US012583843B2

(12) United States Patent
Yang et al.

(10) Patent No.: US 12,583,843 B2
(45) Date of Patent: Mar. 24, 2026

(54) ORGANIC LIGHT-EMITTING DEVICE, METHOD FOR MANUFACTURING SAME, AND COMPOSITION FOR ORGANIC MATERIAL LAYER OF ORGANIC LIGHT-EMITTING DEVICE

(71) Applicant: LT MATERIALS CO., LTD., Yongin-si (KR)

(72) Inventors: Seung-Gyu Yang, Yongin-si (KR); Su-Yeon Kim, Yongin-si (KR); Geon-Yu Park, Yongin-si (KR); Young-Seok No, Yongin-si (KR); Dong-Jun Kim, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 945 days.

(21) Appl. No.: 17/608,881

(22) PCT Filed: Oct. 7, 2020

(86) PCT No.: PCT/KR2020/013664
§ 371 (c)(1),
(2) Date: Nov. 4, 2021

(87) PCT Pub. No.: WO2021/071247
PCT Pub. Date: Apr. 15, 2021

(65) Prior Publication Data

US 2022/0340550 A1 Oct. 27, 2022

(30) Foreign Application Priority Data

Oct. 8, 2019 (KR) ........................ 10-2019-0124527

(51) Int. Cl.
*C07D 405/14* (2006.01)
*C07D 209/82* (2006.01)
(Continued)

(52) U.S. Cl.
CPC ......... *C07D 405/14* (2013.01); *C07D 209/82* (2013.01); *C07D 405/04* (2013.01);
(Continued)

(58) Field of Classification Search
None
See application file for complete search history.

(56) References Cited

U.S. PATENT DOCUMENTS 4,356,429 A 10/1982 Tang
10,158,085 B2 12/2018 Lee et al.
(Continued)

FOREIGN PATENT DOCUMENTS

CN 110194720 A 9/2019
CN 110272427 A 9/2019
(Continued)

OTHER PUBLICATIONS

Computer-generated English-language translation of WO-2021029616-A1.*
(Continued)

*Primary Examiner* — Vu A Nguyen
(74) *Attorney, Agent, or Firm* — Birch, Stewart, Kolasch & Birch, LLP

(57) ABSTRACT

The present specification relates to an organic light emitting device, a method for manufacturing the same, and a composition for an organic material layer.

14 Claims, 20 Drawing Sheets

(51) Int. Cl.

| | |
|---|---|
| ***C07D 405/04*** | (2006.01) |
| ***C07D 409/14*** | (2006.01) |
| ***C07D 487/04*** | (2006.01) |
| ***C07D 491/048*** | (2006.01) |
| ***C07D 495/04*** | (2006.01) |
| ***C07F 7/08*** | (2006.01) |
| ***C07F 9/40*** | (2006.01) |
| ***H10K 50/12*** | (2023.01) |
| ***H10K 50/14*** | (2023.01) |
| ***H10K 50/16*** | (2023.01) |
| ***H10K 50/17*** | (2023.01) |
| ***H10K 50/18*** | (2023.01) |
| ***H10K 85/40*** | (2023.01) |
| ***H10K 85/60*** | (2023.01) |

(52) U.S. Cl.

CPC ......... *C07D 409/14* (2013.01); *C07D 487/04* (2013.01); *C07D 491/048* (2013.01); *C07D 495/04* (2013.01); *C07F 7/0812* (2013.01); *C07F 9/4056* (2013.01); *H10K 50/12* (2023.02); *H10K 50/14* (2023.02); *H10K 50/16* (2023.02); *H10K 50/171* (2023.02); *H10K 85/40* (2023.02); *H10K 85/615* (2023.02); *H10K 85/622* (2023.02); *H10K 85/623* (2023.02); *H10K 85/631* (2023.02); *H10K 85/649* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 50/18* (2023.02)

(56) References Cited

U.S. PATENT DOCUMENTS

| | | | | |
|---|---|---|---|---|
| 10,622,565 | B2 | 4/2020 | Parham et al. | |
| 11,459,316 | B2 * | 10/2022 | Lee | H10K 85/657 |
| 2016/0141505 | A1 | 5/2016 | Park et al. | |
| 2019/0165282 | A1 | 5/2019 | Parham et al. | |
| 2020/0266355 | A1 * | 8/2020 | Park | H10K 85/6572 |
| 2020/0388765 | A1 * | 12/2020 | Lee | C09K 11/06 |
| 2021/0111350 | A1 | 4/2021 | Lui et al. | |

FOREIGN PATENT DOCUMENTS

| | | | | | |
|---|---|---|---|---|---|
| JP | 2016-535942 | A | | 11/2016 | |
| KR | 10-2015-0070860 | A | | 6/2015 | |
| KR | 10-2016-0028524 | A | | 3/2016 | |
| KR | 10-2018-0068869 | A | | 6/2018 | |
| KR | 10-2018-0129656 | A | | 12/2018 | |
| KR | 10-2019-0030963 | A | | 3/2019 | |
| KR | 10-2019-0038109 | A | | 4/2019 | |
| KR | 20190038109 | A | * | 4/2019 | H10L 51/0071 |
| KR | 10-2019-0064010 | | * | 5/2019 | |
| KR | 10-2019-0068103 | A | | 6/2019 | |
| KR | 10-2019-0079339 | A | | 7/2019 | |
| KR | 10-2019-0097650 | | * | 8/2019 | |
| WO | WO-2014050417 | A1 | * | 4/2014 | C07D 209/86 |
| WO | WO 2017/178311 | A1 | | 10/2017 | |
| WO | WO-2021029616 | A1 | * | 2/2021 | C07D 487/04 |

OTHER PUBLICATIONS

Computer-generated English-language translation of WO-2014050417-A1.*

Machine-generated English-language translation of KR-20190038109-A.*

International Search Report for PCT/KR2020/013664 mailed on Feb. 4, 2021.

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials", Advanced Materials, 1994, vol. 6, No. 9, pp. 677-679.

Extended European Search Report dated Oct. 2, 2023 for Application No. 20874005.0.

European Communication pursuant to Article 94(3) EPC for European Application No. 20874005.0, dated Nov. 11, 2025.

* cited by examiner

【FIG. 1】
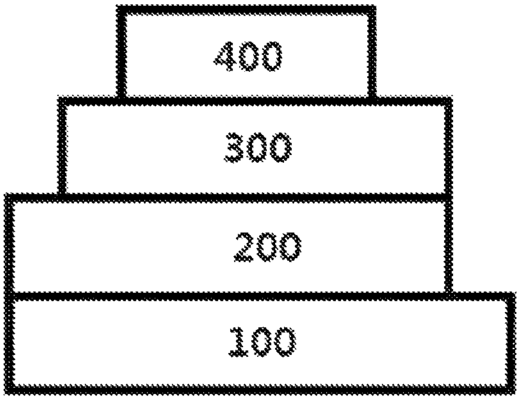
【FIG. 2】
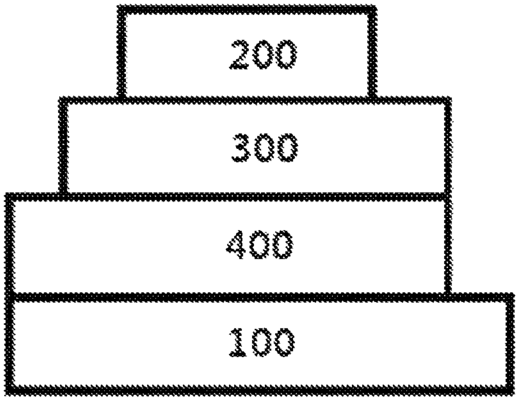

【FIG. 3】
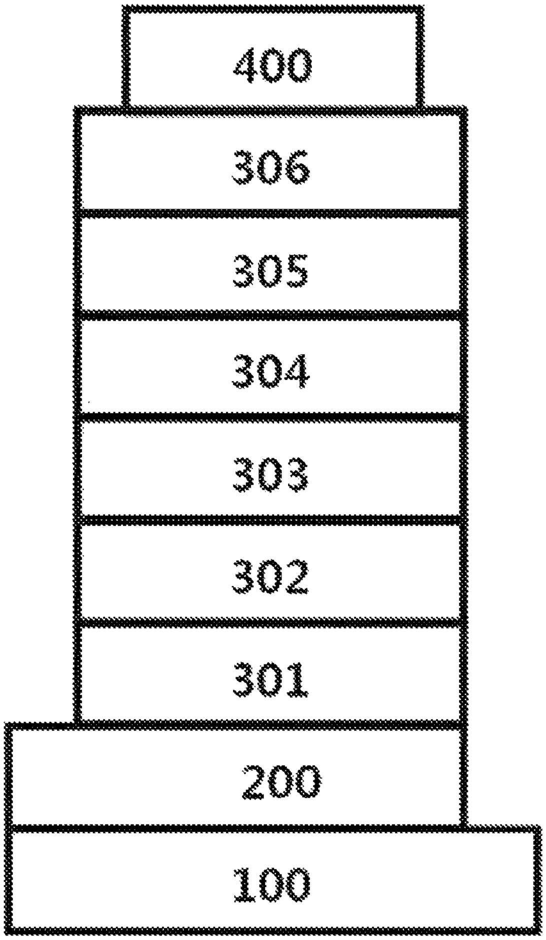

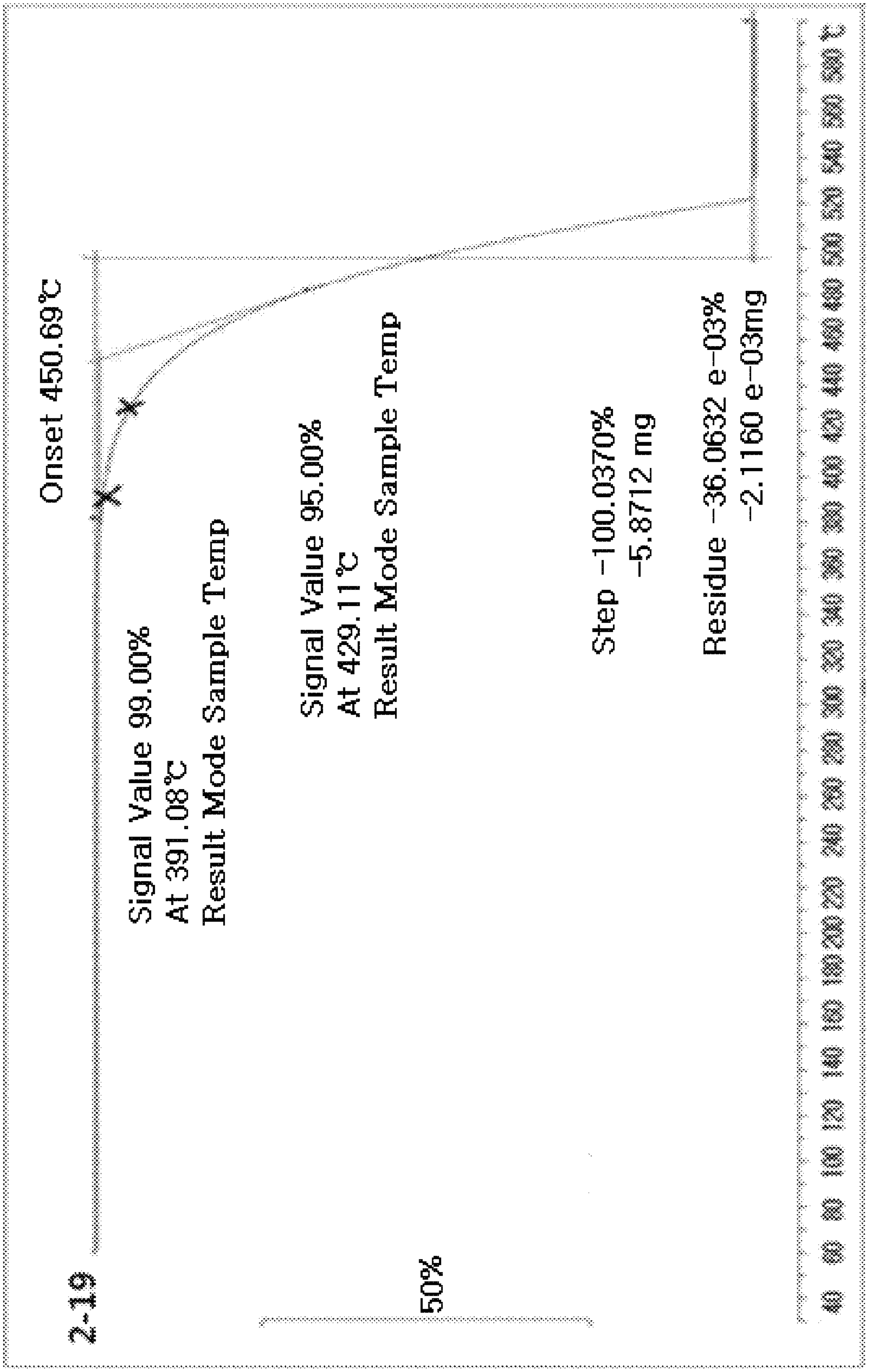
【FIG. 4】

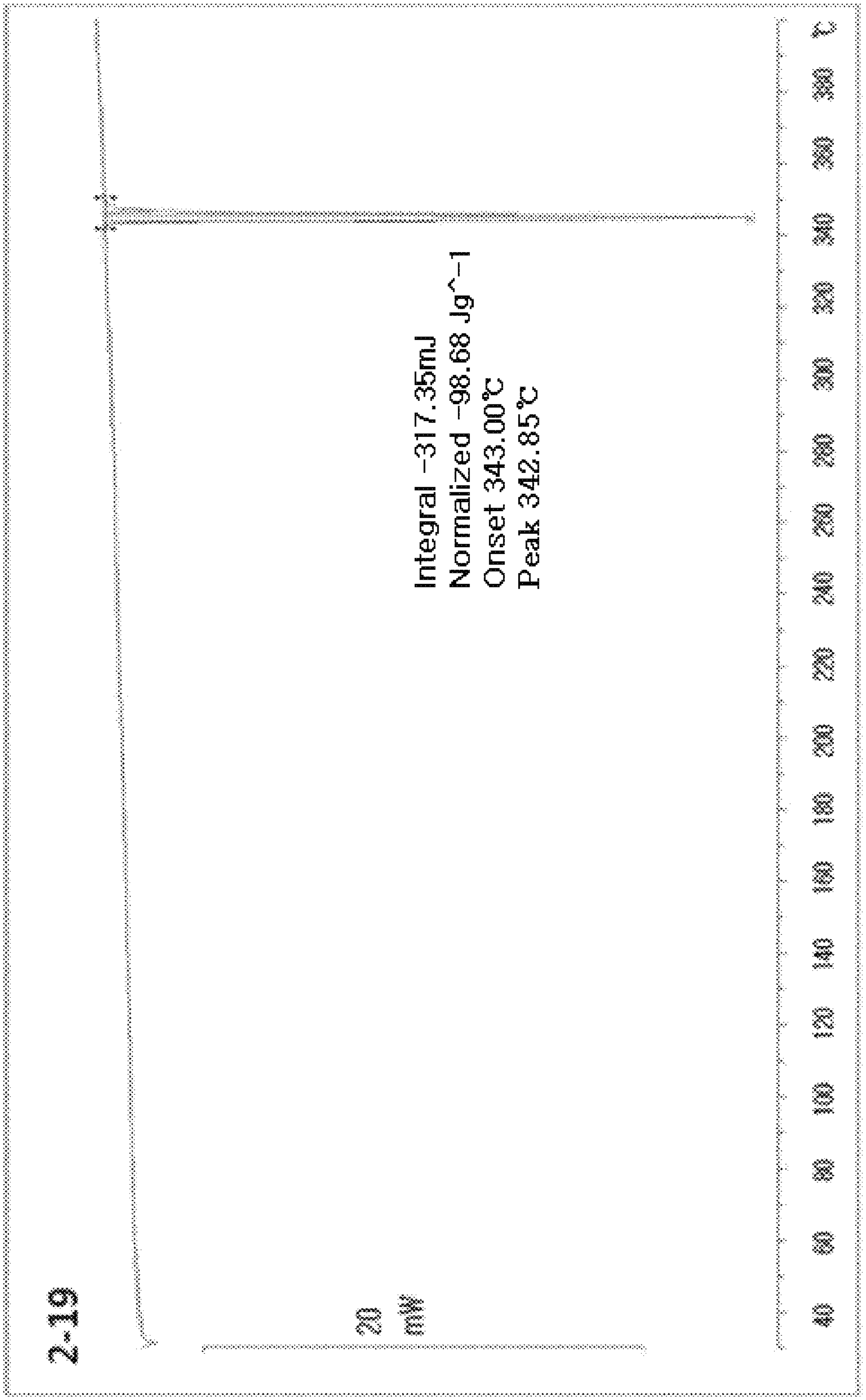
【FIG. 5】

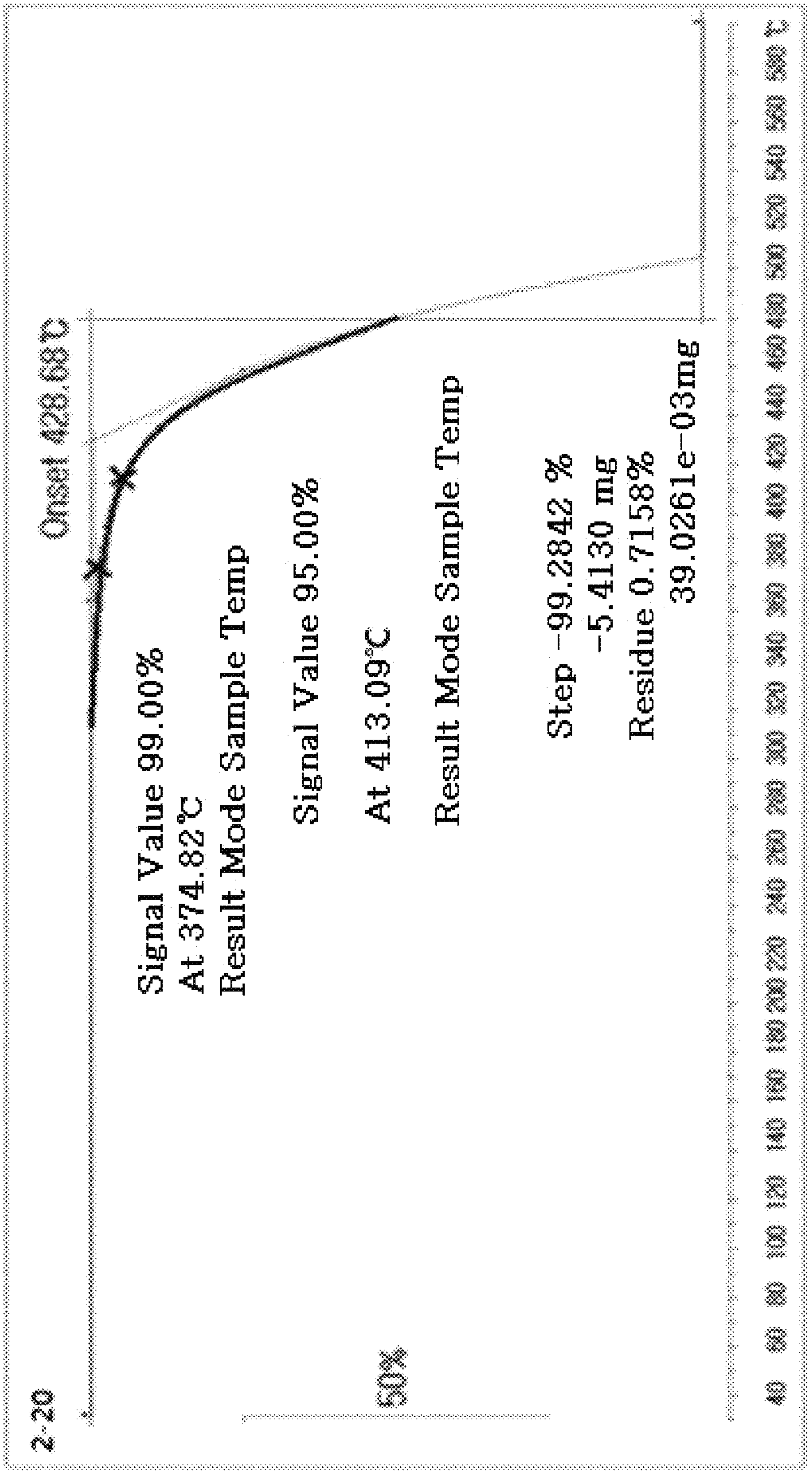
【FIG. 6】

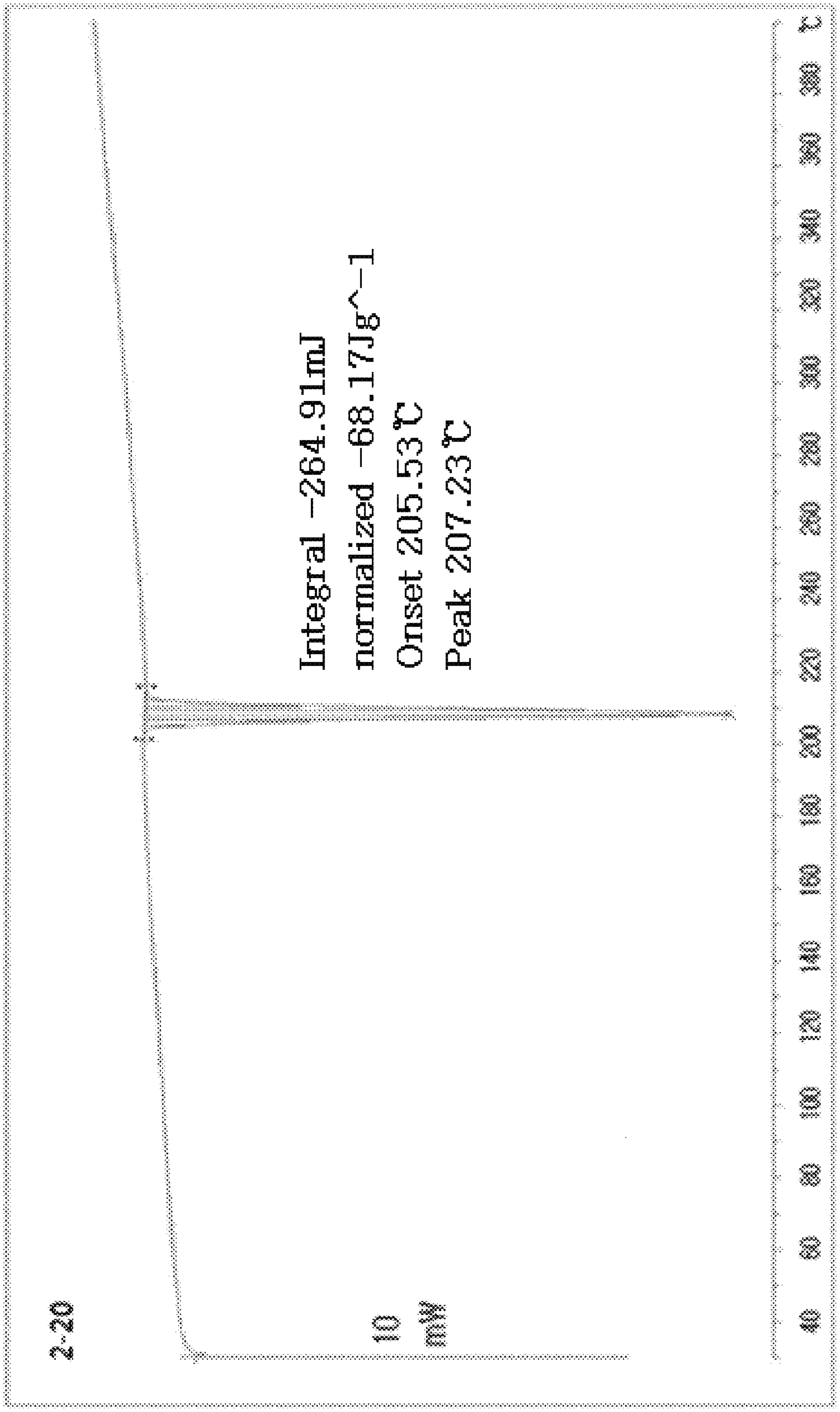
【FIG. 7】

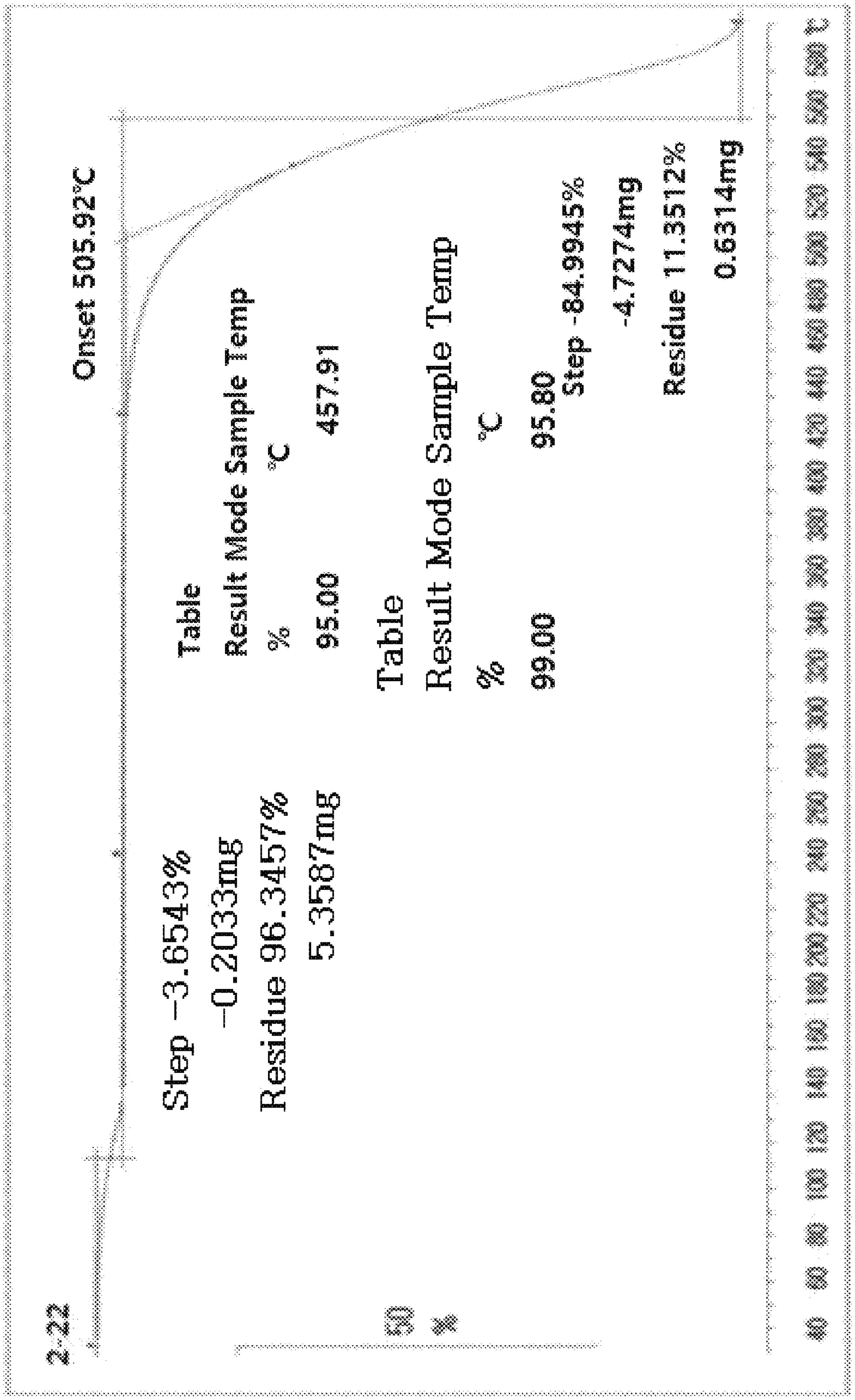
【FIG. 8】

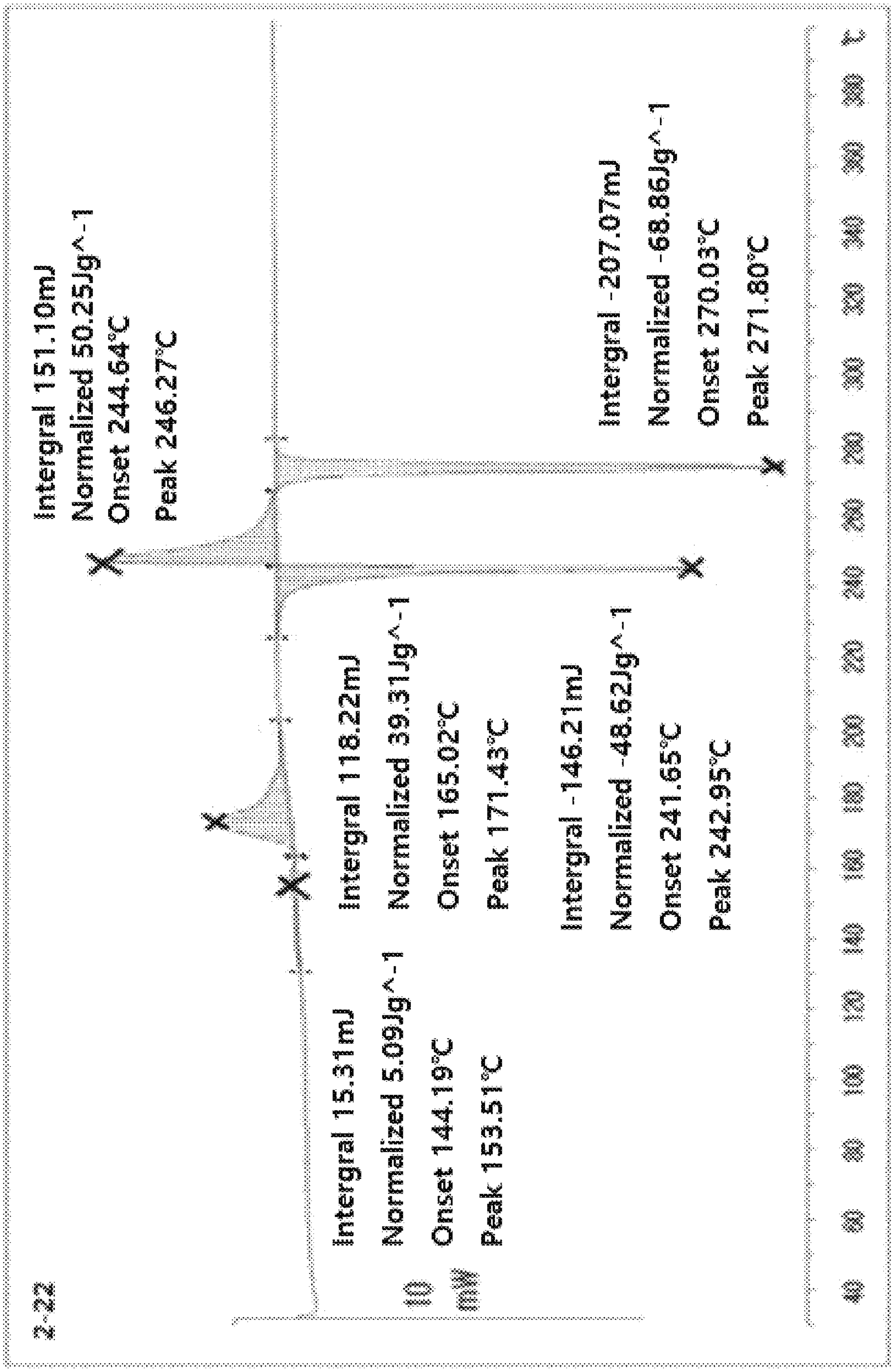
【FIG. 9】

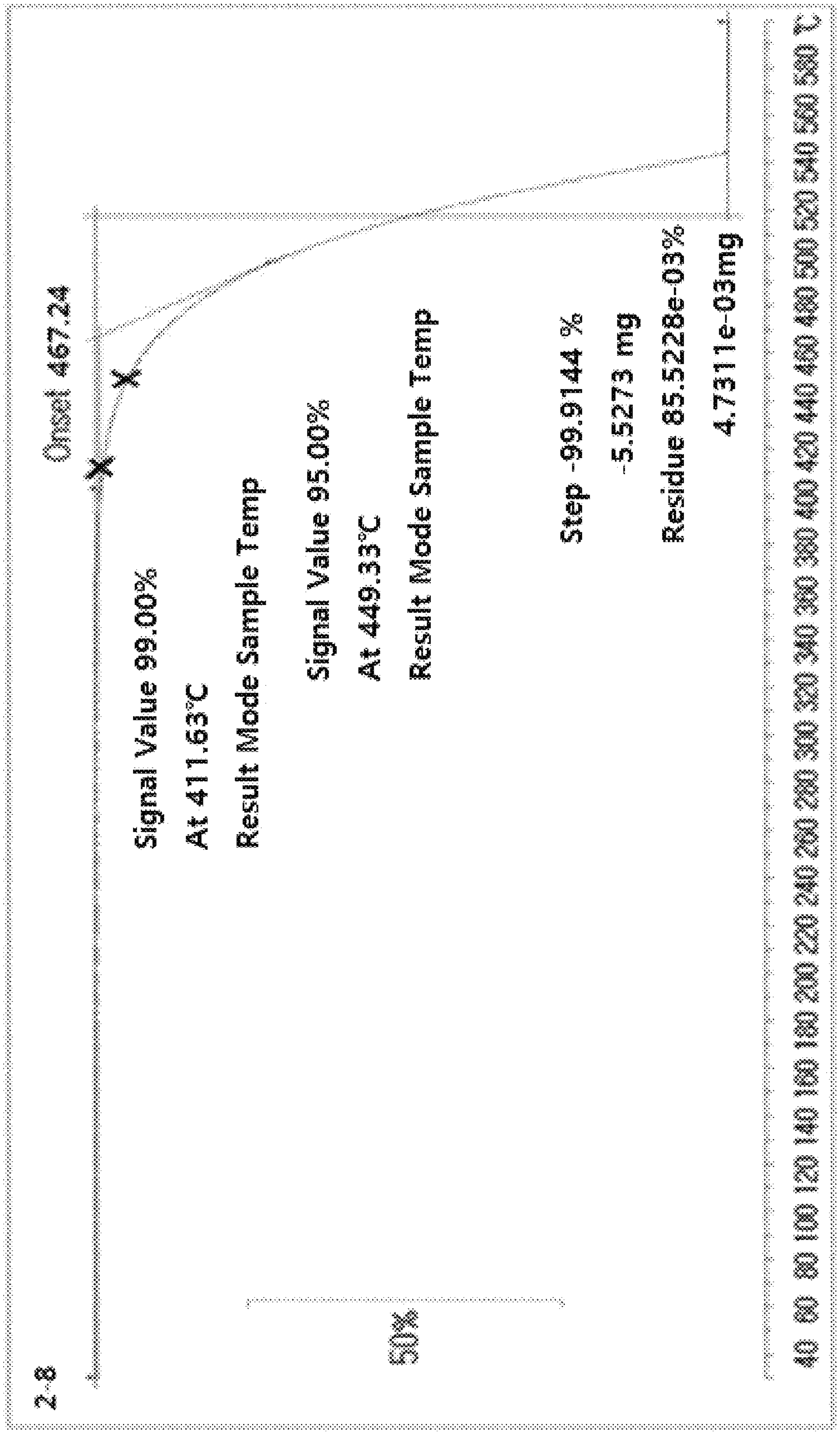
【FIG. 10】

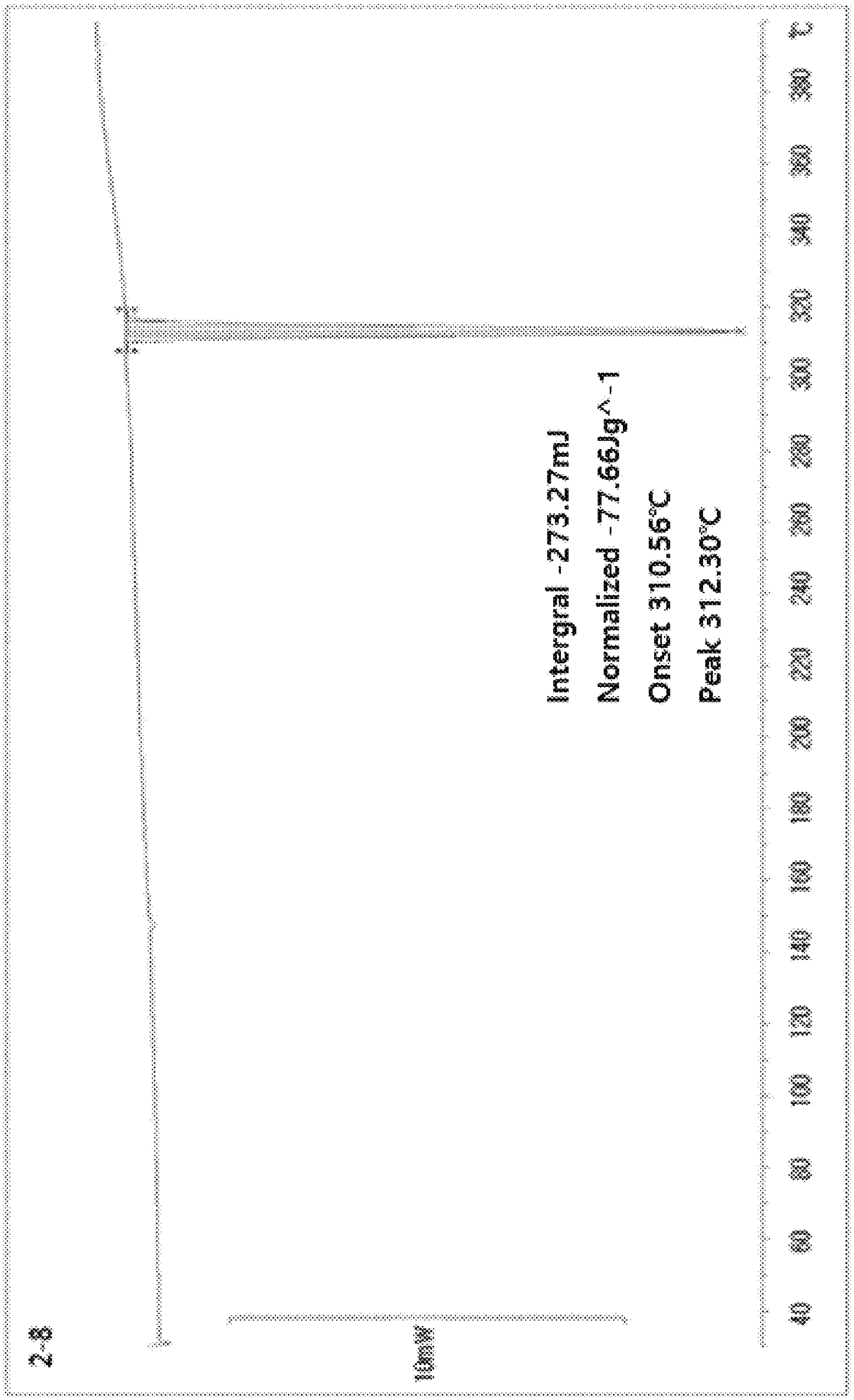
【FIG. 11】

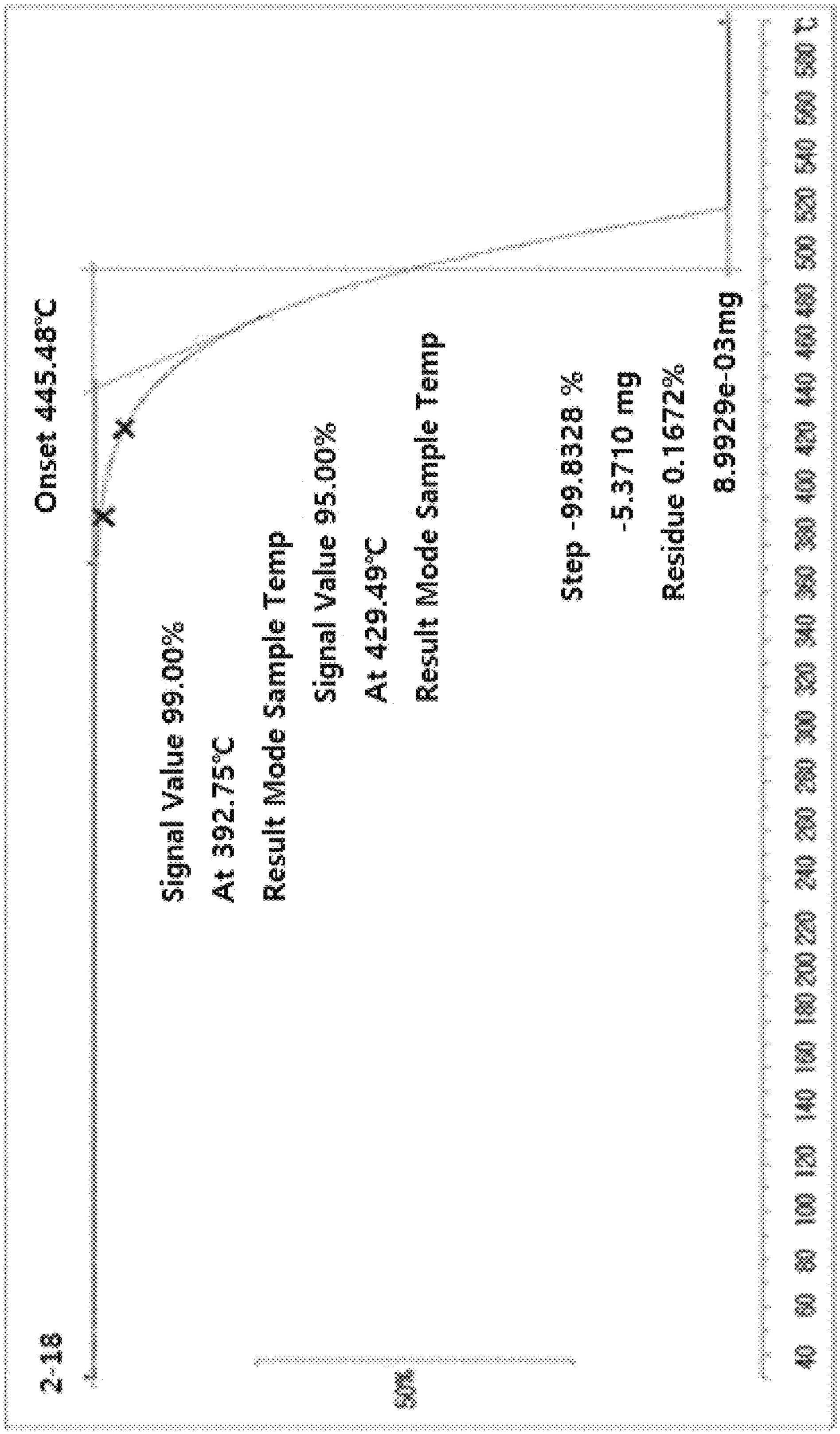
【FIG. 12】

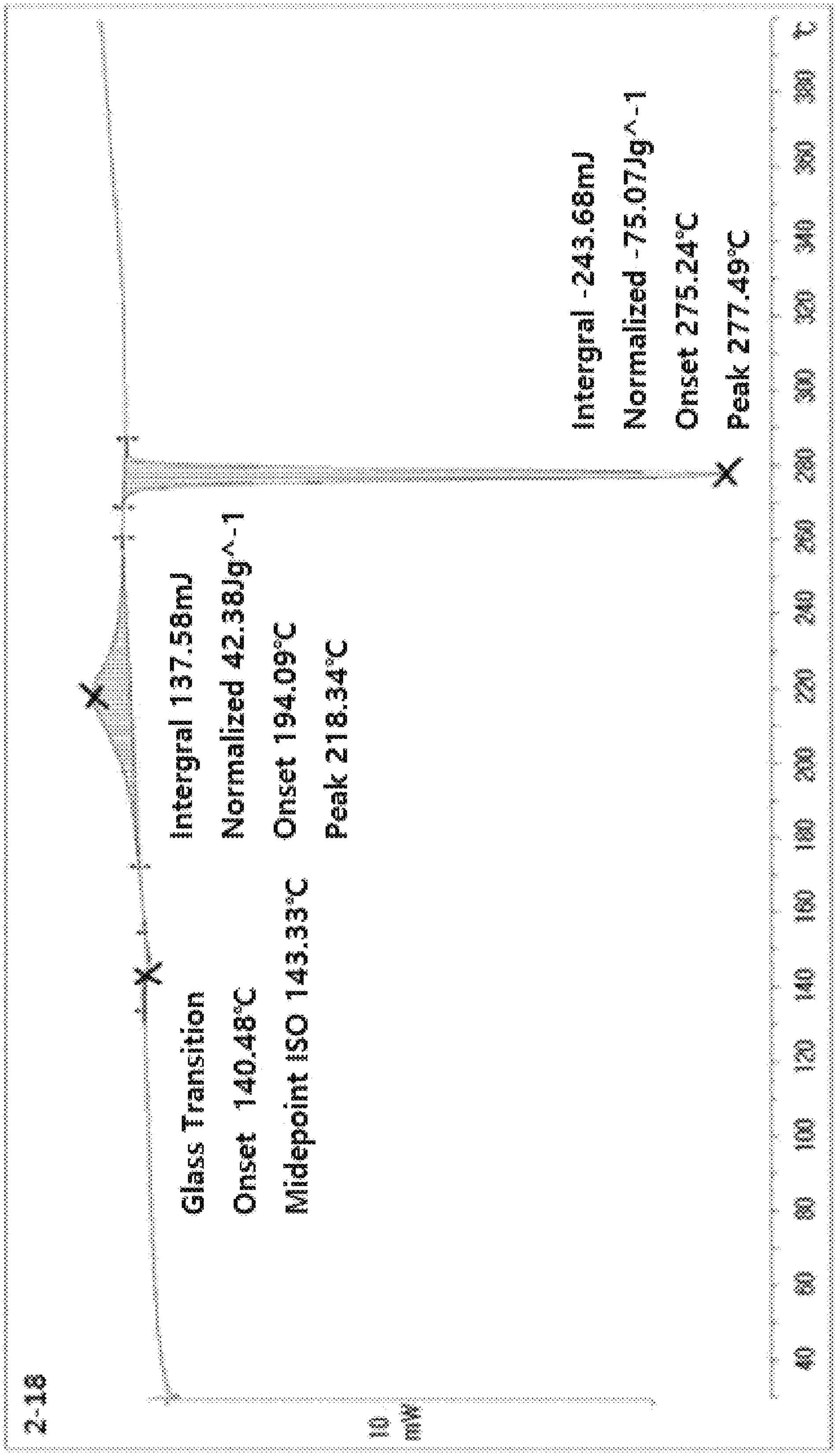
【FIG. 13】

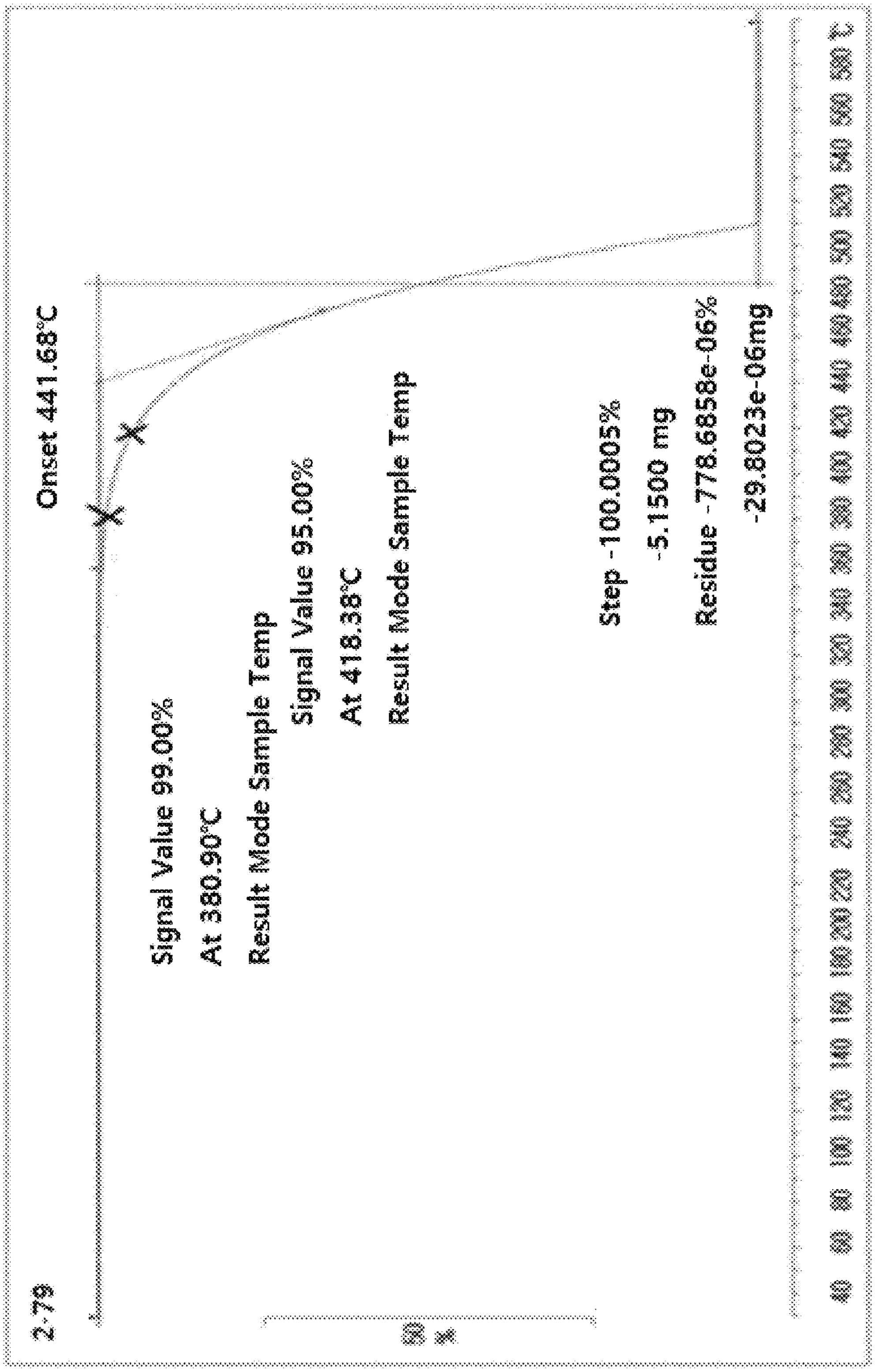
【FIG. 14】

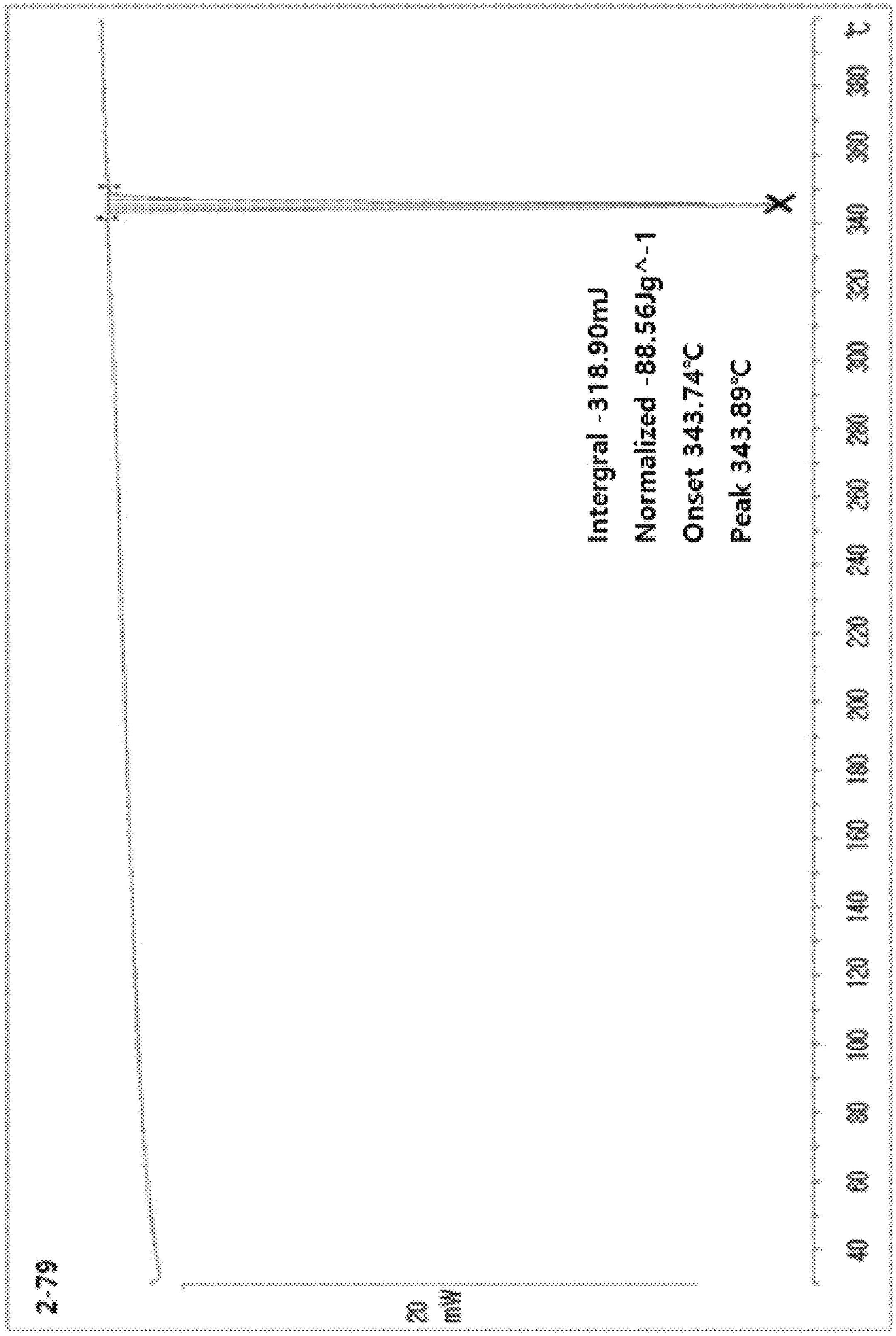
【FIG. 15】

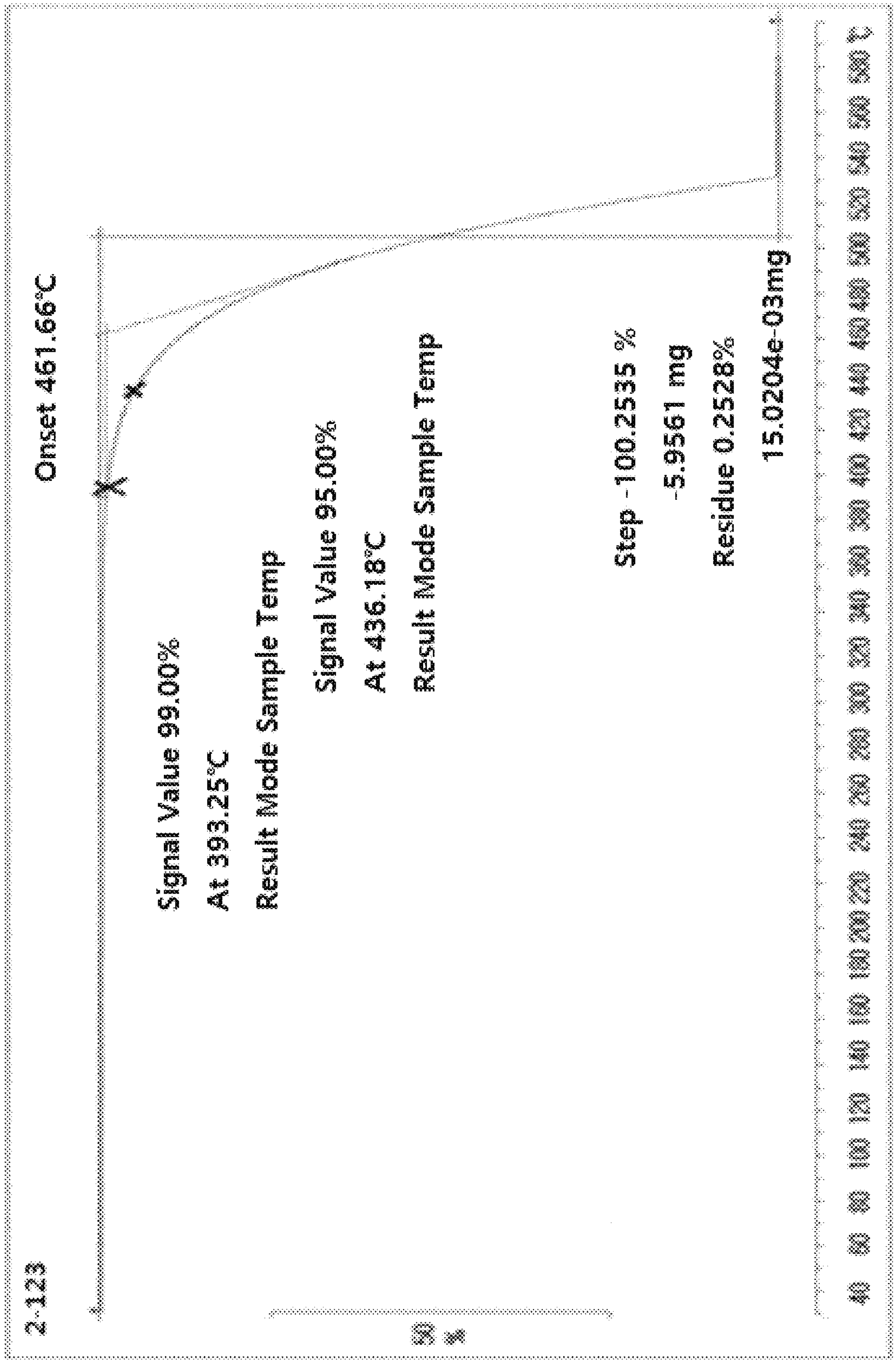
【FIG. 16】

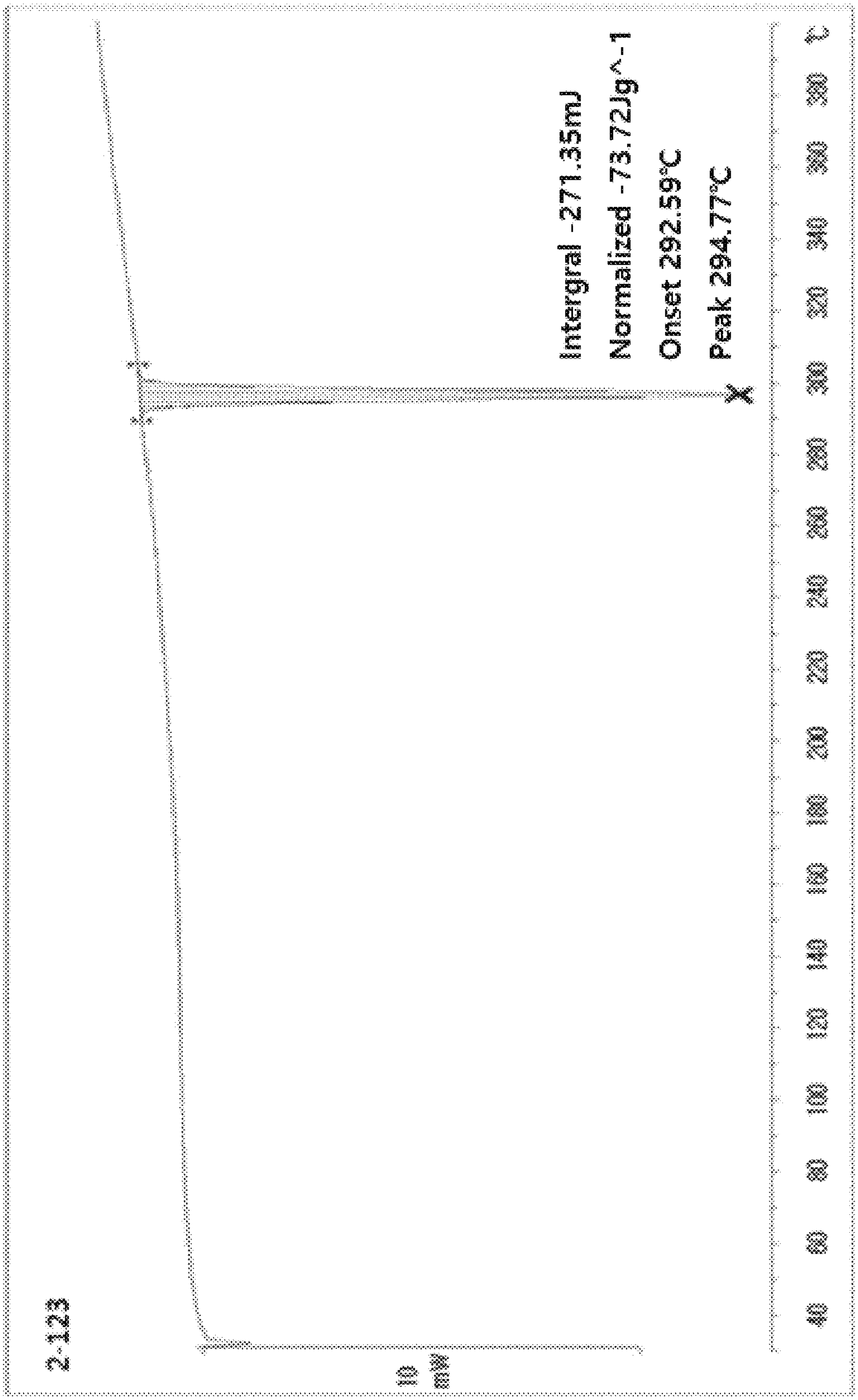
【FIG. 17】

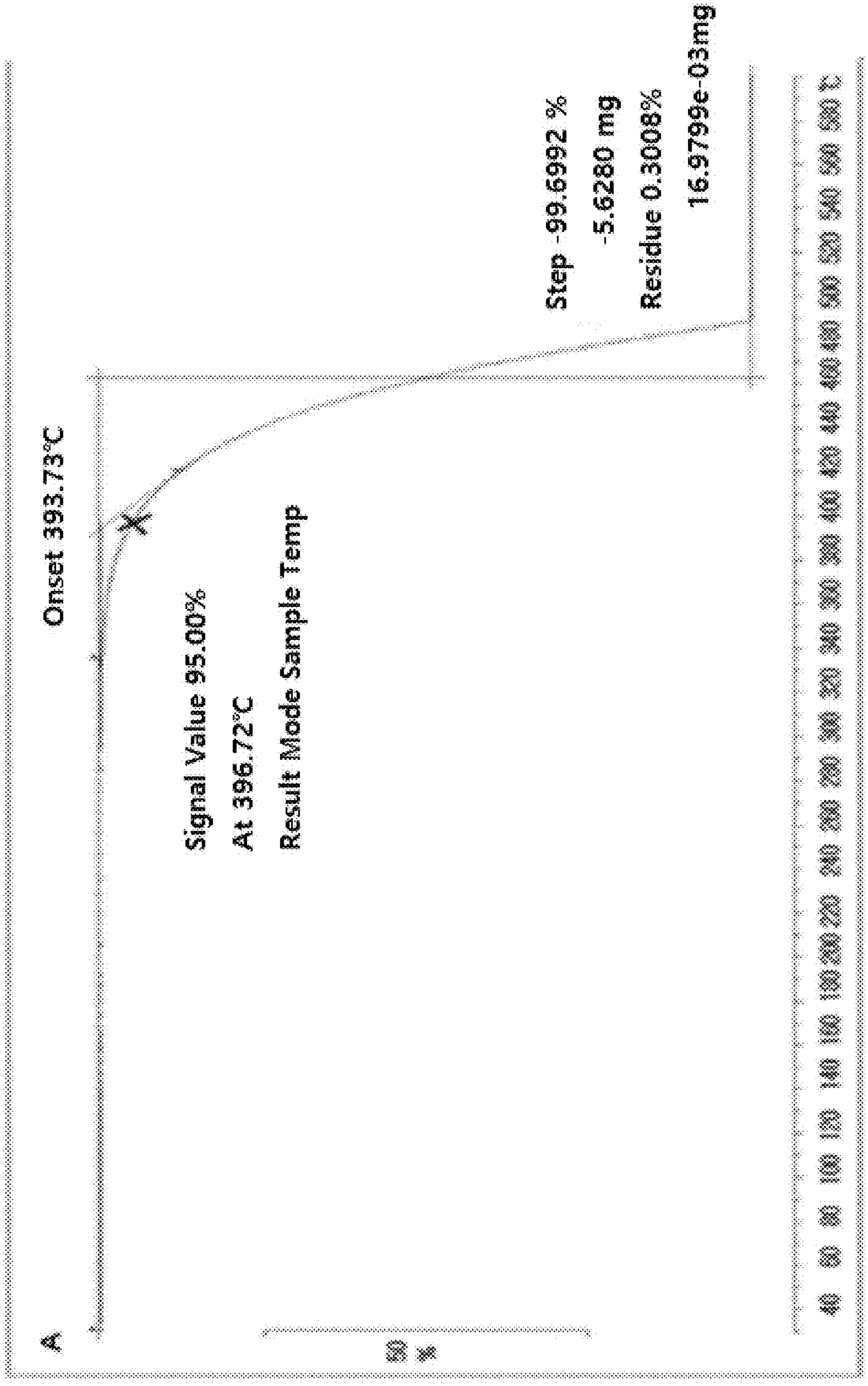
【FIG. 18】

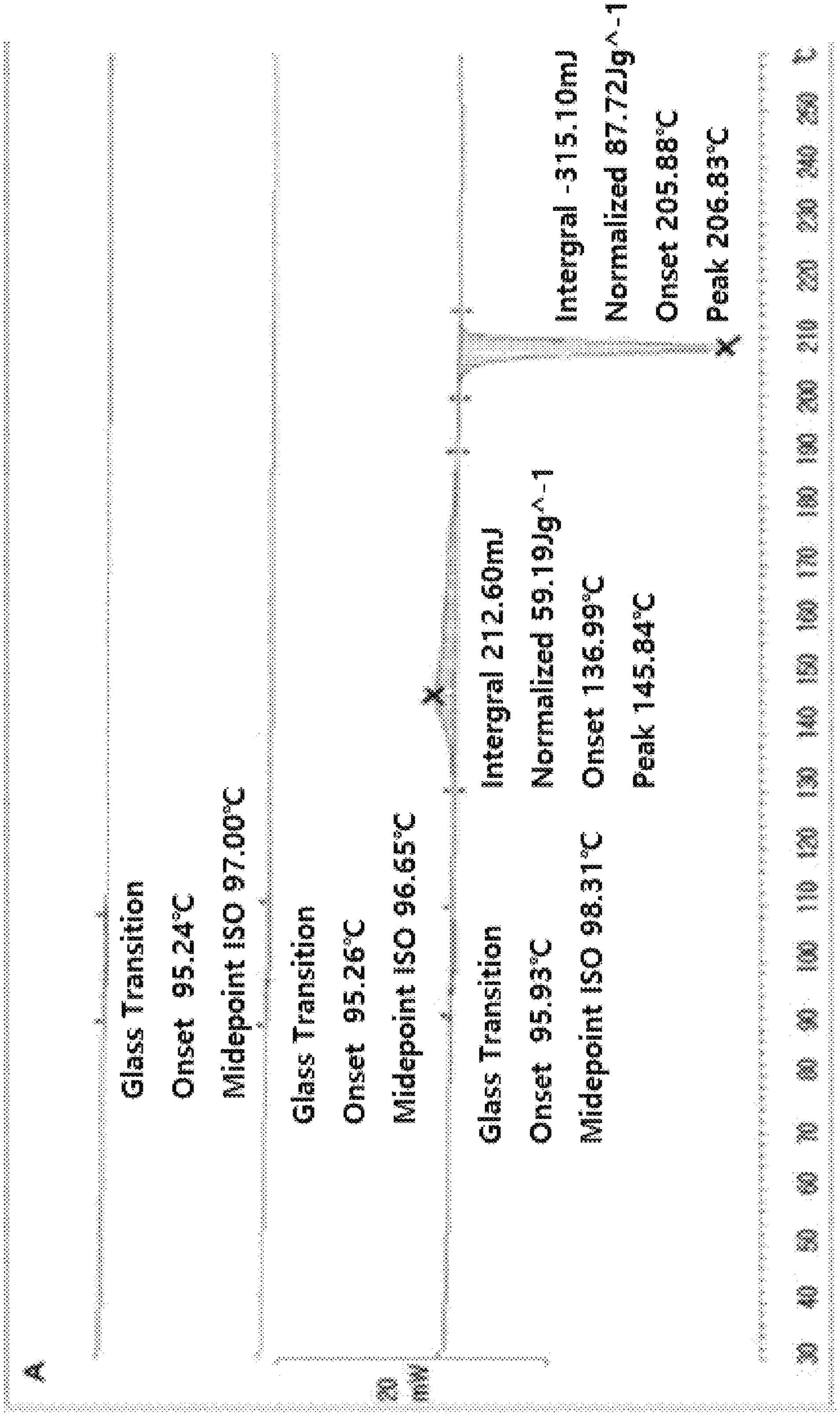
【FIG. 19】

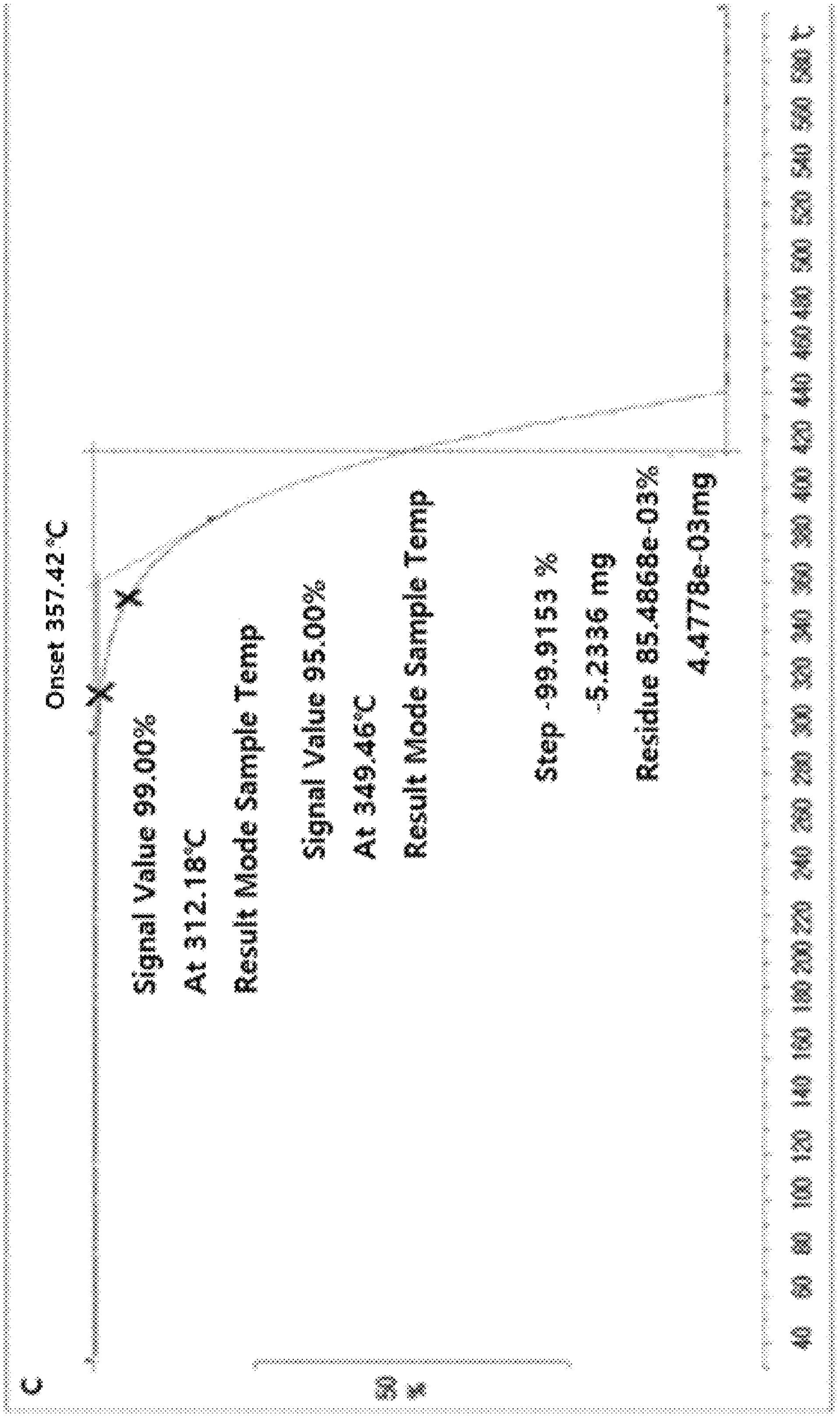
【FIG. 20】

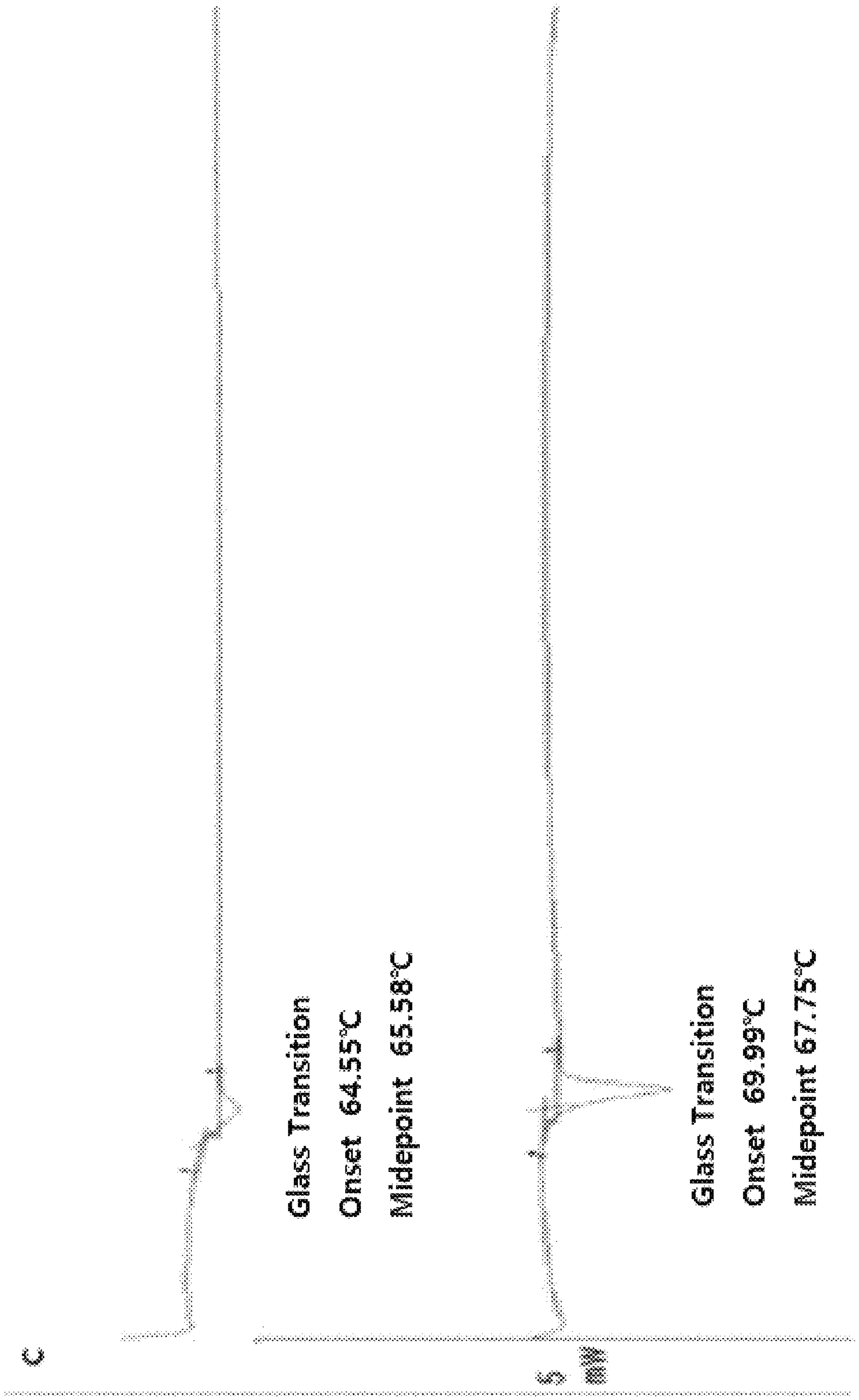
【FIG. 21】

ORGANIC LIGHT-EMITTING DEVICE, METHOD FOR MANUFACTURING SAME, AND COMPOSITION FOR ORGANIC MATERIAL LAYER OF ORGANIC LIGHT-EMITTING DEVICE

TECHNICAL FIELD

This application claims priority to and the benefits of Korean Patent Application No. 10-2019-0124527, filed with the Korean Intellectual Property Office on Oct. 8, 2019, the entire contents of which are incorporated herein by reference.

The present specification relates to an organic light emitting device, a method for manufacturing the same, and a composition for an organic material layer of an organic light emitting device.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents (Patent Document 1) U.S. Pat. No. 4,356,429

DISCLOSURE

Technical Problem

The present application relates to providing an organic light emitting device, a method for manufacturing the same, and a composition for an organic material layer of an organic light emitting device.

Technical Solution

One embodiment of the present application provides an organic light emitting device comprising a first electrode, a second electrode, and one or more organic material layers provided between the first electrode and the second electrode, wherein one or more layers of the organic material layers comprise a heterocyclic compound represented by the following Chemical Formula 1 and a heterocyclic compound represented by the following Chemical Formula 2.

[Chemical Formula 1]

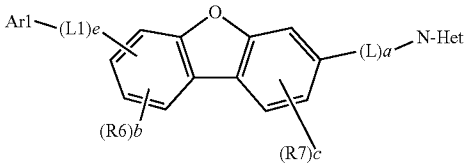

[Chemical Formula 2]

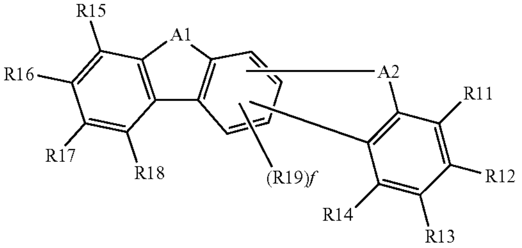

In Chemical Formulae 1 and 2,

N-Het is a monocyclic or polycyclic C2 to C60 heterocyclic group substituted or unsubstituted and comprising one or more Ns, L and L1 are a direct bond; a substituted or unsubstituted C6 to C60 arylene group; or a substituted or unsubstituted C2 to C60 heteroarylene group, Ar1 is a substituted or unsubstituted C6 to C60 aryl group, or represented by the following Chemical Formula 1-A,

[Chemical Formula 1-A]

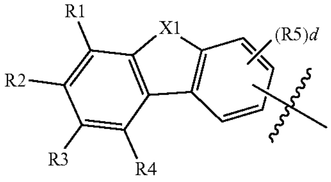

X1 is O; S; or NR22,

R1 to R4 are the same as or different from each other, and each independently hydrogen; a substituted or unsubstituted C1 to C60 alkyl group; a substituted or unsubstituted C6 to C60 aryl group; or a substituted or unsubstituted C2 to C60 heteroaryl group, or two or more groups adjacent to each other bond to each other to form a substituted or unsubstituted C6 to C60 aliphatic or aromatic hydrocarbon ring or a substituted or unsubstituted C2 to C60 heteroring, R5 to R7 and R11 to R19 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(=O)RR'; —SiRR'R" and —NRR', A1 and A2 are the same as or different from each other, and each independently O; S; NRa; or CRbRc, R22, R, R', R" and Ra to Rc are the same as or different from each other, and each independently hydrogen; a substituted or unsubstituted C1 to C60 alkyl group; a substituted or unsubstituted C6 to C60 aryl group; or a substituted or unsubstituted C2 to C60 heteroaryl group, b, c and d are an integer of 0 to 3, f is an integer of 0 to 2, and a and e are an integer of 0 to 5.

In addition, another embodiment of the present application provides a composition for an organic material layer of an organic light emitting device, the composition comprising the heterocyclic compound represented by Chemical Formula 1 and the heterocyclic compound represented by Chemical Formula 2.

Lastly, one embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

Advantageous Effects

A heterocyclic compound according to one embodiment of the present application can be used as a material of an organic material layer of an organic light emitting device. The heterocyclic compound can be used as a material of a hole injection layer, a hole transfer layer, a light emitting layer, an electron transfer layer, an electron injection layer, a charge generation layer or the like in an organic light emitting device. Particularly, a heterocyclic compound represented by Chemical Formula 1 and a compound represented by Chemical Formula 2 can be used as a material of an organic material layer of an organic light emitting device. In addition, when using a heterocyclic compound represented by Chemical Formula 1 and a heterocyclic compound represented by Chemical Formula 2 in an organic light emitting device, a driving voltage of the device can be lowered, light efficiency can be enhanced, and lifetime properties of the device can be enhanced by thermal stability of the compound.

Particularly, the compound of Chemical Formula 1 has a more electron stabilizing structure by a No. 3 position of one side benzene ring of the dibenzofuran structure being substituted with an N-containing ring and another benzene ring not substituted with the N-containing ring of the dibenzofuran structure being substituted with a specific substituent, which provides proper energy level and thermal stability. By using the compounds of Chemical Formula 1, an organic light emitting device with improved lifetime, driving stability and efficiency can be manufactured.

DESCRIPTION OF DRAWINGS

FIG. 1 to FIG. 3 are diagrams each schematically illustrating a lamination structure of an organic light emitting device according to one embodiment of the present application.

FIG. 4 and FIG. 5 are graphs showing thermal stability of Compound 2-19 of the present application.

FIG. 6 and FIG. 7 are graphs showing thermal stability of Compound 2-20 of the present application.

FIG. 8 and FIG. 9 are graphs showing thermal stability of Compound 2-22 of the present application.

FIG. 10 and FIG. 11 are graphs showing thermal stability of Compound 2-8 of the present application.

FIG. 12 and FIG. 13 are graphs showing thermal stability of Compound 2-18 of the present application.

FIG. 14 and FIG. 15 are graphs showing thermal stability of Compound 2-79 of the present application.

FIG. 16 and FIG. 17 are graphs showing thermal stability of Compound 2-123 of the present application.

FIG. 18 and FIG. 19 are graphs showing thermal stability of Compound A.

FIG. 20 and FIG. 21 are graphs showing thermal stability of Compound C.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

In the present specification, a term "substitution" means a hydrogen atom bonding to a carbon atom of a compound being changed to another substituent, and the position of substitution is not limited as long as it is a position at which the hydrogen atom is substituted, that is, a position at which a substituent is capable of substituting, and when two or more substituents substitute, the two or more substituents may be the same as or different from each other.

In the present specification, a "case of a substituent being not indicated in a chemical formula or compound structure" means that a hydrogen atom bonds to a carbon atom. However, since deuterium ($^2$H) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0% or a hydrogen content being 100%. In other words, an expression of "substituent X is hydrogen" does not exclude deuterium unlike a hydrogen content being 100% or a deuterium content being 0%, and therefore, may mean a state in which hydrogen and deuterium are mixed.

In one embodiment of the present application, deuterium is one of isotopes of hydrogen, is an element having deuteron formed with one proton and one neutron as a nucleus, and may be expressed as hydrogen-2, and the elemental symbol may also be written as D or $^{2}$H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

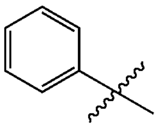 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

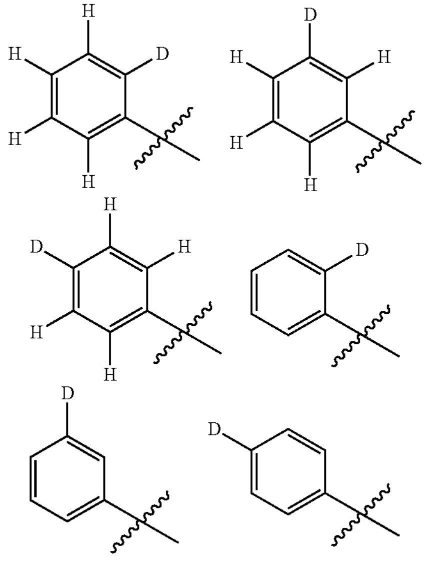

In addition, in one embodiment of the present application, "a phenyl group having a deuterium content of 0%" may mean a phenyl group that does not comprise a deuterium atom, that is, a phenyl group that has 5 hydrogen atoms.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In one embodiment of the present application, R, R' and R" are the same as or different from each other, and may be each independently hydrogen; a substituted or unsubstituted C1 to C60 alkyl group; a substituted or unsubstituted C6 to C60 aryl group; or a substituted or unsubstituted C2 to C60 heteroaryl group.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring group thereof, and the like, but are not limited thereto.

In the present specification, the fluorenyl group may be substituted, and adjacent substituents may bond to each other to form a ring.

When the fluorenyl group is substituted, the following structures may be included, however, the structure is not limited thereto.

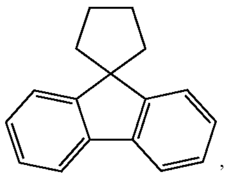
,
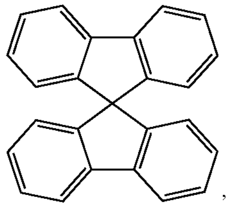
,

-continued

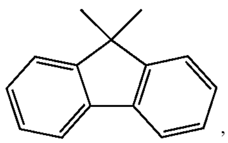
,
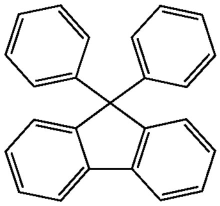
,
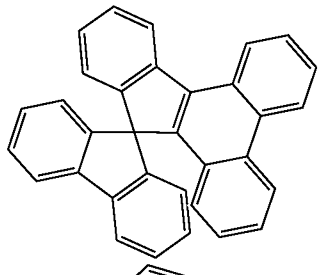
,
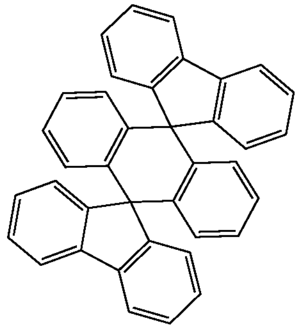

In the present specification, the heteroaryl group comprises S, O, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]

carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except that these are each a divalent group. In addition, the heteroarylene group means the heteroaryl group having two bonding sites, that is, a divalent group. The descriptions on the heteroaryl group provided above may be applied thereto except that these are each a divalent group.

In the present specification, the phosphine oxide group is represented by —P(═O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specifically, the phosphine oxide group may be substituted with an aryl group, and as the aryl group, the examples described above may be used. Examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR104R105R106. R104 to R106 are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that adjacent groups may form, the structures illustrated as the cycloalkyl group, the cycloheteroalkyl group, the aryl group and the heteroaryl group described above may be used except for those that are not a monovalent group.

One embodiment of the present application provides an organic light emitting device comprising a first electrode, a second electrode, and one or more organic material layers provided between the first electrode and the second electrode, wherein one or more layers of the organic material layers comprise a heterocyclic compound represented by Chemical Formula 1 and a heterocyclic compound represented by Chemical Formula 2.

In one embodiment of the present application, Chemical Formula 1 may be represented by any one of the following Chemical Formulae 3 to 6.

[Chemical Formula 3]

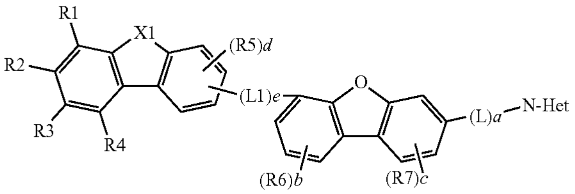

[Chemical Formula 4]

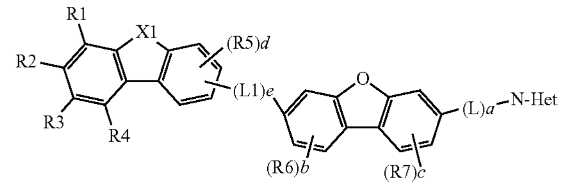

[Chemical Formula 5]

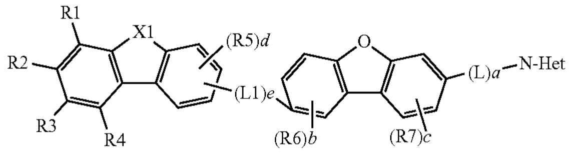

[Chemical Formula 6]

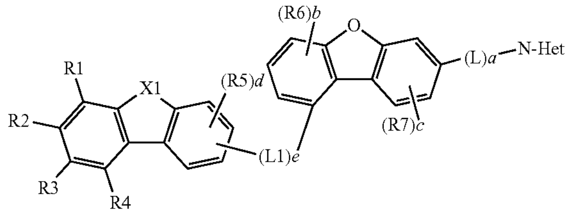

In Chemical Formulae 3 to 6,

N-Het, L, L1, R1 to R7, X1 and a to e have the same definitions as in Chemical Formula 1.

In one embodiment of the present application, Chemical Formula 1 may be represented by any one of the following Chemical Formulae 3-1 to 6-1.

[Chemical Formula 3-1]

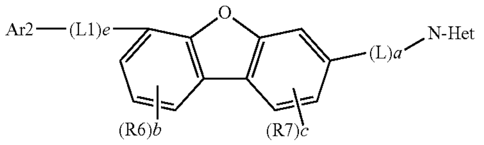

[Chemical Formula 4-1]

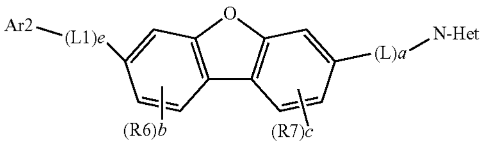

[Chemical Formula 5-1]

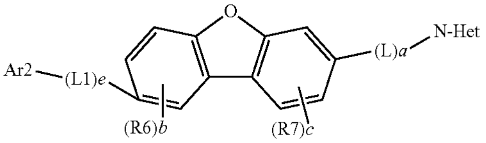

[Chemical Formula 6-1]

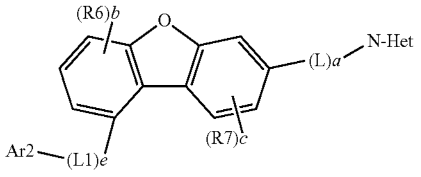

In Chemical Formulae 3-1 to 6-1,

N-Het, L, L1, R6, R7, a to c and e have the same definitions as in Chemical Formula 1, and Ar2 is a substituted or unsubstituted monocyclic or polycyclic C6 to C60 aryl group.

As in the compound of Chemical Formula 1 according to the present application, linearity of the whole material increases when using a No. 3 position of dibenzofuran, which is effective in increasing stability of the whole structure. This is an effect obtained by an azine-based compound that is a substituent having a strong electron withdrawing tendency. Particularly, when substituted with triazine, dibenzofuran at the center of the structure maintains an electron-deficient state, which requires more electrical energy (electrons) to break the bond. Herein, electron withdrawing is stronger as the material has higher linearity, and as electrons in the molecule are concentrated around the triazine structure, an effect of further increasing electron deficiency of the whole structure is obtained. As a result, when driving a device, an effect of preventing a host material from being decomposed by a current flow is obtained.

In one embodiment of the present application, Ar1 is a substituted or unsubstituted C6 to C60 aryl group, or may be represented by Chemical Formula 1-A.

In another embodiment, Ar1 is a substituted or unsubstituted C6 to C40 aryl group, or may be represented by Chemical Formula 1-A.

In another embodiment, Ar1 is a C6 to C40 aryl group, or may be represented by Chemical Formula 1-A.

In another embodiment, Ar1 is a C6 to C20 aryl group, or may be represented by Chemical Formula 1-A.

In another embodiment, Ar1 is a C10 to C20 aryl group, or may be represented by Chemical Formula 1-A.

In another embodiment, Ar1 is a C6 aryl group, or may be represented by Chemical Formula 1-A.

In another embodiment, Ar1 is a phenyl group; a biphenyl group; a terphenyl group; or a triphenylenyl group, or may be represented by Chemical Formula 1-A.

In one embodiment of the present application, Ar2 is a substituted or unsubstituted monocyclic or polycyclic C6 to C60 aryl group.

In another embodiment, Ar2 is a substituted or unsubstituted monocyclic or polycyclic C6 to C40 aryl group.

In another embodiment, Ar2 is a substituted or unsubstituted monocyclic to tetracyclic C6 to C40 aryl group.

In another embodiment, Ar2 is a substituted or unsubstituted monocyclic to pentacyclic C6 to C40 aryl group.

In another embodiment, Ar2 is a substituted or unsubstituted monocyclic C6 to C20 aryl group.

In another embodiment, Ar2 is a substituted or unsubstituted dicyclic C6 to C20 aryl group.

In another embodiment, Ar2 is a substituted or unsubstituted tricyclic C6 to C30 aryl group.

In another embodiment, Ar2 is a substituted or unsubstituted tetracyclic C6 to C40 aryl group.

In another embodiment, Ar2 is a C6 to C40 aryl group.

In another embodiment, Ar2 is a C6 to C20 aryl group.

In another embodiment, Ar2 is a C10 to C20 aryl group.

In another embodiment, Ar2 is a C6 aryl group.

In another embodiment, Ar2 may be a phenyl group; a biphenyl group; a terphenyl group; or a triphenylenyl group.

In one embodiment of the present application, R5 to R7 are the same as or different from each other, and may be each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R" and —NRR'.

In another embodiment, R5 to R7 are the same as or different from each other, and may be each independently selected from the group consisting of hydrogen; halogen; a substituted or unsubstituted C1 to C60 alkyl group; a substituted or unsubstituted C6 to C60 aryl group; a substituted or unsubstituted C2 to C60 heteroaryl group; —P(═O)RR'; —SiRR'R" and —NRR'.

In another embodiment, R5 to R7 are the same as or different from each other, and may be each independently selected from the group consisting of hydrogen; halogen; a substituted or unsubstituted C1 to C60 alkyl group; a substituted or unsubstituted C6 to C40 aryl group; a substituted or unsubstituted C2 to C40 heteroaryl group; —P(═O)RR'; —SiRR'R" and —NRR'.

In another embodiment, R5 to R7 may be hydrogen.

In another embodiment, R5 may be hydrogen.

In another embodiment, R6 may be hydrogen.

In another embodiment, R7 may be hydrogen.

In one embodiment of the present application, L may be a direct bond; a substituted or unsubstituted C6 to C60 arylene group; or a substituted or unsubstituted C2 to C60 heteroarylene group.

In another embodiment, L may be a direct bond; a substituted or unsubstituted C6 to C40 arylene group; or a substituted or unsubstituted C2 to C40 heteroarylene group.

In another embodiment, L may be a direct bond; a substituted or unsubstituted C6 to C40 monocyclic or polycyclic arylene group; or a substituted or unsubstituted C2 to C40 heteroarylene group.

In another embodiment, L may be a direct bond; a substituted or unsubstituted C6 to C40 monocyclic arylene group; or a substituted or unsubstituted C10 to C40 polycyclic arylene group.

In another embodiment, L may be a direct bond; a C6 to C40 monocyclic arylene group; or a C10 to C40 polycyclic arylene group.

In another embodiment, L may be a direct bond; a phenylene group; a biphenylene group; or a naphthylene group.

In another embodiment, L may be a direct bond.

In one embodiment of the present application, L1 may be a direct bond; a substituted or unsubstituted C6 to C60 arylene group; or a substituted or unsubstituted C2 to C60 heteroarylene group.

In another embodiment, L1 may be a direct bond; a substituted or unsubstituted C6 to C40 arylene group; or a substituted or unsubstituted C2 to C40 heteroarylene group.

In another embodiment, L1 may be a direct bond; a substituted or unsubstituted C6 to C40 monocyclic or polycyclic arylene group; or a substituted or unsubstituted C2 to C40 heteroarylene group.

In another embodiment, L1 may be a direct bond; a substituted or unsubstituted C6 to C40 monocyclic arylene group; or a substituted or unsubstituted C10 to C40 polycyclic arylene group.

In another embodiment, L1 may be a direct bond; a C6 to C40 monocyclic arylene group; or a C10 to C40 polycyclic arylene group.

In another embodiment, L1 may be a direct bond; a phenylene group; a biphenylene group; or a naphthylene group.

In one embodiment of the present application, R1 to R4 are the same as or different from each other, and each independently hydrogen; a substituted or unsubstituted C1 to C60 alkyl group; a substituted or unsubstituted C6 to C60 aryl group; or a substituted or unsubstituted C2 to C60 heteroaryl group, or two or more groups adjacent to each other may bond to each other to form a substituted or unsubstituted C6 to C60 aliphatic or aromatic hydrocarbon ring or a substituted or unsubstituted C2 to C60 heteroring.

In another embodiment, R1 to R4 are the same as or different from each other, and each independently hydrogen; a substituted or unsubstituted C1 to C60 alkyl group; a substituted or unsubstituted C6 to C60 aryl group; or a substituted or unsubstituted C2 to C60 heteroaryl group, or two or more groups adjacent to each other may bond to each other to form a substituted or unsubstituted C6 to C60 aromatic hydrocarbon ring.

In another embodiment, R1 to R4 are the same as or different from each other, and each independently hydrogen; a substituted or unsubstituted C1 to C40 alkyl group; a substituted or unsubstituted C6 to C40 aryl group; or a substituted or unsubstituted C2 to C40 heteroaryl group, or two or more groups adjacent to each other may bond to each other to form a substituted or unsubstituted C6 to C40 aromatic hydrocarbon ring.

In another embodiment, R1 to R4 are the same as or different from each other, and each independently hydrogen; a C1 to C40 alkyl group; a C6 to C40 aryl group; or a C2 to C40 heteroaryl group, or two or more groups adjacent to each other may bond to each other to form a C6 to C40 aromatic hydrocarbon ring.

In another embodiment, R1 to R4 are the same as or different from each other, and each independently hydrogen; a C6 to C40 monocyclic aryl group; or a C10 to C40 polycyclic aryl group, or two or more groups adjacent to each other may bond to each other to form a C6 to C40 monocyclic aromatic hydrocarbon ring.

In another embodiment, R1 to R4 are the same as or different from each other, and each independently hydrogen; a phenyl group; a biphenyl group; or a triphenylenyl group, or two or more groups adjacent to each other may bond to each other to form a benzene ring.

In one embodiment of the present application, X1 may be O; S; or NR22.

In one embodiment of the present application, X1 may be O.

In one embodiment of the present application, X1 may be S.

In one embodiment of the present application, X1 may be NR22.

In one embodiment of the present application, R22 may be a substituted or unsubstituted C1 to C60 alkyl group; a substituted or unsubstituted C6 to C60 aryl group; or a substituted or unsubstituted C2 to C60 heteroaryl group.

In another embodiment, R22 may be a C1 to C60 alkyl group; a C6 to C60 aryl group; or a C2 to C60 heteroaryl group.

In another embodiment, R22 may be a C6 to C60 aryl group.

In another embodiment, R22 may be a C6 to C40 monocyclic aryl group.

In another embodiment, R22 may be a phenyl group.

In one embodiment of the present application, Chemical Formula 1-A may be represented by any one of the following Chemical Formulae 1-1 to 1-6.

[Chemical Formula 1-1]

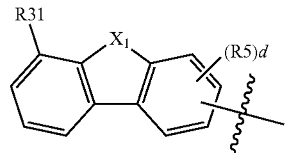

[Chemical Formula 1-2]

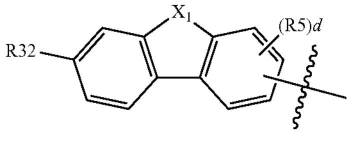

[Chemical Formula 1-3]

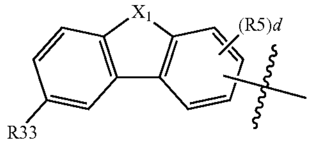

[Chemical Formula 1-4]

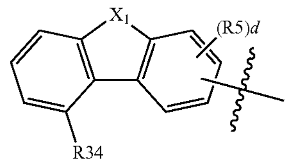

-continued

[Chemical Formula 1-5]

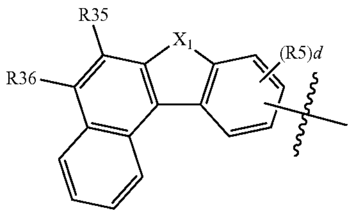

[Chemical Formula 1-6]

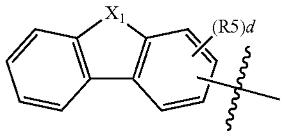

In Chemical Formulae 1-1 to 1-6,

X1, R5 and d have the same definitions as in Chemical Formula 1-A,

means a position linked to L1 of Chemical Formula 1,

R31 to R34 are the same as or different from each other, and each independently a substituted or unsubstituted C1 to C60 alkyl group; a substituted or unsubstituted C6 to C60 aryl group; or a substituted or unsubstituted C2 to C60 heteroaryl group, and R35 and R36 are the same as or different from each other, and each independently hydrogen; a substituted or unsubstituted C1 to C60 alkyl group; a substituted or unsubstituted C6 to C60 aryl group; or a substituted or unsubstituted C2 to C60 heteroaryl group.

In one embodiment of the present application, R31 to R34 are the same as or different from each other, and may be each independently a substituted or unsubstituted C1 to C60 alkyl group; a substituted or unsubstituted C6 to C60 aryl group; or a substituted or unsubstituted C2 to C60 heteroaryl group.

In another embodiment, R31 to R34 are the same as or different from each other, and may be each independently a substituted or unsubstituted C6 to C60 aryl group.

In another embodiment, R31 to R34 are the same as or different from each other, and may be each independently a substituted or unsubstituted C6 to C40 aryl group.

In another embodiment, R31 to R34 are the same as or different from each other, and may be each independently a substituted or unsubstituted C6 to C40 monocyclic or polycyclic aryl group.

In another embodiment, R31 to R34 are the same as or different from each other, and may be each independently a C6 to C40 monocyclic aryl group; or a C10 to C40 polycyclic aryl group.

In another embodiment, R31 to R34 are the same as or different from each other, and may be each independently a phenyl group; or a triphenylenyl group.

In one embodiment of the present application, R35 and R36 may be hydrogen.

In one embodiment of the present application, N-Het may be a monocyclic or polycyclic C2 to C60 heterocyclic group substituted or unsubstituted and comprising one or more Ns.

In another embodiment, N-Het may be a monocyclic or polycyclic C2 to C60 heterocyclic group substituted or unsubstituted and comprising one or more and three or less Ns.

In another embodiment, N-Het may be a monocyclic C2 to C60 heterocyclic group substituted or unsubstituted and comprising one or more and three or less Ns.

In another embodiment, N-Het may be a monocyclic or polycyclic C2 to C40 heterocyclic group substituted or unsubstituted and comprising one or more and three or less Ns.

In another embodiment, N-Het may be a monocyclic C2 to C40 heterocyclic group substituted or unsubstituted and comprising one or more and three or less Ns.

In another embodiment, N-Het may be a monocyclic C2 to C40 heterocyclic group unsubstituted or substituted with one or more substituents selected from the group consisting of a C1 to C20 alkyl group, a C6 to C40 aryl group, a C2 to C40 heteroaryl group, —P(═)ORR' and —SiRR'R" or a substituent linking two or more of the substituents, and comprising one or more and three or less Ns.

In another embodiment, N-Het may be a pyridine group; a pyrimidine group; or a triazine group unsubstituted or substituted with one or more substituents selected from the group consisting of a C1 to C20 alkyl group, a C6 to C40 aryl group, a C2 to C40 heteroaryl group, —P(═)ORR' and —SiRR'R" or a substituent linking two or more of the substituents.

In another embodiment, N-Het may be a pyridine group unsubstituted or substituted with a phenyl group; a pyrimidine group unsubstituted or substituted with a phenyl group; or a triazine group unsubstituted or substituted with one or more substituents selected form the group consisting of a phenyl group unsubstituted or substituted with a triphenylenyl group, a diphenylfluorene group, —P(═)ORR' or —SiRR'R", a biphenyl group, a dibenzofuran group, a dimethylfluorene group and a dibenzothiophene group.

In one embodiment of the present application, N-Het may be selected from among the following structural formulae.

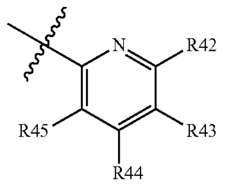
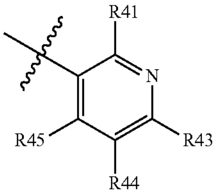
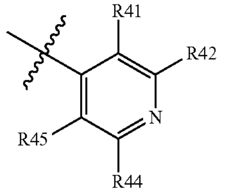
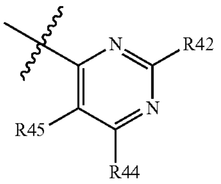
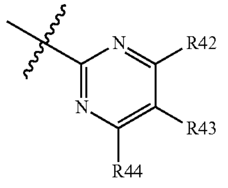
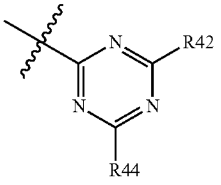

In the structural formulae,

means a position linked to L of Chemical Formula 1, and

R41 to R45 are the same as or different from each other, and each independently hydrogen; a substituted or unsubstituted C1 to C60 alkyl group; a substituted or unsubstituted C6 to C60 aryl group; or a substituted or unsubstituted C2 to C60 heteroaryl group.

In another embodiment, R41 to R45 are the same as or different from each other, and may be each independently hydrogen; a substituted or unsubstituted C1 to C60 alkyl group; a substituted or unsubstituted C6 to C60 aryl group; or a substituted or unsubstituted C2 to C60 heteroaryl group.

In another embodiment, R41 to R45 are the same as or different from each other, and may be each independently hydrogen; a substituted or unsubstituted C1 to C40 alkyl group; a substituted or unsubstituted C6 to C40 aryl group; or a substituted or unsubstituted C2 to C40 heteroaryl group.

In another embodiment, R41 to R45 are the same as or different from each other, and may be each independently hydrogen; a C6 to C40 aryl group unsubstituted or substituted with one or more substituents selected form the group consisting of a C1 to C20 alkyl group, a C6 to C40 aryl group, a C2 to C40 heteroaryl group, —P(=)ORR' and —SiRR'R"; or a C2 to C40 heteroaryl group.

In another embodiment, R41 to R45 are the same as or different from each other, and may be each independently hydrogen; a phenyl group unsubstituted or substituted with one or more substituents selected form the group consisting of a phenyl group, a triphenylenyl group, a diphenylfluorenyl group, —P(=)ORR' and —SiRR'R"; a biphenyl group; a dibenzofuran group; a dibenzothiophene group; or a dimethylfluorenyl group.

In one embodiment of the present application, R, R' and R" are the same as or different from each other, and may be each independently a substituted or unsubstituted C1 to C60 alkyl group; a substituted or unsubstituted C6 to C60 aryl group; or a substituted or unsubstituted C2 to C60 heteroaryl group.

In another embodiment, R, R' and R" are the same as or different from each other, and may be each independently a substituted or unsubstituted C6 to C60 aryl group.

In another embodiment, R, R' and R" are the same as or different from each other, and may be each independently a substituted or unsubstituted C6 to C60 monocyclic or polycyclic aryl group.

In another embodiment, R, R' and R" are the same as or different from each other, and may be each independently a substituted or unsubstituted C6 to C40 monocyclic aryl group.

In another embodiment, R, R' and R" are the same as or different from each other, and may be each independently a C6 to C20 monocyclic aryl group.

In another embodiment, R, R' and R" may be a phenyl group.

In one embodiment of the present application, Chemical Formula 2 may be represented by any one of the following Chemical Formulae 2-1 to 2-6.

[Chemical Formula 2-1]

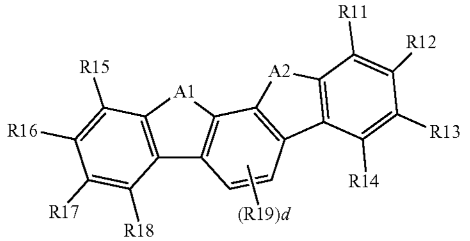

[Chemical Formula 2-2]

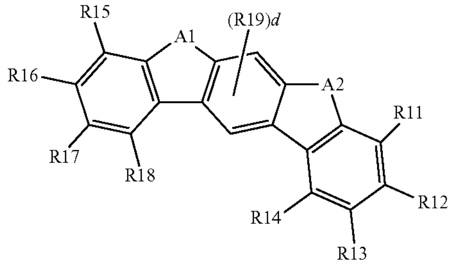

[Chemical Formula 2-3]

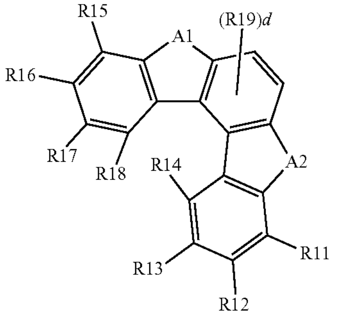

[Chemical Formula 2-4]

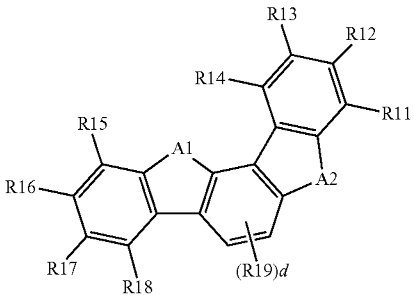

[Chemical Formula 2-5]

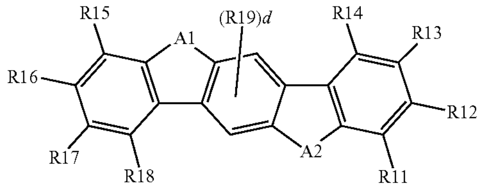

-continued

[Chemical Formula 2-6]

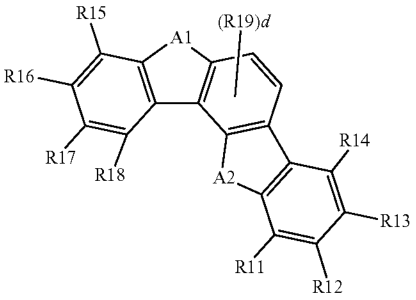

In Chemical Formulae 2-1 to 2-6,

R11 to R19, A1, A2 and d have the same definitions as in Chemical Formula 2.

In one embodiment of the present application, A1 and A2 are the same as or different from each other, and each independently O; S; NRa; or CRbRc.

In one embodiment of the present application, A1 is O; S; NRa; or CRbRc.

In one embodiment of the present application, A2 is O; S; NRa; or CRbRc.

In one embodiment of the present application, A1 is S.

In one embodiment of the present application, A2 is S.

In one embodiment of the present application, A1 is O.

In one embodiment of the present application, A2 is O.

In one embodiment of the present application, A1 is NRa.

In one embodiment of the present application, A2 is NRa.

In one embodiment of the present application, A1 is CRbRc.

In one embodiment of the present application, A2 is CRbRc.

In one embodiment of the present application, Ra may be a substituted or unsubstituted C6 to C60 aryl group; or a substituted or unsubstituted C2 to C60 heteroaryl group.

In one embodiment of the present application, Ra may be a substituted or unsubstituted C6 to C40 aryl group; or a substituted or unsubstituted C2 to C40 heteroaryl group.

In another embodiment, Ra may be a C6 to C40 aryl group unsubstituted or substituted with one or more substituents selected form the group consisting of a C1 to C10 alkyl group, a C6 to C20 aryl group and SiRR'R"; or a C2 to C40 heteroaryl group unsubstituted or substituted with a C6 to C10 aryl group.

In another embodiment, Ra may be a C6 to C20 aryl group unsubstituted or substituted with one or more substituents selected form the group consisting of a C1 to C10 alkyl group, a C6 to C20 aryl group and SiRR'R"; or a C2 to C20 heteroaryl group unsubstituted or substituted with a C6 to C10 aryl group.

In another embodiment, Ra may be a phenyl group unsubstituted or substituted with one or more substituents selected form the group consisting of a phenyl group, a biphenyl group and a triphenylsilyl group; a biphenyl group; a naphthyl group; a terphenyl group; a triphenylenyl group; a dimethylfluorenyl group; a diphenylfluorenyl group; a dibenzofuran group; a dibenzothiophene group; or a carbazole group unsubstituted or substituted with a phenyl group.

In one embodiment of the present application, Rb and Rc are the same as or different from each other, and may be each independently a substituted or unsubstituted C1 to C60 alkyl group.

In another embodiment, Rb and Rc are the same as or different from each other, and may be each independently a substituted or unsubstituted C1 to C40 alkyl group.

In another embodiment, Rb and Rc are the same as or different from each other, and may be each independently a substituted or unsubstituted C1 to C20 alkyl group.

In another embodiment, Rb and Rc are the same as or different from each other, and may be each independently a C1 to C20 alkyl group.

In another embodiment, Rb and Rc are the same as or different from each other, and may be each independently a C1 to C20 linear alkyl group.

In another embodiment, Rb and Rc are the same as or different from each other, and may be each independently a C1 to C10 linear alkyl group.

In another embodiment, Rb and Rc are the same as or different from each other, and may be each independently a C1 to C5 linear alkyl group.

In another embodiment, Rb and Rc may be a methyl group.

In one embodiment of the present application, R11 and R14 to R19 may be hydrogen.

In one embodiment of the present application, Chemical Formula 2 may be represented by any one of the following Chemical Formulae 2-7 to 2-9.

[Chemical Formula 2-7]

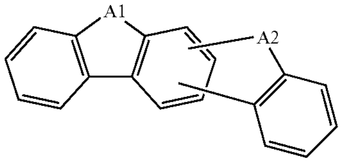

[Chemical Formula 2-8]

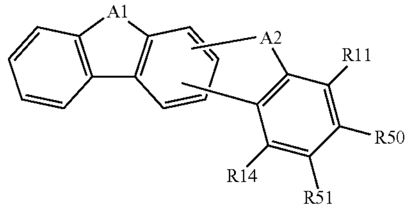

[Chemical Formula 2-9]

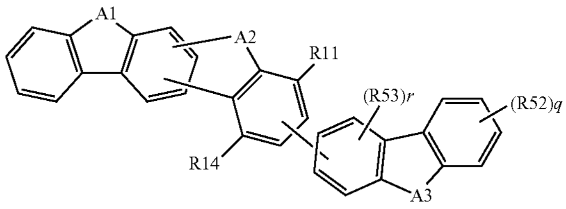

In Chemical Formulae 2-7 to 2-9,

A1, A2, R11 and R14 have the same definitions as in Chemical Formula 2,

A3 is O; S; or NRg,

R50 and R51 are hydrogen; or a substituted or unsubstituted C6 to C60 aryl group, and at least one thereof is a substituted or unsubstituted C6 to C60 aryl group, Rg, R52 and R53 are the same as or different from each other, and each independently hydrogen; a substituted or unsubstituted C1 to C60 alkyl group; a substituted or unsubstituted C6 to C60 aryl group; or a substituted or unsubstituted C2 to C60 heteroaryl group, r is an integer of 0 to 3, and q is an integer of 0 to 4.

In one embodiment of the present application, R50 and R51 may be hydrogen; or a substituted or unsubstituted C6 to C60 aryl group.

In another embodiment, R50 and R51 may be hydrogen; or a substituted or unsubstituted C6 to C40 aryl group.

In another embodiment, R50 and R51 may be hydrogen; or a C6 to C40 aryl group.

In another embodiment, R50 and R51 may be hydrogen; a phenyl group; or a triphenylenyl group.

In one embodiment of the present application, at least one of R50 and R51 may be a substituted or unsubstituted C6 to C60 aryl group.

In one embodiment of the present application, R52 and R53 may be hydrogen.

In one embodiment of the present application, Rg may be a substituted or unsubstituted C6 to C60 aryl group.

In another embodiment, Rg may be a substituted or unsubstituted C6 to C40 aryl group.

In another embodiment, Rg may be a C6 to C40 aryl group.

In another embodiment, Rg may be a phenyl group; or a biphenyl group.

When having a fused-type basic ring as in Chemical Formula 2-7, very fast hole transfer properties are obtained particularly as a host material when used in an organic light emitting device together with the heterocyclic compound of Chemical Formula 1, which lowers threshold voltage and driving voltage of the device allowing driving of the device even at a low voltage.

When having a substituent (R50) in a fused-type ring structure as in Chemical Formula 2-8, a larger structure is obtained compared to Chemical Formula 2-7, and due to the characteristics, the area at the HOMO level is more expanded as the conjugation area becomes wider to the substituent (R50) extended from the basic skeleton. Accordingly, holes are distributed to the wide HOMO level area, and a hole transfer ability may be more stably maintained. In other words, in a case such as Chemical Formula 2-8, overall lifetime properties are more superior although a driving voltage increases to a certain extent.

In Chemical Formula 2-9, a fused-type ring structure is substituted with a heteroaryl group, and, in addition to the properties of maintaining a stable HOMO level through a wide conjugation area as in Chemical Formula 2-8, the substitution by several heteroaryl groups allows a use as an auxiliary means to control a band gap. Particularly, a dibenzofuran/dibenzothiophene group or the like has, although having a slightly increased driving voltage compared to the basic skeleton by having a largest structure, highest structural stability as well as maintaining a higher T1 level, and as a result, lifetime properties of a device are particularly superior.

Effects of more superior efficiency and lifetime are obtained when comprising the compound of Chemical Formula 1 and the compound of Chemical Formula 2 at the same time in the organic material layer of the organic light emitting device. Such results may lead to a forecast that an exciplex phenomenon occurs when comprising the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having a favorable hole transfer ability and an acceptor (n-host) having a favorable electron transfer ability are used as a host of a light emitting layer, holes are injected to the p-host and electrons are injected to the n-host, and therefore, a driving voltage may be lowered, which resultantly helps with enhancement in the lifetime.

According to one embodiment of the present application, Chemical Formula 1 may be represented by any one of the following compounds, but is not limited thereto.

1-1

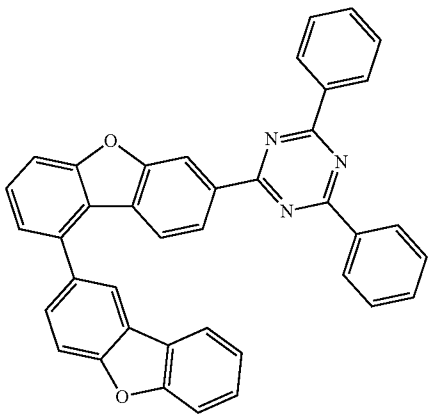

1-2

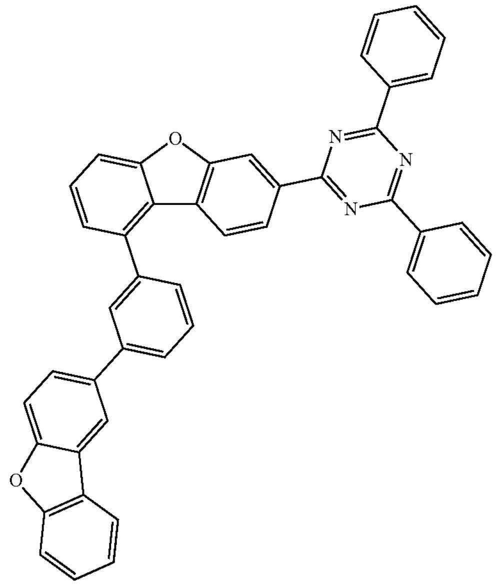

-continued
1-3
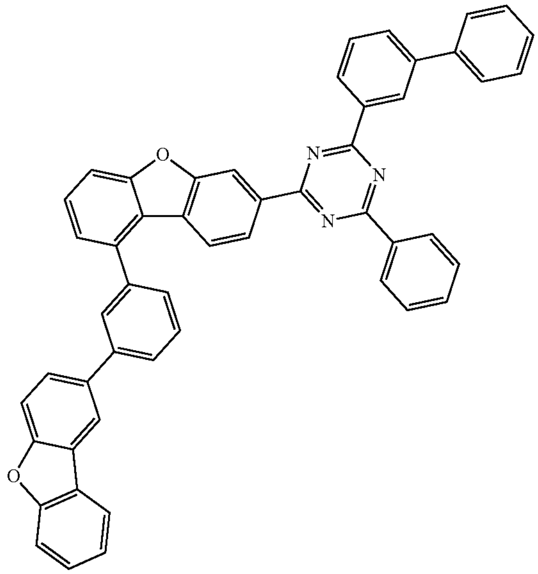
1-4
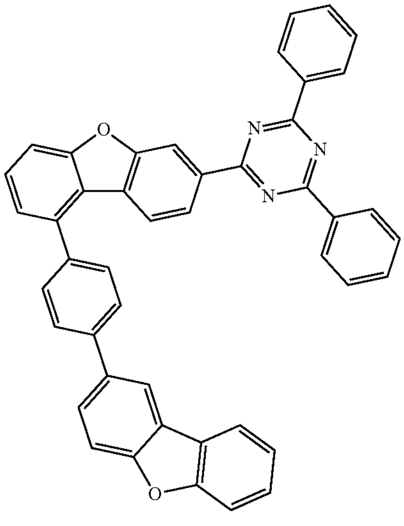
-continued
1-5
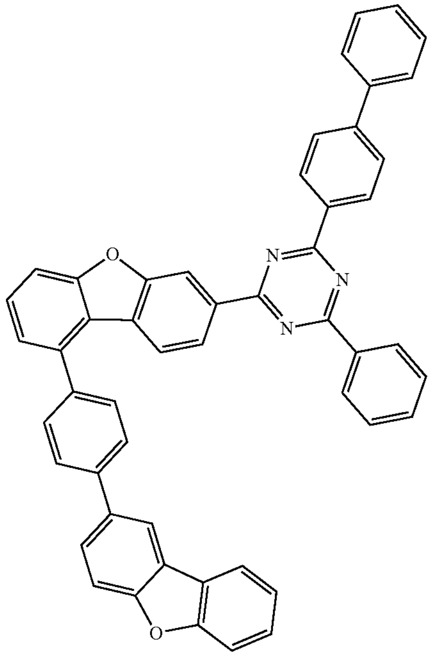
1-6
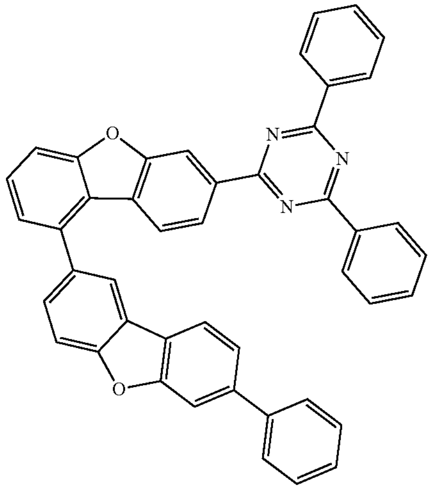
1-7
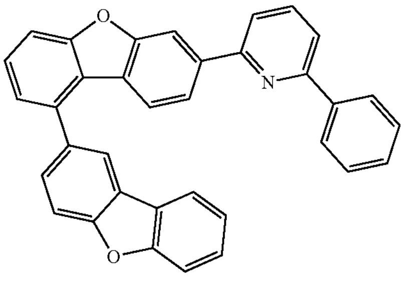

-continued
1-8
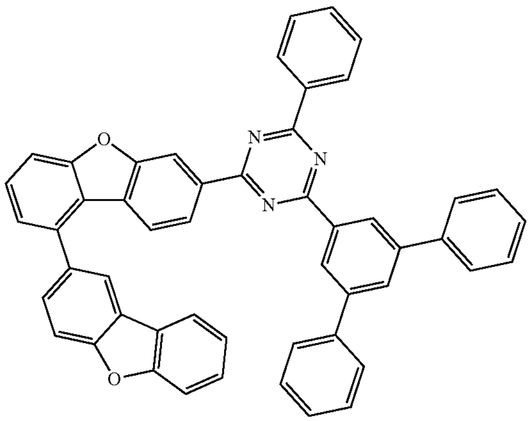
1-9
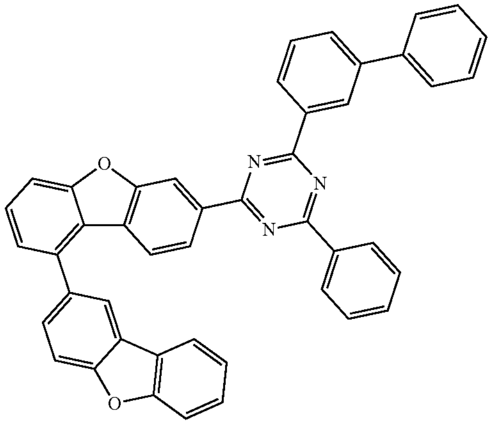
1-10
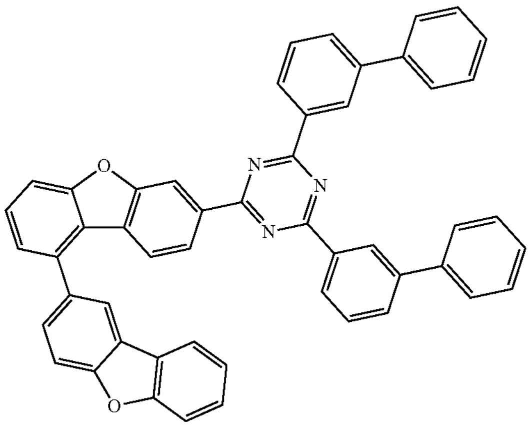
-continued
1-11
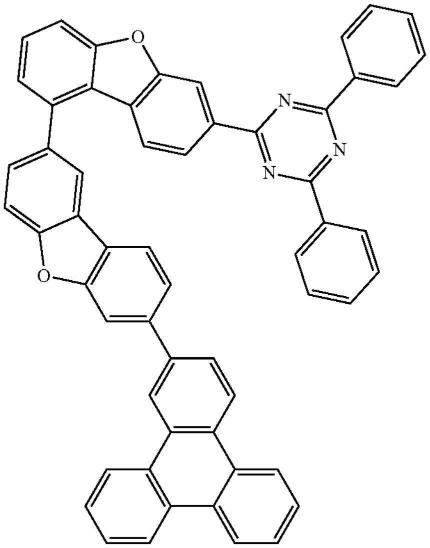
1-12
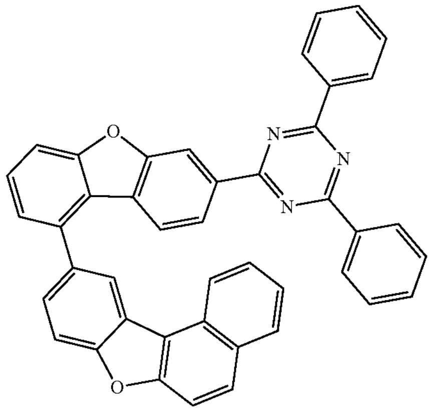
1-13
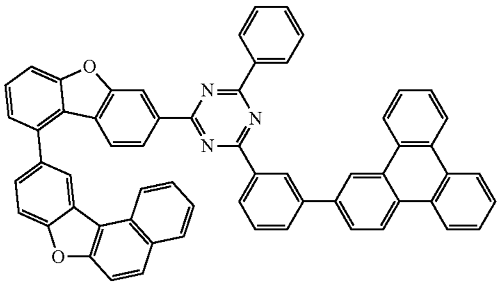

-continued
1-14
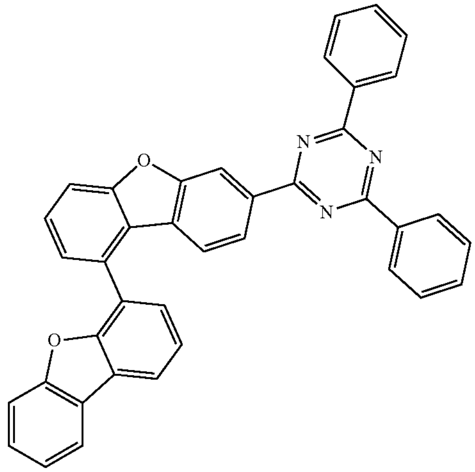
1-15
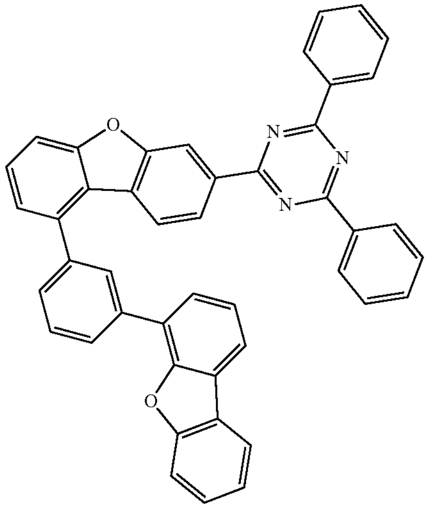
1-16
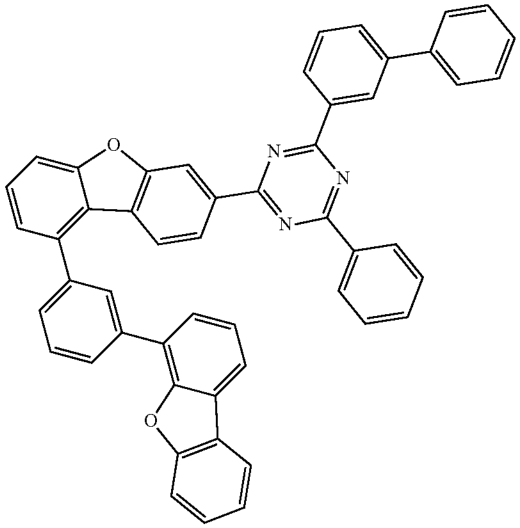
-continued
1-17
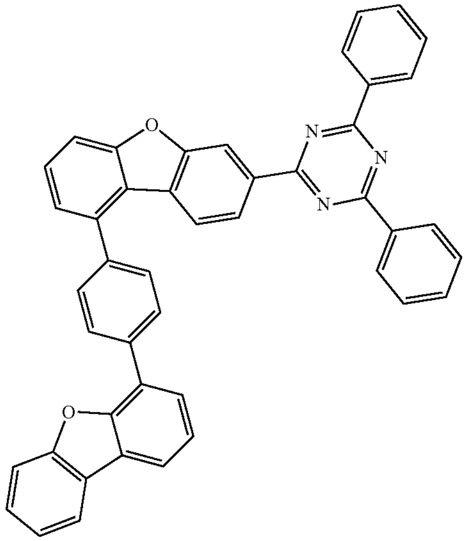
1-18
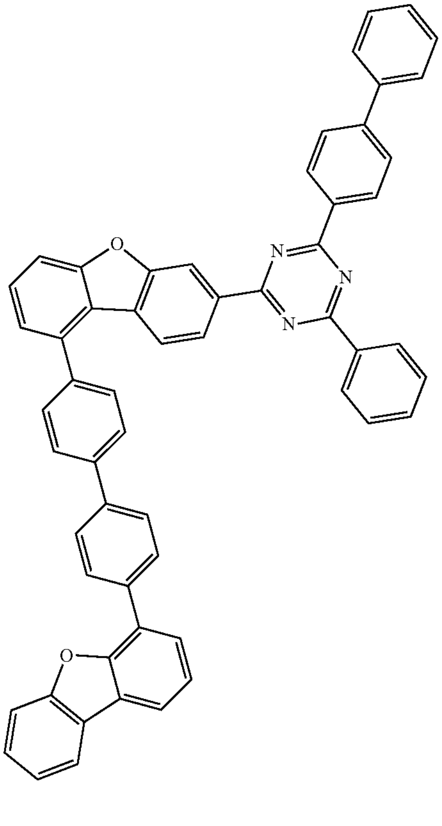

-continued
1-19
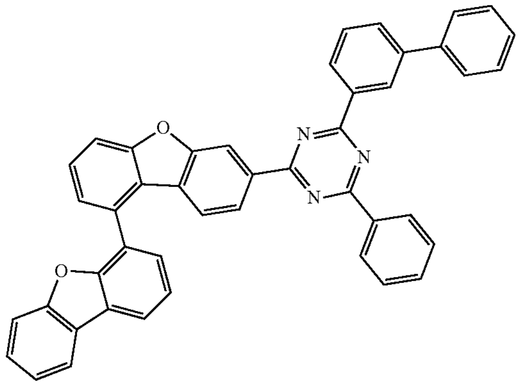
1-20
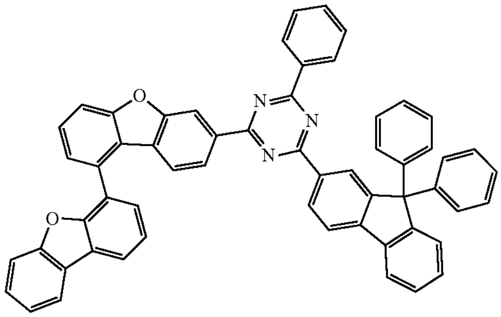
1-21
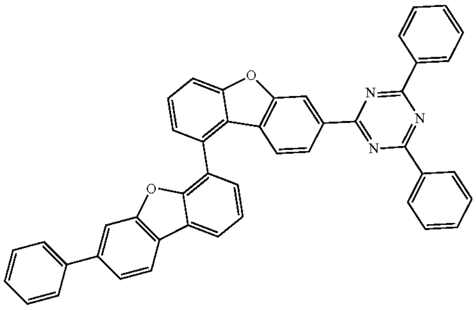
1-22
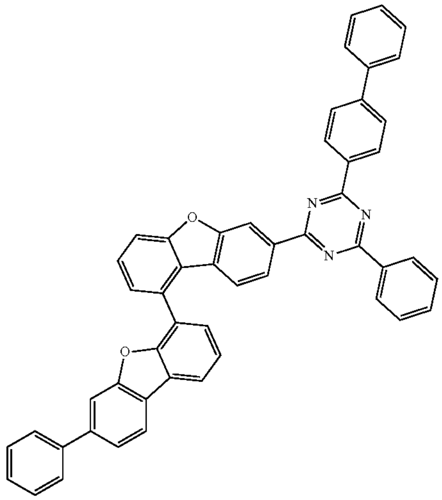
-continued
1-23
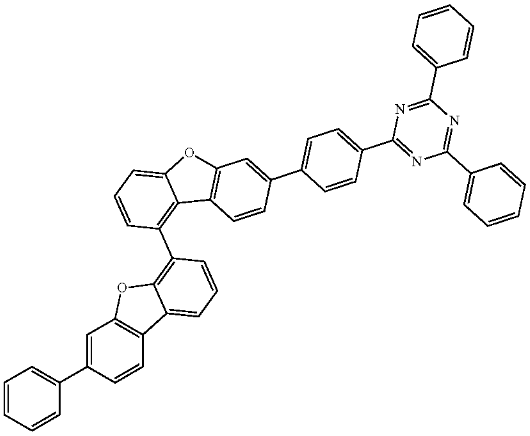
1-24
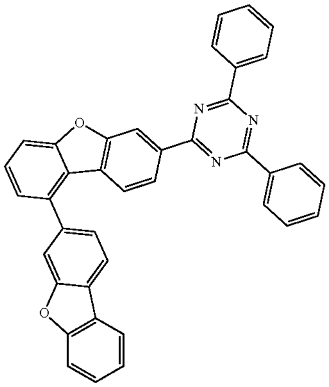
1-25
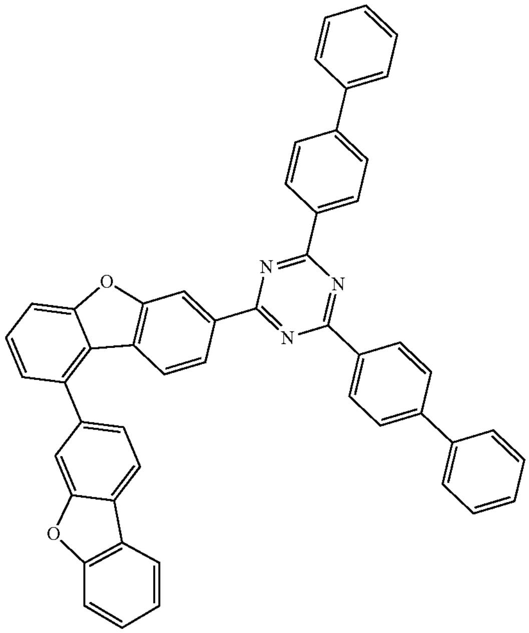

-continued
1-26
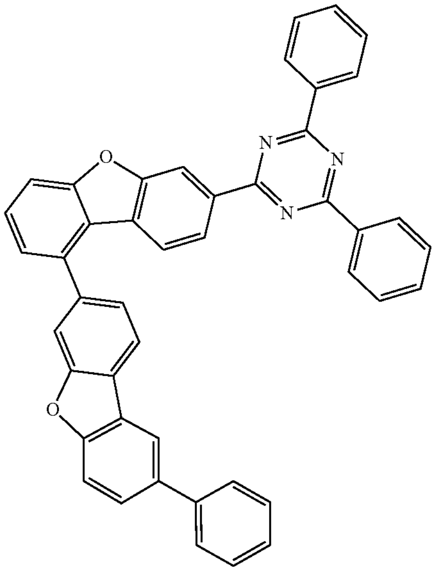
1-27
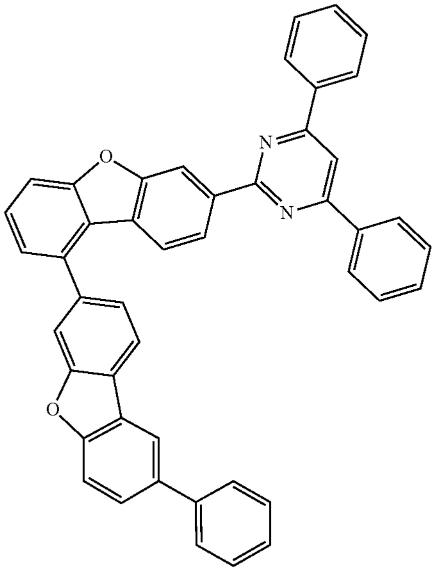
-continued
1-28
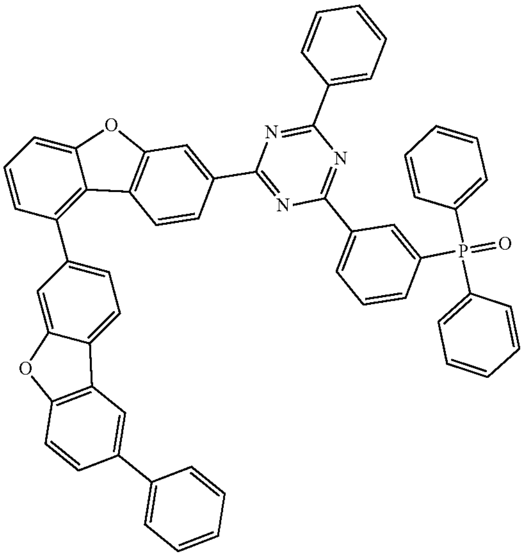
1-29
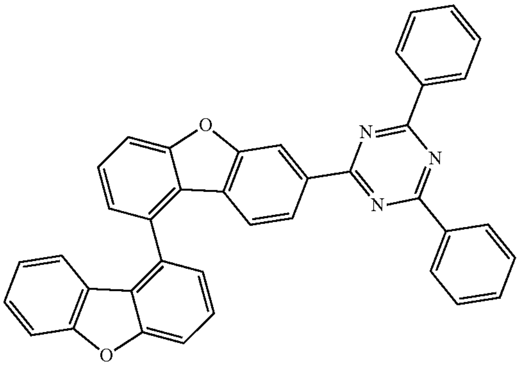
1-30
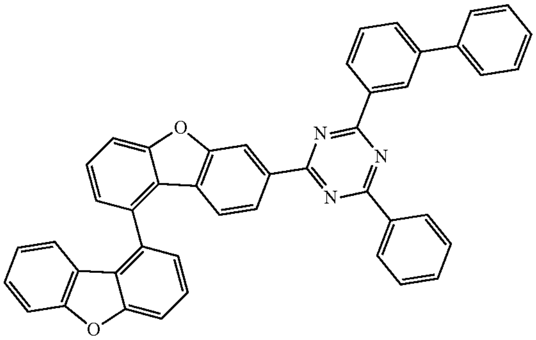

-continued
1-31
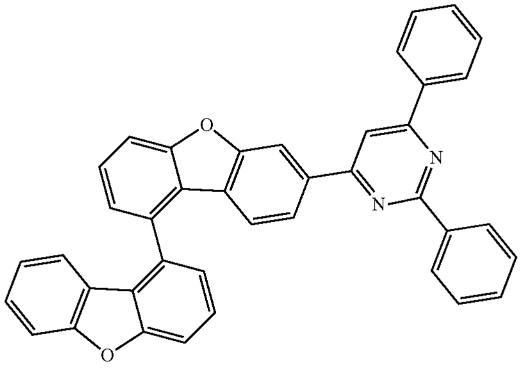
1-32
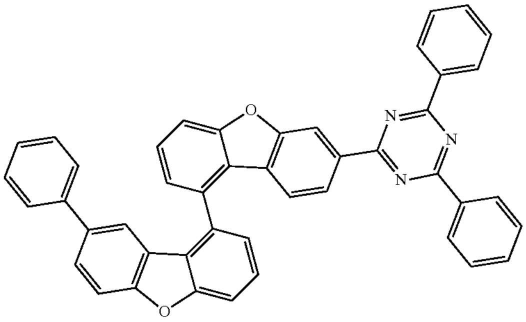
1-33
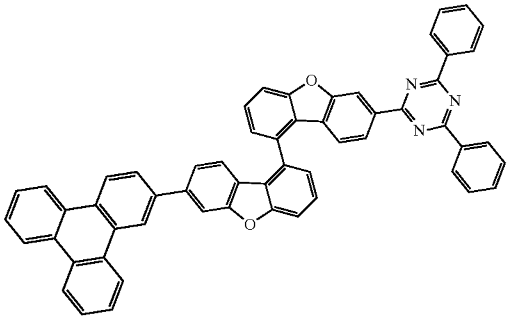
1-34
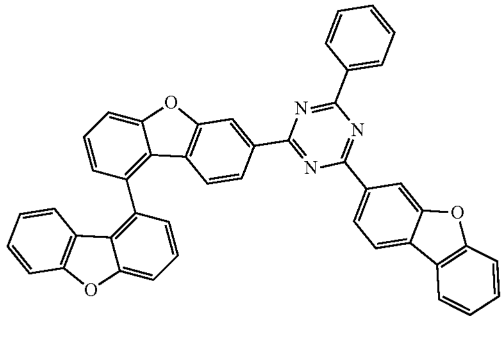
-continued
1-35
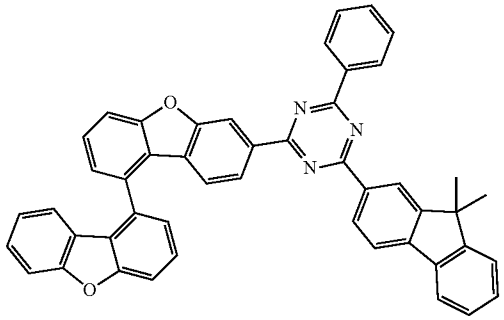
1-36
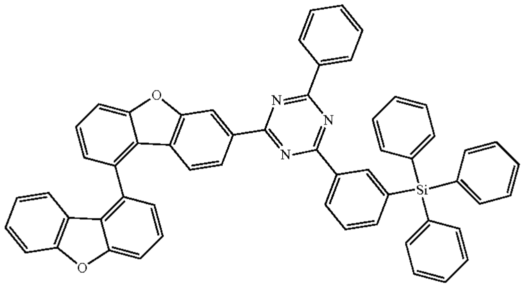
1-37
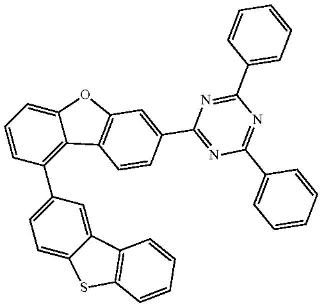
1-38
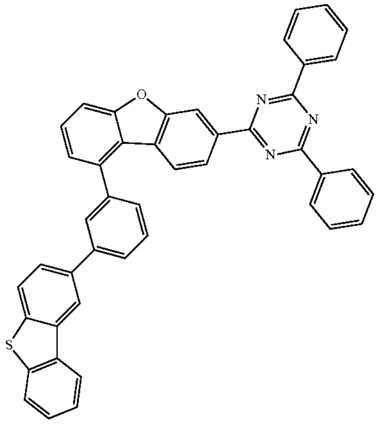

-continued
1-39
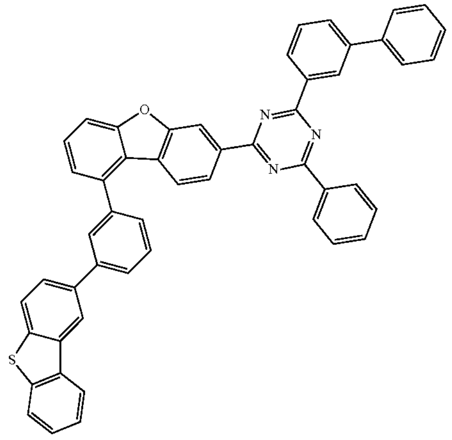
1-40
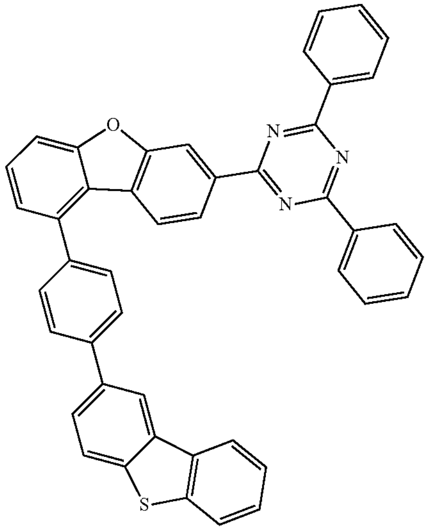
-continued
1-41
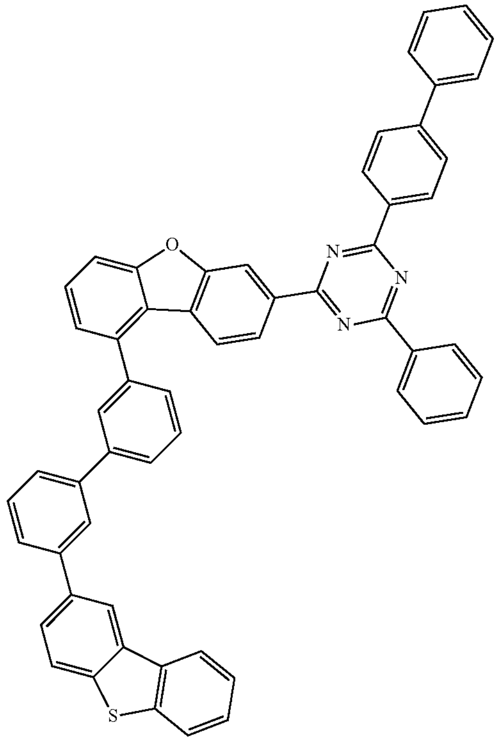
1--42
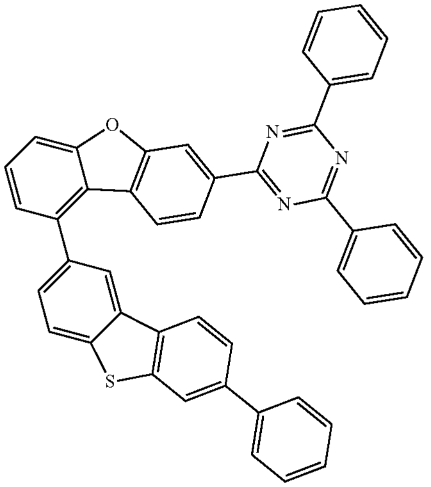
1-43
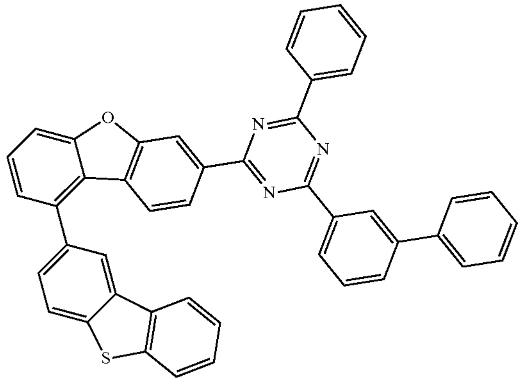

-continued
1-44
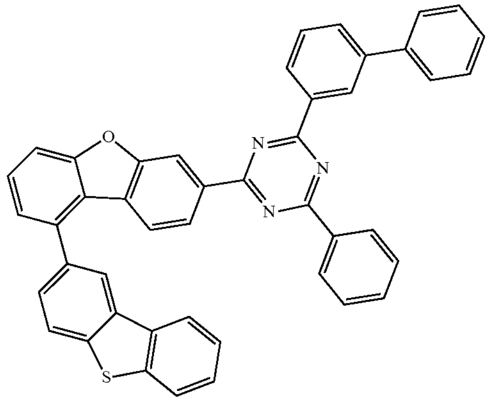
1-45
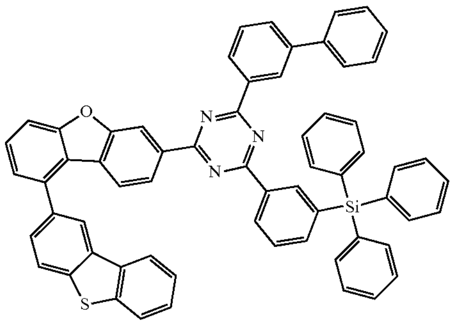
1-46
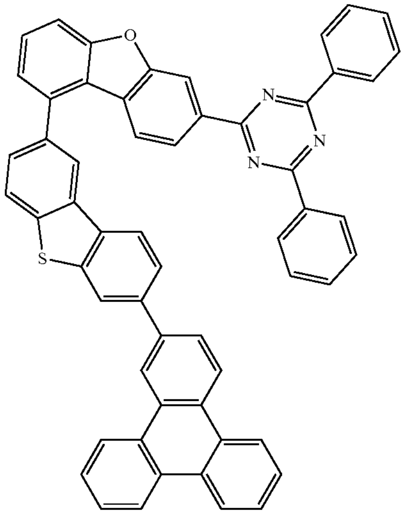
-continued
1-47
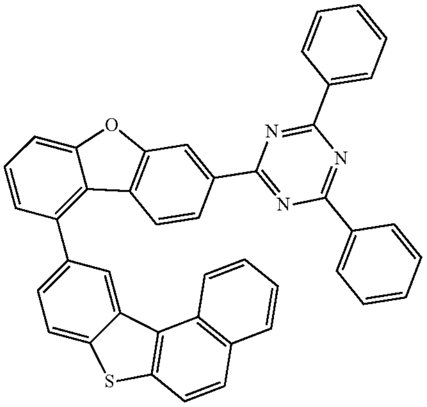
1-48
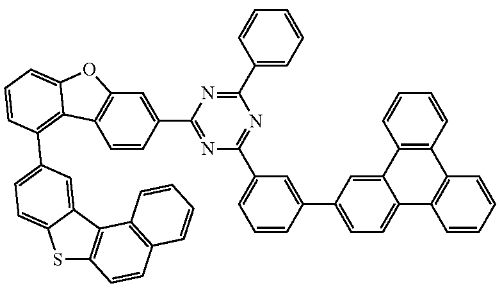
1-49
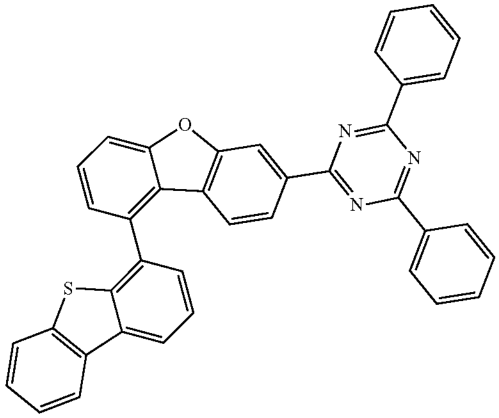

-continued
1-50
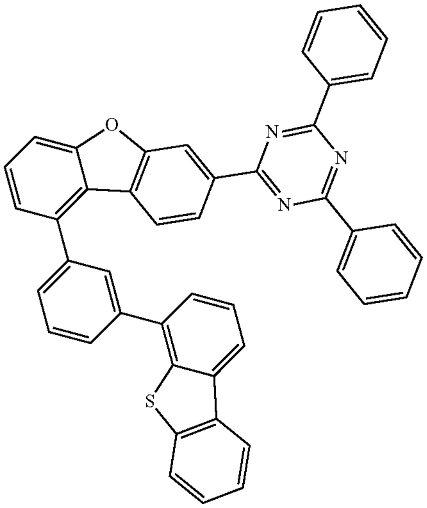
1-51
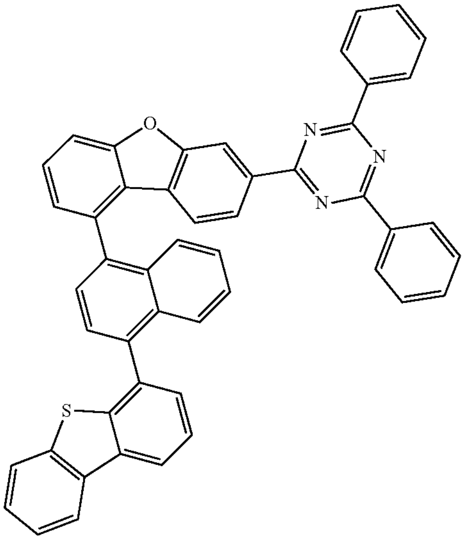
1-52
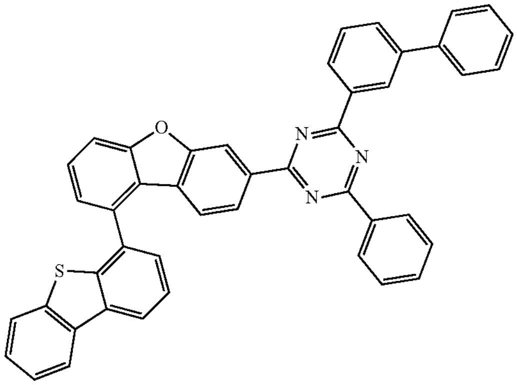
-continued
1-53
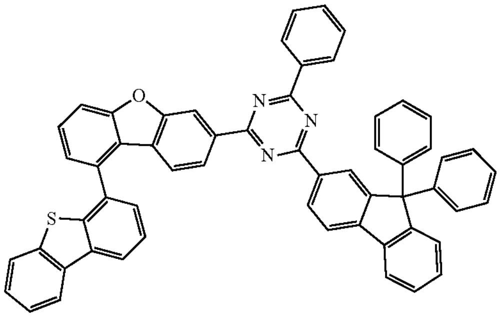
1-54
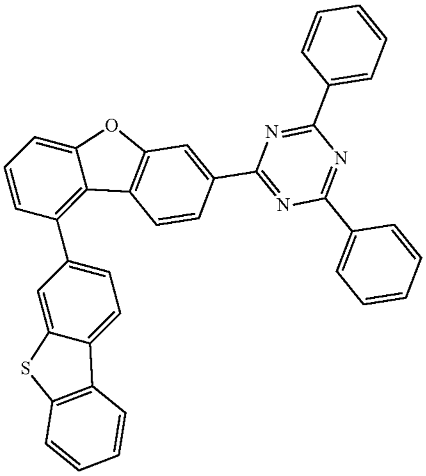
1-55
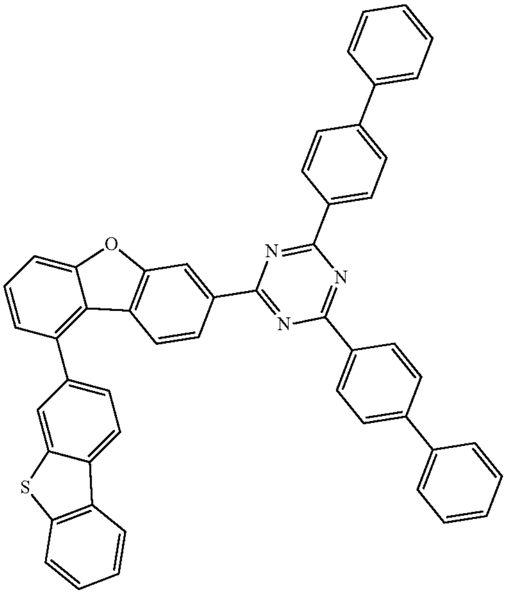

-continued
1-56
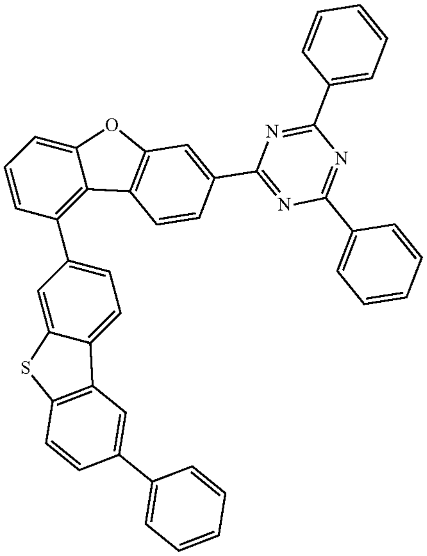
1-57
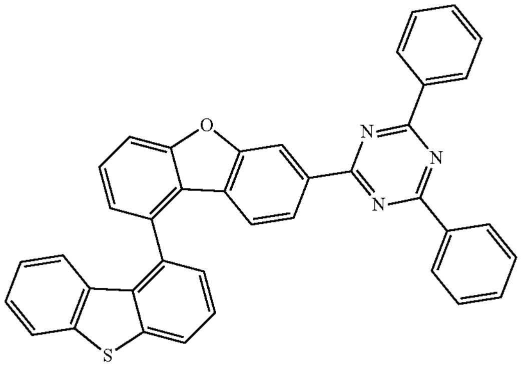
1-58
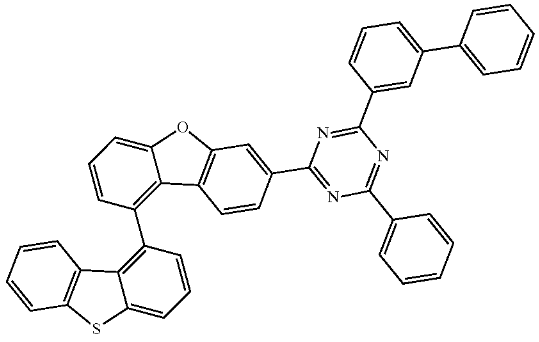
-continued
1-59
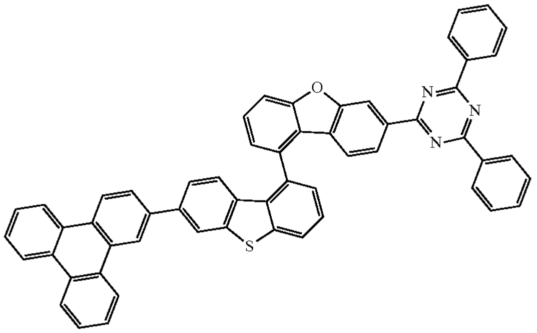
1-60
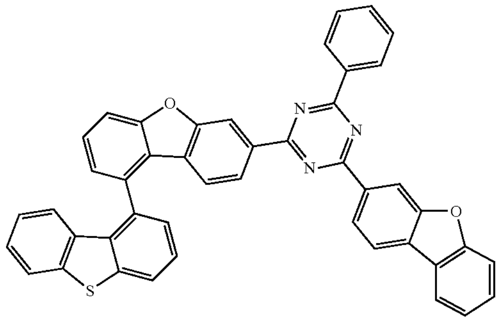
1-61
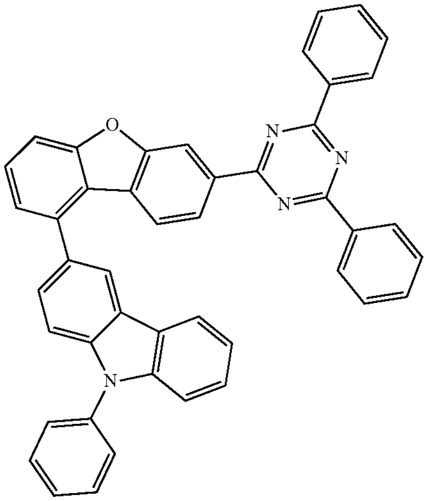

-continued
1-62
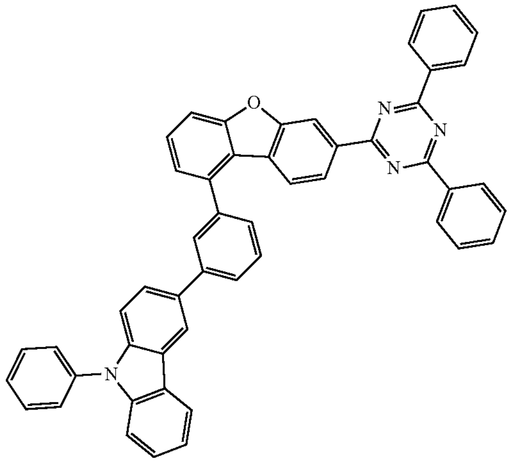
1-63
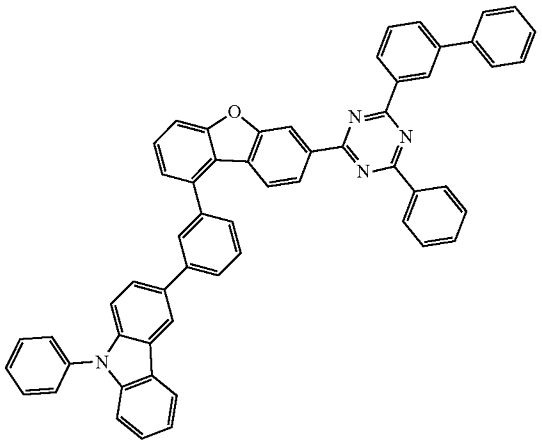
1-64
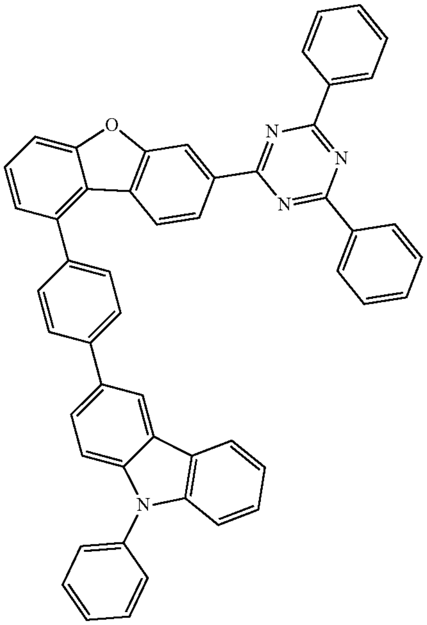
-continued
1-65
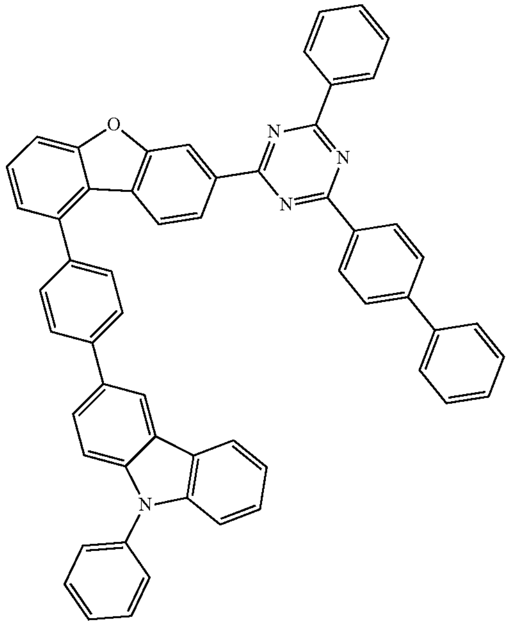
1-66
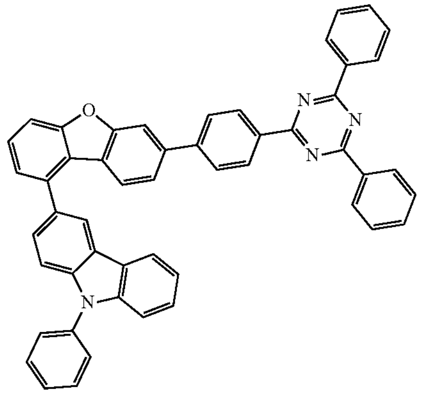
1-67
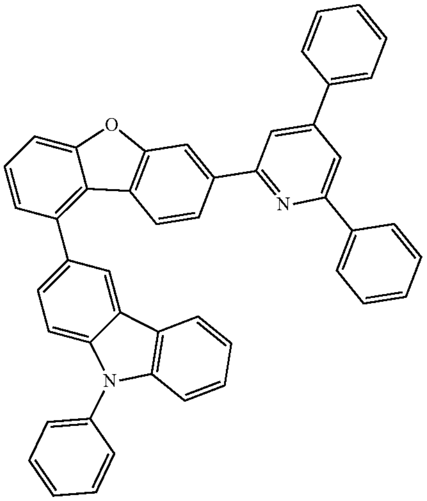

-continued
1-68
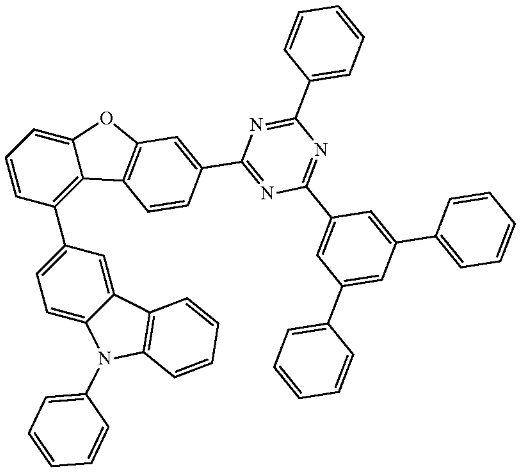
1-69
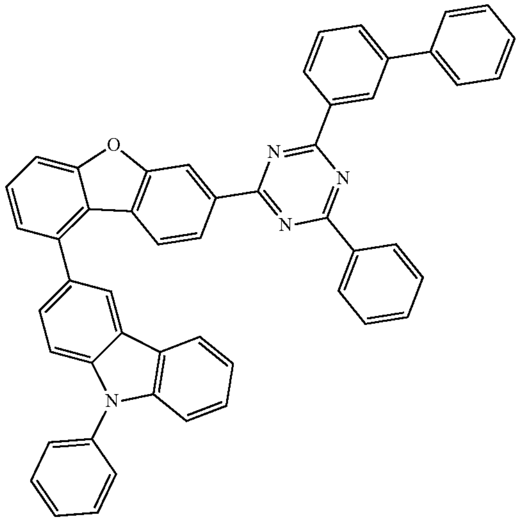
1-70
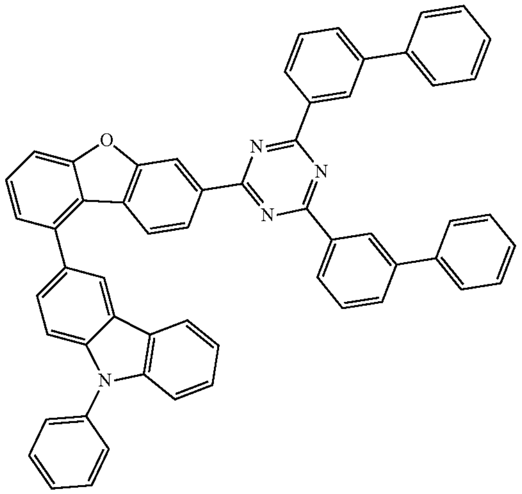
-continued
1-71
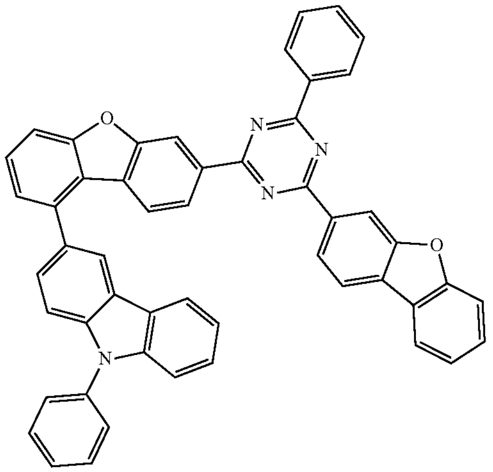
1-72
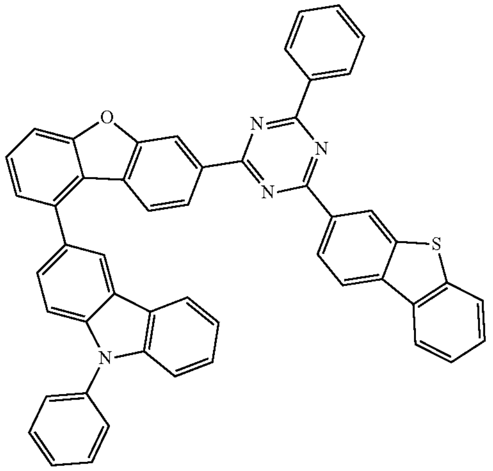
1-73
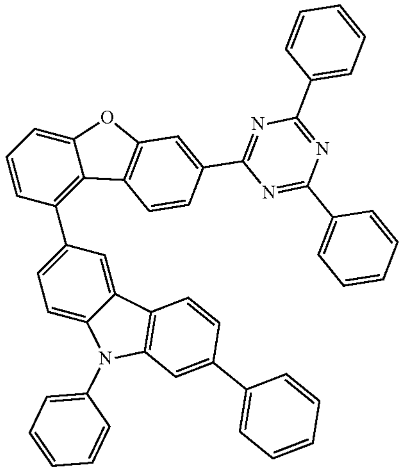

1-74
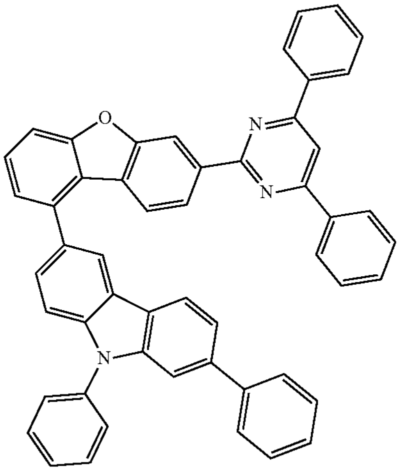
1-75
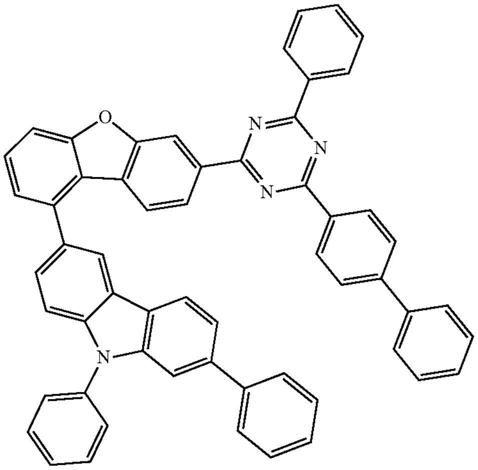
1-76
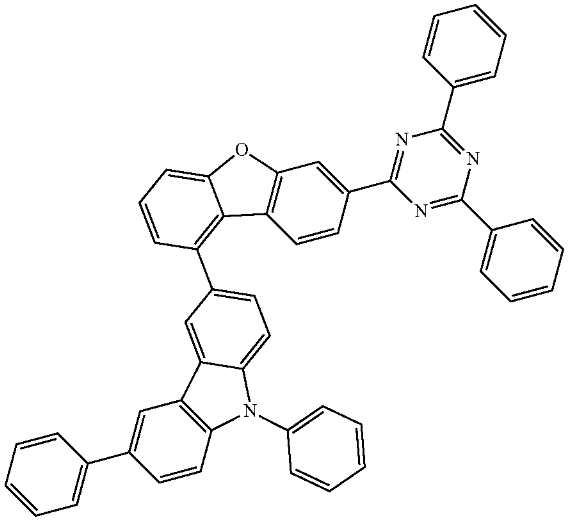
1-77
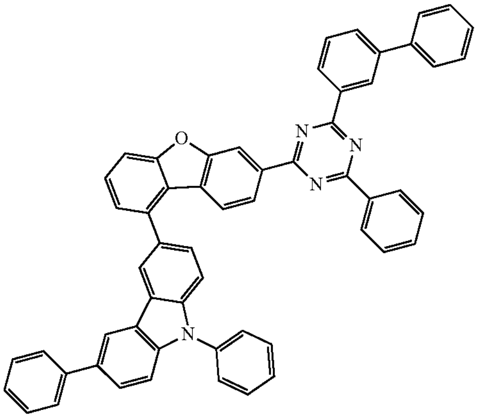
1-78
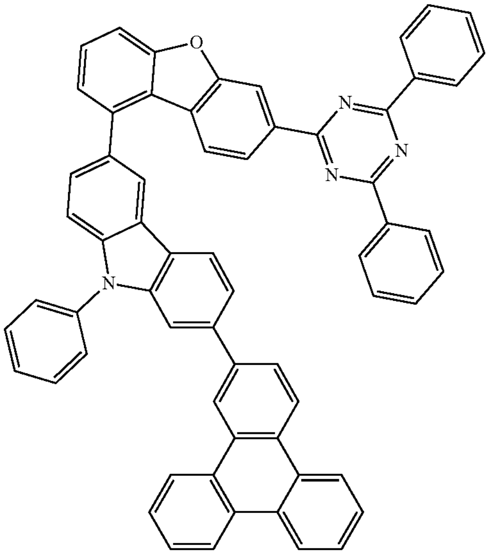
1-79
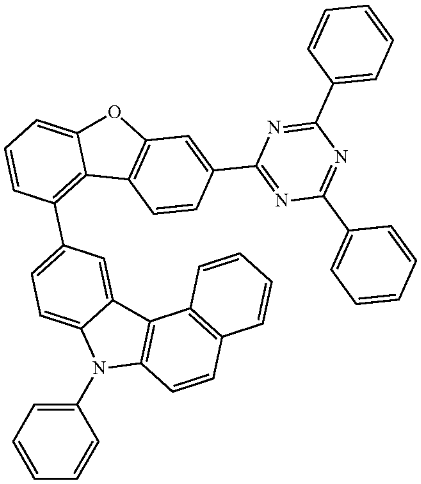

1-80
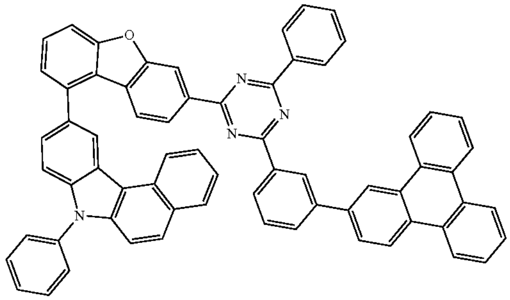
1-81
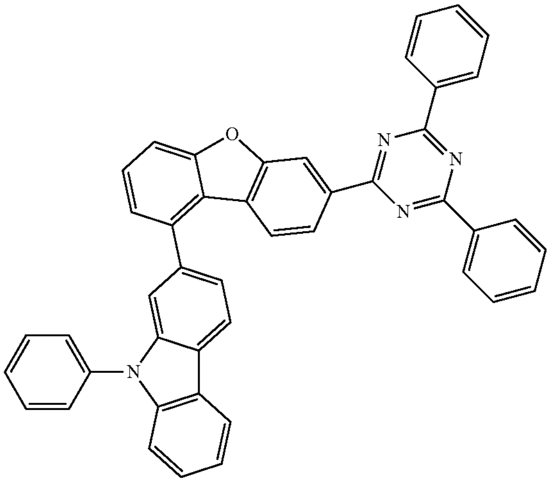
1-82
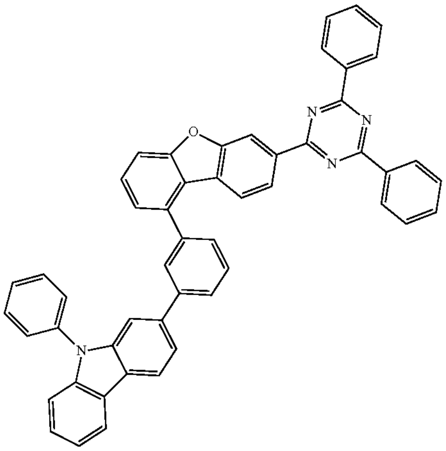
1-83
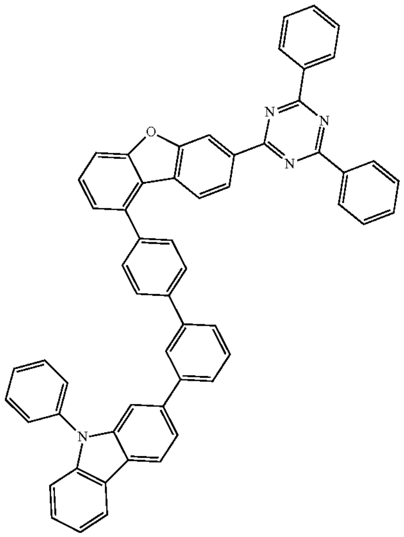
1-84
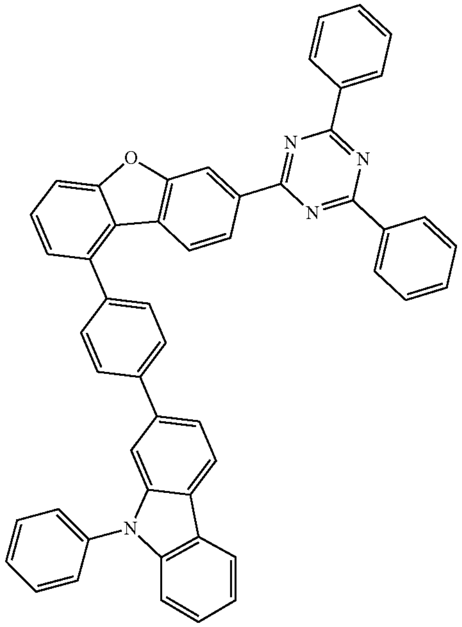

-continued
1-85
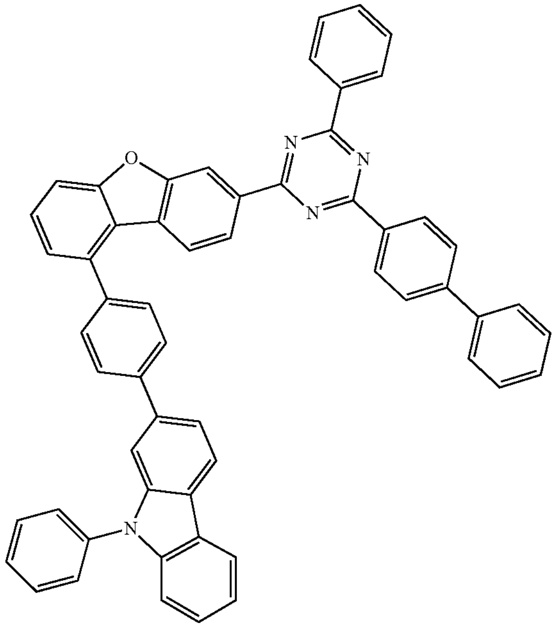
1-86
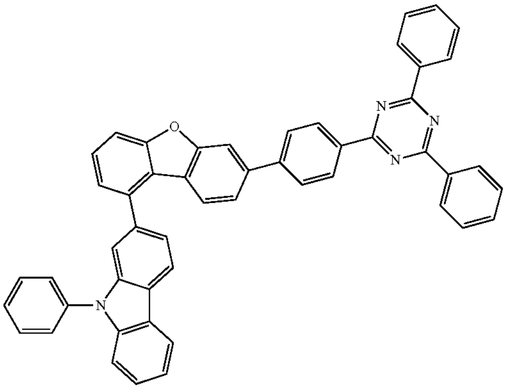
1-87
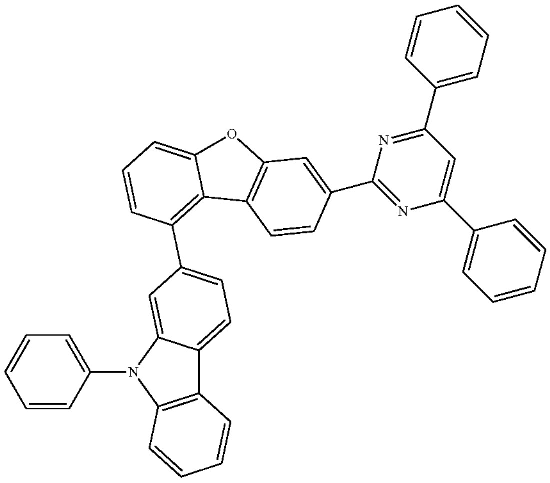
-continued
1-88
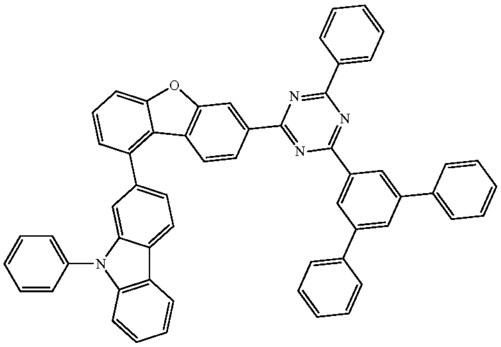
1-89
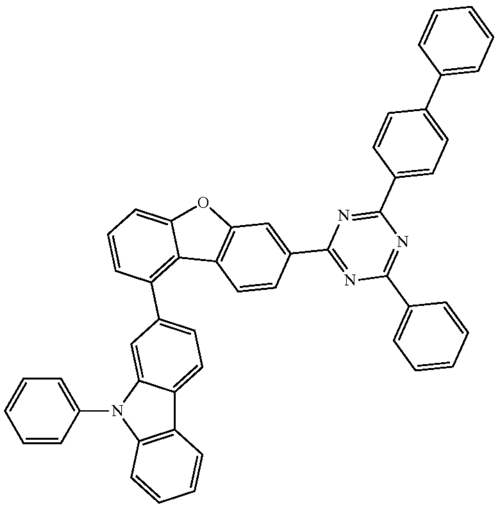
1-90
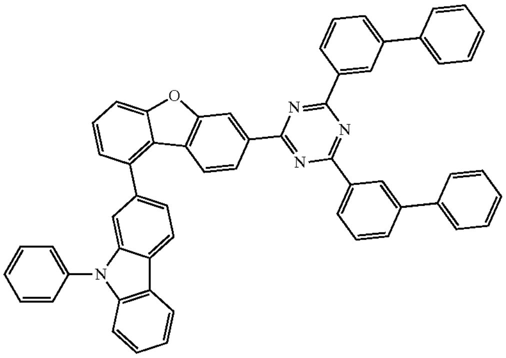
1-91
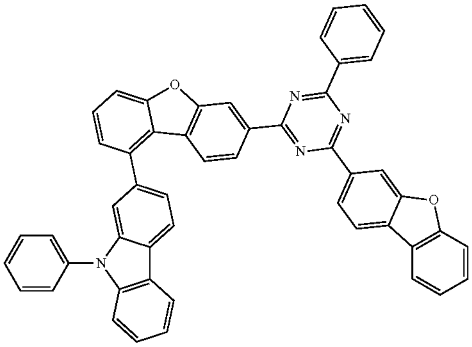

1-92
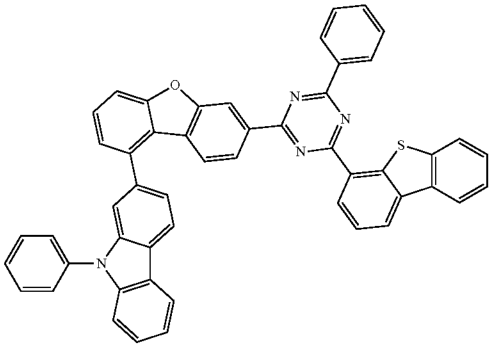
1-93
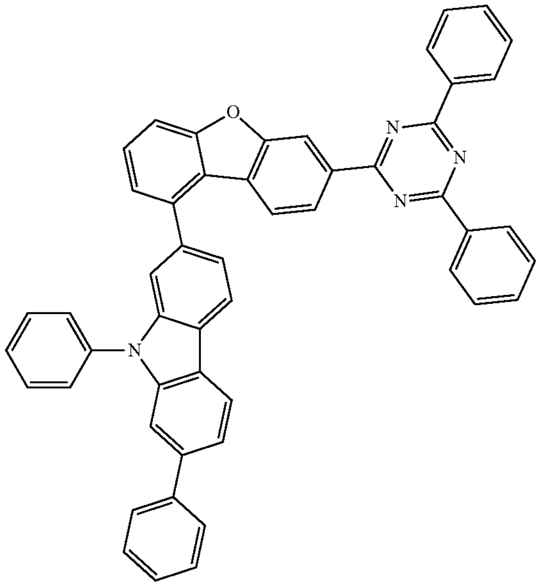
1-94
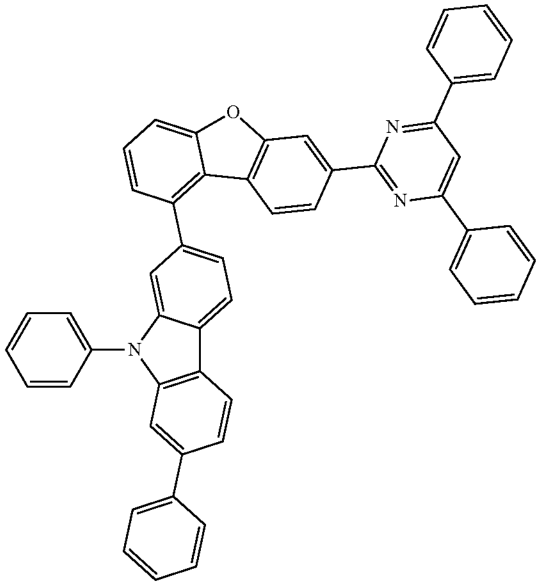
1-95
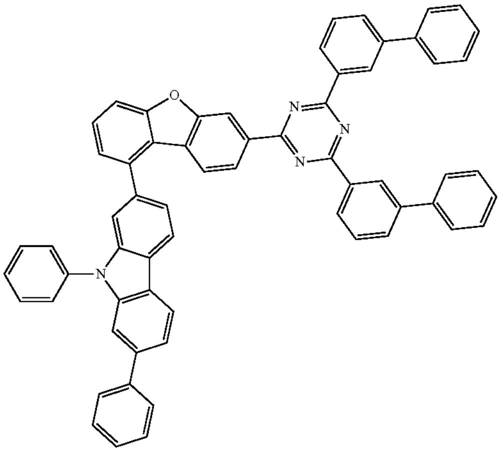
1--96
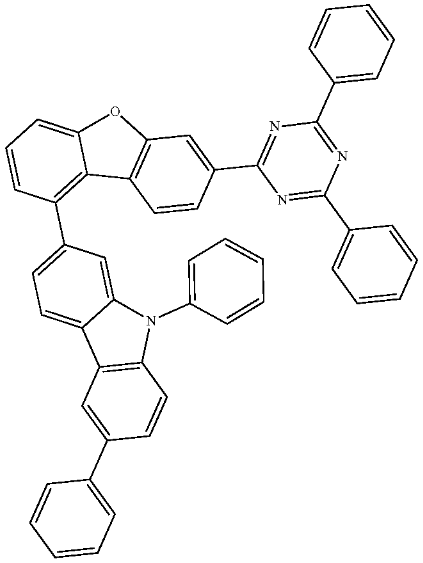
1-97
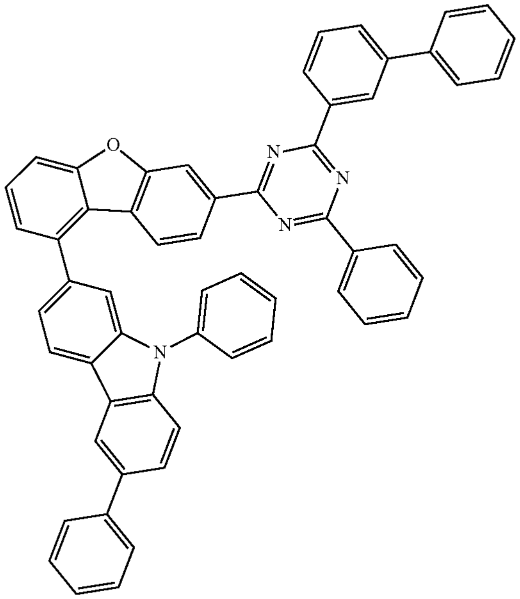

-continued
1-98
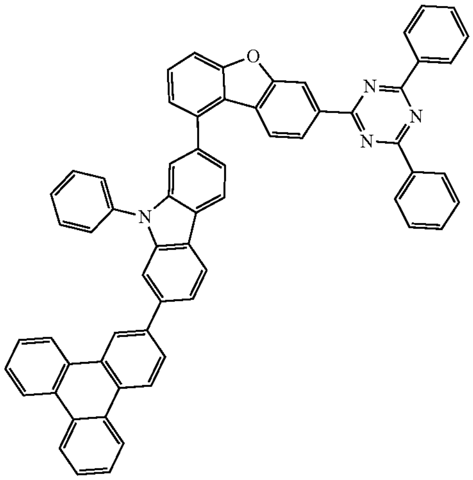
1-99
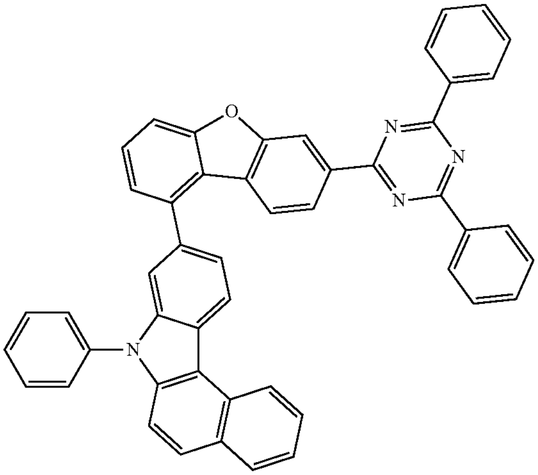
1-100
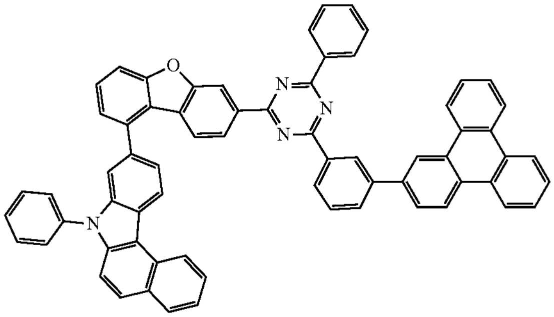
-continued
1-101
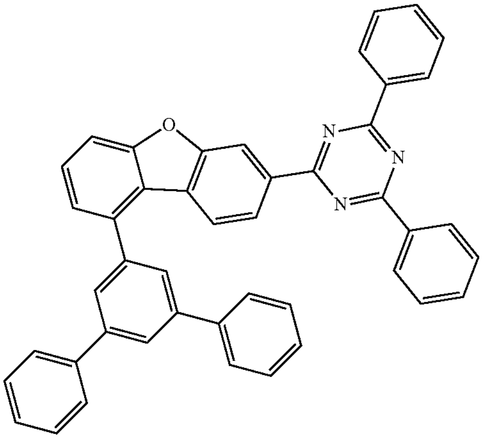
102
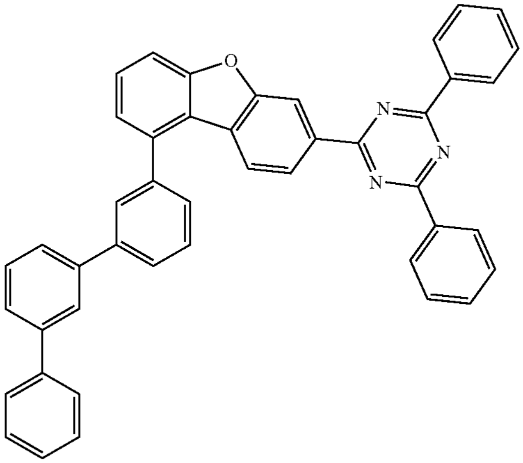
103
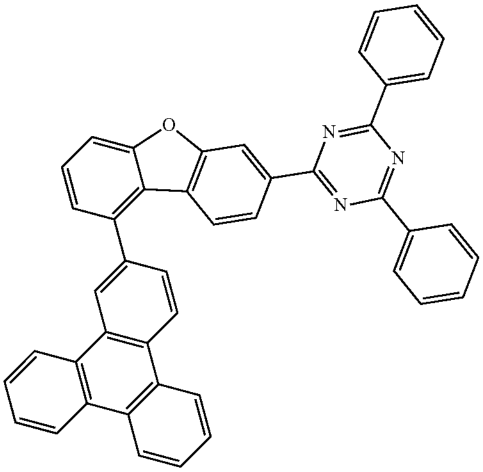

-continued
104
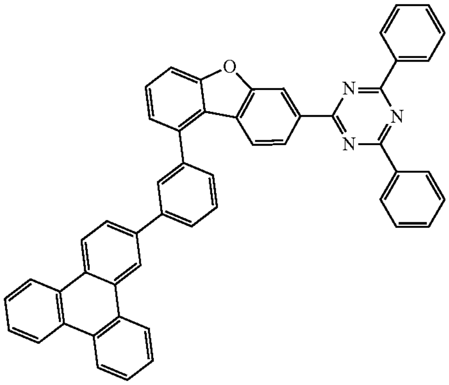
2-1
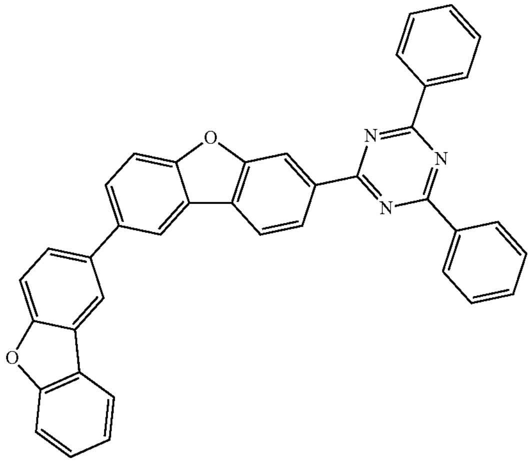
2-2
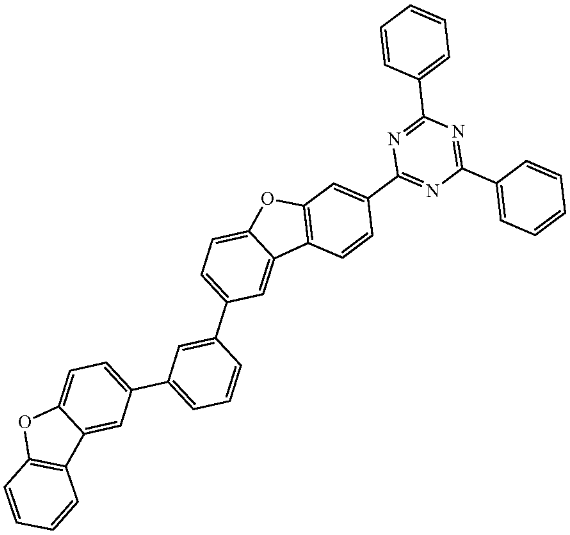
2-3
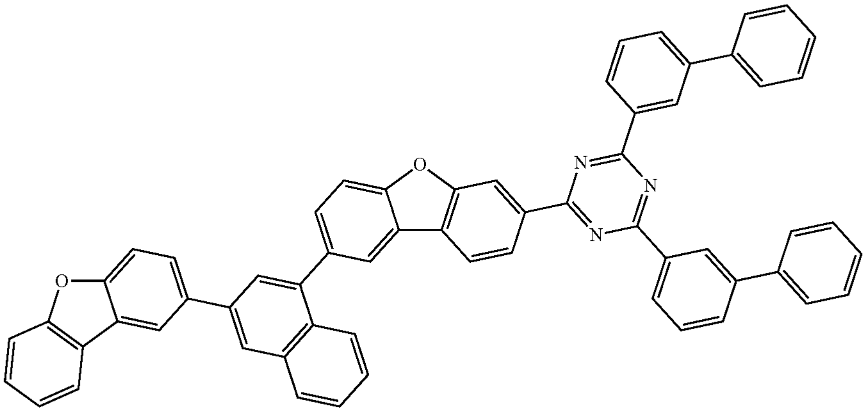

-continued
2-4
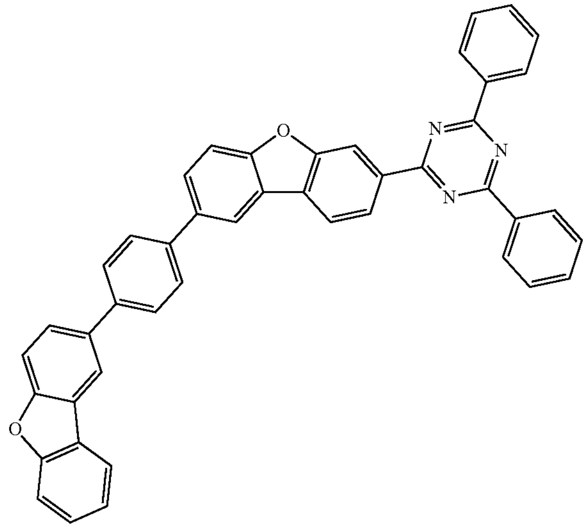
2-5
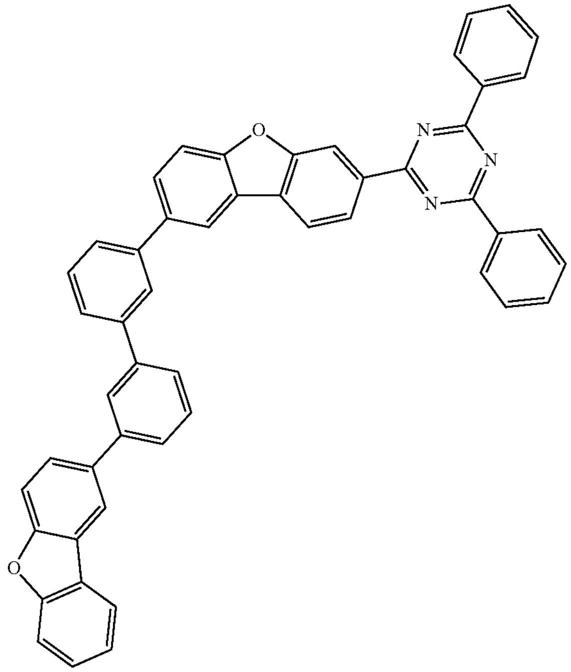
2-6
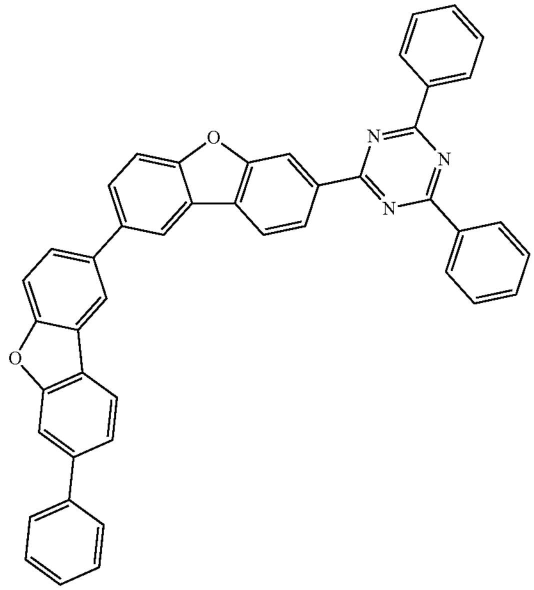
2-7
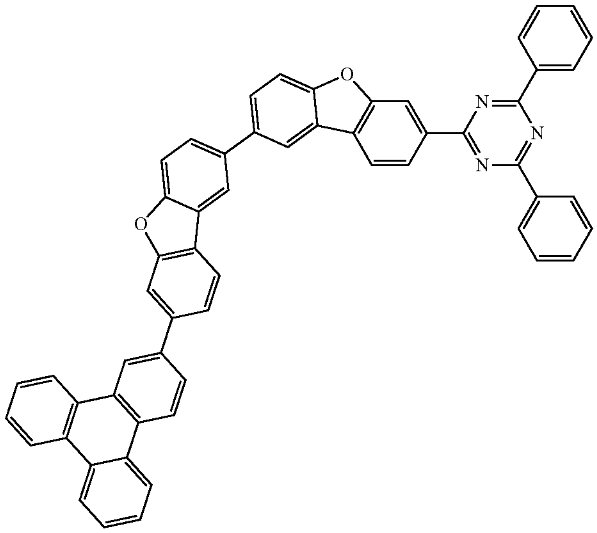

-continued
2-8
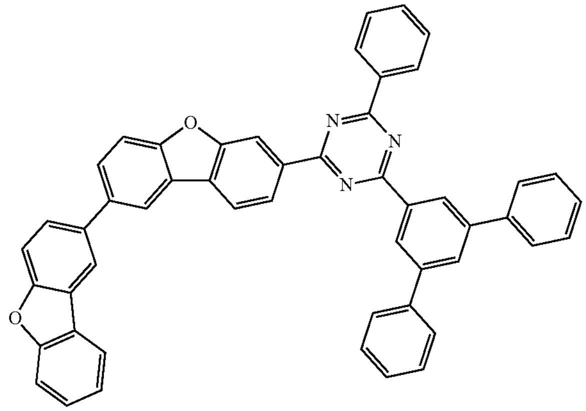
2-9
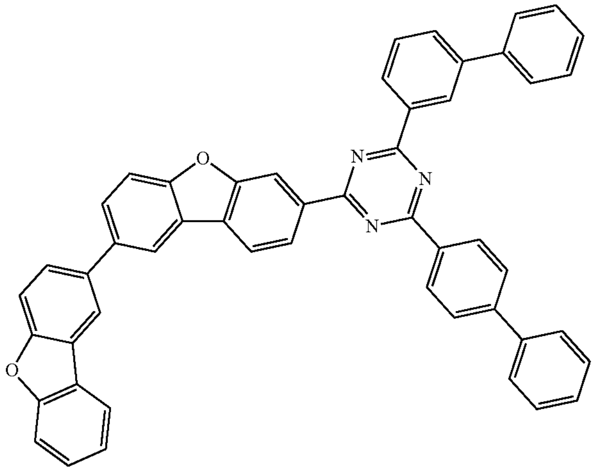
2-10
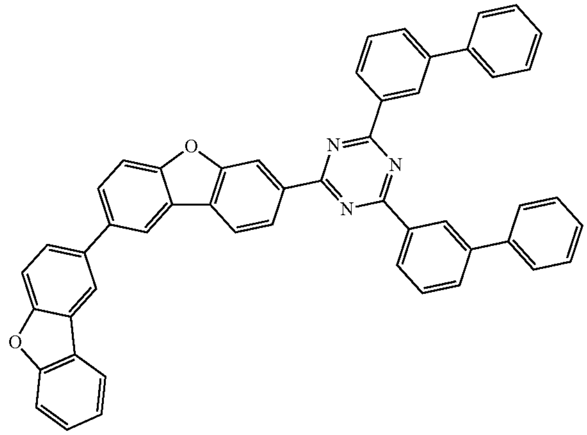
2-11
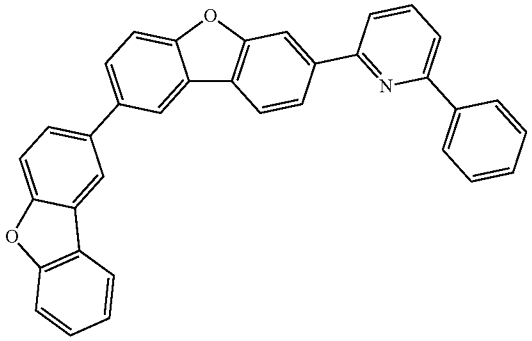
2-12
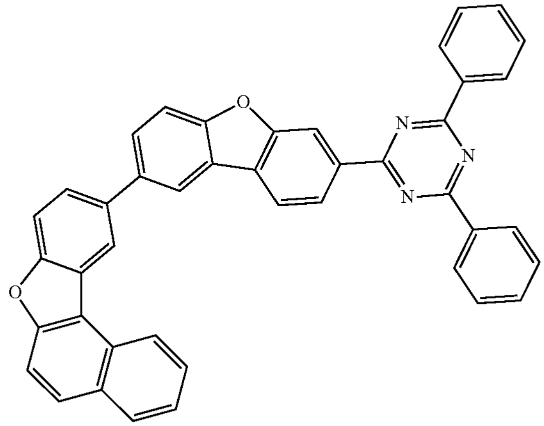

-continued
2-13
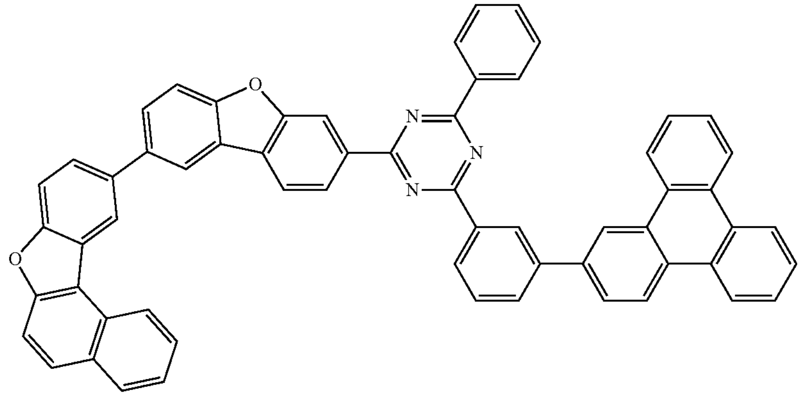
2-14
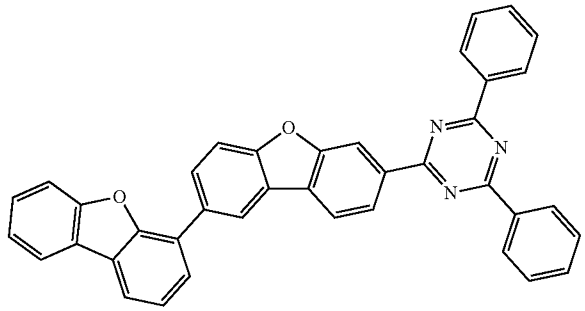
2-15
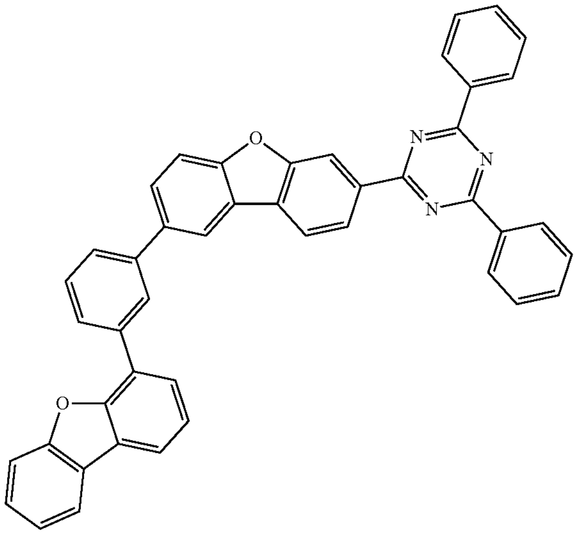
2-16
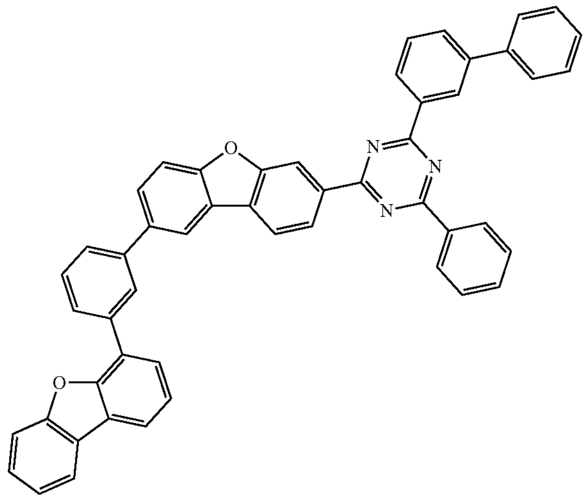
2-17
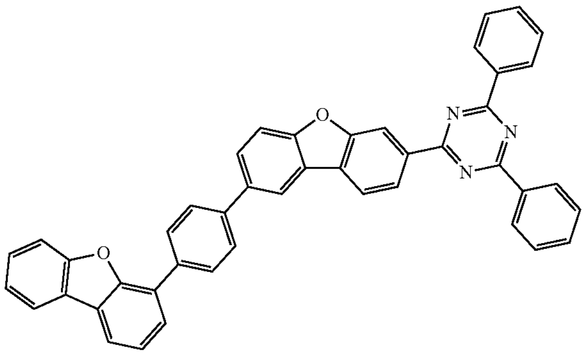

-continued
2-18
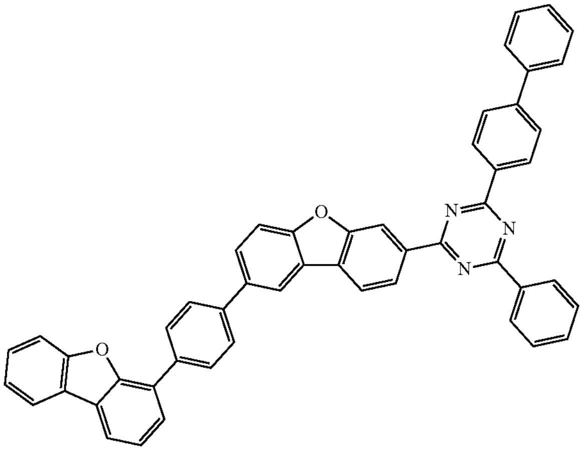
2-19
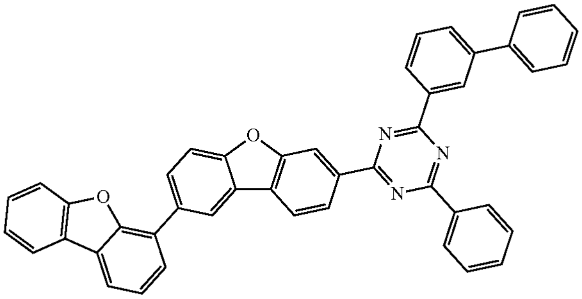
2-20
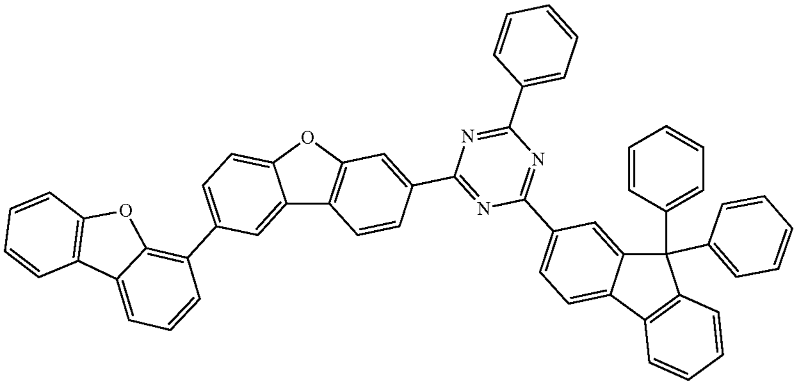
2-21
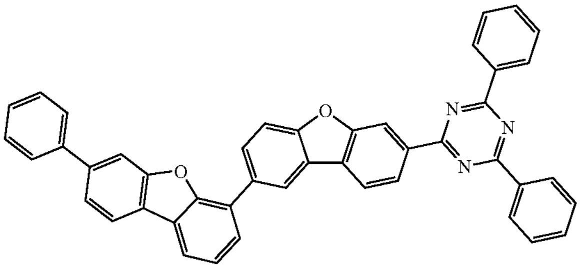
2-22
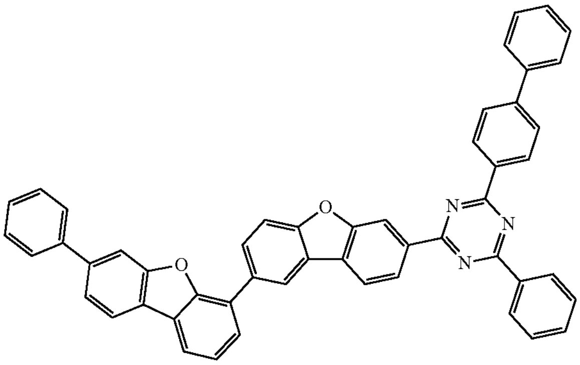
2-23
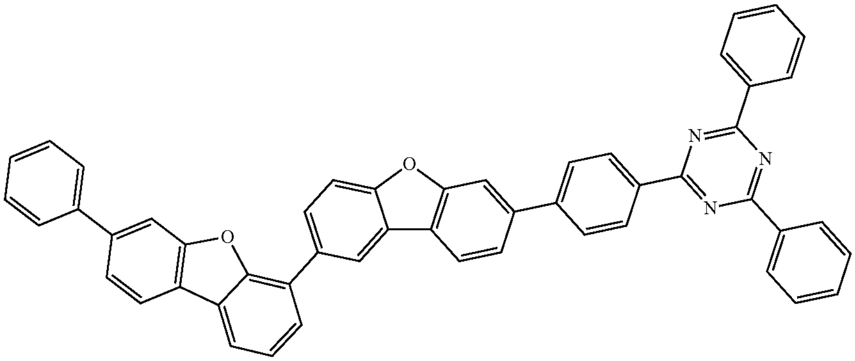

-continued
2-24
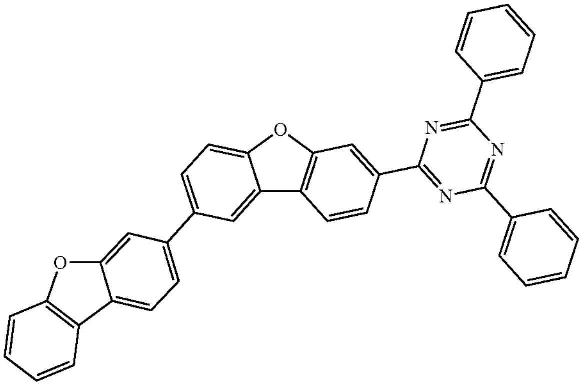
2-25
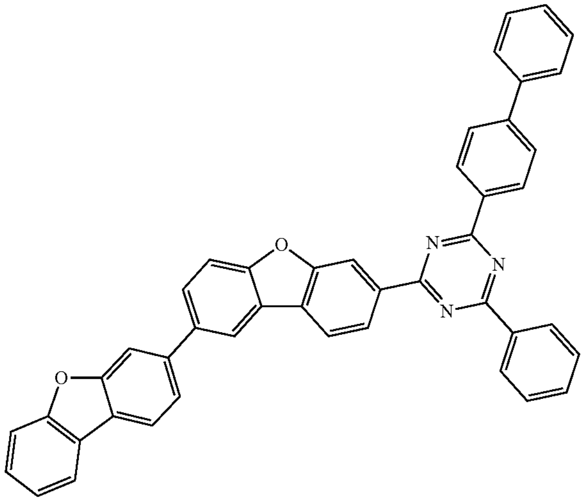
2-26
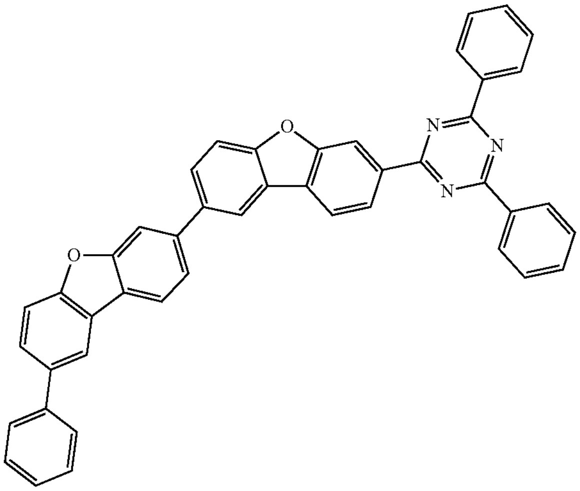
2-27
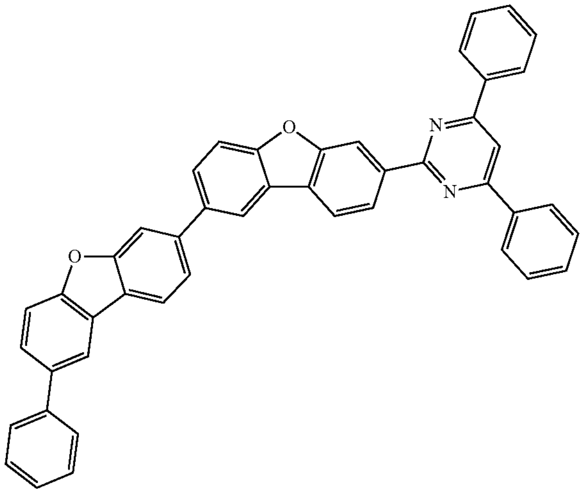
2-28
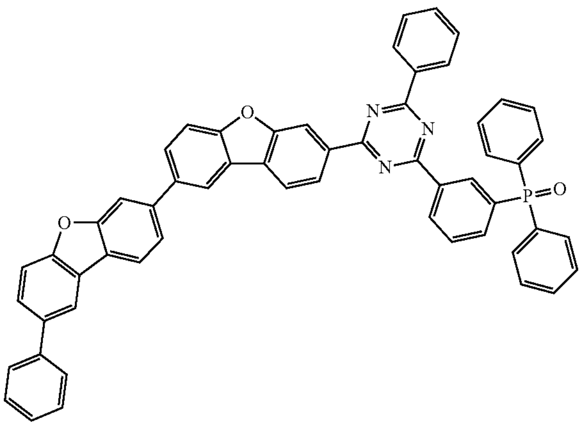
2-29
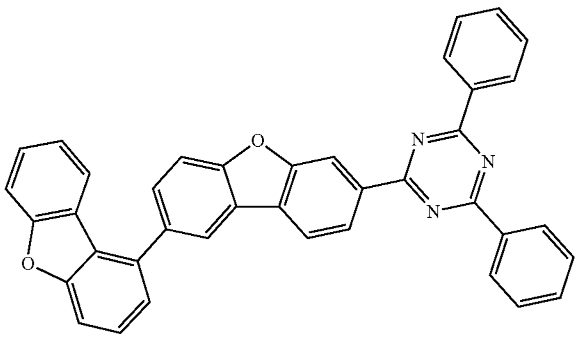

-continued
2-30
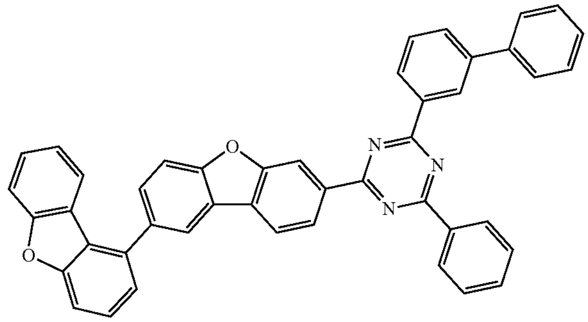
2-31
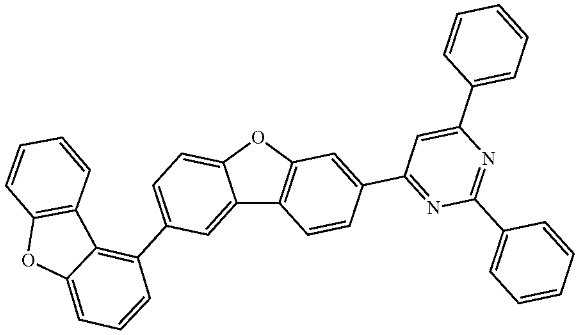
2-32
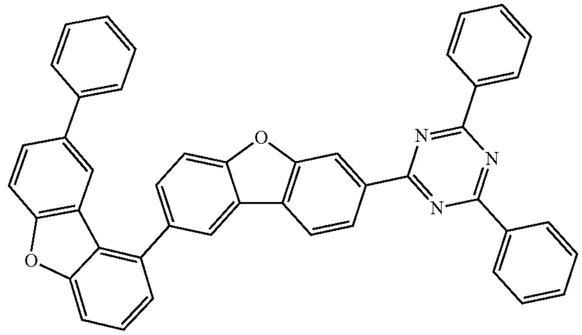
2-33
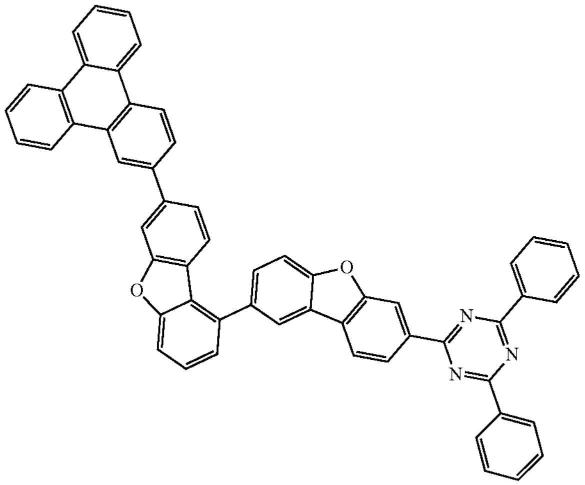
2-34
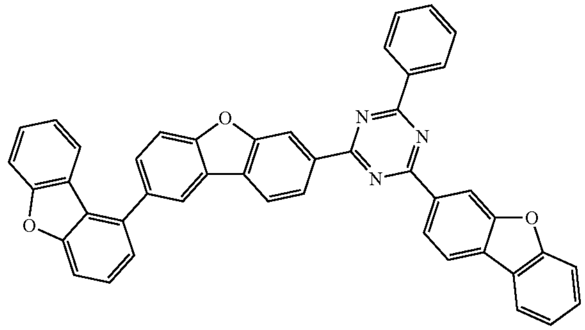
2-35
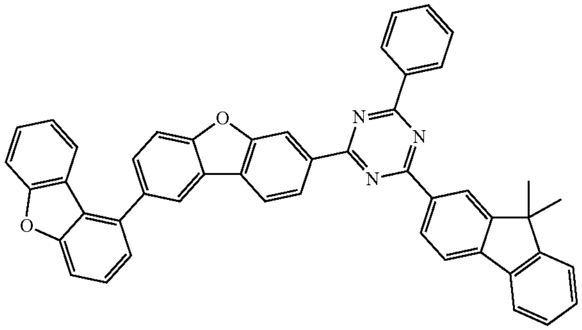

-continued
2-36
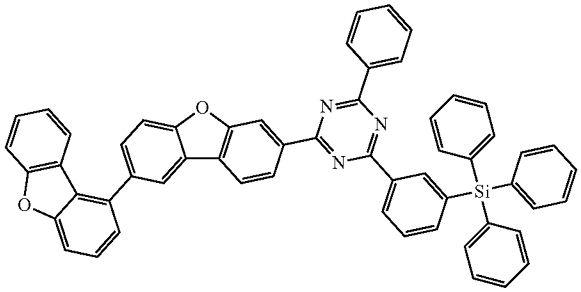
2-37
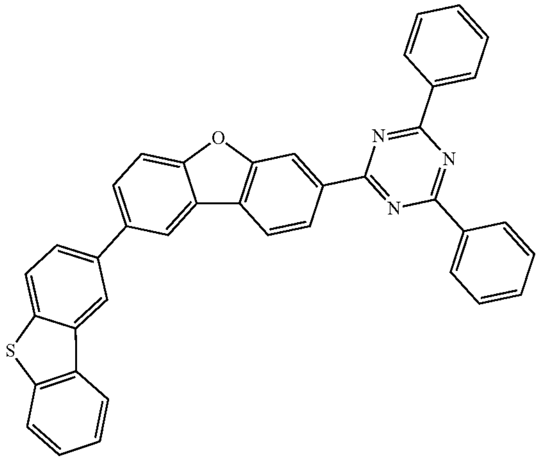
2-38
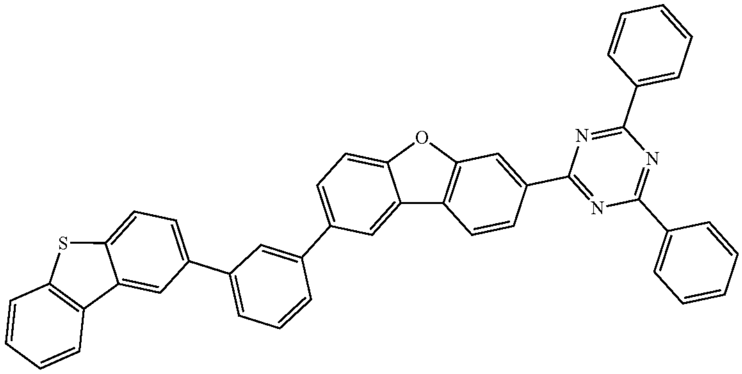
2-39
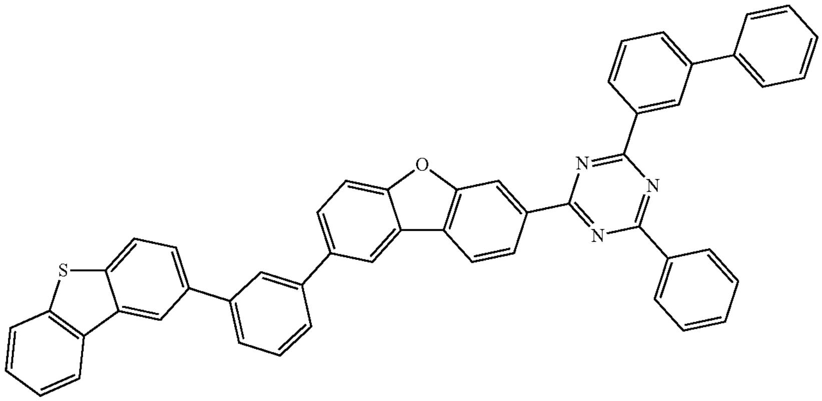

-continued
2-40
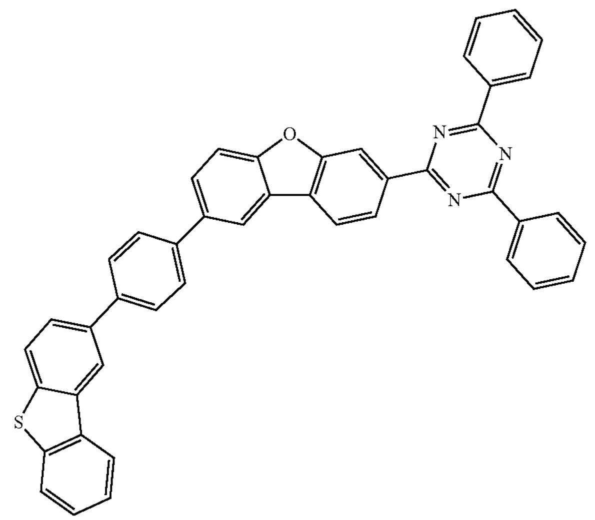
2-41
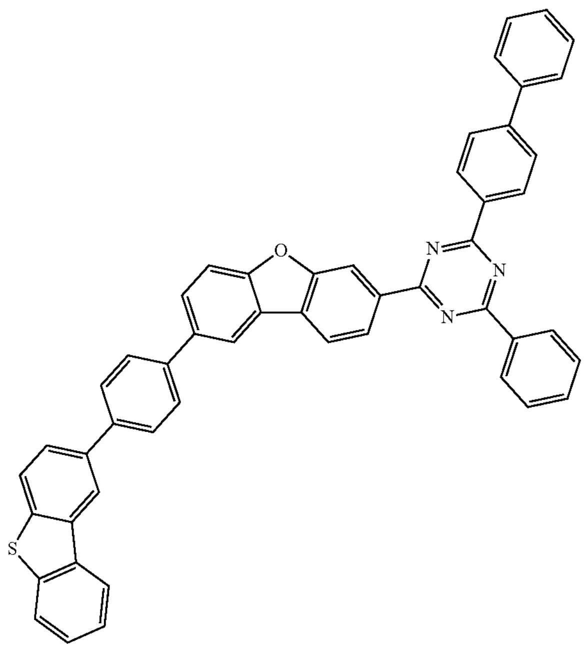
2-42
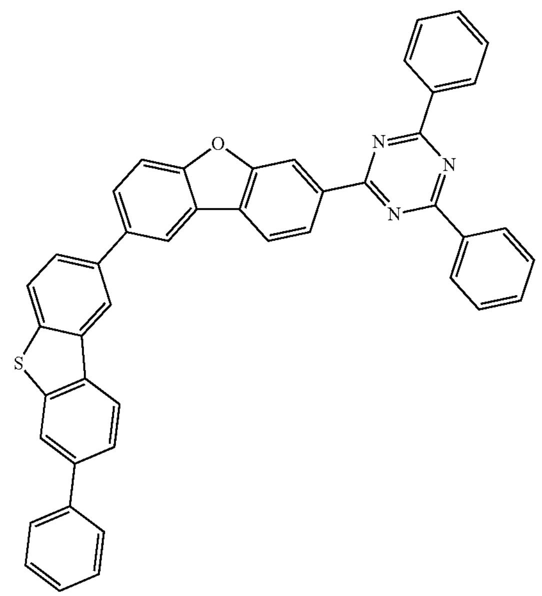
2-43
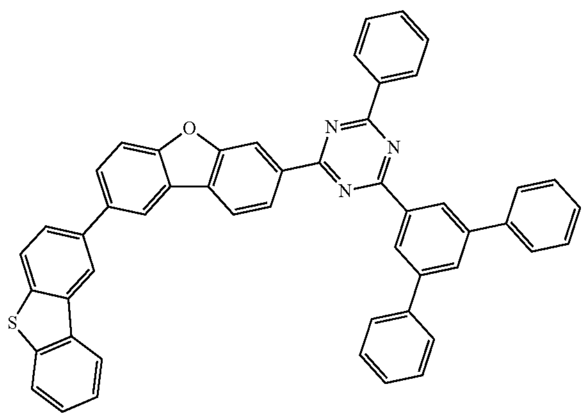

-continued
2-44
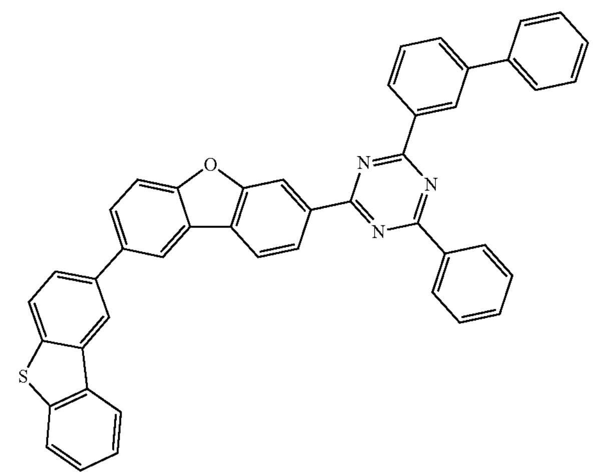
2-45
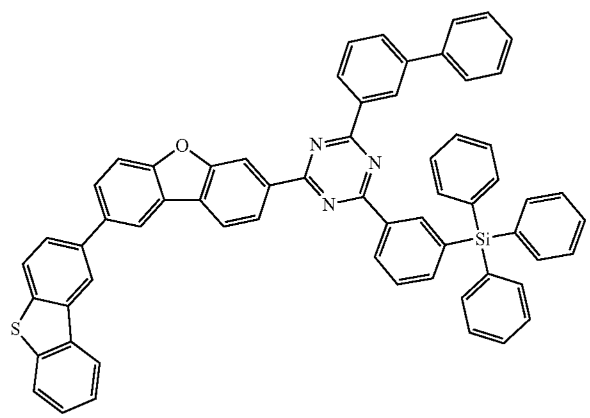
2-46
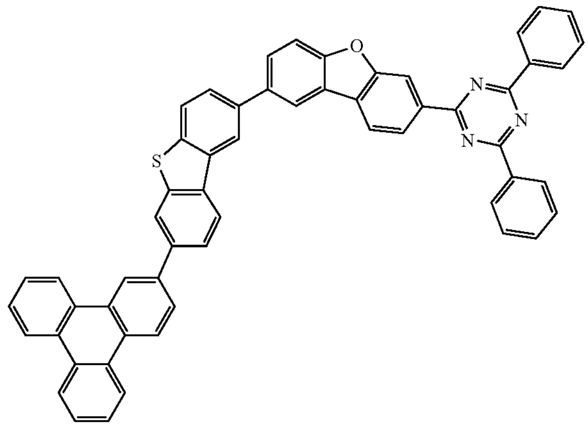
2-47
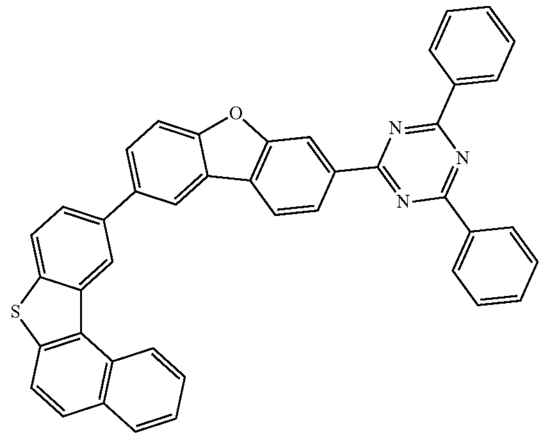
2-48
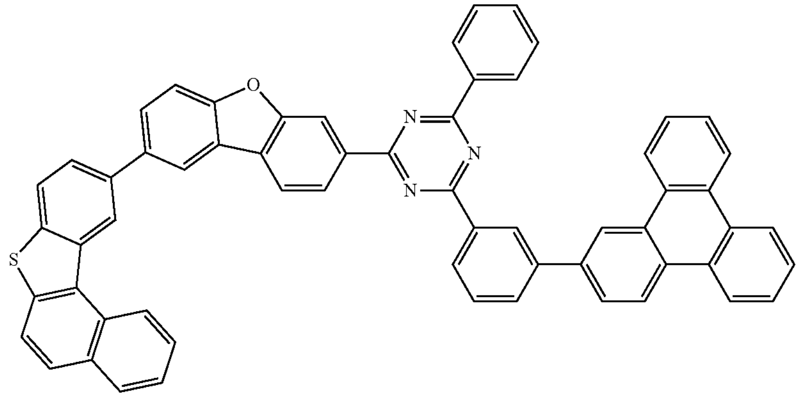

-continued
2-49
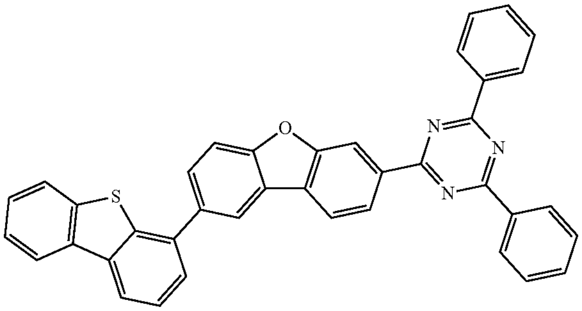
2-50
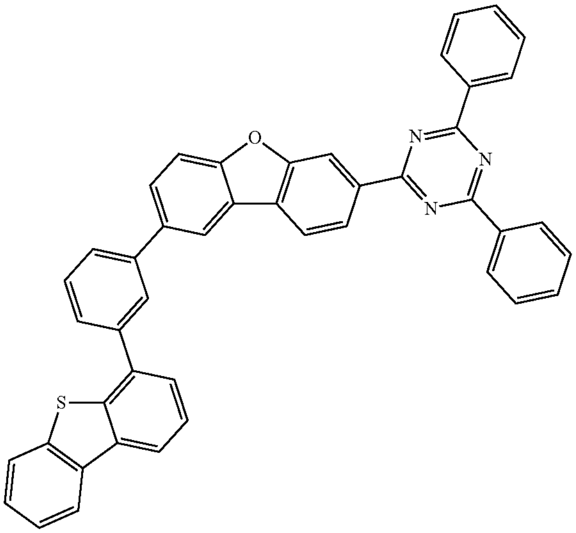
2-51
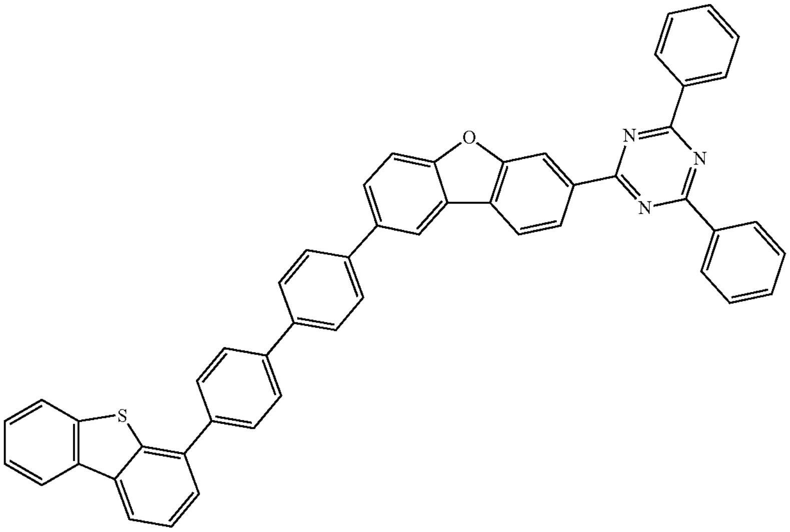
2-52
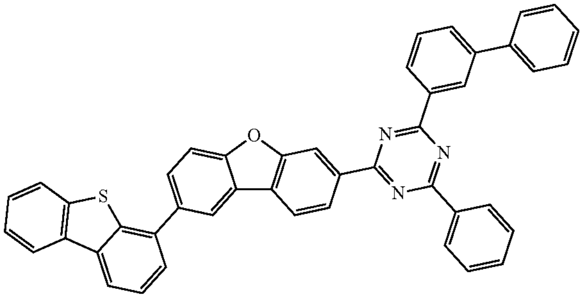
2-53
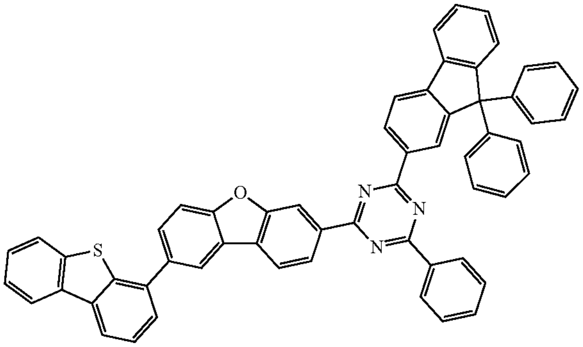

-continued
2-54
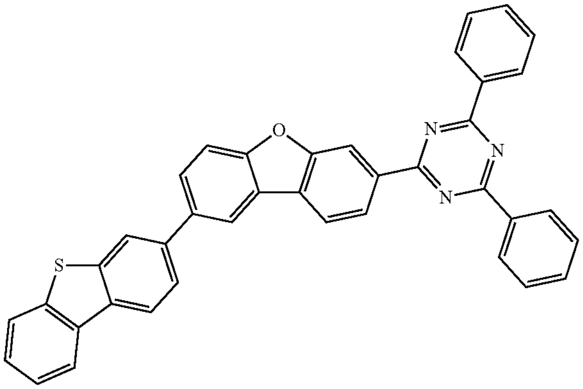
2-55
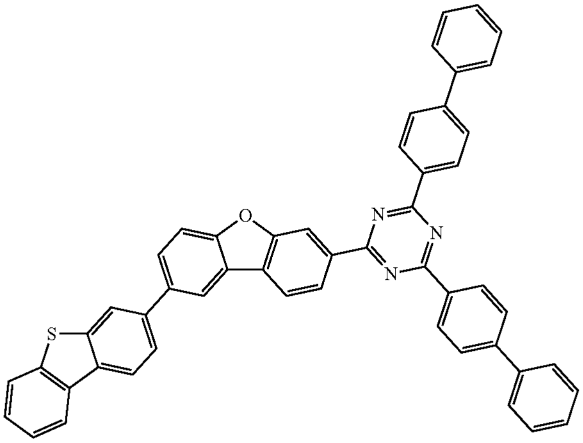
2-56
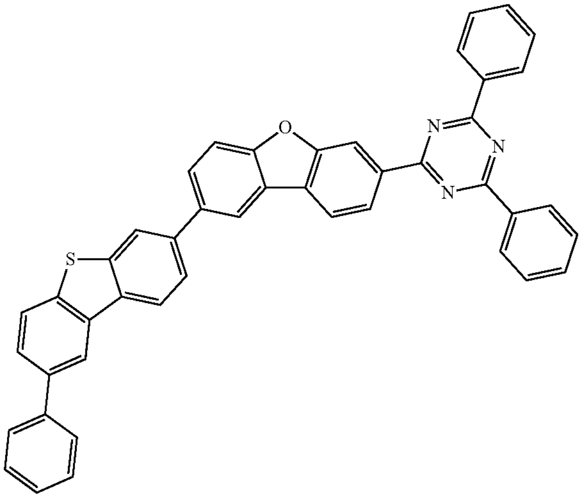
2-57
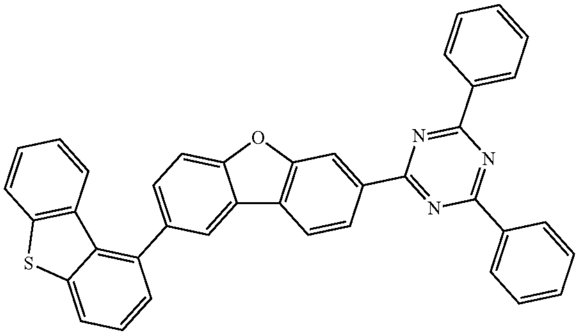
2-58
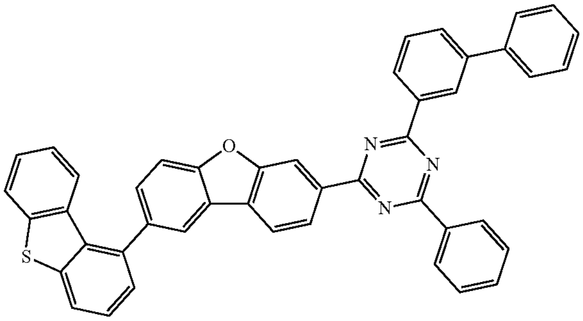
2-59
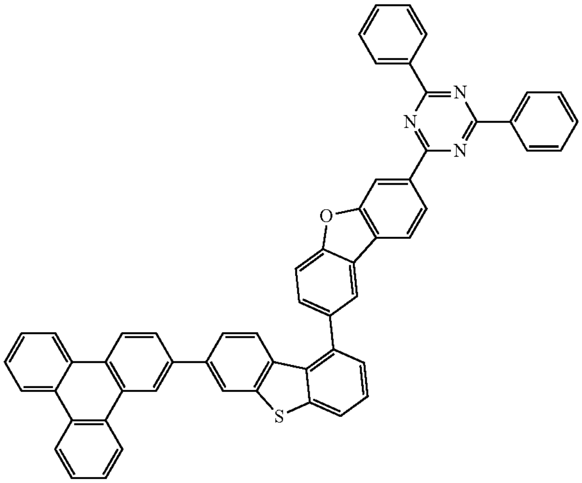

-continued
2-60
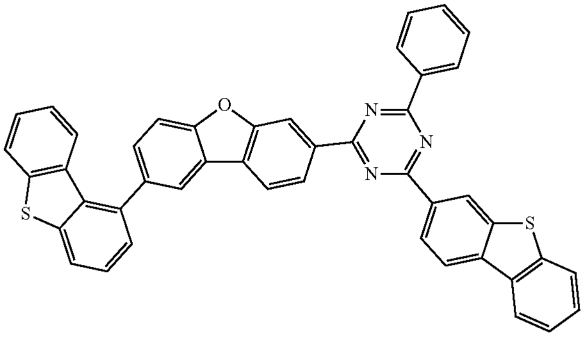
2-61
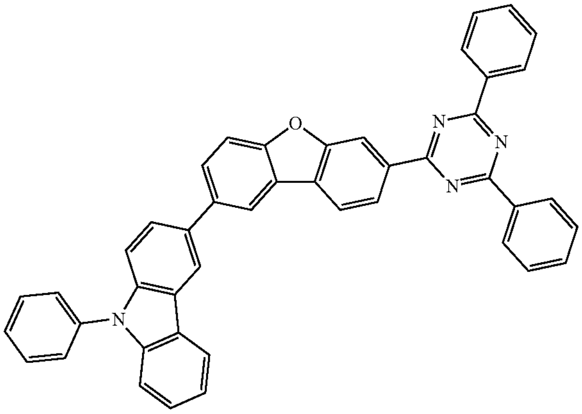
2-62
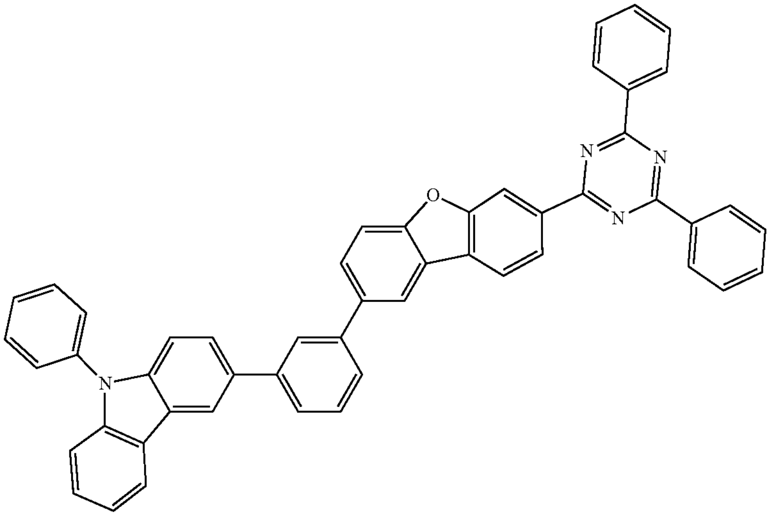
2-63
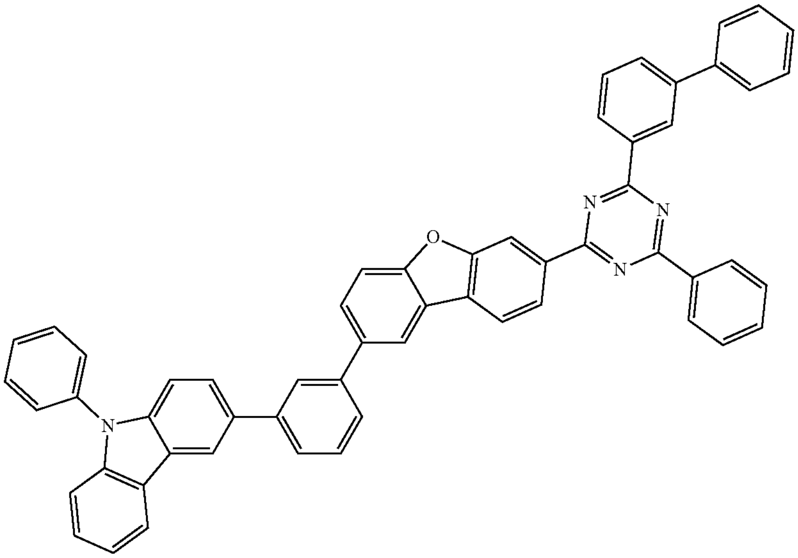

-continued
2-64
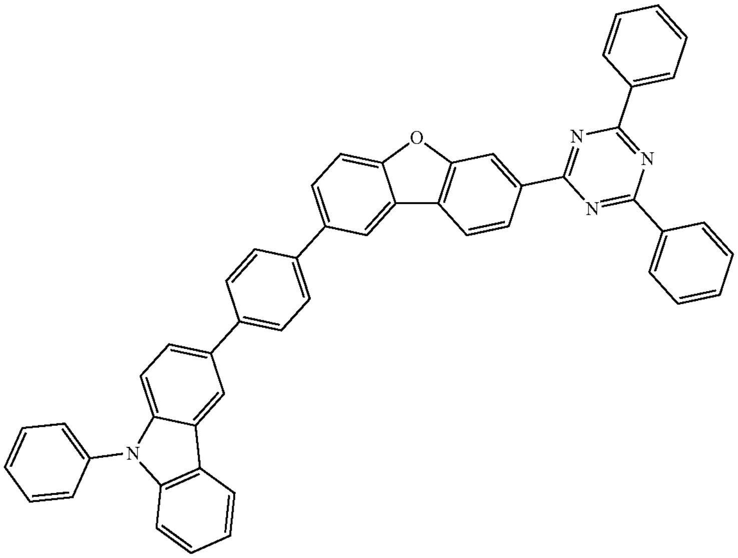
2-65
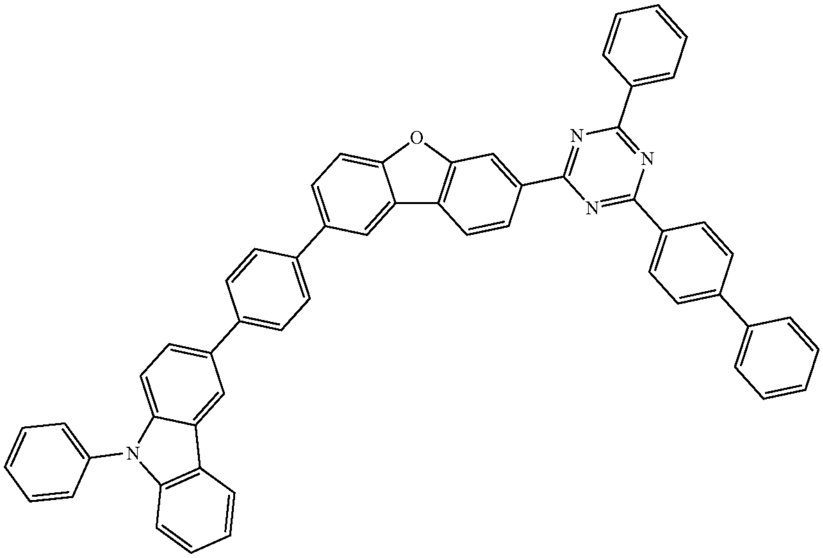
2-66
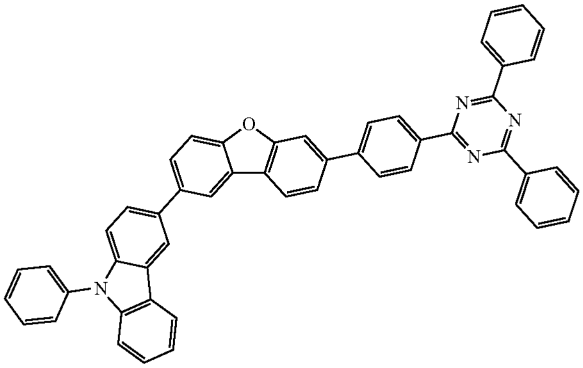
2-67
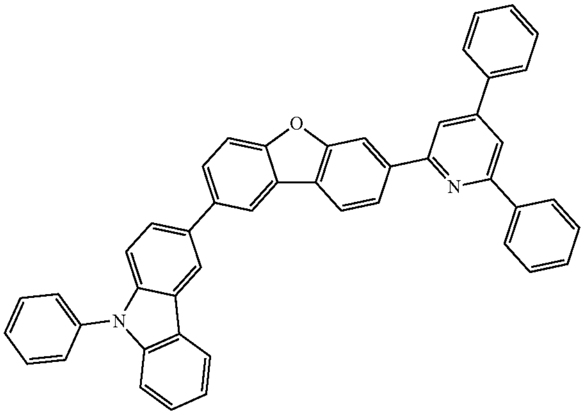

-continued
2-68
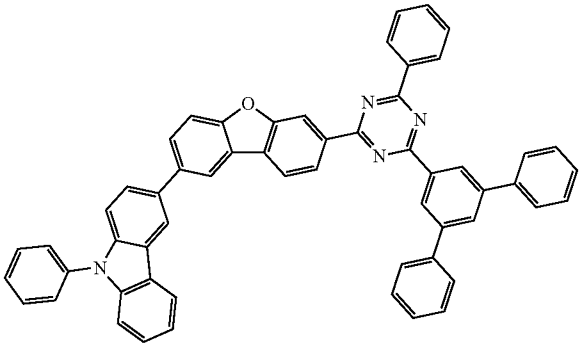
2-69
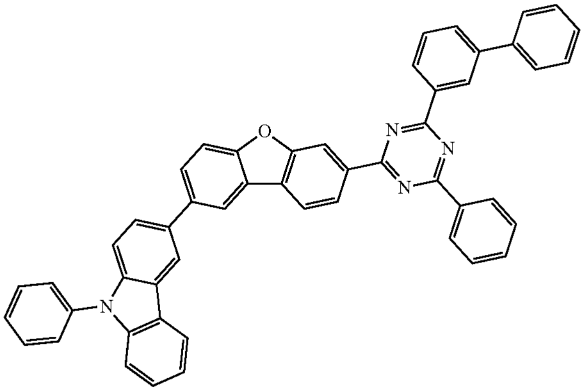
2-70
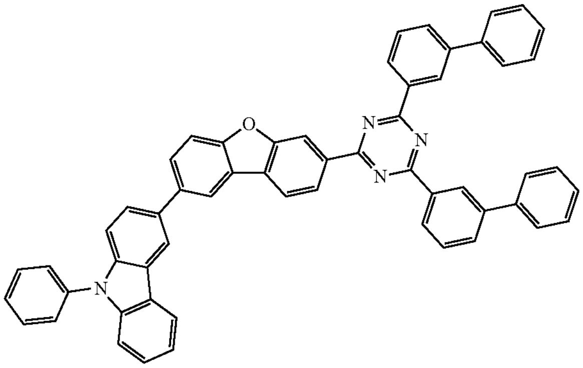
2-71
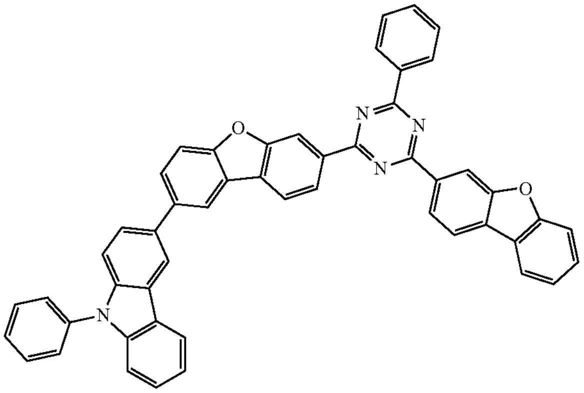
2-72
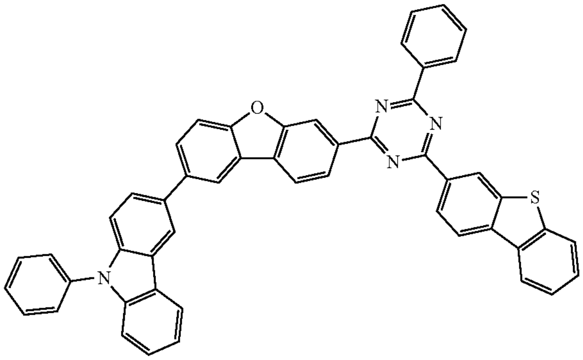
2-73
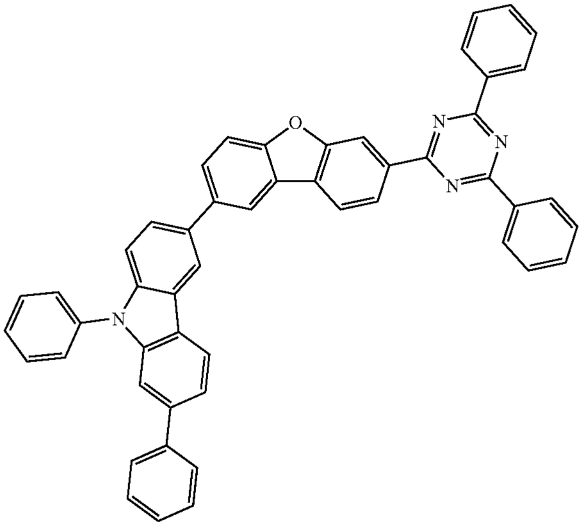

-continued
2-74
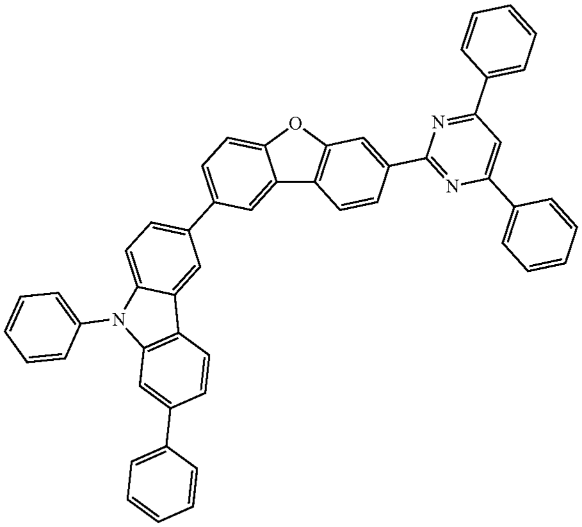
2-75
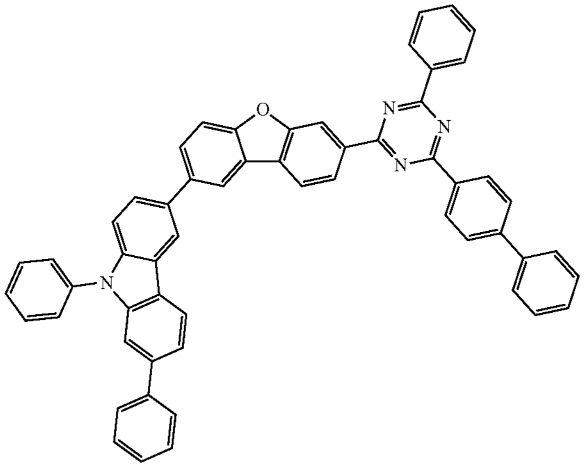
2-76
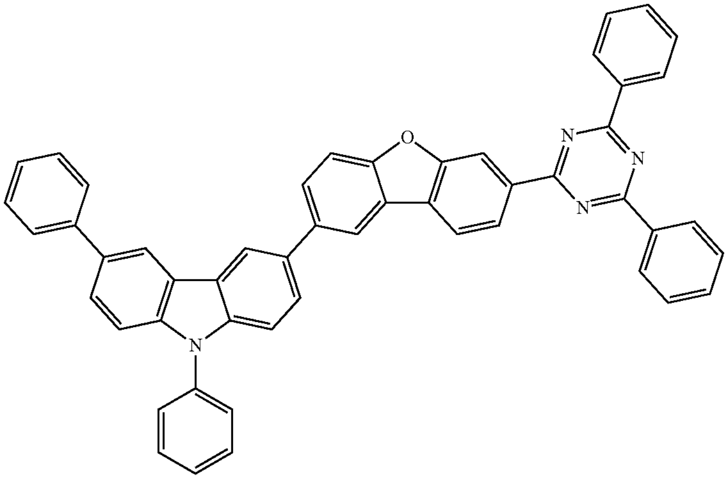
2-77
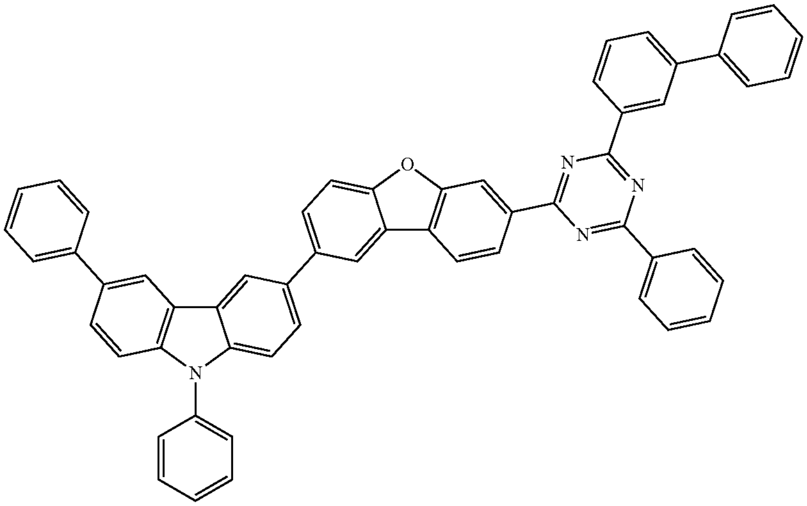

-continued
2-78
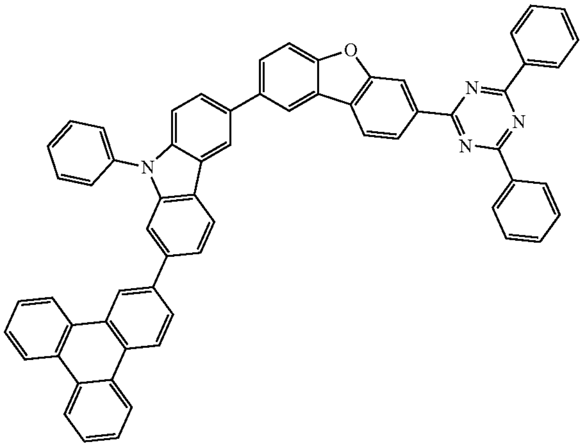
2-79
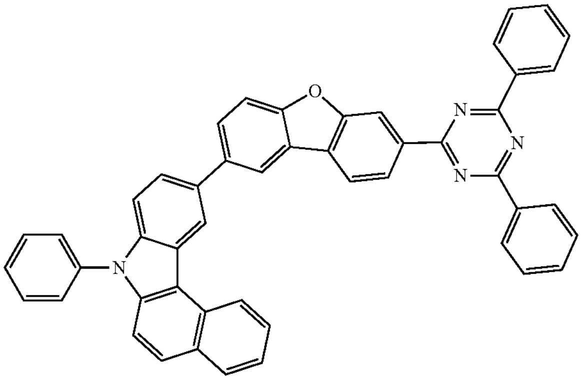
2-80
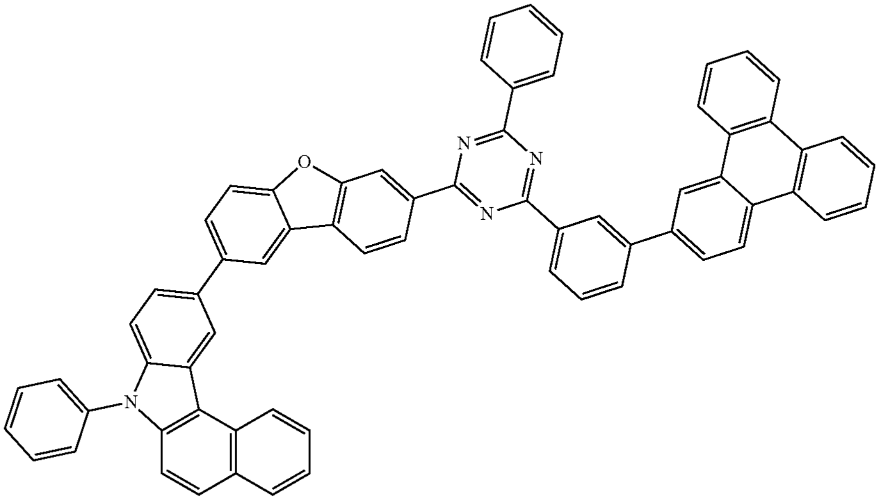
2-81
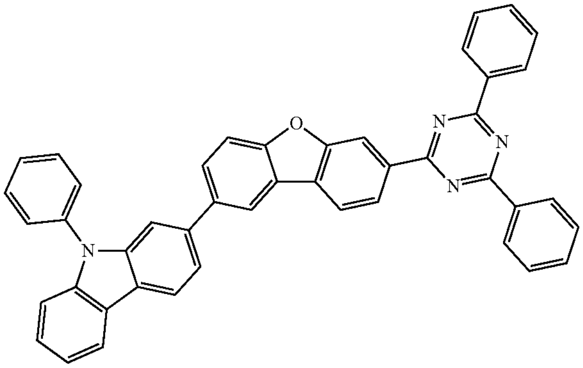
2-82
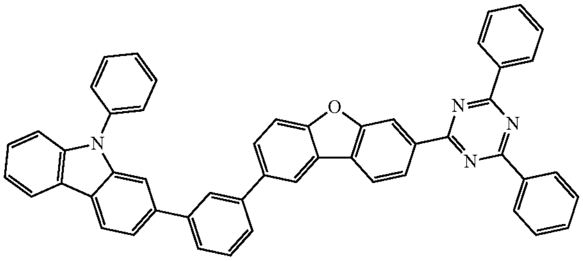

-continued
2-83
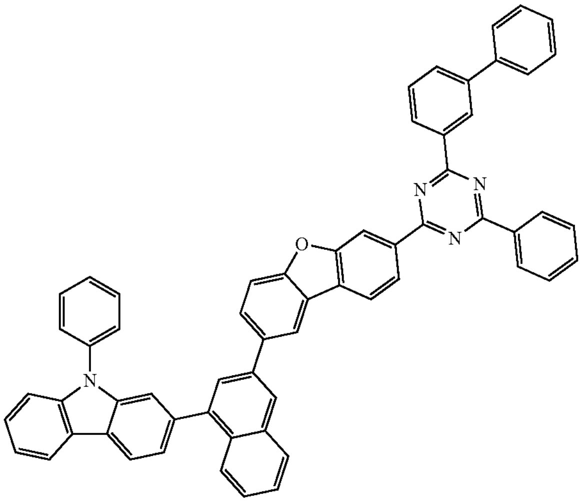
2-84
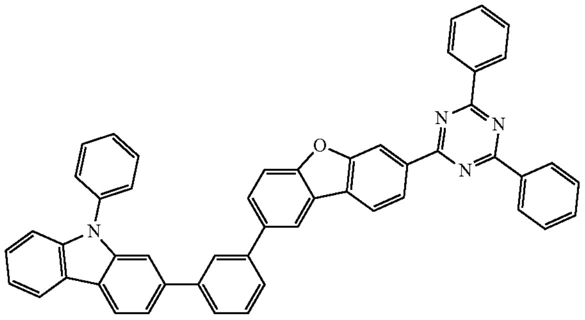
2-85
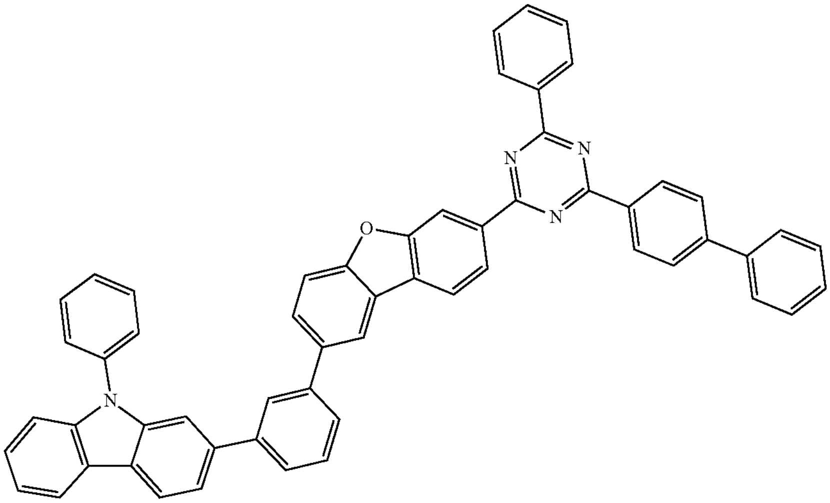
2-86
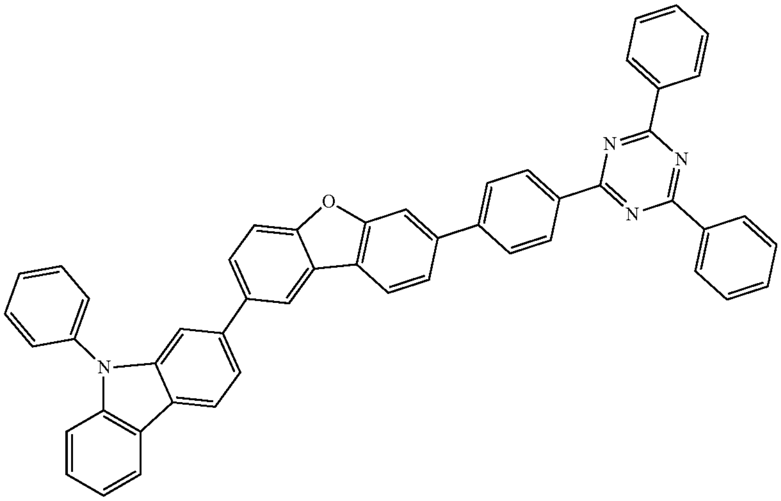

-continued
2-87
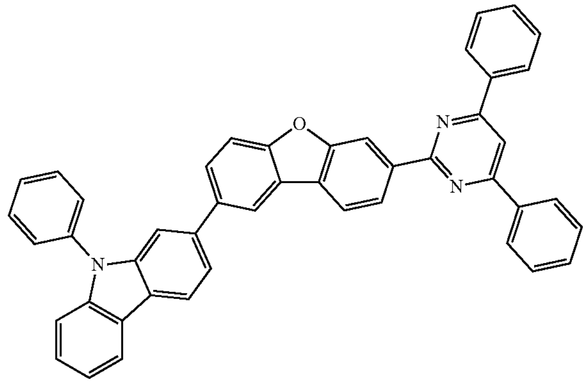
2-88
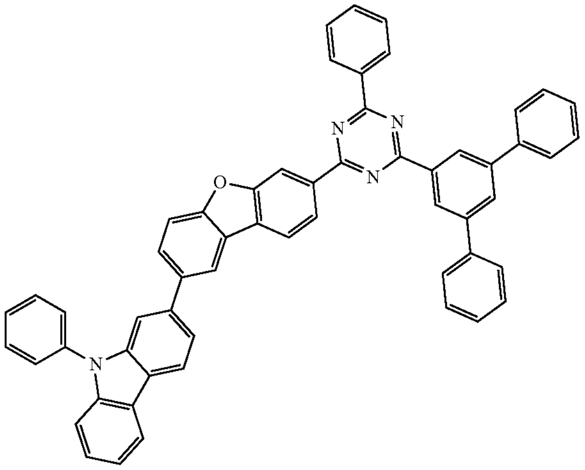
2-89
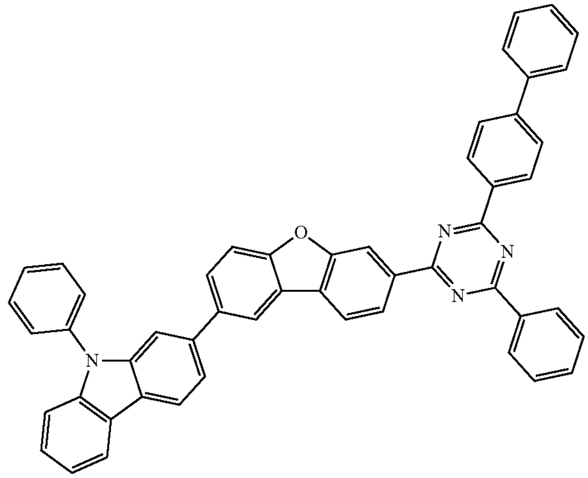
2-90
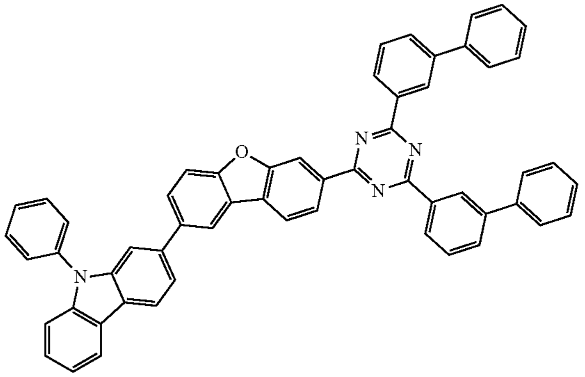
2-91
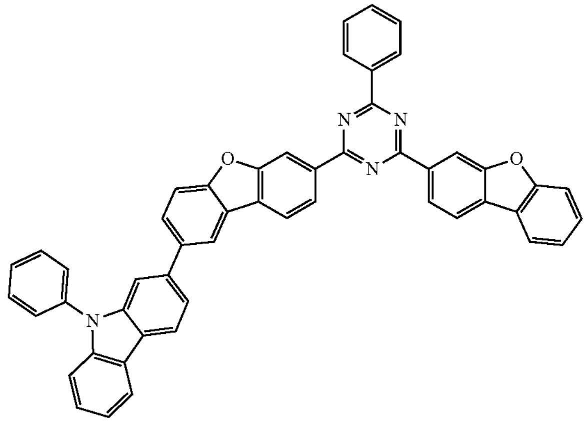
2-92
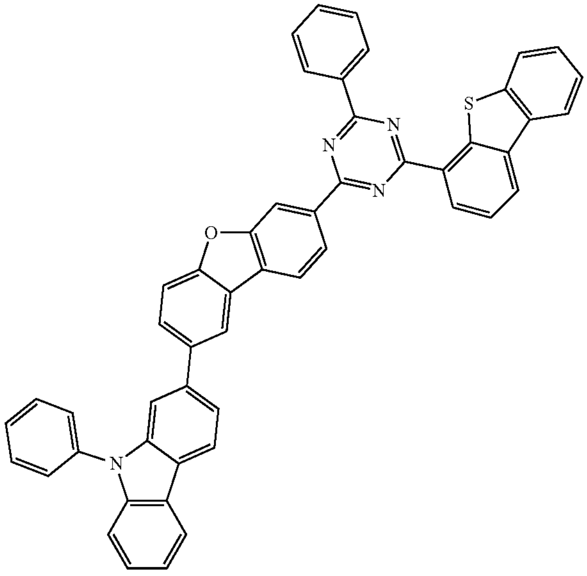

-continued
2-93
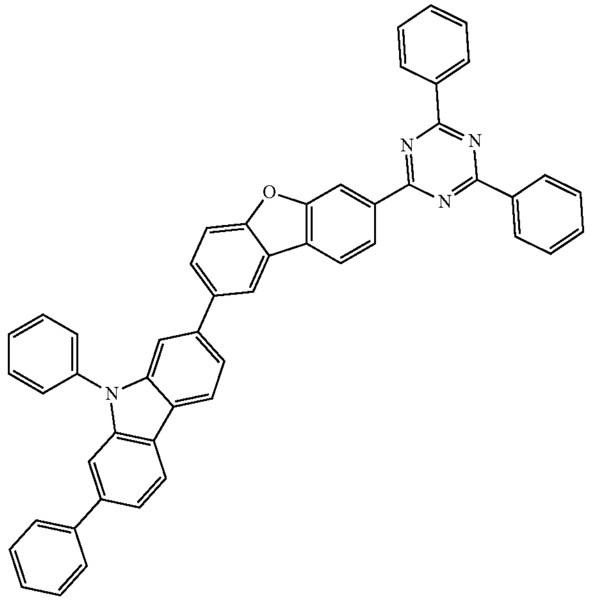
2-94
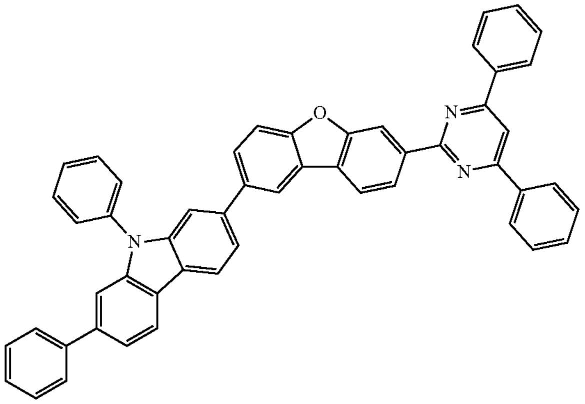
2-95
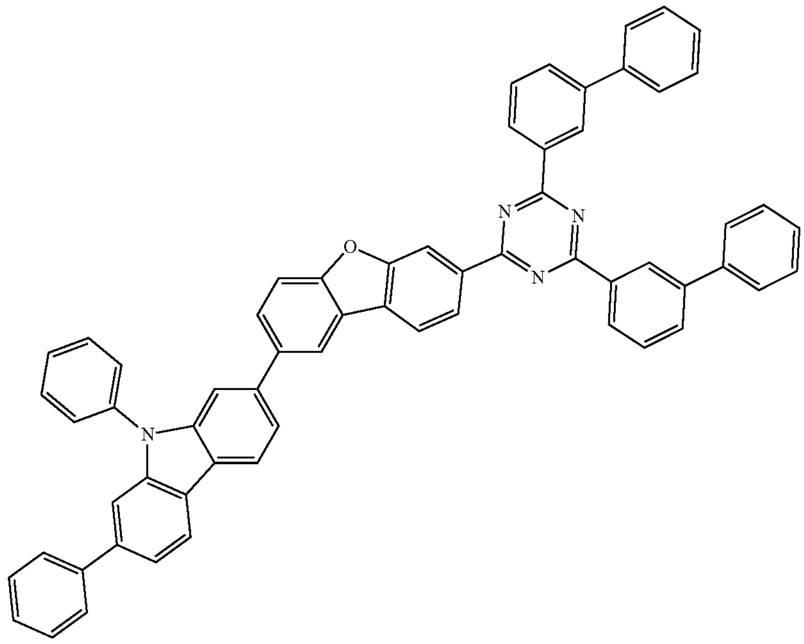

-continued
2-96
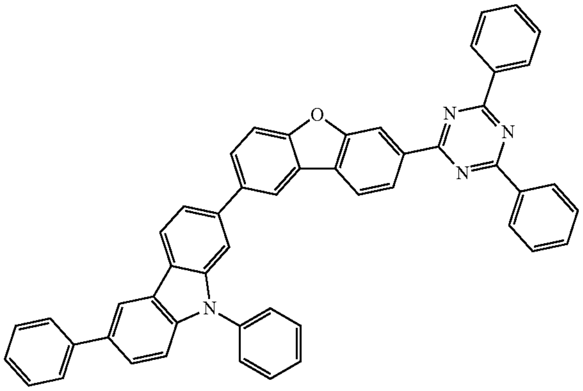
2-97
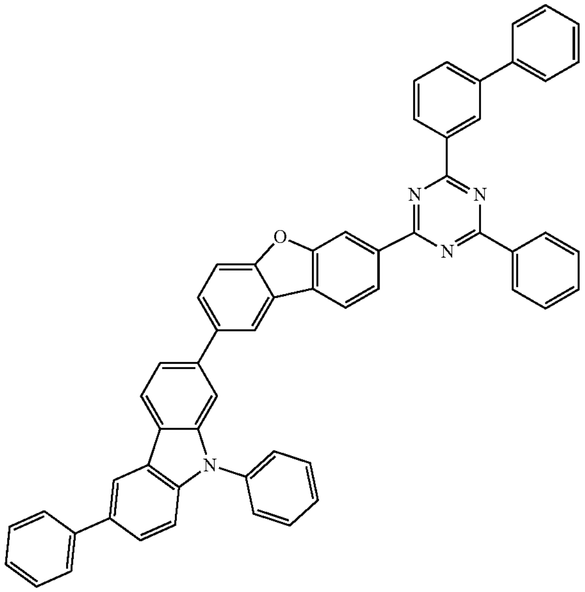
2-98
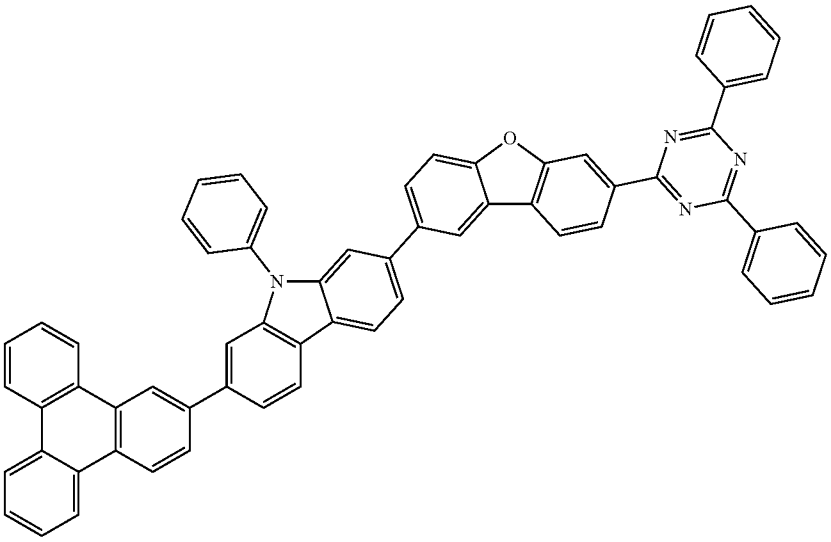

-continued
2-99
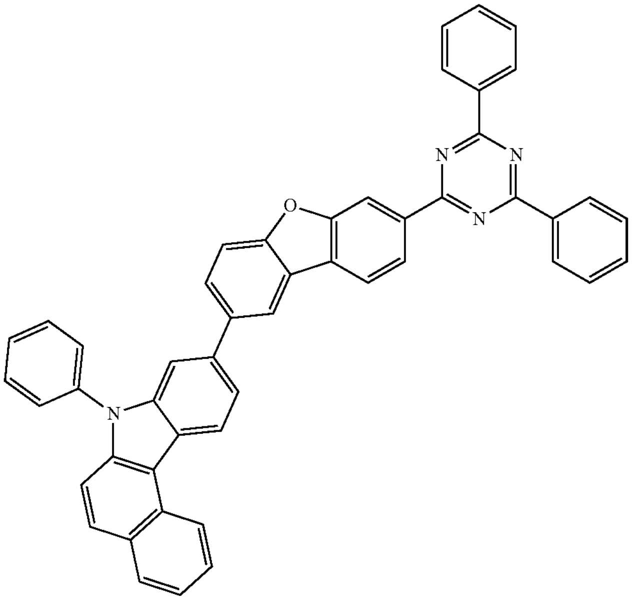
2-100
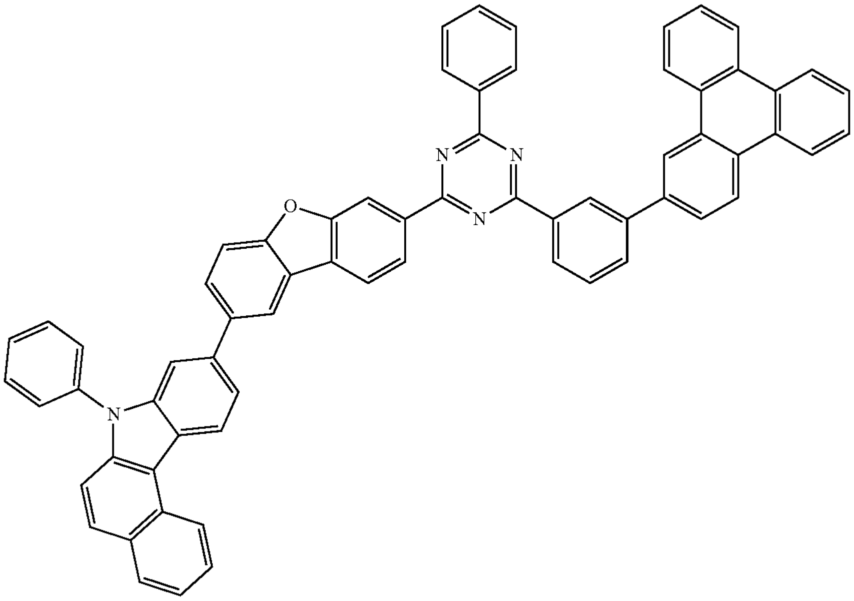
2-101
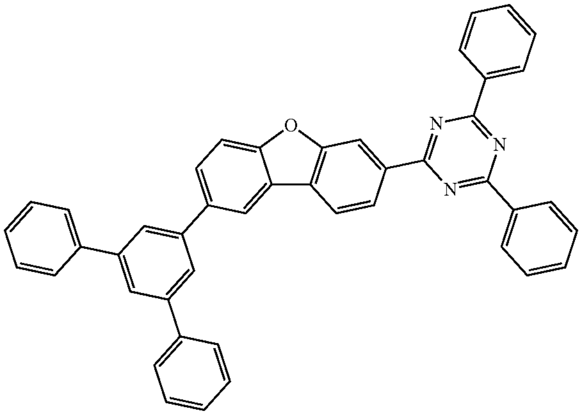
2-102
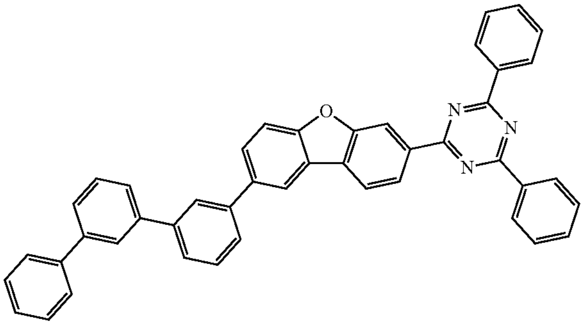

-continued
2-103
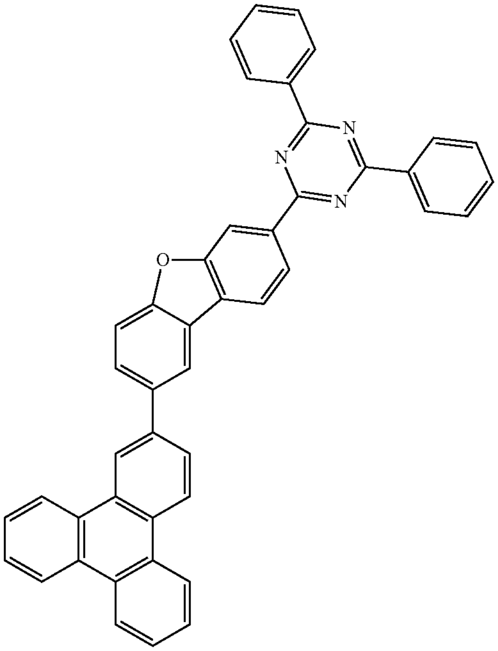
2-104
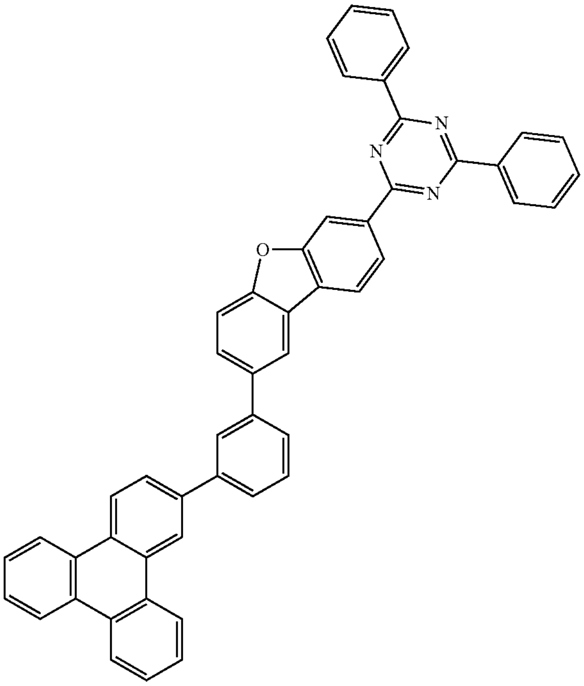
3-1
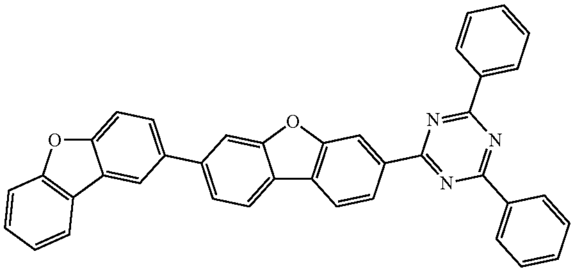
3-2
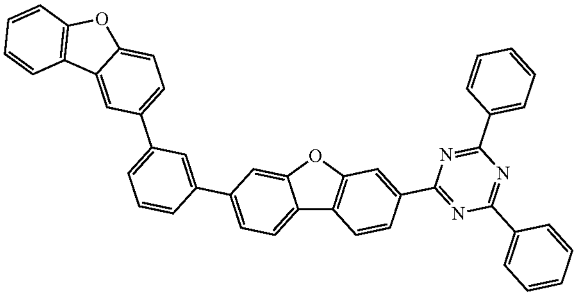
3-3
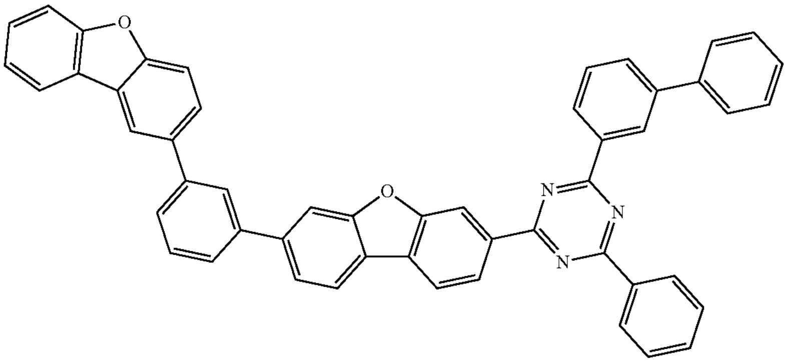

-continued
3-4
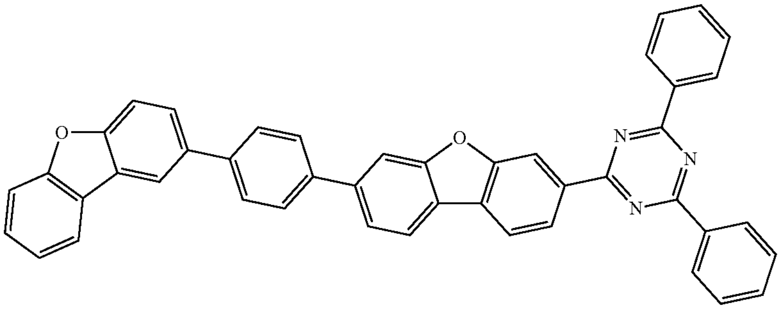
3-5
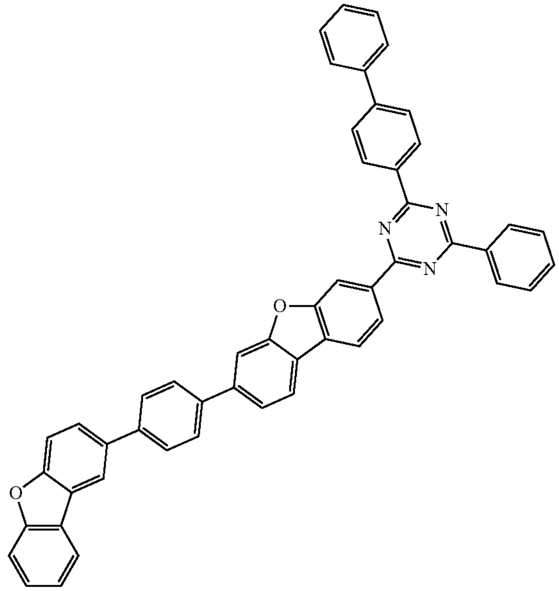
3-6
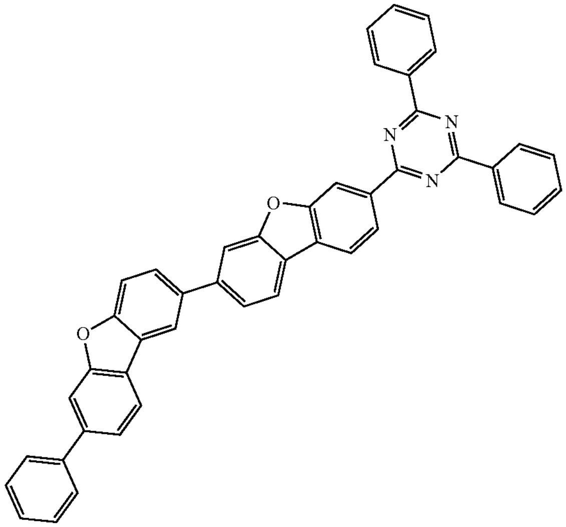
3-7
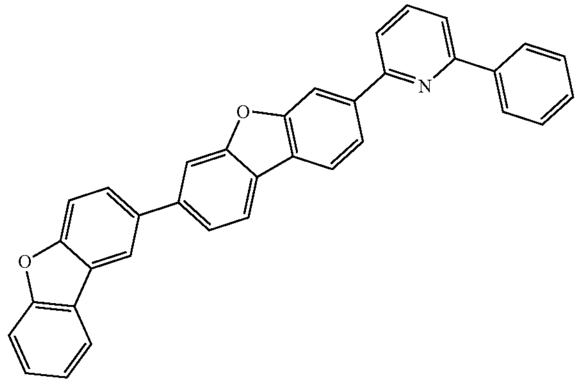
3-8
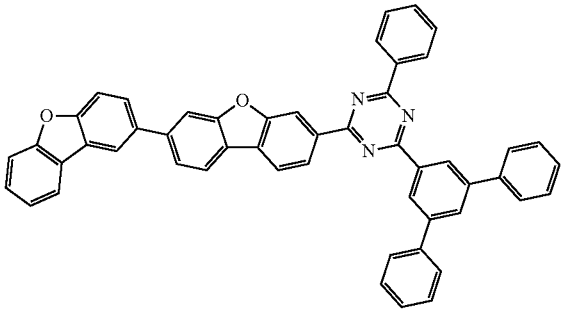
3-9
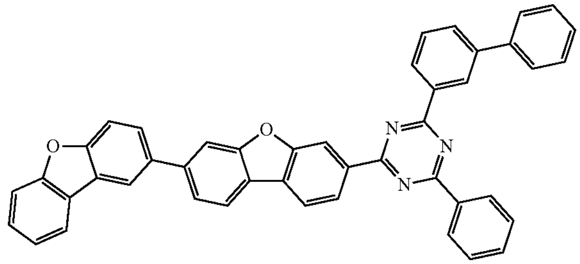
3-10
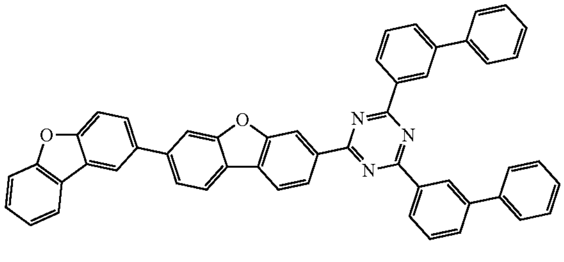

-continued
3-11
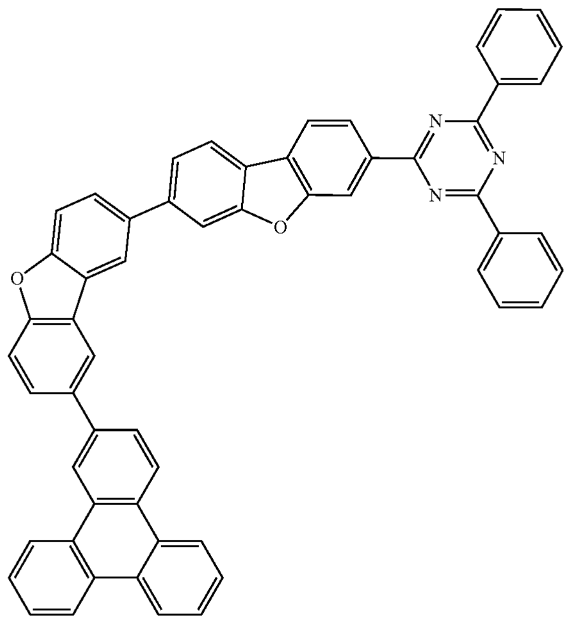
3-12
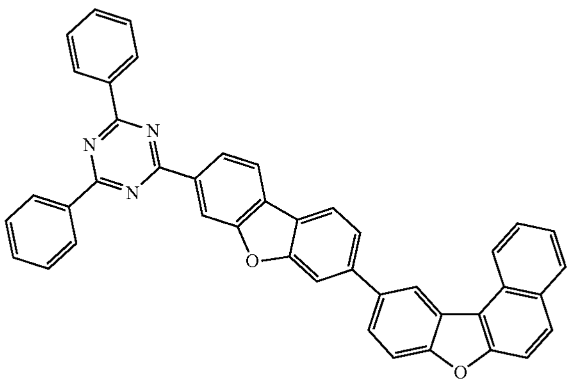
3-13
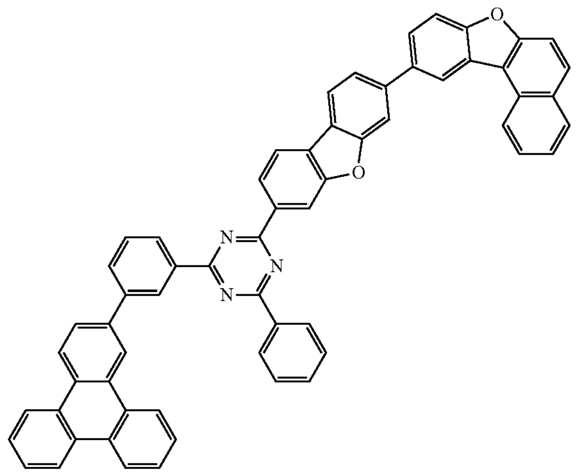
3-14
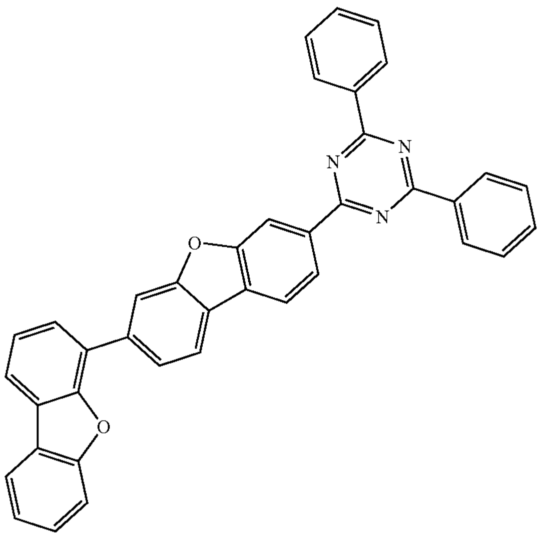
3-15
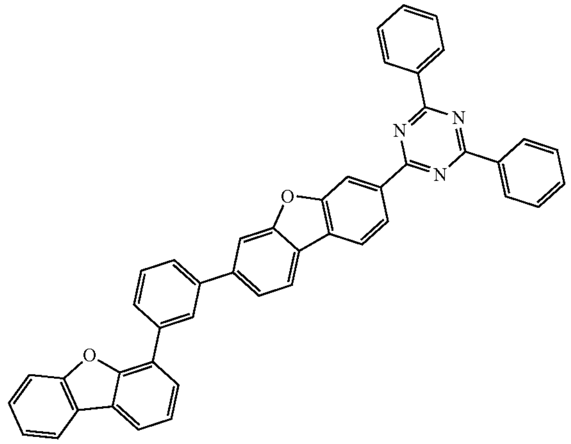

-continued
3-16
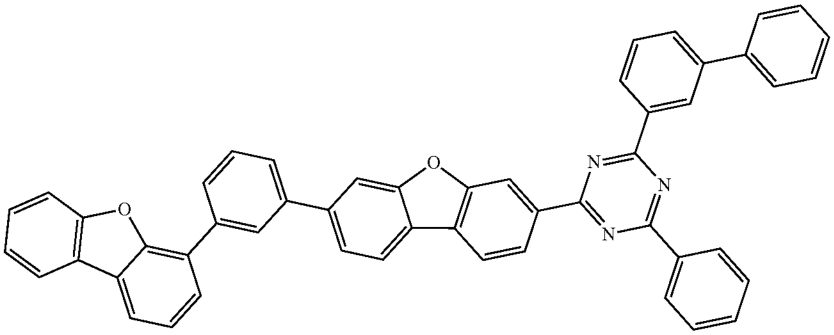
3-17
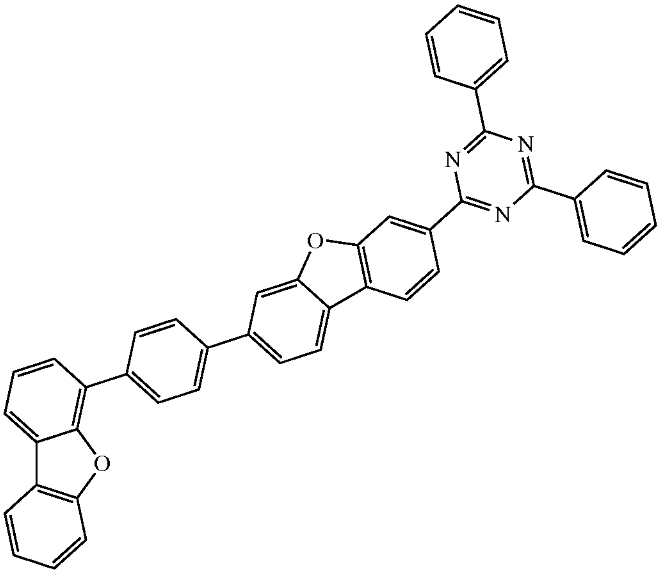
3-18
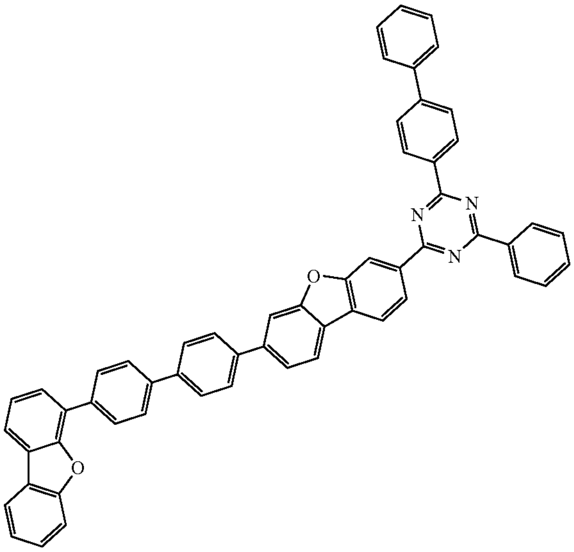

-continued
3-19
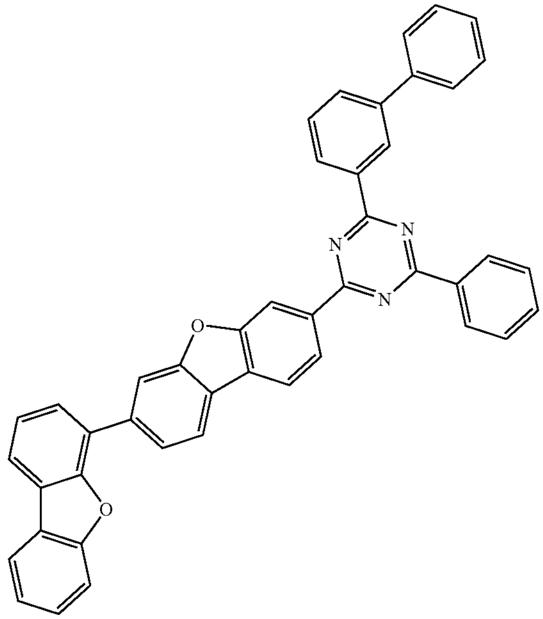
3-20
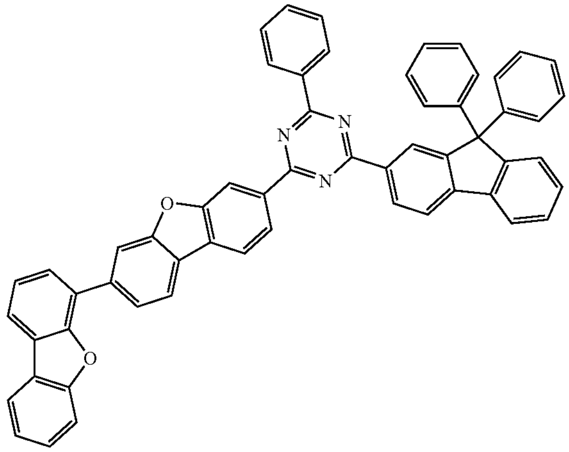
3-21
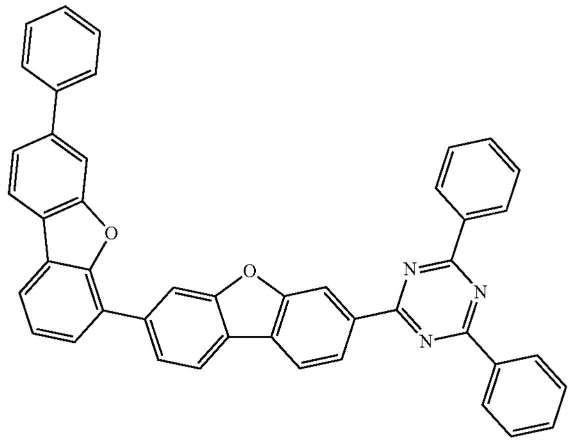
3-22
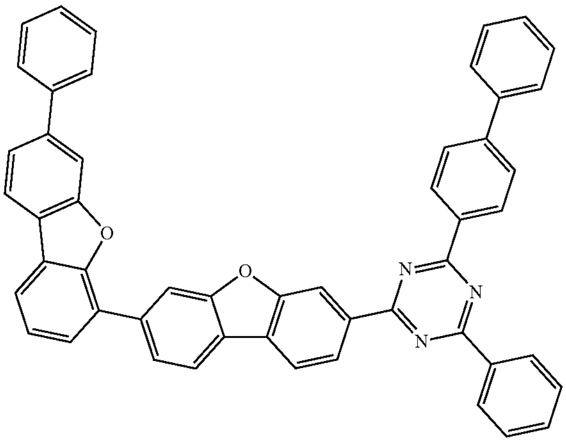
3-23
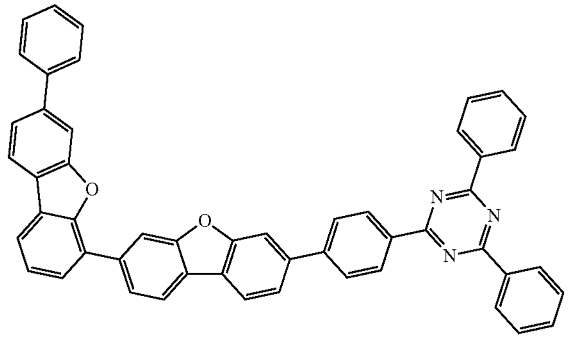
3-24
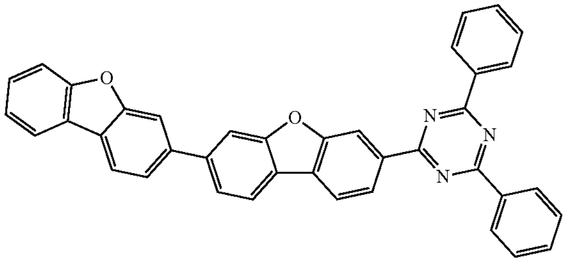

-continued
3-25
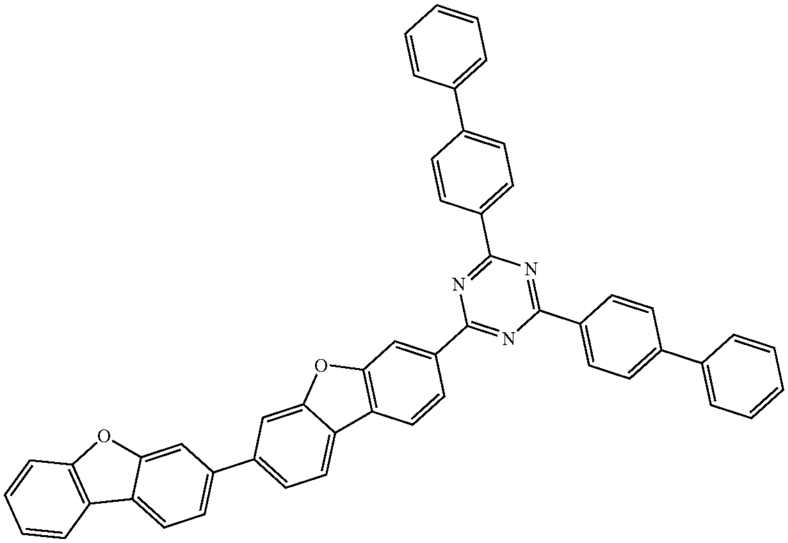
3-26
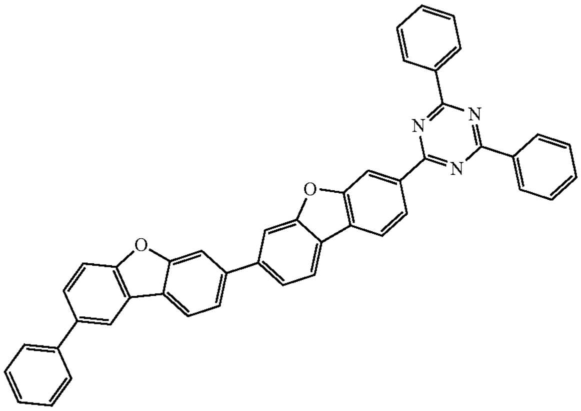
3-37
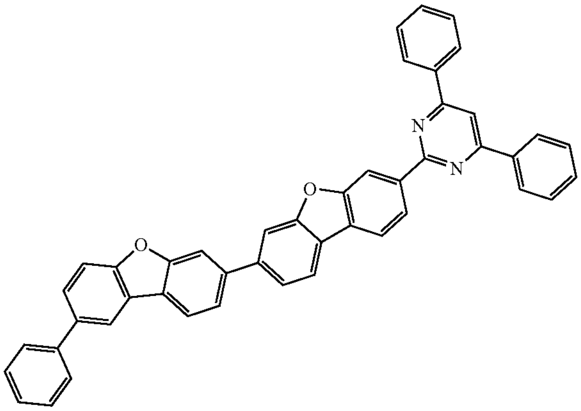
3-28
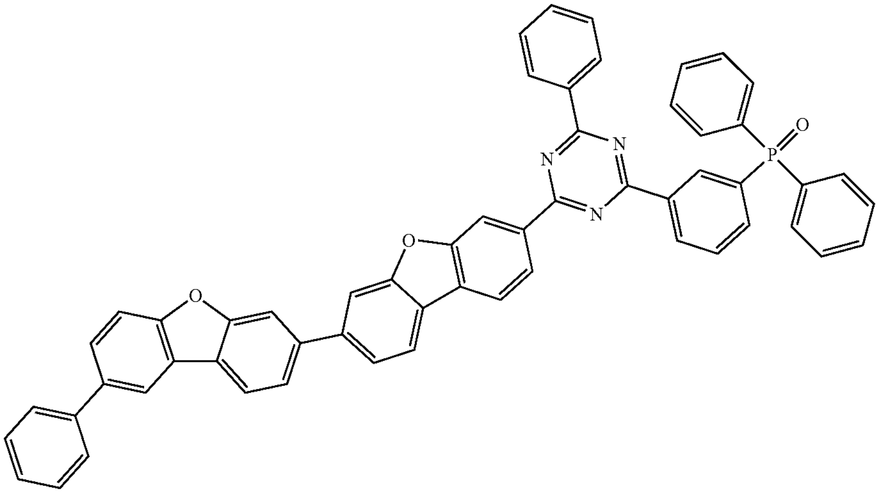

-continued
3-29
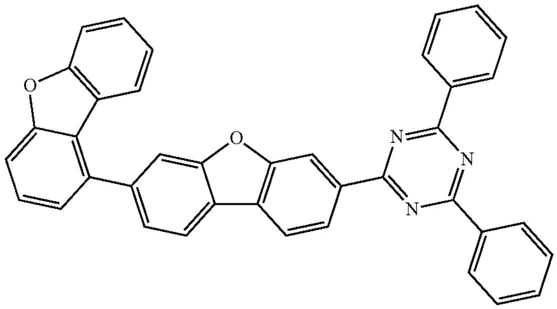
3-30
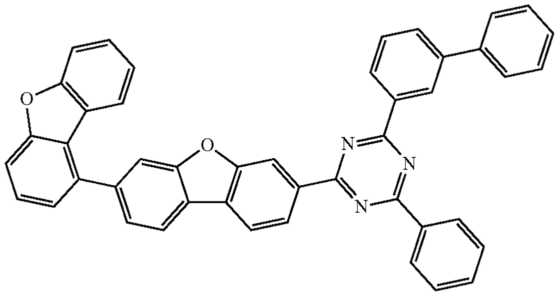
3-31
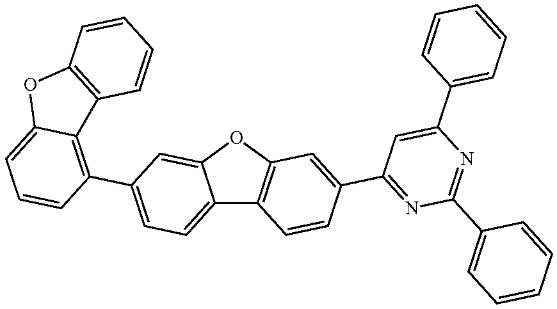
3-32
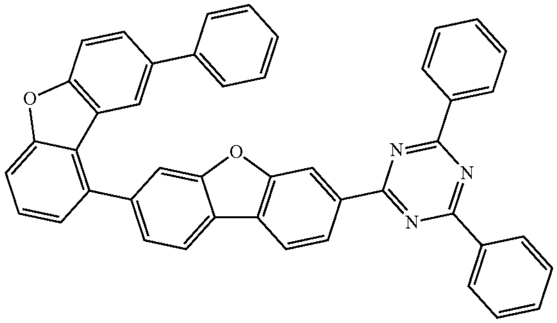
3-33
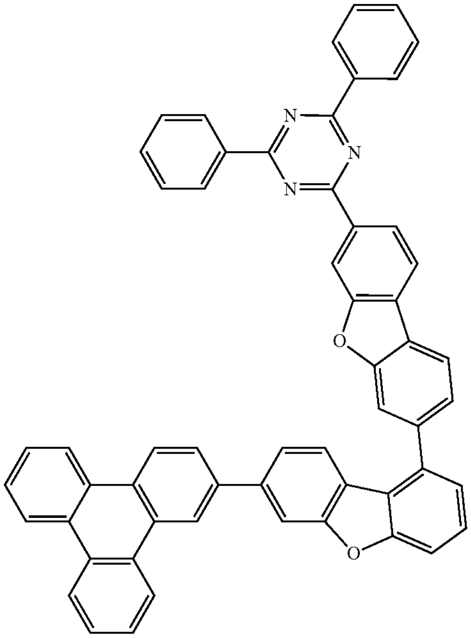
3-34
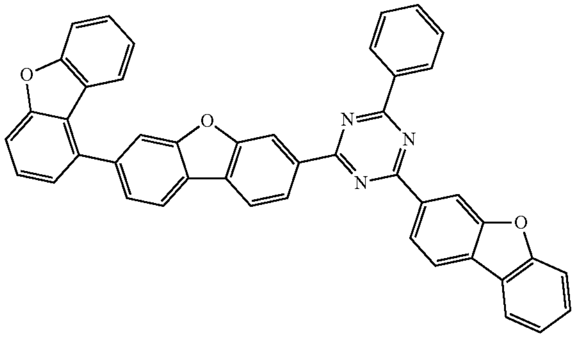

-continued
3-35
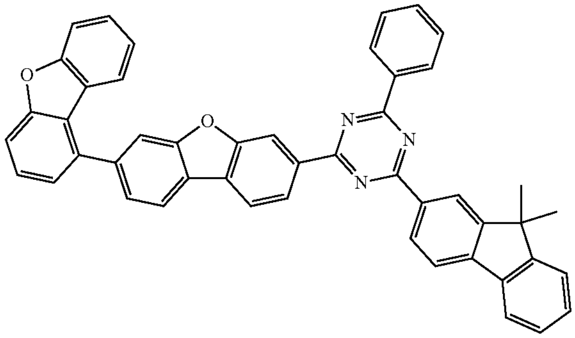
3-36
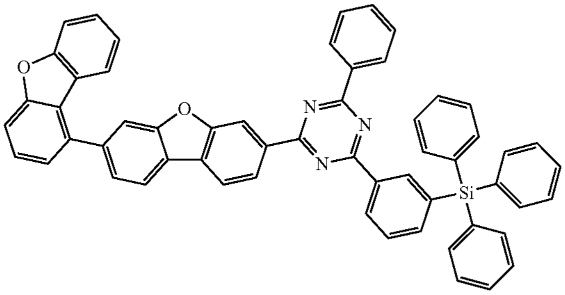
3-37
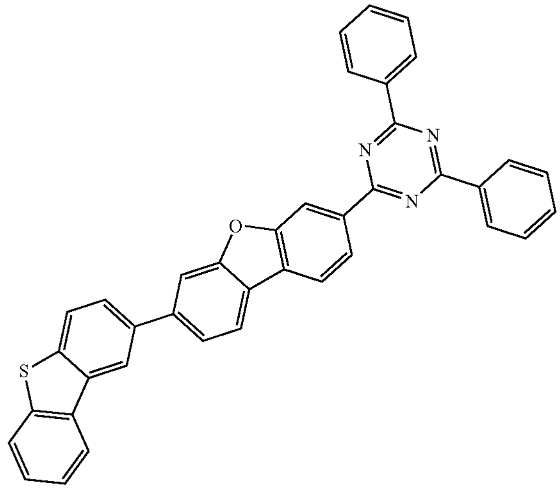
3-38
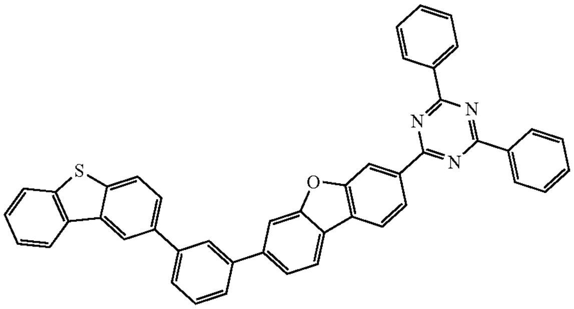
3-39
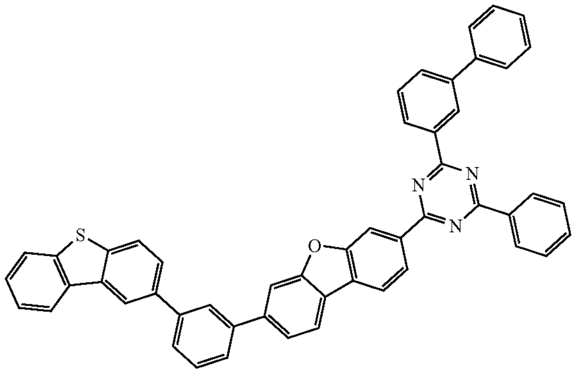
3-40
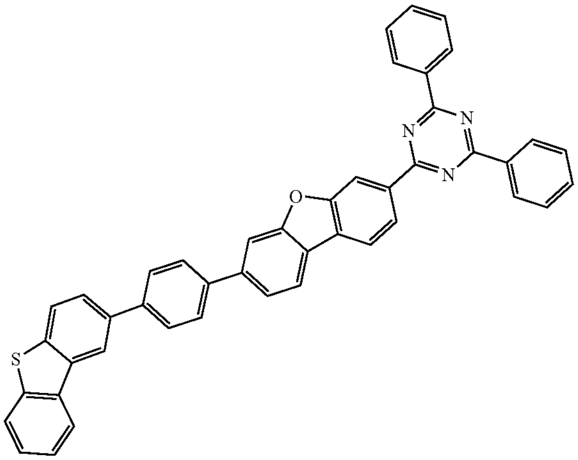

-continued
3-41
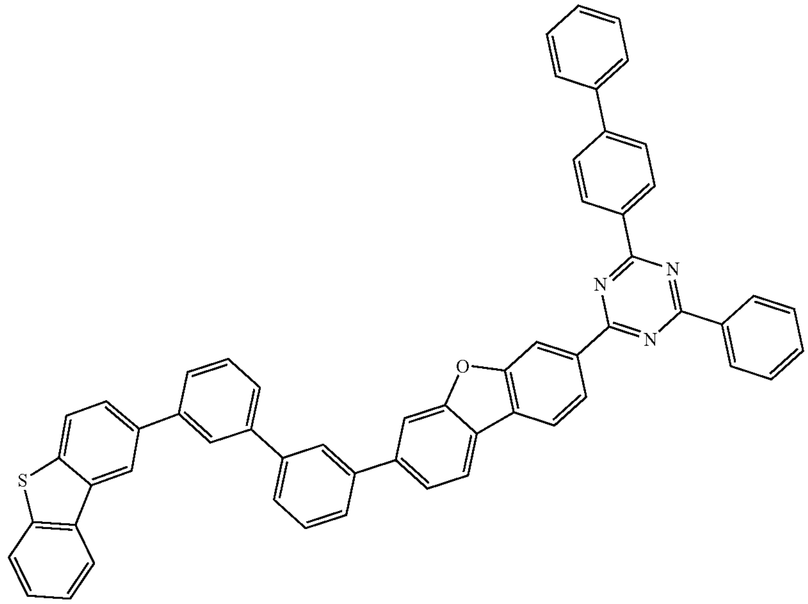
3-42
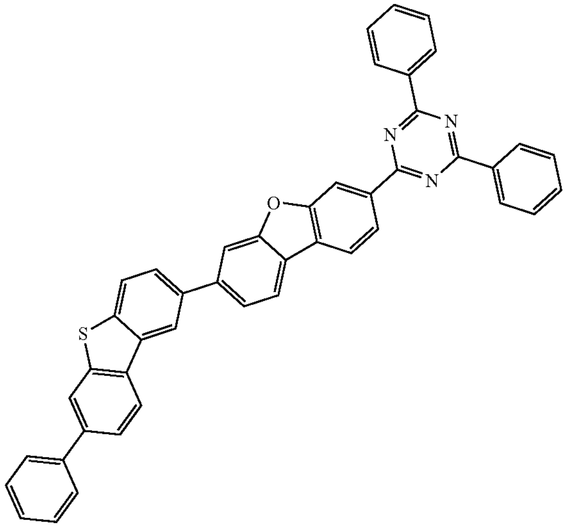
3-43
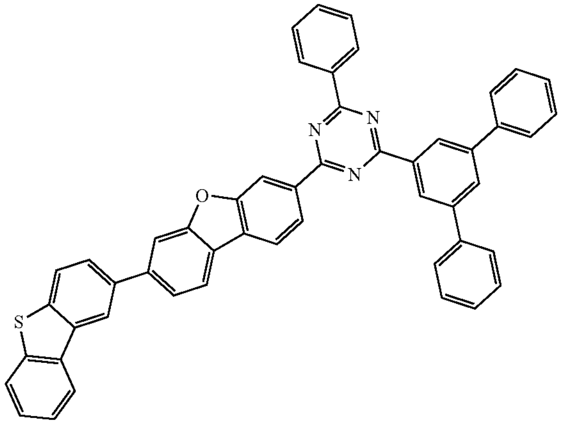

-continued
3-44
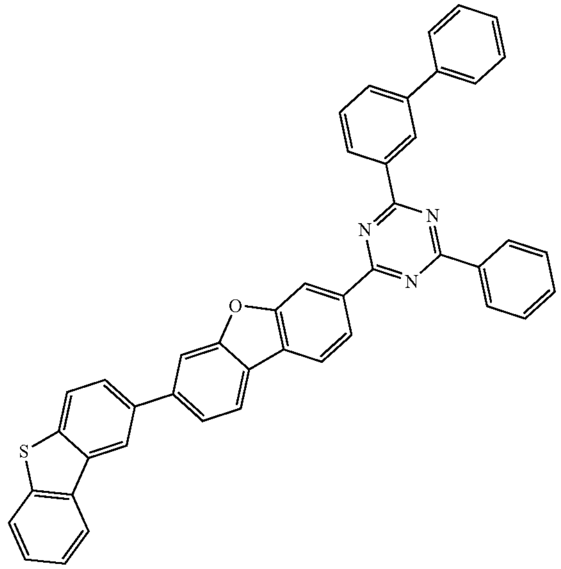
3-45
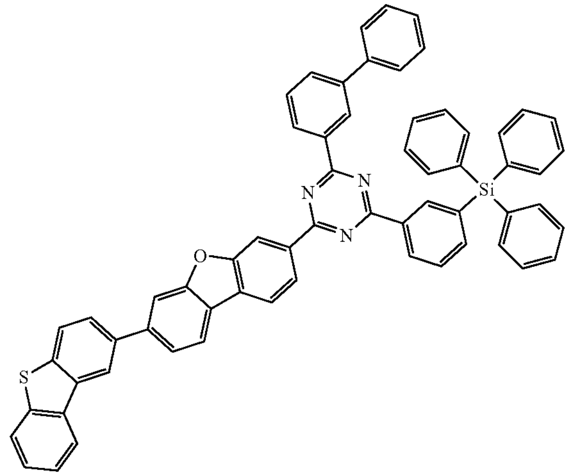
3-46
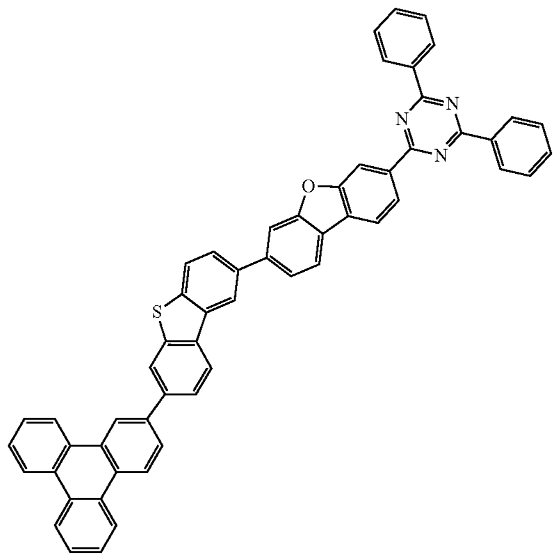
3-47
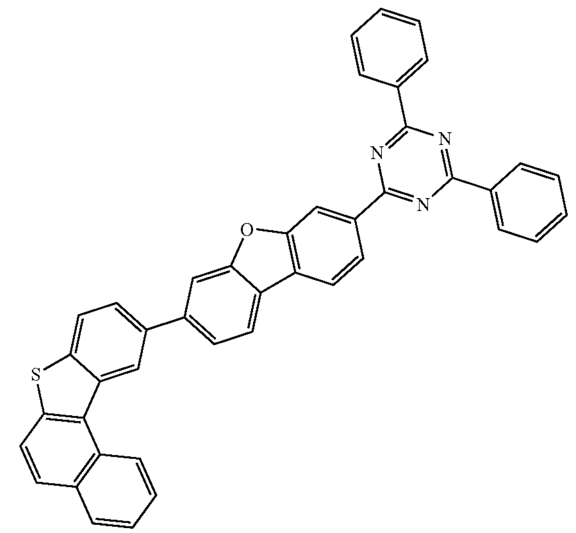
3-48
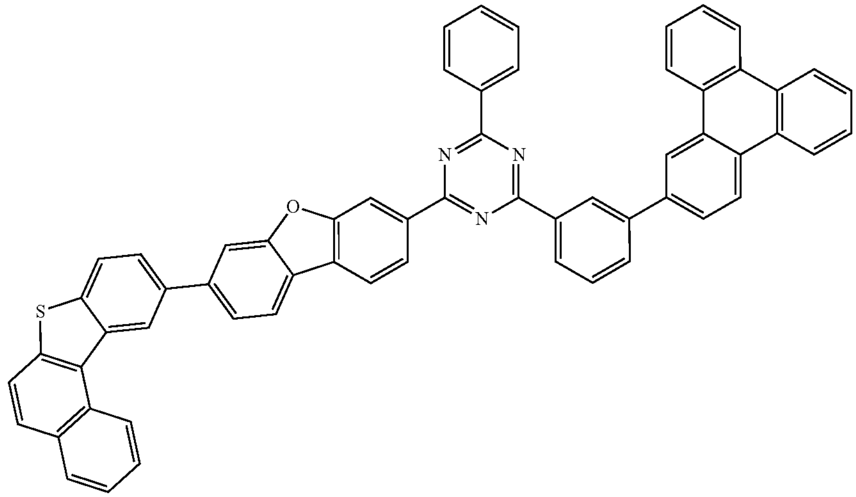

-continued
3-49
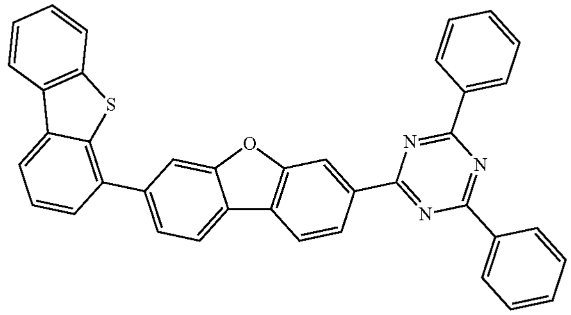
3-50
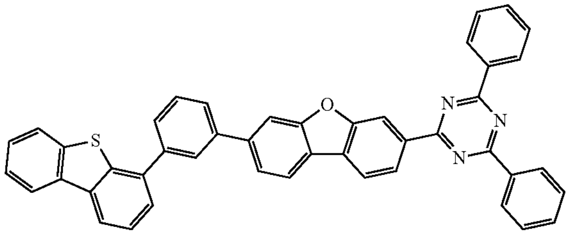
3-51
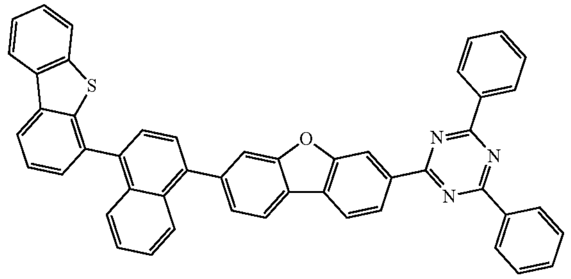
3-52
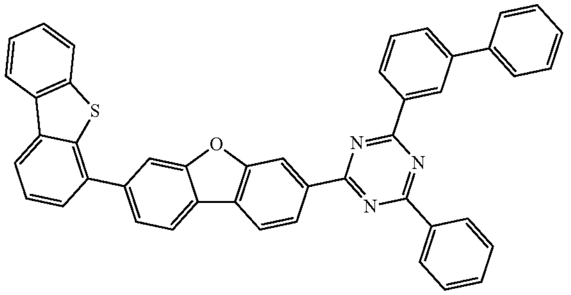
3-53
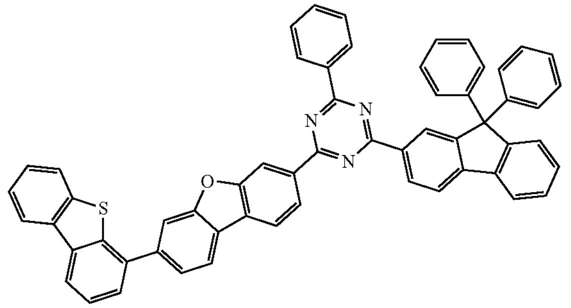
3-54
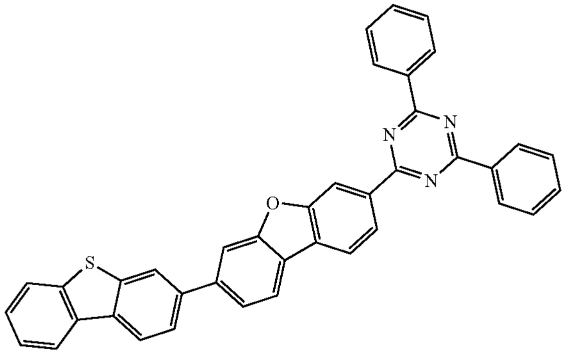
3-55
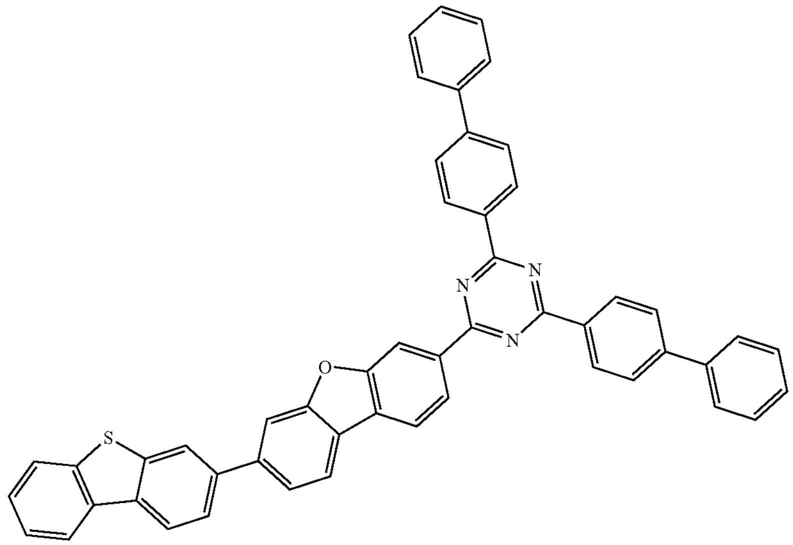

-continued
3-56
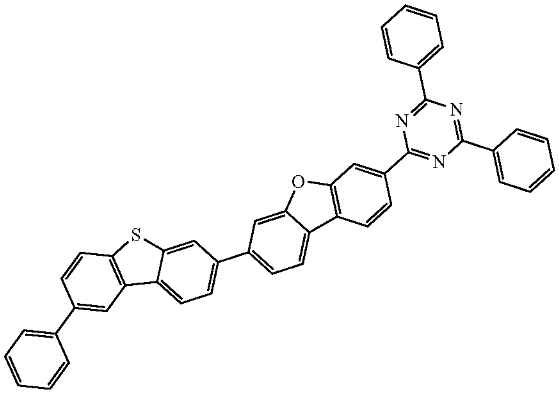
3-57
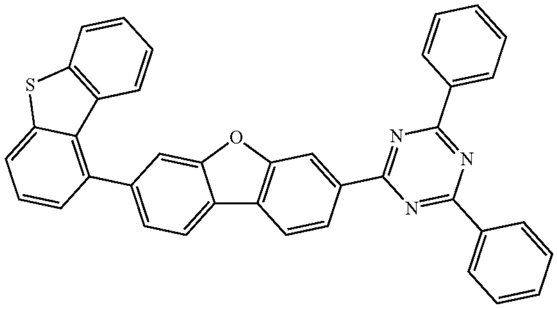
3-58
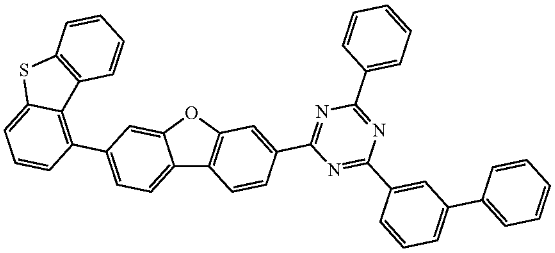
3-59
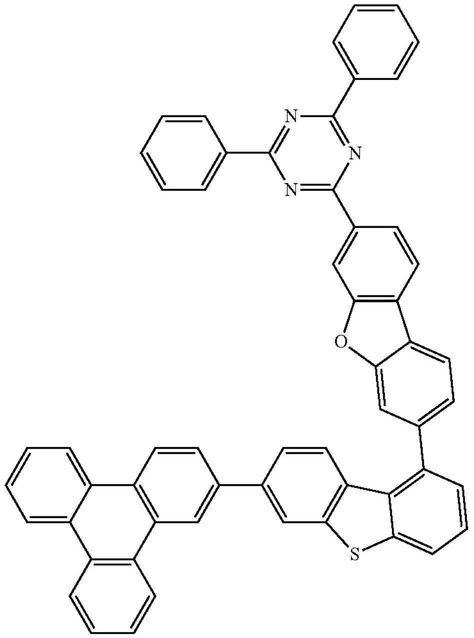
3-60
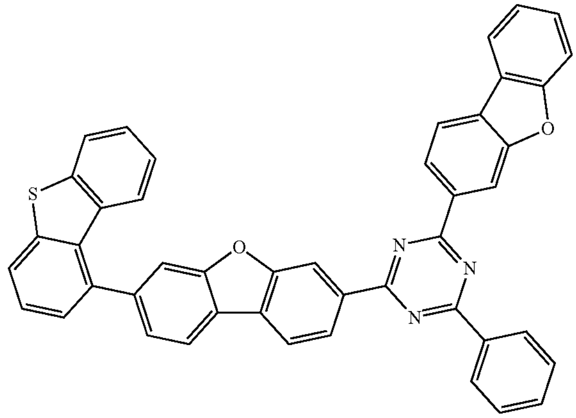
3-61
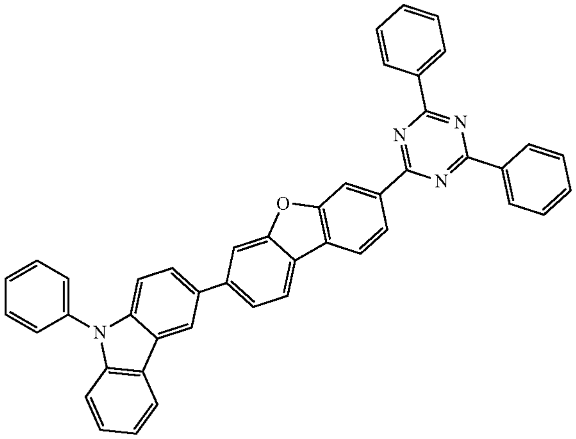

-continued
3-62
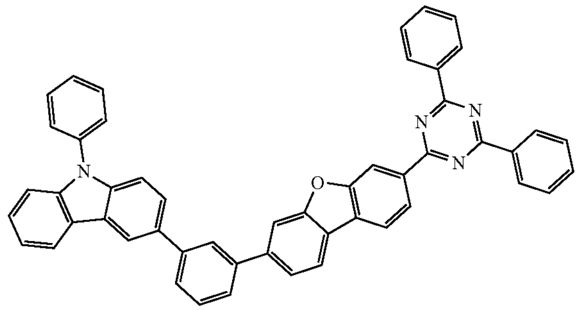
3-63
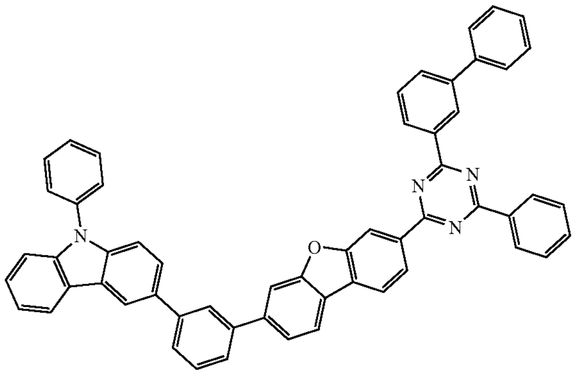
3-64
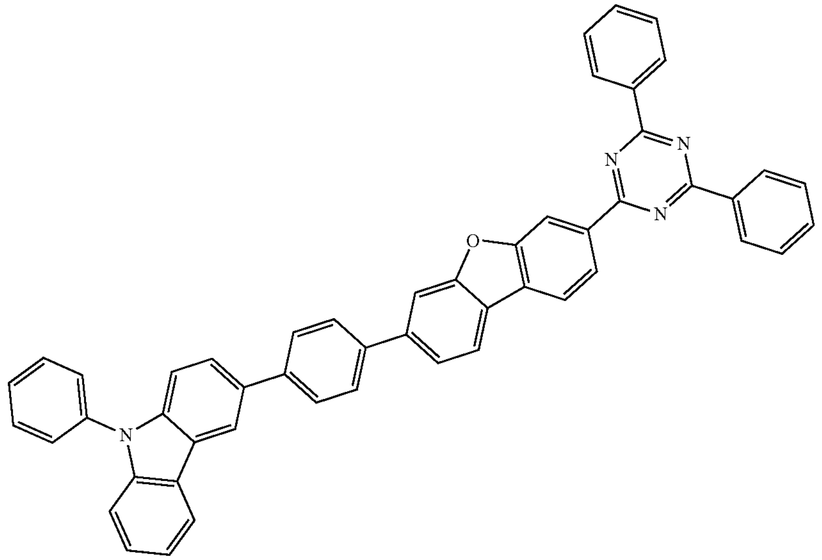
3-65
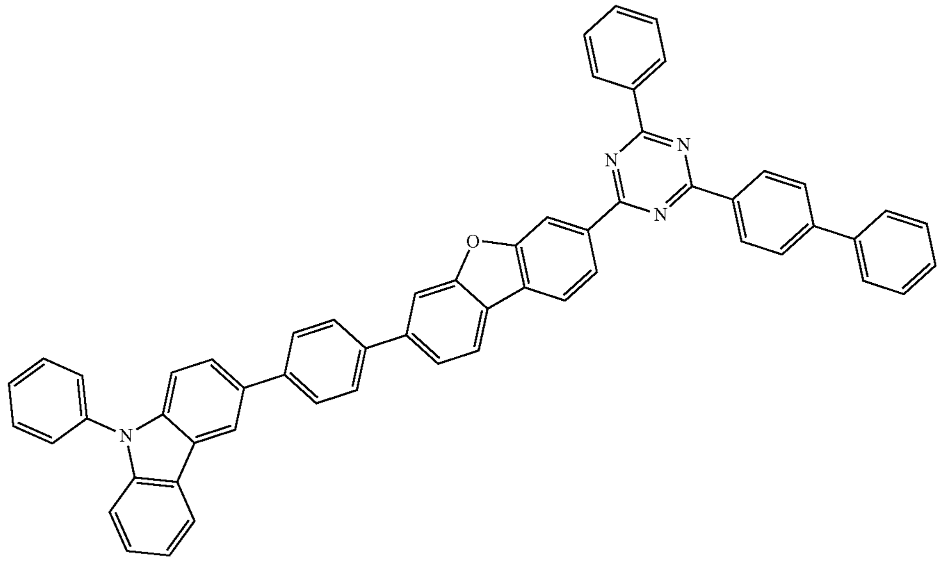

-continued
3-66
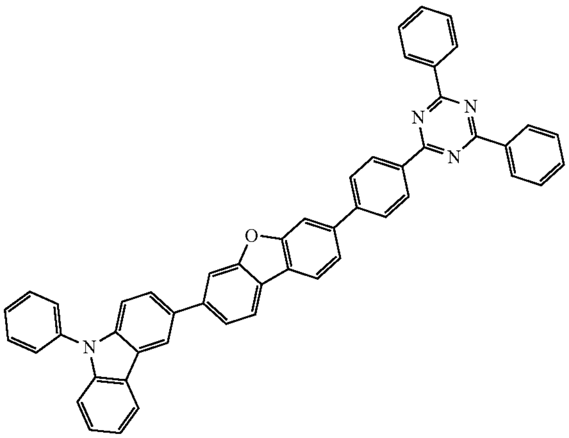
3-67
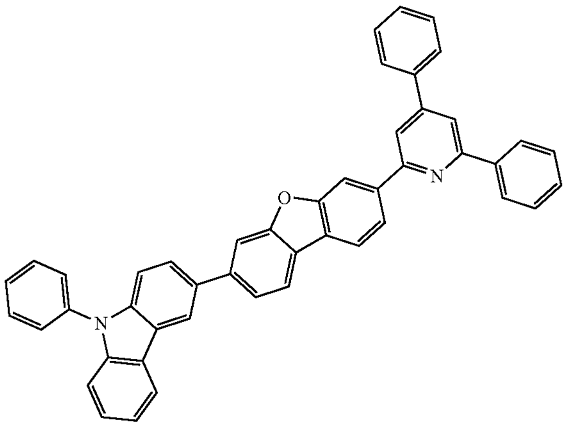
3-68
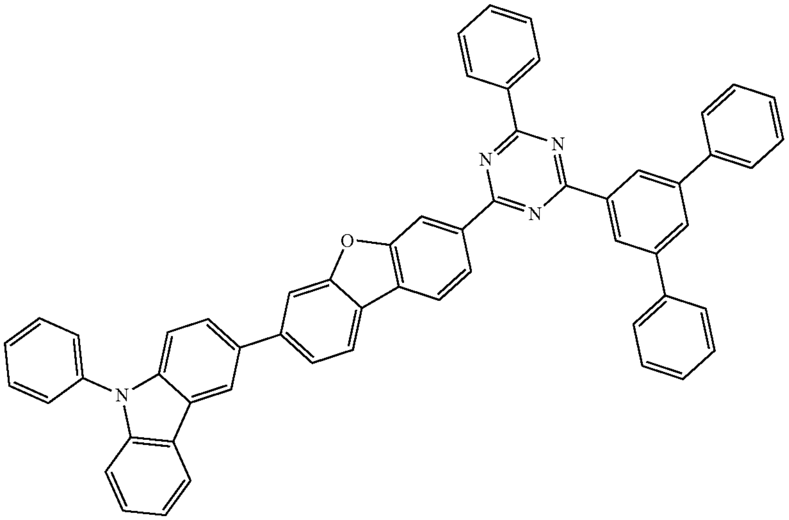
3-69
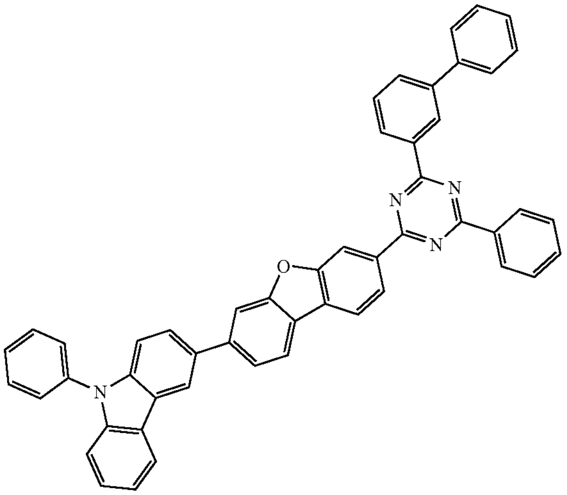
3-70
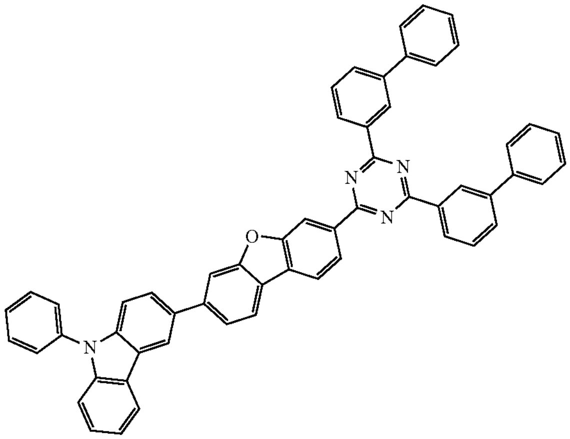

-continued
3-71
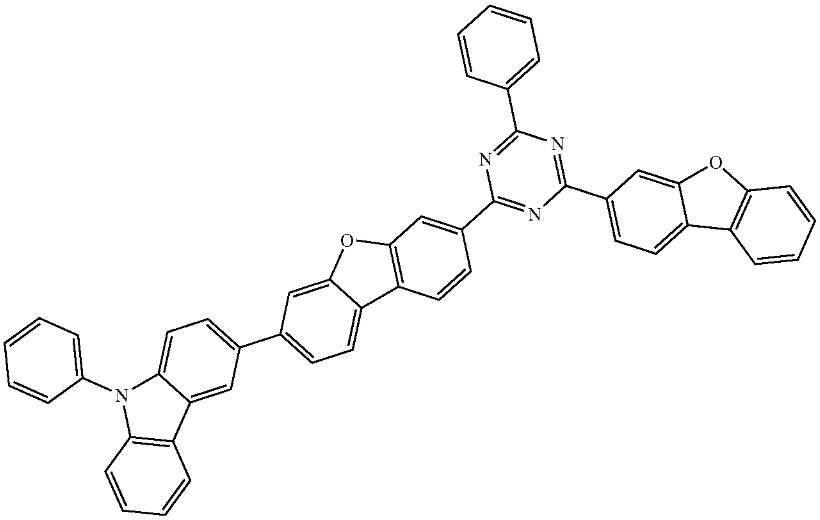
3-72
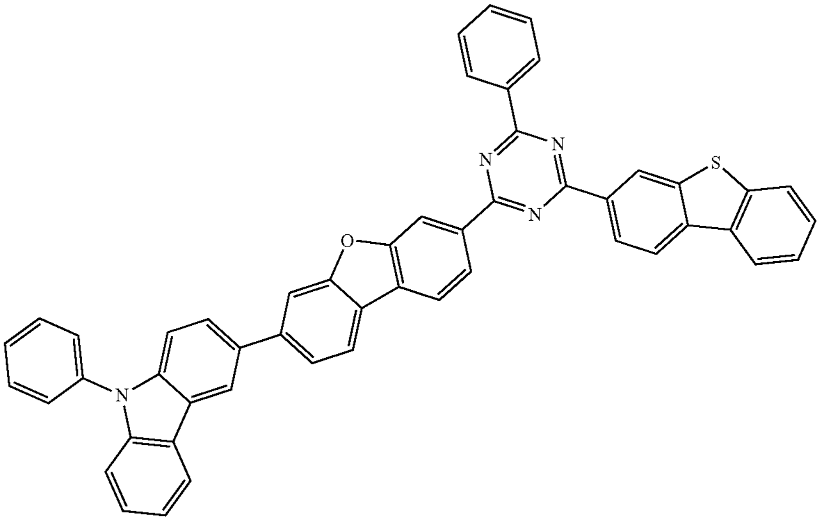
3-73
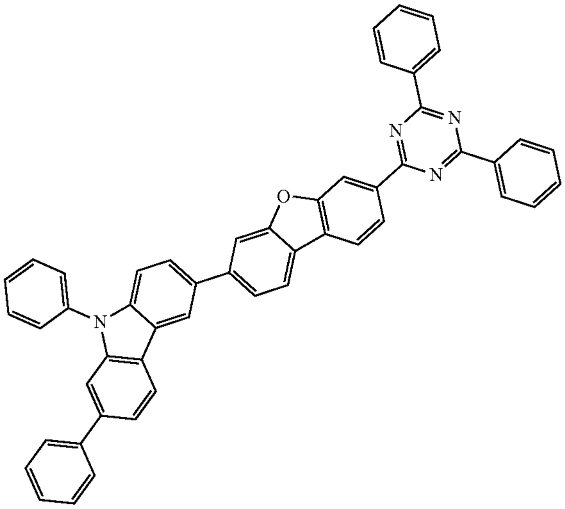
3-74
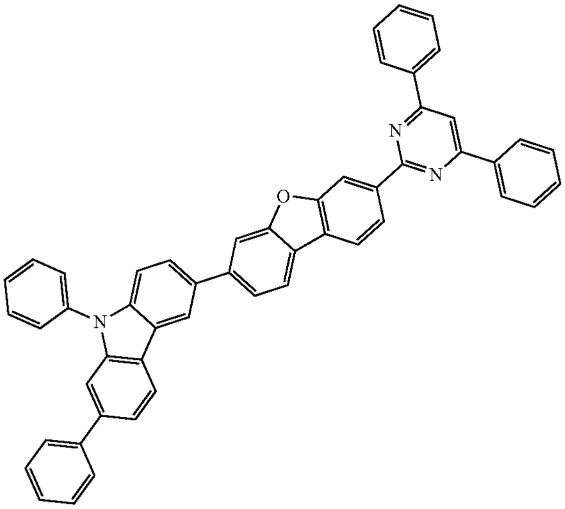

-continued
3-75
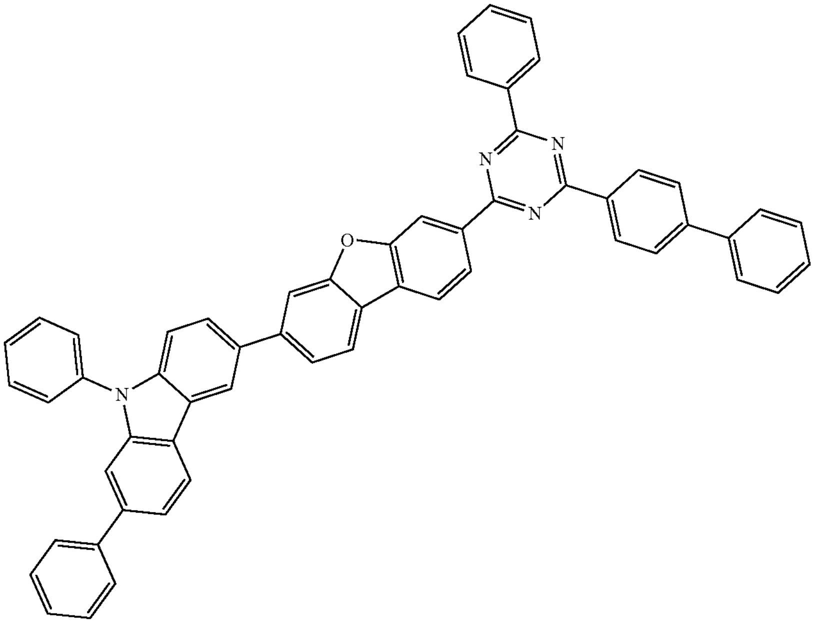
3-76
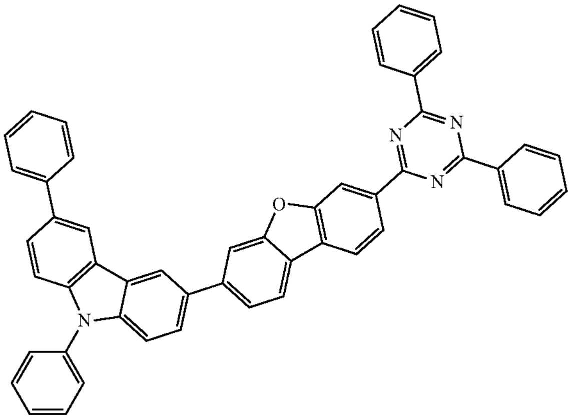
3-77
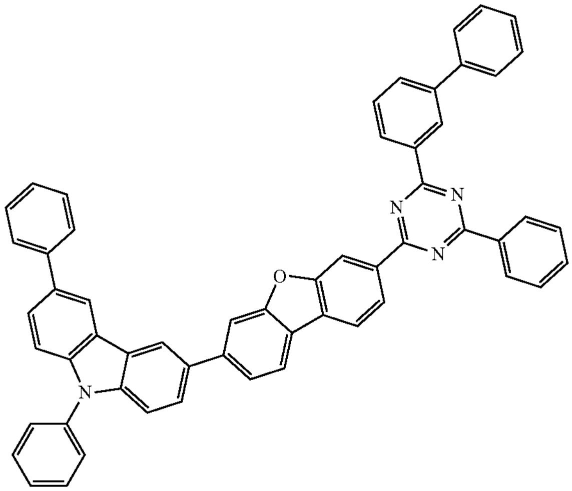
3-78
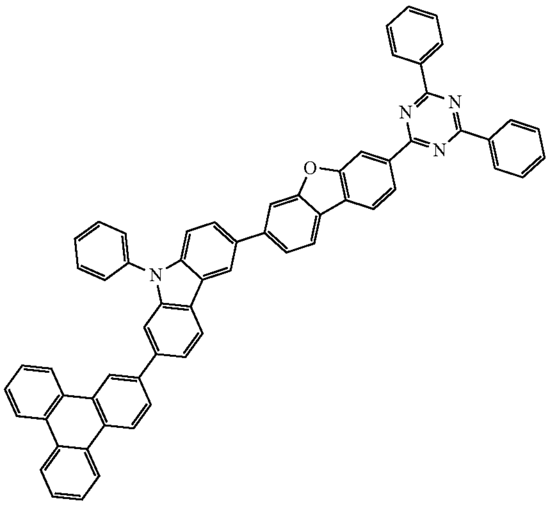
3-79
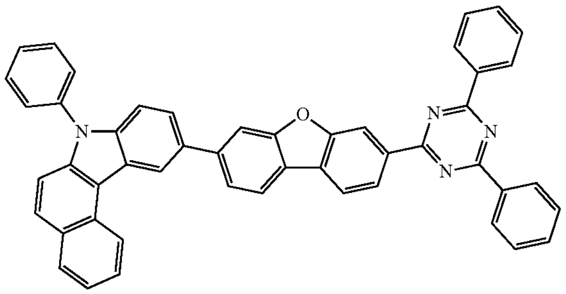

-continued
3-80
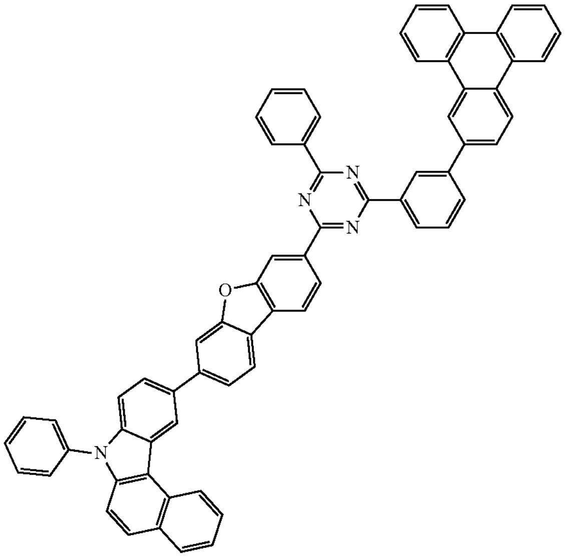
3-81
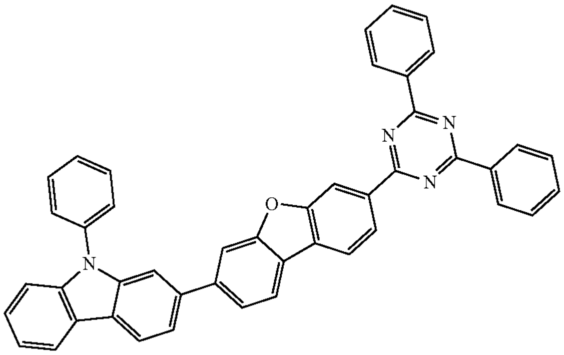
3-82
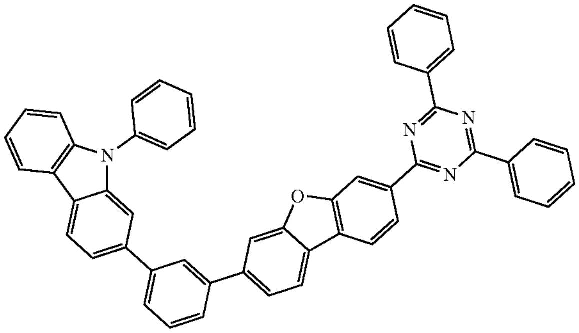
3-83
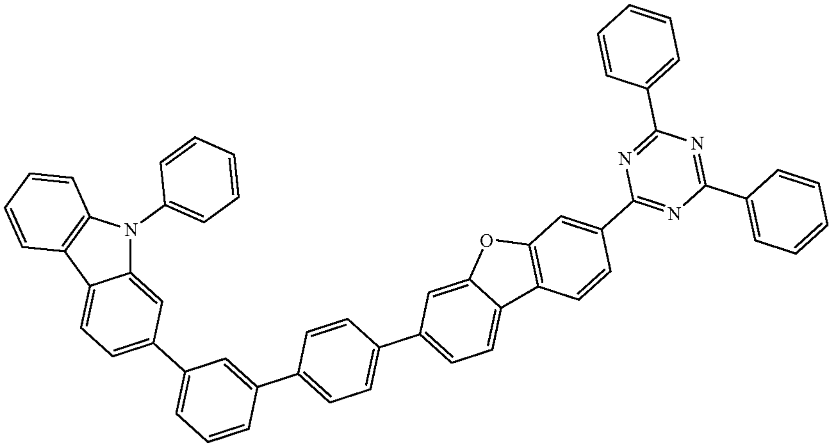

-continued
3-84
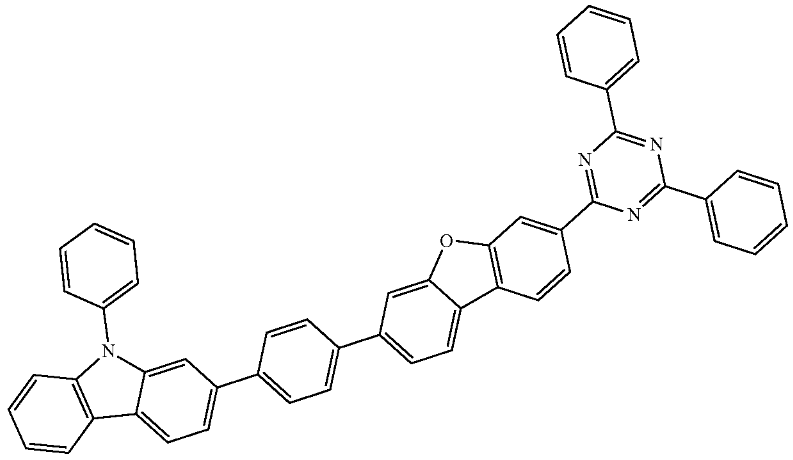
3-85
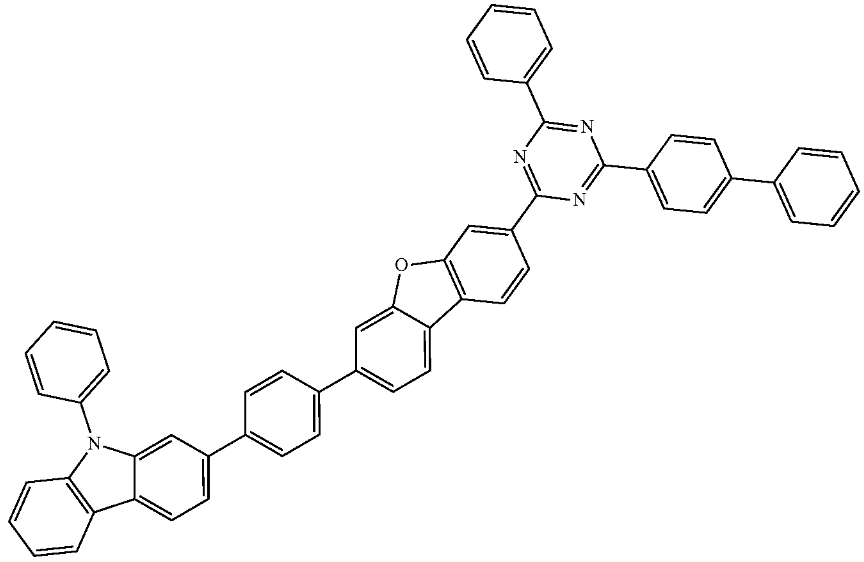
3-86
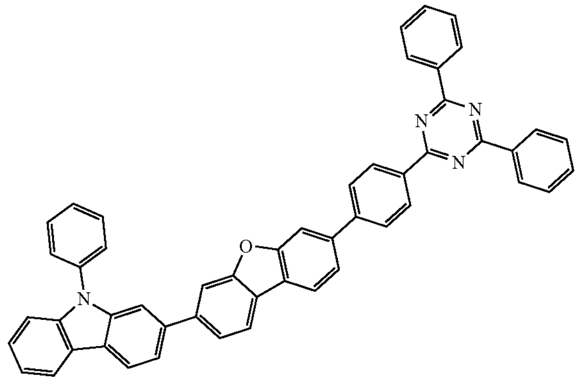
3-87
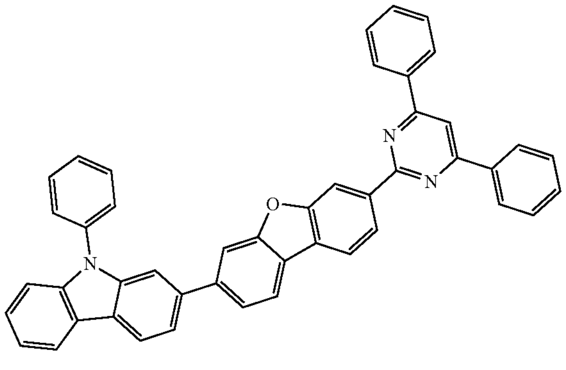

-continued
3-88
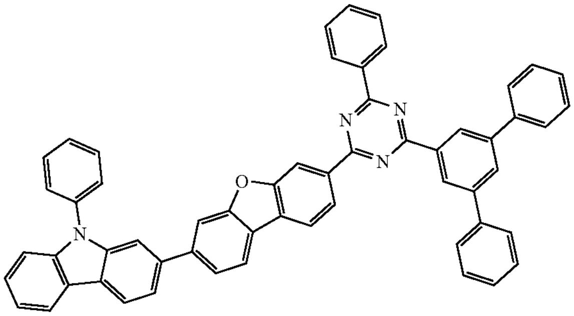
3-89
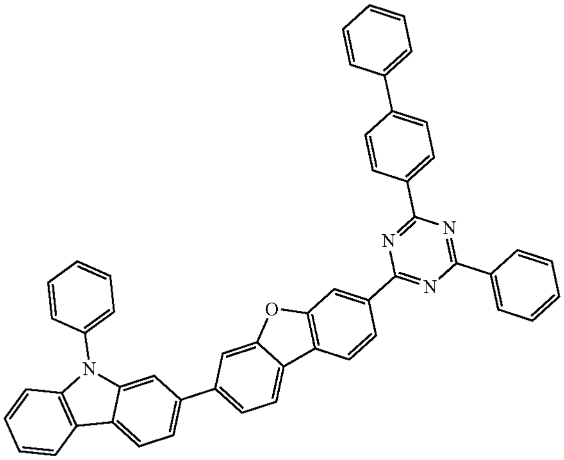
3-90
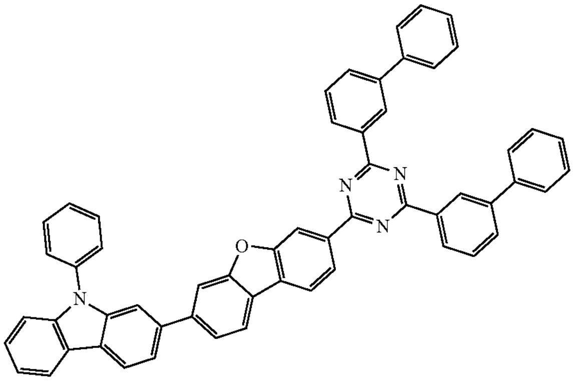
3-91
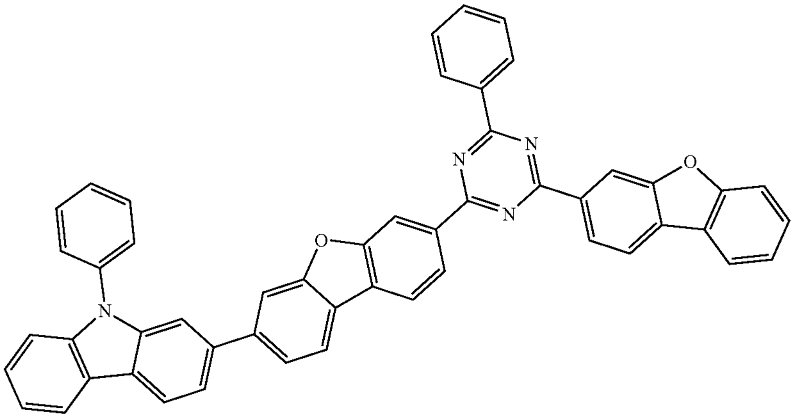
3-92
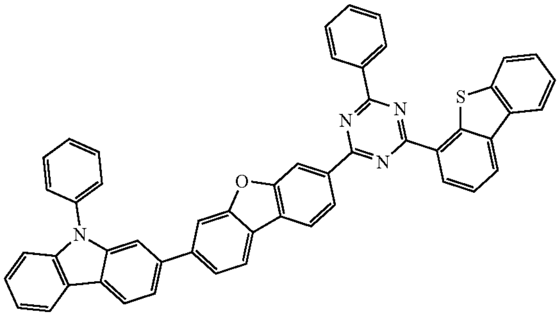

-continued
3-93
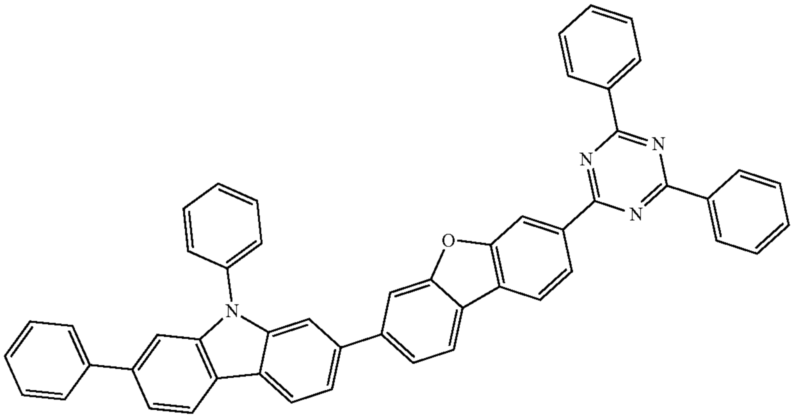
3-94
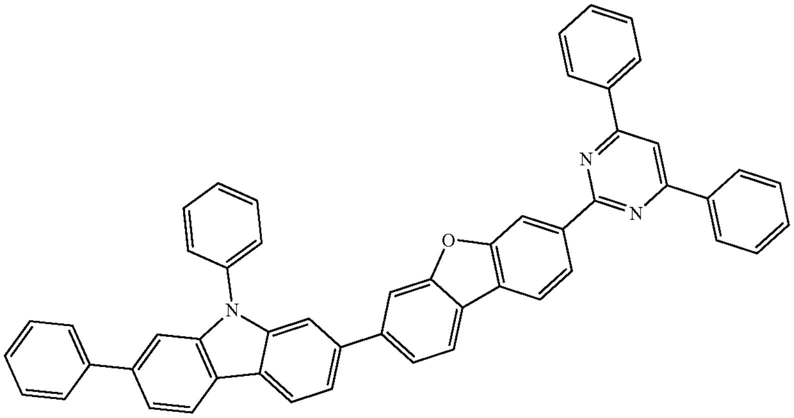
3-95
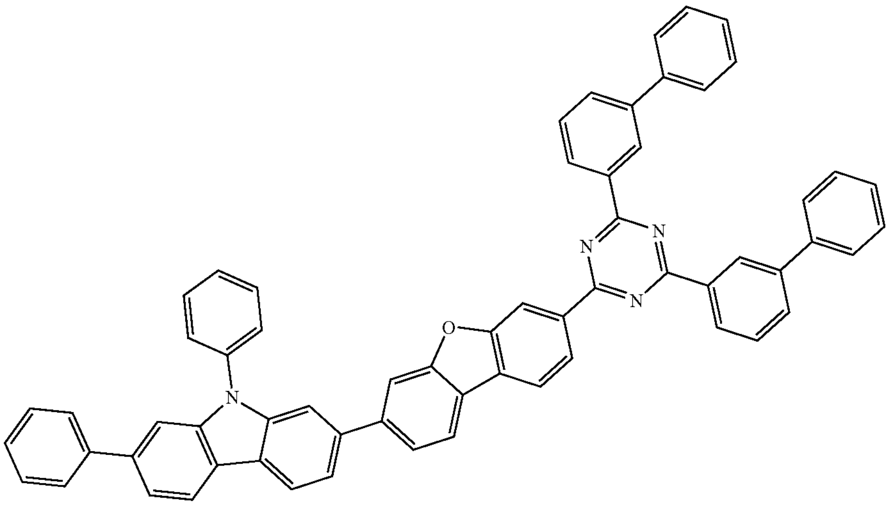

-continued
3-96
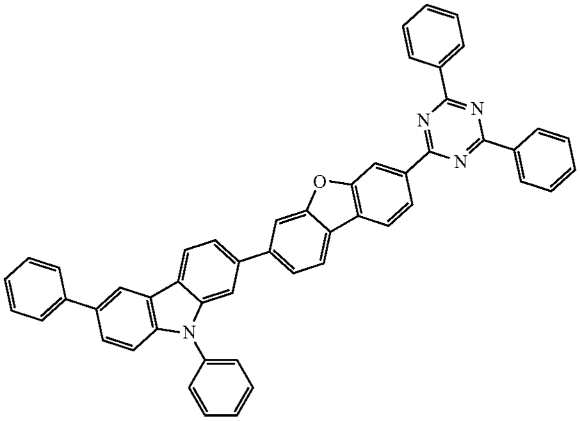
3-97
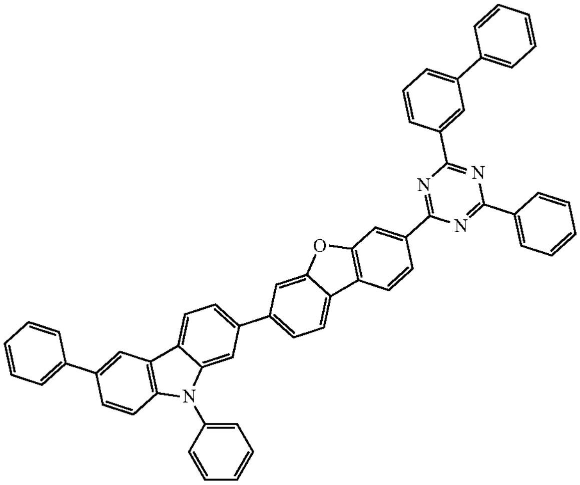
3-98
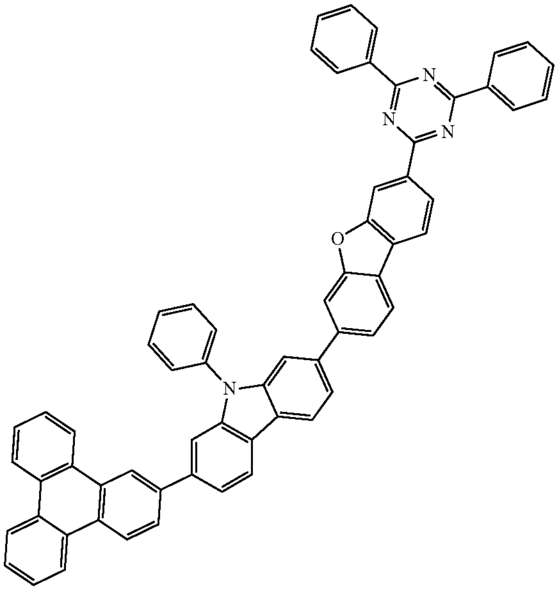
3-99
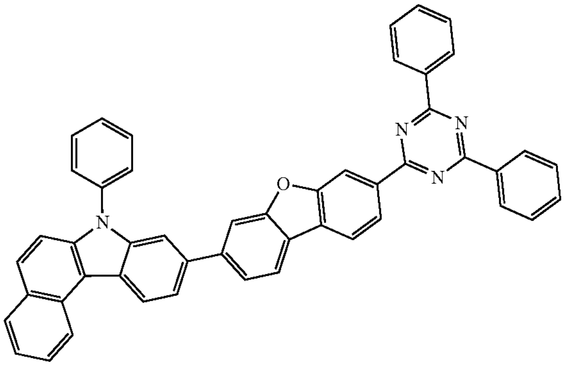

-continued
3-100
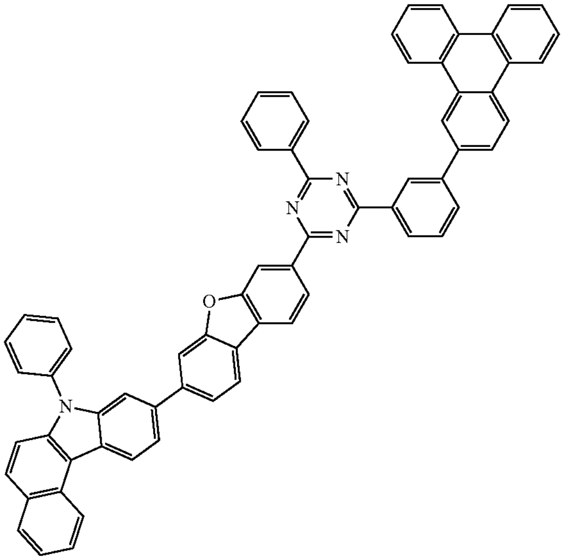
3-101
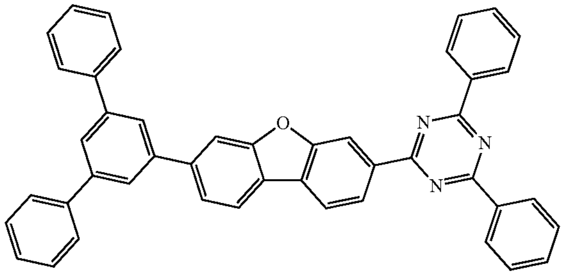
3-102
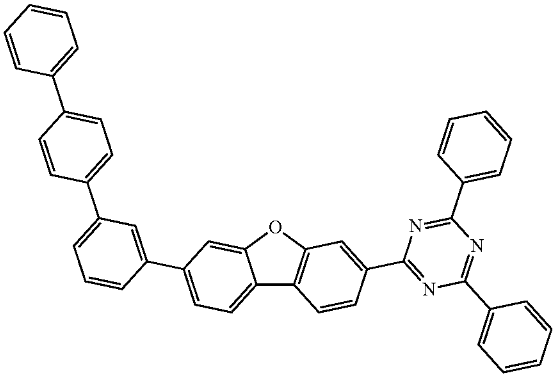
3-103
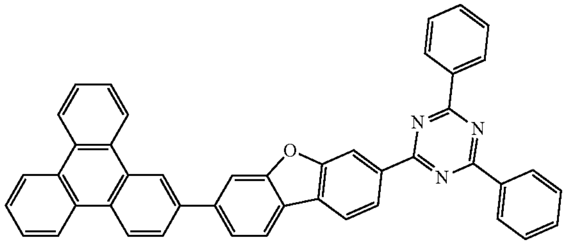
3-104
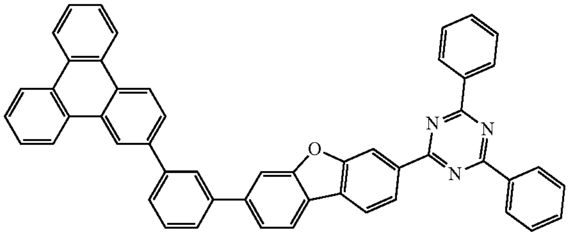

4-1
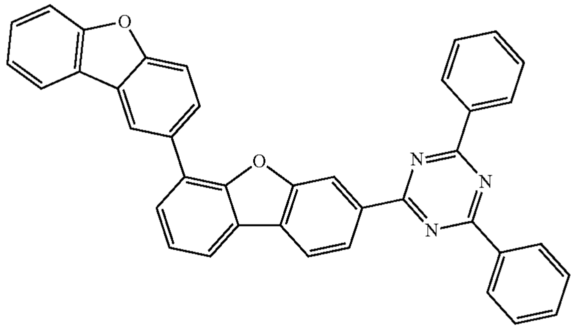
4-2
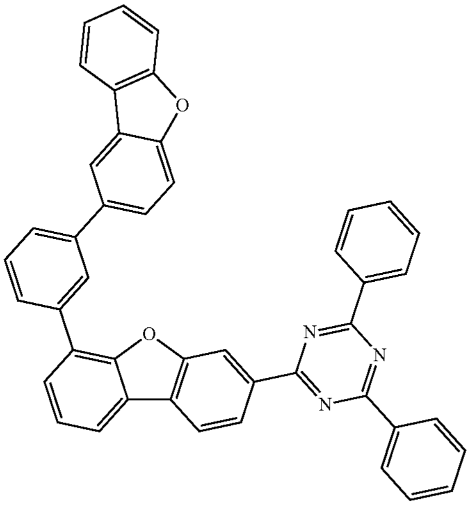
4-3
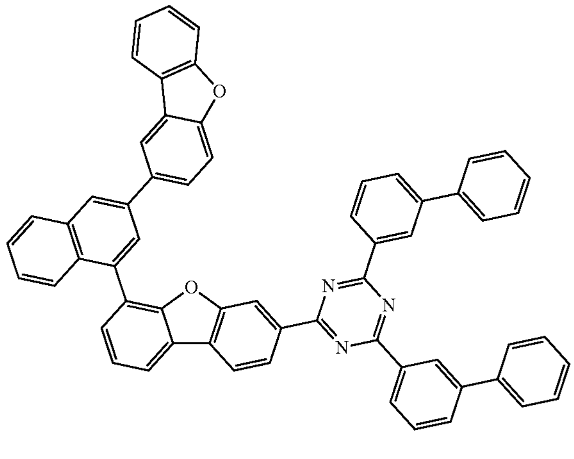
-continued
4-4
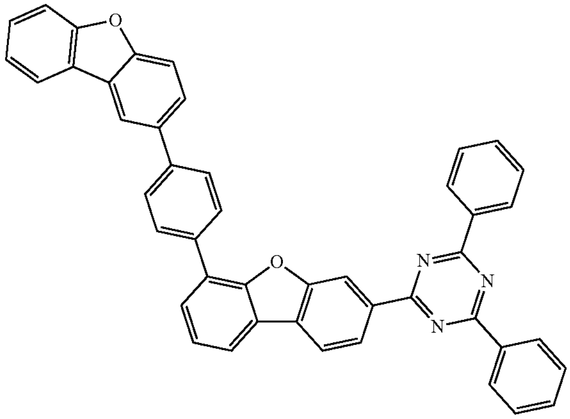
4-5
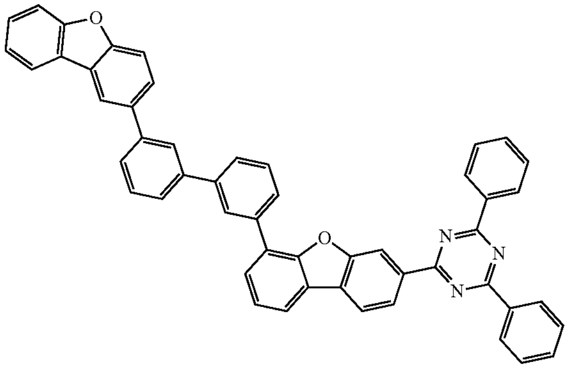
4-6
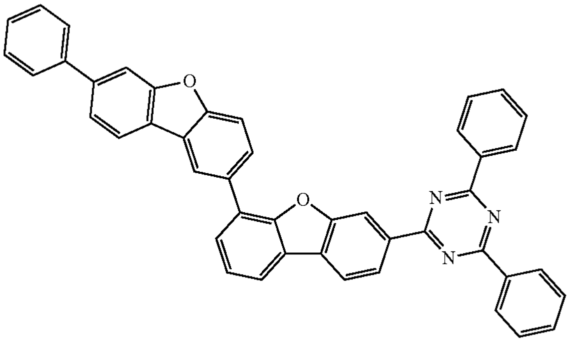
4-7
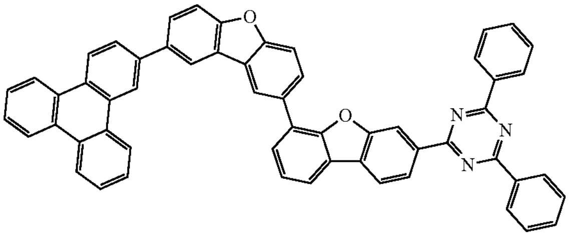

-continued
4-8
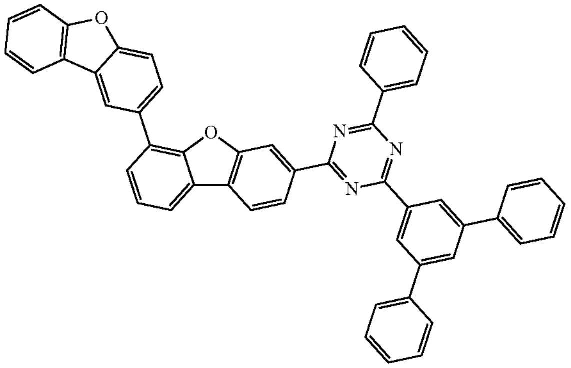
4-9
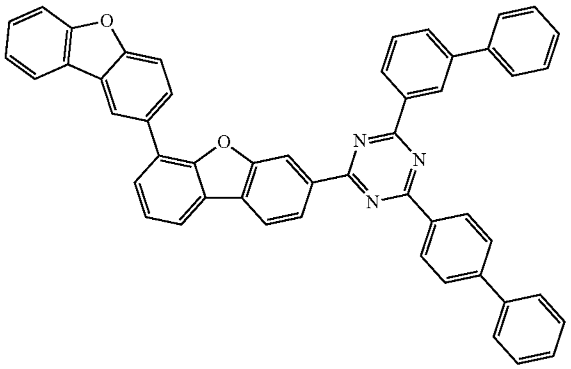
4-10
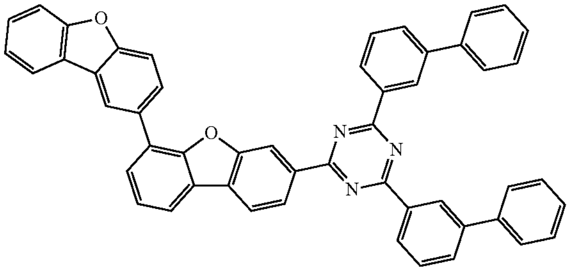
4-11
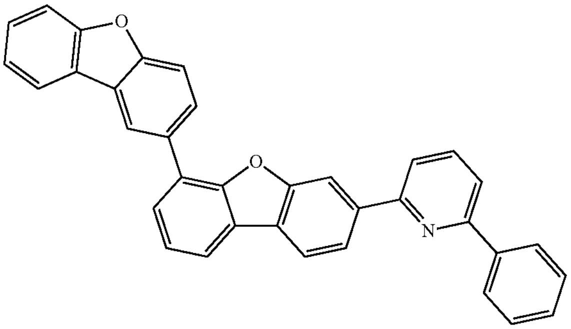
-continued
4-12
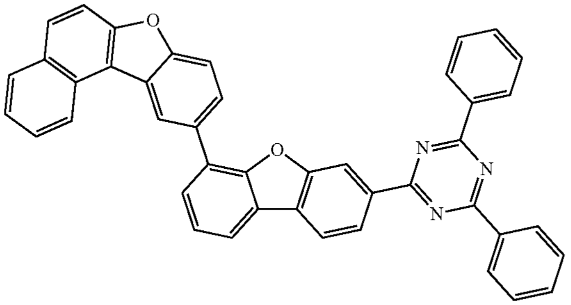
4-13
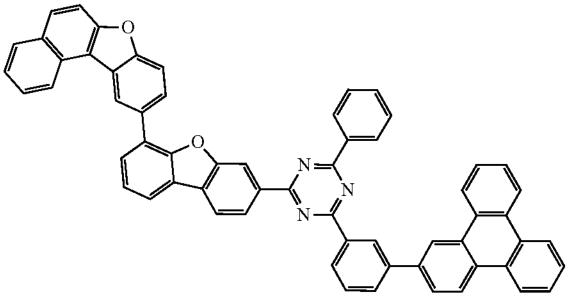
4-14
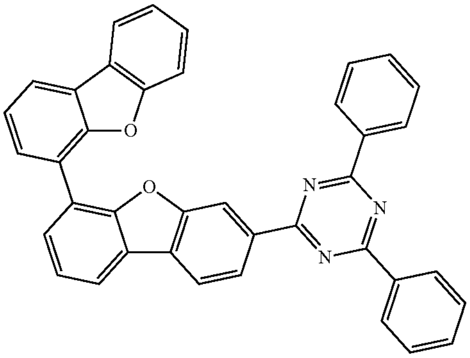
4-15
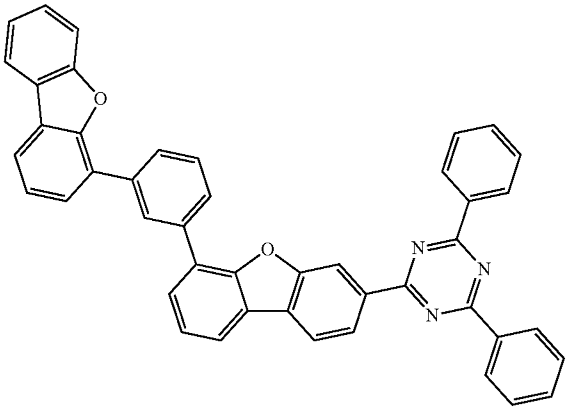

-continued
4-16
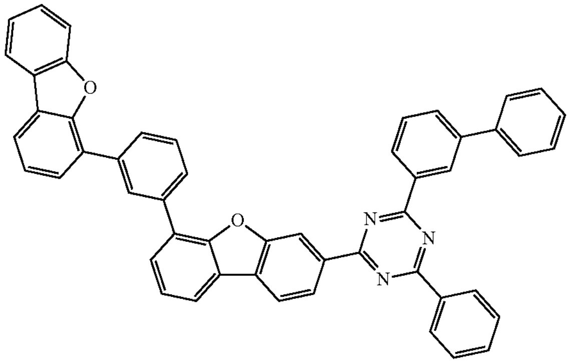
4-17
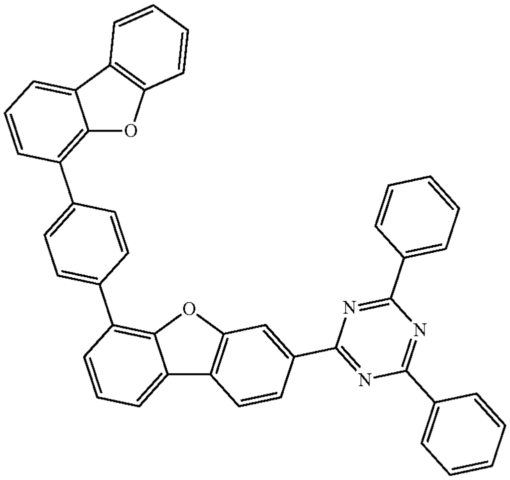
4-18
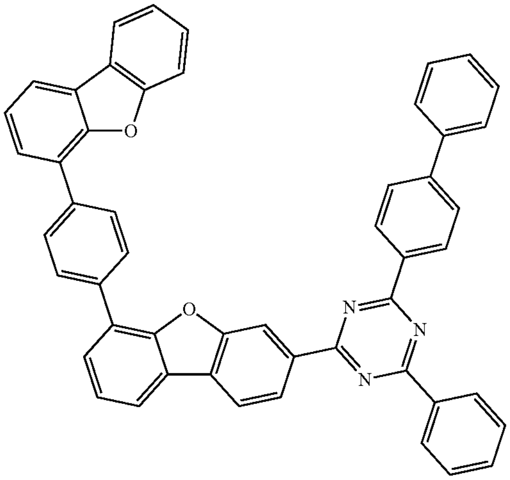
-continued
4-19
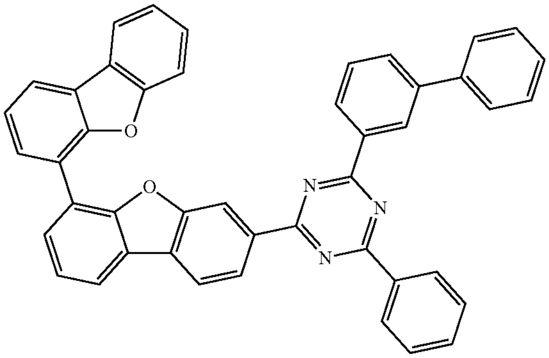
4-20
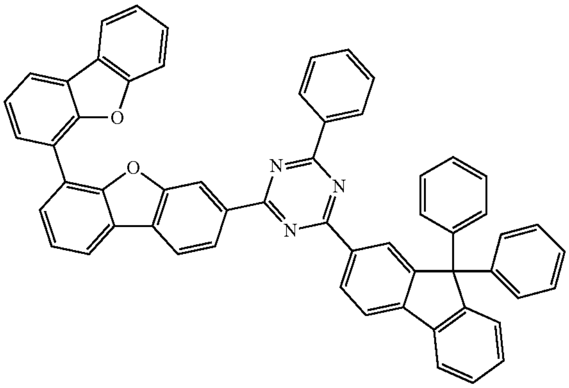
4-21
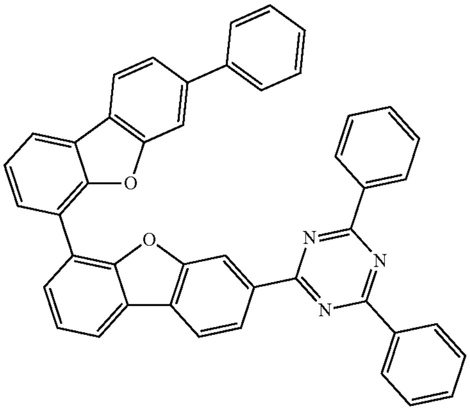

-continued
4-22
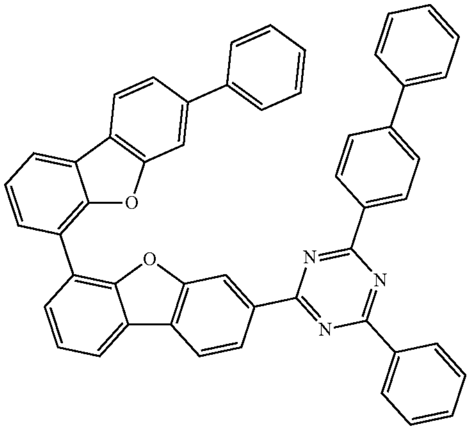
4-23
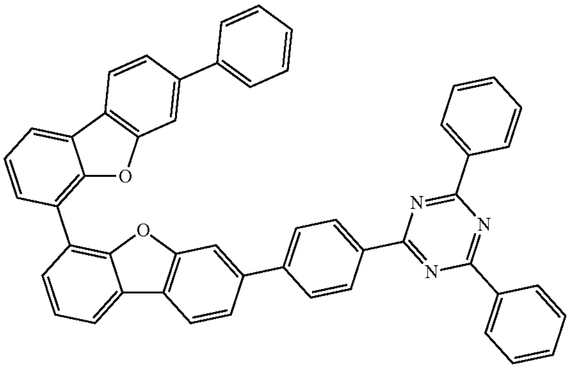
4-24
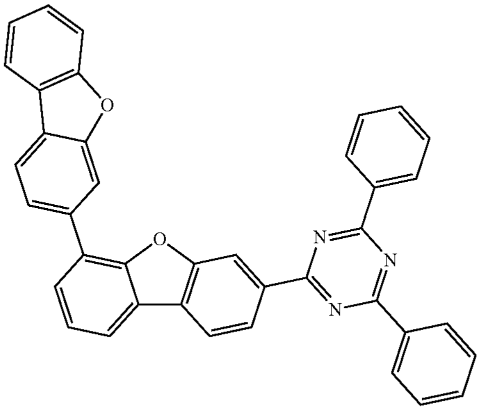
-continued
4-25
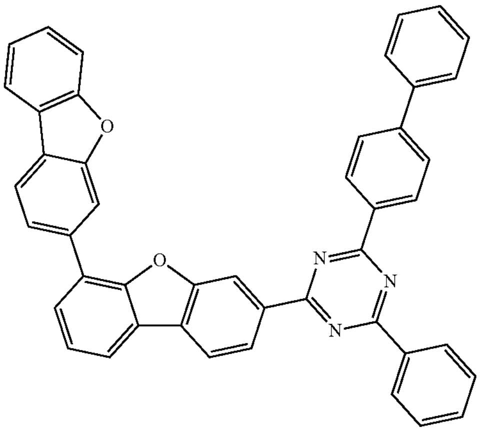
4-26
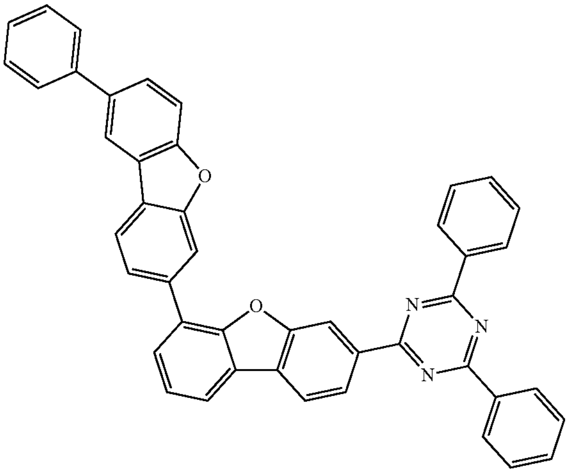
4-27
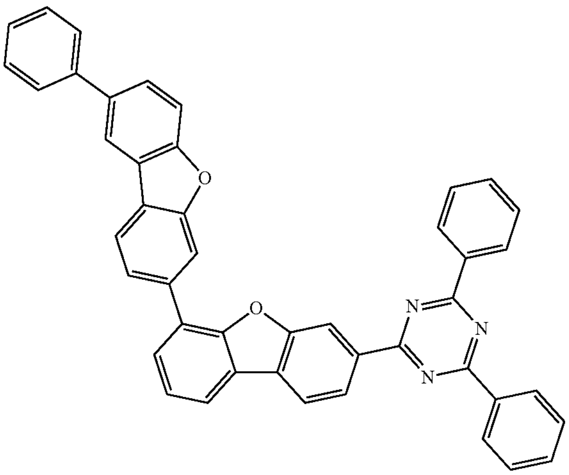

-continued
4-28
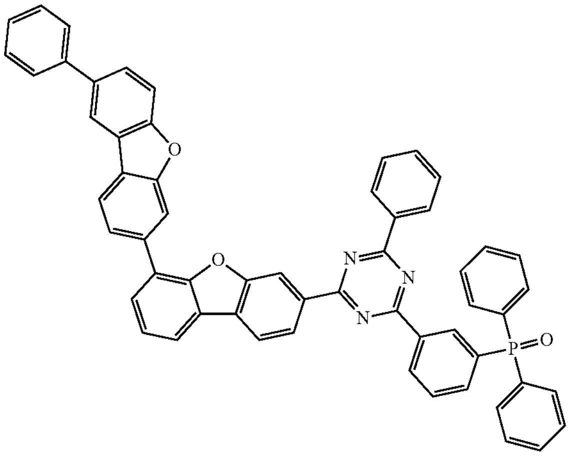
4-29
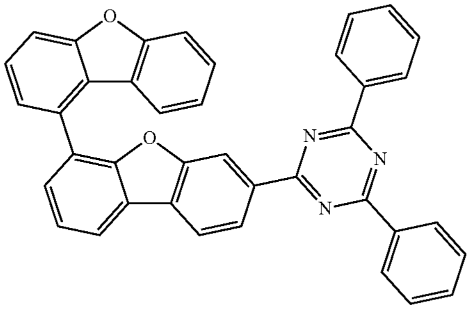
4-30
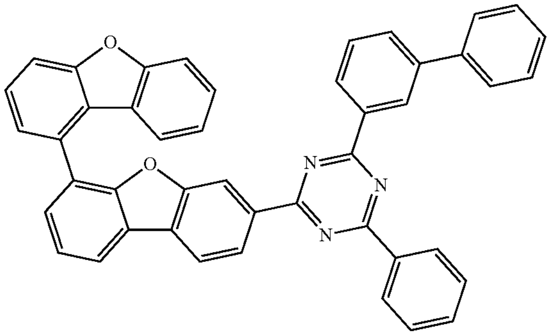
4-31
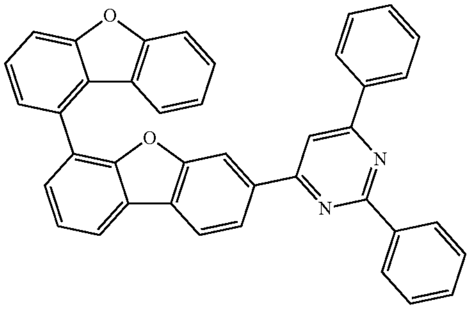
-continued
4-32
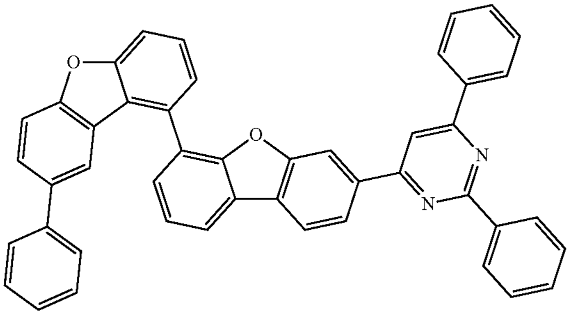
4-33
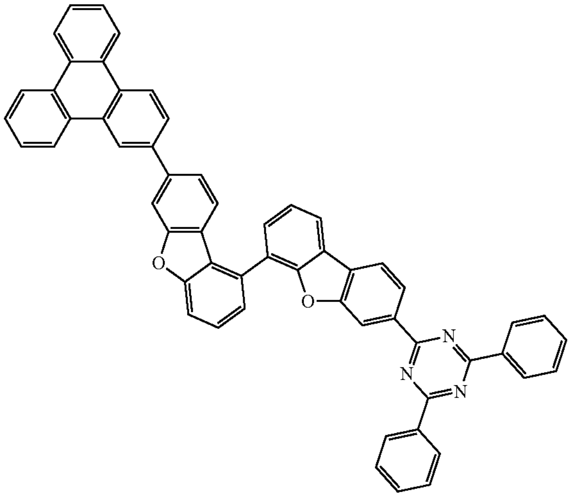
4-34
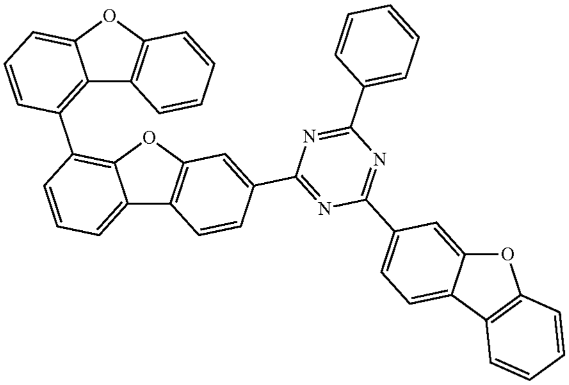

-continued
4-35
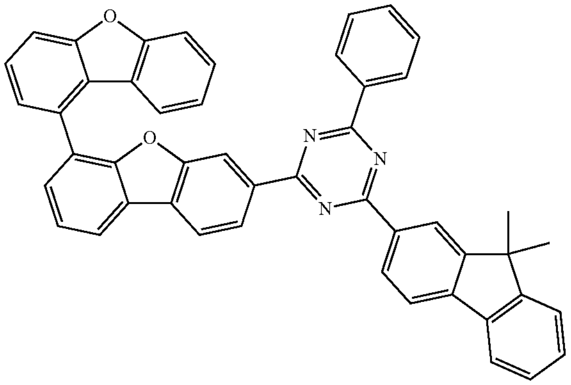
4-36
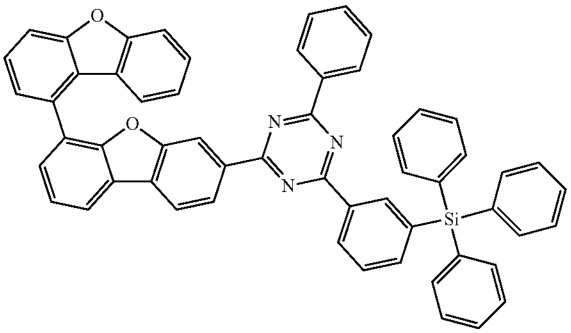
4-37
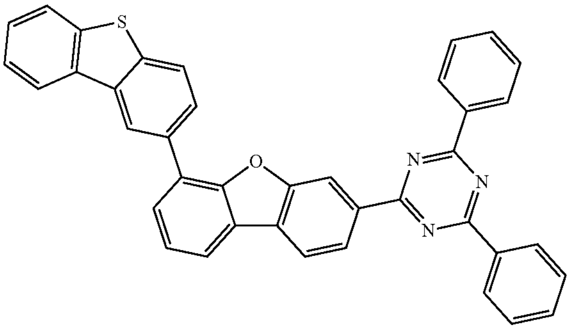
4-38
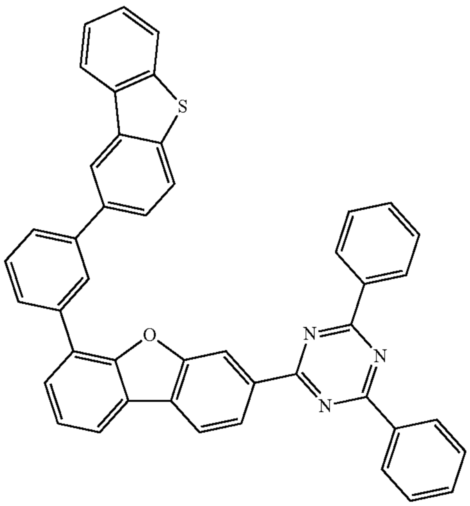
-continued
4-39
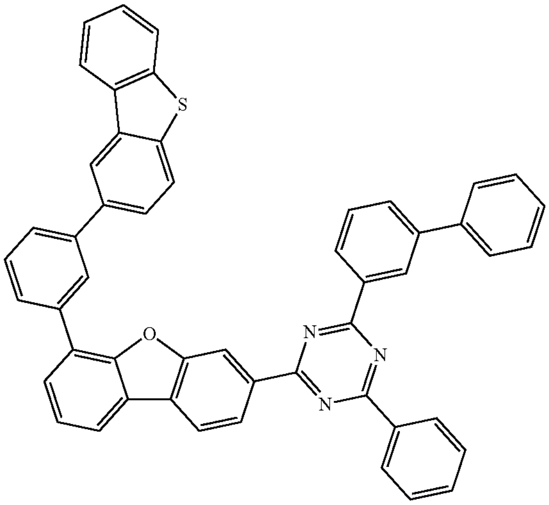
4-40
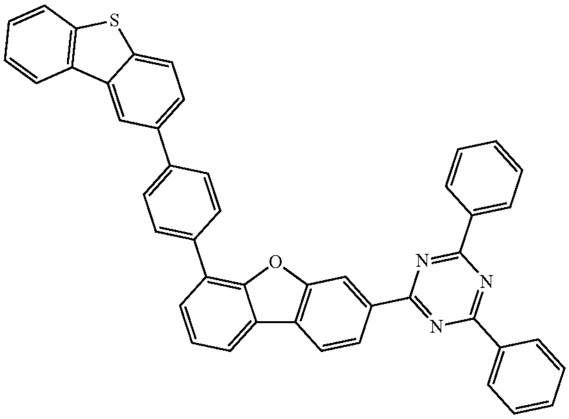
4-41
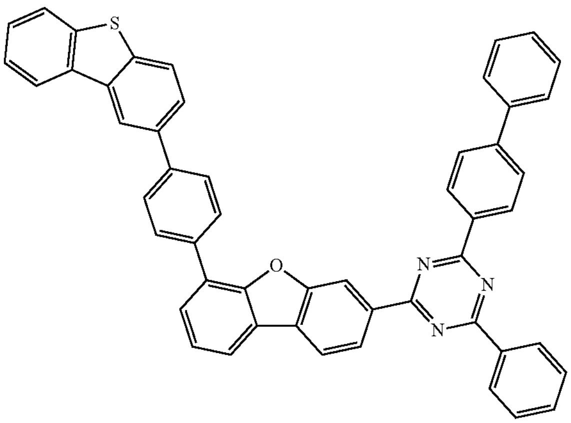

-continued
4-42
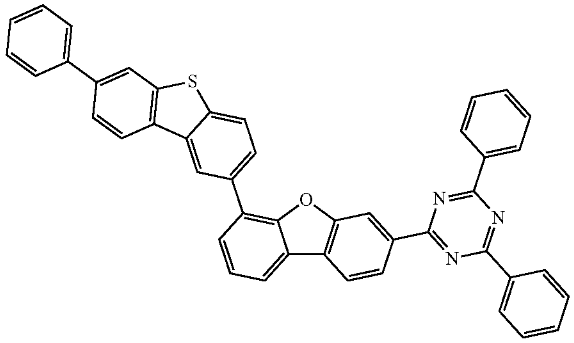
4-43
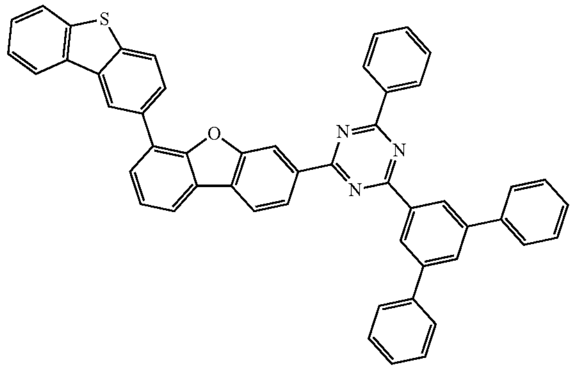
4-44
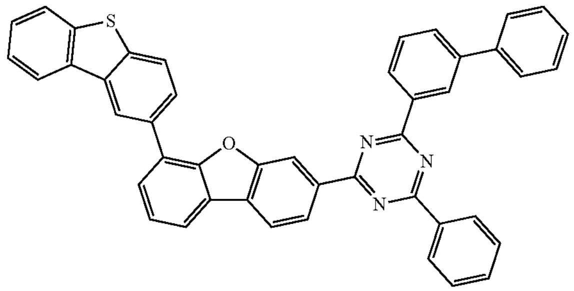
4-45
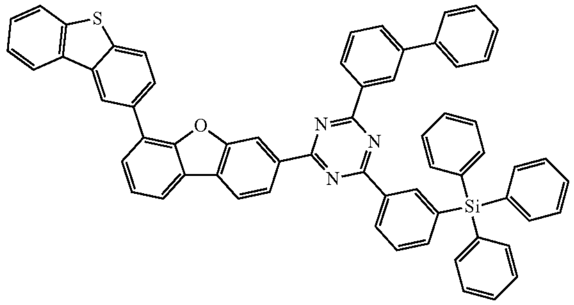
-continued
4-46
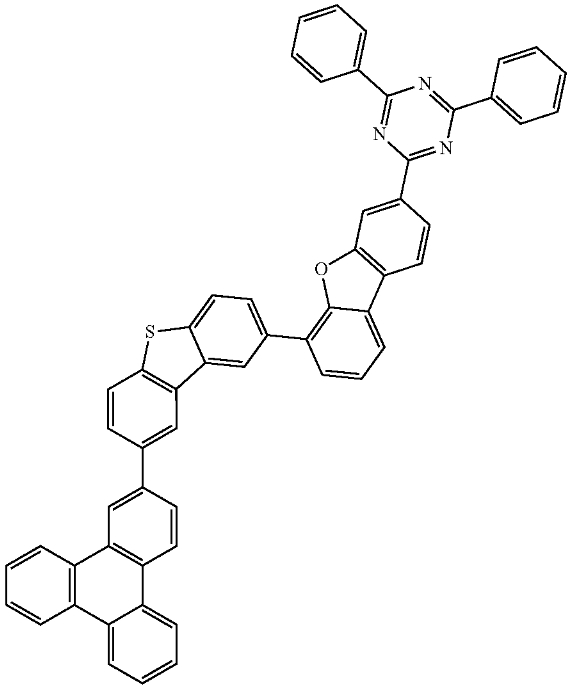
4-47
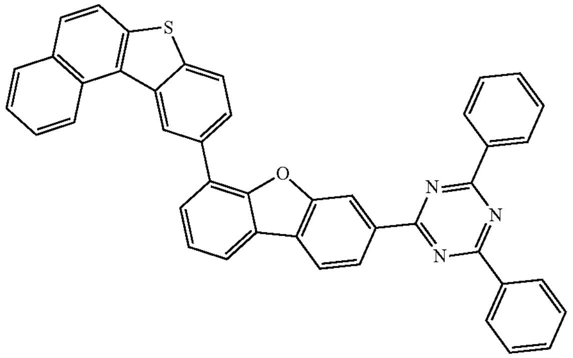
4-48
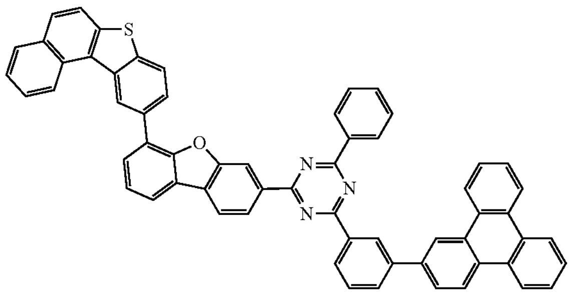

-continued
4-49
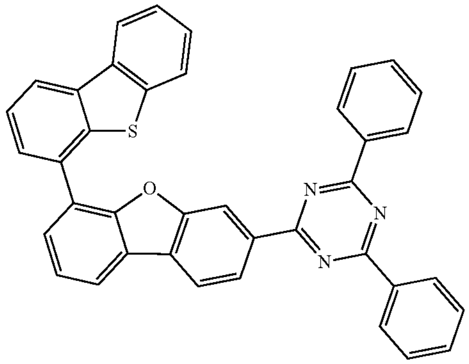
4-50
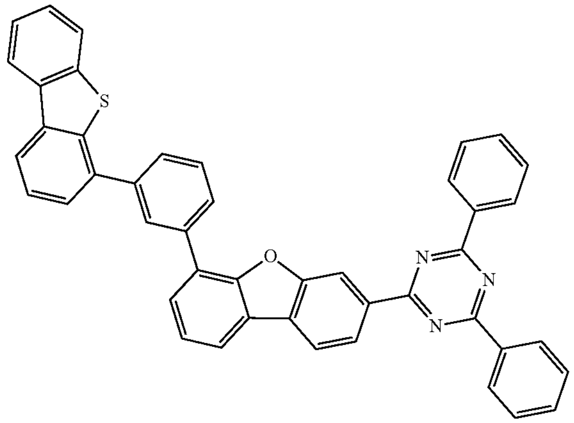
4-51
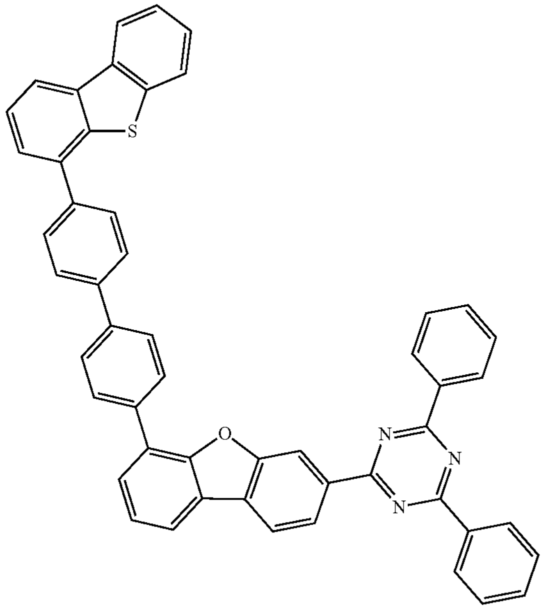
-continued
4-52
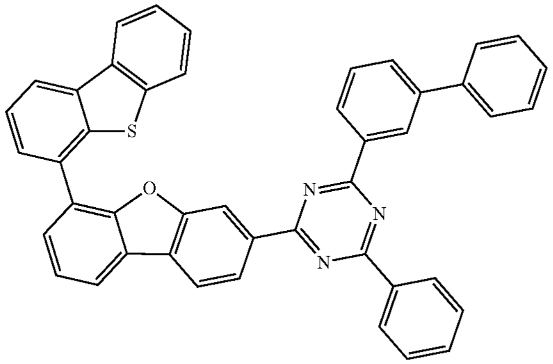
4-53
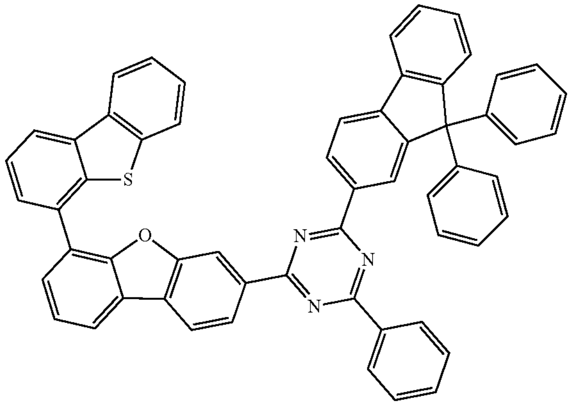
4-54
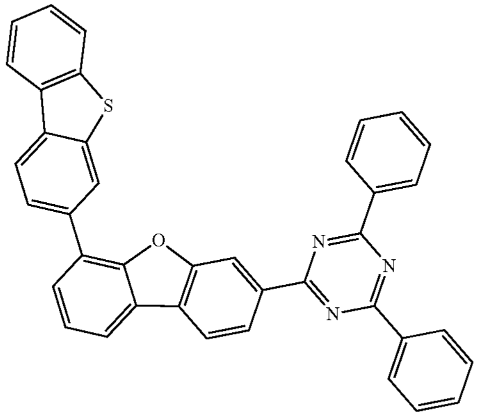

-continued
4-55
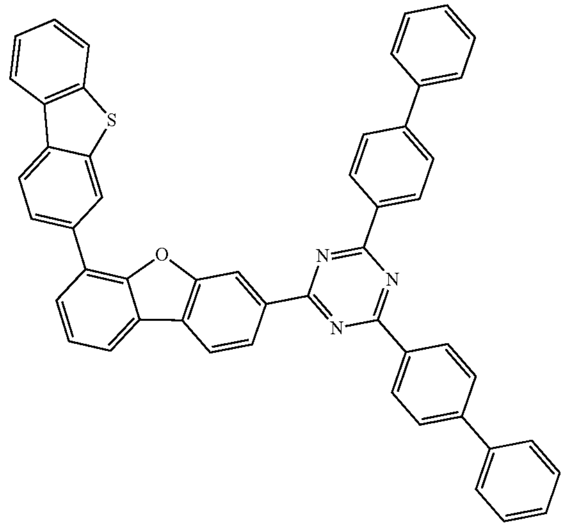
4-56
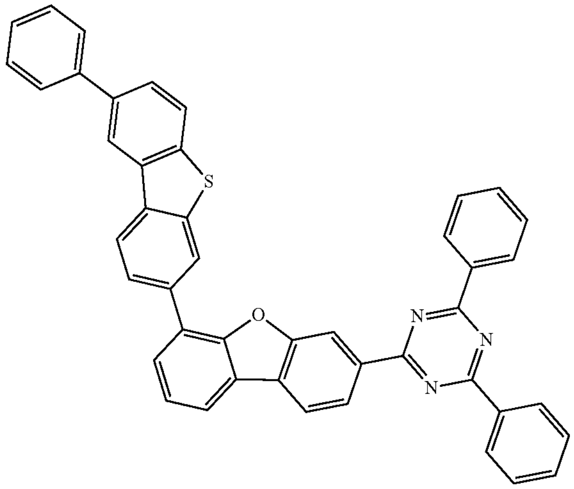
4-57
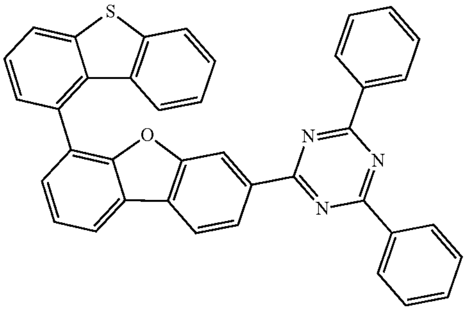
-continued
4-58
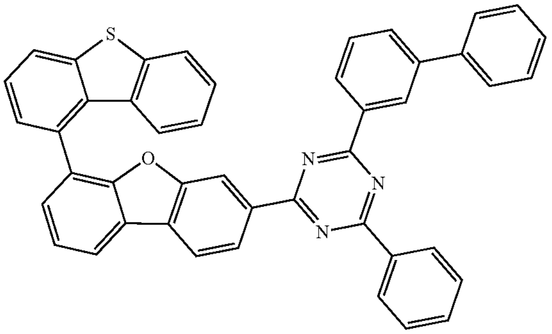
4-59
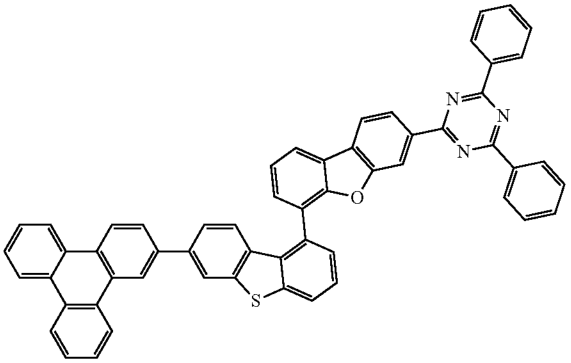
4-60
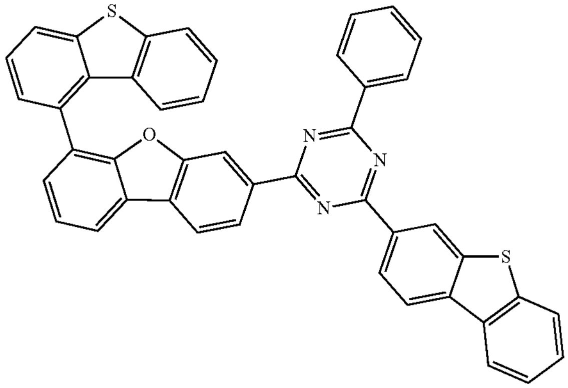
4-61
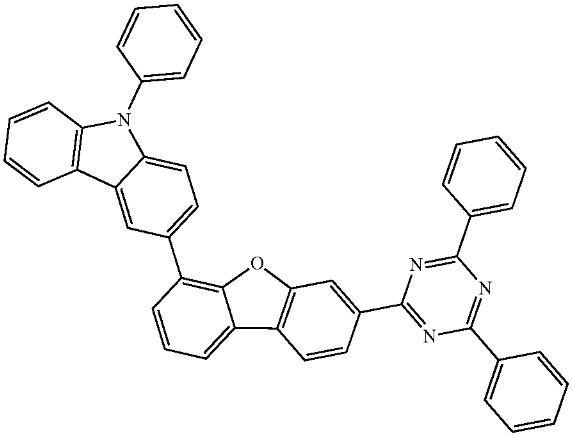

4-62
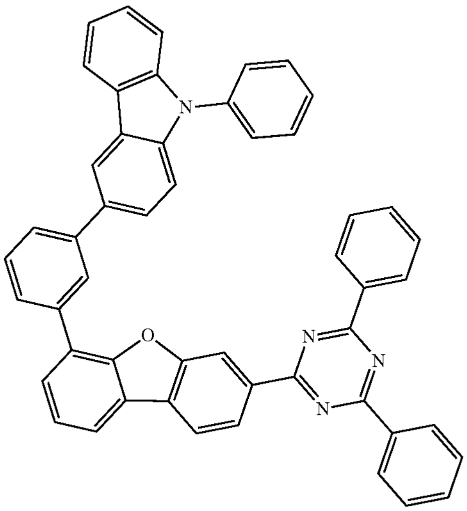
4-63
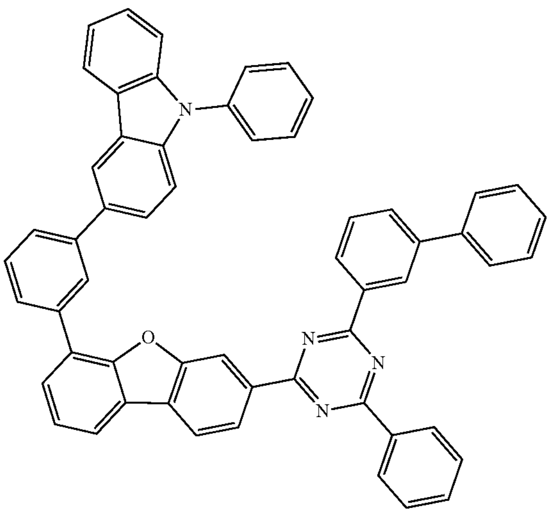
4-64
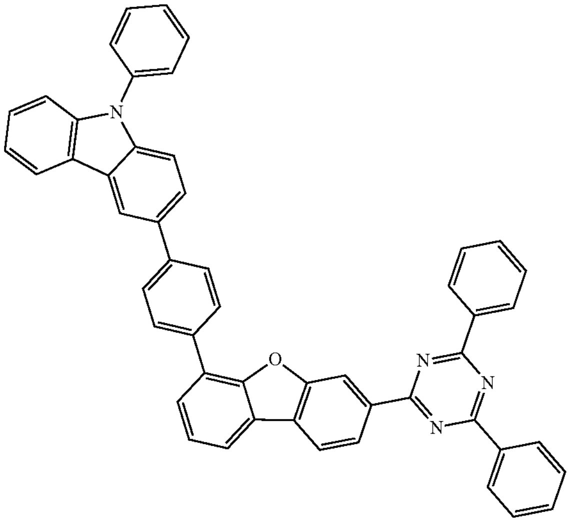
4-65
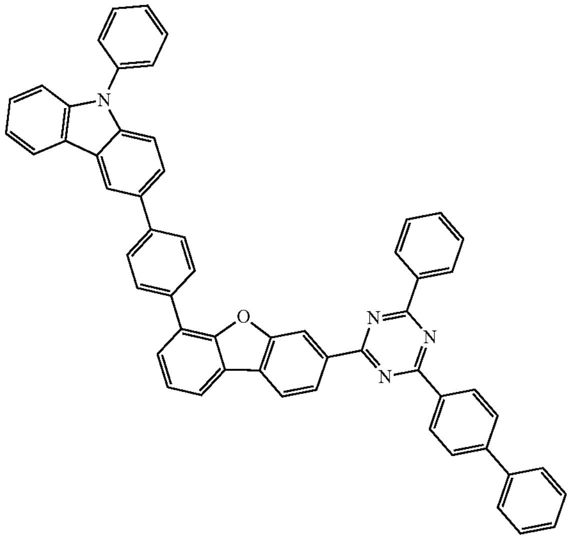
4-66
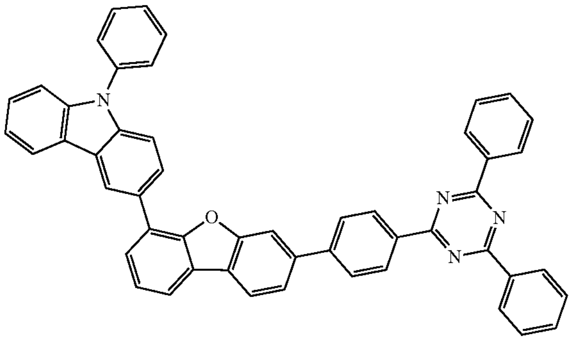
4-67
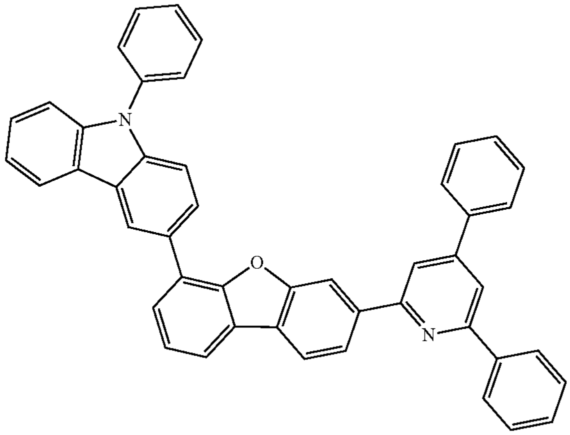

-continued
4-68
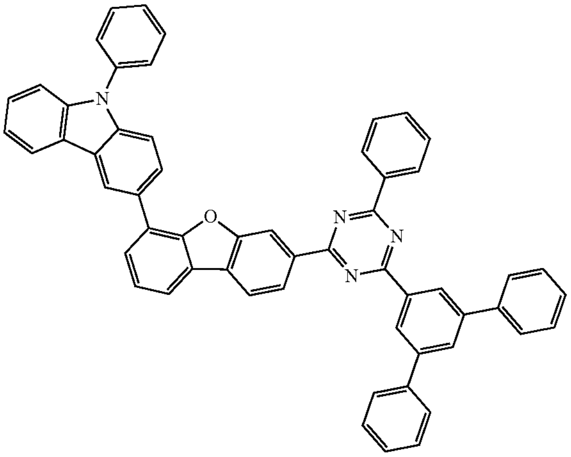
4-69
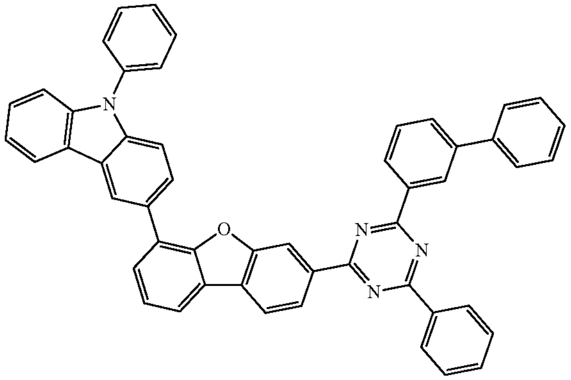
4-70
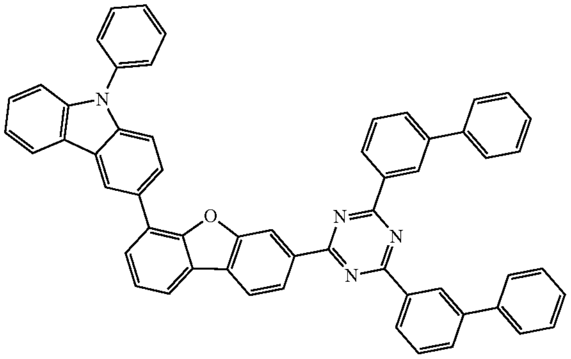
-continued
4-71
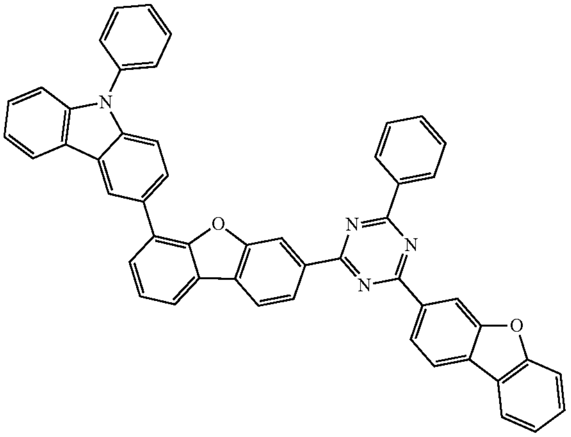
4-72
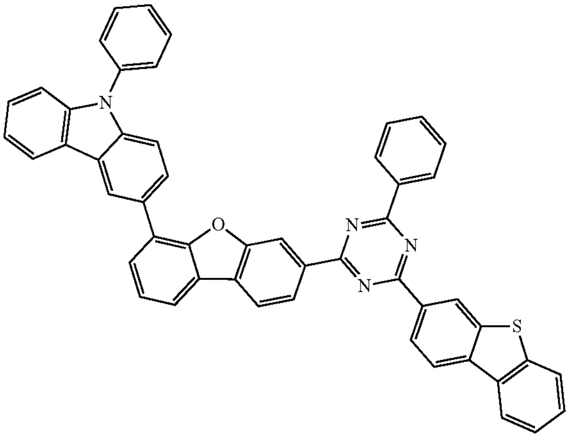
4-73
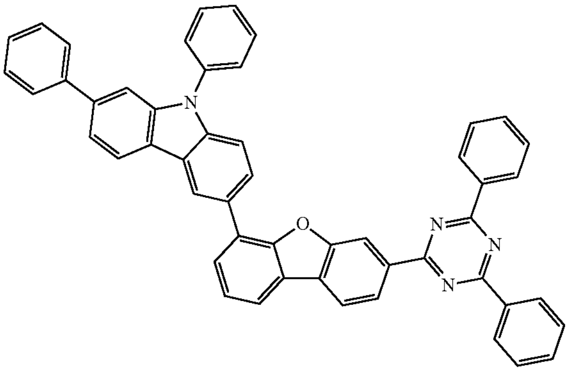

4-74
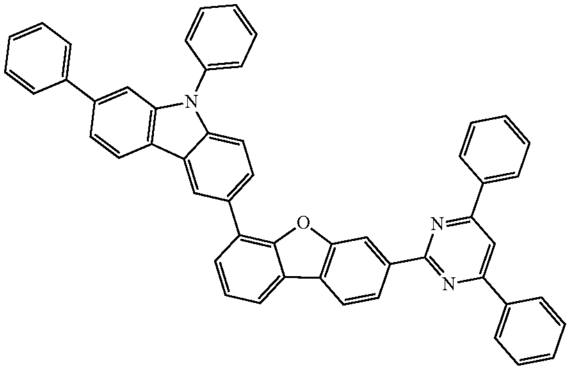
4-75
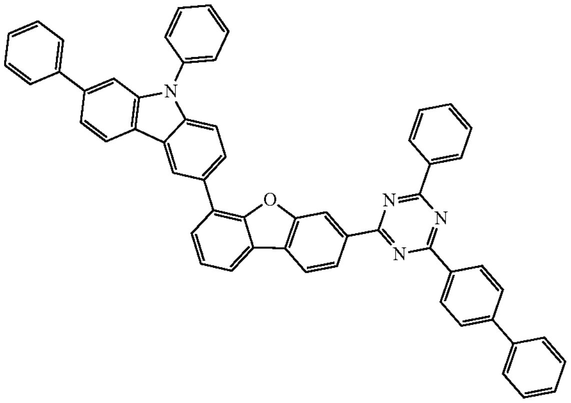
4-76
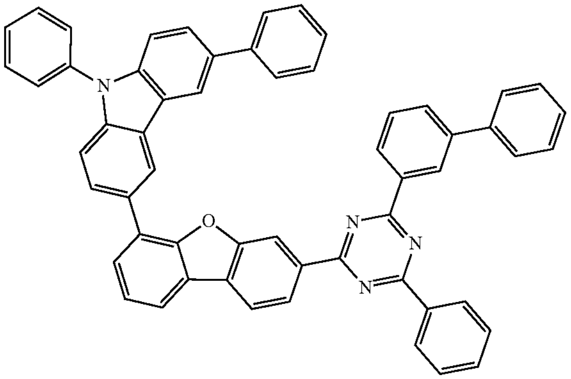
4-77
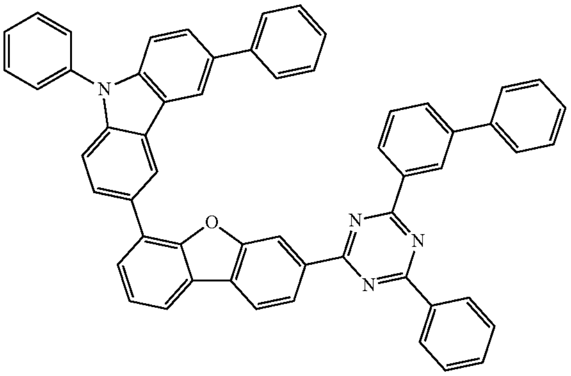
4-78
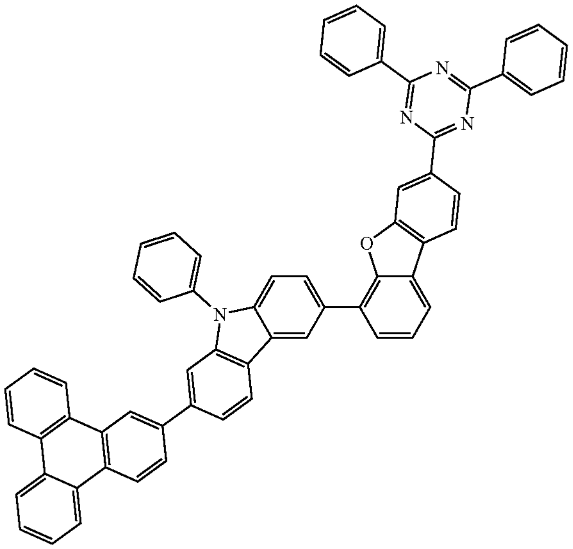
4-79
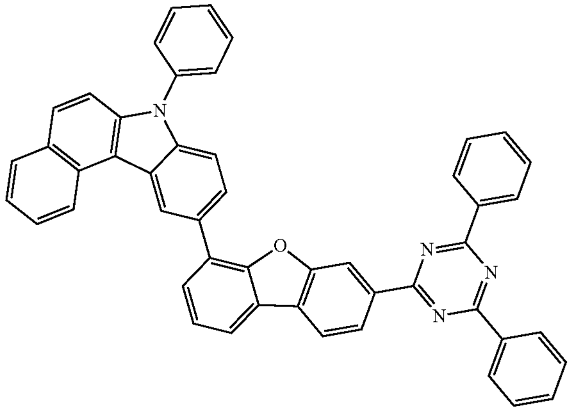
4-80
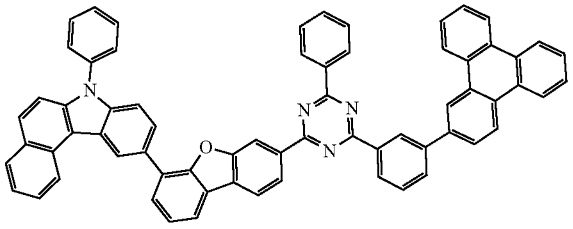

-continued
4-81
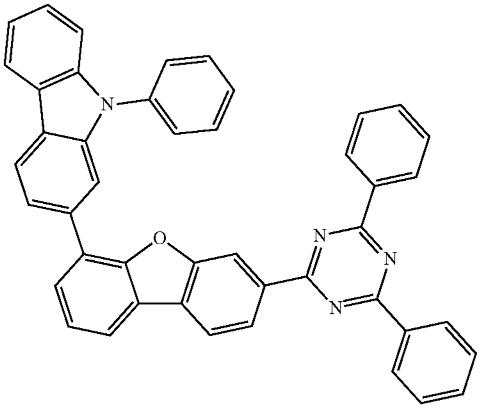
4-82
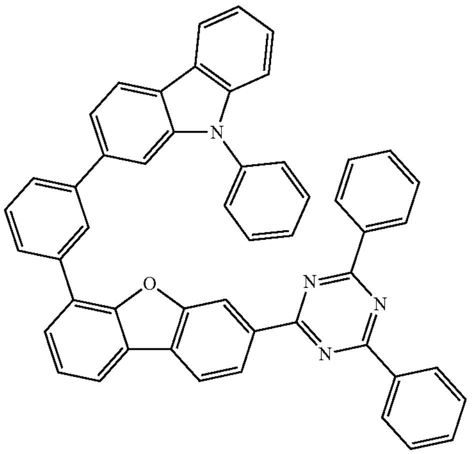
4-83
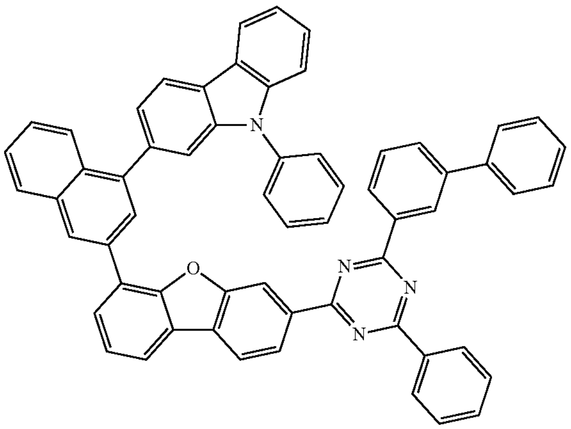
-continued
4-84
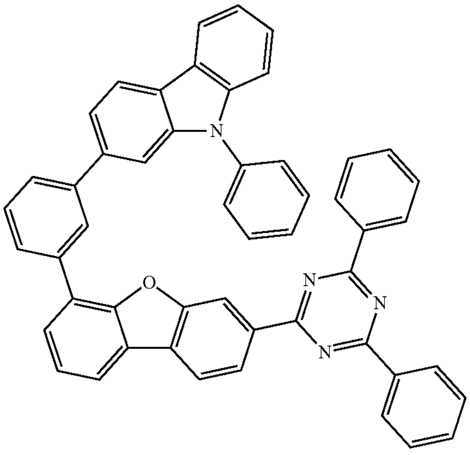
4-85
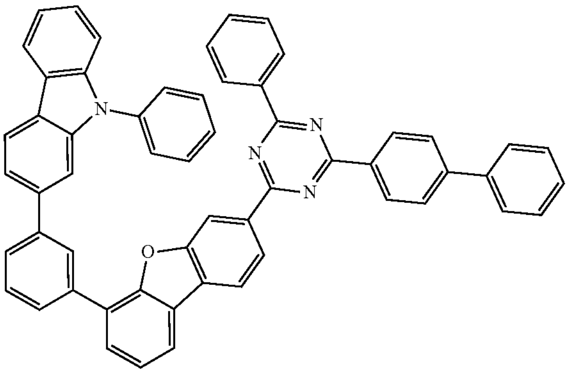
4-86
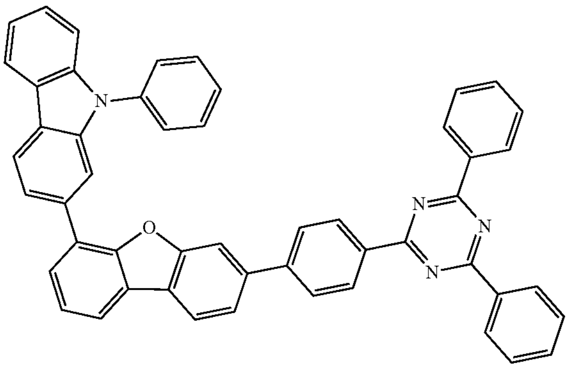

-continued
4-87
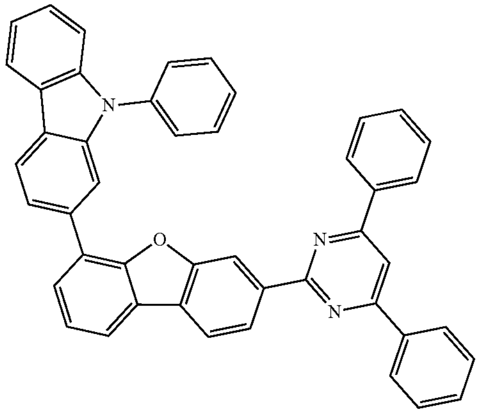
4-88
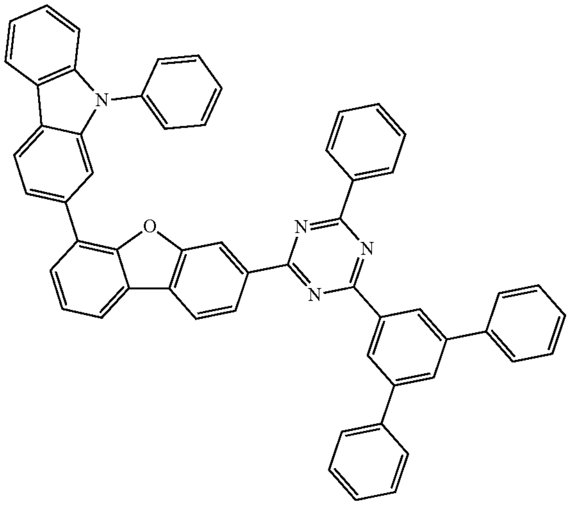
4-89
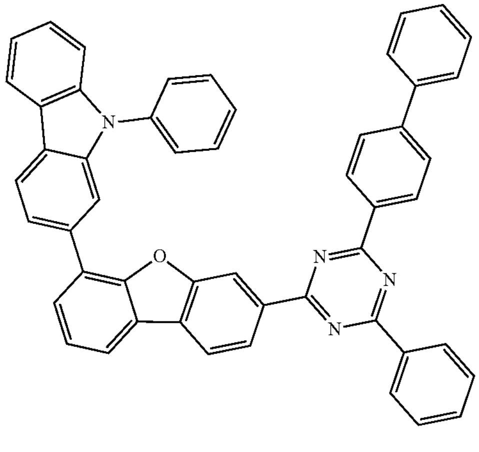
-continued
4-90
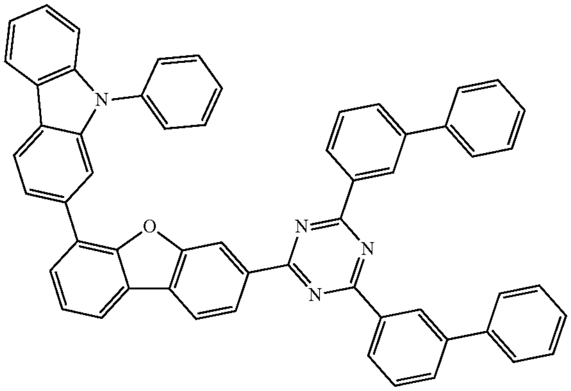
4-91
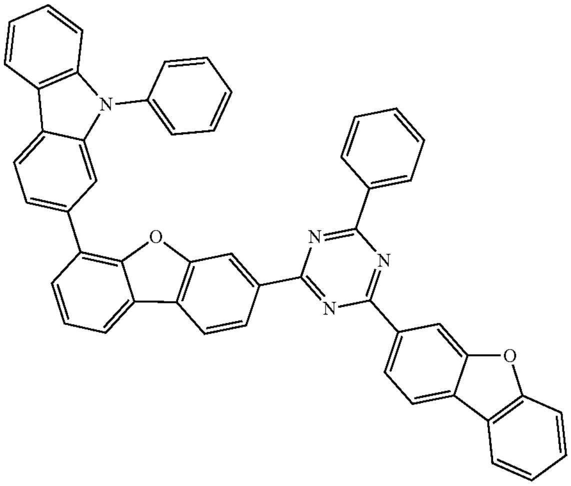
4-92
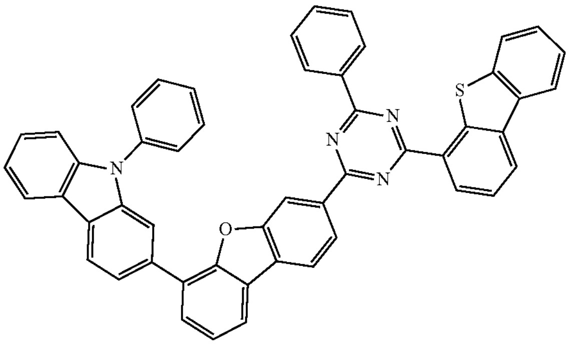

-continued
4-93
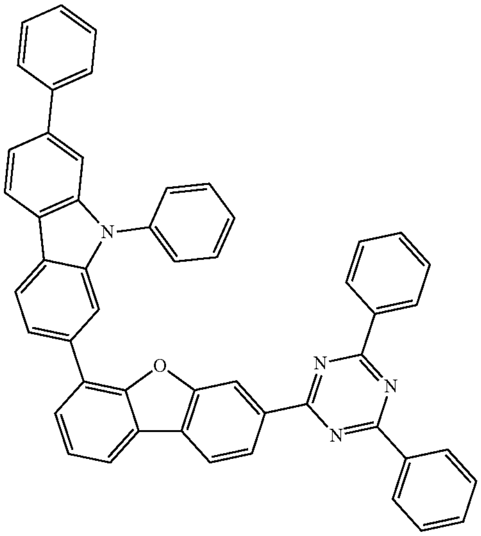
4-94
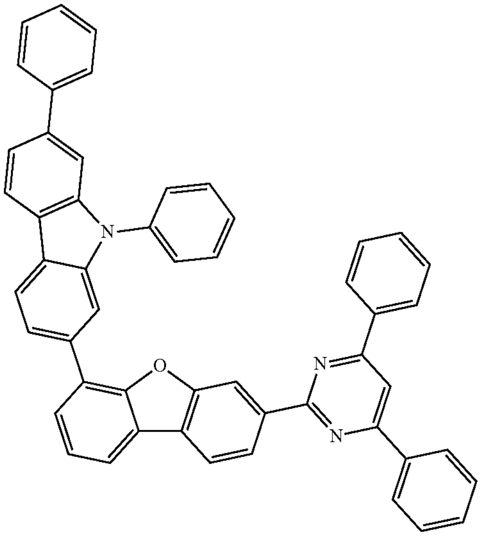
4-95
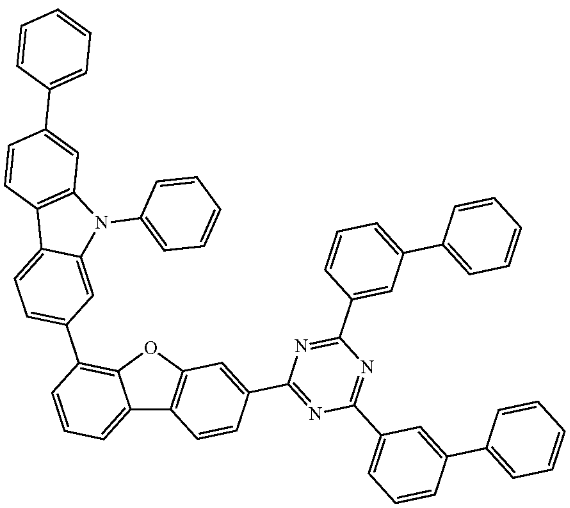
-continued
4-96
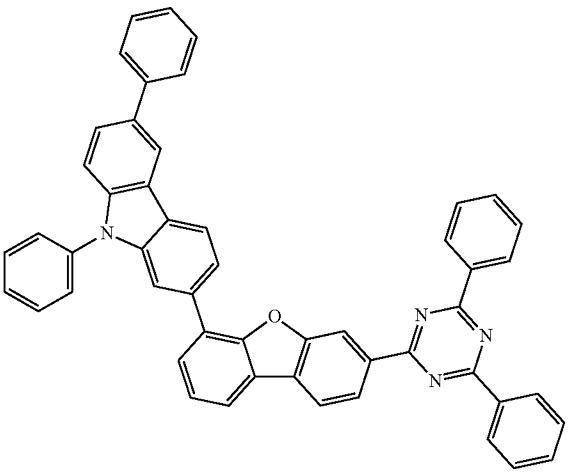
4-97
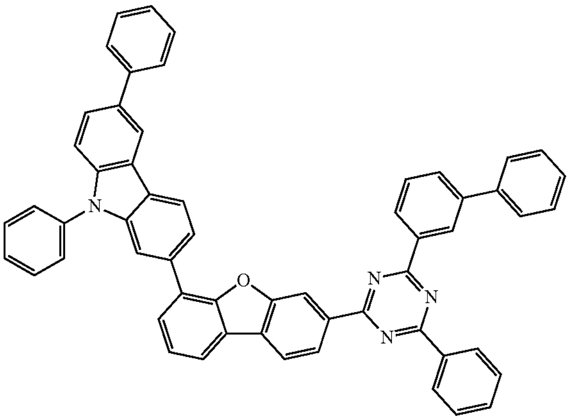
4-98
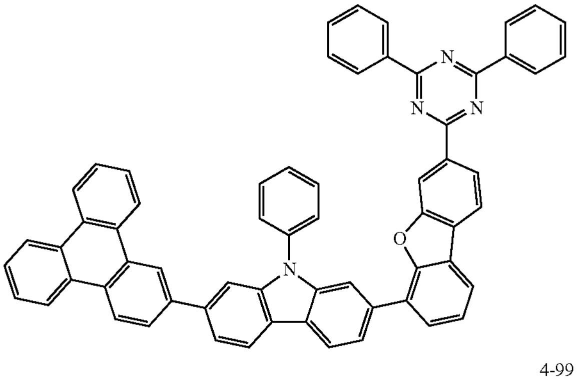
4-99
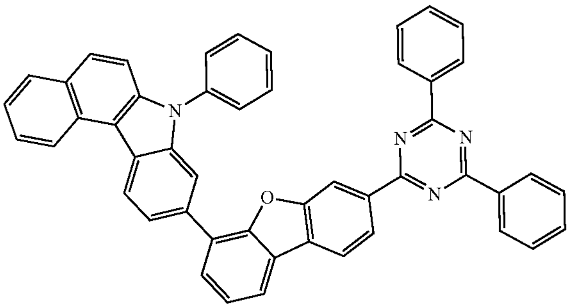

-continued
4-100
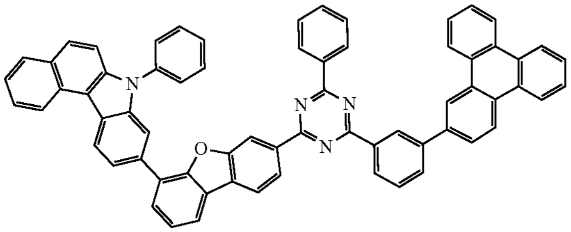
4-101
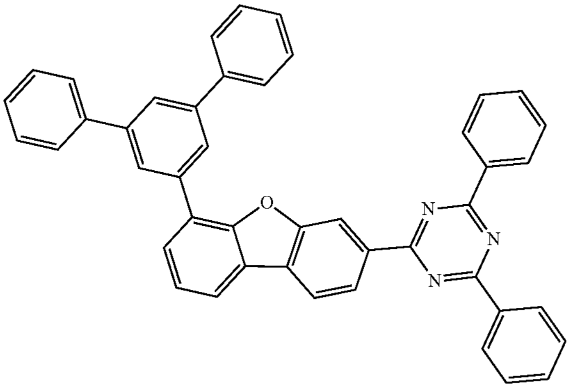
4-102
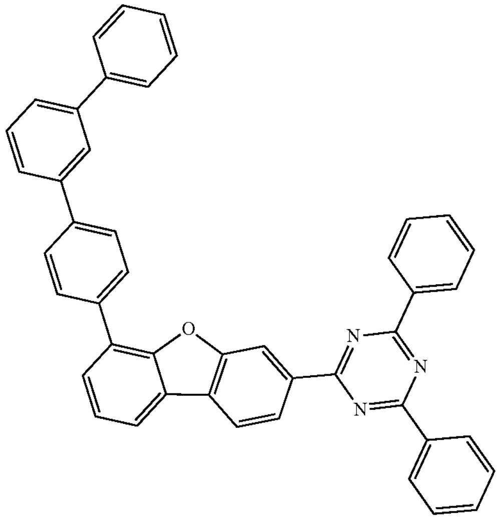
-continued
4-103
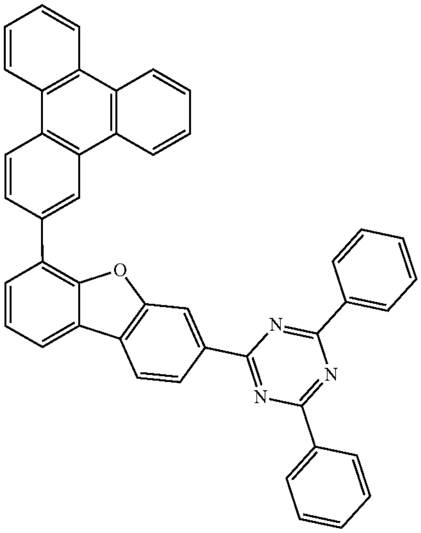
4-104
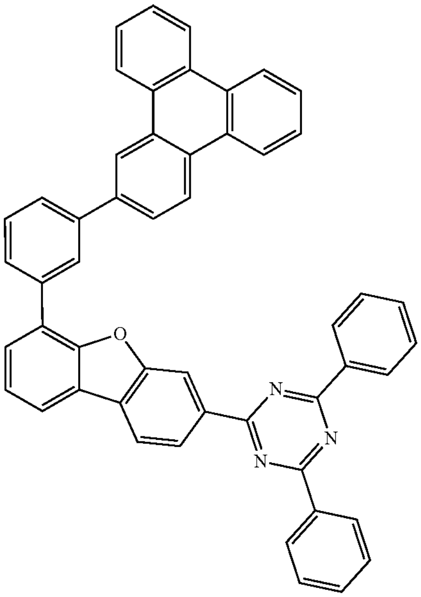
In one embodiment of the present application, Chemical Formula 2 may be represented by any one of the following compounds, but is not limited thereto.

5-1
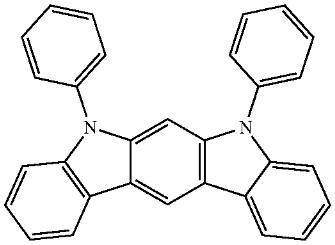
5-2
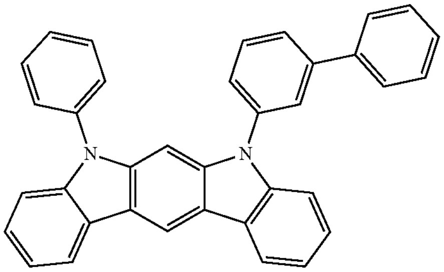
5-3
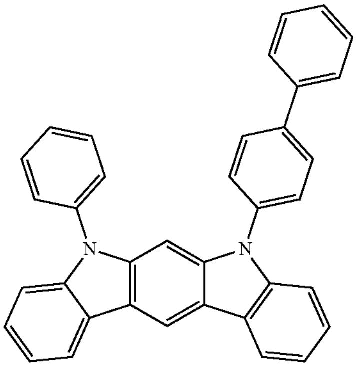
5-4
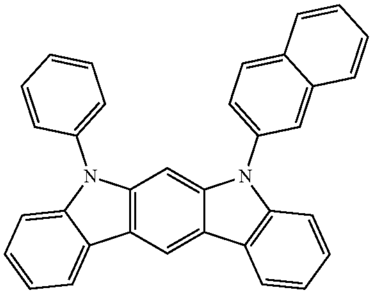
5-5
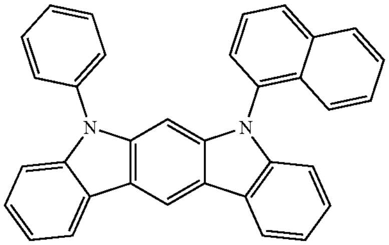
5-6
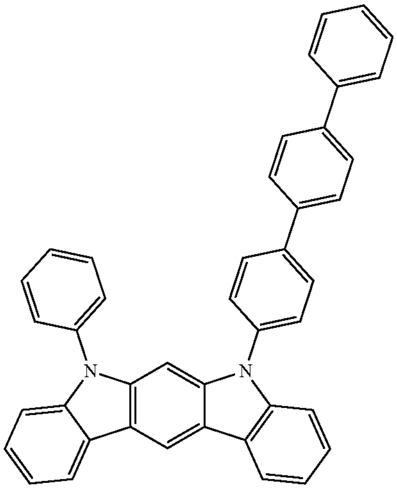
5-7
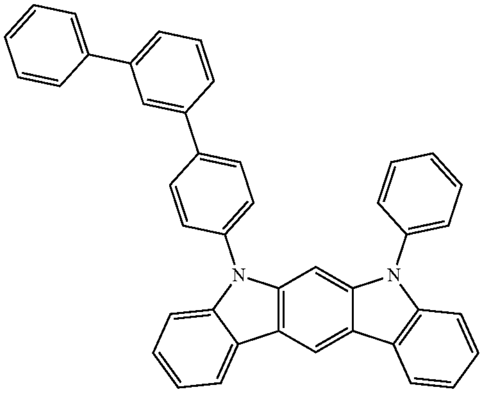
5-8
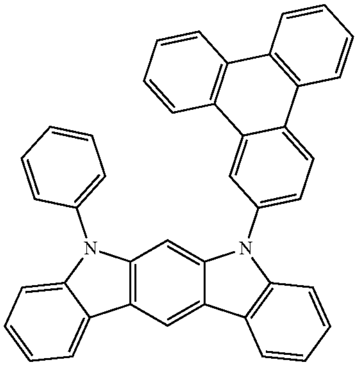

-continued
5-9
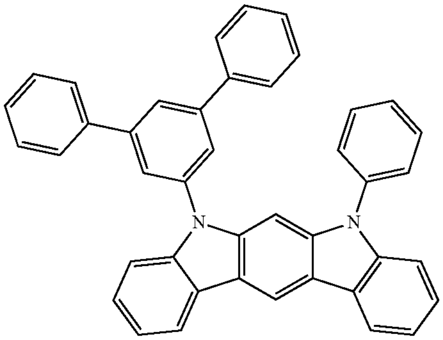
5-10
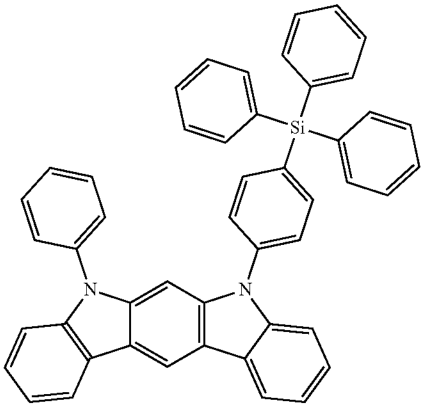
5-11
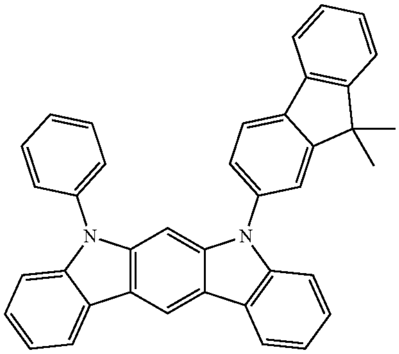
5-12
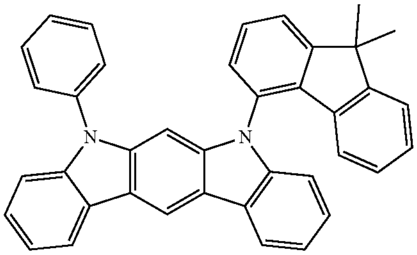
5-13
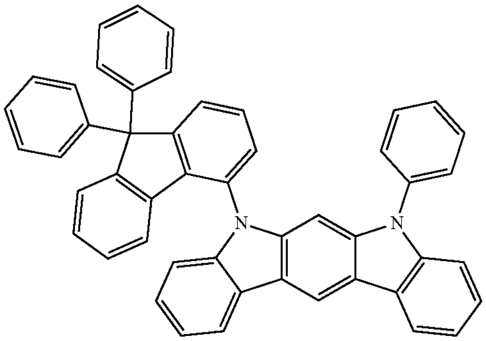
5-14
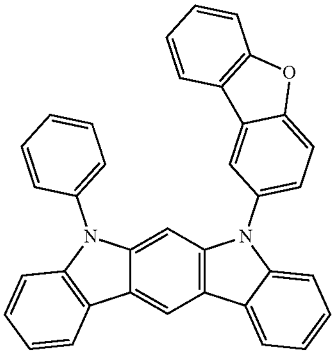
5-15
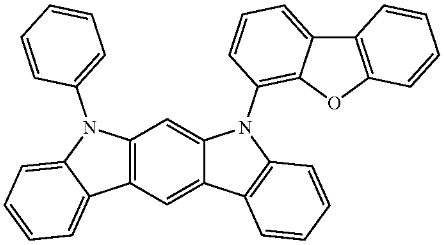
5-16
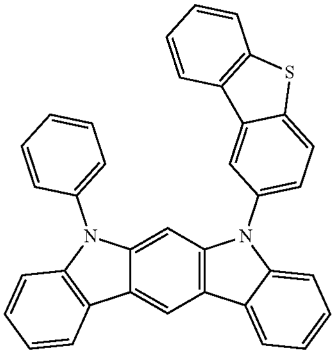

-continued
5-17
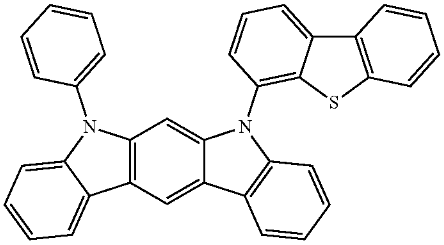
5-18
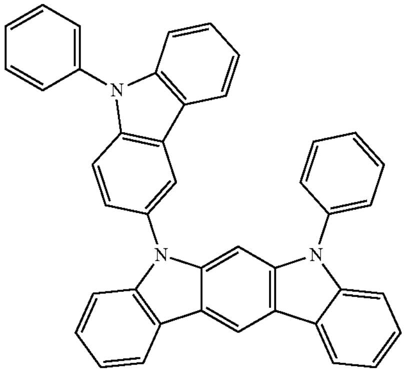
5-19
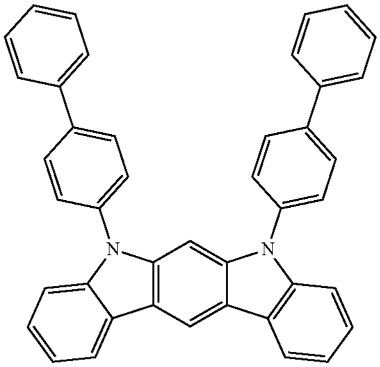
5-20
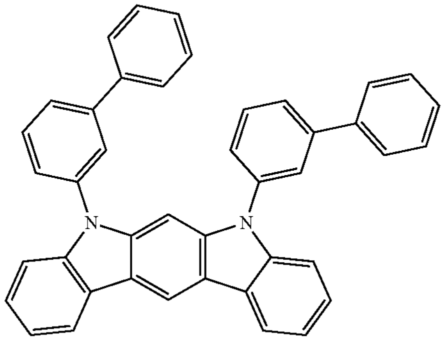
5-21
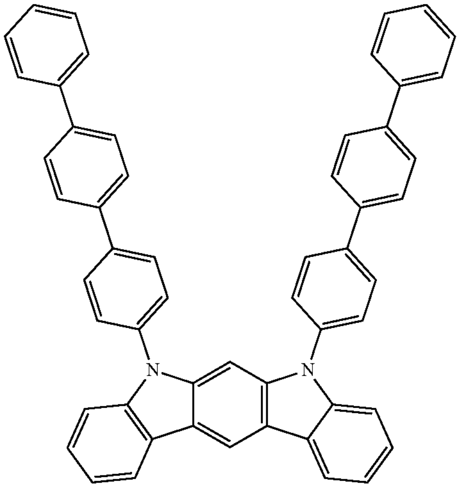
5-22
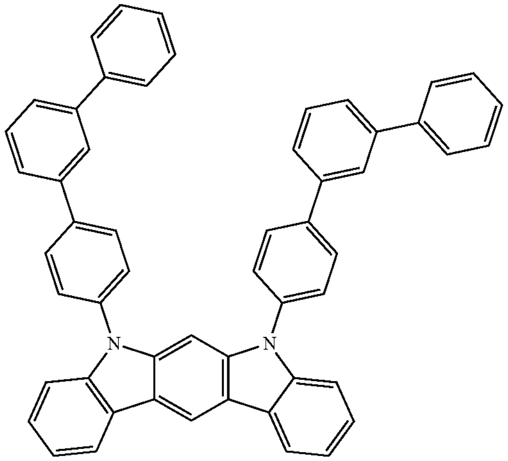
5-23
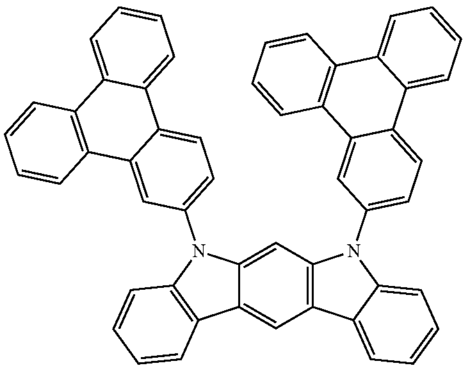
5-24
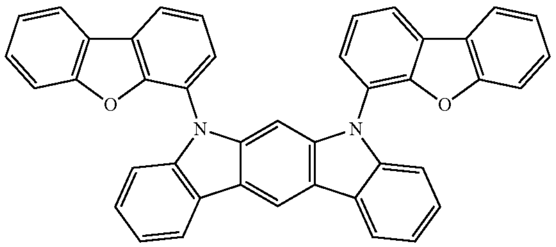

-continued
5-25
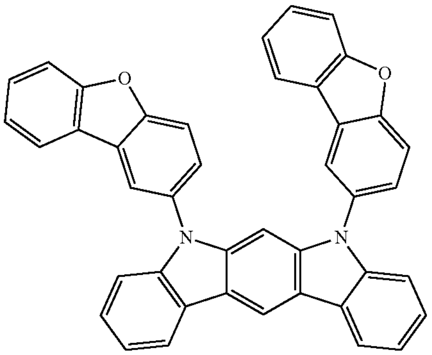
5-26
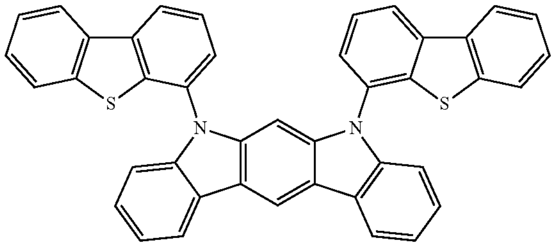
5-27
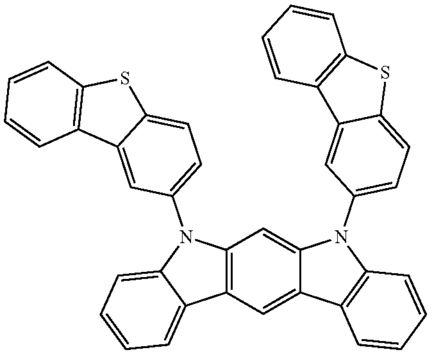
5-28
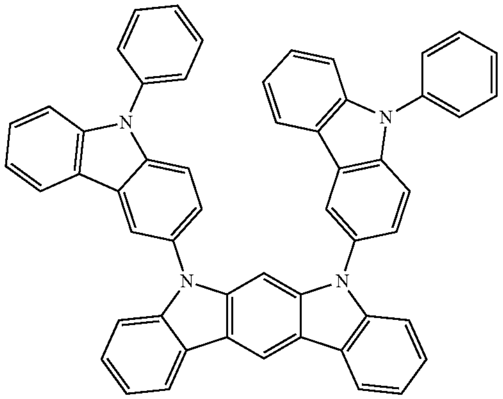
5-29
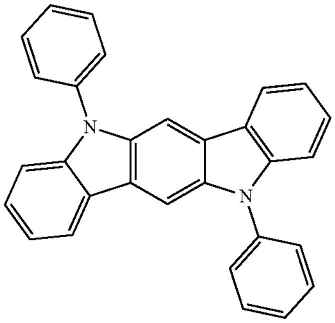
5-30
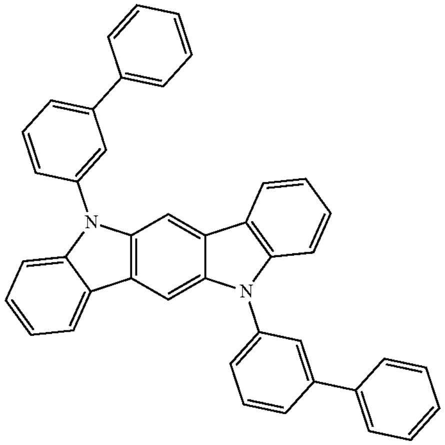

-continued
5-31
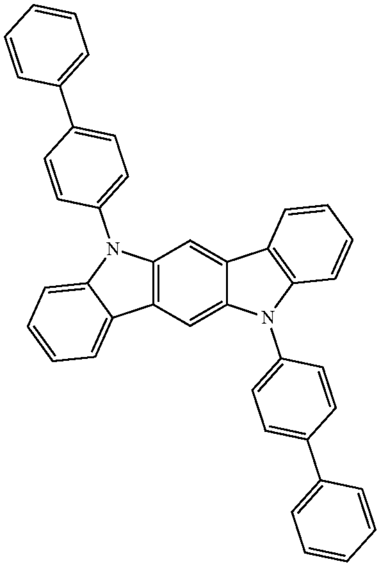
5-32
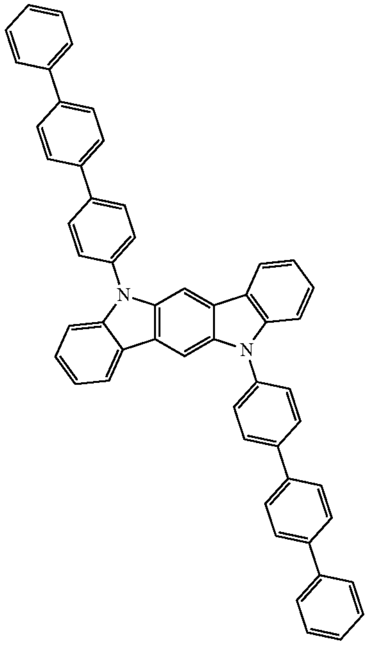
5-33
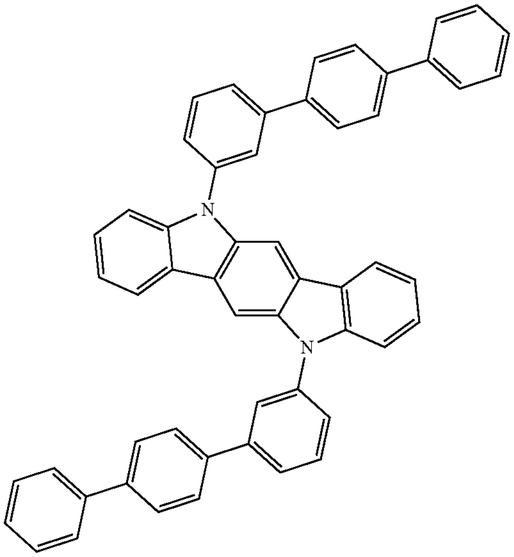
5-34
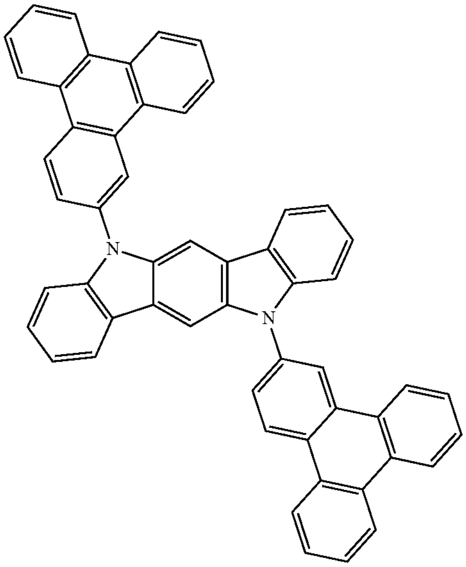

-continued
5-35
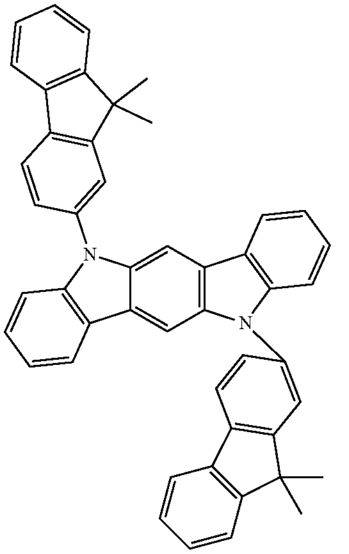
5-36
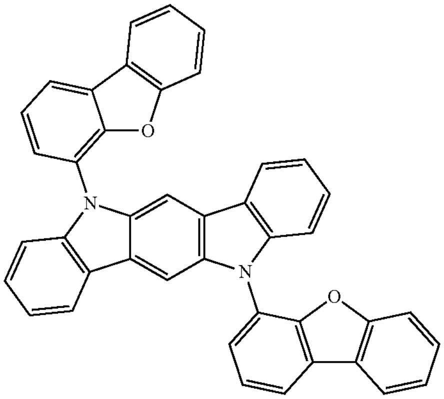
5-37
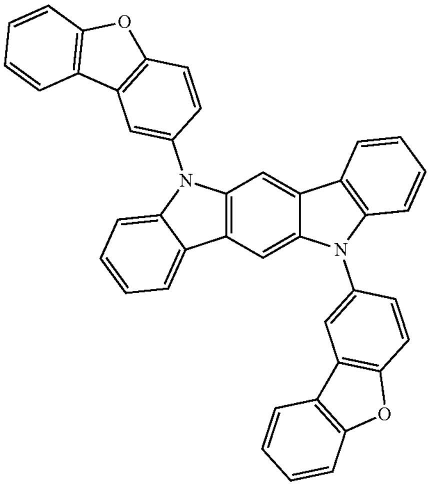
5-38
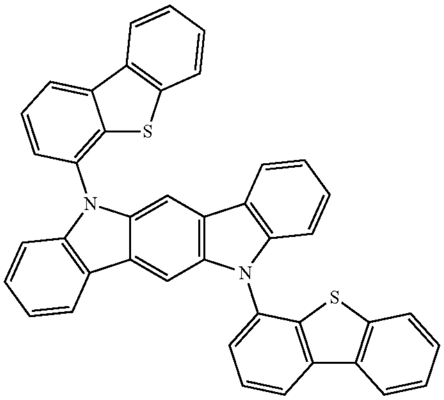
5-39
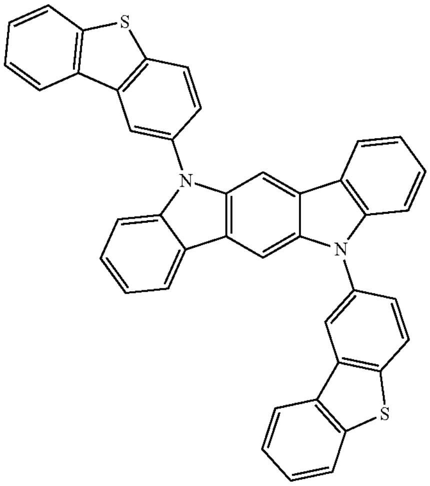
5-40
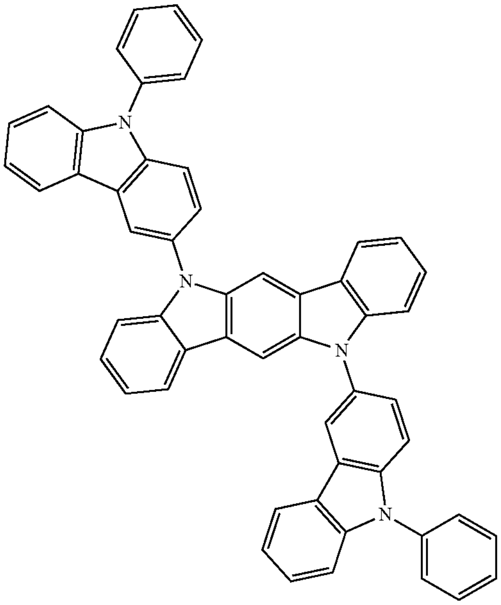

-continued
5-41
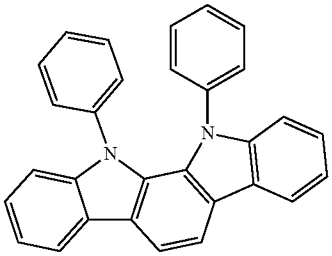
5-42
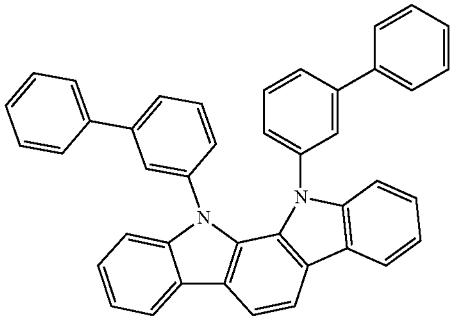
5-43
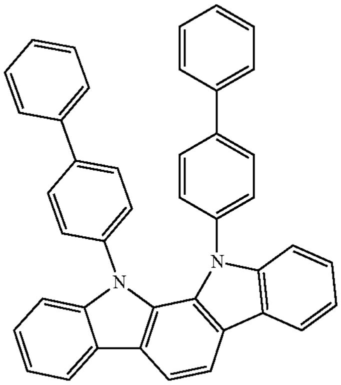
5-44
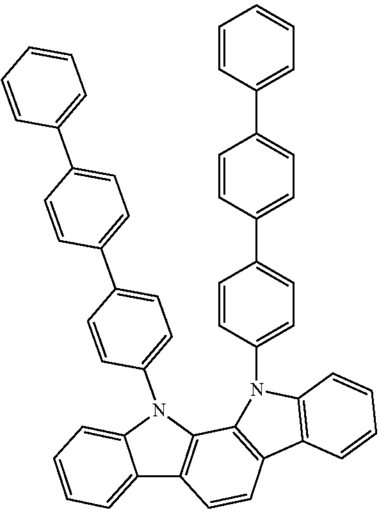
5-45
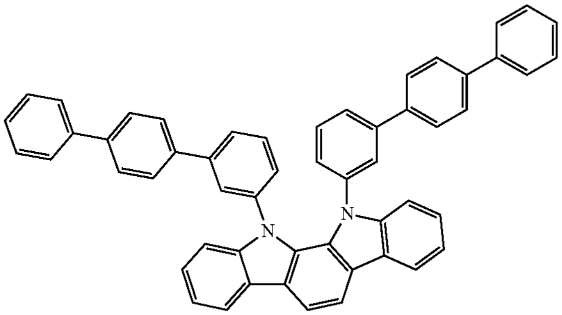
5-46
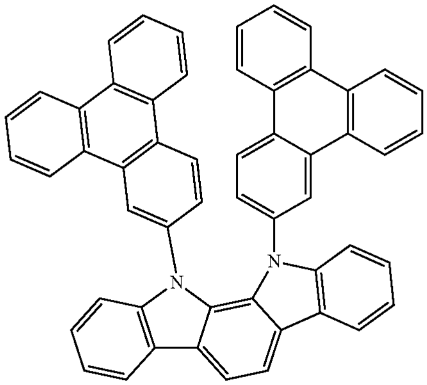

-continued
5-47
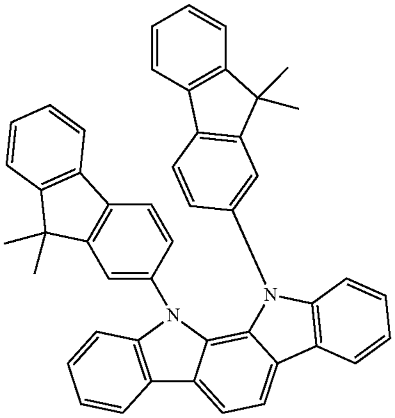
5-48
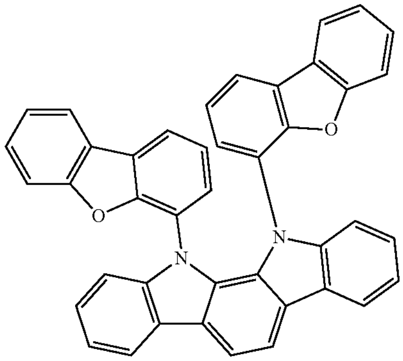
5-49
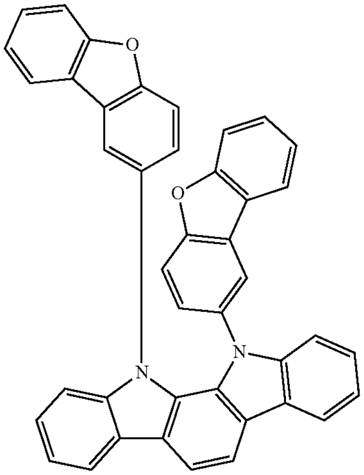
5-50
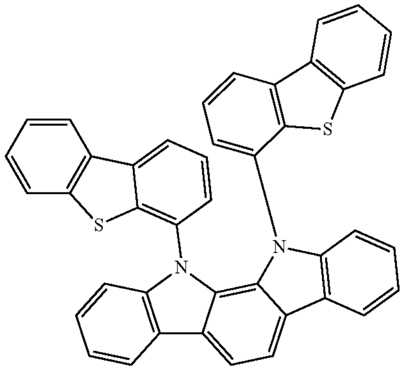
5-51
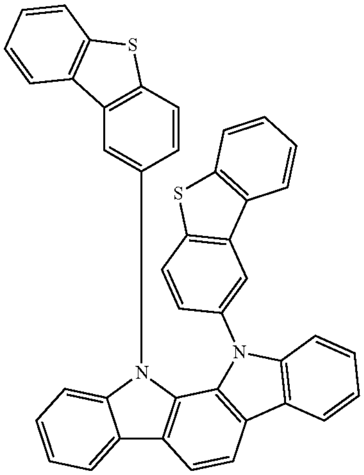
5-52
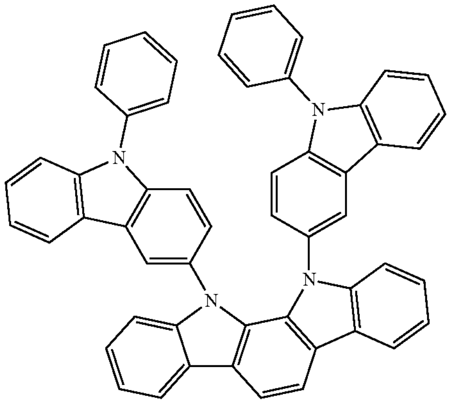

-continued
5-53
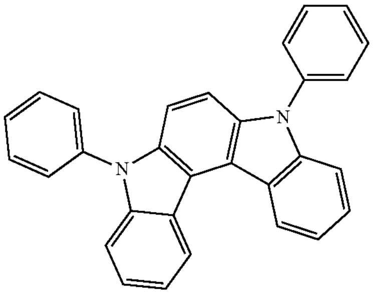
5-54
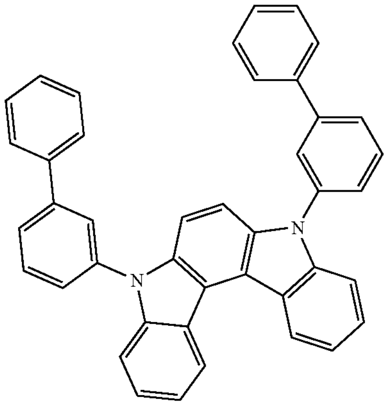
5-55
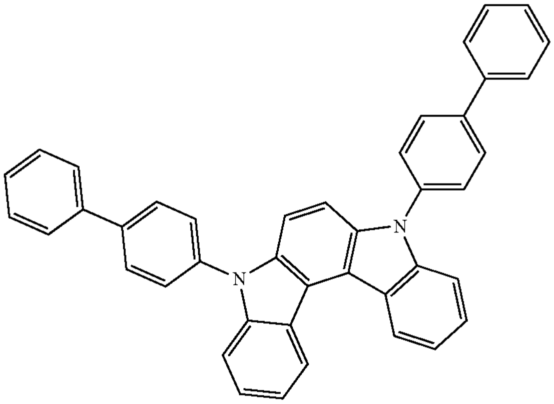
5-56
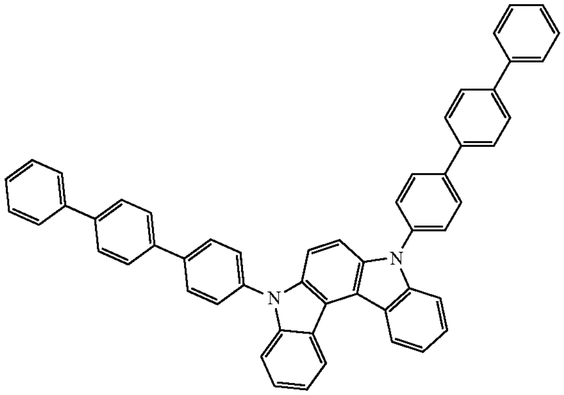
5-57
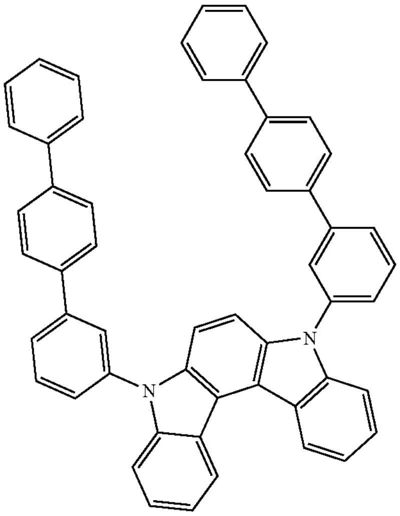
5-58
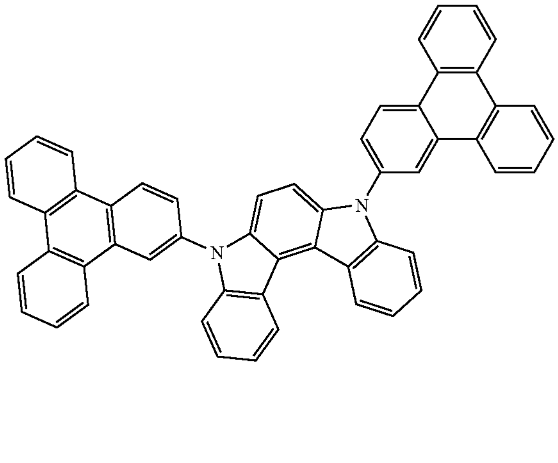

-continued
5-59
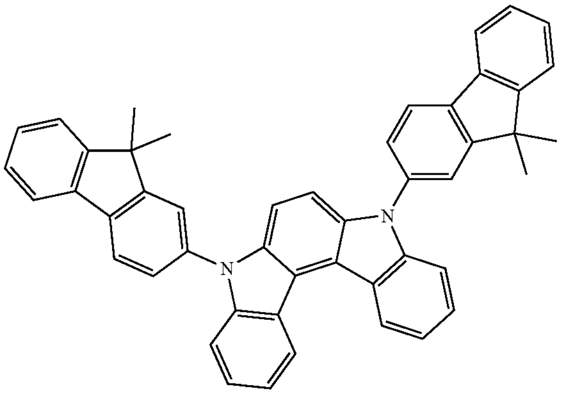
5-60
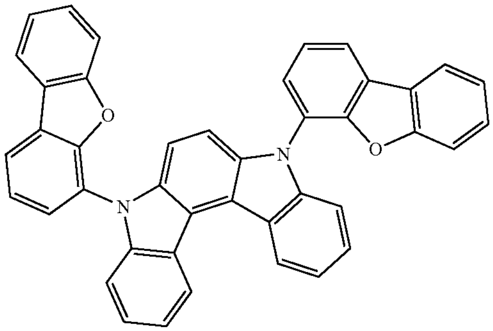
5-61
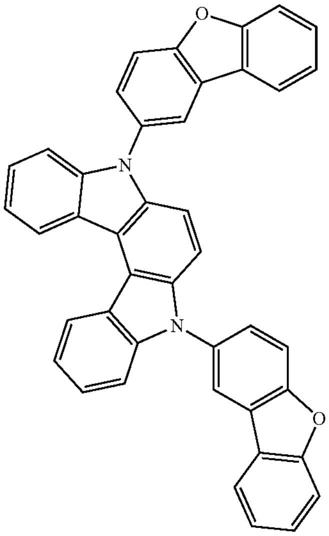
5-62
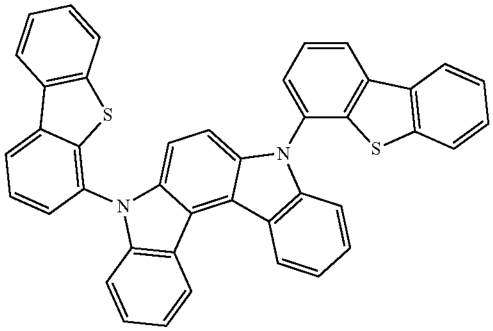
5-63
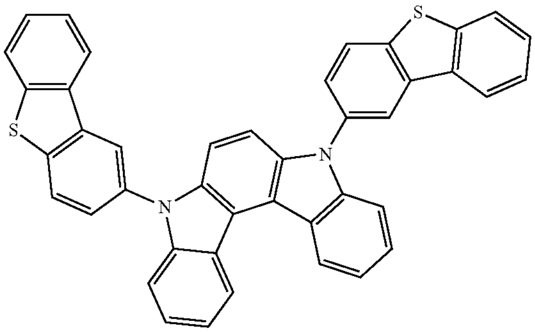
5-64
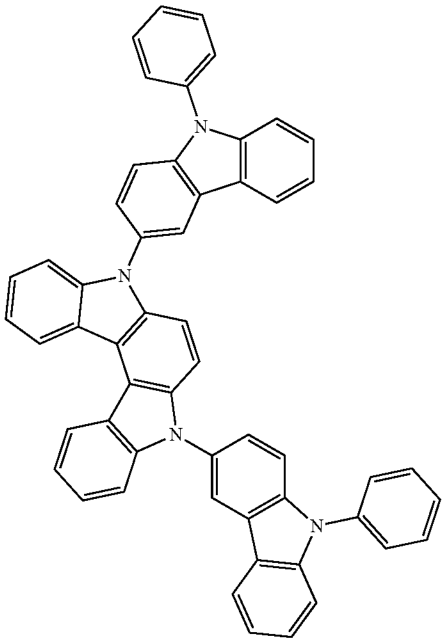

-continued
5-65
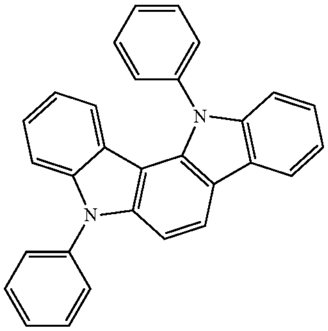
5-66
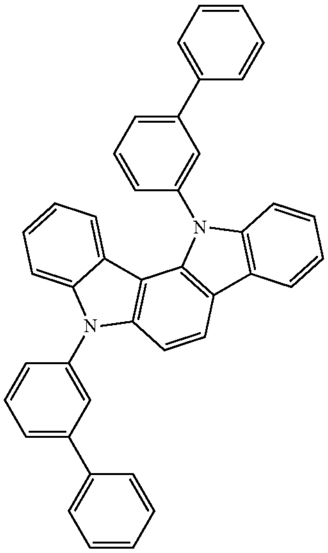
5-67
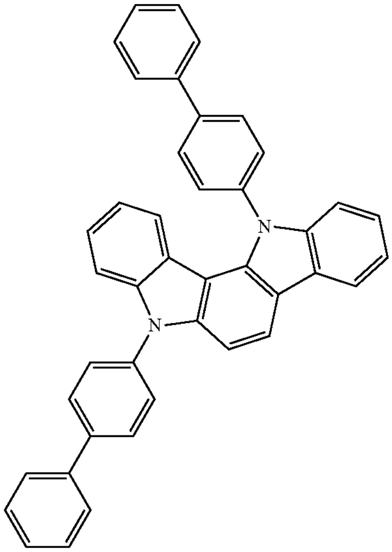
5-68
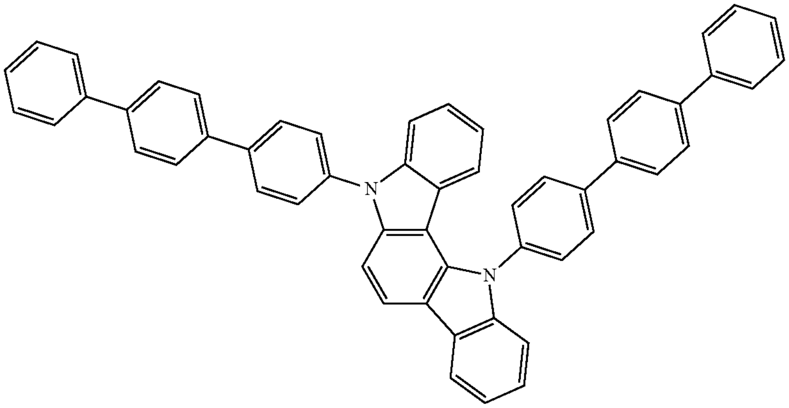

-continued
5-69
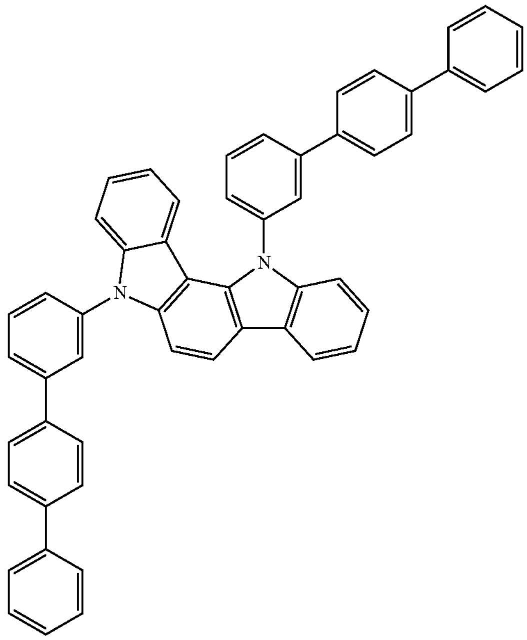
5-70
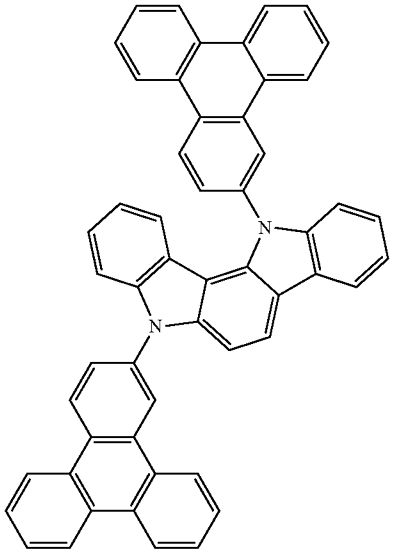
5-71
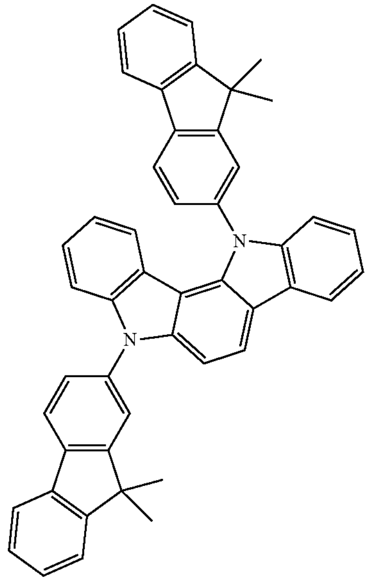
5-72
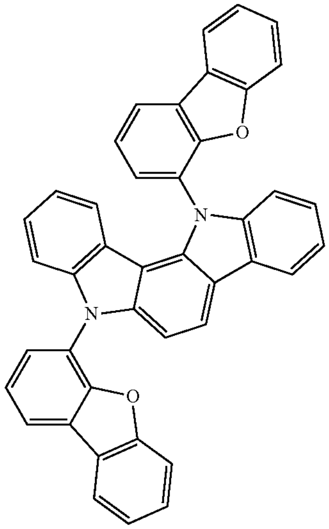

-continued
5-73
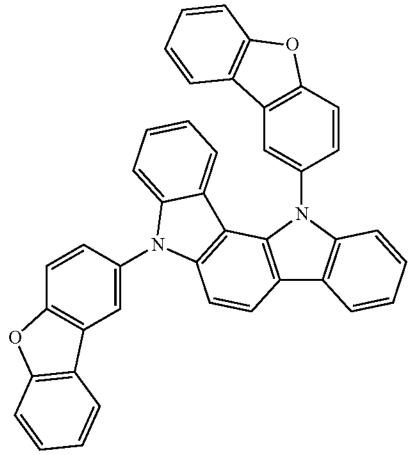
5-74
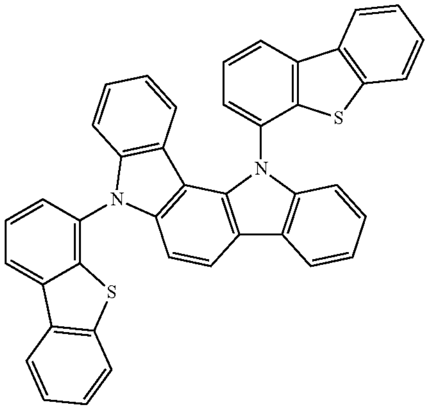
5-75
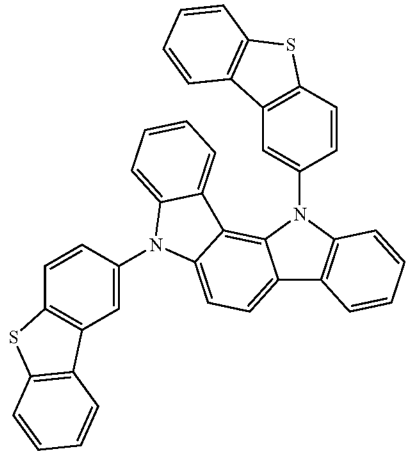
5-76
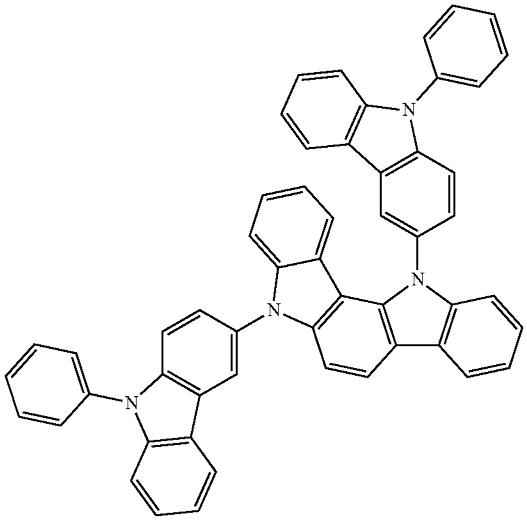
5-77
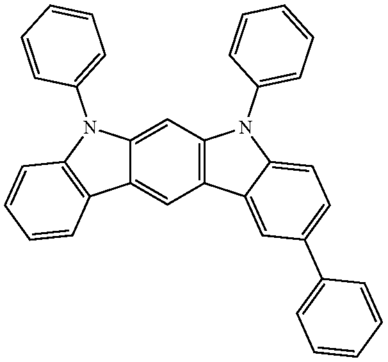
5-78
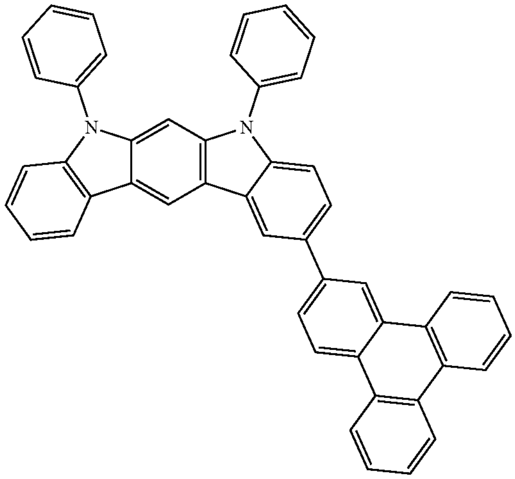

-continued
5-79
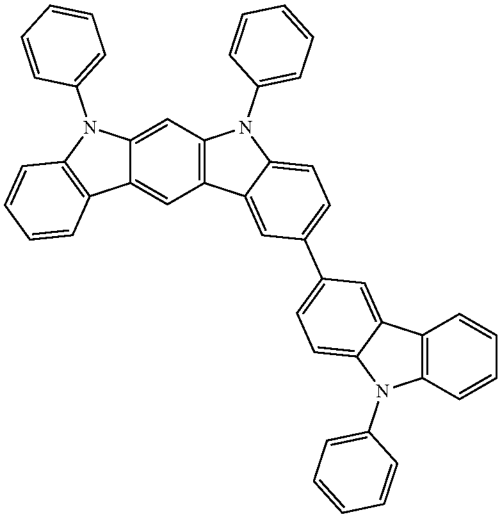
5-80
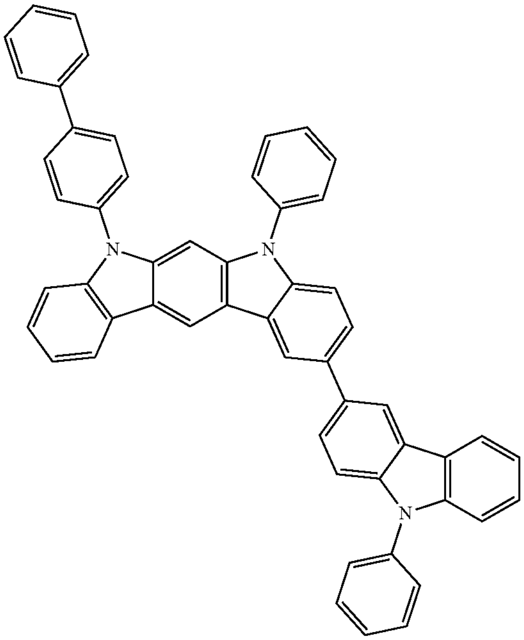
5-81
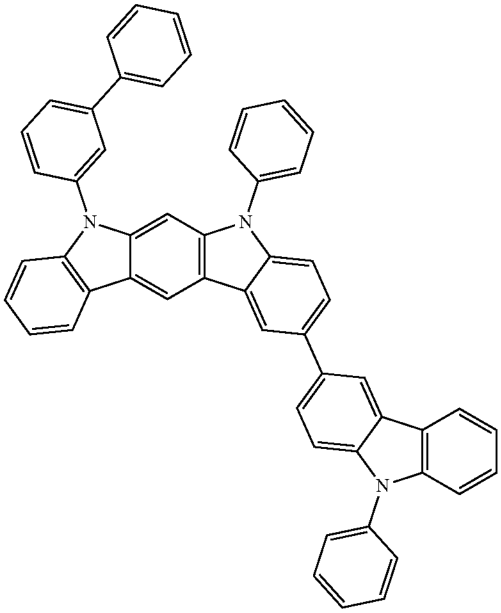
5-82
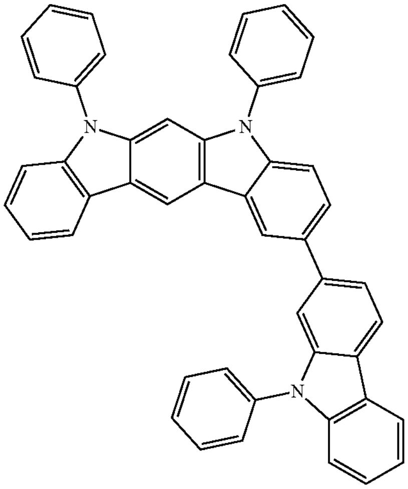

-continued
5-83
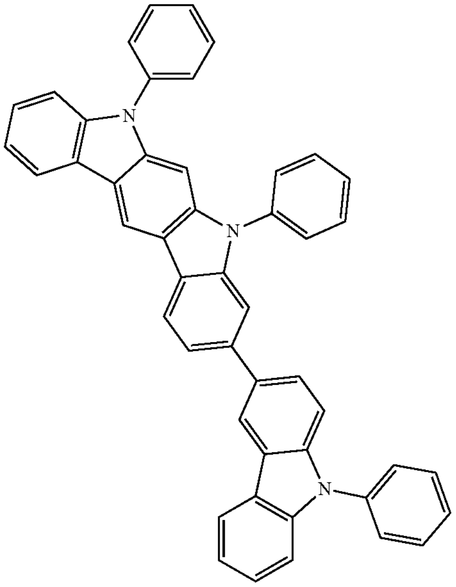
5-84
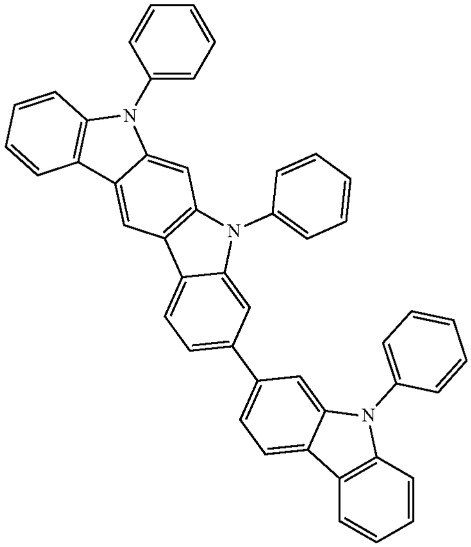
5-85
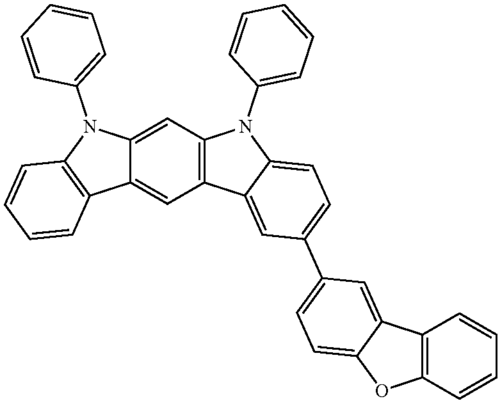
5-86
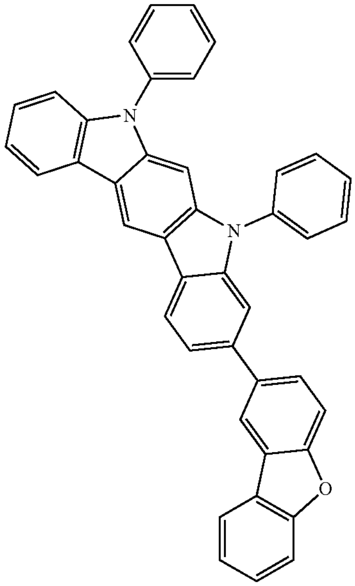

-continued
5-87
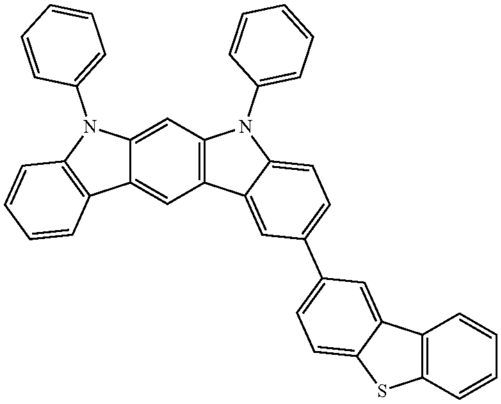
5-88
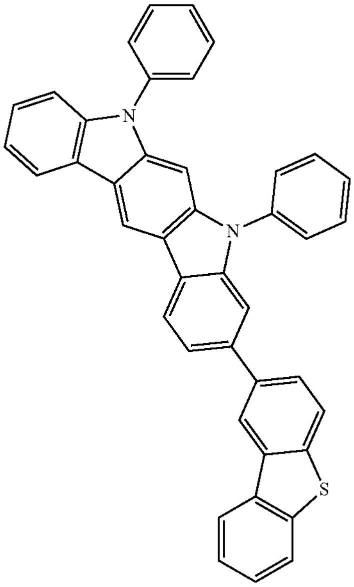
5-89
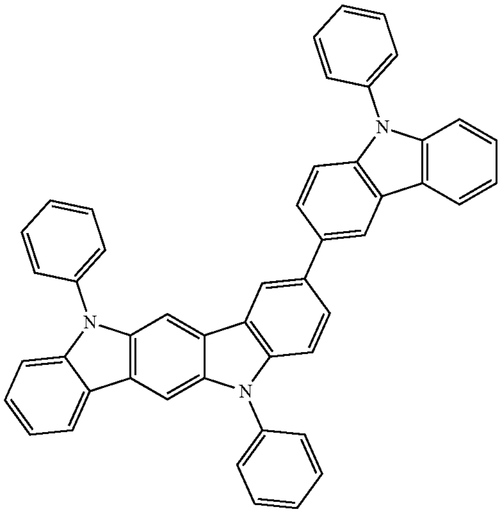
5-90
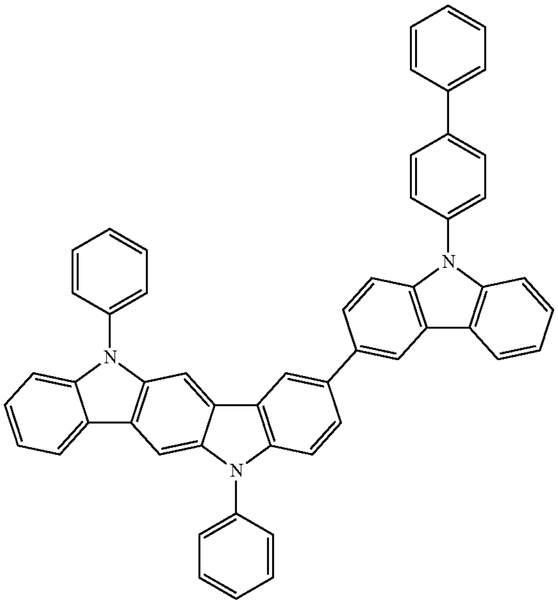

-continued
5-91
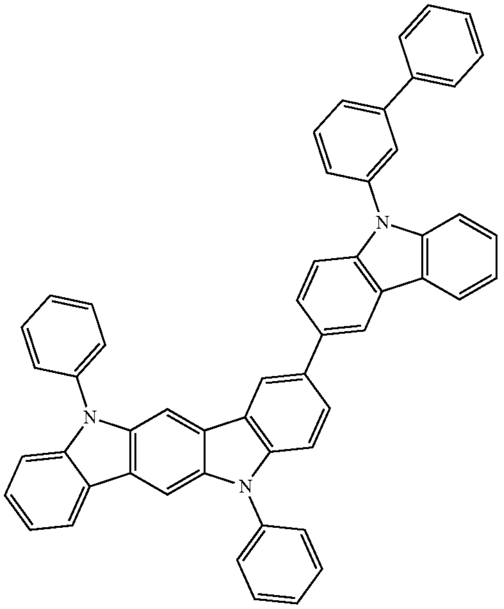
5-92
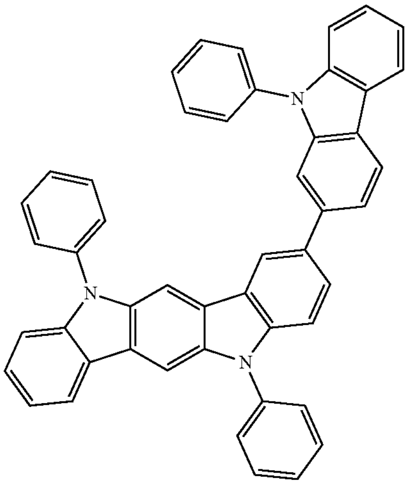
5-93
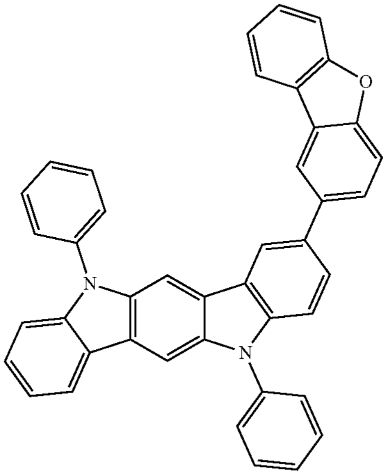
5-94
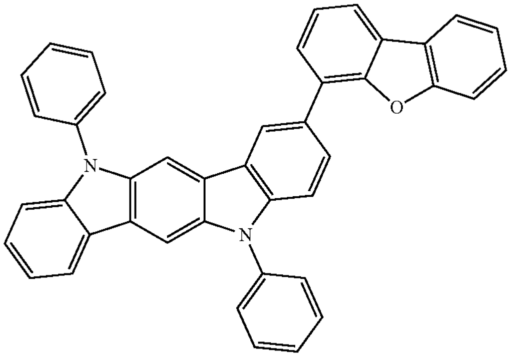
5-95
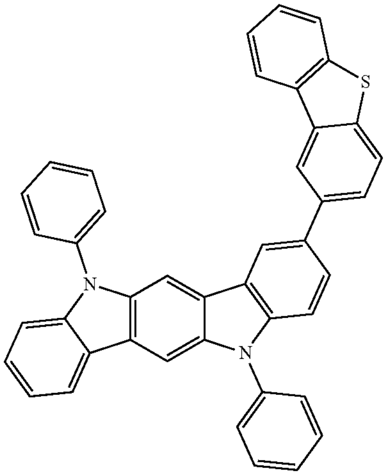
5-96
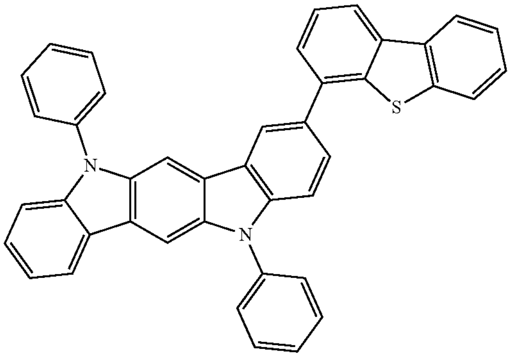

-continued
5-97
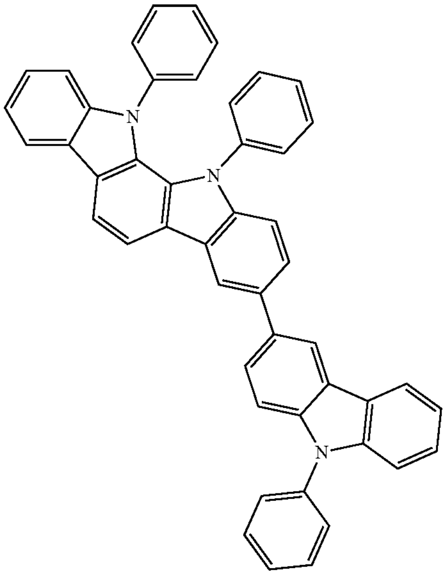
5-98
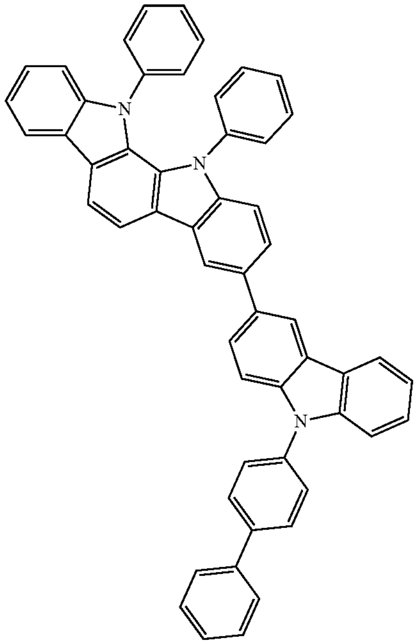
5-99
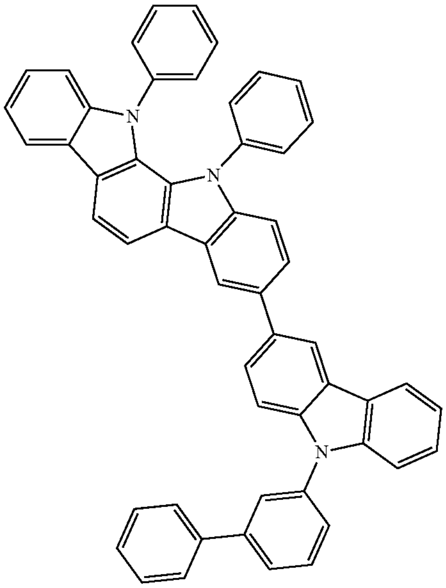
5-100
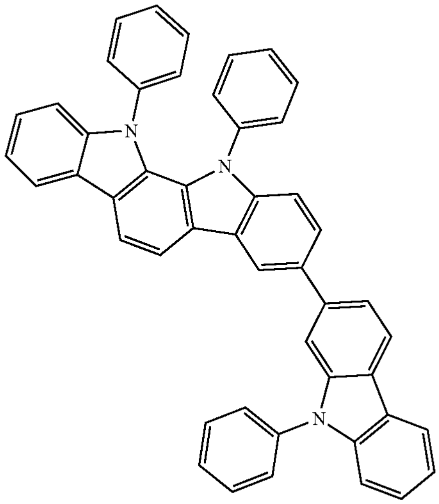
5-101
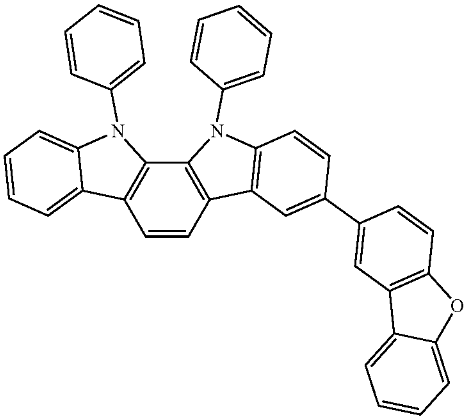
5-102
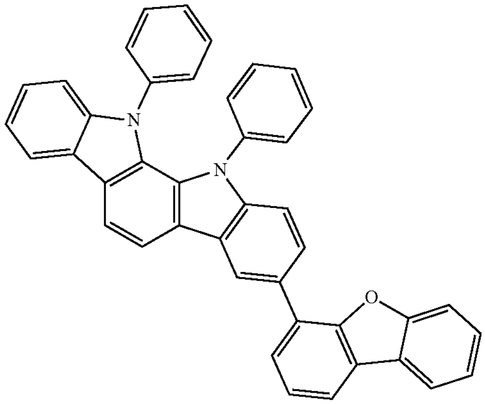

-continued
5-103
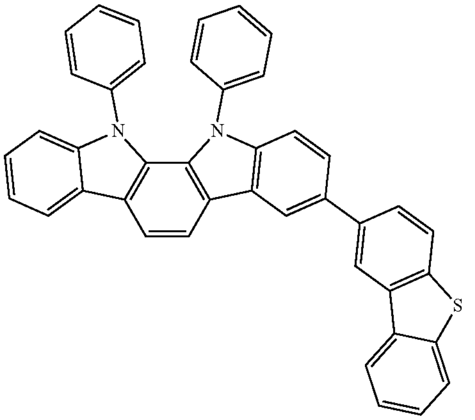
5-104
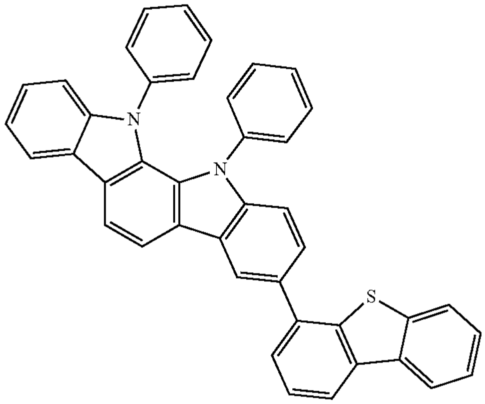
5-105
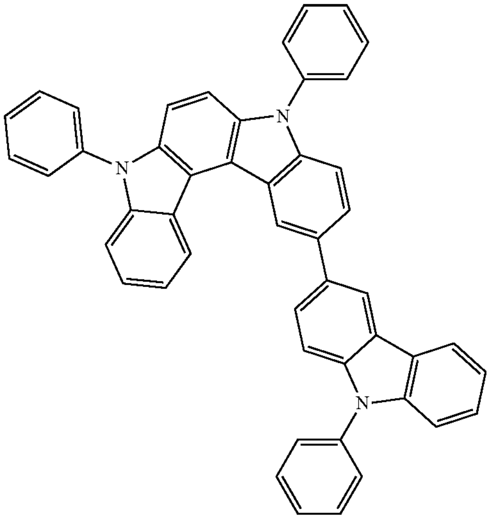
5-106
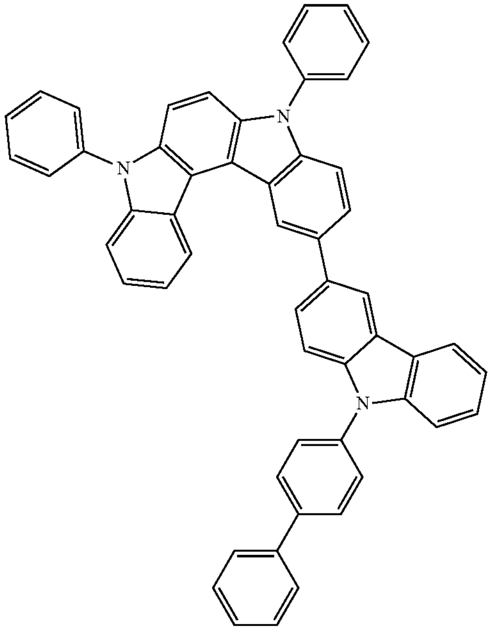
5-107
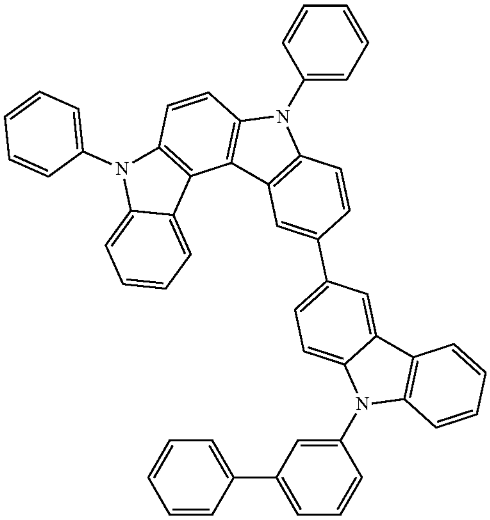
5-108
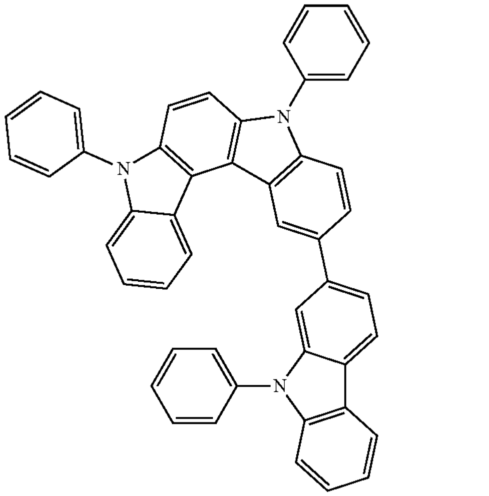

-continued
5-109
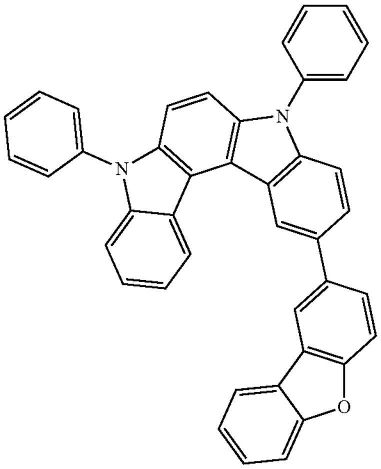
5-110
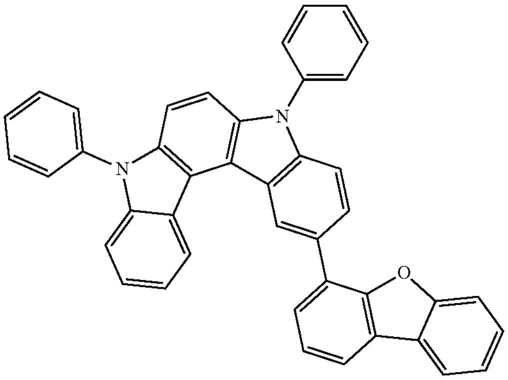
5-111
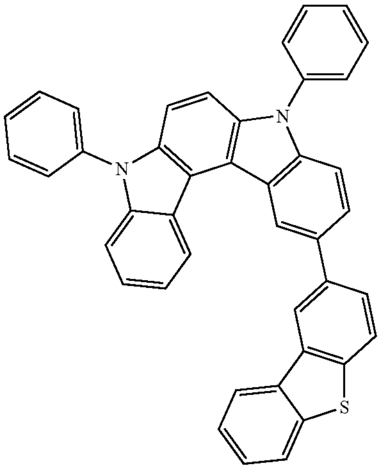
5-112
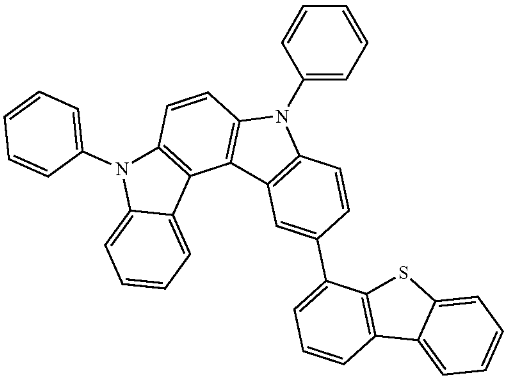
5-113
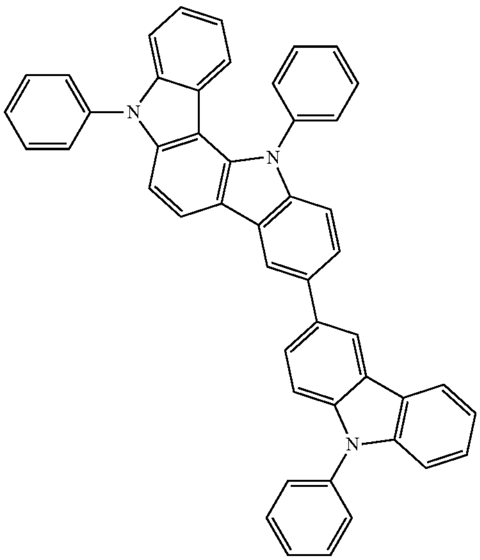
5-114
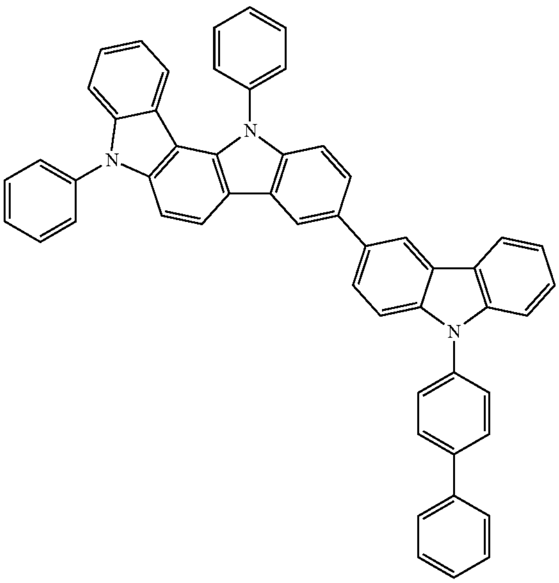

-continued
5-115
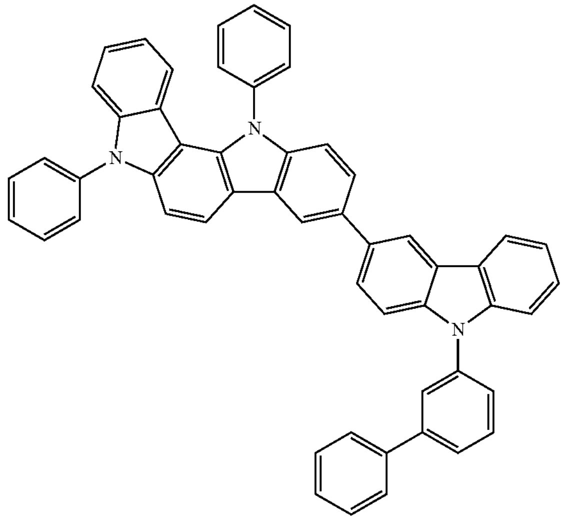
5-116
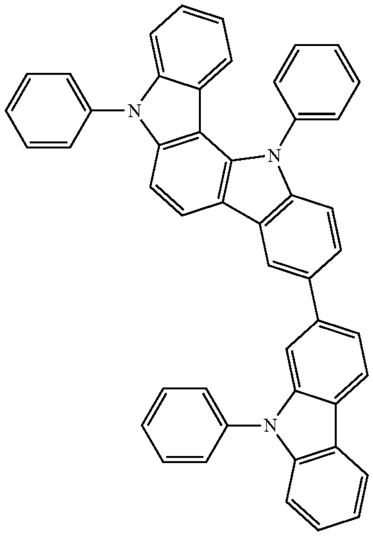
5-117
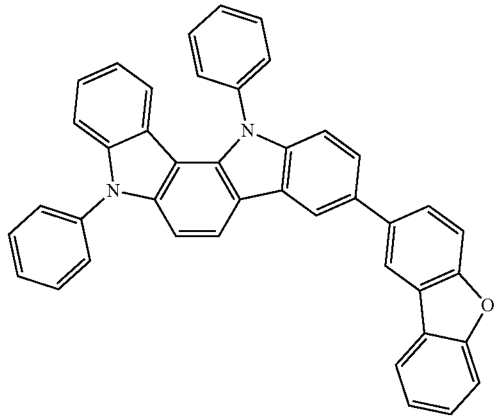
5-118
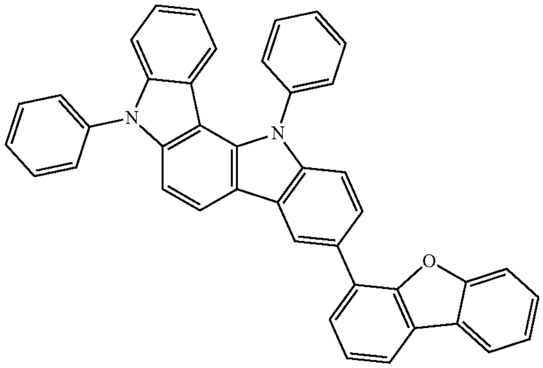
5-119
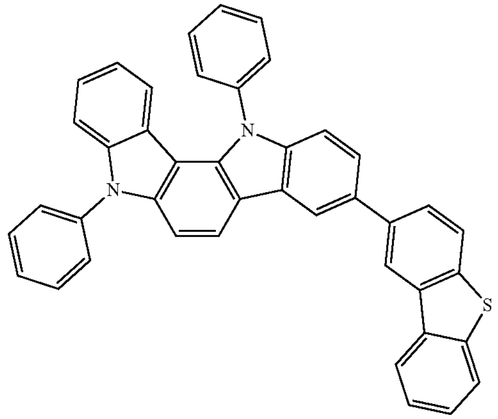
5-120
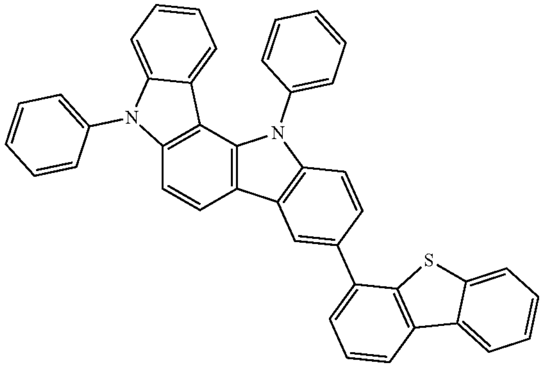

-continued
5-121
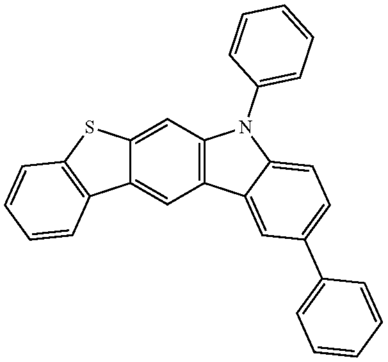
5-122
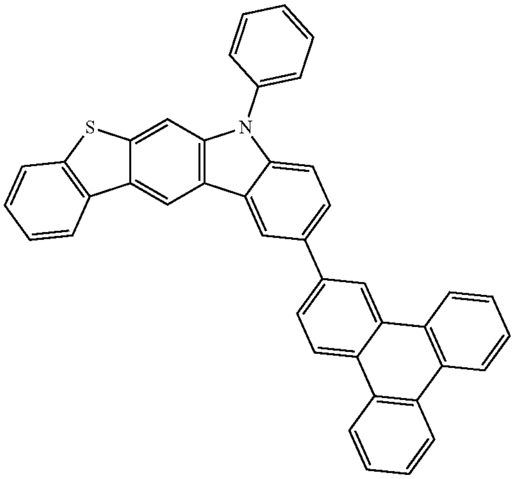
5-123
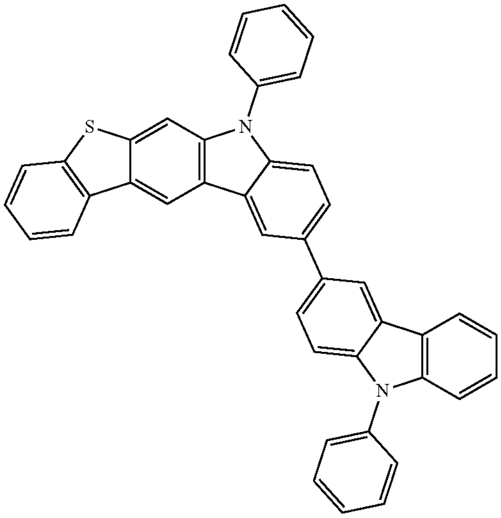
5-124
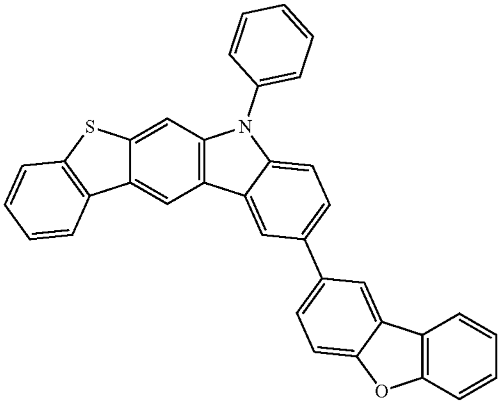
5-125
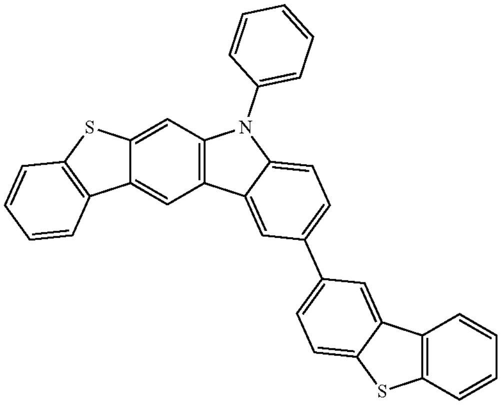
5-126
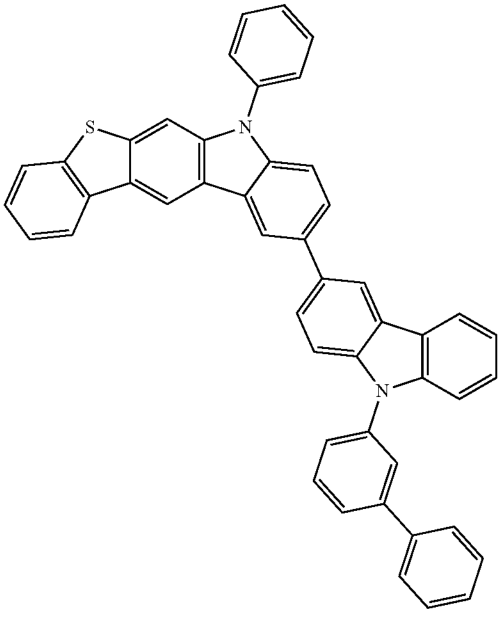

-continued
5-127
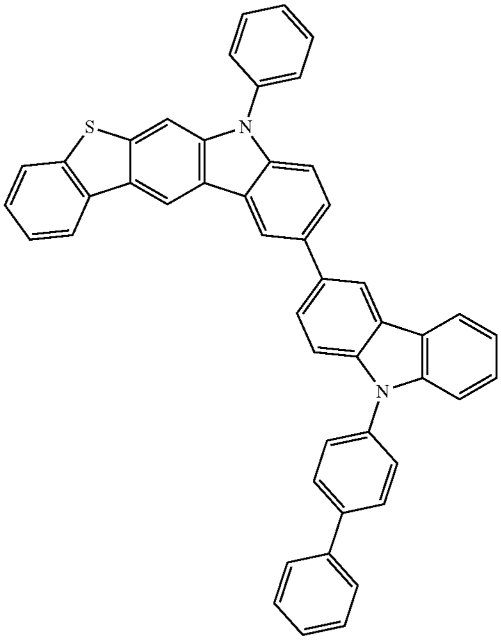
5-128
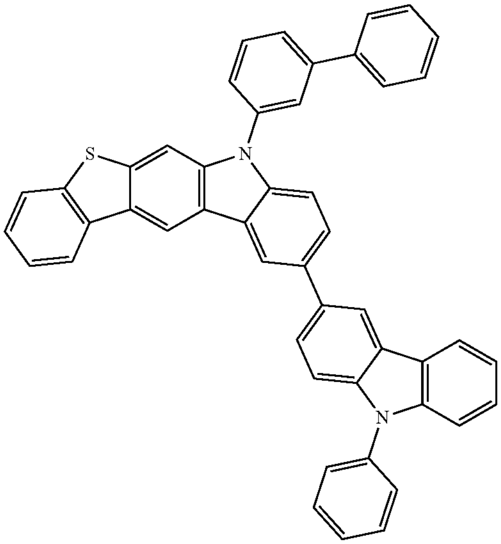
5-129
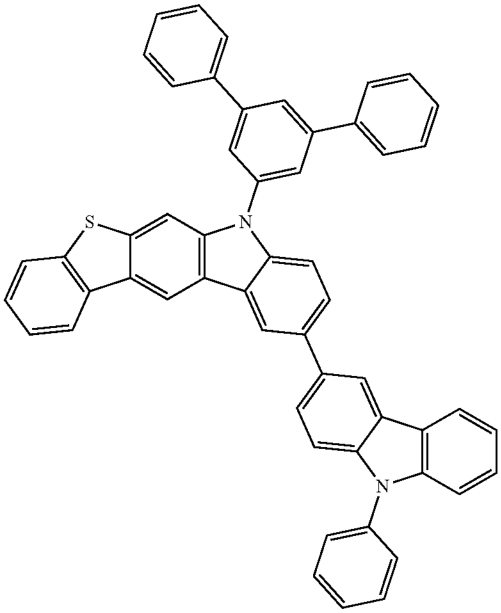
5-130
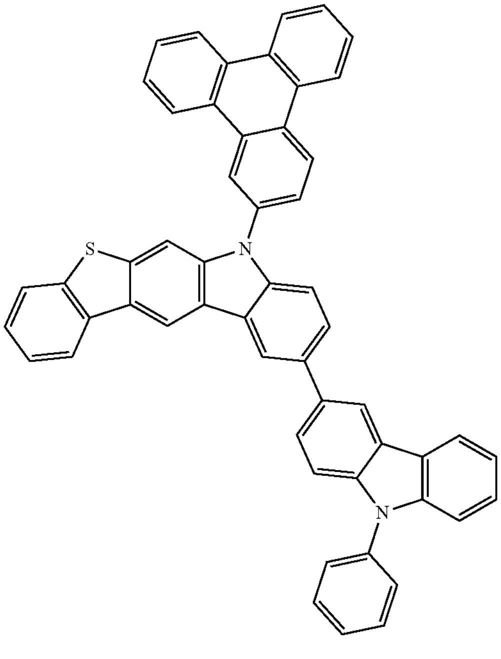

-continued
5-131
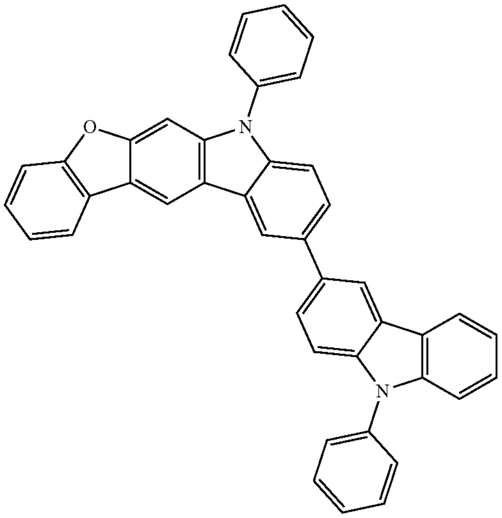
5-132
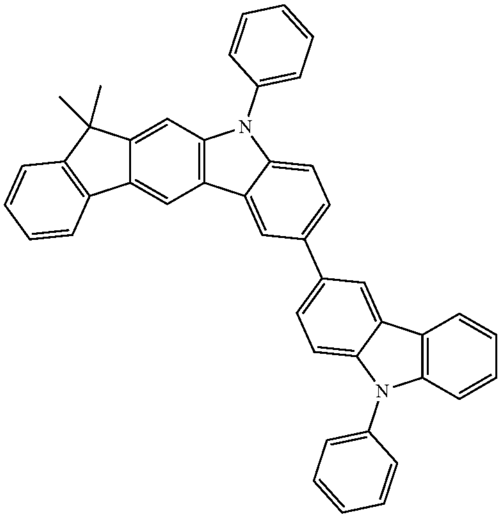
5-133
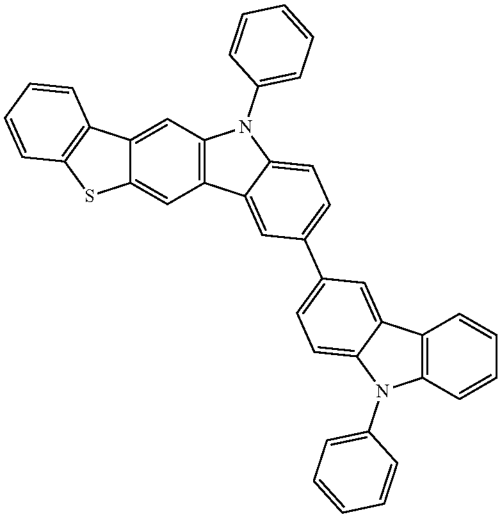
5-134
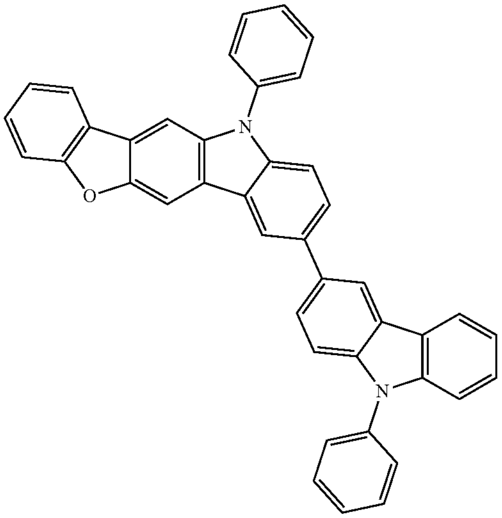
5-135
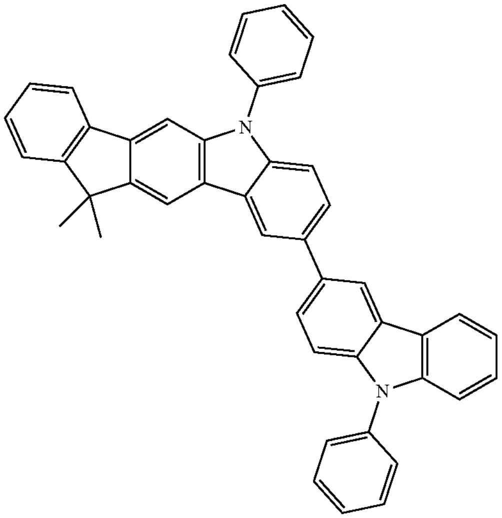
5-136
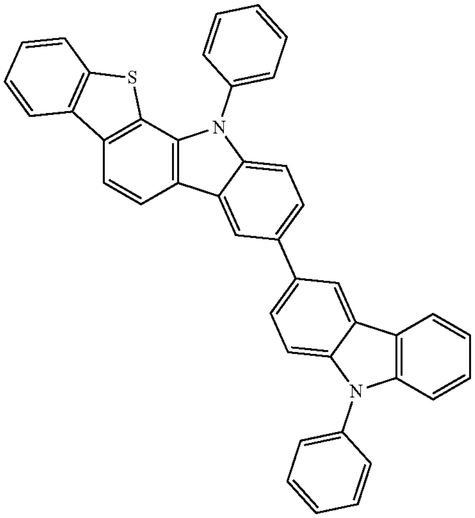

-continued
5-137
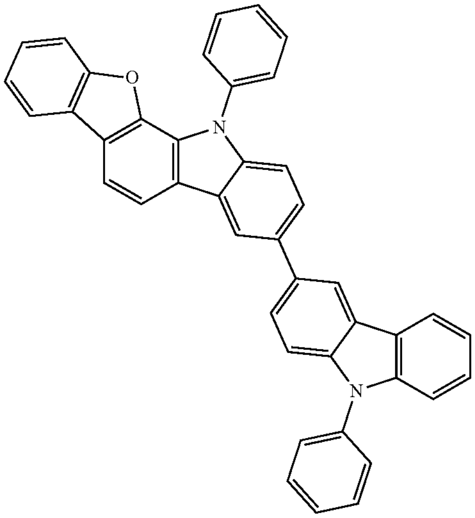
5-138
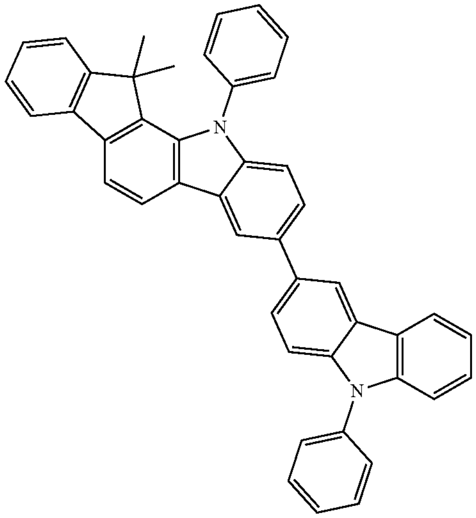
5-139
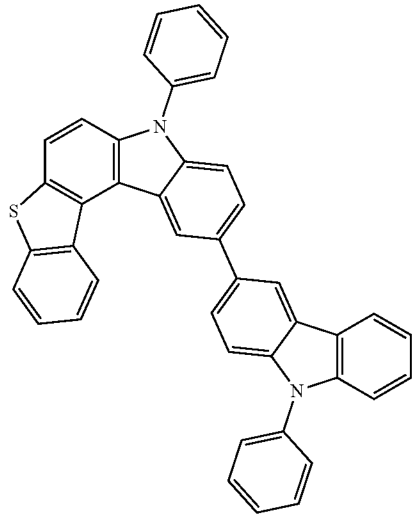
5-140
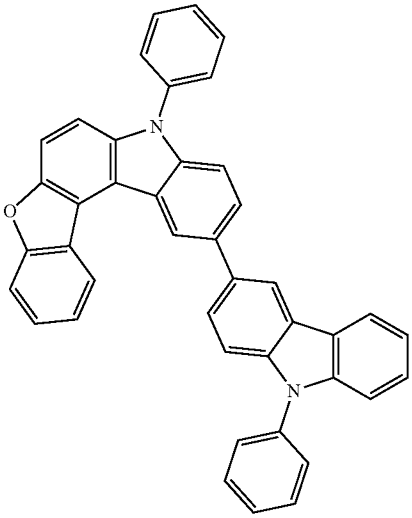
5-141
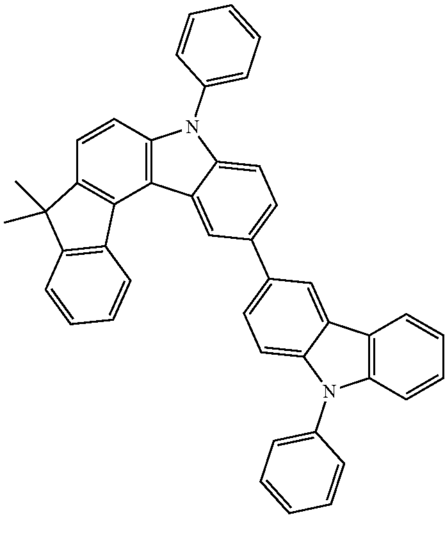
5-142
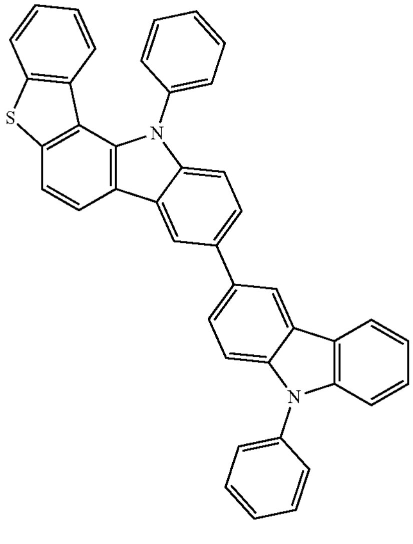

-continued
5-143
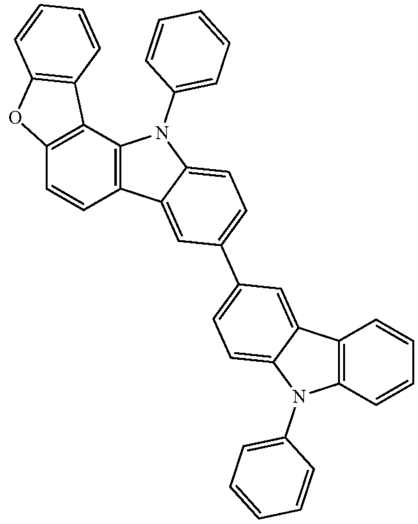
5-144
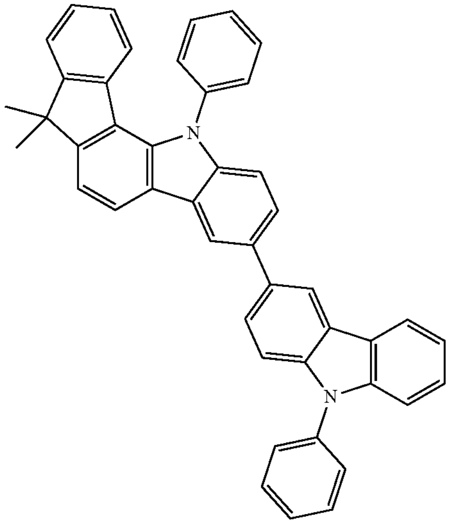
5-145
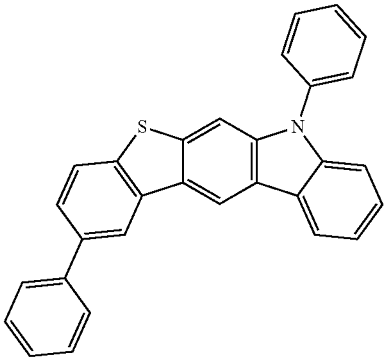
5-146
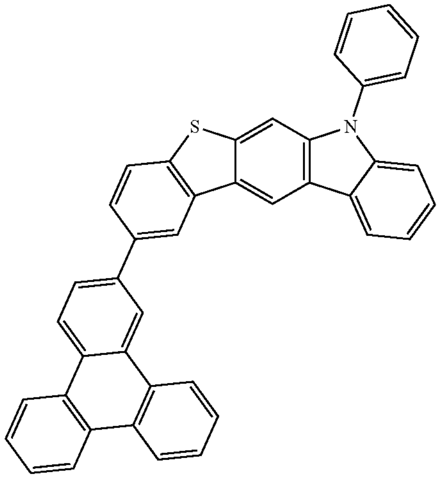
5-147
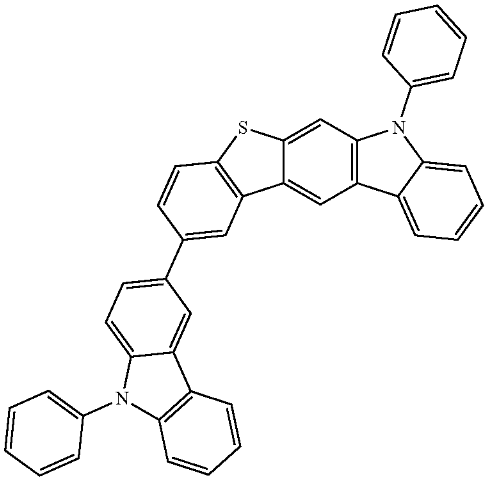
5-148
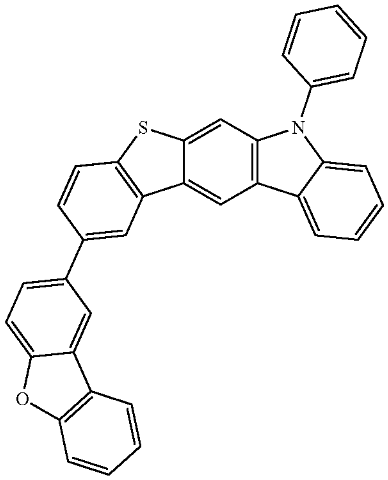

-continued
5-149
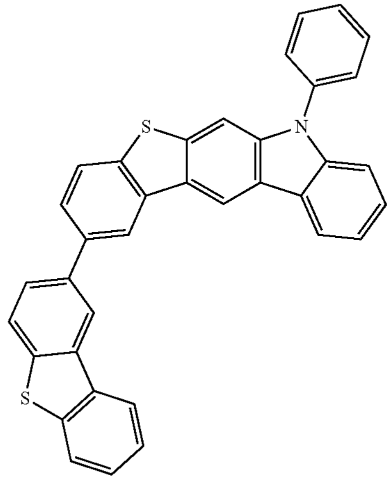
5-150
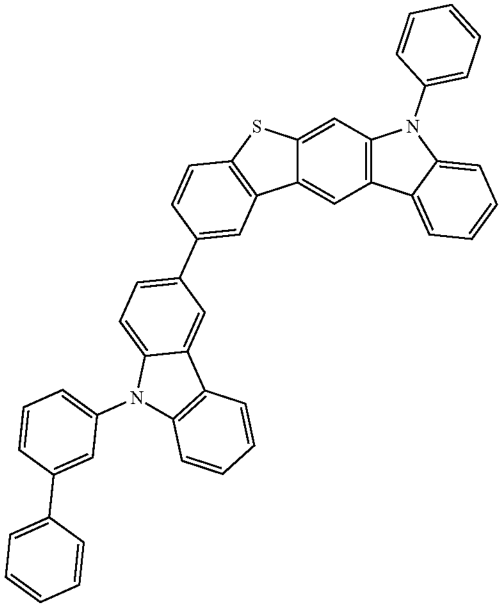
5-151
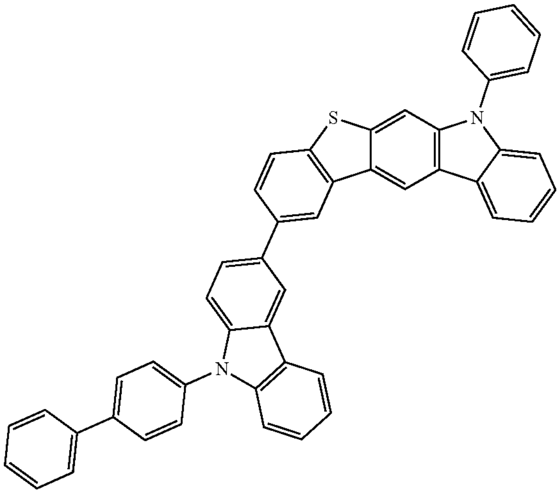
5-152
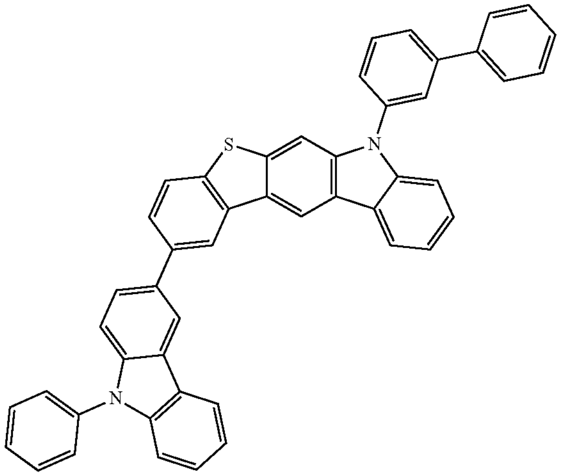

-continued
5-153
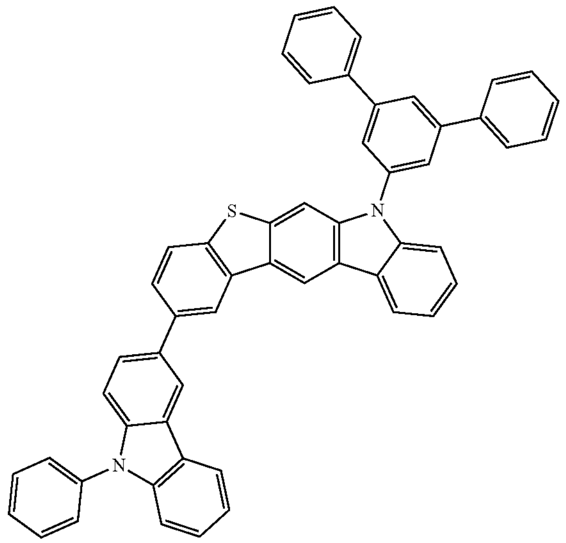
5-154
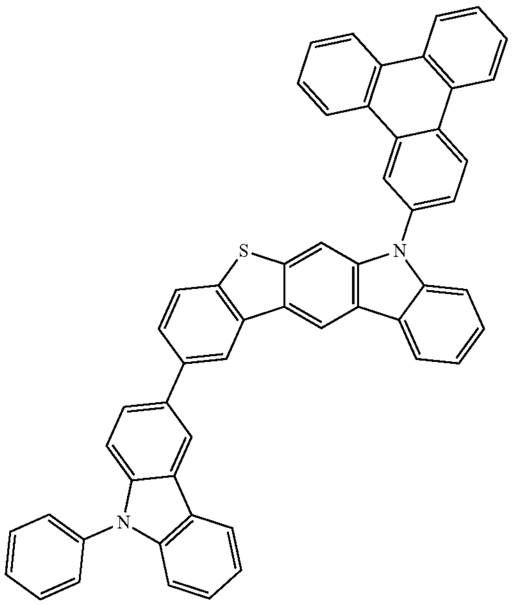
5-155
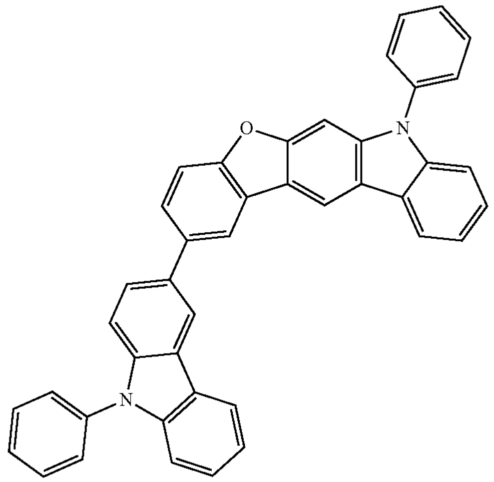
5-156
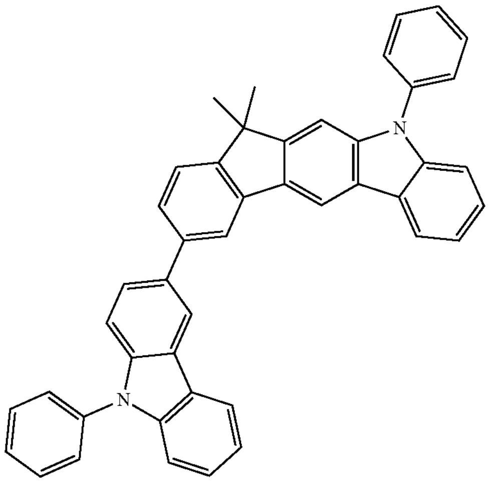
5-157
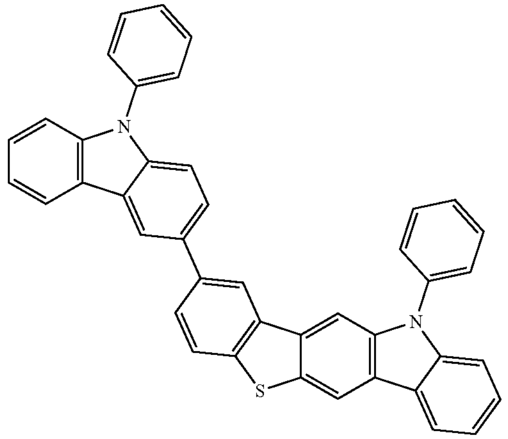
5-158
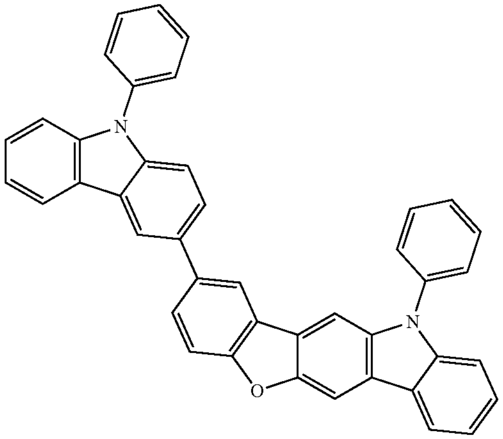

-continued
5-159
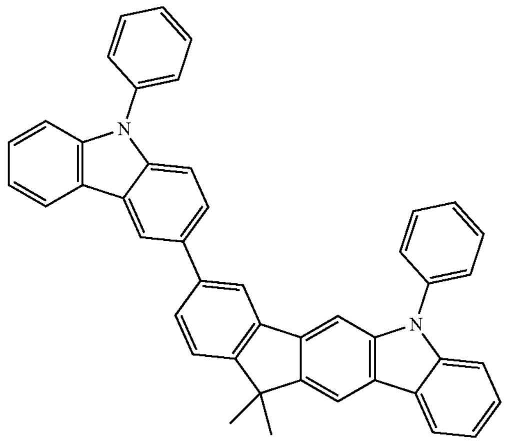
5-160
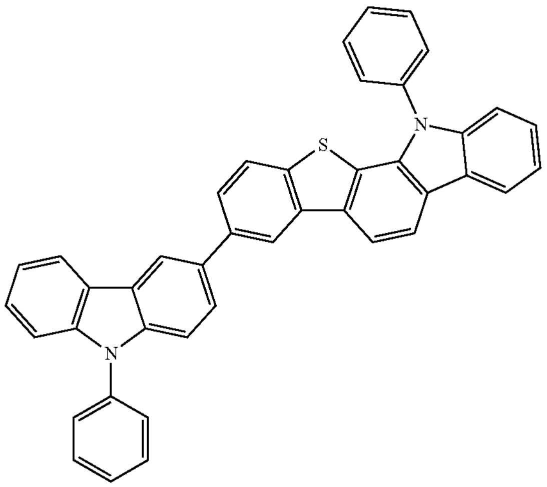
5-161
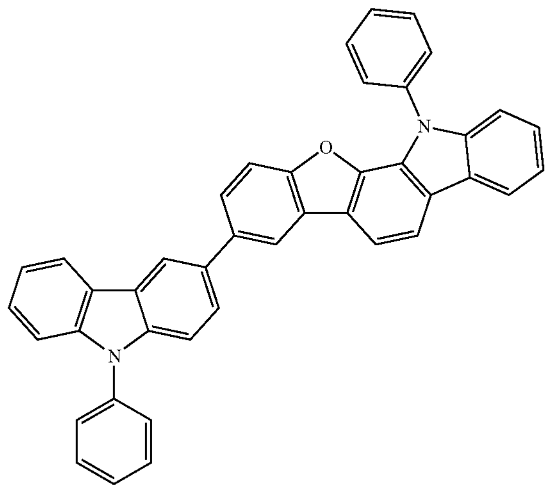
5-162
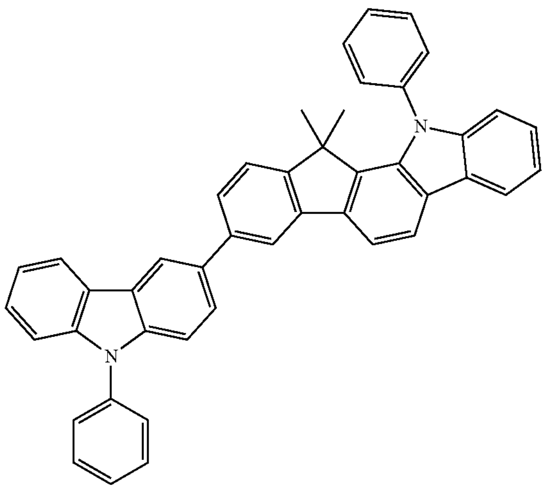
5-163
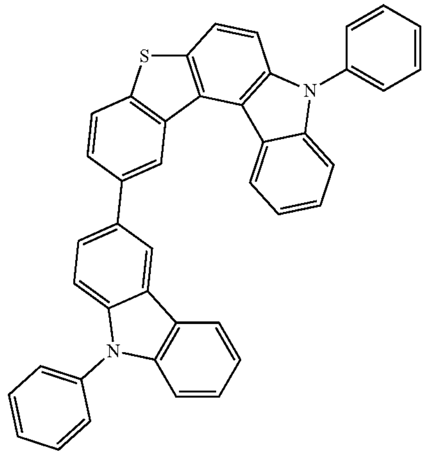
5-164
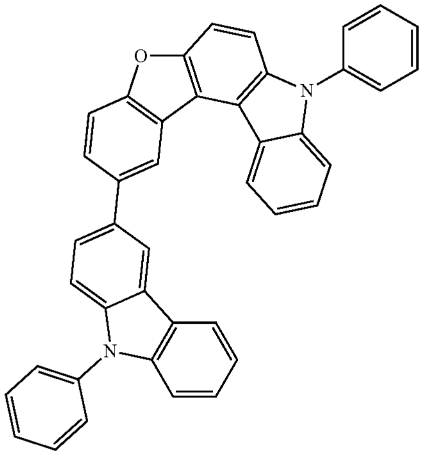

-continued 5-165

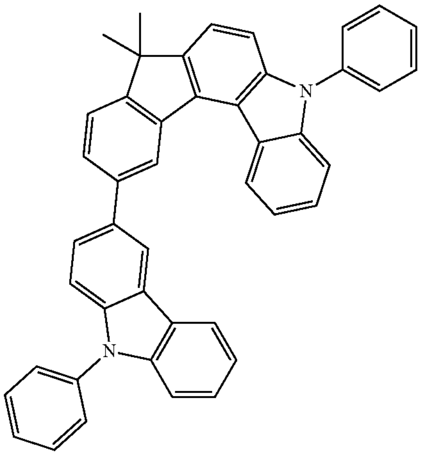

5-166

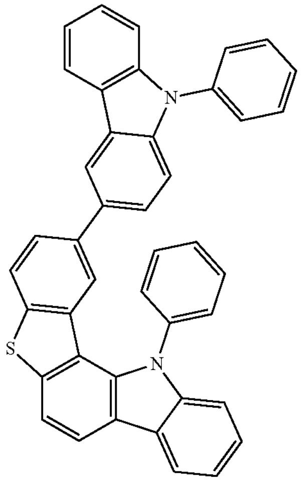

5-167

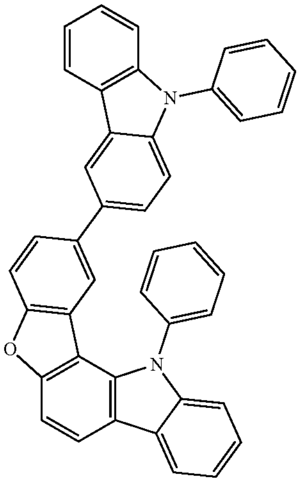

5-168

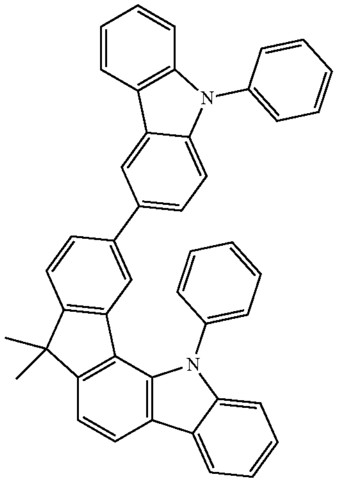

In addition, by introducing various substituents to the structures of Chemical Formulae 1 and 2, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structures of Chemical Formulae 1 and 2, the energy band gap may be finely controlled, and meanwhile, properties at interfaces between organic materials are enhanced, and material applications may become diverse.

Meanwhile, the heterocyclic compound represented by Chemical Formula 2 has a high glass transition temperature (Tg), and has excellent thermal stability. Such an increase in the thermal stability becomes an important factor providing driving stability to a device.

The heterocyclic compound according to one embodiment of the present application may be prepared using a multi-step chemical reaction. Some intermediate compounds are prepared first, and from the intermediate compounds, the heterocyclic compound of Chemical Formula 1 or 2 may be prepared. More specifically, the heterocyclic compound according to one embodiment of the present application may be prepared based on preparation examples to describe later.

In addition, another embodiment of the present application provides a composition for an organic material layer of an organic light emitting device, the composition comprising the heterocyclic compound represented by Chemical Formula 1 and the heterocyclic compound represented by Chemical Formula 2.

Specific descriptions on the heterocyclic compound represented by Chemical Formula 1 and the heterocyclic compound represented by Chemical Formula 2 are the same as the descriptions provided above.

In the composition, the heterocyclic compound represented by Chemical Formula 1: the heterocyclic compound represented by Chemical Formula 2 may have a weight ratio of 1:10 to 10:1, 1:8 to 8:1, 1:5 to 5:1 or 1:2 to 2:1, however, the weight ratio is not limited thereto.

The composition may be used when forming an organic material of an organic light emitting device, and may be more preferably used when forming a host of a light emitting layer.

The composition has a form in which two or more compounds are simply mixed, and materials in a powder state may be mixed before forming the organic material layer of the organic light emitting device, or compounds in a liquid state may be mixed at a proper temperature or higher. The composition is in a solid state below the melting point of each material, and may be maintained in a liquid state when adjusting a temperature.

The composition may further comprise materials known in the art such as solvents and additives.

The organic light emitting device according to one embodiment of the present application may be manufactured using common organic light emitting device manufacturing methods and materials except that one or more organic material layers are formed using the heterocyclic compound represented by Chemical Formula 1 and the heterocyclic compound represented by Chemical Formula 2 described above.

The compound represented by Chemical Formula 1 and the heterocyclic compound represented by Chemical Formula 2 may be formed into an organic material layer using a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

Specifically, the organic light emitting device according to one embodiment of the present application comprises a first electrode, a second electrode, and one or more organic material layers provided between the first electrode and the second electrode, wherein one or more layers of the organic material layers comprise the heterocyclic compound represented by Chemical Formula 1 and the heterocyclic compound represented by Chemical Formula 2.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 and the heterocyclic compound according to Chemical Formula 2 may be used as a material of the blue organic light emitting device.

In one embodiment of the present application, the organic light emitting device may be a green organic light emitting device, and the compound represented by Chemical Formula 1 and the heterocyclic compound represented by Chemical Formula 2 may be used as a material of the green organic light emitting device.

In one embodiment of the present application, the organic light emitting device may be a red organic light emitting device, and the compound represented by Chemical Formula 1 and the heterocyclic compound represented by Chemical Formula 2 may be used as a material of the red organic light emitting device.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

In the organic light emitting device provided in one embodiment of the present application, the organic material layer comprises at least one of a hole blocking layer, an electron injection layer and an electron transfer layer, and the at least one of a hole blocking layer, an electron injection layer and an electron transfer layer comprises the heterocyclic compound represented by Chemical Formula 1 and the heterocyclic compound represented by Chemical Formula 2 at the same time.

In one embodiment of the present application, the organic material layer comprises a light emitting layer, and the light emitting layer comprises the heterocyclic compound represented by Chemical Formula 1 and the heterocyclic compound represented by Chemical Formula 2.

In one embodiment of the present application, the organic material layer comprises a light emitting layer, the light emitting layer comprises a host material, and the host material comprises the heterocyclic compound represented by Chemical Formula 1 and the heterocyclic compound represented by Chemical Formula 2.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

One embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

In the method for manufacturing an organic light emitting device provided in one embodiment of the present application, the forming of organic material layers is forming the heterocyclic compound of Chemical Formula 1 and the heterocyclic compound of Chemical Formula 2 using a thermal vacuum deposition method after pre-mixing.

The pre-mixing means first mixing the heterocyclic compound of Chemical Formula 1 and the heterocyclic compound of Chemical Formula 2 in one source of supply before depositing on the organic material layer. Pre-mixing uses one source of supply instead of two or three sources of supply, and has an advantage of more simplifying a process.

The premixed material may be referred to as the composition for an organic material layer according to one embodiment of the present application.

When pre-mixing as above, unique thermal properties of each material need to be checked before mixing. Herein, depositing a pre-mixed host material from one source of supply may greatly affect deposition conditions comprising a deposition rate depending on the unique thermal properties of the materials. When thermal properties between two or more types of materials that are pre-mixed are not similar and very different, repeatability and reproducibility in a deposition process may not be maintained, which means that an OLED that is all uniform may not be manufactured in one deposition process.

In order to overcome this, electrical properties of the material may be tuned by using a proper combination of basic structure and substituents of each material and in addition thereto, thermal properties of the materials may also be controlled depending on the molecular structure form.

Therefore, by using various substituents in Chemical Formula 2 in addition to the basic skeleton as well as using C—N bonding of fused carbazole as in Chemical Formula 2, diversity of various pre-mixing deposition processes between host-host may be secured by controlling thermal properties of each material as well as attempting to enhance device performance. This has an advantage of securing diversity of a pre-mixing deposition process using three, four or more host materials as well as two compounds as a host.

In the organic light emitting device according to one embodiment of the present application, materials other than the heterocyclic compound of Chemical Formula 1 and the heterocyclic compound of Chemical Formula 2 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MT DATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

<Preparation Example 1> Preparation of Compound 1-1

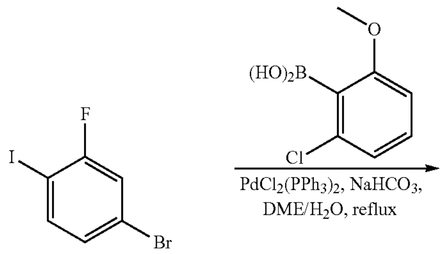

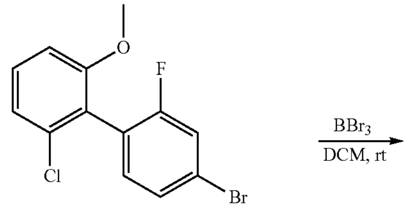

1-1-6

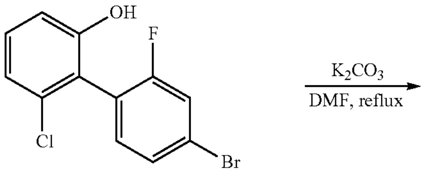

1-1-5

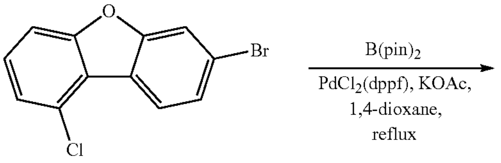

1-1-4

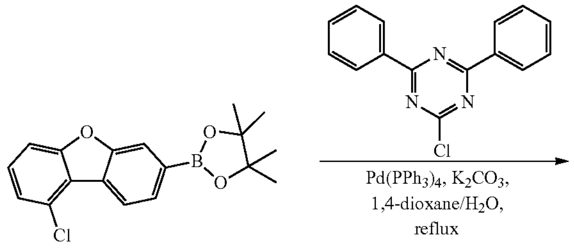

1-1-3

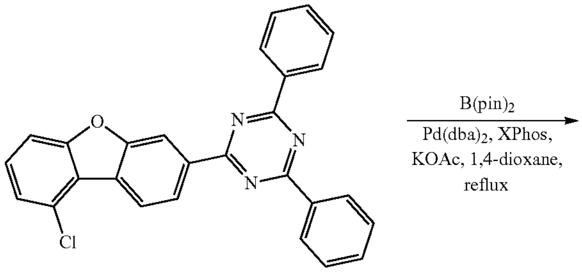

1-1-2

-continued

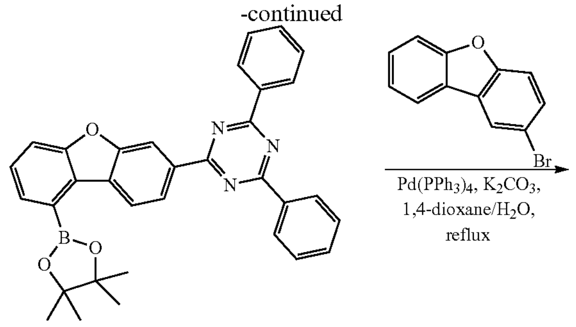

1-1-1

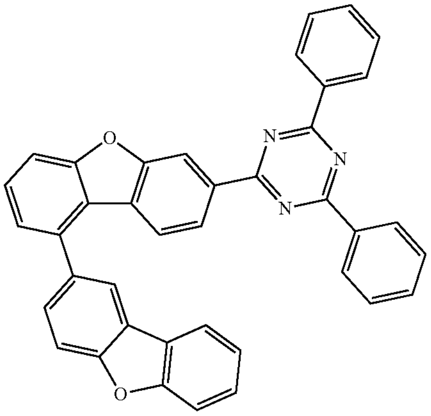

1-1

1) Preparation of Compound 1-1-6

4-Bromo-2-fluoro-1-iodobenzene (200.0 g, 664.7 mM), (2-chloro-6-methoxyphenyl)boronic acid (148.7 g, 794.6 mM), $Pd(PPh)_4$ (38.4 g, 33.2 mM) and $K_2CO_3$ (183.7 g, 1329.4 mM) were dissolved in 1,4-dioxane/$H_2O$ (1 L/200 mL), and refluxed for 24 hours. After the reaction was completed, the result was extracted by introducing distilled water and dichloromethane (DCM) thereto at room temperature, and after drying the organic layer with $MgSO_4$, the solvent was removed using a rotary evaporator. The reaction material was purified by column chromatography (DCM: Hex=1:3) to obtain target Compound 1-1-6 (178 g, 85%).

2) Preparation of Compound 1-1-5

Compound 1-1-6 (178 g, 564.1 mM) and $BBr_3$ (107 mL, 1128.2 mM) were dissolved in DCM (800 mL), and refluxed for 1 hour. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:1) to obtain target Compound 1-1-5 (153.1 g, 90%).

3) Preparation of Compound 1-1-4

Compound 1-1-5 (153 g, 507.4 mM) and $K_2CO_3$ (140.3 g, 1014.8 mM) were dissolved in dimethylformamide (DMF) (800 mL), and refluxed for 4 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:9), and recrystallized with methanol to obtain target Compound 1-1-4 (88.5 g, 62%).

4) Preparation of Compound 1-1-3

Compound 1-1-4 (88.5 g, 314.4 mM), bis(pinacolato) diboron (159.7 g, 628.8 mM), $PdCl_2$(dppf) (23.0 g, 31.4 mM) and KOAc (92.6 g, 943.2 mM) were dissolved in 1,4-dioxane (500 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM: Hex=1:5) to obtain target Compound 1-1-3 (85.7 g, 83%).

5) Preparation of Compound 1-1-2

Compound 1-1-3 (85.0 g, 258.7 mM), 2-chloro-4,6-diphenyl-1,3,5-triazine (69.3 g, 258.7 mM), $Pd(PPh)_4$ (14.9 g, 12.9 mM) and $K_2CO_3$ (71.5 g, 517.4 mM) were dissolved in 1,4-dioxane/$H_2O$ (1000 mL/200 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:4), and recrystallized with methanol to obtain target Compound 1-1-2 (79.7 g, 71%).

6) Preparation of Compound 1-1-1

Compound 1-1-2 (79.0 g, 182.1 mM), bis(pinacolato) diboron (92.5 g, 364.2 mM), $Pd(dba)_2$ (10.5 g, 18.2 mM), XPhos (17.4 g, 36.4 mM) and KOAc (53.6 g, 546.3 mM) were dissolved in 1,4-dioxane (800 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:5) to obtain target Compound 1-1-1 (84.2 g, 88%).

7) Preparation of Compound 1-1

Compound 1-1-1 (15.0 g, 28.5 mM), 2-bromodibenzo[b, d]furan (7.8 g, 31.4 mM), $Pd(PPh)_4$ (1.6 g, 1.4 mM) and $K_2CO_3$ (7.9 g, 57.0 mM) were dissolved in 1,4-dioxane/$H_2O$ (200 mL/40 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM: Hex=1:3), and recrystallized with methanol to obtain target Compound 1-1 (13.2 g, 82%).

Target Compound A was synthesized in the same manner as in Preparation Example 1 except that Intermediate A of the following Table 1 was used instead of 2-chloro-4,6-diphenyl-1,3,5-triazine, and Intermediate B of the following Table 1 was used instead of 2-bromodibenzo[b,d]furan.

TABLE 1

| Compound No. | Intermediate A | Intermediate B | Target compound A | Yield |
|---|---|---|---|---|
| 1-2 | 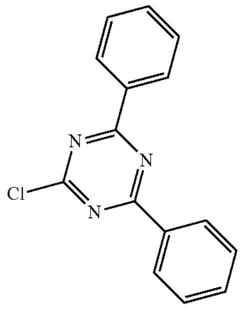 [SMILES: Clc1nc(-c2ccccc2)nc(-c2ccccc2)n1] | 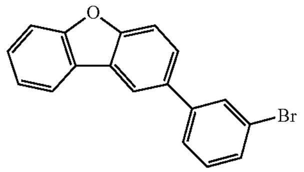 [SMILES: Brc1cccc(-c2ccc3oc4ccccc4c3c2)c1] | 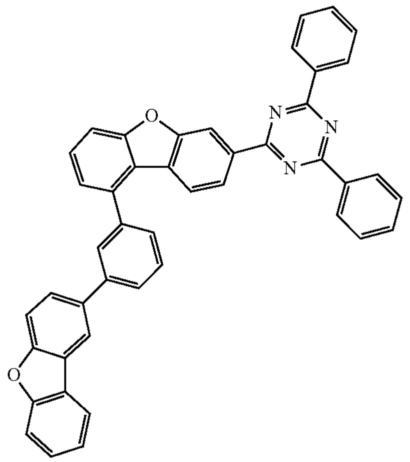 [SMILES: c1ccc(-c2nc(-c3ccccc3)nc(-c3ccc4c(c3)oc3cccc(-c5cccc(-c6ccc7oc8ccccc8c7c6)c5)c34)n2)cc1] | 20% |
| 1-14 | | 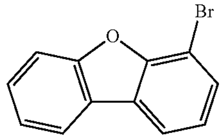 | 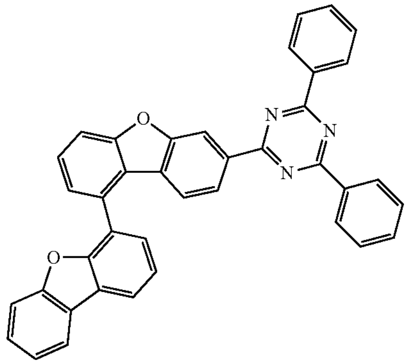 [SMILES: c1ccc(-c2nc(-c3ccccc3)nc(-c3ccc4c(c3)oc3cccc(-c5cccc6c5oc5ccccc56)c34)n2)cc1] | 26% |

TABLE 1-continued
| Compound No. | Intermediate A | Intermediate B | Target compound A | Yield |
| --- | --- | --- | --- | --- |
| 1-18 | | 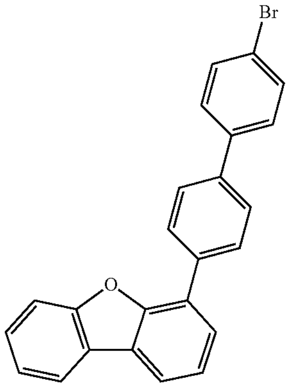 [SMILES: Brc1ccc(-c2ccc(-c3cccc4c3oc3ccccc34)cc2)cc1] | 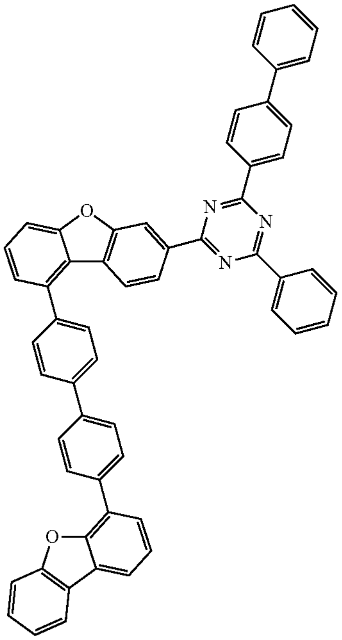 [SMILES: c1ccc(-c2ccc(-c3nc(-c4ccccc4)nc(-c4ccc5c(c4)oc4cccc(-c6ccc(-c7ccc(-c8cccc9c8oc8ccccc89)cc7)cc6)c45)n3)cc2)cc1] | 22% |
| 1-37 | | 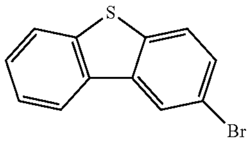 [SMILES: Brc1ccc2sc3ccccc3c2c1] | 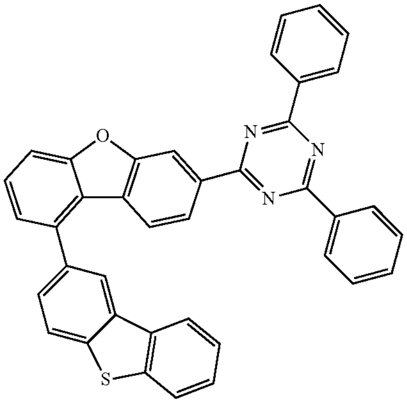 [SMILES: c1ccc(-c2nc(-c3ccccc3)nc(-c3ccc4c(c3)oc3cccc(-c5ccc6sc7ccccc7c6c5)c34)n2)cc1] | 23% |
| 1-38 | 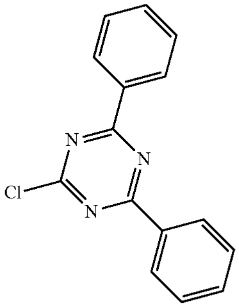 [SMILES: Clc1nc(-c2ccccc2)nc(-c2ccccc2)n1] | 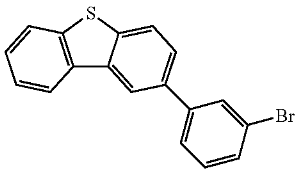 | 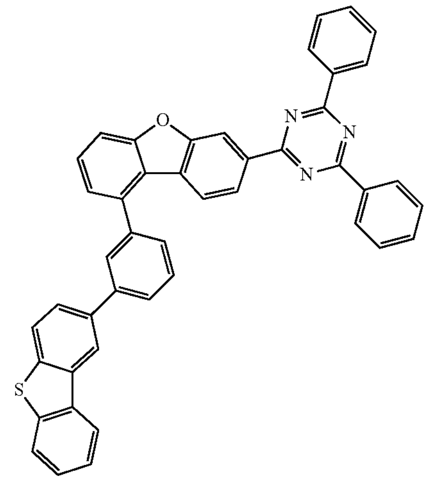 [SMILES: c1ccc(-c2nc(-c3ccccc3)nc(-c3ccc4c(c3)oc3cccc(-c5cccc(-c6ccc7sc8ccccc8c7c6)c5)c34)n2)cc1] | 25% |

TABLE 1-continued
| Compound No. | Intermediate A | Intermediate B | Target compound A | Yield |
|---|---|---|---|---|
| 1-49 | | 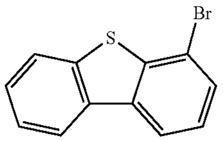 [SMILES: Brc1cccc2c1sc1ccccc12] | 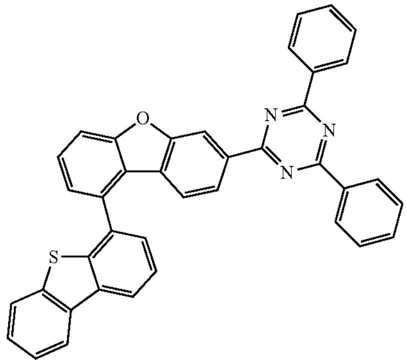 | 24% |
| 1-50 | | 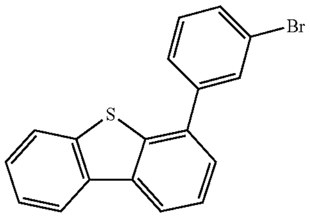 [SMILES: Brc1cccc(-c2cccc3c2sc2ccccc23)c1] | 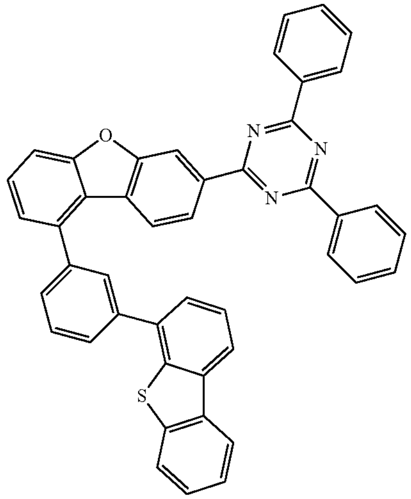 [SMILES: c1ccc(-c2nc(-c3ccccc3)nc(-c3ccc4c(c3)oc3cccc(-c5cccc(-c6cccc7c6sc6ccccc67)c5)c34)n2)cc1] | 22% |
| 1-61 | | 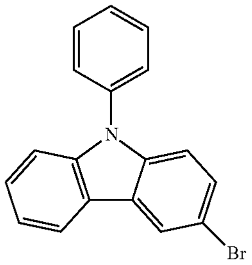 [SMILES: Brc1ccc2c(c1)c1ccccc1n2-c1ccccc1] | 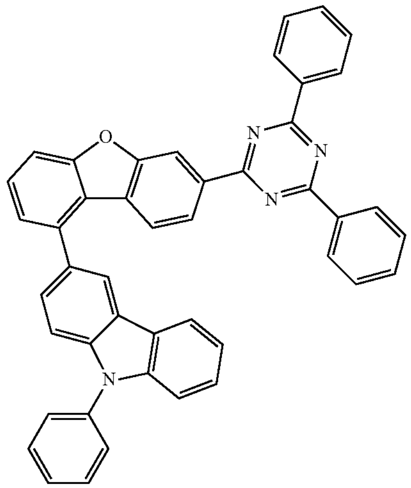 [SMILES: c1ccc(-c2nc(-c3ccccc3)nc(-c3ccc4c(c3)oc3cccc(-c5ccc6c(c5)c5ccccc5n6-c5ccccc5)c34)n2)cc1] | 26% |

TABLE 1-continued
| Compound No. | Intermediate A | Intermediate B | Target compound A | Yield |
|---|---|---|---|---|
| 1-81 | | 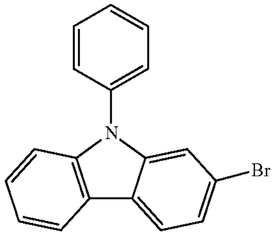 [SMILES: Brc1ccc2c3ccccc3n(-c3ccccc3)c2c1] | 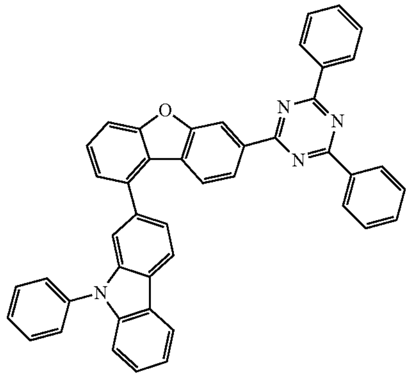 [SMILES: c1ccc(-c2nc(-c3ccccc3)nc(-c3ccc4c(c3)oc3cccc(-c5ccc6c7ccccc7n(-c7ccccc7)c6c5)c34)n2)cc1] | 23% |
<Preparation Example 2> Preparation of Compound 2-1
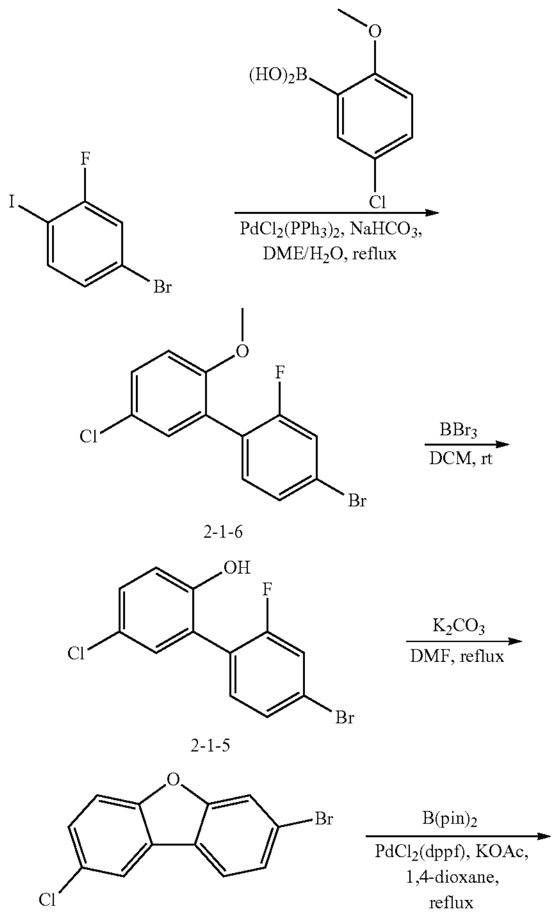
2-1-6
2-1-5
2-1-4
-continued
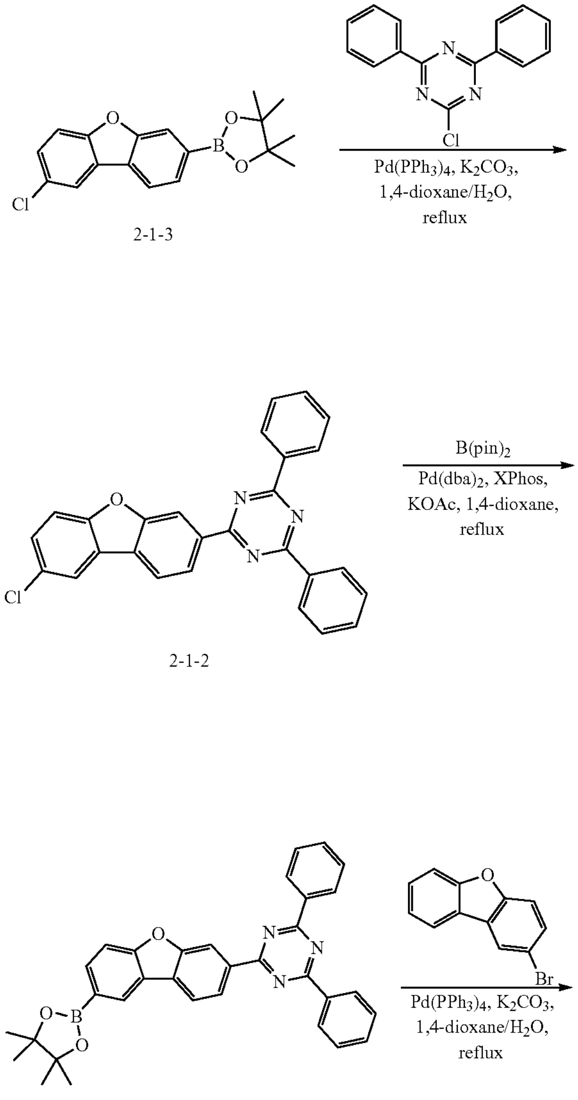
2-1-3
2-1-2
2-1-1

-continued

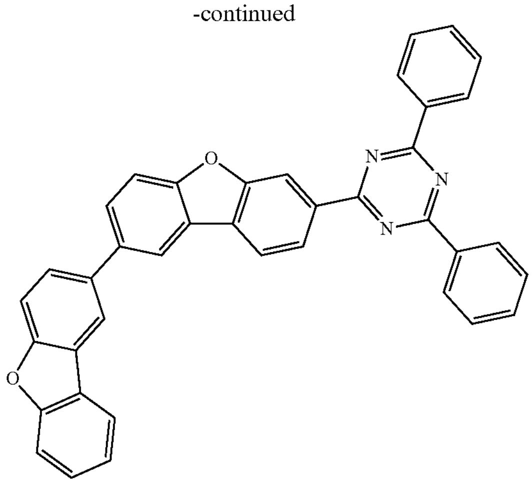

2-1

1) Preparation of Compound 2-1-6

4-Bromo-2-fluoro-1-iodobenzene (200.0 g, 664.7 mM), (5-chloro-2-methoxyphenyl)boronic acid (148.7 g, 794.6 mM), $Pd(PPh)_4$ (38.4 g, 33.2 mM) and $K_2CO_3$ (183.7 g, 1329.4 mM) were dissolved in 1,4-dioxane/$H_2O$ (1 L/200 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:4) to obtain target Compound 2-1-6 (174 g, 83%).

2) Preparation of Compound 2-1-5

Compound 2-1-6 (174 g, 551.4 mM) and $BBr_3$ (105 mL, 1102.8 mM) were dissolved in DCM (800 mL), and refluxed for 1 hour. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:1) to obtain target Compound 2-1-5 (148.0 g, 89%).

3) Preparation of Compound 2-1-4

Compound 2-1-5 (148 g, 491.3 mM) and $K_2CO_3$ (135.8 g, 982.8 mM) were dissolved in DMF (800 mL), and refluxed for 4 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:8), and recrystallized with methanol to obtain target Compound 2-1-4 (78.8 g, 57%).

4) Preparation of Compound 2-1-3

Compound 2-1-4 (78.0 g, 277.1 mM), bis(pinacolato) diboron (140.7 g, 554.2 mM), $PdCl_2(dppf)$ (20.3 g, 27.7 mM) and KOAc (81.6 g, 831.3 mM) were dissolved in 1,4-dioxane (500 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM: Hex=1:5) to obtain target Compound 2-1-3 (77.4 g, 85%).

5) Preparation of Compound 2-1-2

Compound 2-1-3 (77.0 g, 234.3 mM), 2-chloro-4,6-diphenyl-1,3,5-triazine (67.7 g, 234.3 mM), $Pd(PPh)_4$ (13.5 g, 11.7 mM) and $K_2CO_3$ (64.8 g, 468.6 mM) were dissolved in 1,4-dioxane/$H_2O$ (1000 mL/200 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:5), and recrystallized with methanol to obtain target Compound 2-1-2 (74.2 g, 73%).

6) Preparation of Compound 2-1-1

Compound 2-1-2 (74.0 g, 170.6 mM), bis(pinacolato) diboron (86.6 g, 341.2 mM), $Pd(dba)_2$ (9.8 g, 17.1 mM), XPhos (16.3 g, 34.1 mM) and KOAc (50.2 g, 511.8 mM) were dissolved in 1,4-dioxane (800 mL), and refluxed for 24 hours. After the reaction was completed, the result was extracted by introducing distilled water and dichloromethane (DCM) thereto at room temperature, and after drying the organic layer with $MgSO_4$, the solvent was removed using a rotary evaporator. The reaction material was purified by column chromatography (DCM:Hex=1:4) to obtain target Compound 2-1-1 (78.0 g, 87%).

7) Preparation of Compound 2-1

Compound 2-1-1 (15.0 g, 28.5 mM), 2-bromodibenzo[b,d]furan (7.8 g, 31.4 mM), $Pd(PPh)_4$ (1.6 g, 1.4 mM) and $K_2CO_3$ (7.9 g, 57.0 mM) were dissolved in 1,4-dioxane/$H_2O$ (200 mL/40 mL), and refluxed for 24 hours. After the reaction was completed, the result was extracted by introducing distilled water and dichloromethane (DCM) thereto at room temperature, and after drying the organic layer with $MgSO_4$, the solvent was removed using a rotary evaporator. The reaction material was purified by column chromatography (DCM:Hex=1:3), and recrystallized with methanol to obtain target Compound 2-1 (13.7 g, 85%).

Target Compound A was synthesized in the same manner as in Preparation Example 2 except that Intermediate A of the following Table 2 was used instead of 2-chloro-4,6-diphenyl-1,3,5-triazine, and Intermediate B of the following Table 2 was used instead of 2-bromodibenzo[b,d]furan.

TABLE 2
| Compound No. | Intermediate A | Intermediate B | Target compound A | Yield |
|---|---|---|---|---|
| 2-2 | 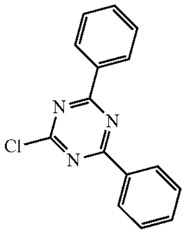 [SMILES: Clc1nc(-c2ccccc2)nc(-c2ccccc2)n1] | 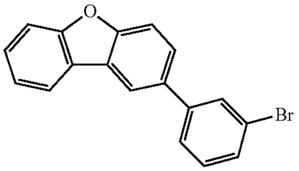 [SMILES: Brc1cccc(-c2ccc3oc4ccccc4c3c2)c1] | 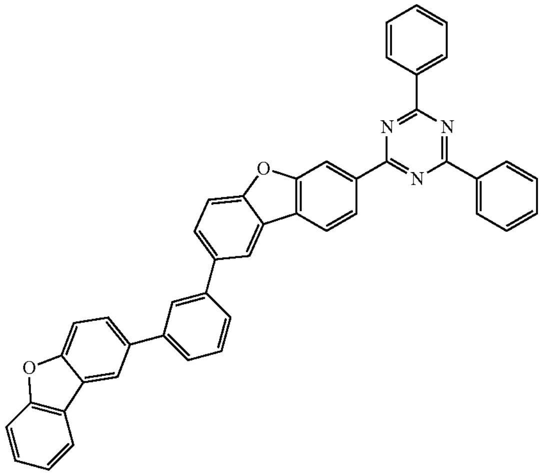 [SMILES: c1ccc(-c2nc(-c3ccccc3)nc(-c3ccc4c(c3)oc3ccc(-c5cccc(-c6ccc7oc8ccccc8c7c6)c5)cc34)n2)cc1] | 21% |
| 2-4 | | 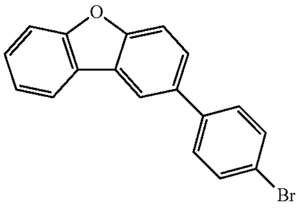 | 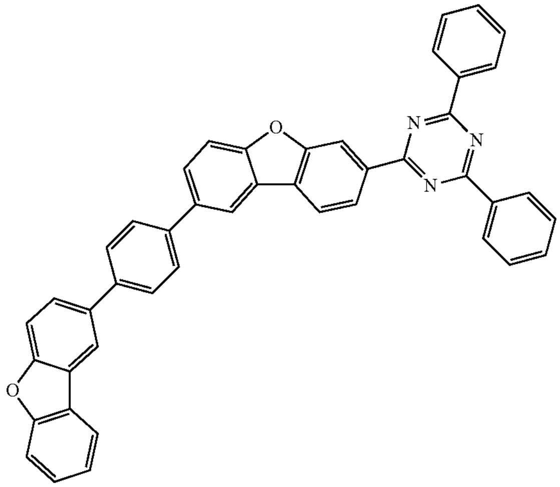 [SMILES: c1ccc(-c2nc(-c3ccccc3)nc(-c3ccc4c(c3)oc3ccc(-c5ccc(-c6ccc7oc8ccccc8c7c6)cc5)cc34)n2)cc1] | 22% |
| 2-14 | | 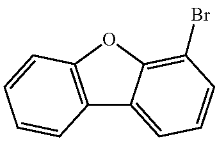 | 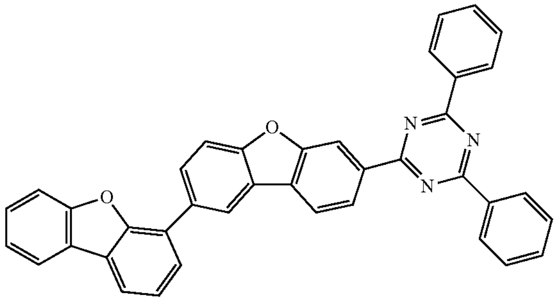 [SMILES: c1ccc(-c2nc(-c3ccccc3)nc(-c3ccc4c(c3)oc3ccc(-c5cccc6c5oc5ccccc56)cc34)n2)cc1] | 25% |

TABLE 2-continued
| Compound No. | Intermediate A | Intermediate B | Target compound A | Yield |
|---|---|---|---|---|
| 2-37 | | 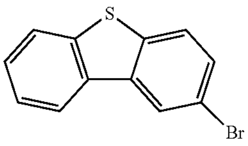 [SMILES: Brc1ccc2sc3ccccc3c2c1] | 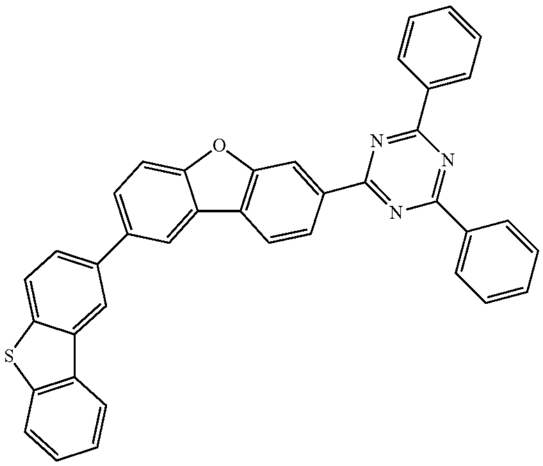 [SMILES: c1ccc(-c2nc(-c3ccccc3)nc(-c3ccc4c(c3)oc3ccc(-c5ccc6sc7ccccc7c6c5)cc34)n2)cc1] | 26% |
| 2-40 | | 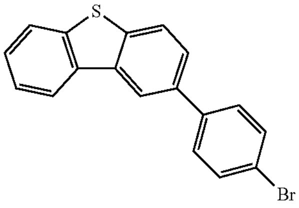 | 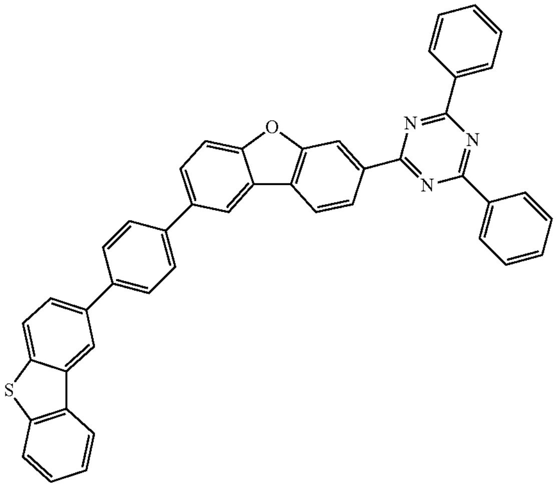 [SMILES: c1ccc(-c2nc(-c3ccccc3)nc(-c3ccc4c(c3)oc3ccc(-c5ccc(-c6ccc7sc8ccccc8c7c6)cc5)cc34)n2)cc1] | 20% |
| 2-49 | 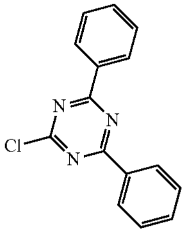 [SMILES: Clc1nc(-c2ccccc2)nc(-c2ccccc2)n1] | 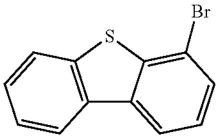 [SMILES: Brc1cccc2c1sc1ccccc12] | 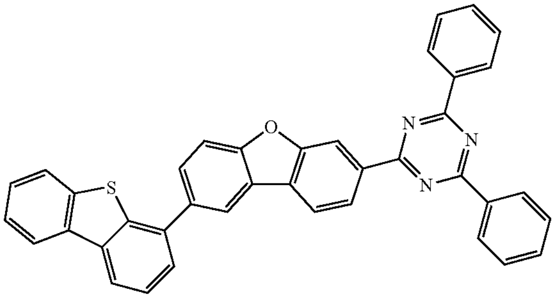 [SMILES: c1ccc(-c2nc(-c3ccccc3)nc(-c3ccc4c(c3)oc3ccc(-c5cccc6c5sc5ccccc56)cc34)n2)cc1] | 25% |

TABLE 2-continued
| Compound No. | Intermediate A | Intermediate B | Target compound A | Yield |
|---|---|---|---|---|
| 2-51 | | 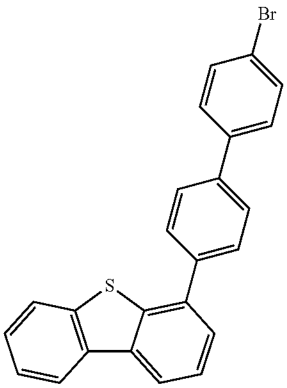 [SMILES: Brc1ccc(-c2ccc(-c3cccc4c3sc3ccccc34)cc2)cc1] | 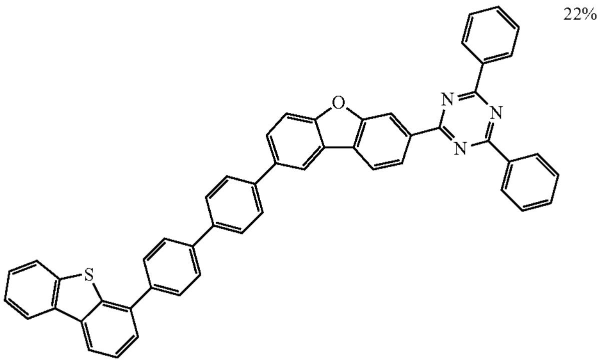 | 22% |
| 2-61 | | 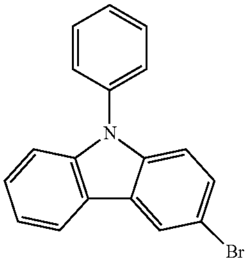 [SMILES: Brc1ccc2c(c1)c1ccccc1n2-c1ccccc1] | 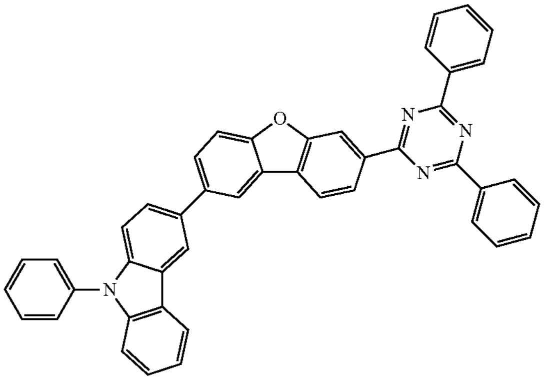 [SMILES: c1ccc(-c2nc(-c3ccccc3)nc(-c3ccc4c(c3)oc3ccc(-c5ccc6c(c5)c5ccccc5n6-c5ccccc5)cc34)n2)cc1] | 26% |
| 2-81 | | 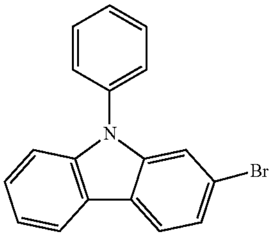 [SMILES: Brc1ccc2c3ccccc3n(-c3ccccc3)c2c1] | 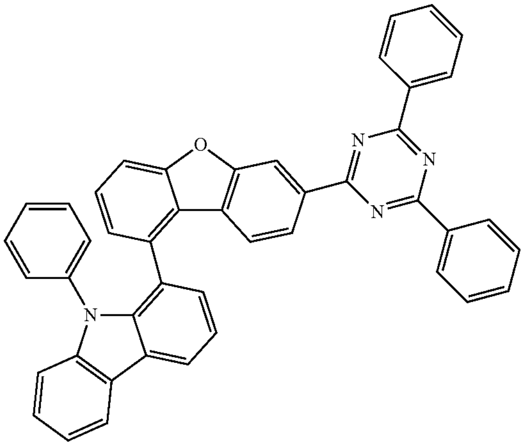 [SMILES: c1ccc(-c2nc(-c3ccccc3)nc(-c3ccc4c(c3)oc3cccc(-c5cccc6c7ccccc7n(-c7ccccc7)c56)c34)n2)cc1] | 23% |

<Preparation Example 3> Preparation of Compound 3-1

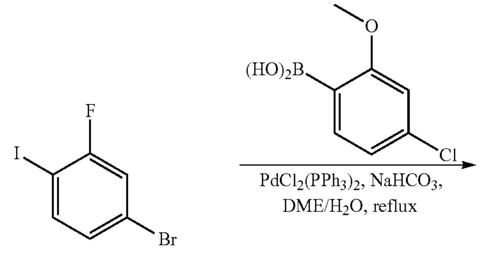

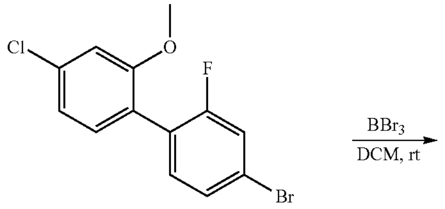

3-1-6

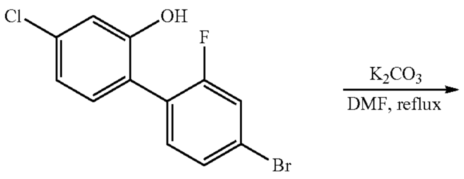

3-1-5

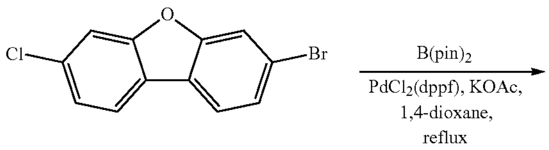

3-1-4

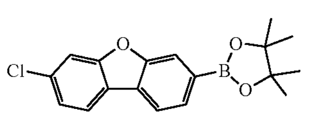

3-1-3

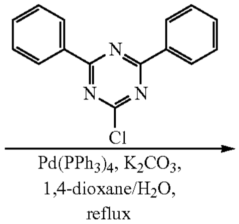

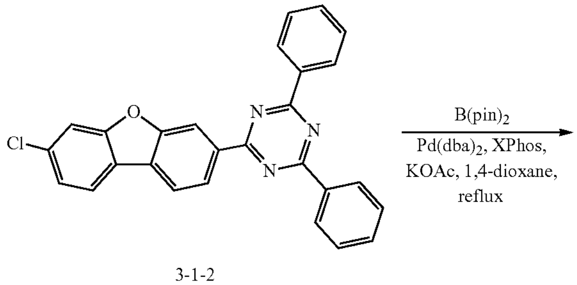

3-1-2

-continued

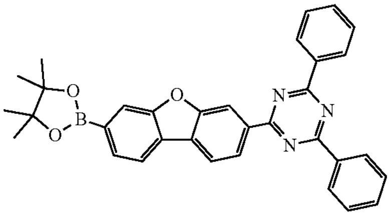

3-1-1

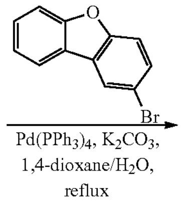

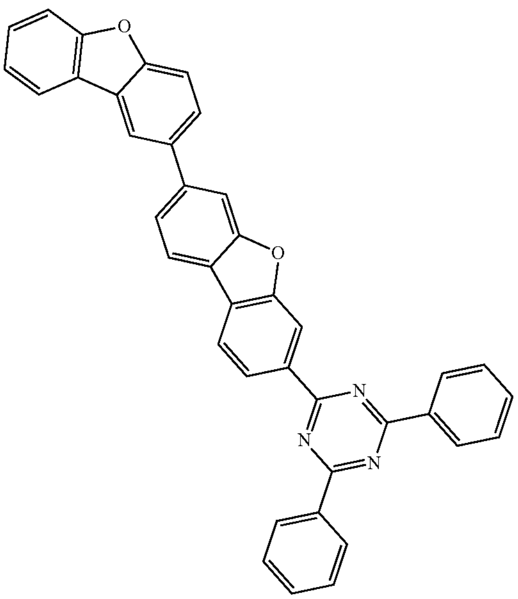

3-1

1) Preparation of Compound 3-1-6

4-Bromo-2-fluoro-1-iodobenzene (200.0 g, 664.7 mM), (4-chloro-2-methoxyphenyl)boronic acid (148.7 g, 794.6 mM), $Pd(PPh)_4$ (38.4 g, 33.2 mM) and $K_2CO_3$ (183.7 g, 1329.4 mM) were dissolved in 1,4-dioxane/$H_2O$ (1 L/200 mL), and refluxed for 24 hours. After the reaction was completed, the result was extracted by introducing distilled water and dichloromethane (DCM) thereto at room temperature, and after drying the organic layer with $MgSO_4$, the solvent was removed using a rotary evaporator. The reaction material was purified by column chromatography (DCM:Hex=1:3) to obtain target Compound 3-1-6 (170 g, 81%).

2) Preparation of Compound 3-1-5

Compound 3-1-6 (170 g, 538.7 mM) and $BBr_3$ (102 mL, 1078 mM) were dissolved in DCM (800 mL), and refluxed for 1 hour. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:1) to obtain target Compound 3-1-5 (148 g, 91%).

3) Preparation of Compound 3-1-4

Compound 3-1-5 (148 g, 490.8 mM) and $K_2CO_3$ (135.6 g, 981.6 mM) were dissolved in DMF (800 mL), and refluxed for 4 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:9), and recrystallized with methanol to obtain target Compound 3-1-4 (84.1 g, 61%).

4) Preparation of Compound 3-1-3

Compound 3-1-4 (84.1 g, 298.8 mM), bis(pinacolato) diboron (151.6 g, 597.5 mM), $PdCl_2$(dppf) (21.9 g, 29.9 mM) and KOAc (88.0 g, 896.4 mM) were dissolved in 1,4-dioxane (500 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM: Hex=1:5) to obtain target Compound 3-1-3 (82.6 g, 84%).

5) Preparation of Compound 3-1-2

Compound 3-1-3 (82.6 g, 251.4 mM), 2-chloro-4,6-diphenyl-1,3,5-triazine (67.3 g, 251.4 mM), $Pd(PPh)_4$ (14.6 g, 12.6 mM) and $K_2CO_3$ (69.49 g, 502.8 mM) were dissolved in 1,4-dioxane/$H_2O$ (1000 mL/200 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:4), and recrystallized with methanol to obtain target Compound 3-1-2 (79.7 g, 71%).

6) Preparation of Compound 3-1-1

Compound 3-1-2 (76.3 g, 175.9 mM), bis(pinacolato) diboron (92.5 g, 351.7 mM), $Pd(dba)_2$ (10.1 g, 17.6 mM), XPhos (16.8 g, 35.2 mM) and KOAc (51.8 g, 527.6 mM) were dissolved in 1,4-dioxane (800 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:5) to obtain target Compound 3-1-1 (79.5 g, 83%).

7) Preparation of Compound 3-1

Compound 3-1-1 (15.0 g, 28.5 mM), 2-bromodibenzo[b,d]furan (7.8 g, 31.4 mM), $Pd(PPh)_4$ (1.6 g, 1.4 mM) and $K_2CO_3$ (7.9 g, 57.0 mM) were dissolved in 1,4-dioxane/$H_2O$ (200 mL/40 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM: Hex=1:3), and recrystallized with methanol to obtain target Compound 3-1 (13.6 g, 85%).

Target Compound A was synthesized in the same manner as in Preparation Example 3 except that Intermediate A of the following Table 3 was used instead of 2-chloro-4,6-diphenyl-1,3,5-triazine, and Intermediate B of the following Table 3 was used instead of 2-bromodibenzo[b,d]furan.

TABLE 3

| Compound No. | Intermediate A | Intermediate B | Target compound A | Yield |
|---|---|---|---|---|
| 3-2 | 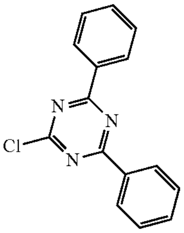 [SMILES: Clc1nc(-c2ccccc2)nc(-c2ccccc2)n1] | 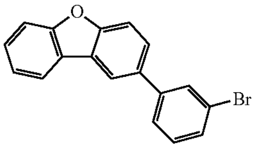 [SMILES: Brc1cccc(-c2ccc3oc4ccccc4c3c2)c1] | 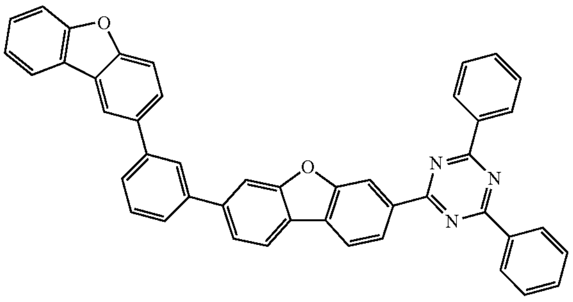 | 21% |
| 3-14 | | 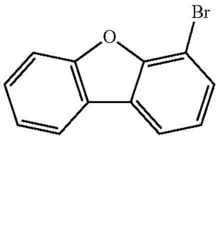 [SMILES: Brc1cccc2c1oc1ccccc12] | 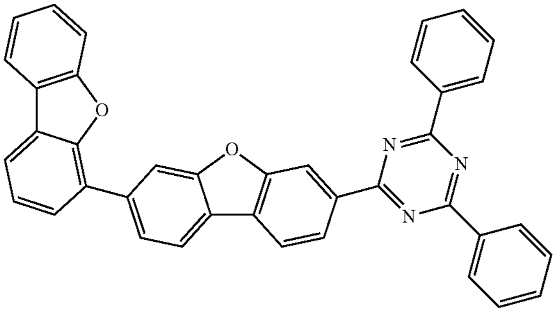 [SMILES: c1ccc(-c2nc(-c3ccccc3)nc(-c3ccc4c(c3)oc3cc(-c5cccc6c5oc5ccccc56)ccc34)n2)cc1] | 25% |

TABLE 3-continued
| Compound No. | Intermediate A | Intermediate B | Target compound A | Yield |
| --- | --- | --- | --- | --- |
| 3-18 | | 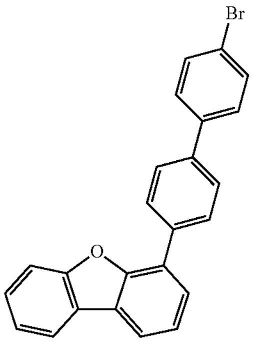 [SMILES: Brc1ccc(-c2ccc(-c3cccc4c3oc3ccccc34)cc2)cc1] | 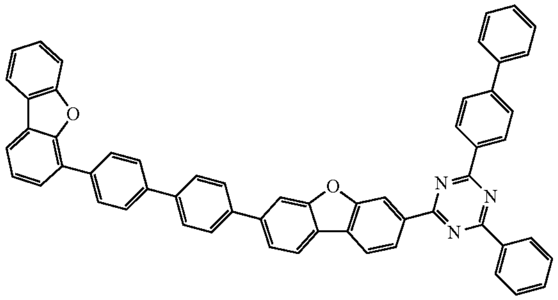 [SMILES: c1ccc(-c2ccc(-c3nc(-c4ccccc4)nc(-c4ccc5c(c4)oc4cc(-c6ccc(-c7ccc(-c8cccc9c8oc8ccccc89)cc7)cc6)ccc45)n3)cc2)cc1] | 24% |
| 3-37 | | 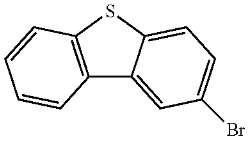 [SMILES: Brc1ccc2sc3ccccc3c2c1] | 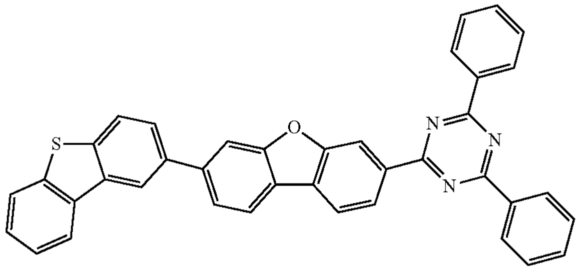 [SMILES: c1ccc(-c2nc(-c3ccccc3)nc(-c3ccc4c(c3)oc3cc(-c5ccc6sc7ccccc7c6c5)ccc34)n2)cc1] | 22% |
| 3-38 | | 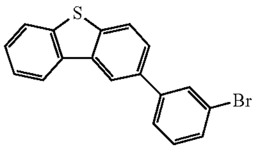 [SMILES: Brc1cccc(-c2ccc3sc4ccccc4c3c2)c1] | 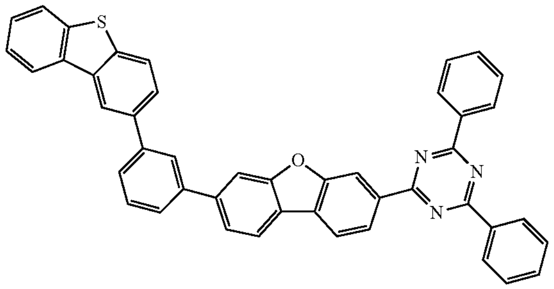 [SMILES: c1ccc(-c2nc(-c3ccccc3)nc(-c3ccc4c(c3)oc3cc(-c5cccc(-c6ccc7sc8ccccc8c7c6)c5)ccc34)n2)cc1] | 23% |
| 3-49 | | 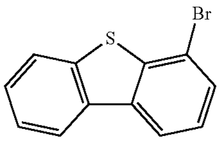 [SMILES: Brc1cccc2c1sc1ccccc12] | 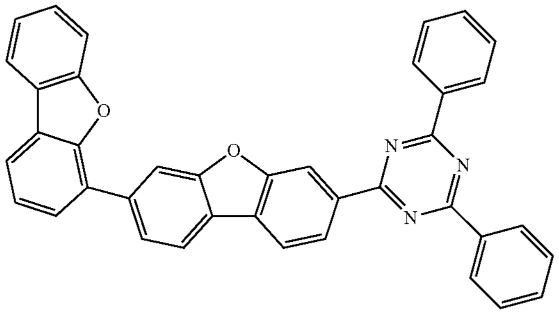 [SMILES: c1ccc(-c2nc(-c3ccccc3)nc(-c3ccc4c(c3)oc3cc(-c5cccc6c5oc5ccccc56)ccc34)n2)cc1] | 26% |
| 3-50 | | 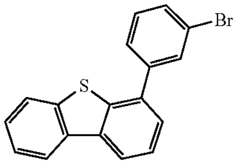 [SMILES: Brc1cccc(-c2cccc3c2sc2ccccc23)c1] | 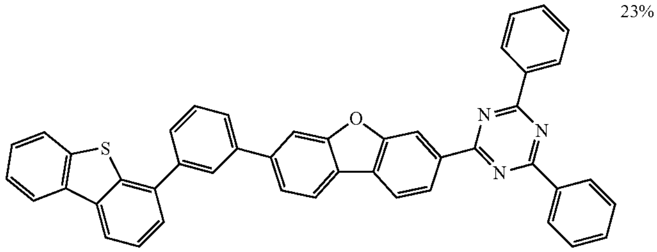 | 23% |

TABLE 3-continued
| Compound No. | Intermediate A | Intermediate B | Target compound A | Yield |
|---|---|---|---|---|
| 3-61 | | 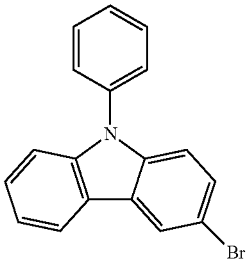 [SMILES: Brc1ccc2c(c1)c1ccccc1n2-c1ccccc1] | 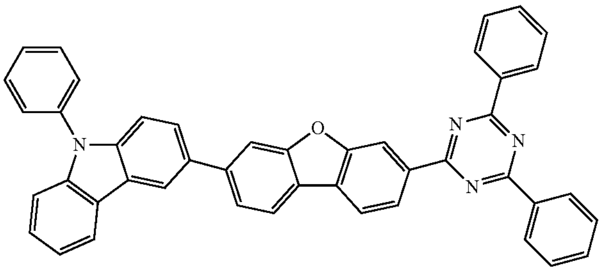 [SMILES: c1ccc(-c2nc(-c3ccccc3)nc(-c3ccc4c(c3)oc3cc(-c5ccc6c(c5)c5ccccc5n6-c5ccccc5)ccc34)n2)cc1] | 24% |
| 3-81 | | 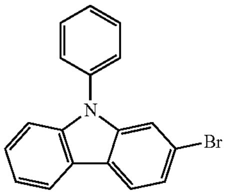 [SMILES: Brc1ccc2c3ccccc3n(-c3ccccc3)c2c1] | 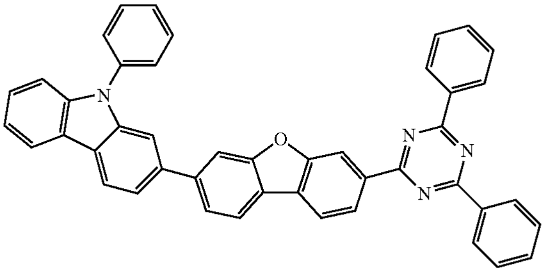 [SMILES: c1ccc(-c2nc(-c3ccccc3)nc(-c3ccc4c(c3)oc3cc(-c5ccc6c7ccccc7n(-c7ccccc7)c6c5)ccc34)n2)cc1] | 23% |
<Preparation Example 4> Preparation of Compound 4-1
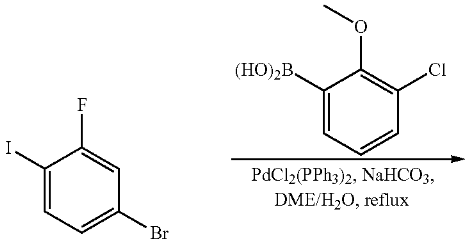
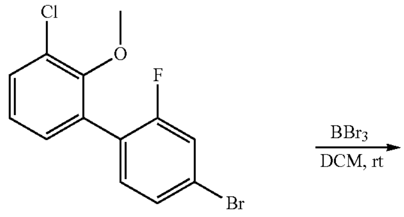
4-1-6
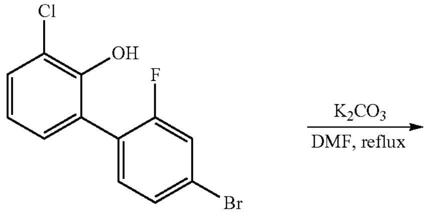
4-1-5
-continued
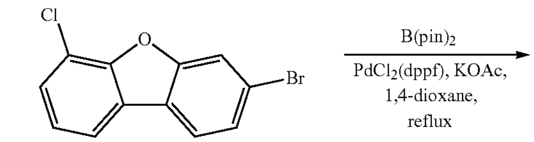
4-1-4
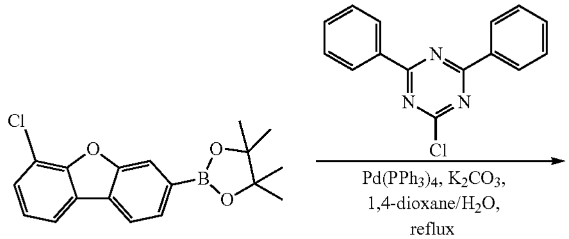
4-1-3
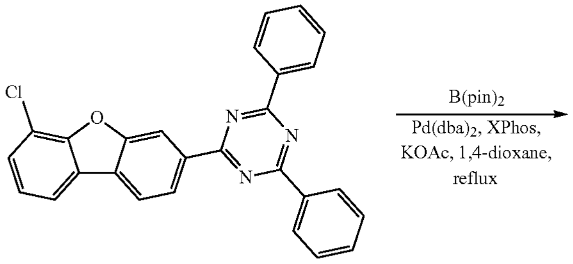
4-1-2

-continued

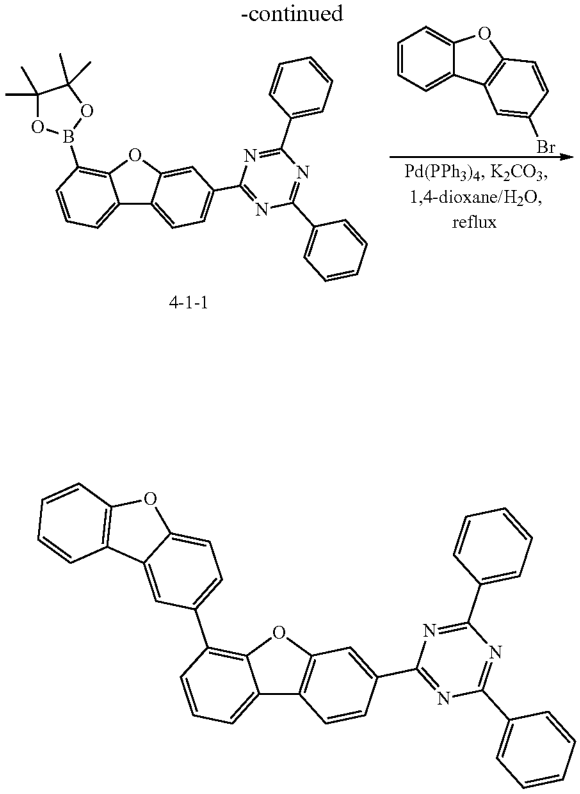

4-1-1

4-1

1) Preparation of Compound 4-1-6

4-Bromo-2-fluoro-1-iodobenzene (200.0 g, 664.7 mM), (3-chloro-2-methoxyphenyl)boronic acid (148.7 g, 794.6 mM), $Pd(PPh)_4$ (38.4 g, 33.2 mM) and $K_2CO_3$ (183.7 g, 1329.4 mM) were dissolved in 1,4-dioxane/$H_2O$ (1 L/200 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:4) to obtain target Compound 4-1-6 (169 g, 81%).

2) Preparation of Compound 4-1-5

Compound 4-1-6 (169 g, 535.5 mM) and $BBr_3$ (103 mL, 1071.0 mM) were dissolved in dichloromethane (DCM) (800 mL), and refluxed for 1 hour. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:1) to obtain target Compound 4-1-5 (145.3 g, 90%).

3) Preparation of Compound 4-1-4

Compound 4-1-5 (145.3 g, 481.9 mM) and $K_2CO_3$ (133.2 g, 963.9 mM) were dissolved in DMF (800 mL), and refluxed for 4 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:8), and recrystallized with methanol to obtain target Compound 4-1-4 (74.6 g, 57%).

4) Preparation of Compound 4-1-3

Compound 4-1-4 (74.6 g, 265.1 mM), bis(pinacolato) diboron (134.6 g, 530.2 mM), $PdCl_2$(dppf) (19.4 g, 26.5 mM) and KOAc (78.1 g, 795.3 mM) were dissolved in 1,4-dioxane (500 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM: Hex=1:5) to obtain target Compound 4-1-3 (76.7 g, 88%).

5) Preparation of Compound 4-1-2

Compound 4-1-3 (76.7 g, 233.28 mM), 2-chloro-4,6-diphenyl-1,3,5-triazine (67.7 g, 233.28 mM), $Pd(PPh)_4$ (13.5 g, 11.7 mM) and $K_2CO_3$ (64.5 g, 466.6 mM) were dissolved in 1,4-dioxane/$H_2O$ (800 mL/160 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:5), and recrystallized with methanol to obtain target Compound 4-1-2 (70.9 g, 70%).

6) Preparation of Compound 4-1-1

Compound 4-1-2 (74.0 g, 163.3 mM), bis(pinacolato) diboron (g, 326.6 mM), $Pd(dba)_2$ (9.4 g, 16.3 mM), XPhos (15.6 g, 32.7 mM) and KOAc (48.1 g, 489.9 mM) were dissolved in 1,4-dioxane (740 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM:Hex=1:4) to obtain target Compound 4-1-1 (72.9 g, 85%).

7) Preparation of Compound 4-1

Compound 4-1-1 (15.0 g, 28.5 mM), 2-bromodibenzo[b,d]furan (7.8 g, 31.4 mM), $Pd(PPh)_4$ (1.6 g, 1.4 mM) and $K_2CO_3$ (7.9 g, 57.0 mM) were dissolved in 1,4-dioxane/$H_2O$ (200 mL/40 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was purified by column chromatography (DCM: Hex=1:3), and recrystallized with methanol to obtain target Compound 4-1 (12.9 g, 80%).

Target Compound A was synthesized in the same manner as in Preparation Example 4 except that Intermediate A of the following Table 4 was used instead of 2-chloro-4,6-diphenyl-1,3,5-triazine, and Intermediate B of the following Table 4 was used instead of 2-bromodibenzo[b,d]furan.

TABLE 4
| Compound No. | Intermediate A | Intermediate B | Target compound A | Yield |
|---|---|---|---|---|
| 4-2 | 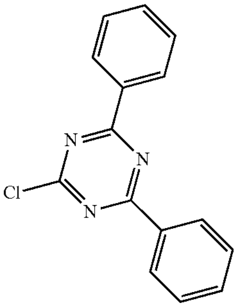 [SMILES: Clc1nc(-c2ccccc2)nc(-c2ccccc2)n1] | 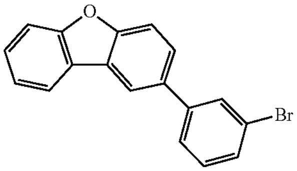 | 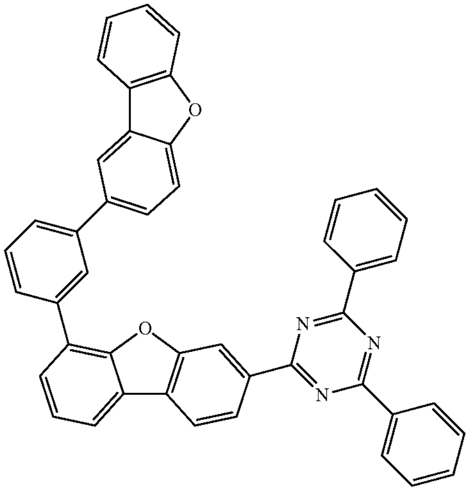 [SMILES: c1ccc(-c2nc(-c3ccccc3)nc(-c3ccc4c(c3)oc3c(-c5cccc(-c6ccc7oc8ccccc8c7c6)c5)cccc34)n2)cc1] | 22% |
| 4-4 | | 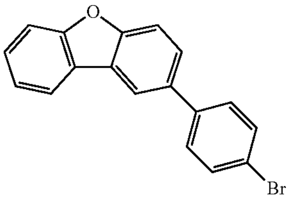 [SMILES: Brc1ccc(-c2ccc3oc4ccccc4c3c2)cc1] | 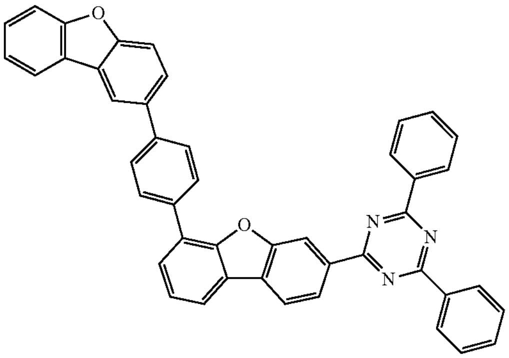 [SMILES: c1ccc(-c2nc(-c3ccccc3)nc(-c3ccc4c(c3)oc3c(-c5ccc(-c6ccc7oc8ccccc8c7c6)cc5)cccc34)n2)cc1] | 23% |
| 4-14 | | 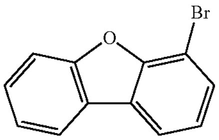 | 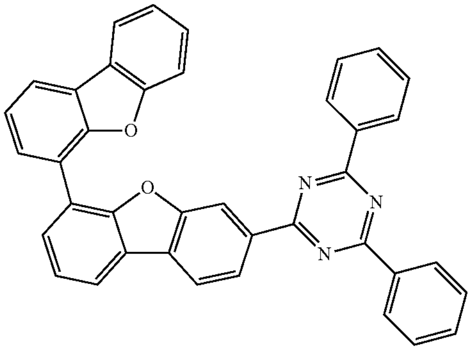 [SMILES: c1ccc(-c2nc(-c3ccccc3)nc(-c3ccc4c(c3)oc3c(-c5cccc6c5oc5ccccc56)cccc34)n2)cc1] | 27% |
| 4-37 | | 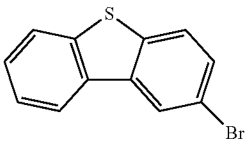 [SMILES: Brc1ccc2sc3ccccc3c2c1] | 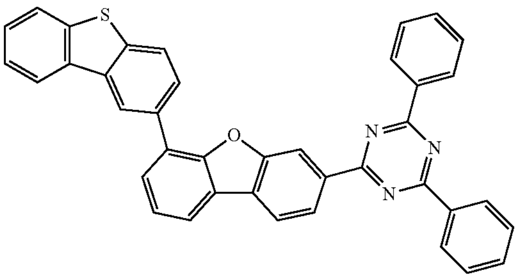 [SMILES: c1ccc(-c2nc(-c3ccccc3)nc(-c3ccc4c(c3)oc3c(-c5ccc6sc7ccccc7c6c5)cccc34)n2)cc1] | 24% |

TABLE 4-continued
| Compound No. | Intermediate A | Intermediate B | Target compound A | Yield |
|---|---|---|---|---|
| 4-40 | | 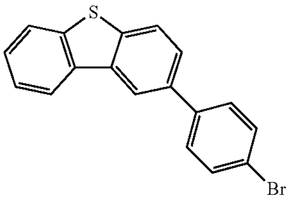 [SMILES: Brc1ccc(-c2ccc3sc4ccccc4c3c2)cc1] | 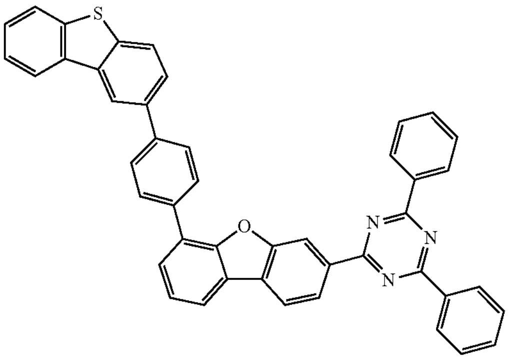 [SMILES: c1ccc(-c2nc(-c3ccccc3)nc(-c3ccc4c(c3)oc3c(-c5ccc(-c6ccc7sc8ccccc8c7c6)cc5)cccc34)n2)cc1] | 20% |
| 4-49 | | 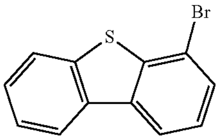 [SMILES: Brc1cccc2c1sc1ccccc12] | 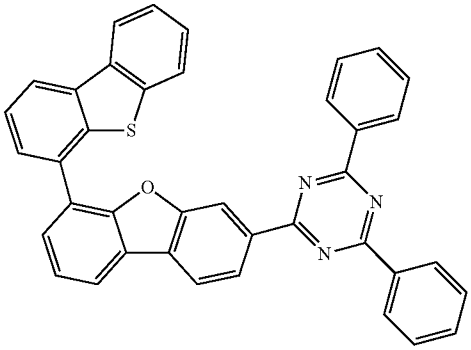 | 25% |
| 4-51 | | 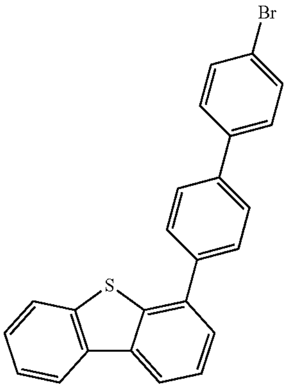 | 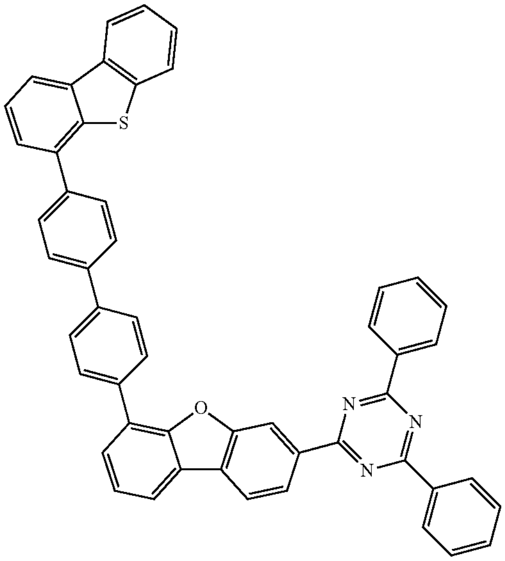 [SMILES: c1ccc(-c2nc(-c3ccccc3)nc(-c3ccc4c(c3)oc3c(-c5ccc(-c6ccc(-c7cccc8c7sc7ccccc78)cc6)cc5)cccc34)n2)cc1] | 22% |

TABLE 4-continued

| Compound No. | Intermediate A | Intermediate B | Target compound A | Yield |
|---|---|---|---|---|
| 4-61 | | 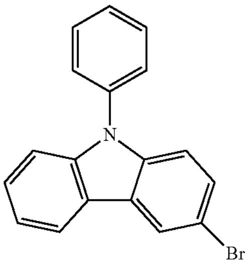 [SMILES: Brc1ccc2c(c1)c1ccccc1n2-c1ccccc1] | 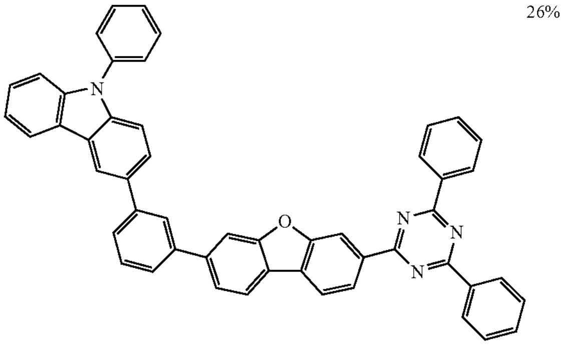 | 26% |
| 4-81 | | 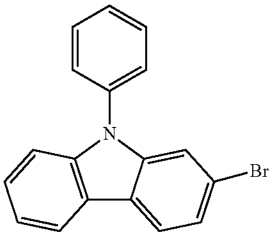 [SMILES: Brc1ccc2c3ccccc3n(-c3ccccc3)c2c1] | 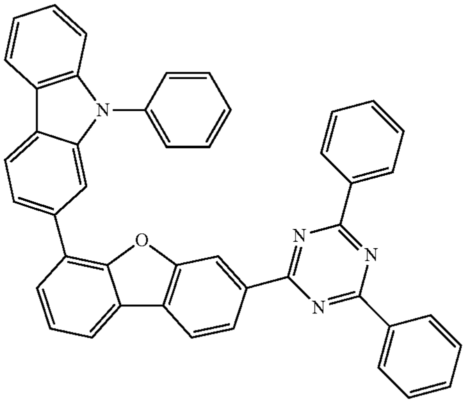 [SMILES: c1ccc(-c2nc(-c3ccccc3)nc(-c3ccc4c(c3)oc3c(-c5ccc6c7ccccc7n(-c7ccccc7)c6c5)cccc34)n2)cc1] | 23% |

<Preparation Example 5> Synthesis of Compound 5-6

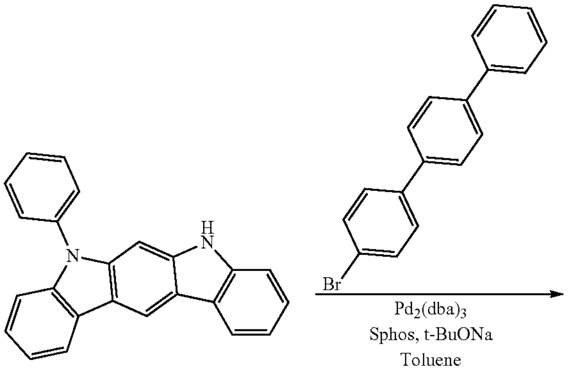

-continued

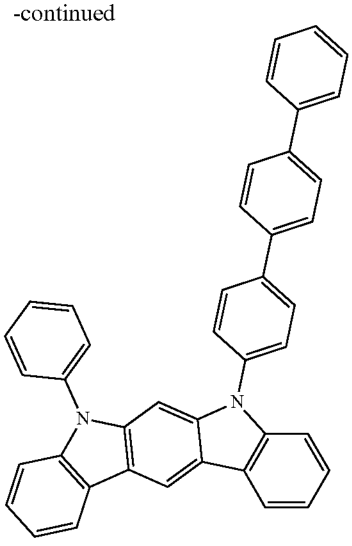

5-6

1) Preparation of Compound 5-6

5-Phenyl-5,7-dihydroindolo[2,3-b]carbazole (6.0 g, 18.05 mM), 4-bromo-1,1';4',1"-terphenyl (6.7 g, 21.66 mM), $Pd_2(dba)_3$ (0.824 g, 0.90 mM), Sphos (0.74 g, 1.80 mM) and t-BuONa (3.47 g, 36.10 mM) were dissolved in 1,4-oxane (60 mL), and refluxed for 24 hours. After the reaction was completed, the result was extracted by introducing distilled water and DCM thereto at room temperature, and after drying the organic layer with $MgSO_4$, the solvent was removed using a rotary evaporator. The reaction material was dissolved in DCB (100 ml) and filtered through silica gel for purification, and recrystallized with methanol to obtain target Compound 5-6 (8.6 g, 85%).

Target Compound A was synthesized in the same manner as in Preparation Example 5 except that Intermediate A of the following Table 5 was used instead of 4-bromo-1,1';4',1"-terphenyl, and Intermediate B of the following Table 5 was used instead of 5-phenyl-5,7-dihydroindolo[2,3-b]carbazole.

TABLE 5

| No. | Intermediate A | Intermediate B |
| --- | --- | --- |
| 5-6 | 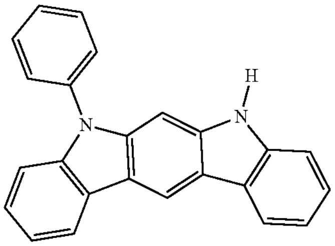 [SMILES: c1ccc(-n2c3ccccc3c3cc4c(cc32)[nH]c2ccccc24)cc1] | 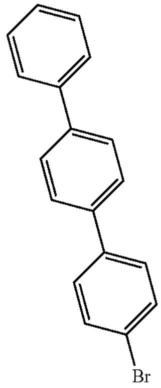 [SMILES: Brc1ccc(-c2ccc(-c3ccccc3)cc2)cc1] |
| 5-19 | 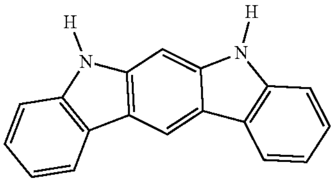 [SMILES: c1ccc2c(c1)[nH]c1cc3[nH]c4ccccc4c3cc12] | 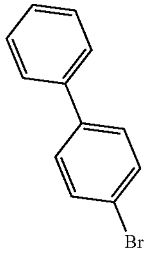 [SMILES: Brc1ccc(-c2ccccc2)cc1] |
| 5-22 | | 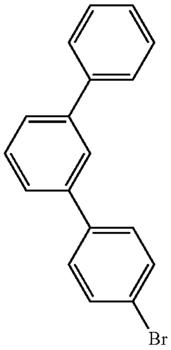 [SMILES: Brc1ccc(-c2cccc(-c3ccccc3)c2)cc1] |
| 5-25 | | 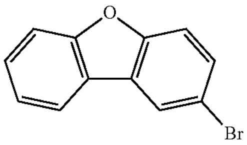 [SMILES: Brc1ccc2oc3ccccc3c2c1] |
| 5-30 | 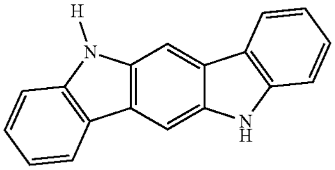 [SMILES: c1ccc2c(c1)[nH]c1cc3c(cc12)[nH]c1ccccc13] | 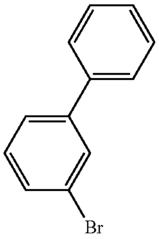 [SMILES: Brc1cccc(-c2ccccc2)c1] |

TABLE 5-continued
| | | |
|---|---|---|
| 5-40 | | 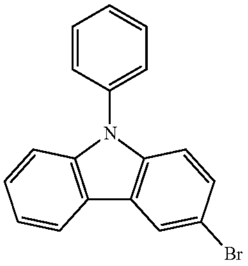 [SMILES: Brc1ccc2c(c1)c1ccccc1n2-c1ccccc1] |
| 5-70 | 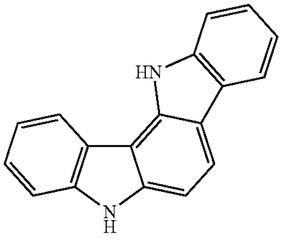 [SMILES: c1ccc2c(c1)[nH]c1c2ccc2[nH]c3ccccc3c21] | 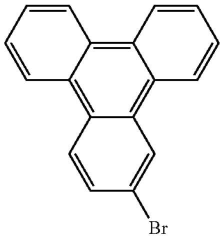 [SMILES: Brc1ccc2c3ccccc3c3ccccc3c2c1] |
| No. | Target Compound A | Yield |
|---|---|---|
| 5-6 | 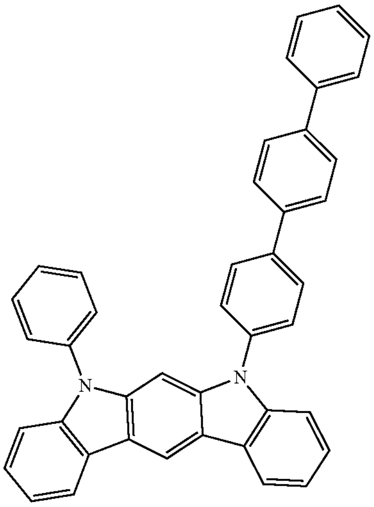 [SMILES: c1ccc(-c2ccc(-c3ccc(-n4c5ccccc5c5cc6c7ccccc7n(-c7ccccc7)c6cc54)cc3)cc2)cc1] | 83% |
| 5-19 | 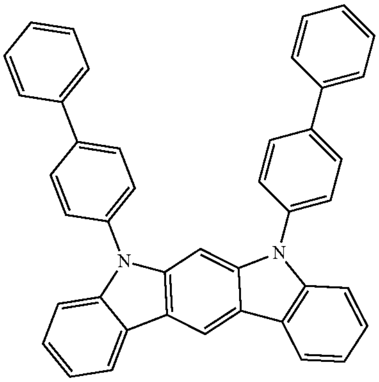 [SMILES: c1ccc(-c2ccc(-n3c4ccccc4c4cc5c6ccccc6n(-c6ccc(-c7ccccc7)cc6)c5cc43)cc2)cc1] | 84% |

TABLE 5-continued
| | | |
|---|---|---|
| 5-22 | 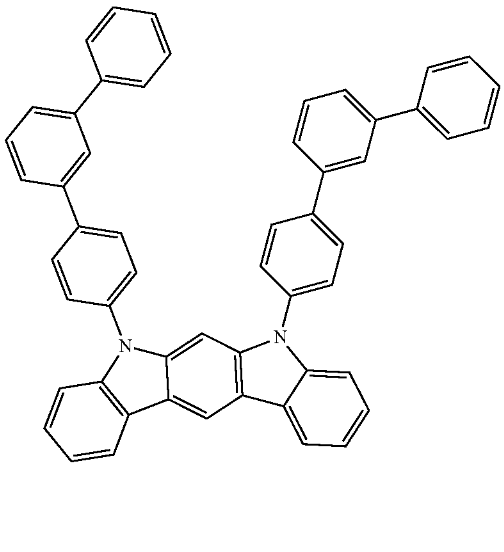 [SMILES: c1ccc(-c2cccc(-c3ccc(-n4c5ccccc5c5cc6c7ccccc7n(-c7ccc(-c8cccc(-c9ccccc9)c8)cc7)c6cc54)cc3)c2)cc1] | 80% |
| 5-25 | 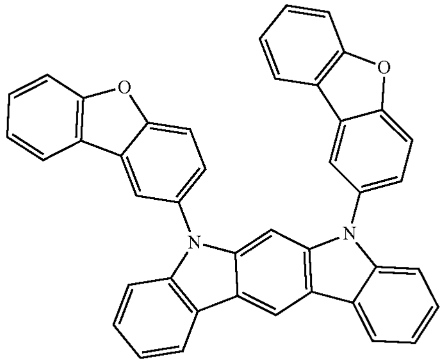 [SMILES: c1ccc2c(c1)oc1ccc(-n3c4ccccc4c4cc5c6ccccc6n(-c6ccc7oc8ccccc8c7c6)c5cc43)cc12] | 81% |
| 5-30 | 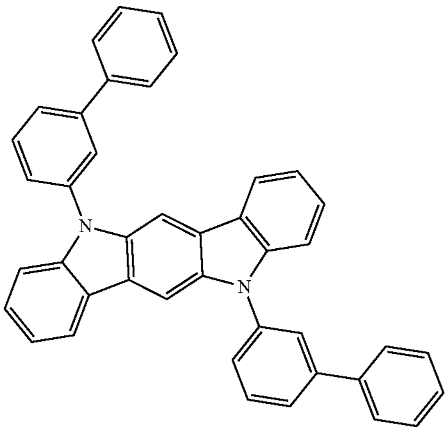 [SMILES: c1ccc(-c2cccc(-n3c4ccccc4c4cc5c(cc43)c3ccccc3n5-c3cccc(-c4ccccc4)c3)c2)cc1] | 80% |

TABLE 5-continued
| | | |
|---|---|---|
| 5-40 | 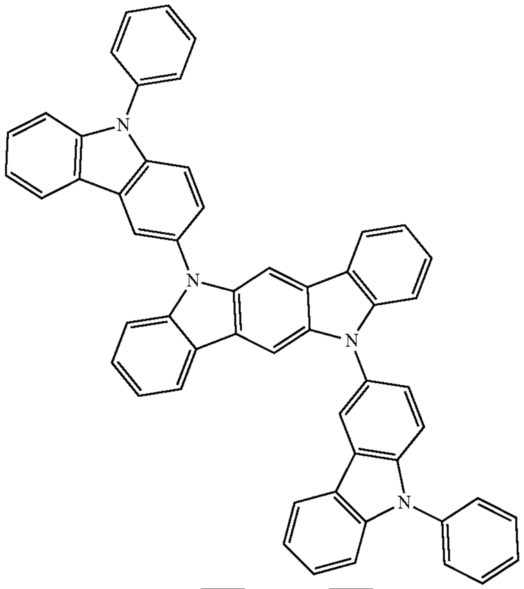 [SMILES: c1ccc(-n2c3ccccc3c3cc(-n4c5ccccc5c5cc6c(cc54)c4ccccc4n6-c4ccc5c(c4)c4ccccc4n5-c4ccccc4)ccc32)cc1] | 74% |
| 5-70 | 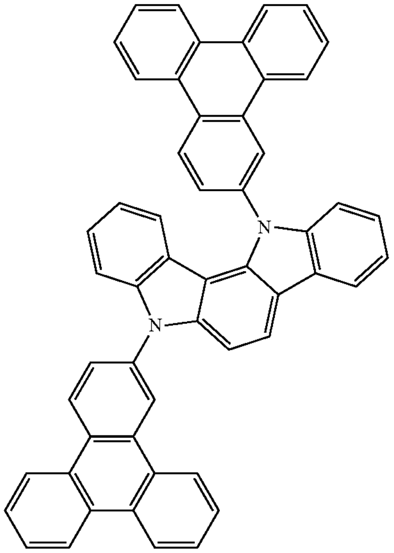 [SMILES: c1ccc2c(c1)c1ccccc1c1cc(-n3c4ccccc4c4c3ccc3c5ccccc5n(-c5ccc6c7ccccc7c7ccccc7c6c5)c34)ccc21] | 82% |
<Preparation Example 6> Synthesis of Compound 5-79
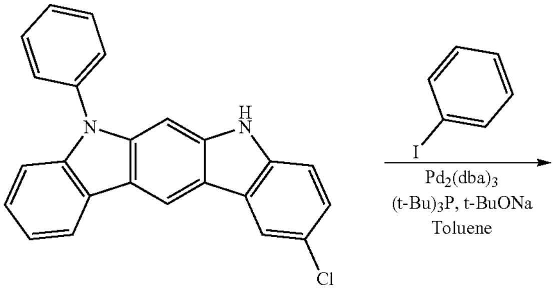
5-79-3
-continued
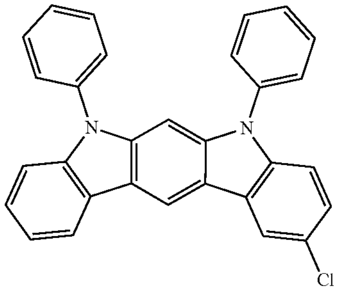
5-79-2
6-1) Preparation of Compound 5-79-2
2-Chloro-7-phenyl-5,7-dihydroindolo[2,3-b]carbazole (7.0 g, 19.08 mM), iodobenzene (4.28 g, 20.99 mM), $Pd_2(dba)_3$ (0.873 g, 0.95 mM), $(t\text{-}Bu)_3P$ (0.58 g, 2.86 mM) and t-BuONa (3.67 g, 38.16 mM) were dissolved in toluene (70 mL), and refluxed for 4 hours. After the reaction was completed, the result was extracted by introducing distilled water and DCM thereto at room temperature, and after drying the organic layer with $MgSO_4$, the solvent was removed using a rotary evaporator.

The reaction material was purified using a MC/HEX column, and the solvent was removed using a rotary evaporator to obtain target Compound 5-79-2 (6.93 g, 82%).

Target Compound C-2 was synthesized in the same manner as in Preparation Example 6-1 except that Intermediate C-3 of the following Table 6 was used instead of 2-chloro-7-phenyl-5,7-dihydroindolo[2,3-b]carbazole.

TABLE 6

| Compound No. | Intermediate C-3 | Intermediate D-3 | Target compound C-2 | Yield |
|---|---|---|---|---|
| 5-79-2 | 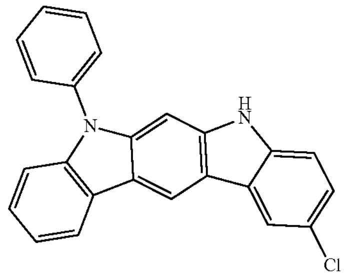 [SMILES: Clc1ccc2[nH]c3cc4c(cc3c2c1)c1ccccc1n4-c1ccccc1] | 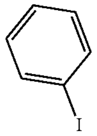 | 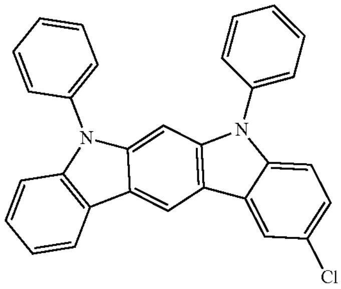 [SMILES: Clc1ccc2c(c1)c1cc3c4ccccc4n(-c4ccccc4)c3cc1n2-c1ccccc1] | 82% |
| 5-113-2 | 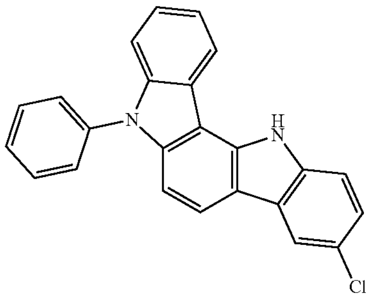 [SMILES: Clc1ccc2[nH]c3c(ccc4c3c3ccccc3n4-c3ccccc3)c2c1] | | 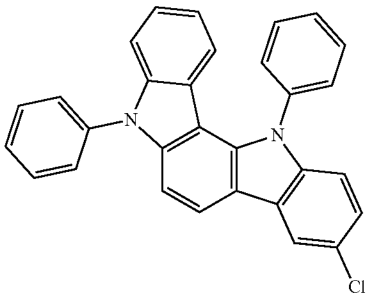 [SMILES: Clc1ccc2c(c1)c1ccc3c(c4ccccc4n3-c3ccccc3)c1n2-c1ccccc1] | 85% |
| 5-123-2 | 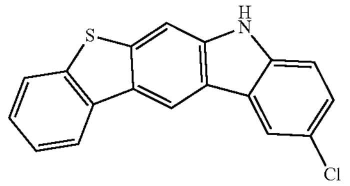 [SMILES: Clc1ccc2[nH]c3cc4sc5ccccc5c4cc3c2c1] | | 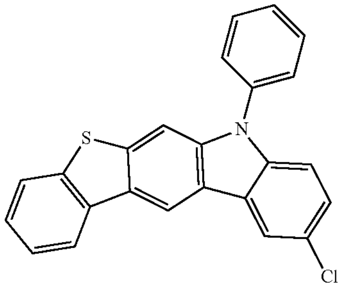 [SMILES: Clc1ccc2c(c1)c1cc3c(cc1n2-c1ccccc1)sc1ccccc13] | 81% |
| 5-142-2 | 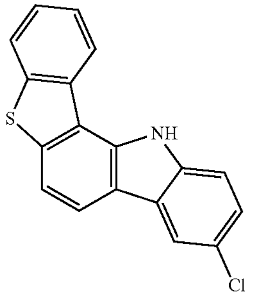 [SMILES: Clc1ccc2[nH]c3c(ccc4sc5ccccc5c43)c2c1] | | 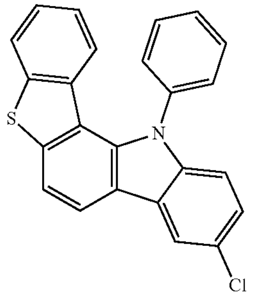 [SMILES: Clc1ccc2c(c1)c1ccc3sc4ccccc4c3c1n2-c1ccccc1] | 80% |

6-2) Preparation of Compound 5-79-1

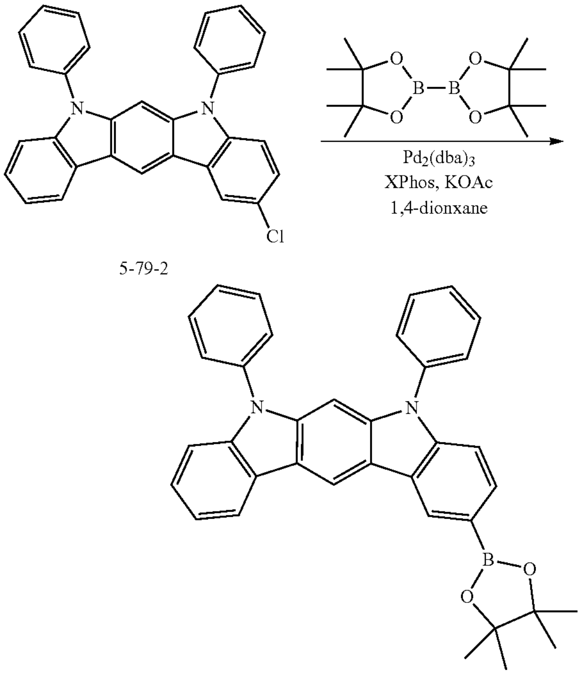

5-79-2

5-79-1

2-Chloro-5,7-diphenyl-5,7-dihydroindolo[2,3-b]carbazole (6.93 g, 15.65 mM), bispinacolatodiborane (5.96 g, 23.47 mM), $Pd_2(dba)_3$ (1.43 g, 1.56 mM), XPhos (1.49 g, 3.13 mM) and KOAc (4.61 g, 46.94 mM) were dissolved in 1,4-oxane (70 mL), and refluxed for 5 hours. After the reaction was completed, the result was extracted by introducing distilled water and DCM thereto at room temperature, and after drying the organic layer with $MgSO_4$, the solvent was removed using a rotary evaporator. The reaction material was purified using a MC/HEX column, and the filtrate was vacuum concentrated to obtain target Compound 5-79-1 (6.8 g, 81%).

Target Compound C-1 was synthesized in the same manner as in Preparation Example 6-2 except that Intermediate C-2 of the following Table 7 was used instead of 2-chloro-5,7-diphenyl-5,7-dihydroindolo[2,3-b]carbazole.

TABLE 7

| Compound No. | Intermediate C-2 | Target compound C-1 | Yield |
|---|---|---|---|
| 5-79-1 | 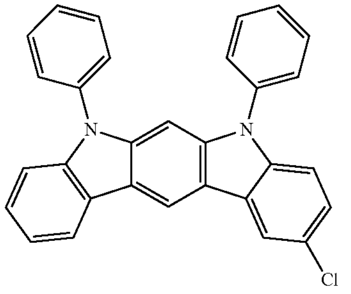 [SMILES: Clc1ccc2c(c1)c1cc3c4ccccc4n(-c4ccccc4)c3cc1n2-c1ccccc1] | 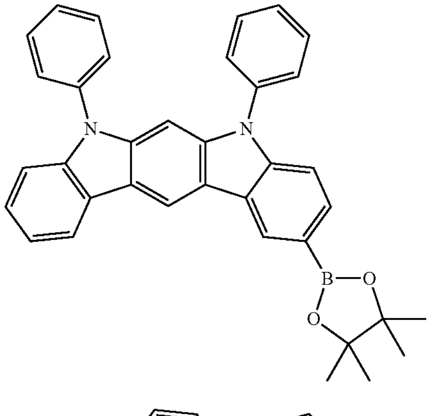 | 81% |
| 5-113-1 | 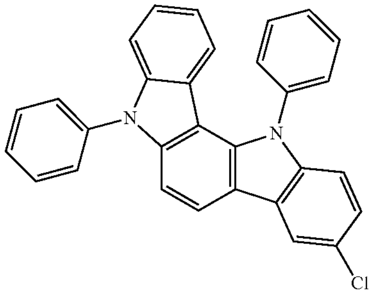 [SMILES: Clc1ccc2c(c1)c1ccc3c(c4ccccc4n3-c3ccccc3)c1n2-c1ccccc1] | 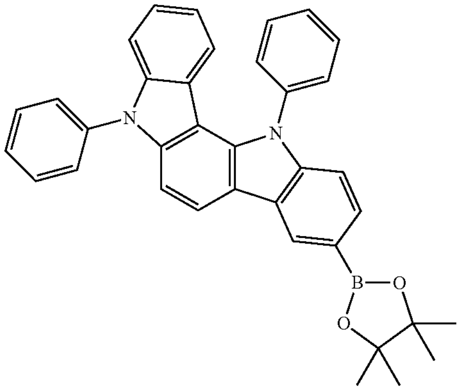 [SMILES: CC1(C)OB(c2ccc3c(c2)c2ccc4c(c5ccccc5n4-c4ccccc4)c2n3-c2ccccc2)OC1(C)C] | 80% |

TABLE 7-continued
| Compound No. | Intermediate C-2 | Target compound C-1 | Yield |
|---|---|---|---|
| 5-123-1 | 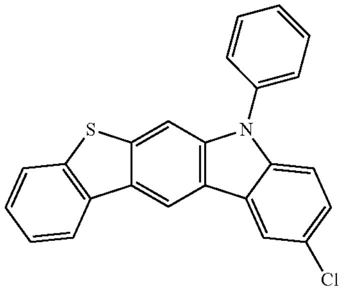 [SMILES: Clc1ccc2c(c1)c1cc3c(cc1n2-c1ccccc1)sc1ccccc13] | 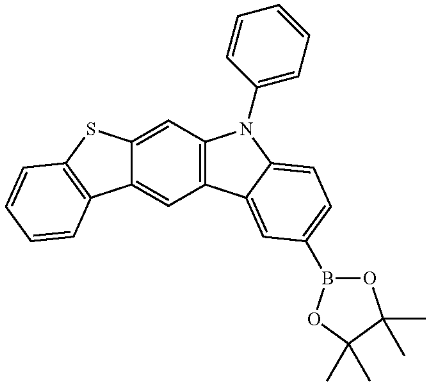 [SMILES: CC1(C)OB(c2ccc3c(c2)c2cc4c(cc2n3-c2ccccc2)sc2ccccc24)OC1(C)C] | 75% |
| 5-142-1 | 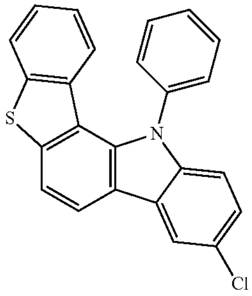 [SMILES: Clc1ccc2c(c1)c1ccc3sc4ccccc4c3c1n2-c1ccccc1] | 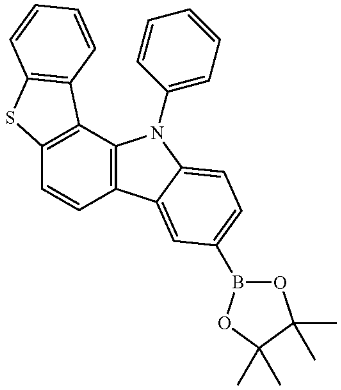 [SMILES: CC1(C)OB(c2ccc3c(c2)c2ccc4sc5ccccc5c4c2n3-c2ccccc2)OC1(C)C] | 76% |
6-3) Preparation of Compound 5-79
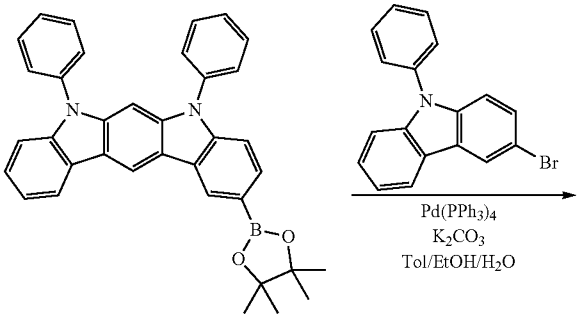
5-79-1
-continued
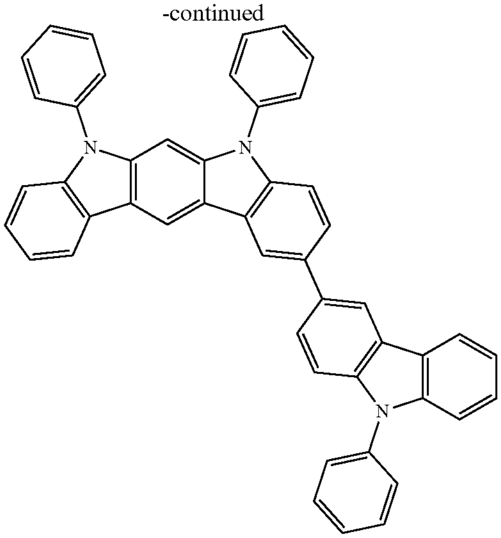
5-79
5,7-Diphenyl-2-(4,4,5,5-tetramethyl-1,3,2-dioxaboranyl)-5,7-dihydroindolo[2,3-b]carbazole (6.8 g, 12.72 mM), 3-bromo-9-phenyl-carbazole (4.51 g, 14.00 mM), $Pd(PPh_3)_4$ (0.74 g, 0.64 mM) and $K_2CO_3$ (3.52 g, 25.45 mM) were dissolved in toluene (70 mL)/ethanol (15 mL)/water (15 mL), and refluxed for 4 hours. After the reaction was completed, the result was extracted by introducing distilled water and DCM thereto at room temperature, and after drying the organic layer with $MgSO_4$, the solvent was removed using a rotary evaporator. The reaction material was purified using a MC/HEX column, and the filtrate was vacuum concentrated to obtain target Compound 5-79 (6.61 g, 80%).

Target Compound C was synthesized in the same manner as in Preparation Example 6-3 except that Intermediate C-1 of the following Table 8 was used instead of 5,7-diphenyl-2-(4,4,5,5-tetramethyl-1,3,2-dioxaboranyl)-5,7-dihydroindolo[2,3-b]carbazole, and Intermediate D-1 of the following Table 8 was used instead of 3-bromo-9-phenyl-carbazole.

TABLE 8

| Compound No. | Intermediate C-1 | Intermediate D-1 | Target compound C | Yield |
|---|---|---|---|---|
| 5-77 | 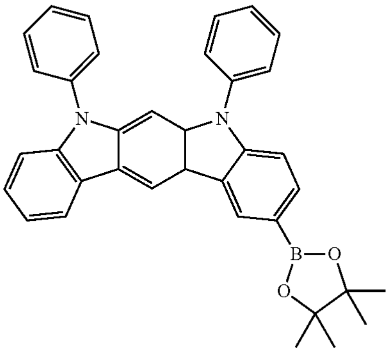 [SMILES: CC1(C)OB(c2ccc3c(c2)C2C=c4c(n(-c5ccccc5)c5ccccc45)=CC2N3c2ccccc2)OC1(C)C] | 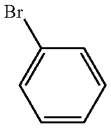 | 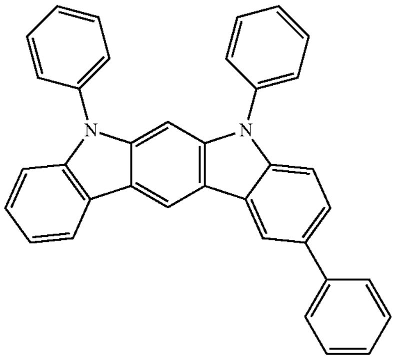 [SMILES: c1ccc(-c2ccc3c(c2)c2cc4c5ccccc5n(-c5ccccc5)c4cc2n3-c2ccccc2)cc1] | 83% |
| 5-78 | 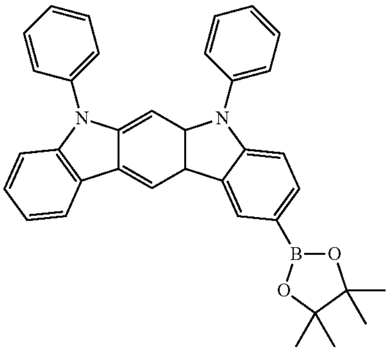 [SMILES: CC1(C)OB(c2ccc3c(c2)C2C=c4c(n(-c5ccccc5)c5ccccc45)=CC2N3c2ccccc2)OC1(C)C] | 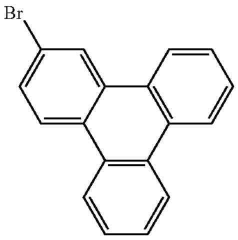 [SMILES: Brc1ccc2c3ccccc3c3ccccc3c2c1] | 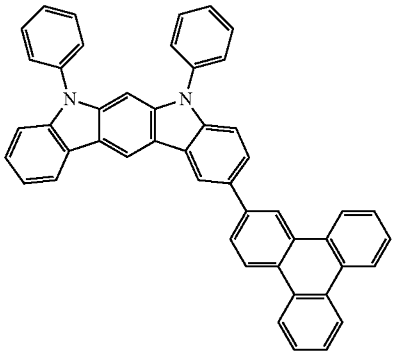 [SMILES: c1ccc(-n2c3ccccc3c3cc4c5cc(-c6ccc7c8ccccc8c8ccccc8c7c6)ccc5n(-c5ccccc5)c4cc32)cc1] | 83% |
| 5-79 | 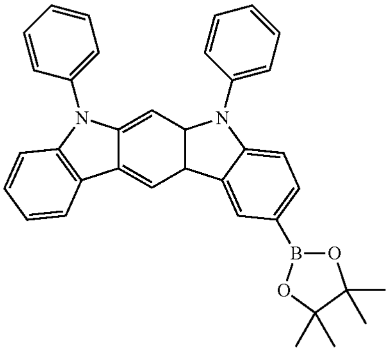 | 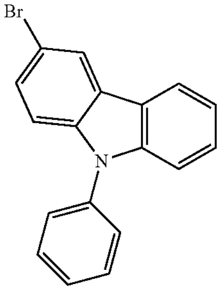 [SMILES: Brc1ccc2c(c1)c1ccccc1n2-c1ccccc1] | 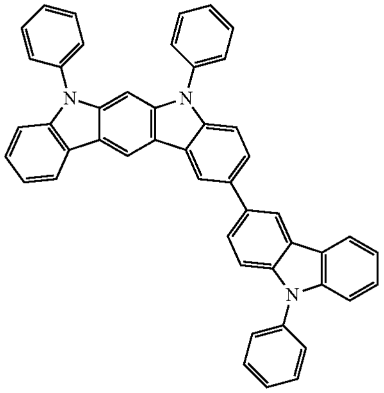 [SMILES: c1ccc(-n2c3ccccc3c3cc(-c4ccc5c(c4)c4cc6c7ccccc7n(-c7ccccc7)c6cc4n5-c4ccccc4)ccc32)cc1] | 80% |

TABLE 8-continued
| Compound No. | Intermediate C-1 | Intermediate D-1 | Target compound C | Yield |
| --- | --- | --- | --- | --- |
| 5-113 | 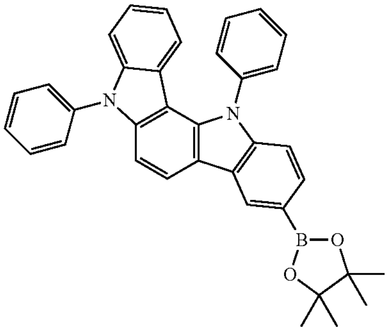 [SMILES: CC1(C)OB(c2ccc3c(c2)c2ccc4c(c5ccccc5n4-c4ccccc4)c2n3-c2ccccc2)OC1(C)C] | | 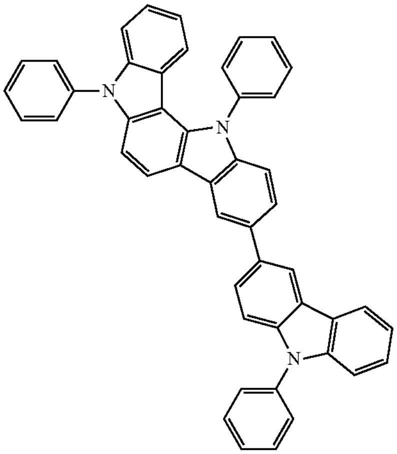 [SMILES: c1ccc(-n2c3ccccc3c3cc(-c4ccc5c(c4)c4ccc6c(c7ccccc7n6-c6ccccc6)c4n5-c4ccccc4)ccc32)cc1] | 82% |
| 5-123 | 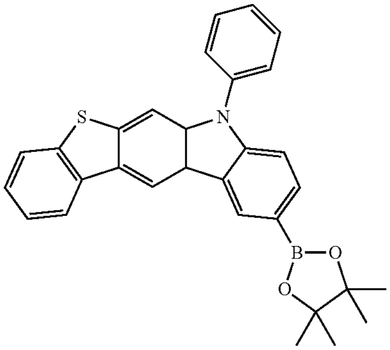 [SMILES: CC1(C)OB(c2ccc3c(c2)C2C=c4c(sc5ccccc45)=CC2N3c2ccccc2)OC1(C)C] | | 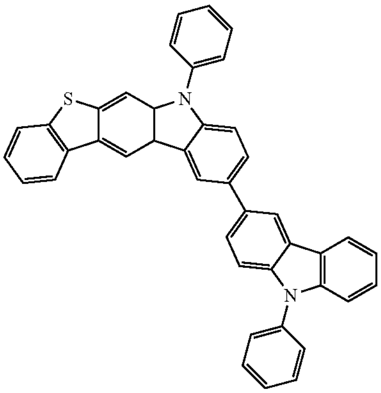 [SMILES: C1=c2sc3ccccc3c2=CC2c3cc(-c4ccc5c(c4)c4ccccc4n5-c4ccccc4)ccc3N(c3ccccc3)C12] | 75% |
| 5-142 | 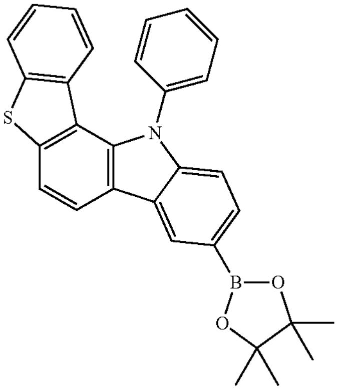 [SMILES: CC1(C)OB(c2ccc3c(c2)c2ccc4sc5ccccc5c4c2n3-c2ccccc2)OC1(C)C] | | 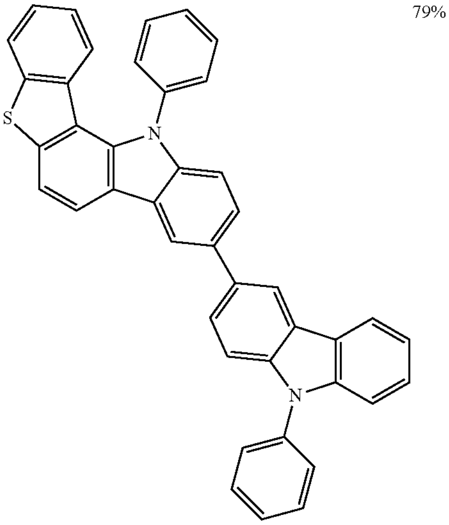 | 79% |

The compounds of Chemical Formula 1 and the compounds of Chemical Formula 2 other than those prepared in the preparation examples were also prepared in the same manner. Synthesis identification data of the compounds prepared above are as described in the following [Table 9] and [Table 10].

TABLE 9

| Compound No. | $^1$H NMR ($CDCl_3$, 200 Mz) |
|---|---|
| 1-1 | δ = 8.28 (4H, d), 7.95 (1H, d), 7.89 (1H, d), 7.62-7.81 (8H, m), 7.32-7.51 (9H, m) |
| 1-2 | δ = 8.28 (4H, d), 7.95 (1H, d), 7.89 (1H, d), 7.32-7.81 (21H, m) |
| 1-14 | δ = 8.28 (4H, d), 7.95 (1H, d), 7.89 (1H, d), 7.85 (1H, d), 7.81 (1H, d), 7.75 (2H, d), 7.66 (1H, d), 7.64 (1H, s), 7.62 (1H, d), 7.32-7.51 (10H, m) |
| 1-18 | δ = 8.28 (2H, d), 7.81-7.89 (6H, m) 7.66 (2H, d), 7.51-7.60 (8H, m), 7.25-7.41 (17H, m) |
| 1-37 | δ = 8.45 (1H, d), 8.28 (4H, d), 7.95-8.00 (4H, m), 7.86 (1H, d), 7.75 (2H, d), 7.64 (1H, s), 7.62 (1H, d), 7.41-7.52 (9H, m) |
| 1-38 | δ = 8.45 (1H, d), 8.28 (4H, d), 7.95-8.00 (4H, m), 7.86 (1H, d), 7.75 (2H, d), 7.70 (1H, s), 7.41-7.64 (14H, m) |
| 1-49 | δ = 8.45 (1H, d), 8.41 (1H, d), 8.28 (4H, d), 8.20 (1H, d), 7.98 (1H, d), 7.95 (1H, d), 7.75 (2H, d), 7.41-7.64 (12H, m) |
| 1-50 | δ = 8.45 (1H, d), 8.41 (1H, d), 8.28 (4H, d), 8.20 (1H, d), 7.98 (1H, d), 7.95 (1H, d), 7.75 (2H, d), 7.70 (1H, s), 7.41-7.62 (15H, m) |
| 1-61 | δ = 8.28 (4H, d), 8.18 (1H, d), 8.12 (1H, d), 8.00 (1H, d), 7.95 (1H, d), 7.77 (1H, s), 7.75 (2H, d), 7.41-7.77 (16H, m), 7.29 (1H, t) |
| 1-81 | δ = 8.49 (1H, d), 8.28 (4H, d), 8.12 (1H, d), 8.10 (1H, d), 7.95 (1H, d), 7.75 (2H, d), 7.41-7.64 (17H, m), 7.29 (1H, t) |
| 2-1 | δ = 8.28 (4H, d), 7.95 (1H, d), 7.89 (1H, d), 7.64-7.81 (9H, m), 7.32-7.51 (8H, m) |
| 2-2 | δ = 8.28 (4H, d), 7.95 (1H, d), 7.89 (1H, d), 7.32-7.81 (21H, m) |
| 2-4 | δ = 8.28 (4H, d), 7.95 (1H, d), 7.89 (1H, d), 7.64-7.81 (9H, m), 7.25-7.51 (12H, m) |
| 2-14 | δ = 8.28 (4H, d), 7.64-7.95 (10H, m), 7.32-7.51 (9H, m) |
| 2-37 | δ = 8.45 (1H, d), 8.28 (4H, d), 7.95-8.00 (4H, m), 7.71-7.86 (5H, m), 7.64 (1H, s), 7.41-7.51 (5H, m) |
| 2-40 | δ = 8.45 (1H, d), 8.28 (4H, d), 7.95-8.00 (4H, m), 7.71-7.86 (5H, m), 7.64 (1H, s), 7.41-7.52 (8H, m), 7.25 (4H, s) |
| 2-49 | δ = 8.45 (1H, d), 8.41 (1H, d), 8.28 (4H, d), 8.20 (1H, d), 7.98 (1H, d), 7.95 (1H, d), 7.71-7.81 (4H, m), 7.41-7.64 (10H, m) |
| 2-51 | δ = 8.45 (1H, d), 8.41 (1H, d), 8.28 (4H, d), 8.20 (1H, d), 7.98 (1H, d), 7.95 (1H, d), 7.71-7.81 (4H, m), 7.41-7.64 (10H, m), 7.25 (8H, s) |
| 2-61 | δ = 8.28 (4H, d), 8.18 (1H, d), 8.12 (1H, d), 8.00 (1H, d), 7.95 (1H, d), 7.71-7.81 (5H, m), 7.41-7.64 (14H, m), 7.29 (1H, t) |
| 2-81 | δ = 8.49 (1H, d), 8.28 (4H, d), 8.12 (1H, d), 8.10 (1H, d), 7.95 (1H, d), 7.71-7.81 (4H, m), 7.41-7.64 (15H, m), 7.29 (1H, t) |
| 3-1 | δ = 8.28 (4H, d), 7.95 (2H, d), 7.89 (1H, d), 7.64-7.81 (8H, m), 7.32-7.51 (8H, m) |
| 3-2 | δ = 8.36 (4H, m), 7.98-7.73 (12H, m), 7.61-7.50 (9H, m), 7.39-7.31 (2H, m) |
| 3-14 | δ = 8.36 (4H, m), 8.08-7.98 (5H, m), 7.82 (2H, d), 7.76 (2H, s), 7.54-7.50 (8H, m) 7.39-7.31 (2H, m) |
| 3-18 | δ = 8. 36 (2H, m), 8.08-7.96 (7H, m), 7.82-7.76 (6H, m), 7.54-7.31 (20H, m) |
| 3-37 | δ = 8.45 (1H, d), 8.36 (4H, m), 8.12 (2H, m), 8.03-7.93 (4H, m), 7.82 (2H, d), 7.76 (2H, s), 7.56-7.49 (8H, m) |
| 3-38 | δ = 8.45 (1H, d), 8.36 (4H, m), 8.12 (2H, m), 8.03-7.93 (5H, m), 7.8207.73 (5H, m) 7.61-7.49 (10H, m) |
| 3-49 | δ = 8.55 (1H, d), 8.45 (1H, d), 8.36-8.32 (5H, m) 8.03 (2H, d), 7.93 (1H, d), 7.82-7.78 (5H, m), 7.56-7.49 (8H, m) |
| 3-50 | δ = 8.55 (1H, d), 8.45 (1H, d), 8.36-8.32 (5H, m), 8.03 (2H, d), 7.93-7.91 (2H, m), 7.82-7.70 (6H, m), 7.61-7.49 (10H, m) |
| 3-61 | δ = 8.36-8.30 (5H, m), 8.19 (1H, d), 8.13 (1H, d), 8.03 (2H, d), 7.89 (1H, s), 7.82 (2H, d), 7.76 (2H, s), 7.62-7.50 (13H, m), 7.20 (1H, t) |
| 3-81 | δ = 8.62 (1H, d), 8.36 (4H, m), 8.22-8.19 (2H, m), 8.03 (2H, d), 7.82 (2H, d), 7.76-7.74 (3H, m), 7.62-7.50 (10H, m), 7.20 (1H, t) |

TABLE 9-continued

| Compound No. | $^1$H NMR ($CDCl_3$, 200 Mz) |
|---|---|
| 4-1 | δ = 8.28 (4H, d), 7.64-7.95 (10H, m), 7.32-7.51 (9H, m) |
| 4-2 | δ = 8.36 (4H, m), 8.08-7.73 (11H, m), 7.61 (2H, d), 7.54-7.50 (8H, m), 7.39 (1H, t), 7.31 (1H, t) |
| 4-4 | δ = 8.36 (4H, m), 8.08-7.94 (4H, m), 7.88 (1H, d), 7.83-7.76 (4Hm), 7.54-7.50 (8H, m), 7.39-7.25 (6H, m), |
| 4-14 | δ = 8.36 (4H, m), 8.08 (2H, d), 8.03-7.98 (4H, m), 7.82 (1H, d), 7.76 (1H, s), 7.54-7.50 (9H, m), 7.39 (1H, t), 7.31 (1H, t) |
| 4-37 | δ = 8.45 (1H, d), 8.36 (4H, m), 8.12-7.99 (6H, m), 7.93 (1H, d), 7.82 (1H, d), 7.76 (1H, s), 7.56-7.49 (9H, m), |
| 4-40 | δ = 8.45 (1H, d), 8.36 (4H, m), 8.12-7.99 (8H, m), 7.93 (1H, d), 7.82 (1H, d), 7.76 (1H, d), 7.59-7.46 (9H, m), 7.25 (4H, s) |
| 4-49 | δ = 8.55 (1H, d), 8.45 (1H, d), 8.36 (4H, m), 8.08 (1H, d), 8.03-8.02 (2H, m), 7.93 (1H, d), 7.82 (1H, d) 7.76 (1H, s), 7.70 (1H, t), 7.56-7.49 (10H, m) |
| 4-51 | δ = 8.55 (1H, d), 8.45 (1H, d), 8.36-8.32 (5H, m), 8.08 (1H, d), 8.03-8.02 (2H, m), 7.93 (1H, d), 7.82 (1H, d), 7.76 (1H, s), 7.70 (1H, t), 7.56-7.49 (9H, m), 7.24 (8H, s) |
| 4-61 | δ = 8.36-8.30 (5H, m), 8.19 (1H, d), 8.13-8.03 (4H, m), 7.89 (1H, s), 7.82 (1H, d), 7.76 (1H, s), 7.62-7.48 (14H, m), 7.20 (1H, t) |
| 4-81 | δ = 8.62 (1H, d), 8.36 (4H, m), 8.22 (2H, t), 8.08-8.02 (3H, m), 7.82 (1H, d), 7.76 (1H, s) 7.74 (1H, s), 7.62-7.48 (14H, m), 7.20 (1H, t) |
| 5-6 | δ = 8.55 (1H, d), 8.19 (1H, d), 7.94-7.91 (5H, m), 7.75 (2H, d), 7.62-7.35 (13H, m), 7.25-7.16 (6H, m) |
| 5-19 | δ = 8.55 (1H, d), 8.19 (1H, d), 7.94-7.91 (9H, m), 7.75 (4H, d) 7.58-7.35 (11H, m) 7.20-7.16 (2H, m) |
| 5-22 | δ = 8.55 (1H, d), 8.19 (1H, d), 7.94-7.91 (11H, m), 7.75-7.73 (6H, m) 7.61-7.35 (15H, m) 7.20-7.16 (2H, m) |
| 5-25 | δ = 8.55 (1H, d), 8.19 (1H, d), 7.98-7.94 (3H, m), 7.74 (2H, d) 7.61-7.50 (7H, m), 7.40-7.31 (8H, m), 7.20-7.16 (2H, m) |
| 5-30 | δ = 8.55 (1H, d), 8.21-8.19 (3H, m), 7.94 (1H, d), 7.75-7.35 (21H, m), 7.20-7.16 (2H, m) |
| 5-40 | δ = 8.55 (3H, d), 8.19 (1H, d), 7.94 (3H, d), 7.72-7.47 (18H, m), 7.38-7.35 (5H, m), 7.20-7.16 (4H, m) |
| 5-70 | δ = 9.08-9.06 (4H, d), 8.55 (1H, d), 8.33-8.19 (5H, m), 8.00-7.94 (5H, m), 7.70-7.52 (14H, m), 7.35 (1H, t), 7.20-7.16 (2H, m) |
| 5-77 | δ = 8.30 (1H, d), 8.19 (1H, d), 8.13 (1H, d), 7.89 (1H, s), 7.75 (2H, d), 7.62-7.41 (17H, m), 7.20 (1H, t) |
| 5-78 | δ = 9.27 (1H, s), 8.79 (1H, d), 8.37-8.30 (5H, m), 8.19-8.13 (2H, d), 7.89 (1H, s), 7.70-7.50 (18H, m), 7.40 (1H, s), 7.20 (1H, t) |
| 5-79 | δ = 8.30 (2H, d), 8.19-8.13 (4H, m), 7.89 (2H, s), 7.62-7.50 (20H, m), 7.40 (1H, s), 7.20 (2H, t) |
| 5-113 | δ = 8.55 (1H, d), 8.39 (2H, d), 8.19-8.12 (4H, m), 7.94 (1H, d), 7.89 (2H, s), 7.62-7.50 (17H, m), 7.35 (1H, t), 7.20-7.16 (3H, m) |
| 5-123 | δ = 8.45 (1H, d), 8.30 (2H, d), 8.19-8.13 (3H, m), 7, 93-7.89 (4H, m), 7.78 (1H, s), 7.62-7.49 (13H, m), 7.20 (1H, t) |
| 5-142 | δ = 8.45 (1H, d), 8.30 (2H, d), 8.19-8.08 (4H, m), 7.93 (1H, d), 7.89 (2H, s), 7.80 (1H, d), 7.62-7.49 (14H, m), 7.20 (1H, t) |

TABLE 10

| Compound | FD-MS |
|---|---|
| 1-1 | m/z = 565.18 ($C_{39}H_{23}N_3O_2$ = 565.62) |
| 1-2 | m/z = 641.21 ($C_{45}H_{27}N_3O_2$ = 641.71) |
| 1-14 | m/z = 565.18 ($C_{39}H_{23}N_3O_2$ = 565.62) |
| 1-18 | m/z = 793.27 (C57$H_{35}N_3O_2$ = 793.91) |
| 1-37 | m/z = 581.16 ($C_{39}H_{23}N_3OS$ = 581.68) |
| 1-38 | m/z = 657.19 ($C_{45}H_{27}N_3OS$ = 657.78) |
| 1-49 | m/z = 581.16 ($C_{39}H_{23}N_3OS$ = 581.68) |
| 1-50 | m/z = 657.19 ($C_{45}H_{27}N_3OS$ = 657.78) |
| 1-61 | m/z = 640.23 ($C_{45}H_{28}N_4O$ = 640.73) |
| 1-81 | m/z = 640.23 ($C_{45}H_{28}N_4O$ = 640.73) |
| 2-1 | m/z = 565.18 ($C_{39}H_{23}N_3O_2$ = 565.62) |
| 2-2 | m/z = 641.21 ($C_{45}H_{27}N_3O_2$ = 641.71) |
| 2-4 | m/z = 641.21 ($C_{45}H_{27}N_3O_2$ = 641.71) |
| 2-14 | m/z = 565.18 ($C_{39}H_{23}N_3O_2$ = 565.62) |
| 2-37 | m/z = 581.16 ($C_{39}H_{23}N_3OS$ = 581.68) |

TABLE 10-continued

| Compound | FD-MS |
|---|---|
| 2-40 | m/z = 657.19 ($C_{45}H_{27}N_3OS$ = 657.78) |
| 2-49 | m/z = 581.16 ($C_{39}H_{23}N_3OS$ = 581.68) |
| 2-51 | m/z = 733.22 ($C_{51}H_{31}N_3OS$ = 733.88) |
| 2-61 | m/z = 640.23 ($C_{45}H_{28}N_4O$ = 640.73) |
| 2-81 | m/z = 640.23 ($C_{45}H_{28}N_4O$ = 640.73) |
| 3-1 | m/z = 565.18 ($C_{39}H_{23}N_3O_2$ = 565.62) |
| 3-2 | m/z = 641.21 ($C_{45}H_{27}N_3O_2$ = 641.71) |
| 3-14 | m/z = 565.18 ($C_{39}H_{23}N_3O_2$ = 565.62) |
| 3-18 | m/z = 793.27 ($C_{57}H_{35}N_3O_2$ = 793.91) |
| 3-37 | m/z = 581.16 ($C_{39}H_{23}N_3OS$ = 581.68) |
| 3-38 | m/z = 657.19 ($C_{45}H_{27}N_3OS$ = 657.78) |
| 3-49 | m/z = 581.16 ($C_{39}H_{23}N_3OS$ = 581.68) |
| 3-50 | m/z = 657.19 ($C_{45}H_{27}N_3OS$ = 657.78) |
| 3-61 | m/z = 640.23 ($C_{45}H_{28}N_4O$ = 640.73) |
| 3-81 | m/z = 640.23 ($C_{45}H_{28}N_4O$ = 640.73) |
| 4-1 | m/z = 565.18 ($C_{39}H_{23}N_3O_2$ = 565.62) |
| 4-2 | m/z = 641.21 ($C_{45}H_{27}N_3O_2$ = 641.71) |
| 4-4 | m/z = 641.21 ($C_{45}H_{27}N_3O_2$ = 641.71) |
| 4-14 | m/z = 565.18 ($C_{39}H_{23}N_3O_2$ = 565.62) |
| 4-37 | m/z = 581.16 ($C_{39}H_{23}N_3OS$ = 581.68) |
| 4-40 | m/z = 657.19 ($C_{45}H_{27}N_3OS$ = 657.78) |
| 4-49 | m/z = 581.16 ($C_{39}H_{23}N_3OS$ = 581.68) |
| 4-51 | m/z = 733.22 ($C_{51}H_{31}N_3OS$ = 733.88) |
| 4-61 | m/z = 640.23 ($C_{45}H_{28}N_4O$ = 640.73) |
| 4-81 | m/z = 640.23 ($C_{45}H_{28}N_4O$ = 640.73) |
| 5-6 | m/z = 560.23 (C42H28N2 = 560.70) |
| 5-19 | m/z = 560.23 (C42H28N2 = 560.70) |
| 5-22 | m/z = 712.29 (C54H36N2 = 712.90) |
| 5-25 | m/z = 588.18 (C42H24N2O = 588.67) |
| 5-30 | m/z = 560.23 (C42H28N2 = 560.70) |
| 5-40 | m/z = 738.28 (C54H34N4 = 738.89) |
| 5-70 | m/z = 708.26 (C54H32N2 = 708.86) |
| 5-77 | m/z = 484.19 (C36H24N2 = 484.60) |
| 5-78 | m/z = 634.24 (C48H30N2 = 634.78) |
| 5-79 | m/z = 649.25 (C48H31N3 = 649.80) |
| 5-113 | m/z = 649.25 (C48H31N3 = 649.80) |
| 5-123 | m/z = 590.18 (C42H26N2S = 590.74) |
| 5-142 | m/z = 590.18 (C42H26N2S = 590.74) |

<Experimental Example 1> Manufacture of Organic Light Emitting Device

A glass substrate on which indium tin oxide (ITO) was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. As the light emitting layer, a heterocyclic compound described in the following Table 11 was deposited to 400 Å as a host, and as a green phosphorescent dopant, $Ir(ppy)_3$ was doped and deposited by 7% with respect to the light emitting layer deposition thickness. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, $T_{90}$ was measured when standard luminance was 6,000 cd/m$^2$ through a lifetime measurement system (M6000) manufactured by McScience Inc.

Results of measuring driving voltage, light emission efficiency, color coordinate (CIE) and lifetime of the organic light emitting devices manufactured above are as shown in the following Table 11.

TABLE 11

| | Light Emitting Layer Compound | Driving Voltage (V) | Efficiency (cd/A) | Color Coordinate (x, y) | Life-time ($T_{90}$) |
|---|---|---|---|---|---|
| Reference Example 1 | Ref. 1 | 6.14 | 38.9 | (0.236, 0.687) | 133 |
| Reference Example 2 | Ref. 2 | 6.54 | 35.3 | (0.236, 0.666) | 69 |
| Reference Example 3 | Ref. 3 | 4.85 | 43.4 | (0.237, 0.677) | 85 |
| Reference Example 4 | Ref. 4 | 2.91 | 29.7 | (0.233, 0.683) | 50 |
| Reference Example 5 | Ref. 5 | 6.66 | 35.8 | (0.233, 0.681) | 64 |
| Reference Example 6 | Ref. 6 | 6.15 | 34.9 | (0.233, 0.671) | 77 |
| Reference Example 7 | 5-6 | 2.52 | 28.3 | (0.272, 0.678) | 34 |
| Reference Example 8 | 5-19 | 2.65 | 29.9 | (0.273, 0.682) | 35 |
| Reference Example 9 | 5-22 | 2.57 | 30.4 | (0.271, 0.691) | 35 |
| Reference Example 10 | 5-25 | 2.60 | 30.9 | (0.274, 0.677) | 36 |
| Reference Example 11 | 5-30 | 2.50 | 31.2 | (0.272, 0.675) | 39 |
| Reference Example 12 | 5-40 | 2.51 | 28.2 | (0.272, 0.670) | 34 |
| Reference Example 13 | 5-70 | 2.63 | 29.7 | (0.273, 0.673) | 35 |
| Reference Example 14 | 5-77 | 3.02 | 28.1 | (0.276, 0.666) | 39 |
| Reference Example 15 | 5-78 | 3.14 | 29.2 | (0.277, 0.672) | 40 |
| Reference Example 16 | 5-79 | 3.51 | 31.2 | (0.262, 0.673) | 41 |
| Reference Example 17 | 5-113 | 3.49 | 33.0 | (0.271, 0.671) | 41 |
| Reference Example 18 | 5-123 | 3.42 | 32.1 | (0.278, 0.673) | 43 |
| Reference Example 19 | 5-142 | 3.39 | 33.7 | (0.274, 0.678) | 44 |
| Reference Example 20 | 1-1 | 4.31 | 53.2 | (0.247, 0.667) | 227 |
| Reference Example 21 | 1-2 | 4.30 | 55.8 | (0.241, 0.671) | 224 |

TABLE 11-continued

| | Light Emitting Layer Compound | Driving Voltage (V) | Efficiency (cd/A) | Color Coordinate (x, y) | Life-time ($T_{90}$) |
|---|---|---|---|---|---|
| Reference Example 22 | 1-14 | 4.45 | 52.7 | (0.251, 0.674) | 225 |
| Reference Example 23 | 1-18 | 4.38 | 54.0 | (0.240, 0.672) | 228 |
| Reference Example 24 | 1-37 | 4.34 | 54.1 | (0.242, 0.673) | 232 |
| Reference Example 25 | 1-38 | 4.31 | 55.2 | (0.231, 0.681) | 238 |
| Reference Example 26 | 1-49 | 4.41 | 53.7 | (0.241, 0.683) | 233 |
| Reference Example 27 | 1-50 | 4.39 | 55.0 | (0.231, 0.674) | 241 |
| Reference Example 28 | 1-61 | 4.15 | 50.4 | (0.231, 0.684) | 195 |
| Reference Example 29 | 1-81 | 4.12 | 50.8 | (0.246, 0.677) | 190 |
| Reference Example 30 | 2-1 | 4.19 | 56.4 | (0.244, 0.677) | 263 |
| Reference Example 31 | 2-2 | 4.18 | 58.2 | (0.243, 0.683) | 266 |
| Reference Example 32 | 2-4 | 4.28 | 55.4 | (0.249, 0.691) | 264 |
| Reference Example 33 | 2-14 | 4.27 | 56.8 | (0.228, 0.682) | 268 |
| Reference Example 34 | 2-37 | 4.20 | 57.9 | (0.244, 0.673) | 271 |
| Reference Example 35 | 2-40 | 4.21 | 57.3 | (0.229, 0.682) | 274 |
| Reference Example 36 | 2-49 | 4.28 | 56.1 | (0.239, 0.673) | 270 |
| Reference Example 37 | 2-51 | 4.26 | 56.2 | (0.233, 0.678) | 278 |
| Reference Example 38 | 2-61 | 3.95 | 51.3 | (0.238, 0.675) | 219 |
| Reference Example 39 | 2-81 | 3.99 | 51.0 | (0.240, 0.681) | 214 |
| Reference Example 40 | 3-1 | 4.34 | 54.9 | (0.245, 0.687) | 233 |
| Reference Example 41 | 3-2 | 4.36 | 56.8 | (0.244, 0.675) | 228 |
| Reference Example 42 | 3-14 | 4.35 | 53.5 | (0.249, 0.683) | 229 |
| Reference Example 43 | 3-18 | 4.38 | 54.1 | (0.243, 0.673) | 234 |
| Reference Example 44 | 3-37 | 4.37 | 54.5 | (0.251, 0.684) | 241 |
| Reference Example 45 | 3-38 | 4.43 | 55.1 | (0.247, 0.675) | 239 |
| Reference Example 46 | 3-49 | 4.48 | 55.4 | (0.248, 0.682) | 240 |
| Reference Example 47 | 3-50 | 4.45 | 55.1 | (0.245, 0.686) | 244 |
| Reference Example 48 | 3-61 | 4.17 | 50.6 | (0.243, 0.679) | 208 |
| Reference Example 49 | 3-81 | 4.23 | 49.8 | (0.242, 0.668) | 200 |
| Reference Example 50 | 4-1 | 4.20 | 55.8 | (0.247, 0.685) | 259 |
| Reference Example 51 | 4-2 | 4.21 | 57.9 | (0.241, 0.668) | 261 |
| Reference Example 52 | 4-4 | 4.29 | 55.3 | (0.251, 0.672) | 262 |
| Reference Example 53 | 4-14 | 4.28 | 56.0 | (0.240, 0.674) | 260 |
| Reference Example 54 | 4-37 | 4.19 | 57.3 | (0.242, 0.683) | 264 |
| Reference Example 55 | 4-40 | 4.21 | 56.5 | (0.231, 0.667) | 270 |
| Reference Example 56 | 4-49 | 4.31 | 55.6 | (0.241, 0.671) | 261 |
| Reference Example 57 | 4-51 | 4.27 | 55.7 | (0.231, 0.682) | 273 |
| Reference Example 58 | 4-61 | 3.99 | 51.1 | (0.231, 0.677) | 214 |

TABLE 11-continued

| | Light Emitting Layer Compound | Driving Voltage (V) | Efficiency (cd/A) | Color Coordinate (x, y) | Life-time ($T_{90}$) |
|---|---|---|---|---|---|
| Reference Example 59 | 4-81 | 4.01 | 50.3 | (0.246, 0.673) | 206 |

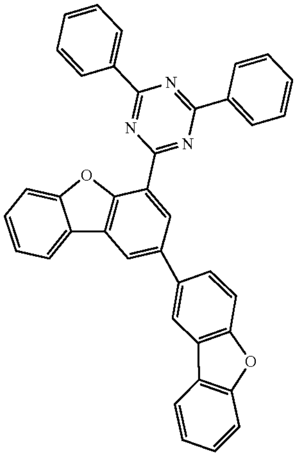 [SMILES: c1ccc(-c2nc(-c3ccccc3)nc(-c3cc(-c4ccc5oc6ccccc6c5c4)cc4c3oc3ccccc34)n2)cc1]
Ref. 1

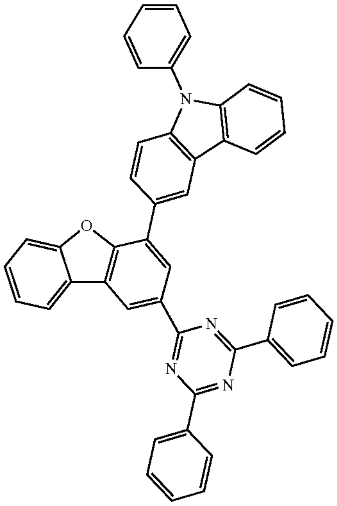 [SMILES: c1ccc(-c2nc(-c3ccccc3)nc(-c3cc(-c4ccc5c(c4)c4ccccc4n5-c4ccccc4)c4oc5ccccc5c4c3)n2)cc1]
Ref. 2

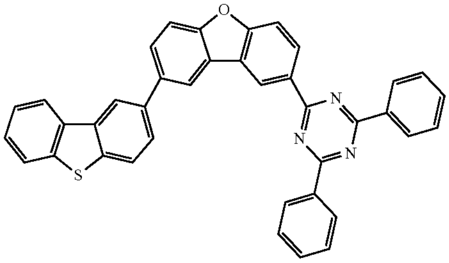 [SMILES: c1ccc(-c2nc(-c3ccccc3)nc(-c3ccc4oc5ccc(-c6ccc7sc8ccccc8c7c6)cc5c4c3)n2)cc1]
Ref. 3

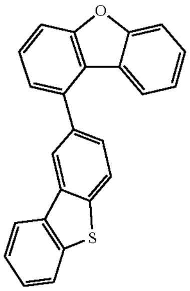 [SMILES: c1ccc2c(c1)oc1cccc(-c3ccc4sc5ccccc5c4c3)c12]
Ref. 4

TABLE 11-continued

| | Light Emitting Layer Compound | Driving Voltage (V) | Efficiency (cd/A) | Color Coordinate (x, y) | Life-time ($T_{90}$) |
|---|---|---|---|---|---|
| Ref. 5 | 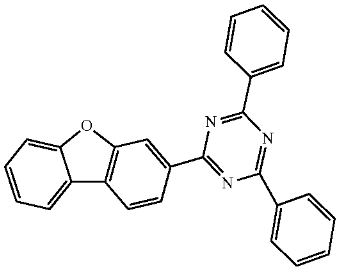 [SMILES: c1ccc(-c2nc(-c3ccccc3)nc(-c3ccc4c(c3)oc3ccccc34)n2)cc1] | | | | |
| Ref. 6 | 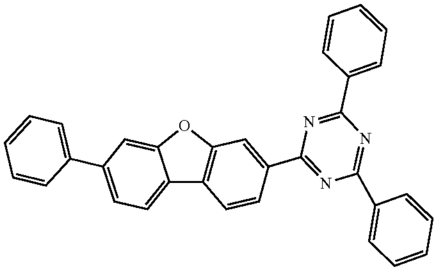 [SMILES: c1ccc(-c2ccc3c(c2)oc2cc(-c4nc(-c5ccccc5)nc(-c5ccccc5)n4)ccc23)cc1] | | | | |

<Experimental Example 2>—Manufacture of Organic Light Emitting Device

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. As the light emitting layer, one type of compound described as Chemical Formula 1 and one type of compound described as Chemical Formula 2 were premixed, and deposited to 400 Å in one source of supply as a host, and as a green phosphorescent dopant, $Ir(ppy)_3$ was doped and deposited by 7% with respect to the light emitting layer deposition thickness. After that, BCP was deposited to 60 Å as a hole blocking layer, and $Alq_3$ was deposited to 200 Å thereon as an electron transfer layer.

Lastly, an electron injection layer was formed on the electron transfer layer by depositing lithium fluoride (LiF) to a thickness of 10 Å, and then a cathode was formed on the electron injection layer by depositing an aluminum (A1) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, $T_{90}$ was measured when standard luminance was 6,000 cd/m$^2$ through a lifetime measurement system (M6000) manufactured by McScience Inc.

Results of measuring driving voltage, light emission efficiency, color coordinate (CIE) and lifetime of the organic light emitting devices manufactured according to the present disclosure are as shown in the following Table 12.

TABLE 12

| | Light Emitting Layer Compound | | Ratio | Driving Voltage (V) | Efficiency (cd/A) | Color Coordinate (x, y) | Life-time ($T_{90}$) |
|---|---|---|---|---|---|---|---|
| Comparative Example 20 | 1-1 | A | 1:1 | 4.78 | 54.2 | (0.276, 0.672) | 316 |
| Comparative Example 21 | | C | 1:1 | 5.49 | 48.1 | (0.277, 0.688) | 302 |
| Comparative Example 22 | | D | 1:1 | 4.99 | 51.3 | (0.278, 0.681) | 298 |
| Comparative Example 23 | | E | 1:1 | 6.63 | 43.2 | (0.282, 0.670) | 239 |
| Comparative Example 24 | 2-1 | A | 1:1 | 4.74 | 56.0 | (0.269, 0.672) | 311 |
| Comparative Example 25 | | B | 1:1 | 6.11 | 44.7 | (0.283, 0.677) | 237 |
| Comparative Example 26 | 2-14 | C | 1:1 | 5.61 | 47.2 | (0.278, 0.675) | 286 |
| Comparative Example 27 | 3-1 | A | 1:1 | 4.76 | 53.8 | (0.282, 0.673) | 291 |
| Comparative Example 28 | 3-49 | B | 1:1 | 6.22 | 41.5 | (0.282, 0.672) | 227 |
| Comparative Example 29 | 4-1 | B | 1:1 | 5.96 | 43.4 | (0.282, 0.681) | 254 |
| Comparative Example 30 | | E | 1:1 | 6.71 | 39.3 | (0.276, 0.688) | 208 |
| Comparative Example 31 | Ref. 1 | 5-19 | 1:1 | 5.63 | 55.0 | (0.285, 0.682) | 231 |
| Comparative Example 32 | Ref. 2 | 5-113 | 1:1 | 6.10 | 53.1 | (0.279, 0.671) | 165 |
| Comparative Example 33 | Ref. 5 | 5-6 | 1:1 | 6.09 | 47.4 | (0.267, 0.683) | 172 |
| Comparative Example 34 | Ref. 6 | 5-6 | 1:1 | 5.69 | 46.7 | (0.274, 0.680) | 184 |
| Example 41 | 1-1 | 5-6 | 1:8 | 4.65 | 56.2 | (0.244, 0.712) | 324 |
| Example 42 | | | 1:5 | 4.51 | 59.4 | (0.242, 0.712) | 345 |
| Example 43 | | | 1:2 | 4.06 | 81.5 | (0.247, 0.711) | 501 |
| Example 44 | | | 1:1 | 3.76 | 84.6 | (0.258, 0.718) | 532 |
| Example 45 | | | 2:1 | 3.82 | 85.2 | (0.249, 0.717) | 564 |
| Example 46 | | | 5:1 | 4.29 | 74.3 | (0.245, 0.709) | 421 |
| Example 47 | | | 8:1 | 4.58 | 55.2 | (0.249, 0.722) | 375 |
| Example 48 | 1-1 | 5-113 | 1:3 | 4.47 | 74.2 | (0.261, 0.724) | 437 |
| Example 49 | | | 1:2 | 4.16 | 79.7 | (0.252, 0.723) | 490 |
| Example 50 | | | 1:1 | 3.81 | 83.4 | (0.248, 0.722) | 523 |
| Example 51 | | | 2:1 | 3.77 | 84.9 | (0.255, 0.719) | 540 |
| Example 52 | | | 3:1 | 4.19 | 74.3 | (0.248, 0.718) | 427 |
| Example 53 | 1-49 | 5-123 | 1:2 | 4.16 | 78.5 | (0.247, 0.716) | 483 |
| Example 54 | | | 1:1 | 3.75 | 84.9 | (0.245, 0.708) | 551 |
| Example 55 | | | 2:1 | 3.84 | 83.5 | (0.254, 0.708) | 539 |
| Example 56 | 2-1 | 5-19 | 1:2 | 4.06 | 77.1 | (0.253, 0.722) | 462 |
| Example 57 | | | 1:1 | 3.68 | 86.4 | (0.255, 0.719) | 575 |
| Example 58 | | | 2:1 | 3.74 | 84.9 | (0.253, 0.717) | 542 |
| Example 59 | 2-14 | 5-30 | 1:2 | 3.97 | 80.2 | (0.246, 0.715) | 501 |
| Example 60 | | | 1:1 | 3.62 | 91.5 | (0.244, 0.717) | 633 |
| Example 61 | | | 2:1 | 3.73 | 85.0 | (0.245, 0.715) | 562 |
| Example 62 | 2-14 | 5-142 | 1:2 | 4.08 | 76.3 | (0.248, 0.719) | 471 |
| Example 61 | | | 1:1 | 3.71 | 84.2 | (0.250, 0.717) | 547 |
| Example 62 | | | 2:1 | 3.83 | 81.9 | (0.246, 0.717) | 526 |
| Example 63 | 2-49 | 5-123 | 1:2 | 4.02 | 76.1 | (0.255, 0.722) | 458 |
| Example 64 | | | 1:1 | 3.75 | 85.3 | (0.253, 0.721) | 565 |
| Example 65 | | | 2:1 | 3.79 | 85.2 | (0.253, 0.719) | 557 |
| Example 66 | 2-61 | 5-142 | 1:2 | 3.87 | 81.4 | (0.251, 0.723) | 513 |
| Example 67 | | | 1:1 | 3.57 | 94.6 | (0.249, 0.720) | 678 |

TABLE 12-continued

| | Light Emitting Layer Compound | | Ratio | Driving Voltage (V) | Efficiency (cd/A) | Color Coordinate (x, y) | Lifetime ($T_{90}$) |
|---|---|---|---|---|---|---|---|
| Example 68 | | | 2:1 | 3.63 | 90.7 | (0.249, 0.719) | 616 |
| Example 69 | 3- | 5-19 | 1:2 | 4.16 | 75.2 | (0.250, 0.722) | 452 |
| Example 70 | 14 | | 1:1 | 3.76 | 85.8 | (0.249, 0.721) | 571 |
| Example 71 | | | 2:1 | 3.89 | 82.3 | (0.246, 0.721) | 535 |
| Example 72 | 3- | 5-6 | 1:2 | 4.11 | 76.0 | (0.248, 0.729) | 447 |
| Example 73 | 49 | | 1:1 | 3.69 | 90.1 | (0.248, 0.727) | 611 |
| Example 74 | | | 2:1 | 3.78 | 86.6 | (0.246, 0.726) | 579 |
| Example 75 | 3- | 5- | 1:2 | 4.02 | 77.9 | (0.246, 0.722) | 483 |
| Example 76 | 49 | 113 | 1:1 | 3.59 | 93.9 | (0.245, 0.720) | 637 |
| Example 77 | | | 2:1 | 3.68 | 90.7 | (0.245, 0.718) | 619 |
| Example 78 | 4- | 5-6 | 1:2 | 3.92 | 79.4 | (0.248, 0.718) | 462 |
| Example 79 | 14 | | 1:1 | 3.65 | 95.2 | (0.247, 0.716) | 673 |
| Example 80 | | | 2:1 | 3.74 | 84.4 | (0.245, 0.715) | 547 |
| Example 81 | 4- | 5- | 1:2 | 3.85 | 83.6 | (0.244, 0.720) | 535 |
| Example 82 | 49 | 113 | 1:1 | 3.59 | 96.7 | (0.244, 0.712) | 688 |
| Example 81 | | | 2:1 | 3.72 | 86.2 | (0.246, 0.711) | 571 |

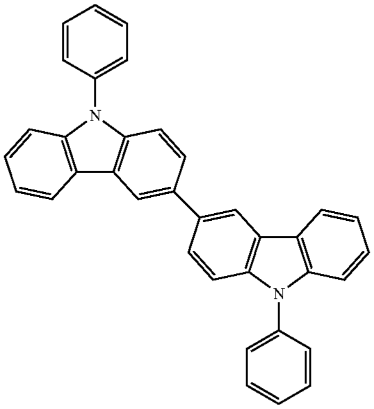 [SMILES: c1ccc(-n2c3ccccc3c3cc(-c4ccc5c(c4)c4ccccc4n5-c4ccccc4)ccc32)cc1]

A

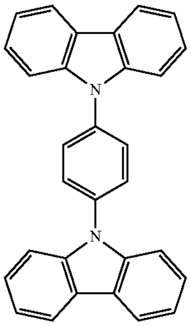 [SMILES: c1ccc2c(c1)c1ccccc1n2-c1ccc(-n2c3ccccc3c3ccccc32)cc1]

B

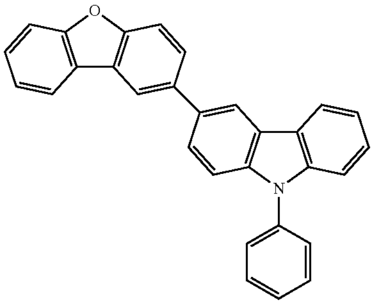 [SMILES: c1ccc(-n2c3ccccc3c3cc(-c4ccc5oc6ccccc6c5c4)ccc32)cc1]

C

TABLE 12-continued

| | Light Emitting Layer Compound | Ratio | Driving Voltage (V) | Efficiency (cd/A) | Color Coordinate (x, y) | Lifetime ($T_{90}$) |
|---|---|---|---|---|---|---|

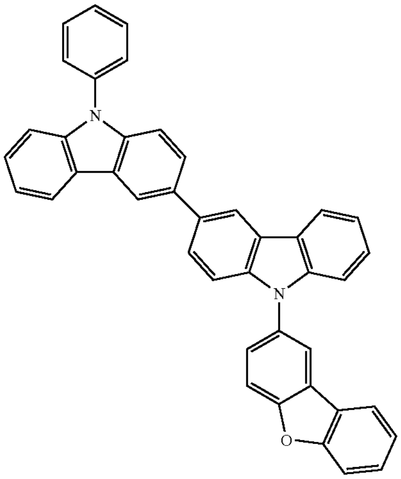 [SMILES: c1ccc(-n2c3ccccc3c3cc(-c4ccc5c(c4)c4ccccc4n5-c4ccc5oc6ccccc6c5c4)ccc32)cc1]

D

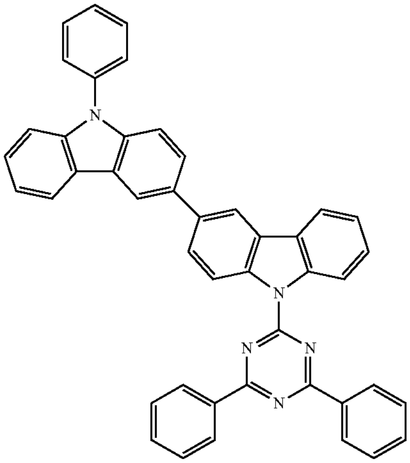 [SMILES: c1ccc(-c2nc(-c3ccccc3)nc(-n3c4ccccc4c4cc(-c5ccc6c(c5)c5ccccc5n6-c5ccccc5)ccc43)n2)cc1]

E

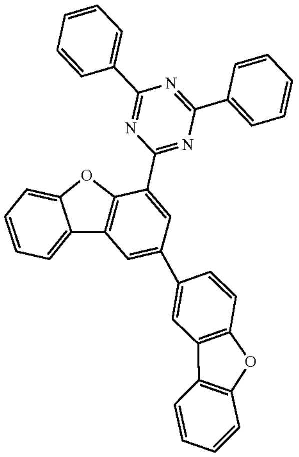 [SMILES: c1ccc(-c2nc(-c3ccccc3)nc(-c3cc(-c4ccc5oc6ccccc6c5c4)cc4c3oc3ccccc34)n2)cc1]

Ref. 1

TABLE 12-continued

| Light Emitting Layer Compound | Ratio | Driving Voltage (V) | Efficiency (cd/A) | Color Coordinate (x, y) | Lifetime ($T_{90}$) |
|---|---|---|---|---|---|
| 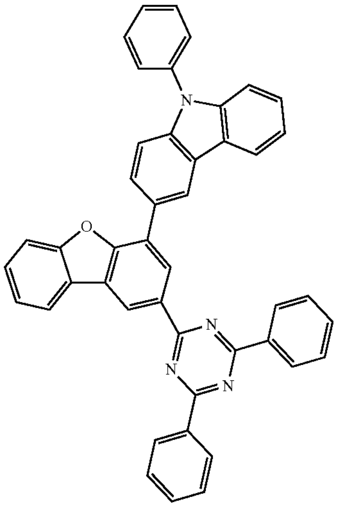 [SMILES: c1ccc(-c2nc(-c3ccccc3)nc(-c3cc(-c4ccc5c(c4)c4ccccc4n5-c4ccccc4)c4oc5ccccc5c4c3)n2)cc1] | | | | | Ref. 2 |
| 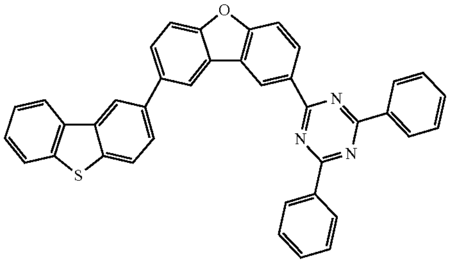 [SMILES: c1ccc(-c2nc(-c3ccccc3)nc(-c3ccc4oc5ccc(-c6ccc7sc8ccccc8c7c6)cc5c4c3)n2)cc1] | | | | | Ref. 3 |
| 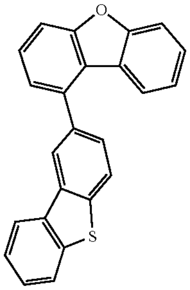 [SMILES: c1ccc2c(c1)oc1cccc(-c3ccc4sc5ccccc5c4c3)c12] | | | | | Ref. 4 |
| 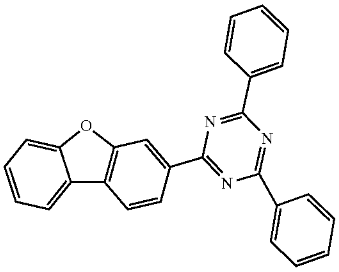 [SMILES: c1ccc(-c2nc(-c3ccccc3)nc(-c3ccc4c(c3)oc3ccccc34)n2)cc1] | | | | | Ref. 5 |
| 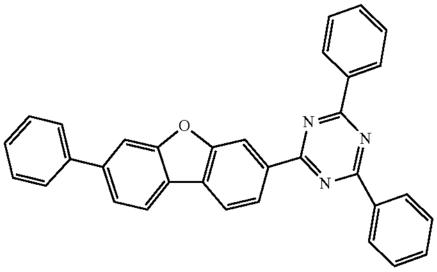 [SMILES: c1ccc(-c2ccc3c(c2)oc2cc(-c4nc(-c5ccccc5)nc(-c5ccccc5)n4)ccc23)cc1] | | | | | Ref. 6 |

As seen from the results of Table 12, the organic electroluminescent device using the light emitting layer material of the organic electroluminescent device of the present disclosure had lower driving voltage, enhanced light emission efficiency, and significantly improved lifetime as well compared to Comparative Examples 20 to 30.

From the results of Table 11 (comprising the compounds each alone) and Table 12 (comprising the heterocyclic compound of Chemical Formula 1 and the heterocyclic compound of Chemical Formula 2 at the same time), it was seen that effects or more superior efficiency and lifetime were obtained when comprising the compound of Chemical Formula 1 and the compound of Chemical Formula 2 at the same time. Such results may lead to a forecast that an exciplex phenomenon occurs when comprising the two compounds at the same time.

Particularly, Table 11 shows the organic light emitting devices comprising Chemical Formula 1 or Chemical Formula 2 of the present application each alone, and it was identified that very inferior performance was obtained particularly when using Chemical Formula 2 alone, and it was identified that, through combining Chemical Formula 1 of the present application and Chemical Formula 2 of the present application as in Table 12, a higher level of performance was accomplished by forming an exciplex form, strengthening a hole transfer ability, and reducing resistance against receiving holes from the hole transfer layer.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having a favorable hole transfer ability and an acceptor (n-host) having a favorable electron transfer ability are used as a host of a light emitting layer, holes are injected to the p-host and electrons are injected to the n-host, and therefore, a driving voltage may be lowered, which resultantly helps with enhancement in the lifetime. In the disclosure of the present application, it was identified that superior device properties were obtained when, as a light emitting layer host, using the heterocyclic compound of Chemical Formula 2 as a donor role and the heterocyclic compound of Chemical Formula 1 as an acceptor role.

The structure of Chemical Formula 1 of the disclosure of the present application is a structure having high electronegativity, and having a more stable structure with dibenzofuran and dibenzothiophene, and a fused arylene group. The structure has high electron mobility as well, and therefore, receives electrons from an electron transfer layer and transfers the electrons to a dopant, and forms an exciplex with a p-type host, an electron donor, to have higher efficiency through reverse intersystem crossing. Particularly, it was identified that, even under an environment where reverse intersystem crossing occurs, high structural stability that the fused cyclic group has delayed material deterioration even when many electrons are introduced to the light emitting layer, and a longer lifetime was obtained.

In addition, in the present disclosure, the light emitting host formed with a plurality of types of compounds was deposited after the compounds were pre-mixed and formed in one source of supply (Experimental Example 2, Table 12). Herein, there is an advantage of fully maintaining uniformity of the thin film surface and thin film properties since the deposition is not performed many times. In addition, through simplifying the process, a device with improved efficiency, driving voltage and lifetime are able to be obtained as well as reducing overall process costs.

As seen from Table 12, the fused carbazole structure as the heterocyclic compound structure of Chemical Formula 2 of the present application is a structure comprising two carbazoles or one carbazole and heteroring, and has strong electron donor properties due to the unshared electron pairs present in the nitrogen and the heteroatom of the carbazole.

In other words, as seen from Table 12, it was identified that overall driving voltage/efficiency/lifetime were superior compared when using the heterocyclic compound corresponding to Chemical Formula 1 of the present application and one of the compounds corresponding to Compounds A to E (biscarbazole type; or structure in which carbazole and heteroring bond).

In addition, through the π-conjugation over a wide area corresponding to the whole basic skeleton, a wide area HOMO level is obtained compared to the non-fused carbazole compound, and wider hole distribution is obtained. Accordingly, properties of fast hole transfer were identified when driving the device, and through this, an advantage of also improving current efficiency was identified by lowering a driving voltage of the device as well as lowering the threshold voltage.

In addition, fused carbazole as in Chemical Formula 2 has a form in which pentagonal to hexagonal rings are fused through π-π bonds. This has a structure with minimal intramolecular distortion (rigid structure), and thereby shows high thermal stability ($T_{d95}$: 400° C. or higher, high $T_g$). High thermal stability becomes a favorable factor in overcoming a harsh high vacuum and high temperature condition of an organic light emitting device (OLED) deposition process, and is also advantageous against device deterioration when driving the device for a long period of time. Accordingly, it was seen that the fused carbazole structure like the structure of Chemical Formula 2 is a basic structure that may become a material of favorable lifetime based on low voltage, high efficiency and high thermal stability.

In addition, when pre-mixing as in Table 12, unique thermal properties of each material need to be checked before mixing. Herein, depositing a pre-mixed host material from one source of supply may greatly affect deposition conditions comprising a deposition rate depending on the unique thermal properties of the materials. When thermal properties between two or more types of materials pre-mixed are not similar and very different, repeatability and reproducibility in a deposition process may not be maintained, which means that an OLED that is all uniform may not be manufactured in one deposition process.

In order to overcome this, electrical properties of the material may be tuned by using a proper combination of basic structure and substituents of each material and in addition thereto, thermal properties of the materials may also be controlled depending on the molecular structure form.

Therefore, by using various substituents in Chemical Formula 2 in addition to the basic skeleton as well as using C—N bonding of fused carbazole as in Chemical Formula 2, diversity of various pre-mixing deposition processes between host-host may be secured by controlling thermal properties of each material as well as attempting to enhance device performance. This has an advantage of securing diversity of a pre-mixing deposition process using three, four or more host materials as well as two compounds as a host.

In addition, when driving an OLED, inside the device is exposed to various types of heat for a long period of time due to thermal energy generated by non-radiative emission caused from device driving for a long period of time and thermal energy generated from resistance to the current flow. Unlike metals, organic materials have very low thermal resistance, and therefore, thermal stability of the material needs to be secured through accurate thermal stability data. In addition, a deposition process of an OLED device is also conducted at a high temperature under a high vacuum state, and materials having low thermal stability are already deteriorated in the deposition process, and driving as an OLED may not be possible at all. Accordingly, in building an OLED, checking thermal stability of materials forming the device is very important preliminary work.

The fused carbazole structure described in Chemical Formula 2 has a form in which several pentagonal/hexagonal rings strongly linked by δ-δ bonds are fused and has a very rigid structure, and therefore, has temperatures of high Tg of 100° C. or higher and very high Td (95%) of 400° C. or higher. From this, it is seen that the material is capable of sufficiently endure a harsh high vacuum/high temperature state of an OLED deposition process, and has stability enough to prevent device deterioration even after driving the device for a long period of time.

FIG. 4 to FIG. 21 are thermal analysis data on each material of Chemical Formula 2 measured using a TGA/DSC apparatus of Mettler Toledo. The measured $Td_{95}$ was measured while raising the temperature from 30° C. to 600° C. by heating so that the temperature rises by 10 K per minute. Among the thermal properties such as glass transition temperature (Tg), crystallization temperature (Tc), melting temperature (Tm) and decomposition temperature (Td/95%) corresponding to Chemical Formula 2, long-term driving of the device and stability of the high vacuum deposition process were identified first through checking the glass transition temperature and the decomposition temperature.

FIG. 4 and FIG. 5 are graphs showing thermal stability of Compound 2-19 of the present application, FIG. 6 and FIG. 7 are graphs showing thermal stability of Compound 2-20 of the present application, FIG. 8 and FIG. 9 are graphs showing thermal stability of Compound 2-22 of the present application, FIG. 10 and FIG. 11 are graphs showing thermal stability of Compound 2-8 of the present application, FIG. 12 and FIG. 13 are graphs showing thermal stability of Compound 2-18 of the present application, FIG. 14 and FIG. 15 are graphs showing thermal stability of Compound 2-79 of the present application, and FIG. 16 and FIG. 17 are graphs showing thermal stability of Compound 2-123 of the present application.

In addition, FIG. 18 and FIG. 19 are graphs showing thermal stability of Compound A, and FIG. 20 and FIG. 2119 are graphs showing thermal stability of Compound C.

In the graphs of FIG. 4 to FIG. 21 showing thermal stability, $Td_{95}$ is a point of measuring a temperature when 95% of the mass remains after applying a temperature, and when $Td_{95}$ is high, it means being stable even at a high temperature.

As identified by comparing FIG. 4 to FIG. 17, and FIG. 18 to FIG. 21, it was identified that $Td_{95}$ was measured to be 400° C. or lower in Compound A (FIG. 18 and FIG. 19) and Compound C (FIG. 20 and FIG. 21) having a biscarbazole structure, which showed lower thermal stability compared to the fused carbazole compounds.

Accordingly, it was identified that comprising the heterocyclic compound of Chemical Formula 1 and the heterocyclic compound of Chemical Formula 2 at the same time is a basic structure sufficiently effective for manufacturing a device having a purposes of low voltage/high efficiency or an OLED having properties of high efficiency/long lifetime or low voltage/long lifetime.

The invention claimed is:

1. An organic light emitting device comprising:

a first electrode;

a second electrode; and one or more organic material layers provided between the first electrode and the second electrode, wherein one or more layers of the organic material layers comprise a heterocyclic compound represented by the following Chemical Formula 1, and a heterocyclic compound represented by any one of the following Chemical Formulas 2-7 to 2-9:

[Chemical Formula 1]

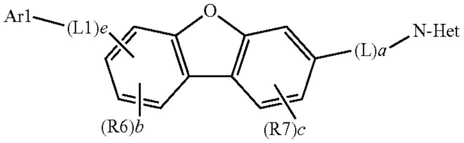

[Chemical Formula 2-7]

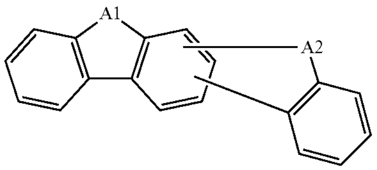

[Chemical Formula 2-8]

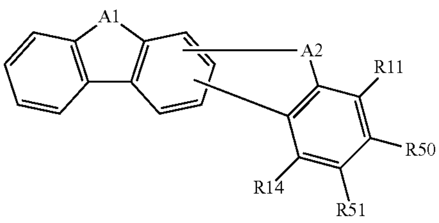

-continued

[Chemical Formula 2-9]

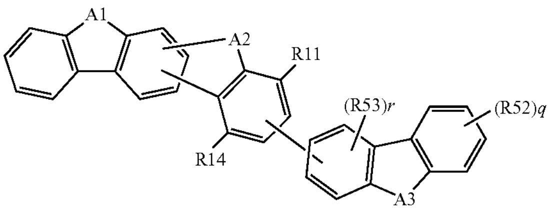

in Chemical Formulae 1 and 2-7 to 2-9,

N-Het is a pyridine group unsubstituted or substituted with one or more substituents selected from the group consisting of a C1 to C20 alkyl group, a C6 to C40 aryl group, a C2 to C40 heteroaryl group comprising S or O as a heteroatom, —P(═)ORR' and —SiRR'R" or a substituent linking two or more of the substituents; a pyrimidine group unsubstituted or substituted with one or more substituents selected from the group consisting of a C1 to C20 alkyl group, a C6 to C40 aryl group, a C2 to C40 heteroaryl group comprising S or O as a heteroatom, —P(═)ORR' and —SiRR'R" or a substituent linking two or more of the substituents; or a triazine group unsubstituted or substituted with one or more substituents selected from the group consisting of a C1 to C20 alkyl group, a C6 to C40 aryl group, a C2 to C40 heteroaryl group comprising S or O as a heteroatom, —P(═)ORR' and —SiRR'R" or a substituent linking two or more of the substituents, L and L1 are a direct bond; a C6 to C60 monocyclic arylene group; or a C10 to C60 polycyclic arylene group, Ar1 is a substituted or unsubstituted C10 to C60 aryl group, or represented by the following Chemical Formula 1-A;

[Chemical Formula 1-A]

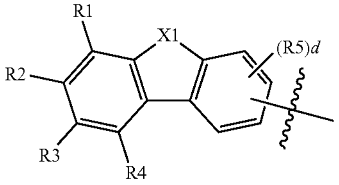

X1 is O; S; or NR22;

R1 to R4 are the same as or different from each other, and each independently hydrogen; a substituted or unsubstituted C1 to C40 alkyl group; a substituted or unsubstituted C6 to C40 aryl group; or a substituted or unsubstituted C2 to C40 heteroaryl group, or two or more groups adjacent to each other bond to each other to form a substituted or unsubstituted C6 to C40 aromatic hydrocarbon ring, A3 is O; S; or NRg;

R50 and R51 are the same as or different from each other, and each independently hydrogen; a phenyl group; or a triphenylenyl group, and at least one thereof is a phenyl group or a triphenylenyl group, Rg is a substituted or unsubstituted C6 to C60 aryl group, R11, R14, R52 and R53 are hydrogen, r is an integer of 0 to 3;

q is an integer of 0 to 4,

R5 to R7 are the same as or different from each other, and each independently selected from the group consisting of hydrogen; and deuterium;

A1 and A2 are the same as or different from each other, and each independently O; S; NRa; or CRbRc;

at least one of A1 and A2 is O; S; or CRbRc;

R22, R, R', and R" are the same as or different from each other, and each independently a C6 to C40 aryl group, Ra is a phenyl group unsubstituted or substituted with one or more substituents selected form the group consisting of a phenyl group, a biphenyl group and a triphenylsilyl group; a biphenyl group; a naphthyl group; a terphenyl group; a triphenylenyl group; a dimethylfluorenyl group; a diphenylfluorenyl group; a dibenzofuran group; a dibenzothiophene group; or a carbazole group unsubstituted or substituted with a phenyl group, Rb and Rc are the same as or different from each other, and each independently C1 to C20 alkyl group, b, c and d are an integer of 0 to 3;

and a and e are an integer of 0 to 5,

"substituted or unsubstituted" means being substituted with one or more substituents selected from the group consisting of C1 to C60 linear or branched alkyl; C6 to C60 monocyclic or polycyclic aryl; C2 to C60 monocyclic or polycyclic heteroaryl; —SiRR'R"; and —P(═O)RR'; or being unsubstituted, or being substituted with a substituent linking two or more substituents selected from among the substituents illustrated above, or being unsubstituted.

2. The organic light emitting device of claim 1, wherein Chemical Formula 1 is represented by any one of the following Chemical Formulae 3 to 6:

[Chemical Formula 3]

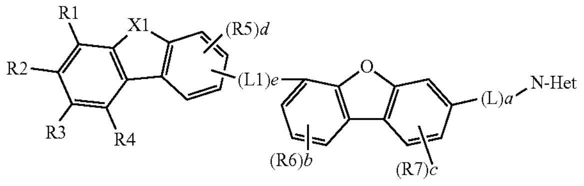

[Chemical Formula 4]

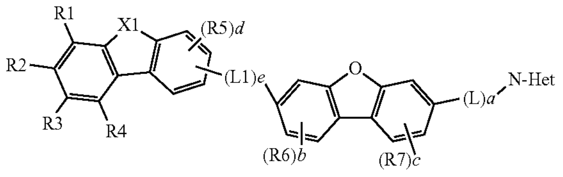

[Chemical Formula 5]

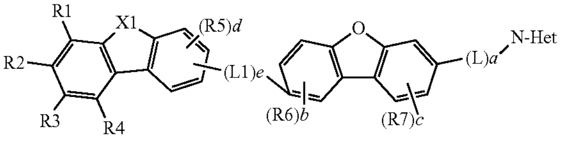

-continued

[Chemical Formula 6]

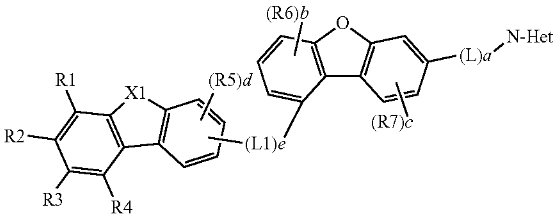

in Chemical Formulae 3 to 6,

N-Het, L, L1, R1 to R7, X1 and a to e have the same definitions as in Chemical Formula 1.

3. The organic light emitting device of claim 1, wherein Chemical Formula 1 is represented by any one of the following Chemical Formulae 3-1 to 6-1:

[Chemical Formula 3-1]

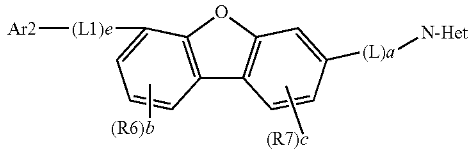

[Chemical Formula 4-1]

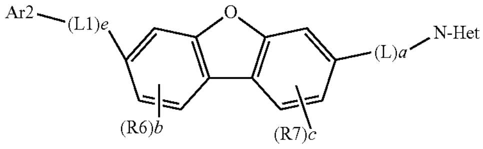

[Chemical Formula 5-1]

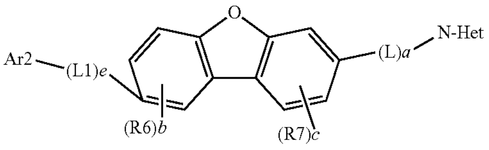

[Chemical Formula 6-1]

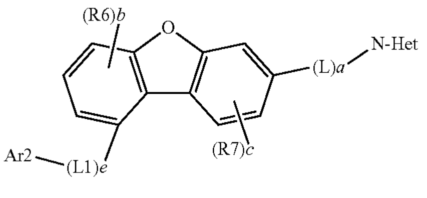

in Chemical Formulae 3-1 to 6-1,

N-Het, L, L1, R6, R7, a to c and e have the same definitions as in Chemical Formula 1; and Ar2 is a substituted or unsubstituted C10 to C60 aryl group.

4. The organic light emitting device of claim 1, wherein R5 to R7 are hydrogen.

5. The organic light emitting device of claim 1, wherein Chemical Formula 1 is represented by any one of the following compounds:

1-1
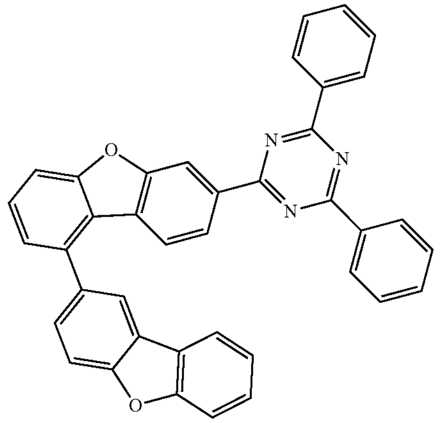
1-2
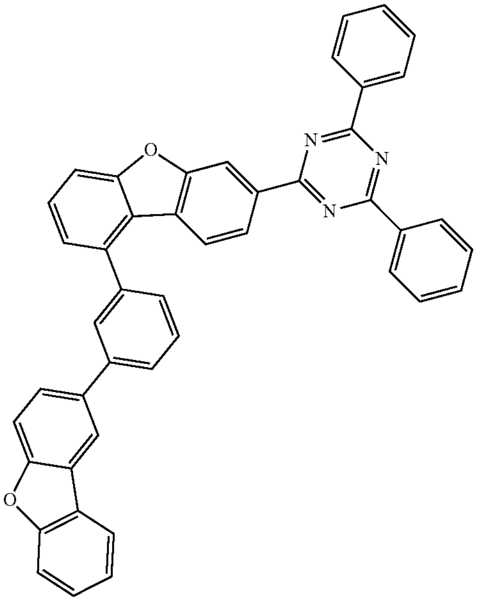
1-3
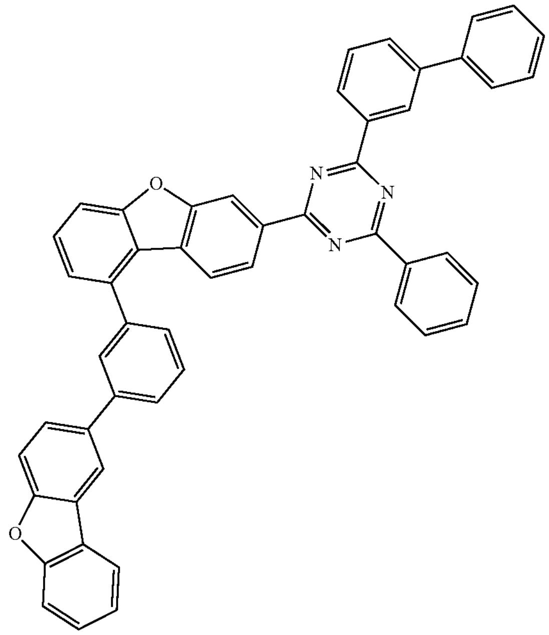
1-4
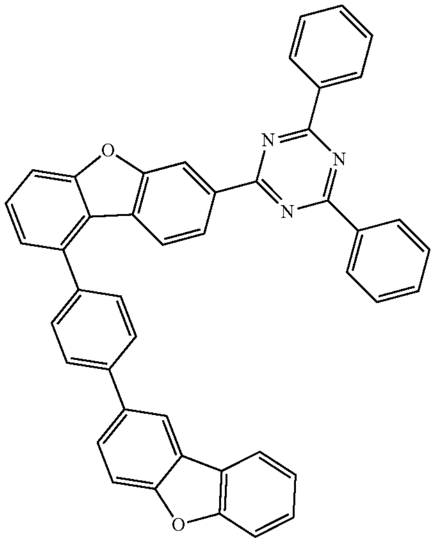

-continued
1-5
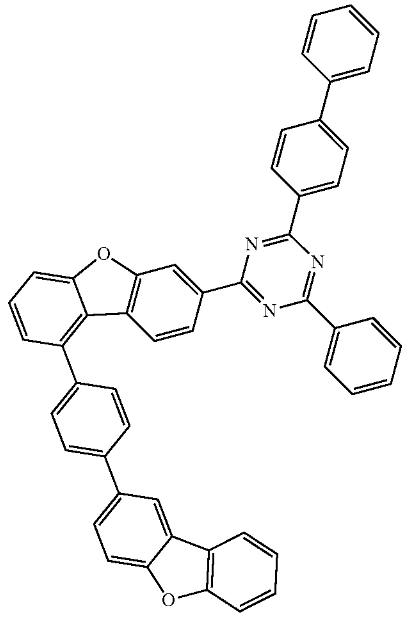
1-6
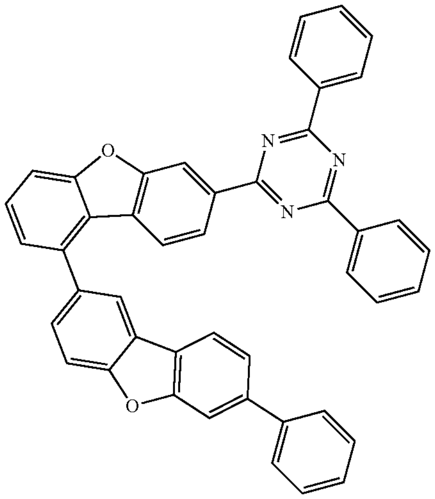
1-7
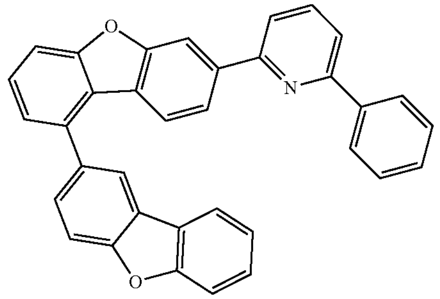
1-8
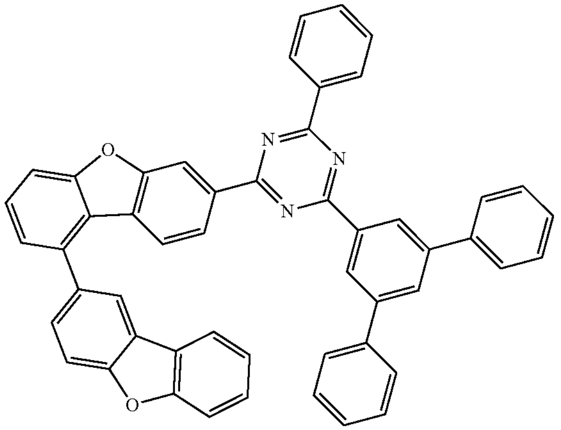
1-9
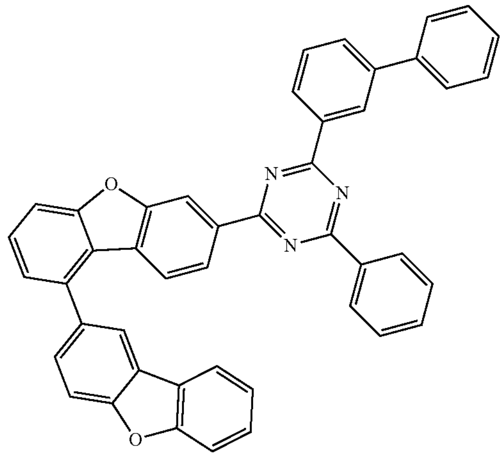
1-10
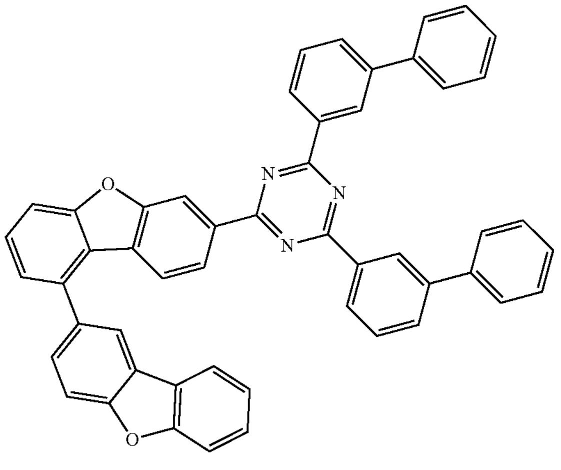

-continued
1-11
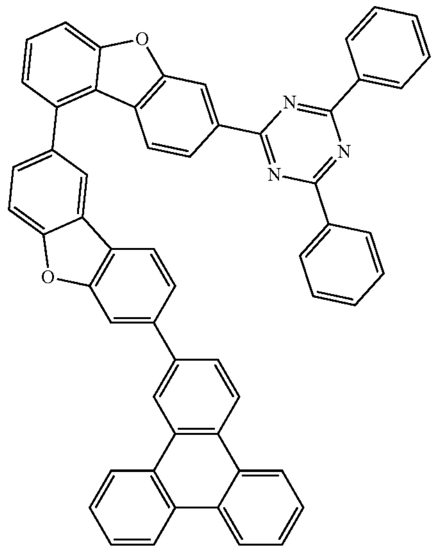
1-12
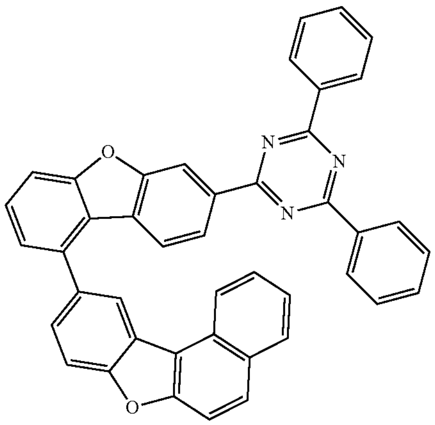
1-13
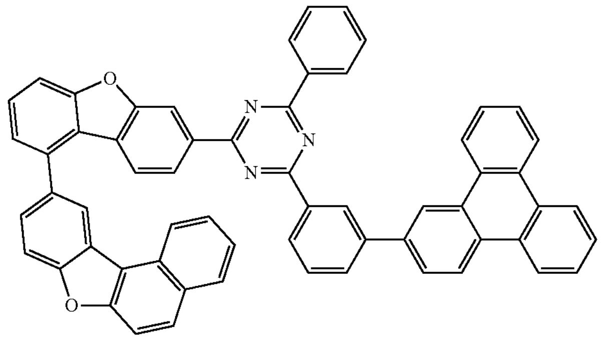
1-14
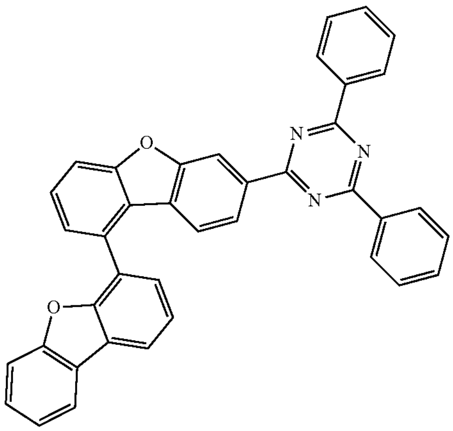
1-15
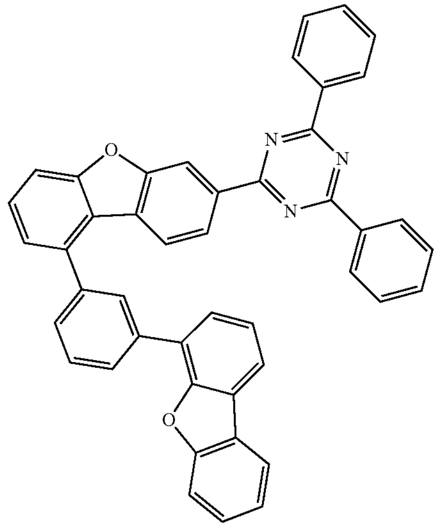
1-16
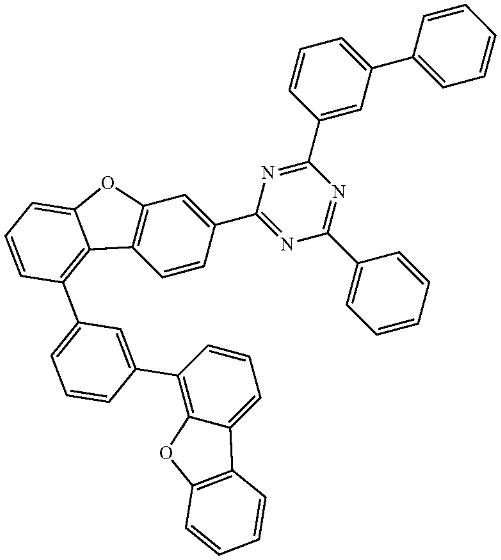

-continued
1-17
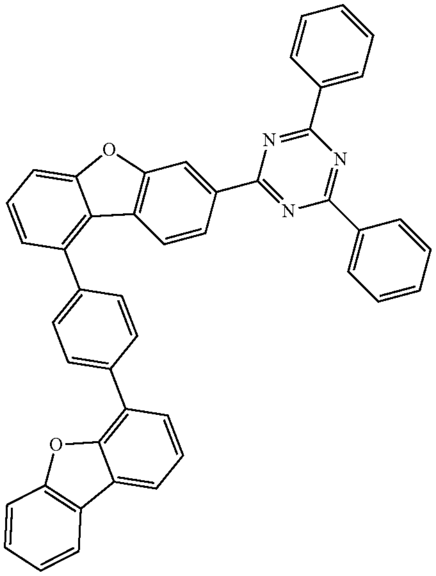
1-18
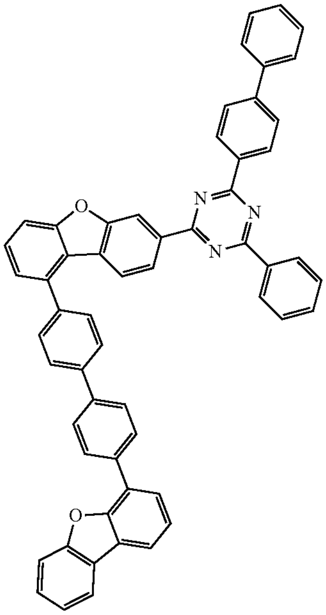
1-19
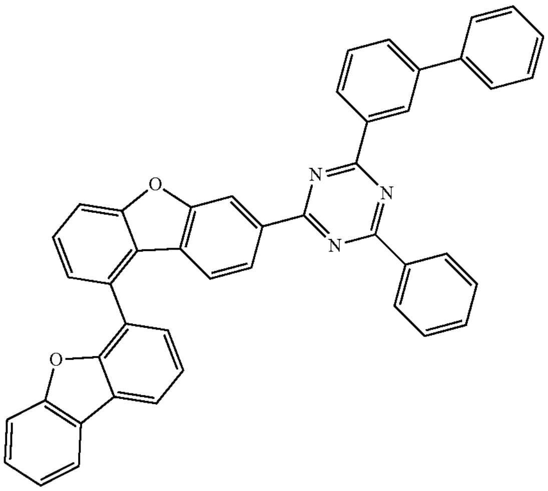
1-20
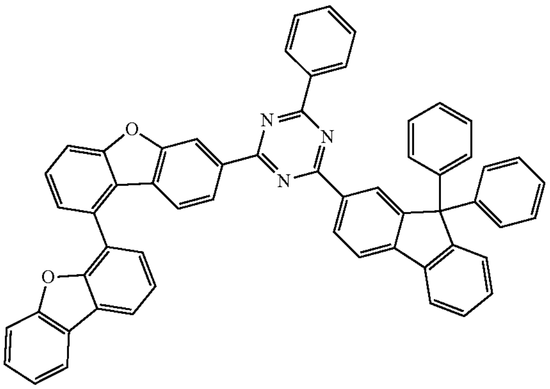
1-21
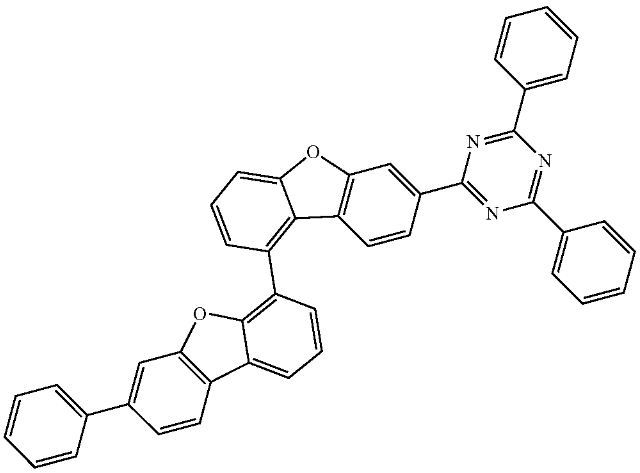

-continued
1-22
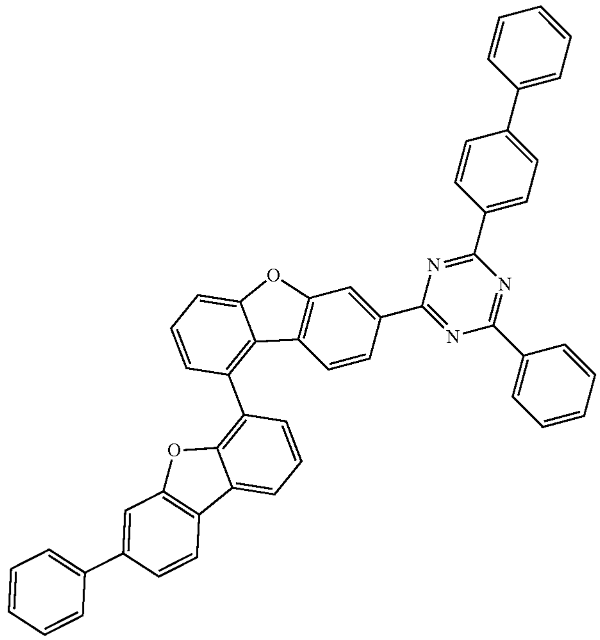
1-23
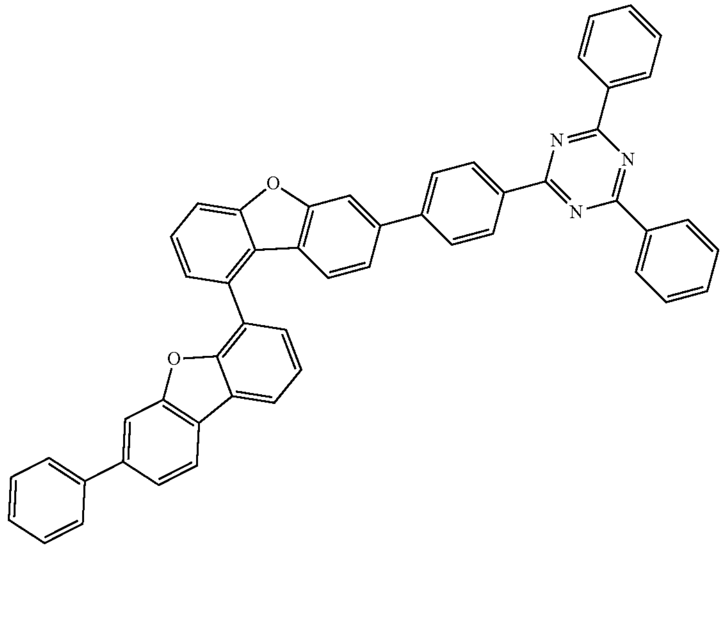

-continued
1-24
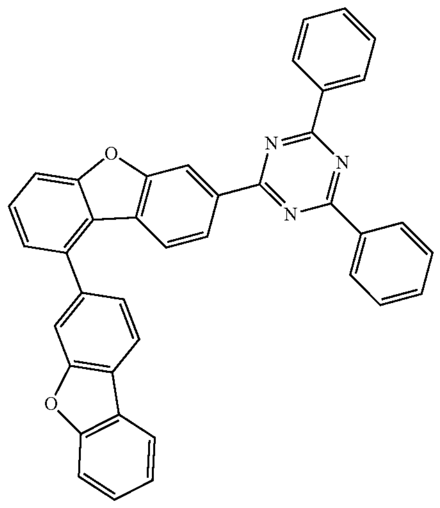
1-25
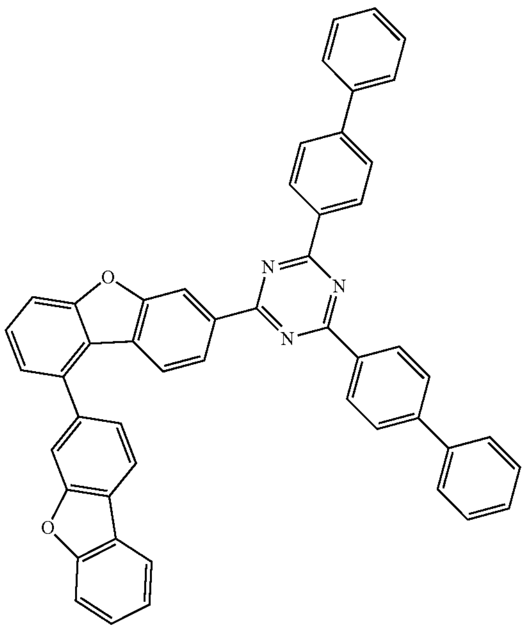
1-26
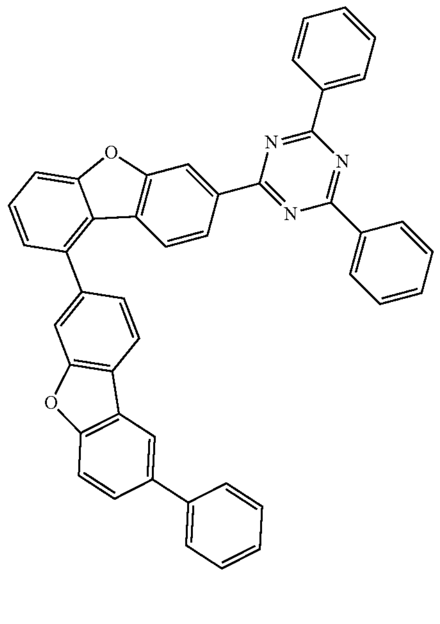
1-27
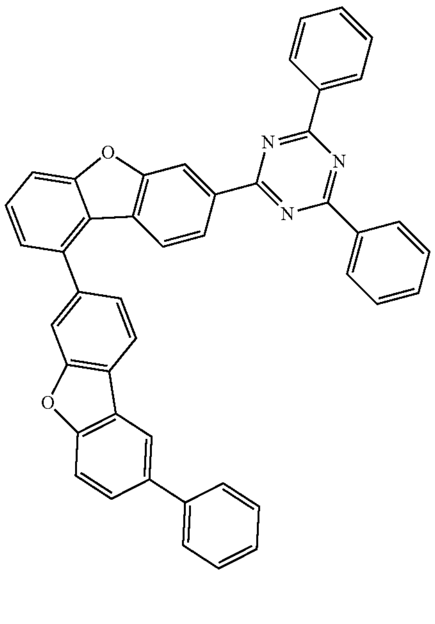

-continued
1-28
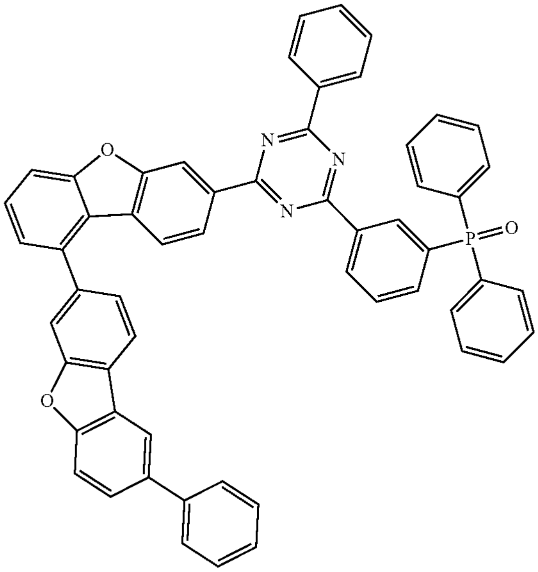
1-29
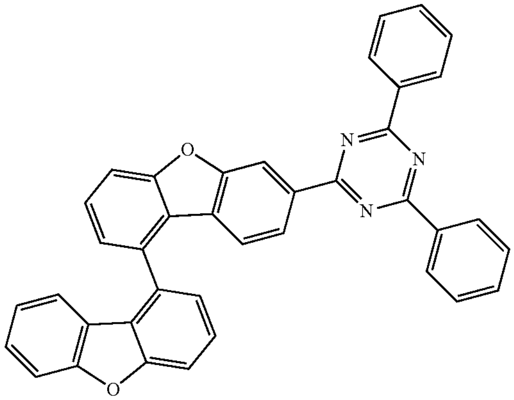
1-30
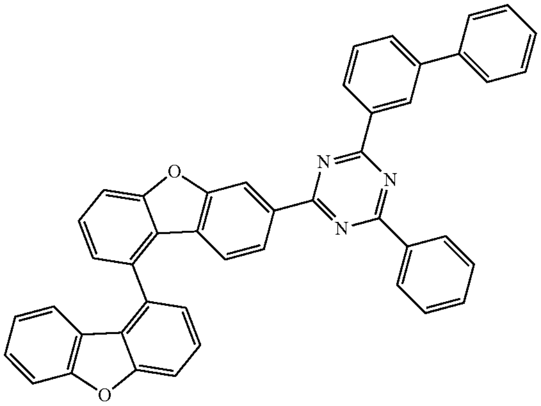
1-31
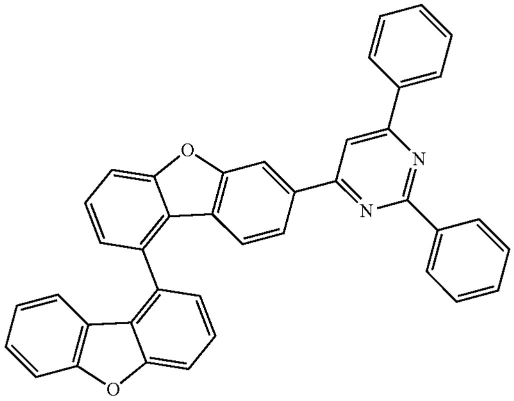
1-32
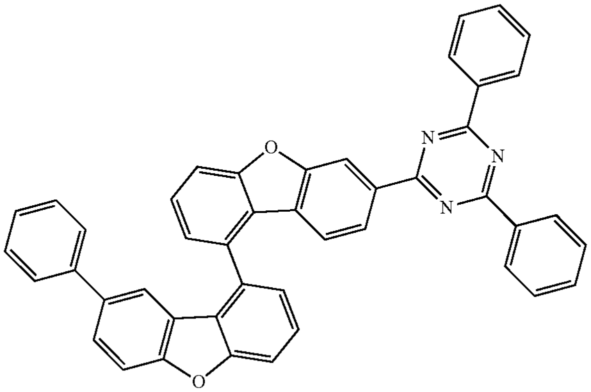
1-33
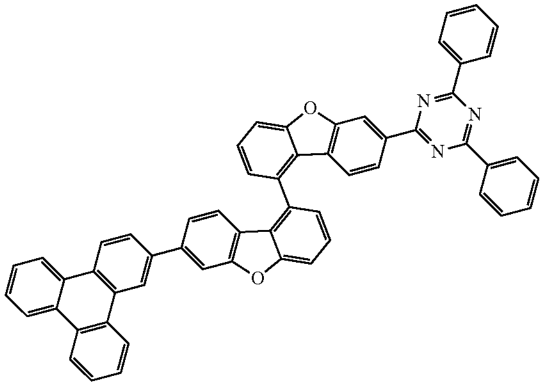

-continued
1-34
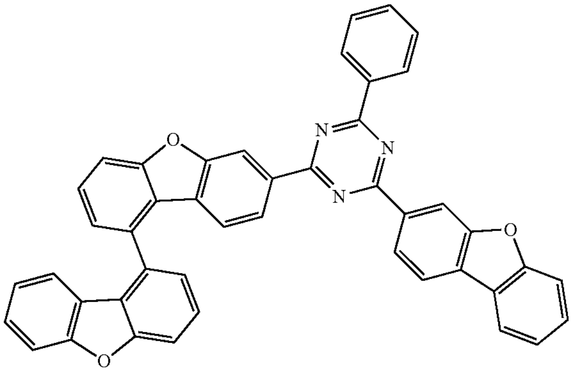
1-35
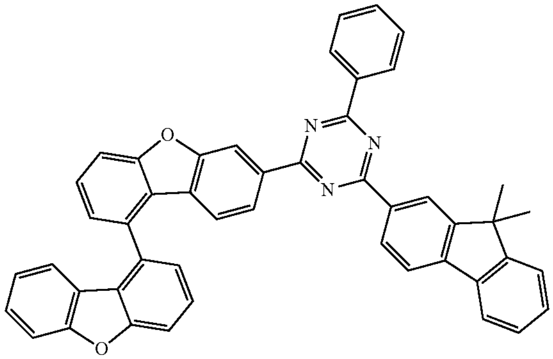
1-36
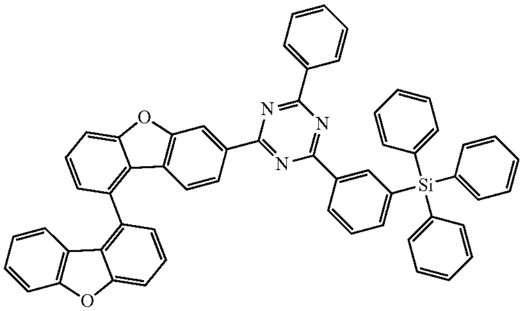
1-37
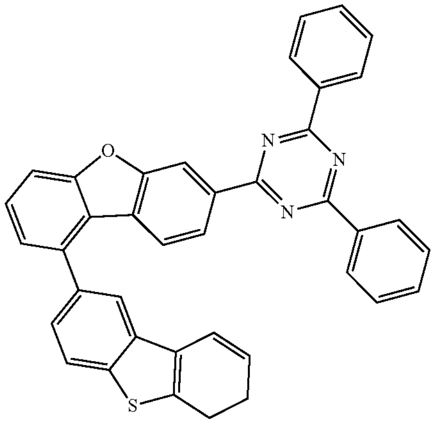
1-38
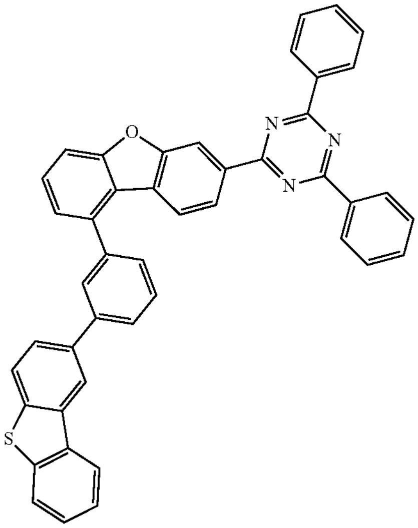
1-39
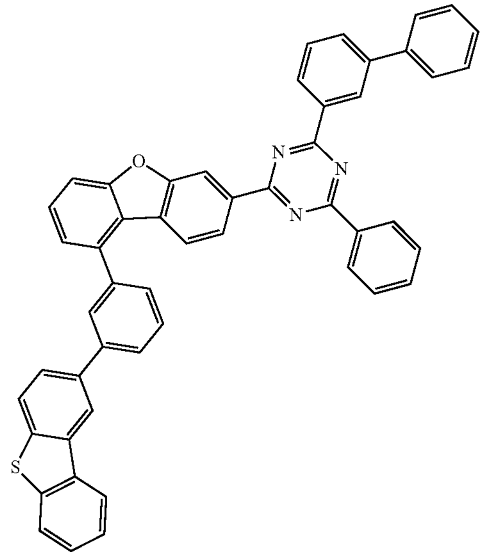

-continued
1-40
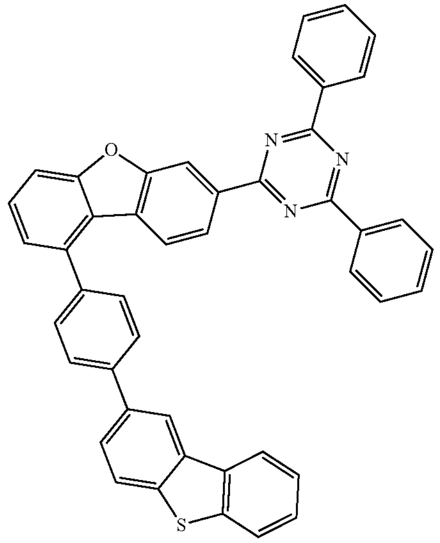
1-41
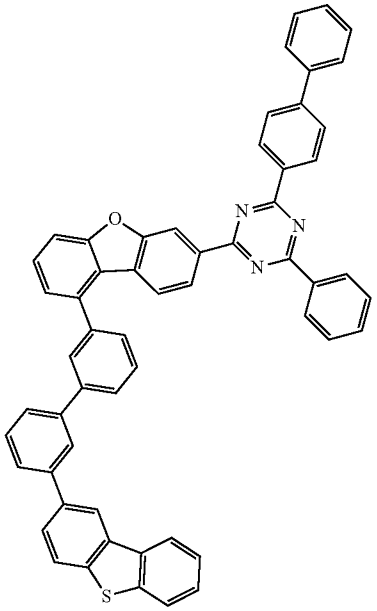
1-42
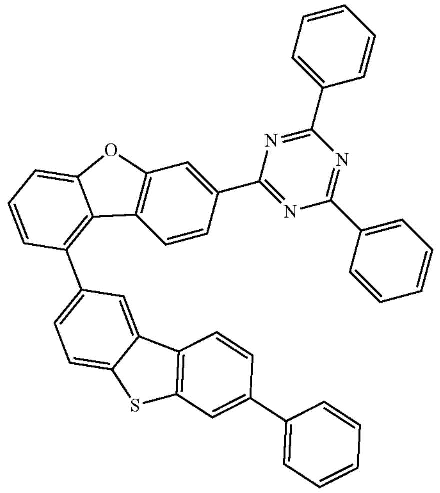
1-43
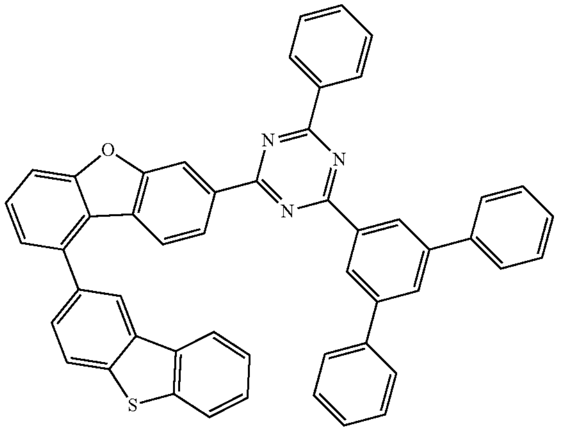
1-44
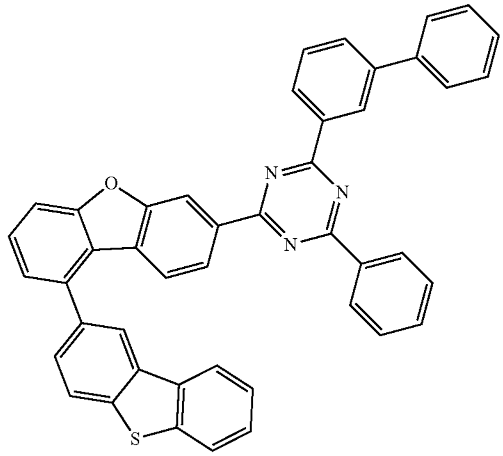

-continued
1-45
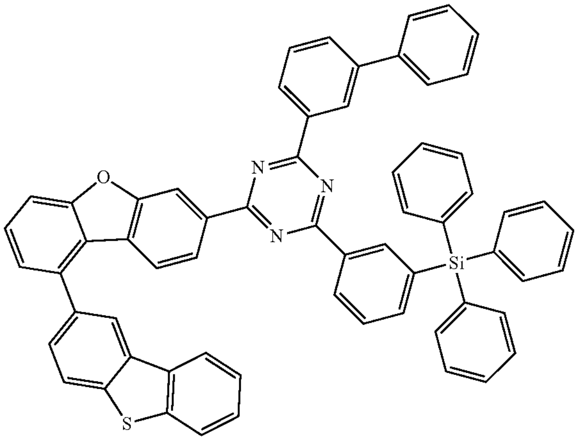
1-46
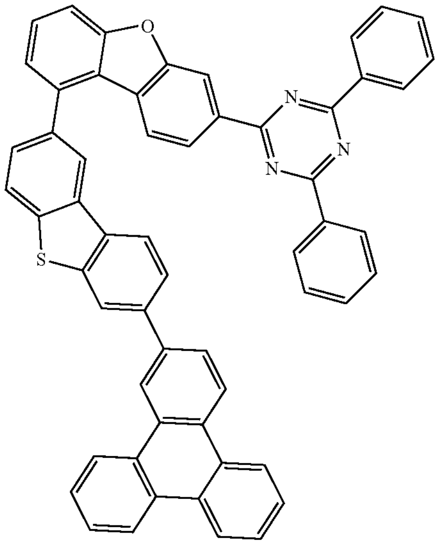
1-47
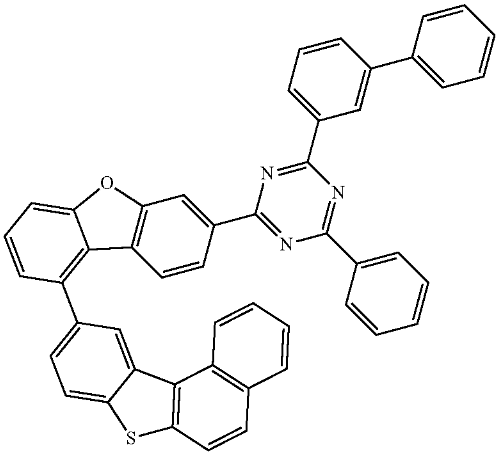
1-48
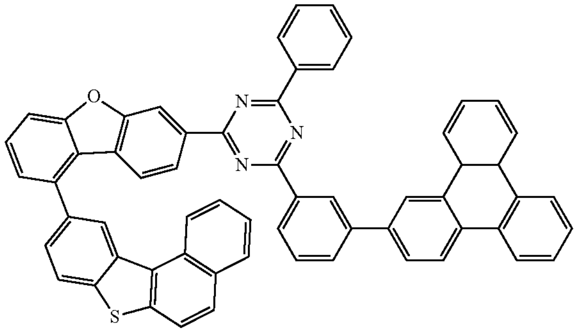
1-49
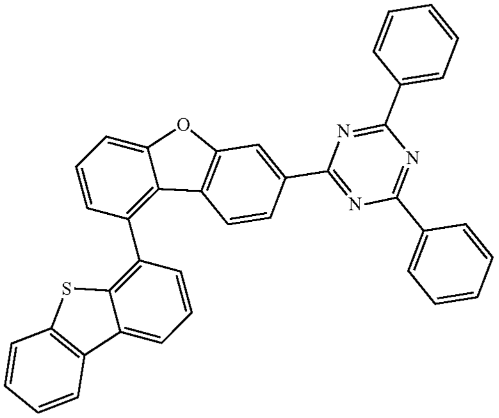
1-50
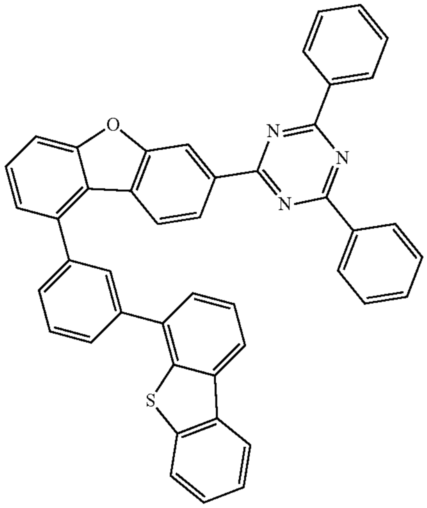

-continued
1-51
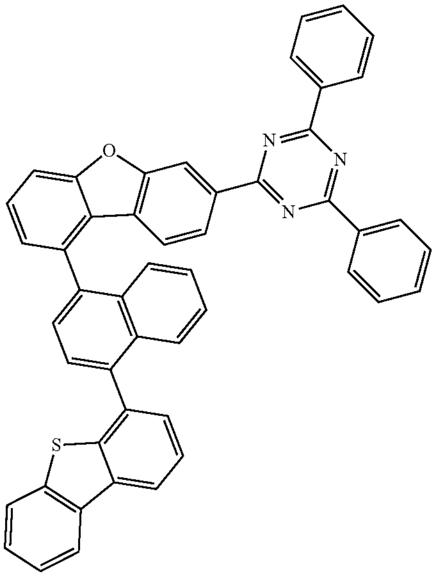
1-52
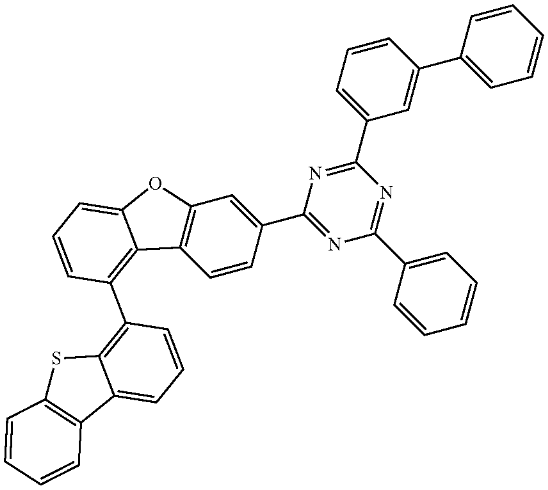
1-53
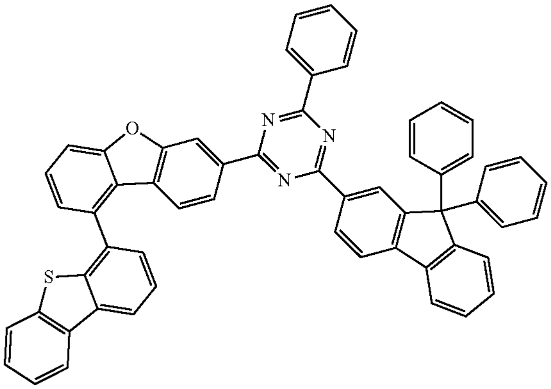
1-54
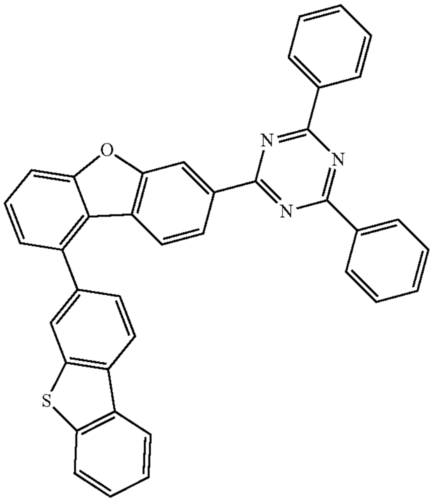

-continued
1-55
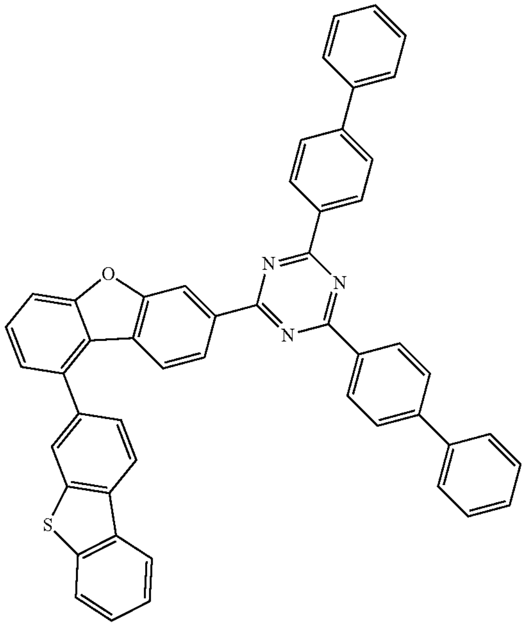
1-56
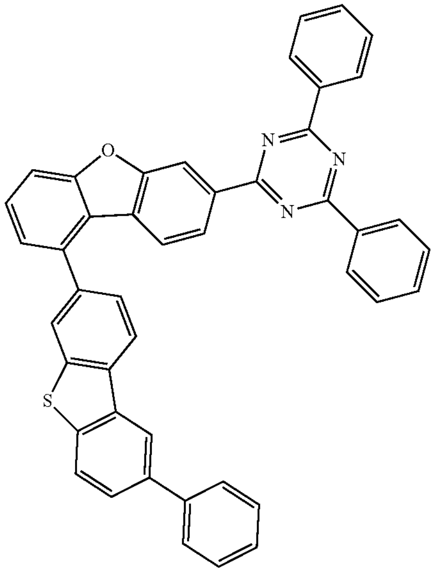
1-57
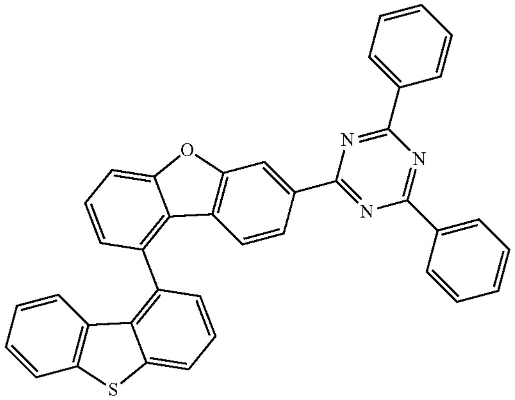
1-58
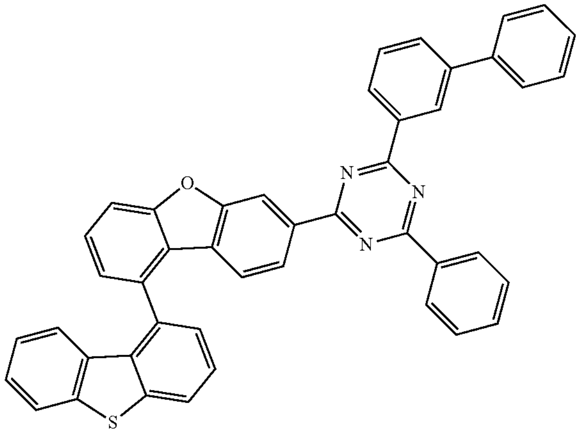
1-59
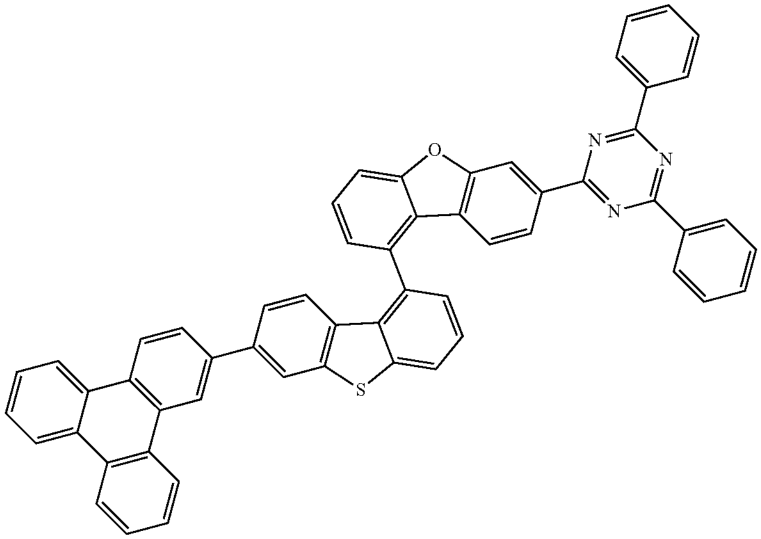

-continued
1-60
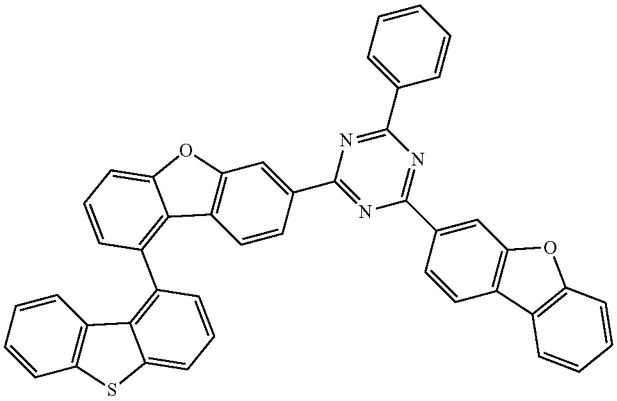
1-61
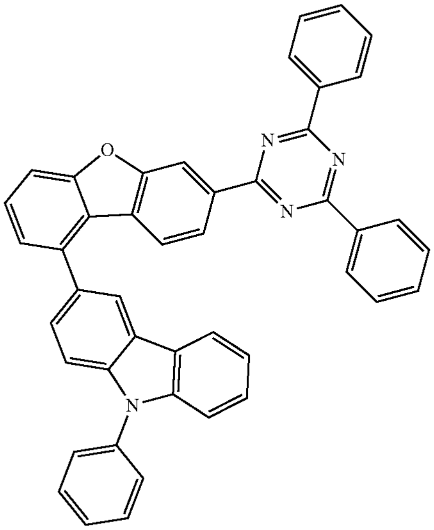
1-62
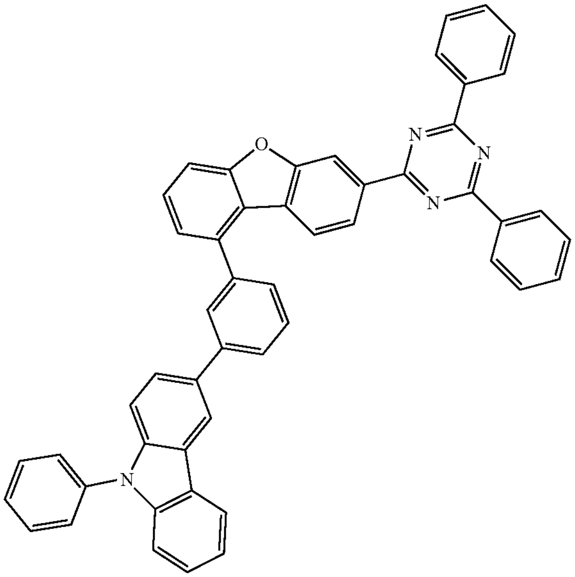
1-63
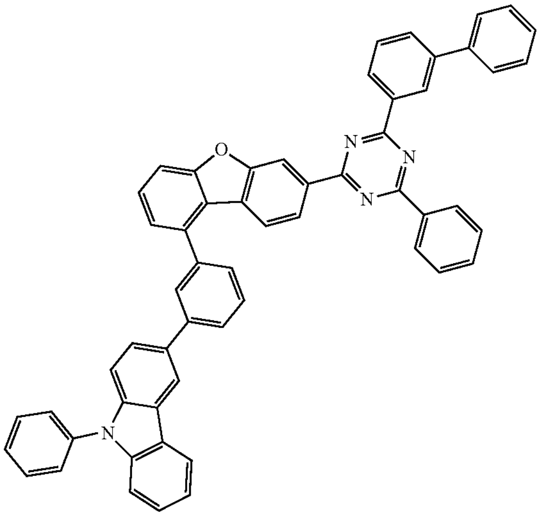
1-64
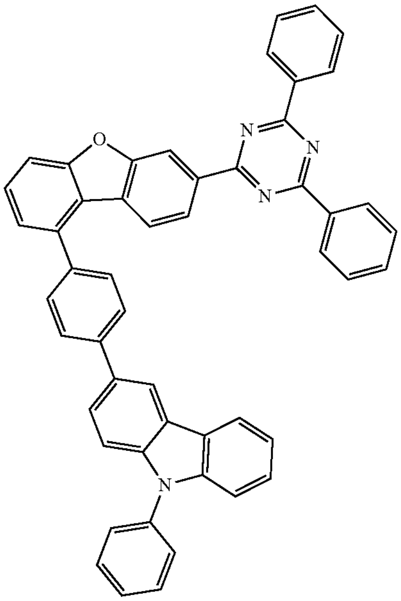

-continued
1-65
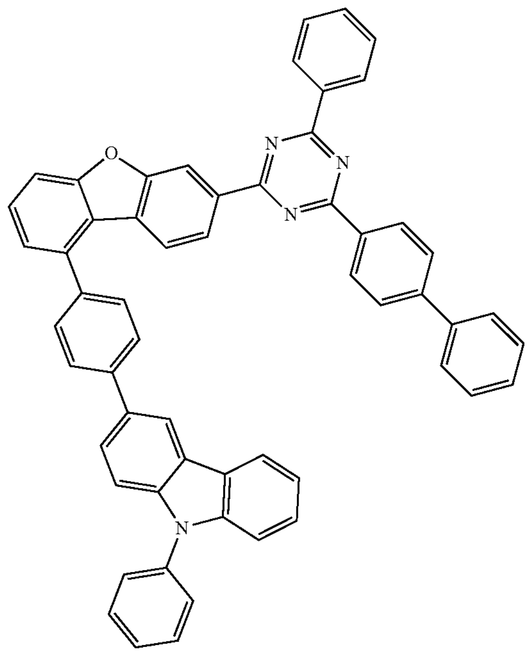
1-66
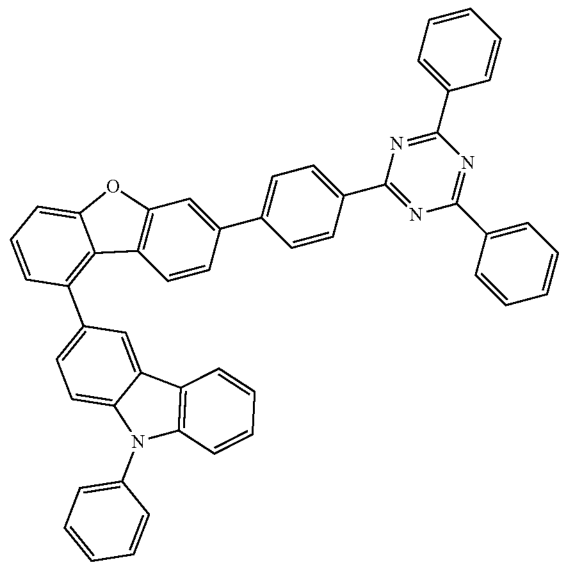
1-67
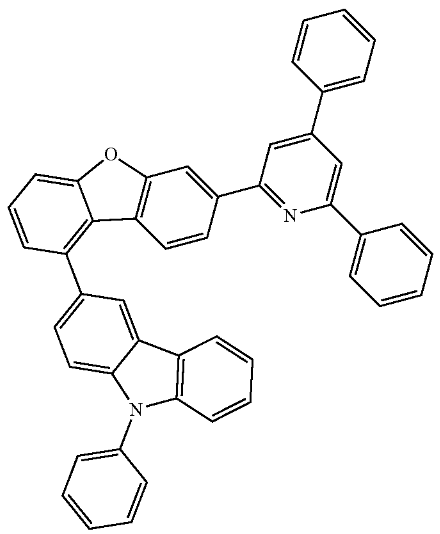
1-68
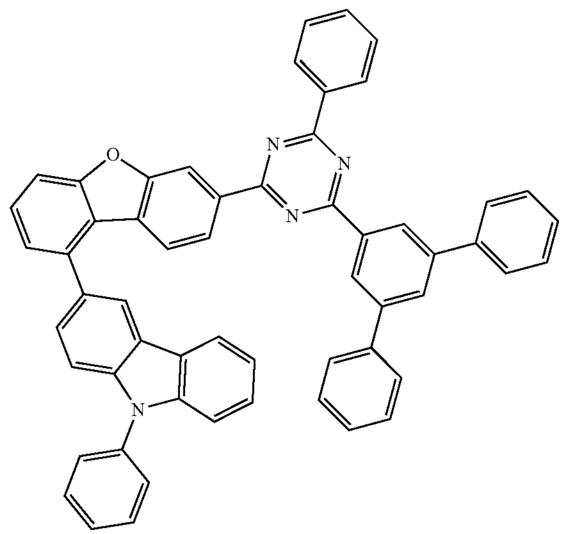

-continued
1-69
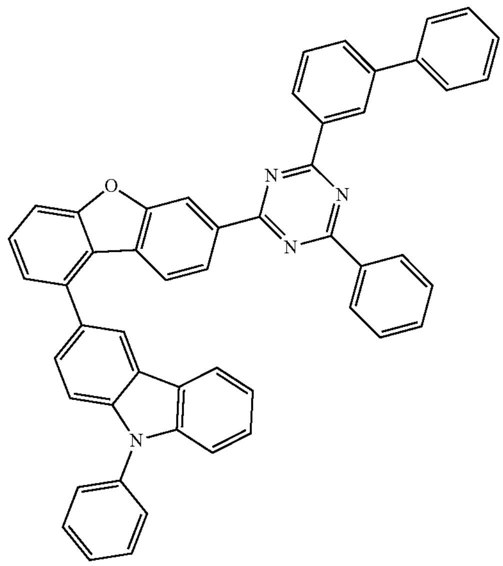
1-70
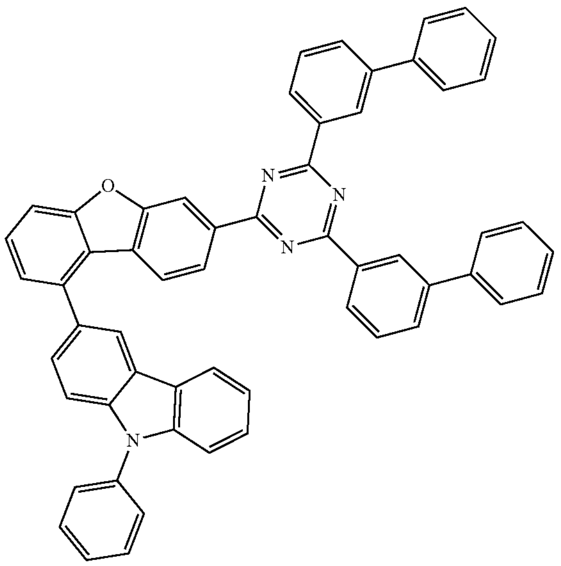
1-71
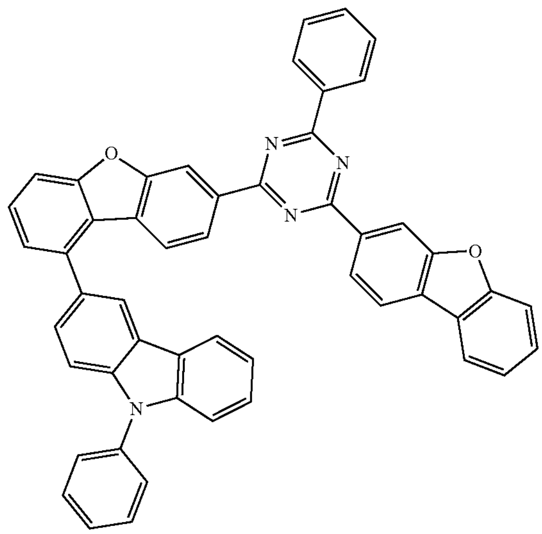
1-72
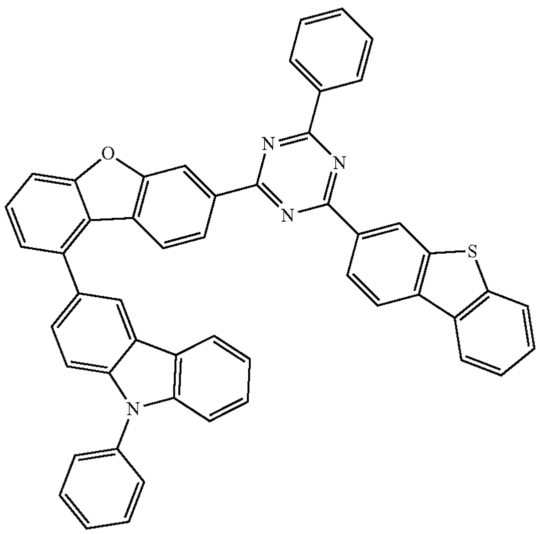
1-73
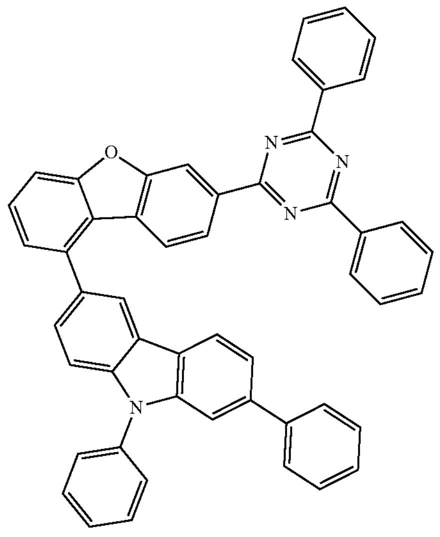
1-74
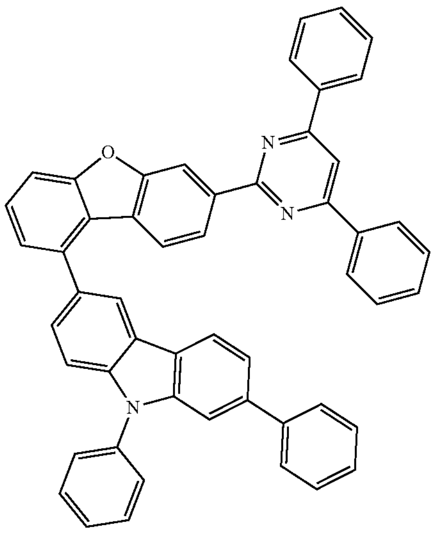

-continued
1-75
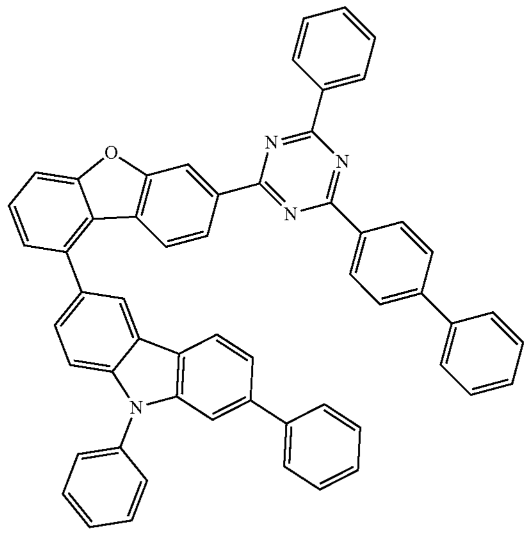
1-76
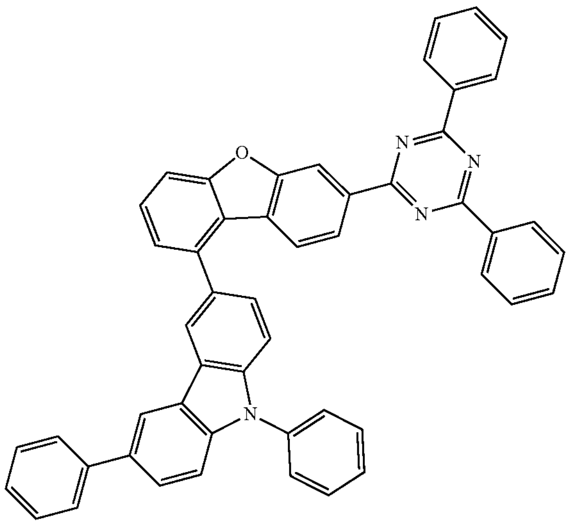
1-77
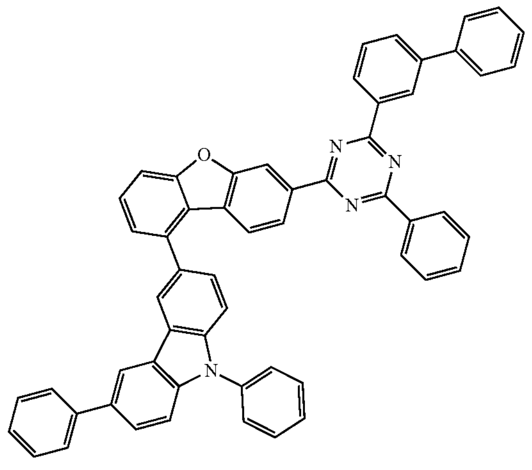
1-78
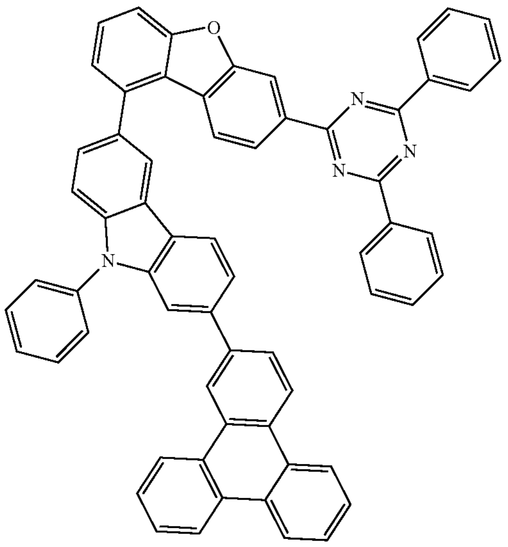
1-79
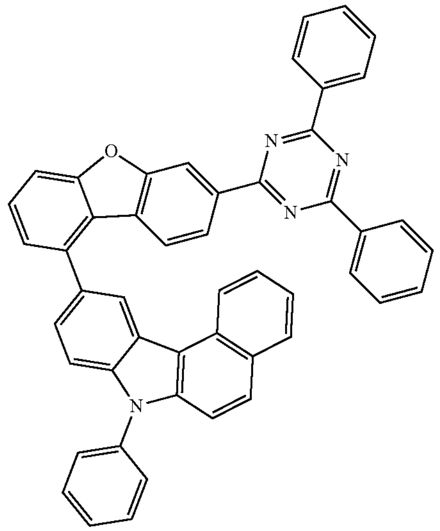
1-80
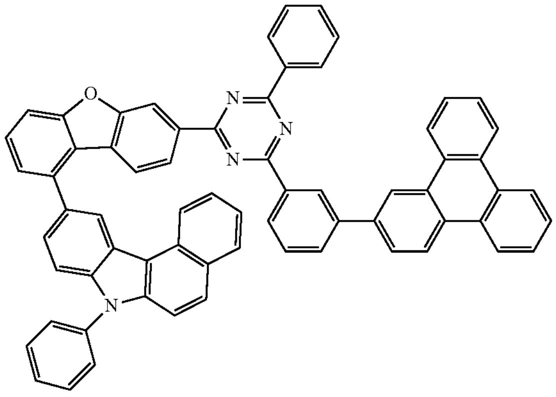

-continued
1-81
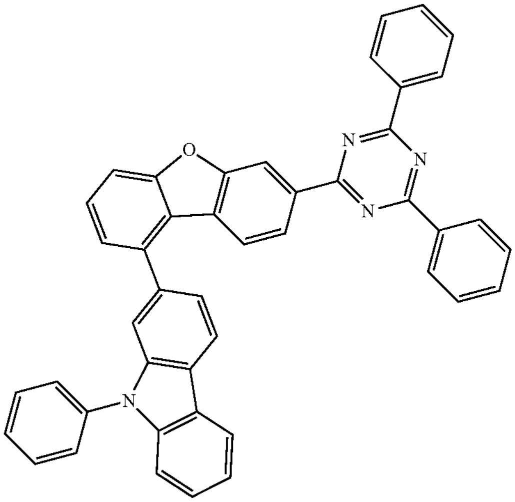
1-82
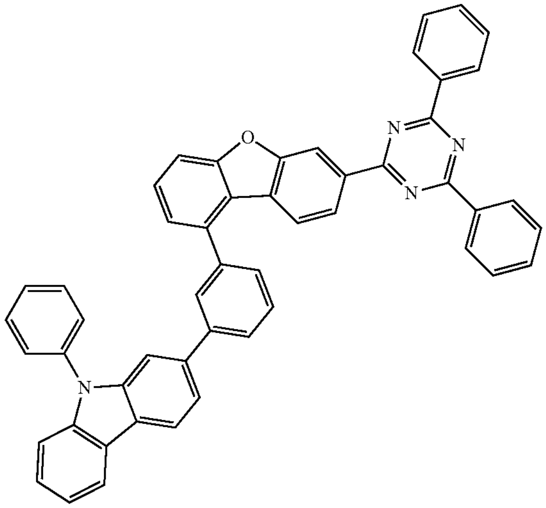
1-83
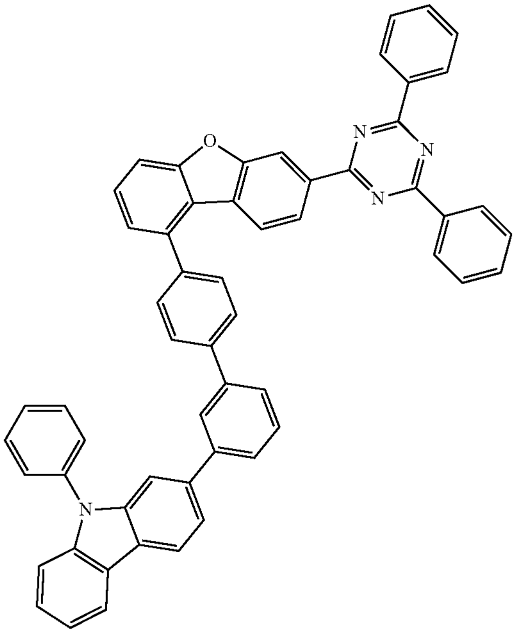
1-84
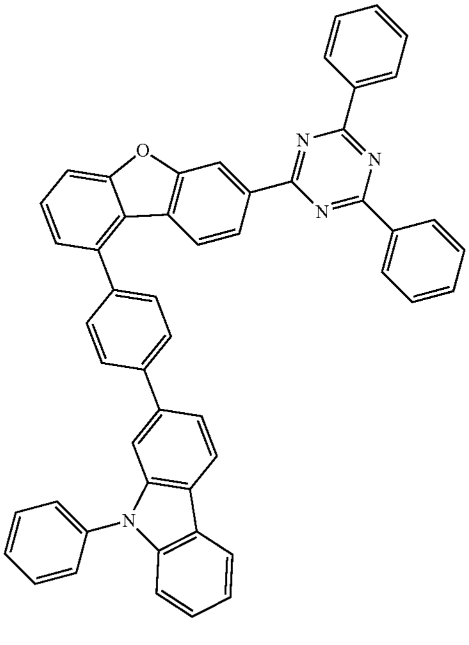

-continued
1-85
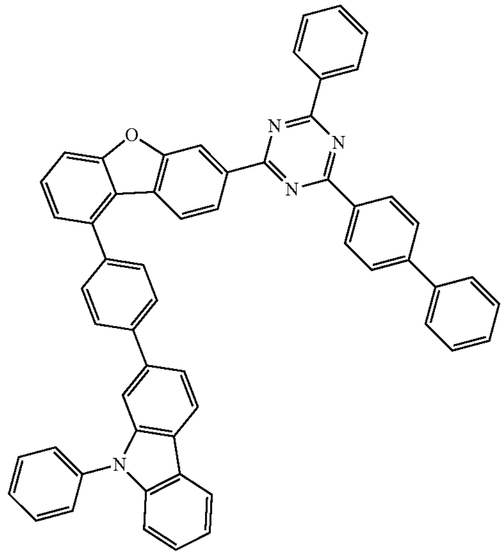
1-86
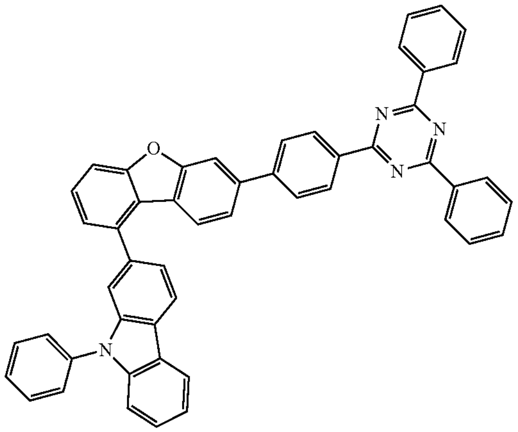
1-87
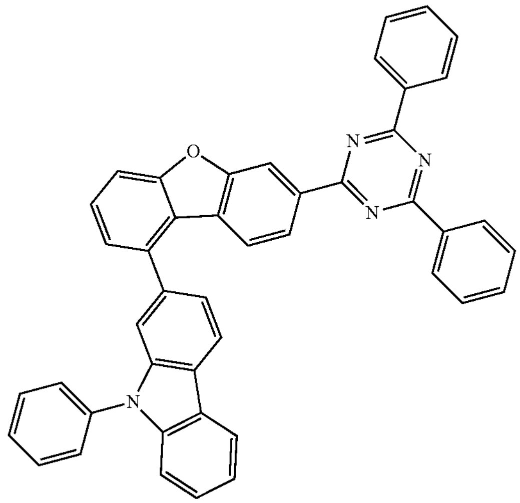
1-88
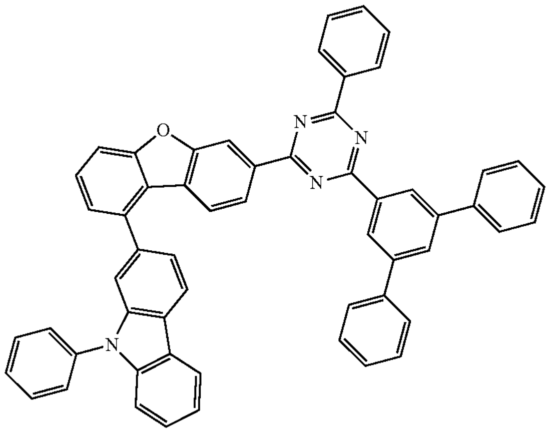

-continued
1-89
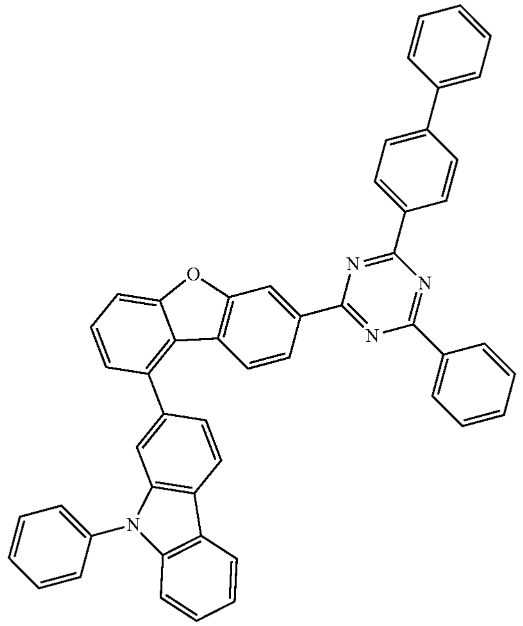
1-90
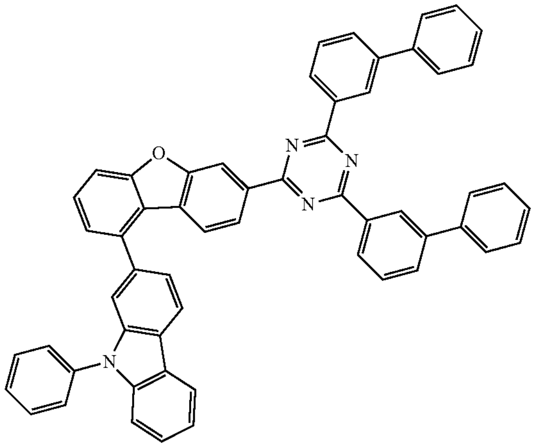
1-91
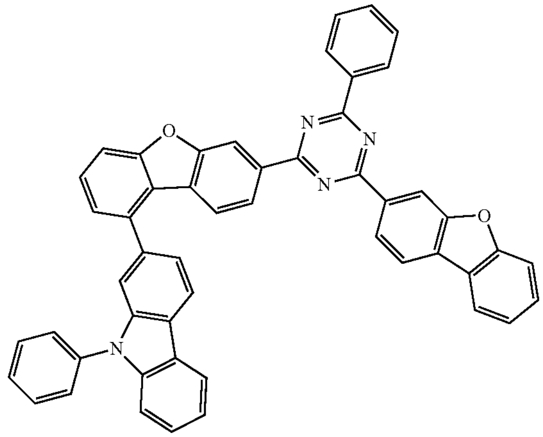
1-92
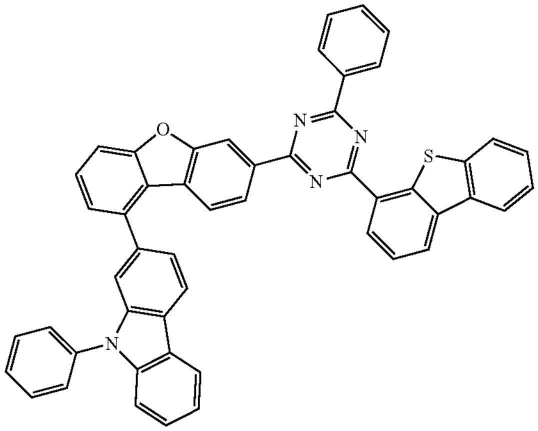

-continued
1-93
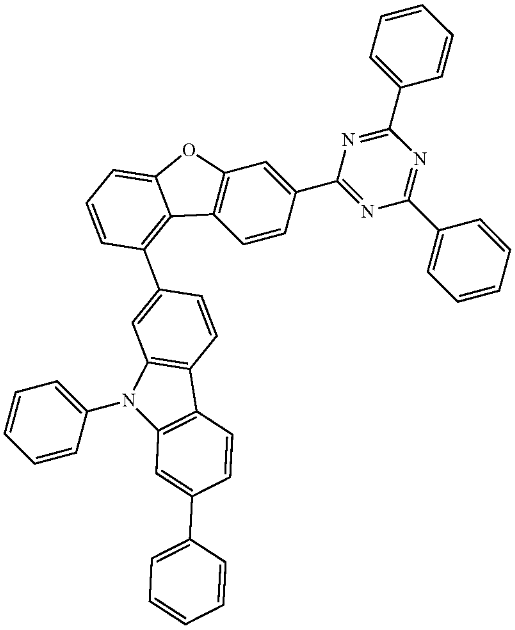
1-94
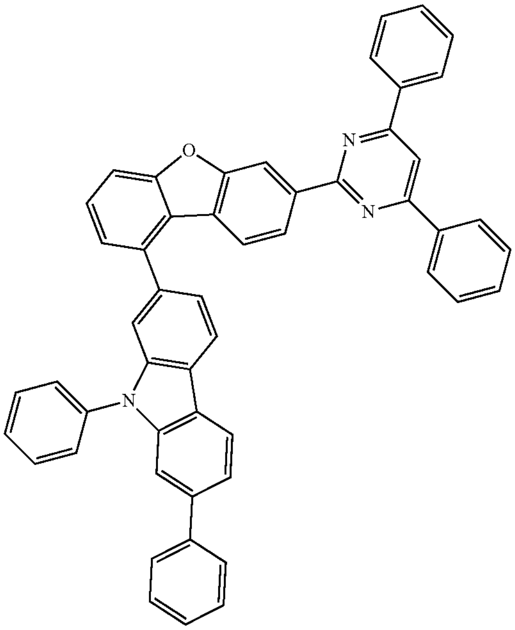
1-95
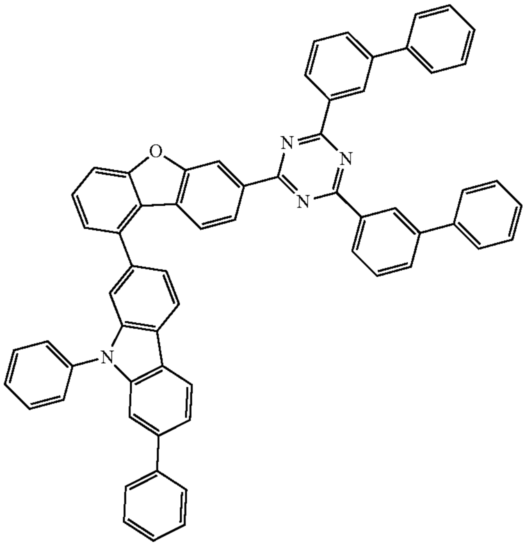
1-96
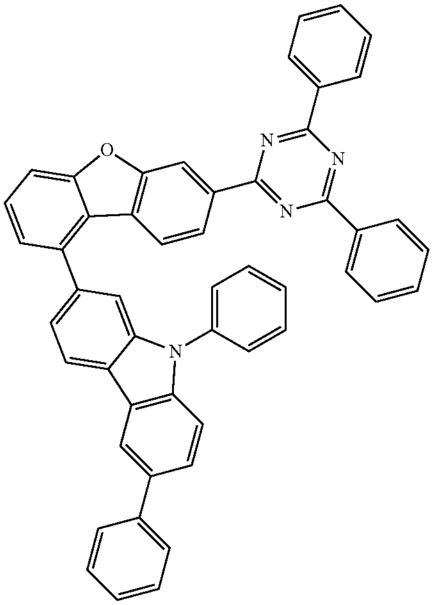

-continued
1-97
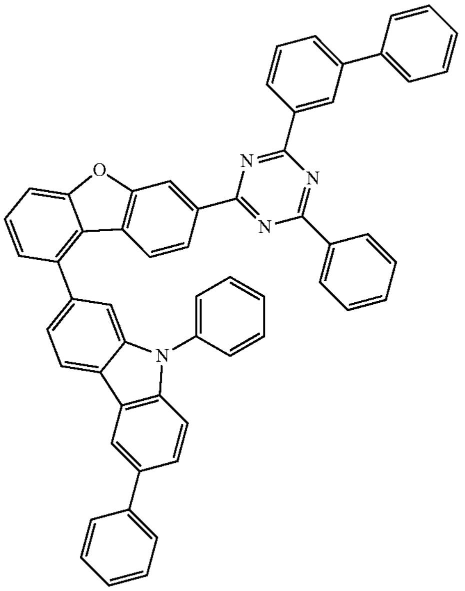
1-98
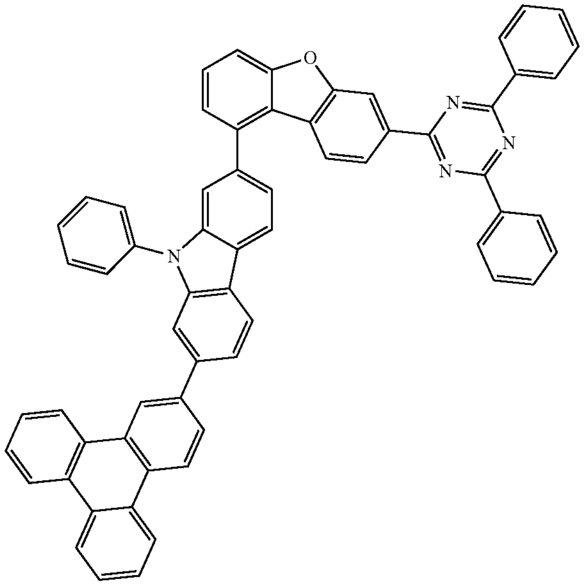
1-99
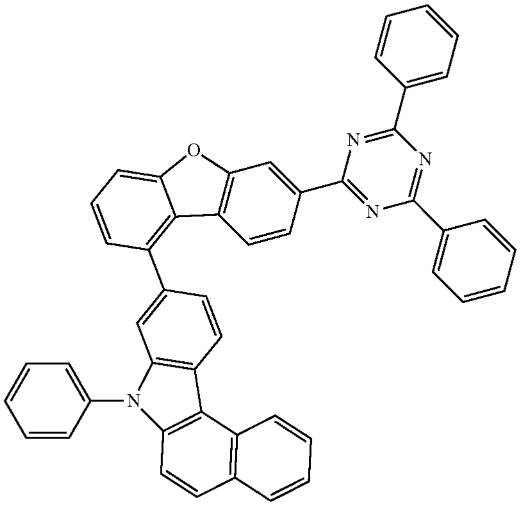
1-100
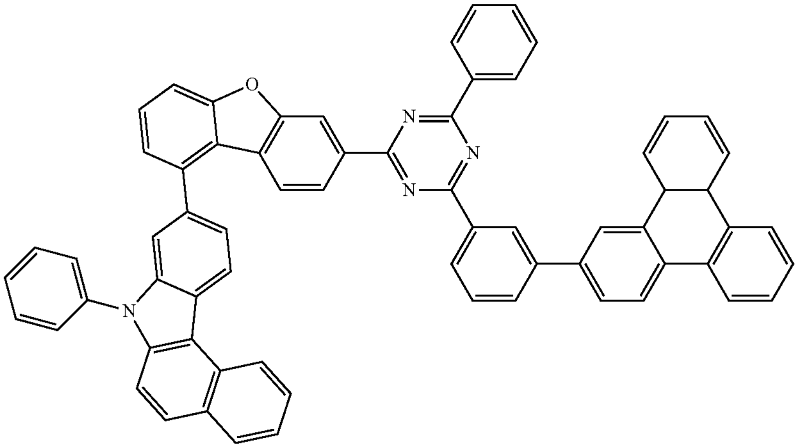

-continued
1-101
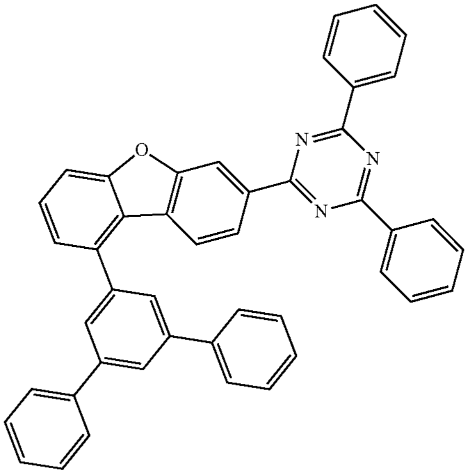
1-102
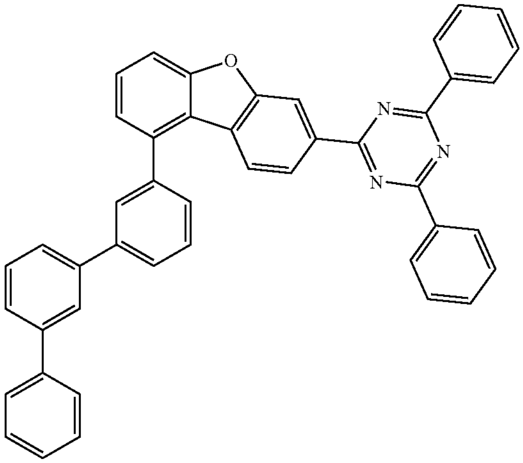
1-103
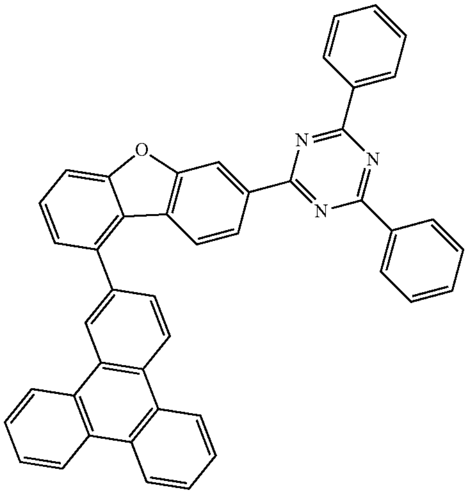
1-104
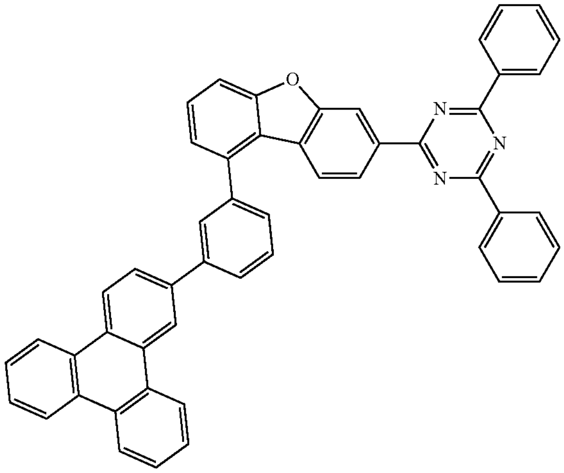

2-1
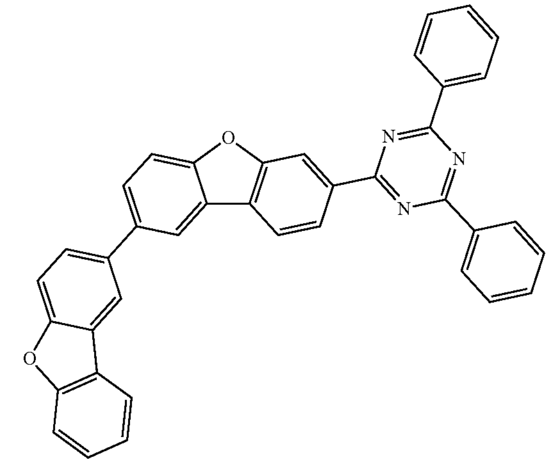
2-2
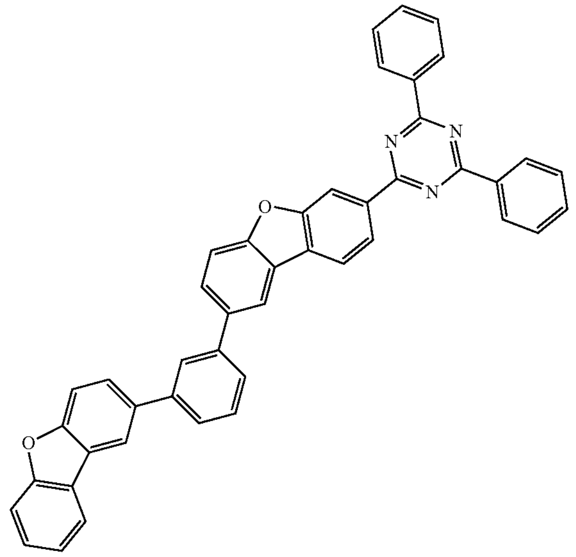
2-3
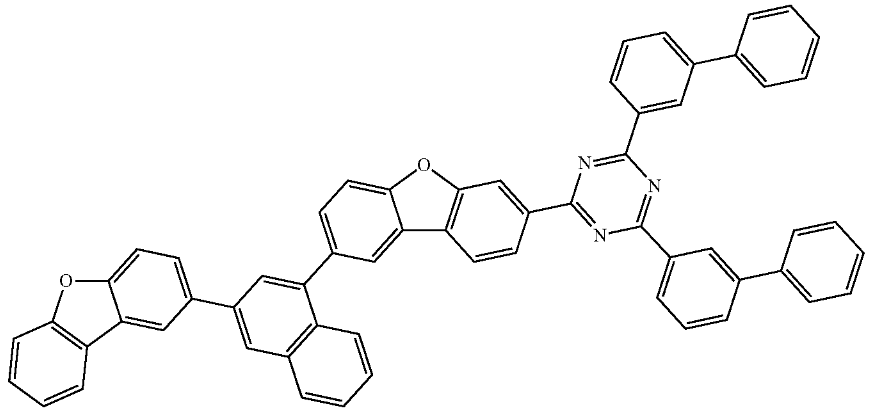
2-4
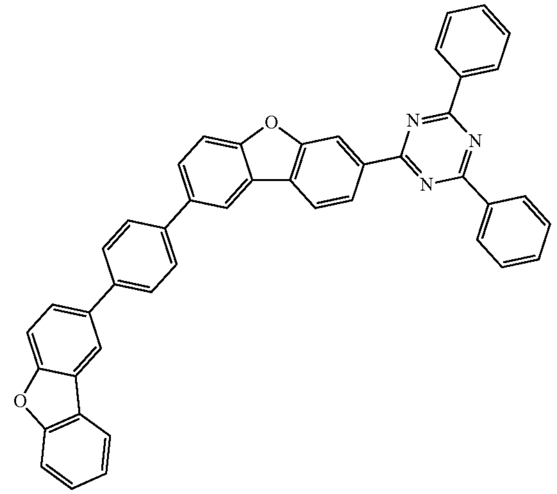
2-5
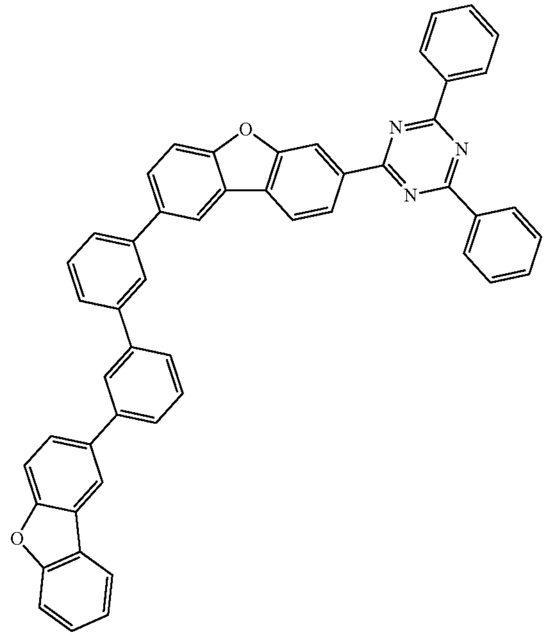

-continued
2-6
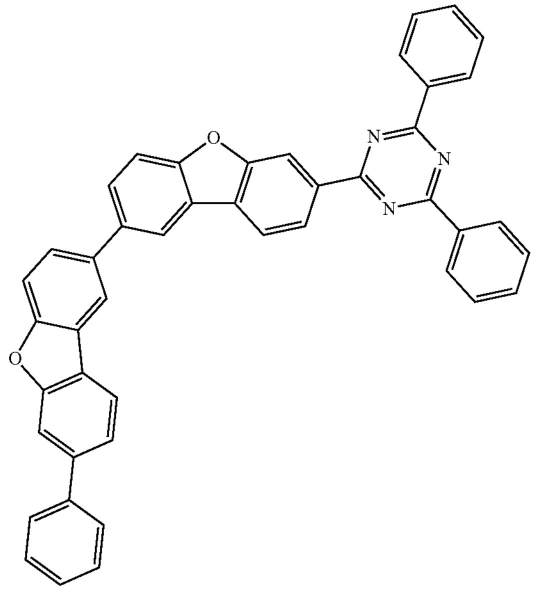
2-7
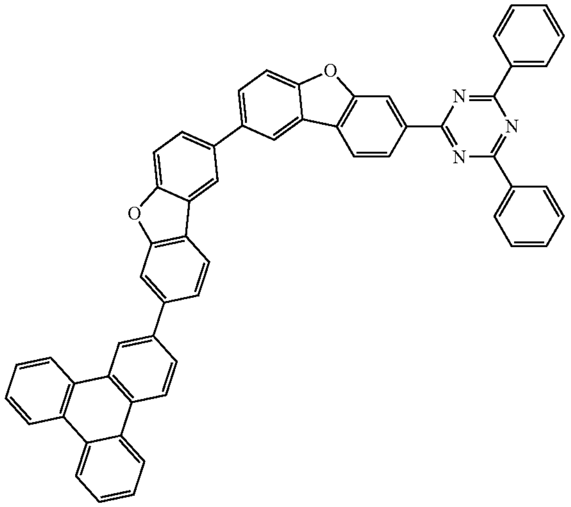
2-8
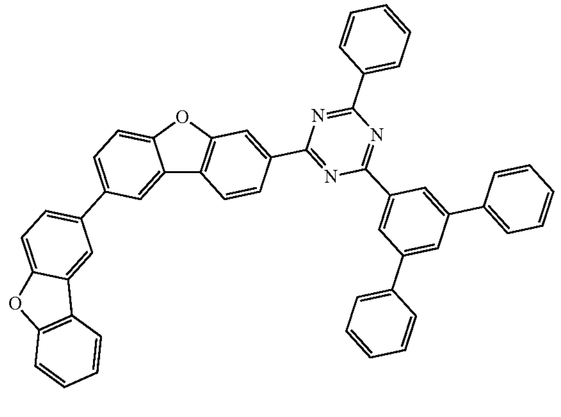
2-9
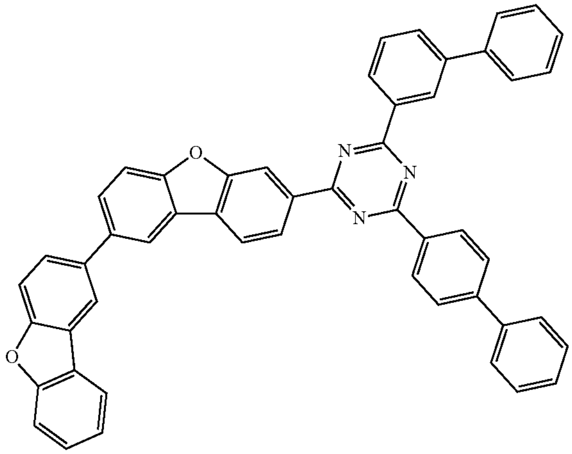
2-10
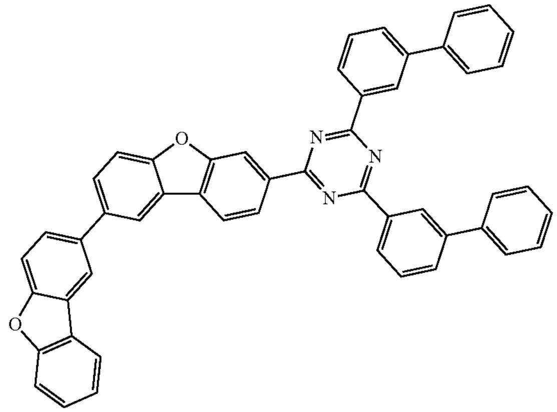
2-11
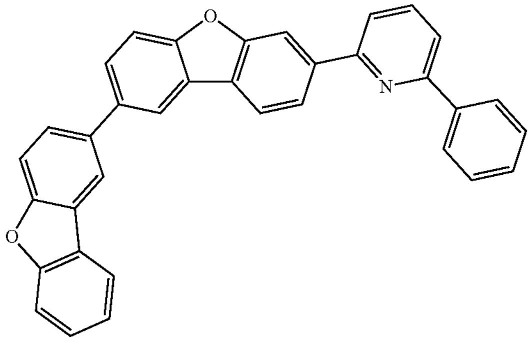

-continued
2-12
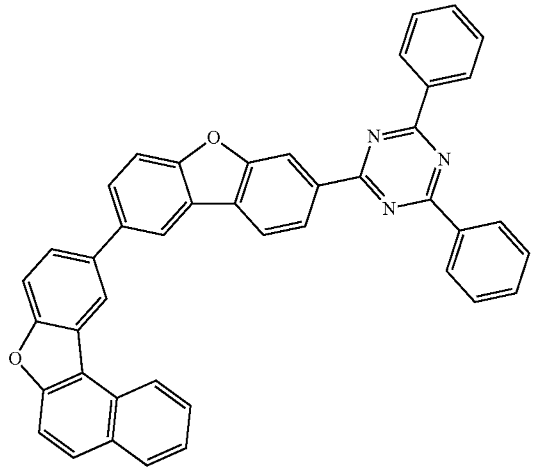
2-13
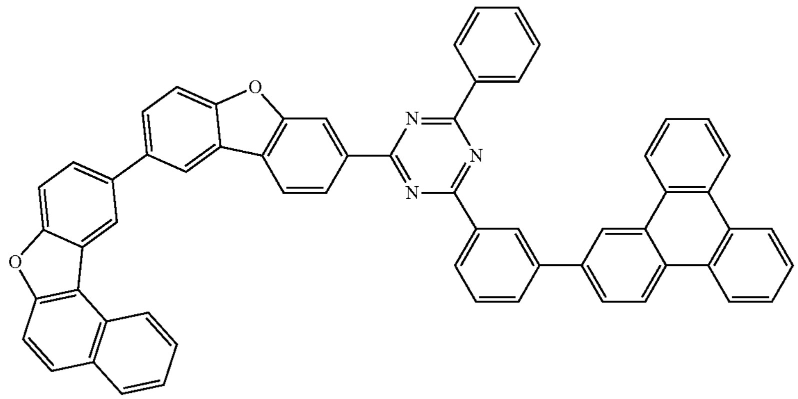
2-14
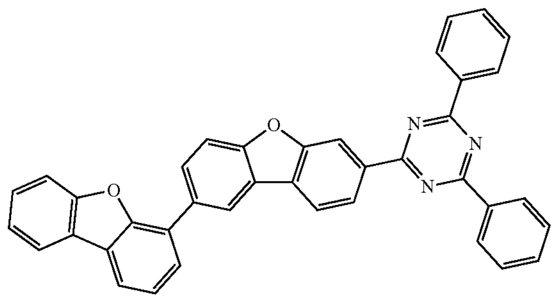
2-15
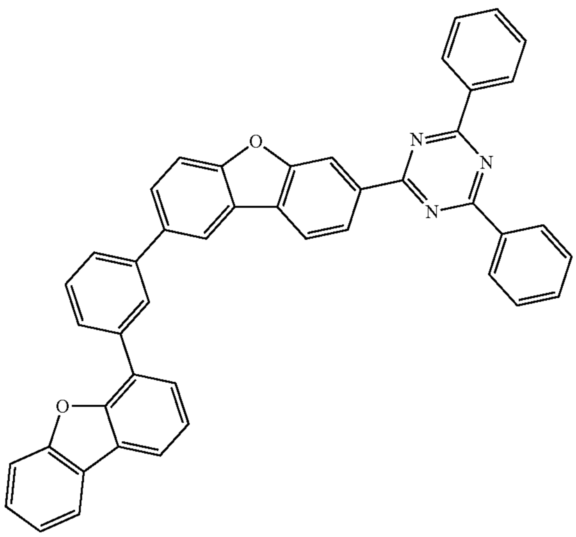

-continued
2-16
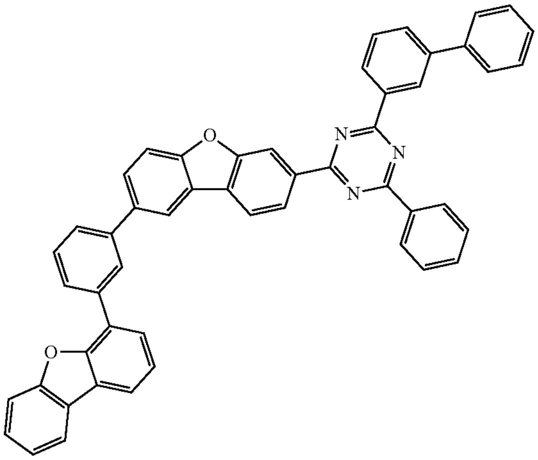
2-17
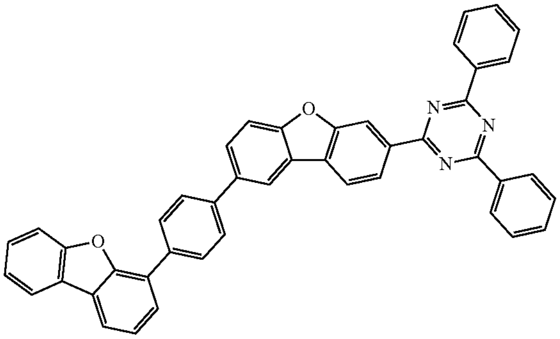
2-18
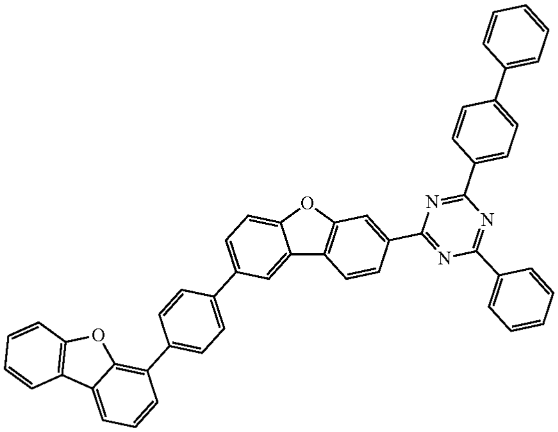
2-19
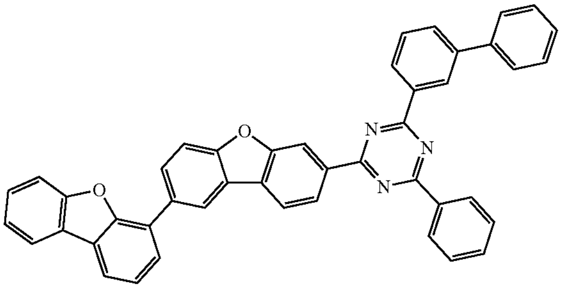
2-20
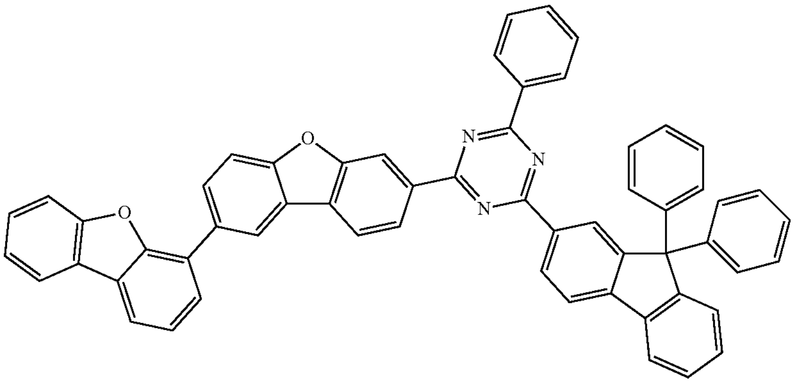

-continued
2-21
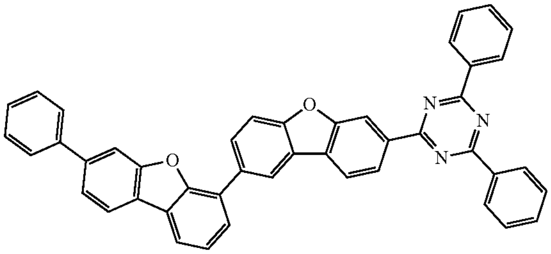
2-22
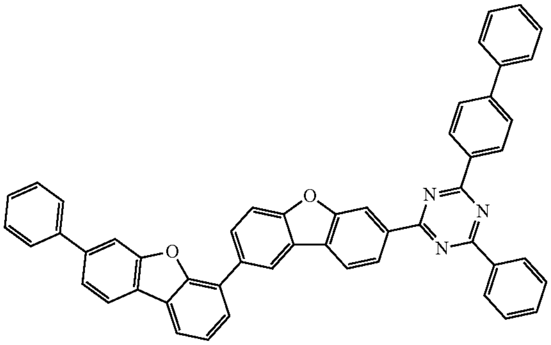
2-23
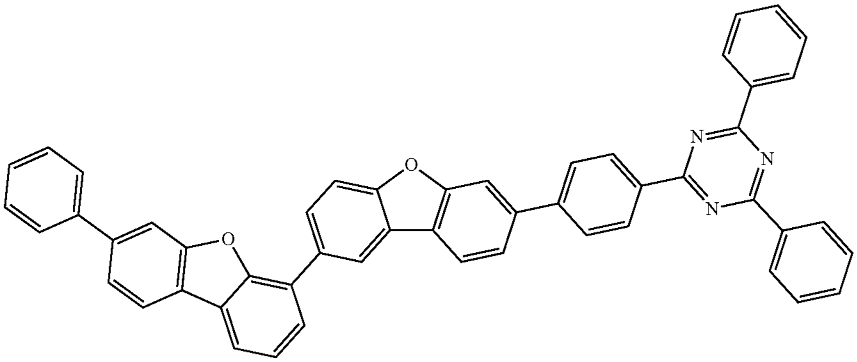
2-24
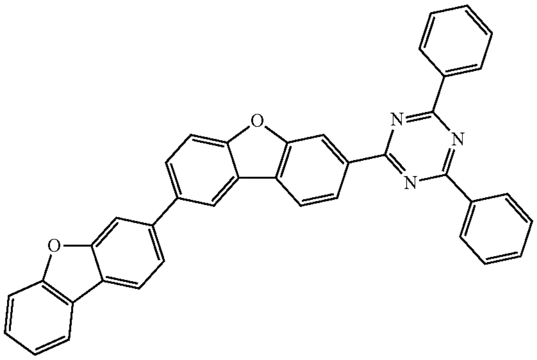
2-25
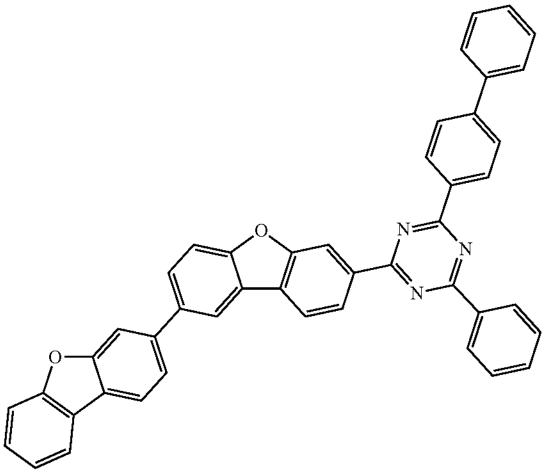

-continued
2-26
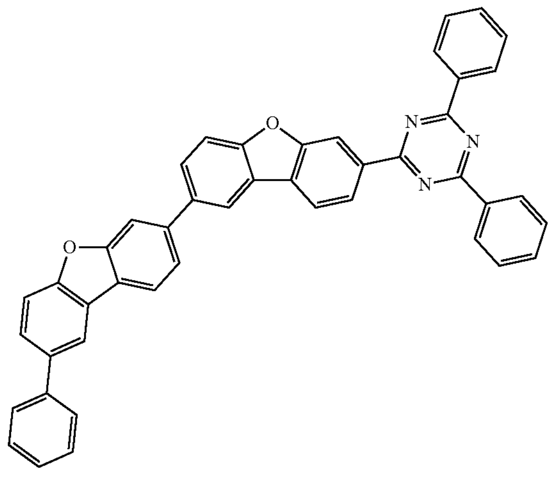
2-27
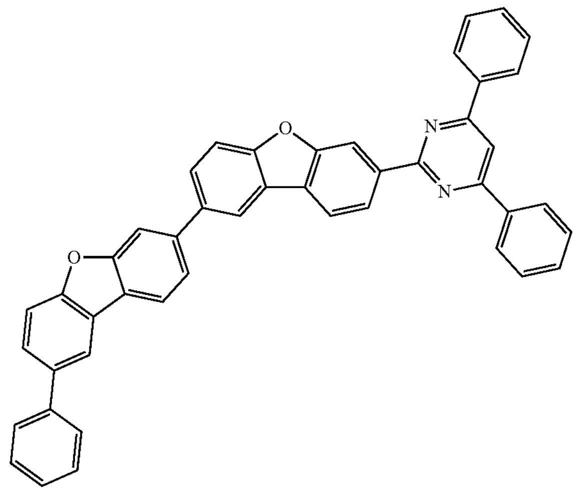
2-28
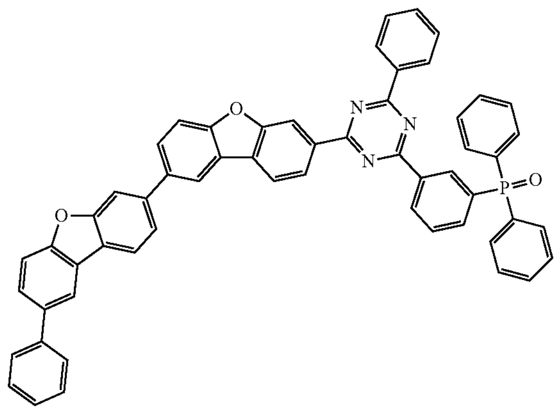
2-29
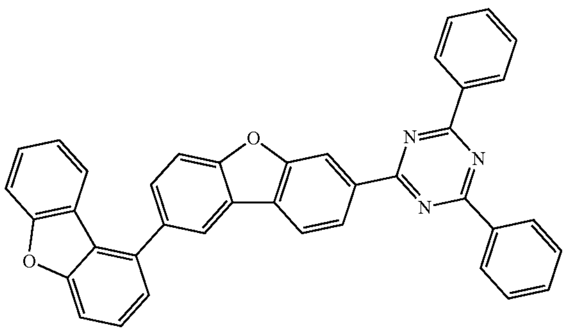
2-30
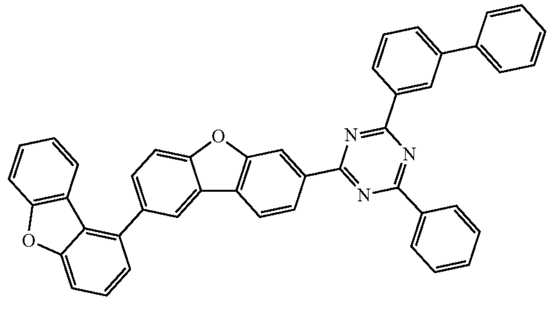
2-31
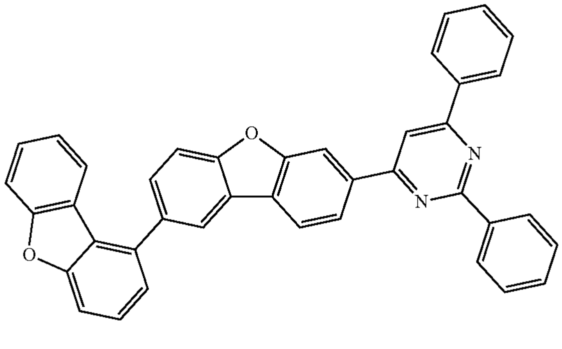

-continued
2-32
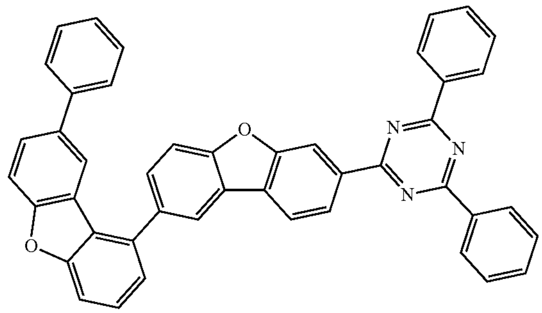
2-33
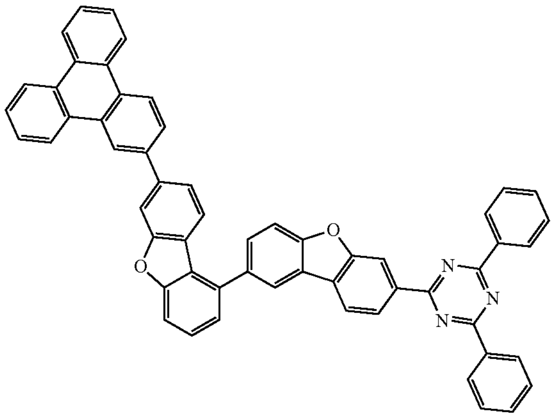
2-34
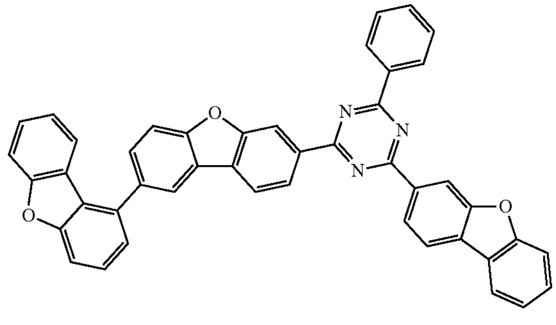
2-35
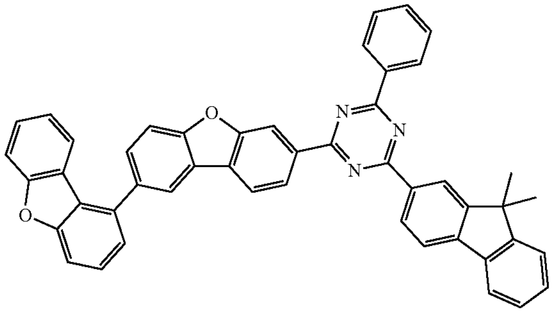
2-36
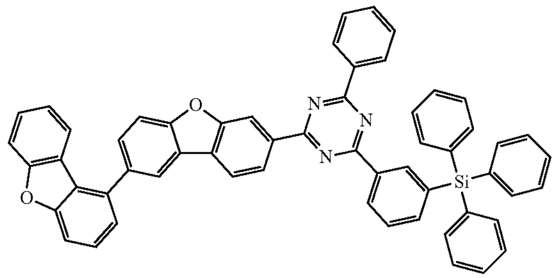
2-37
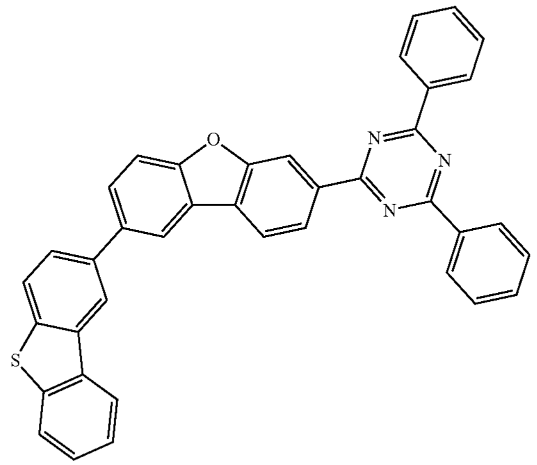
2-38
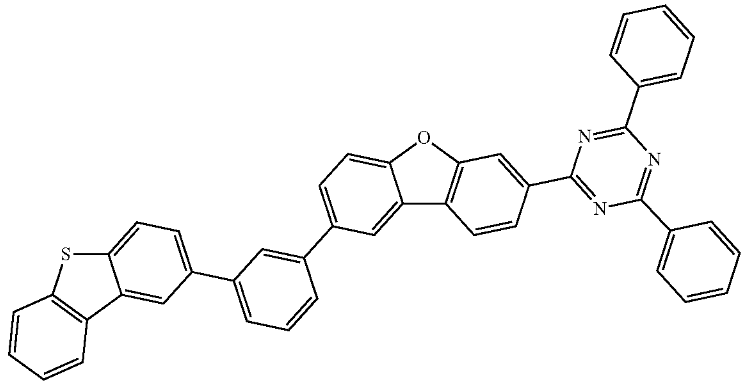

-continued
2-39
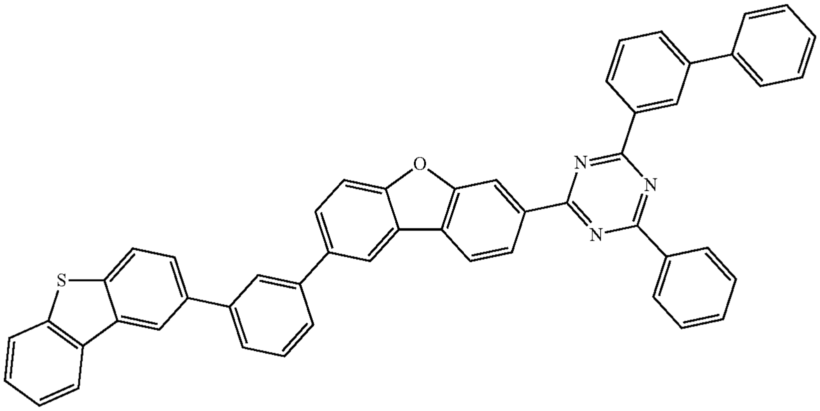
2-40
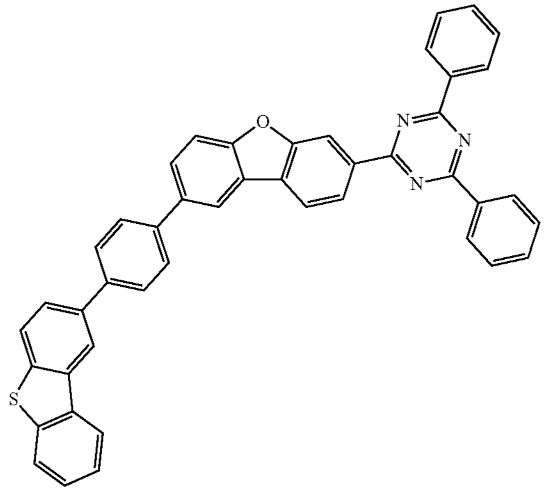
2-41
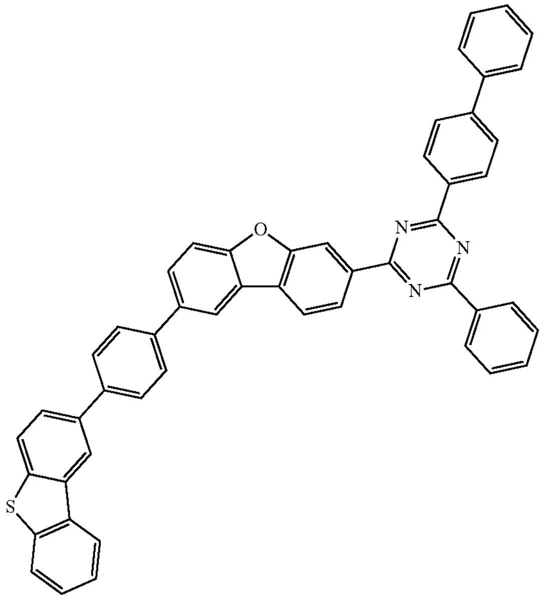
2-42
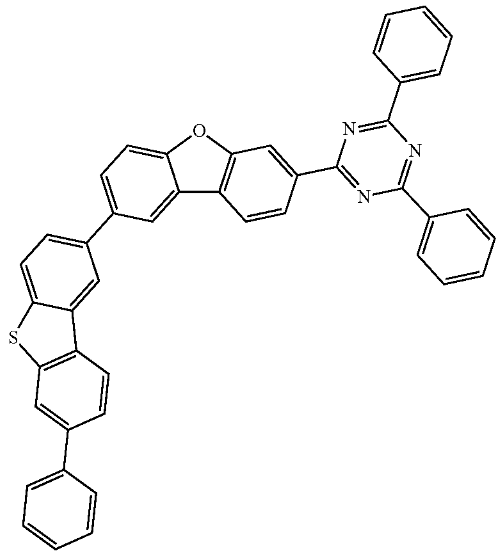
2-43
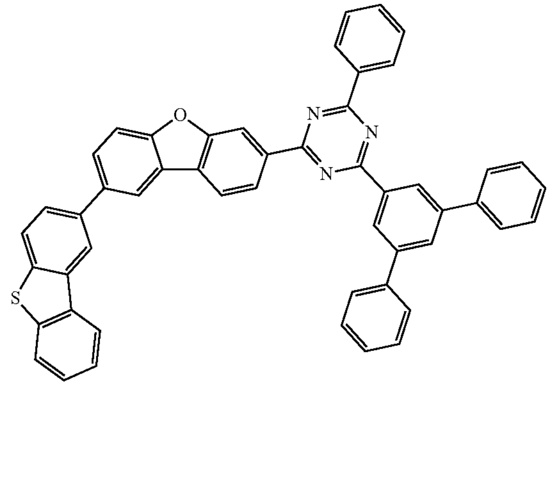

-continued
2-44
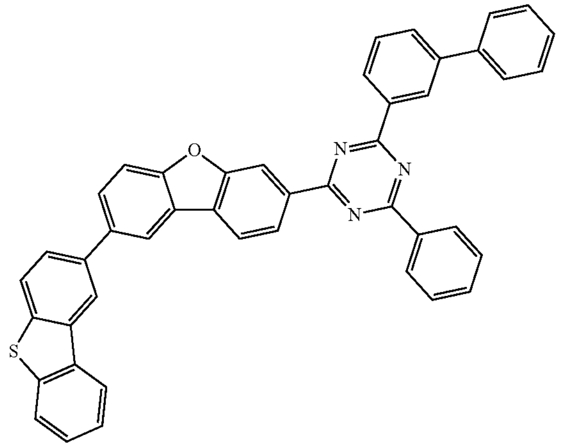
2-45
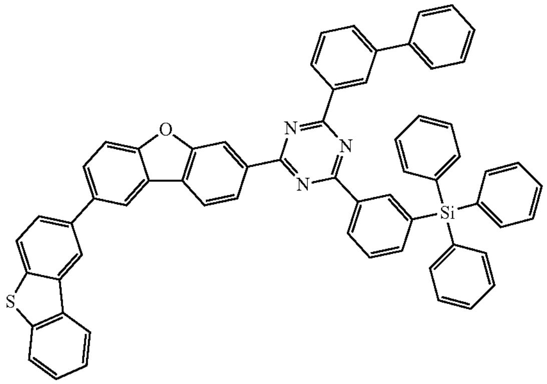
2-46
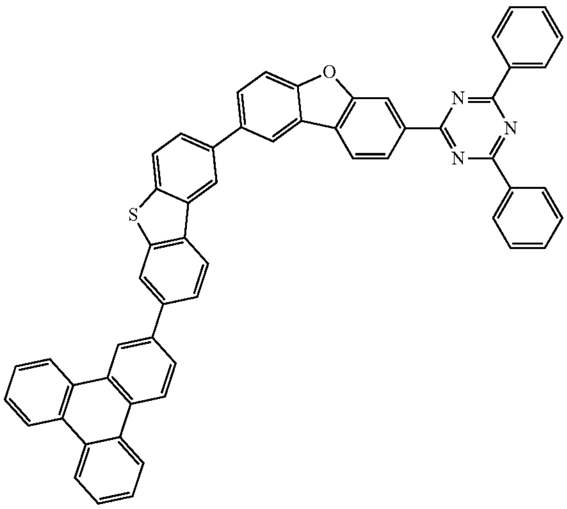
2-47
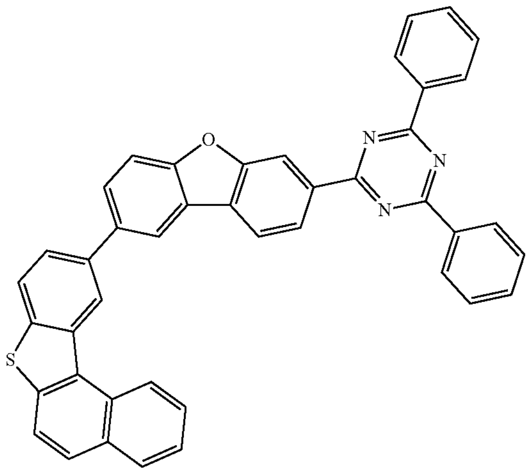
2-48
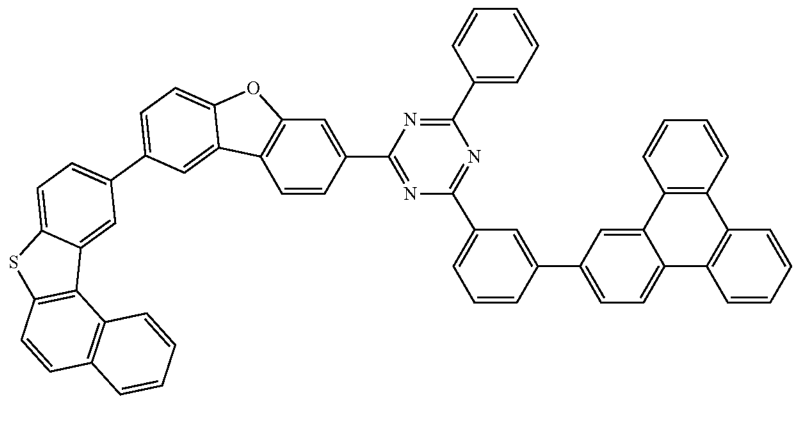

-continued
2-49
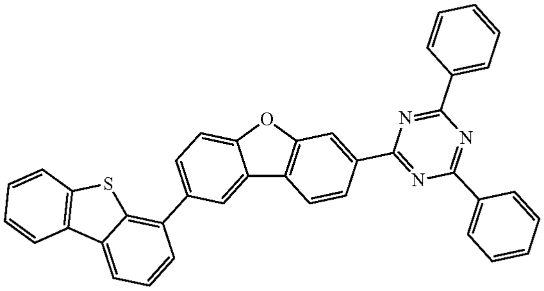
2-50
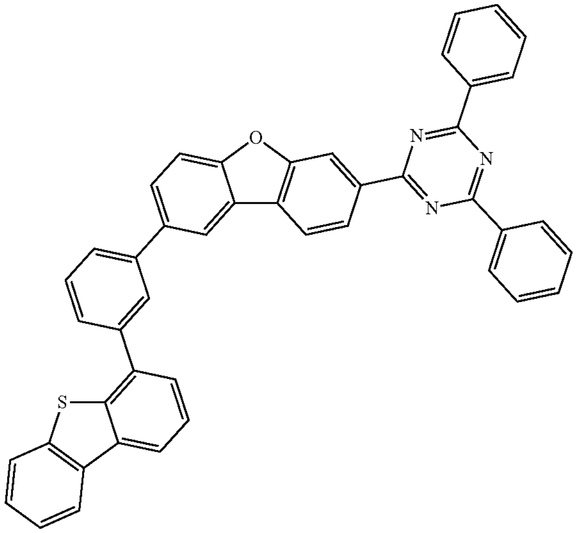
2-51
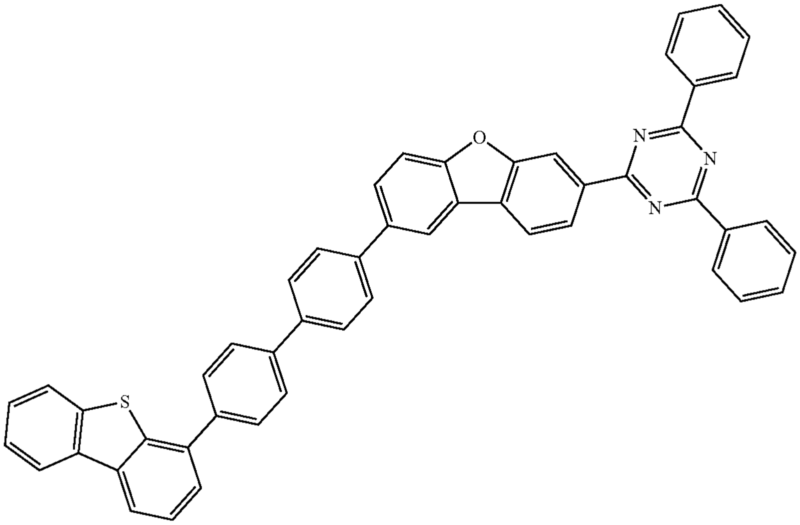
2-52
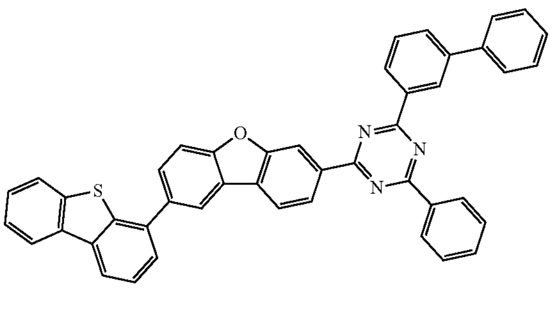
2-53
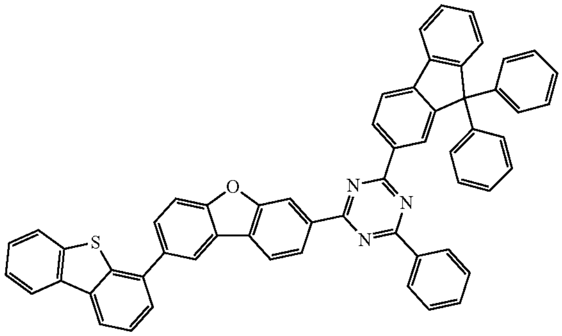

-continued
2-54
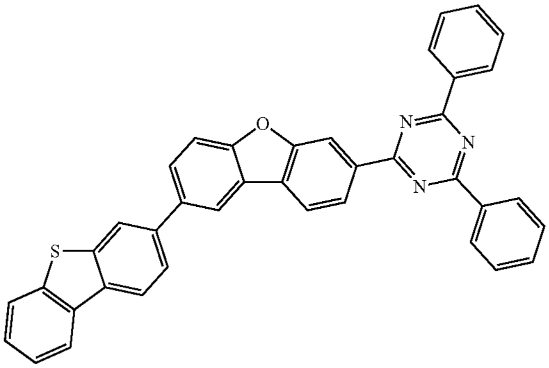
2-55
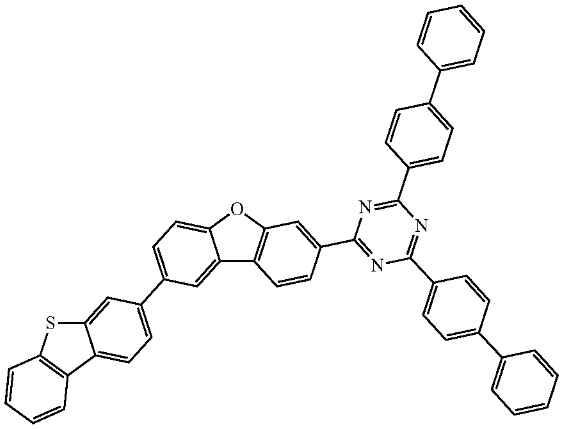
2-56
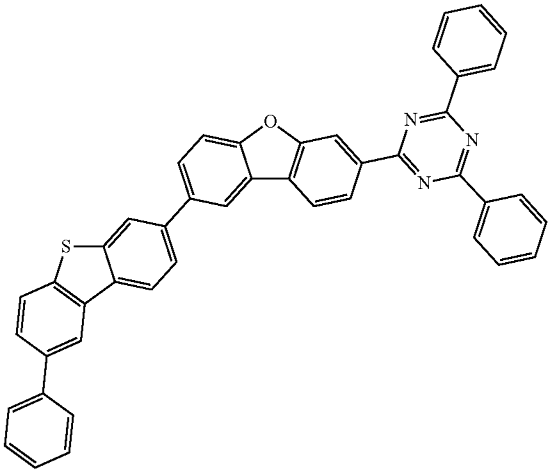
2-57
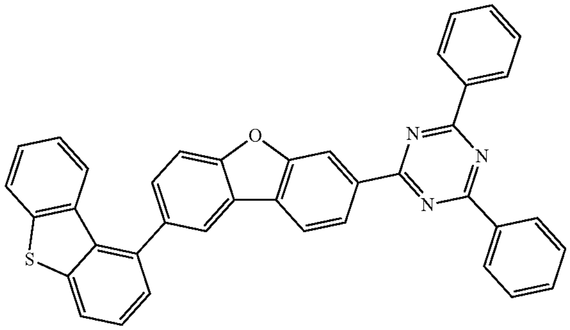
2-58
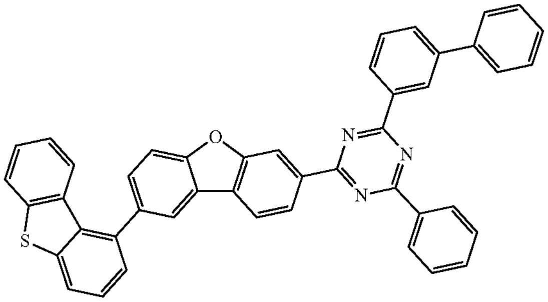
2-59
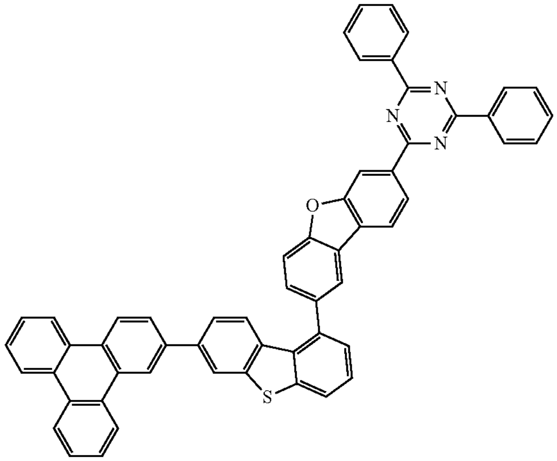

-continued
2-60
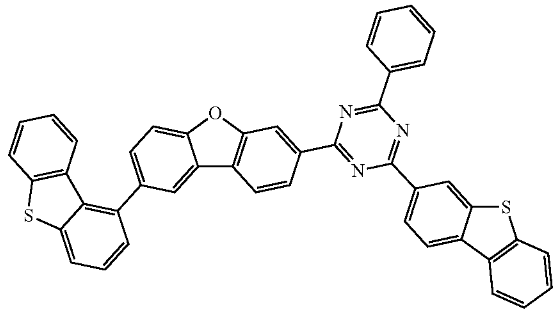
2-61
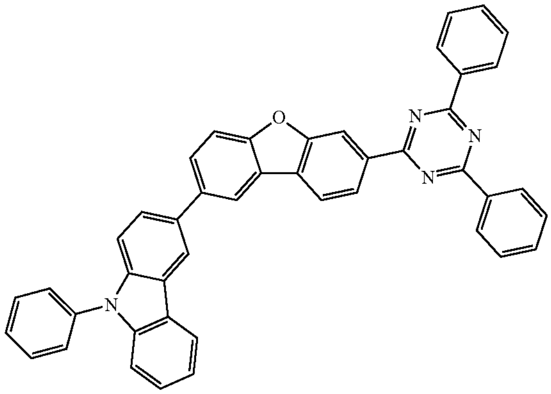
2-62
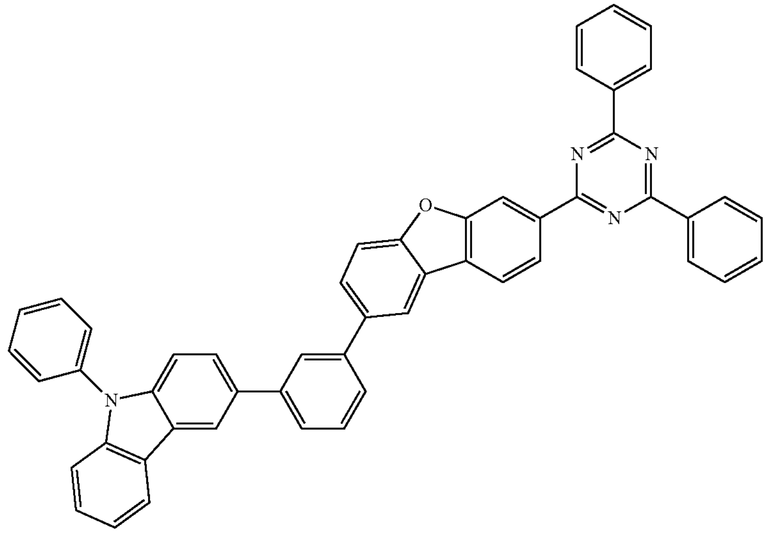
2-63
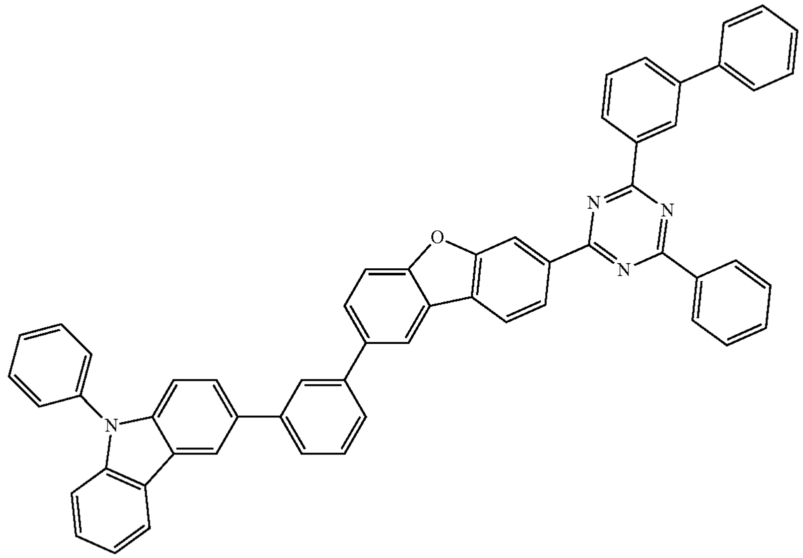

-continued
2-64
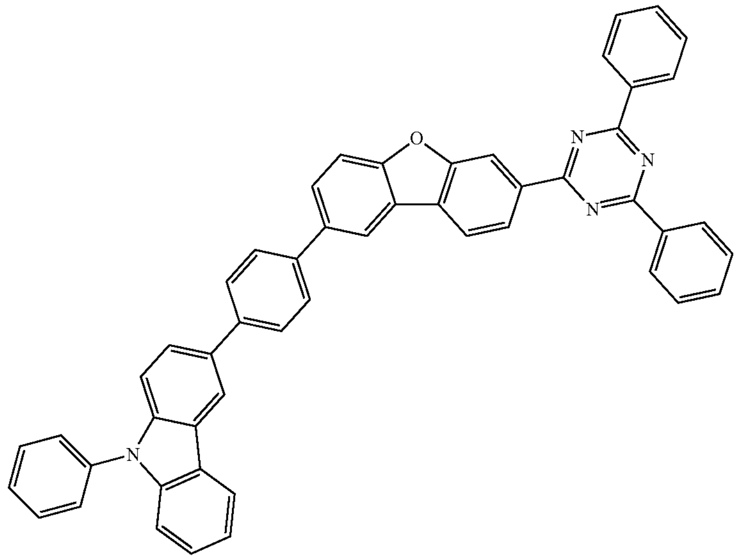
2-65
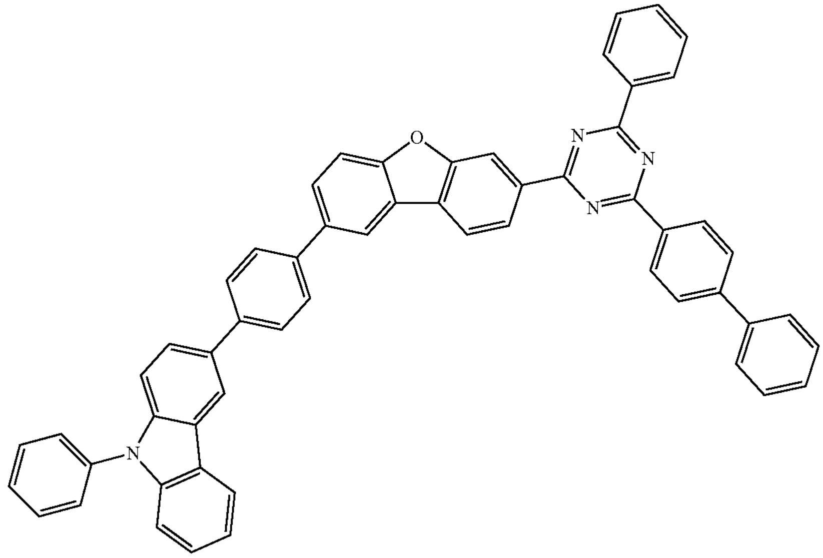
2-66
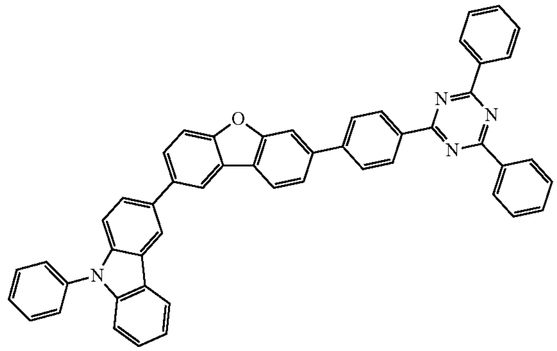
2-67
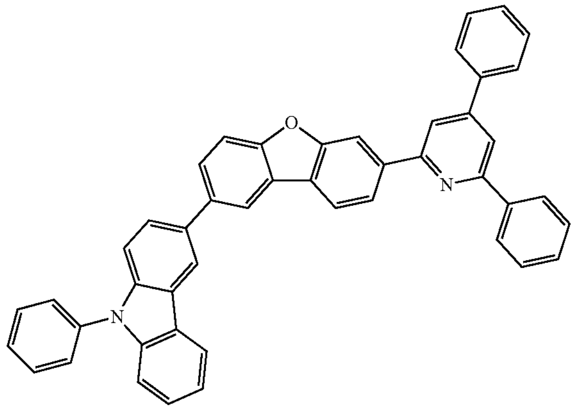

-continued
2-68
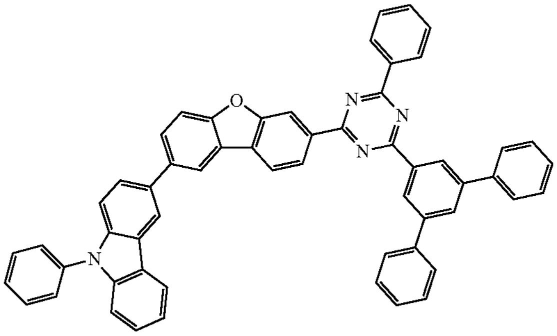
2-69
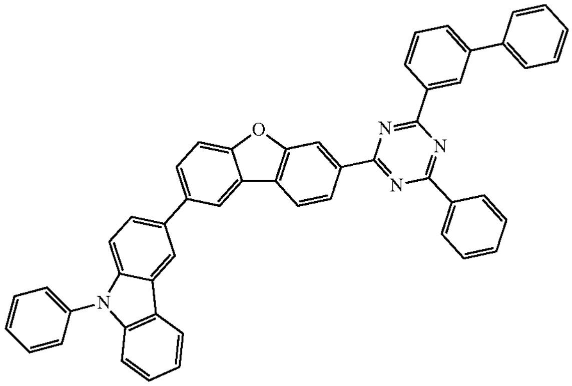
2-70
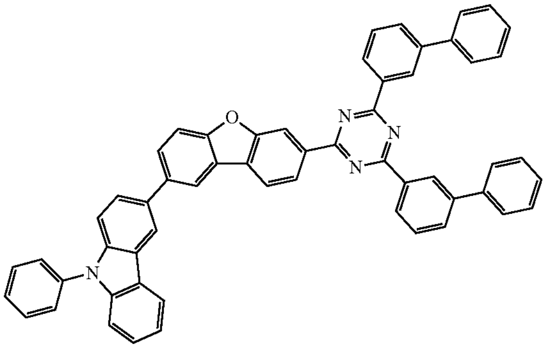
2-71
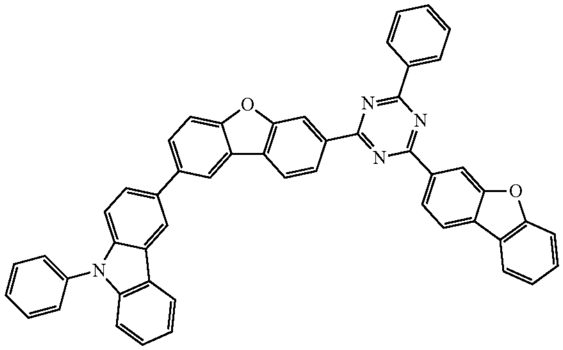
2-72
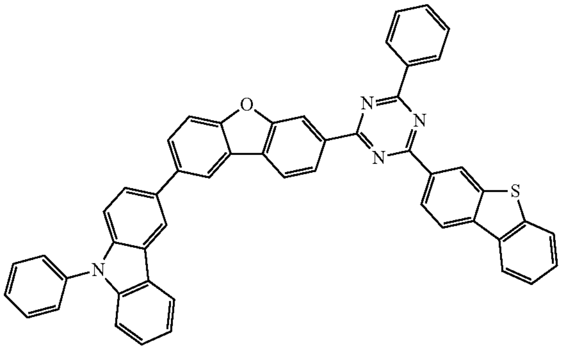
2-73
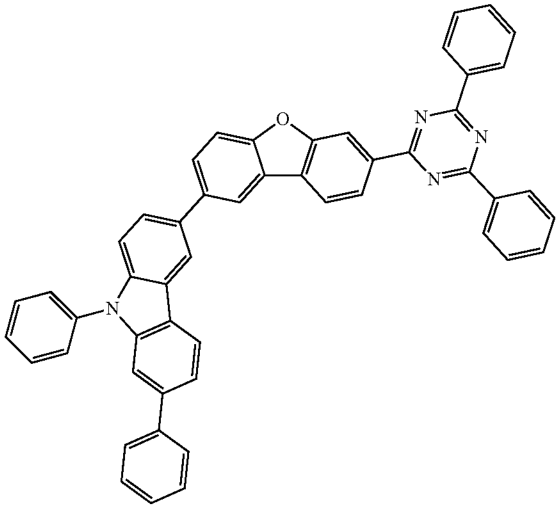

-continued
2-74
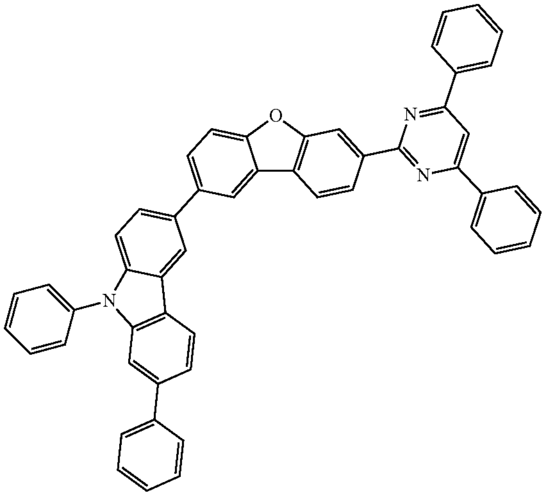
2-75
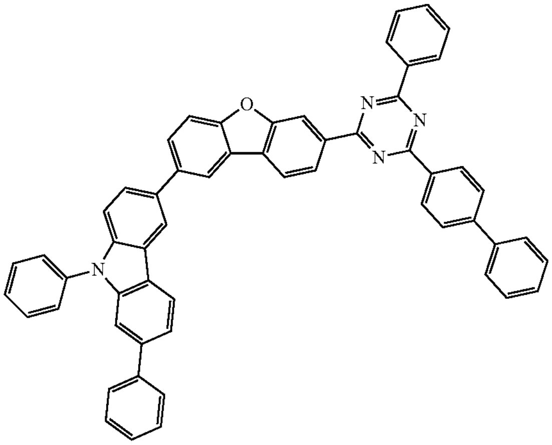
2-76
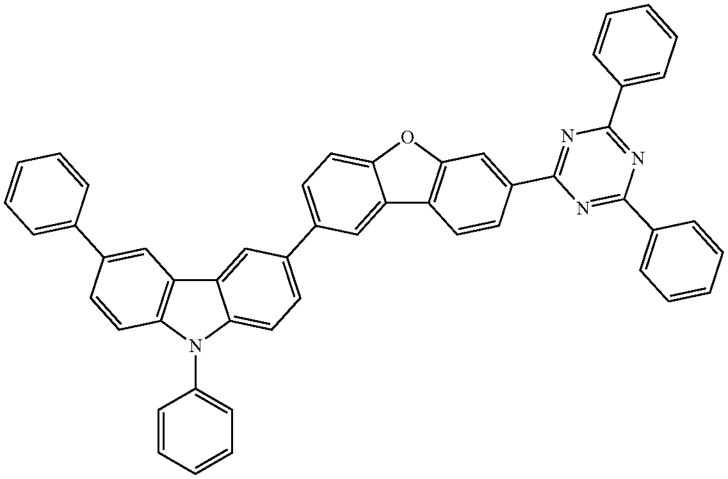
2-77
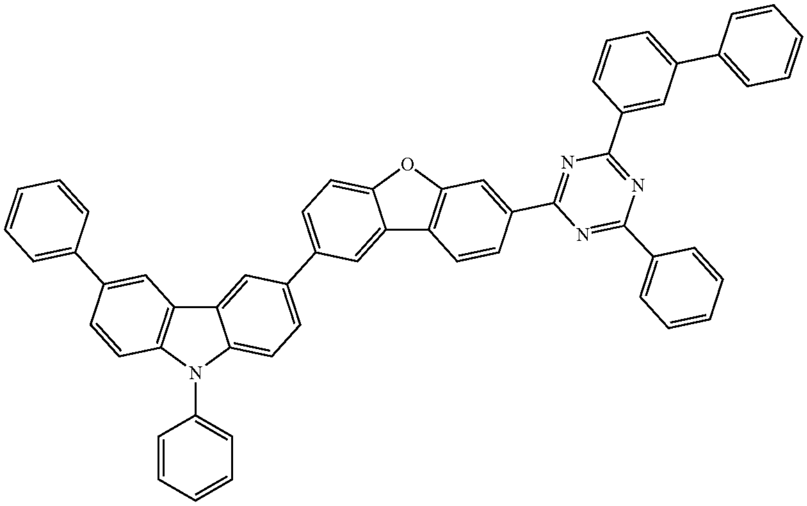

-continued
2-78
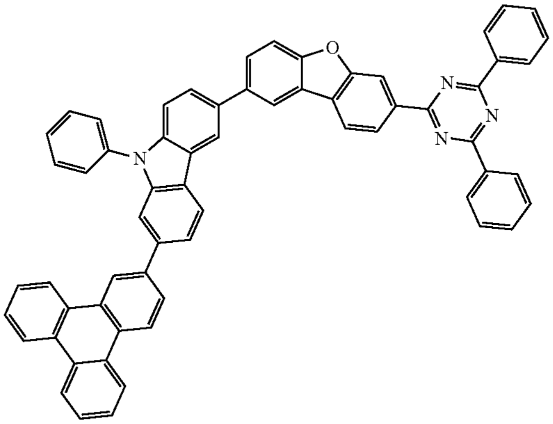
2-79
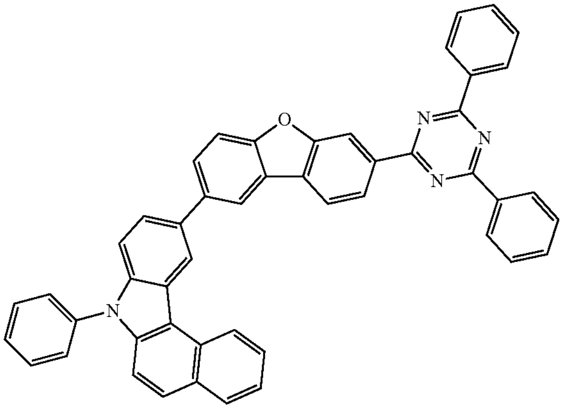
2-80
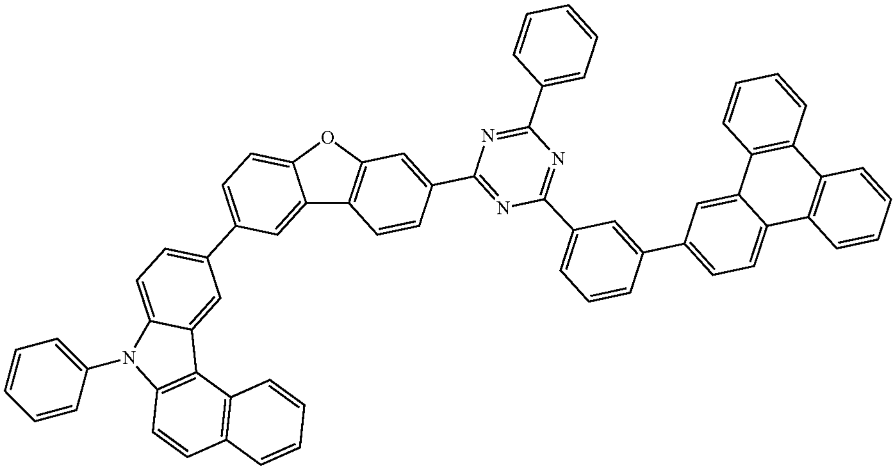
2-81
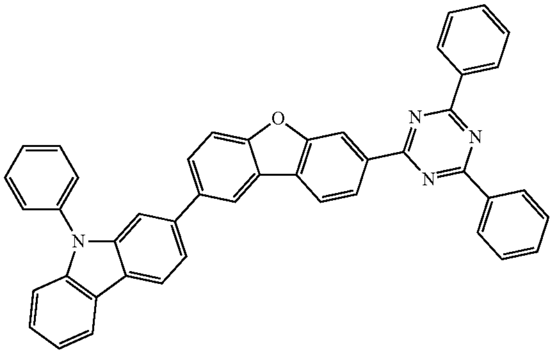
2-82
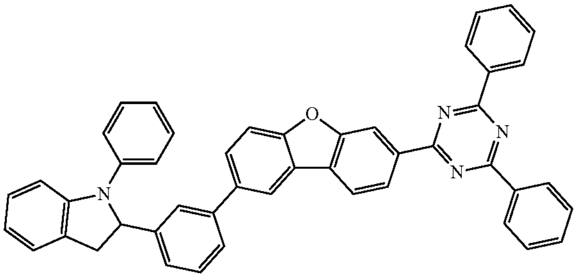

-continued
2-83
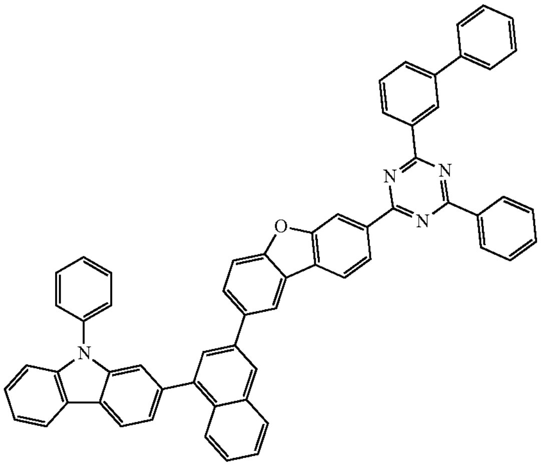
2-84
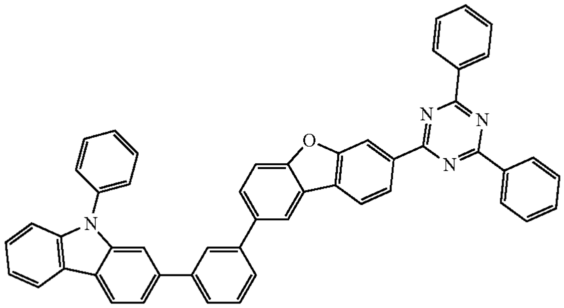
2-85
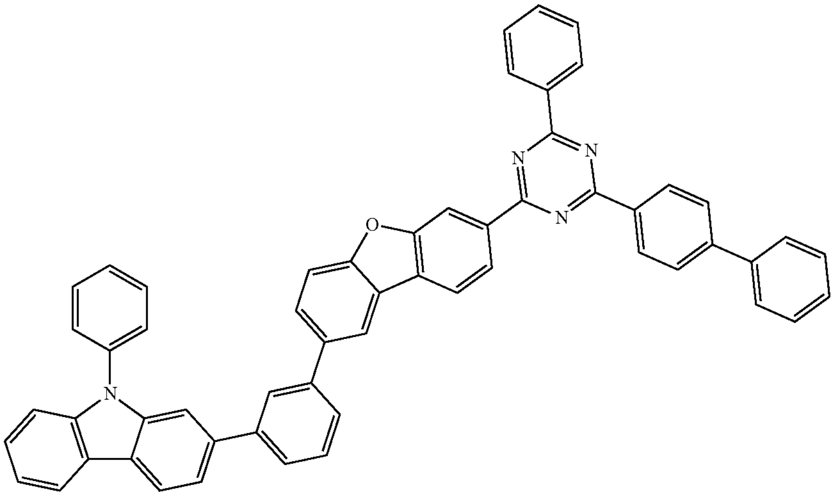
2-86
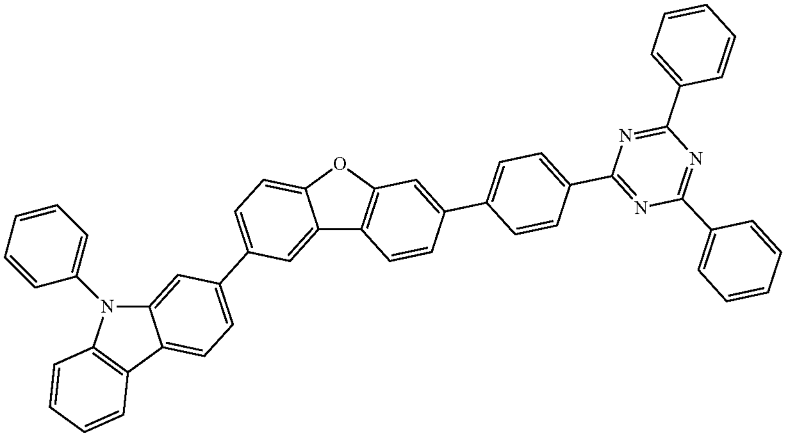

-continued
2-87
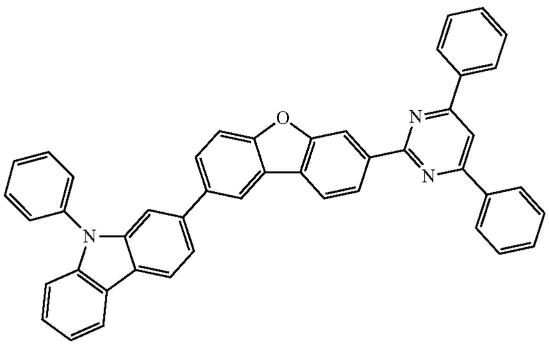
2-88
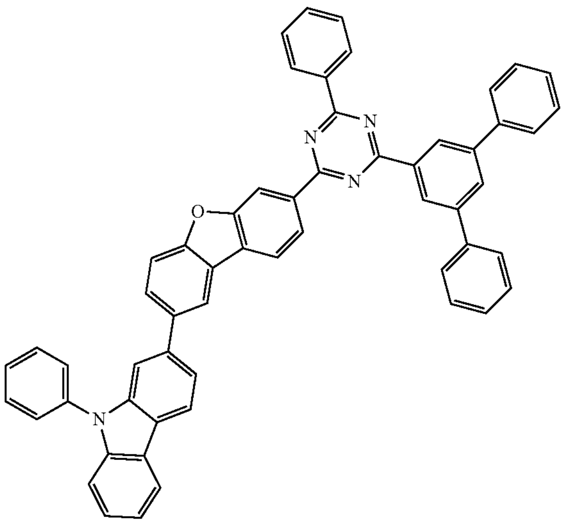
2-89
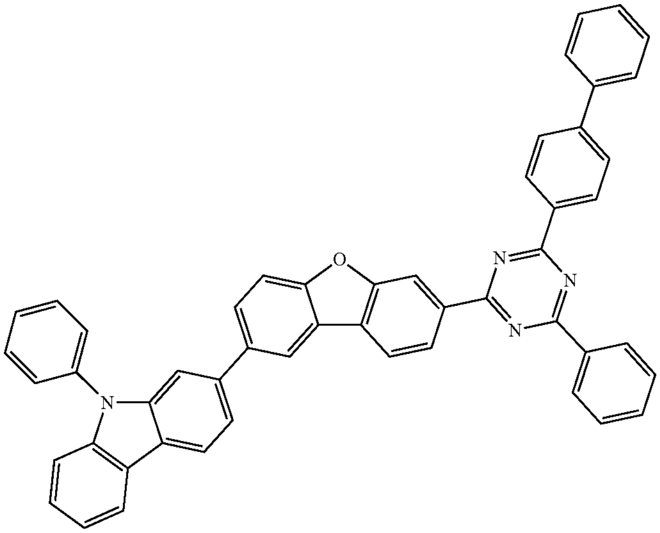
2-90
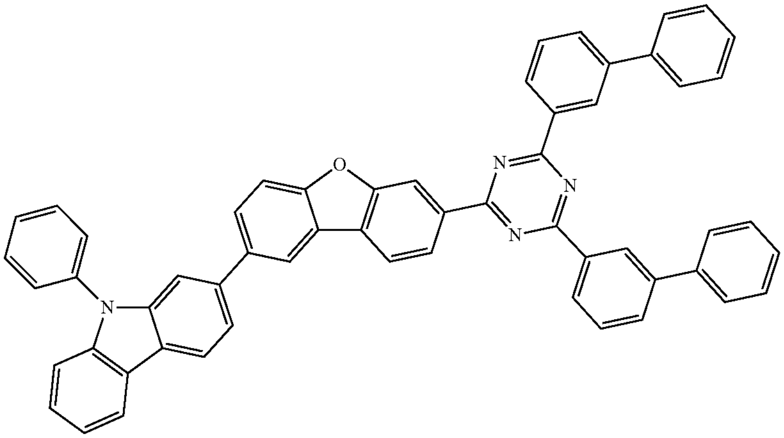

-continued
2-91
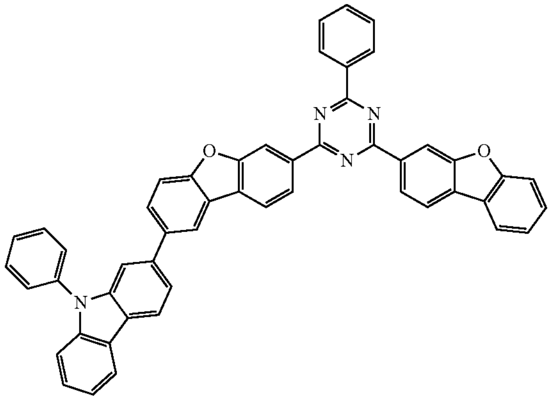
2-92
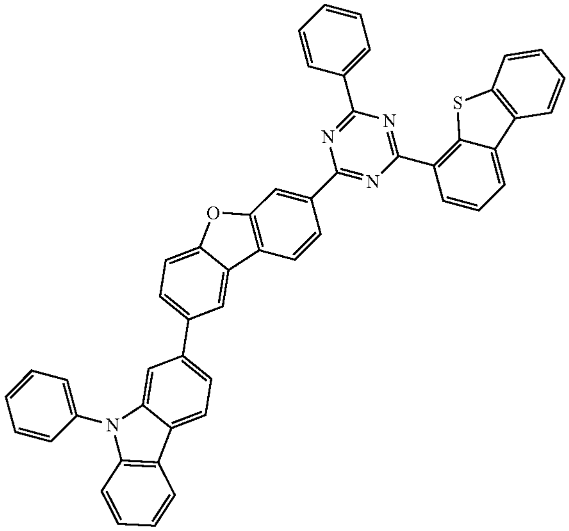
2-93
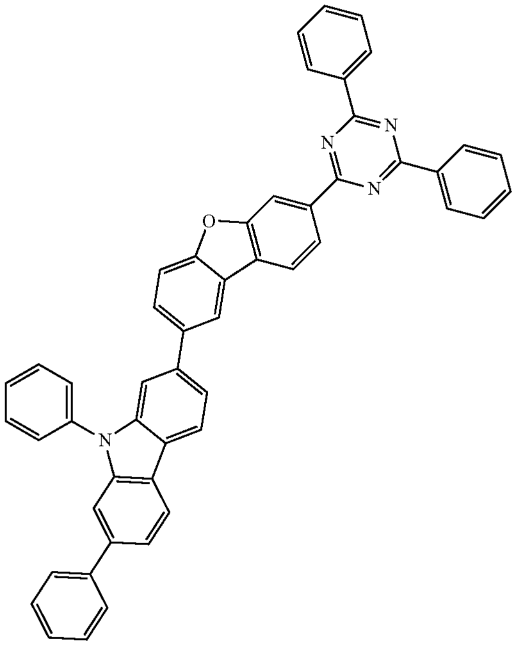
2-94
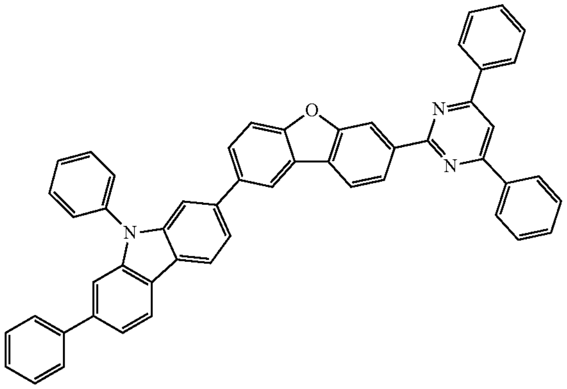

-continued
2-95
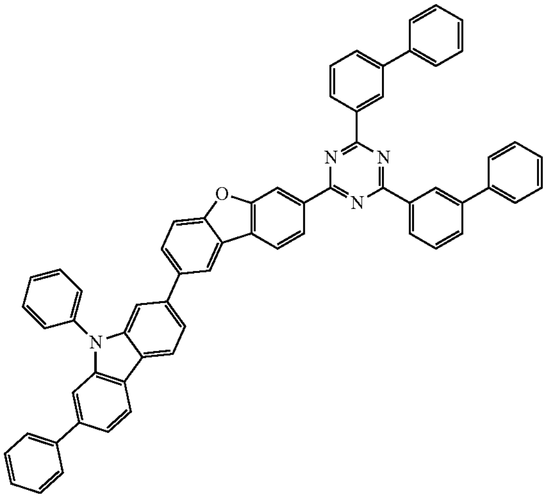
2-96
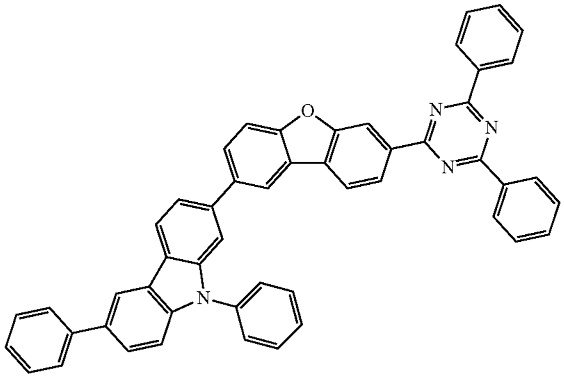
2-97
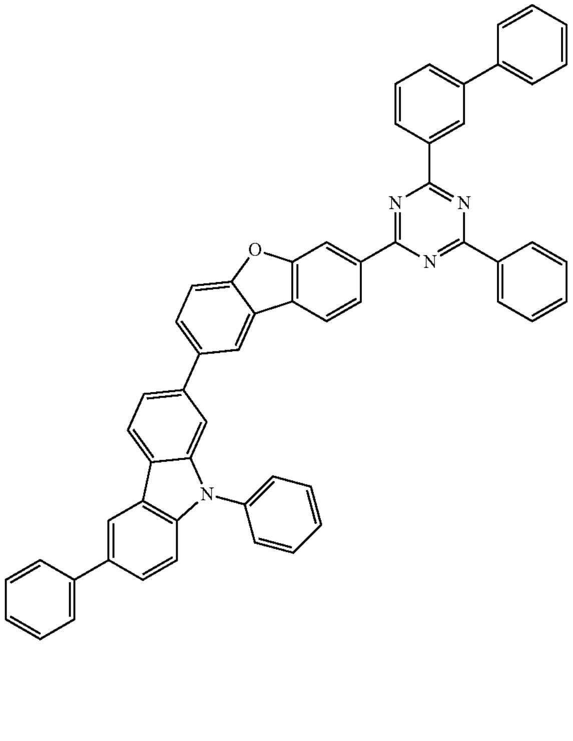

-continued
2-98
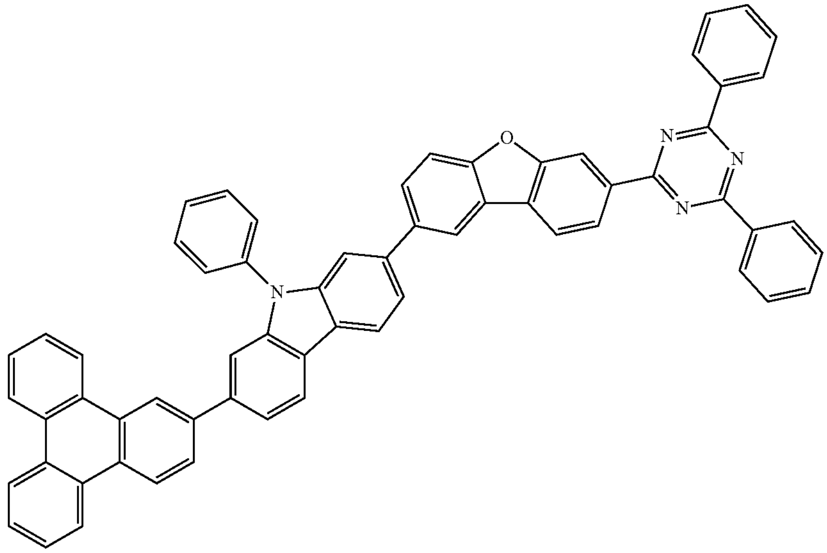
2-99
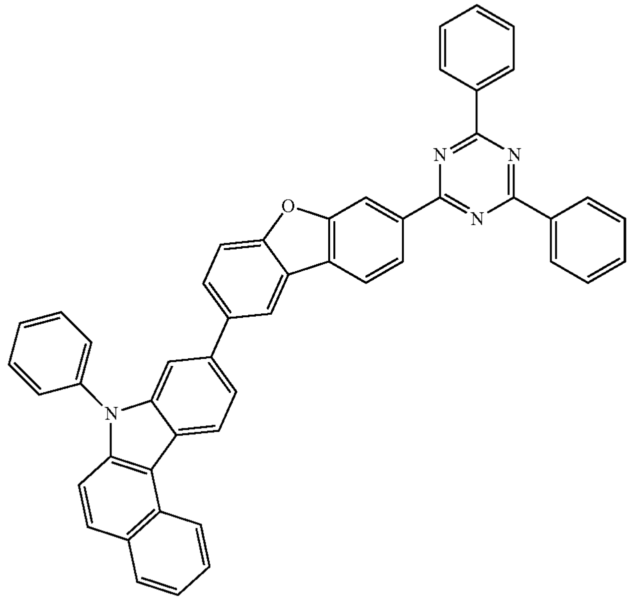

-continued
2-100
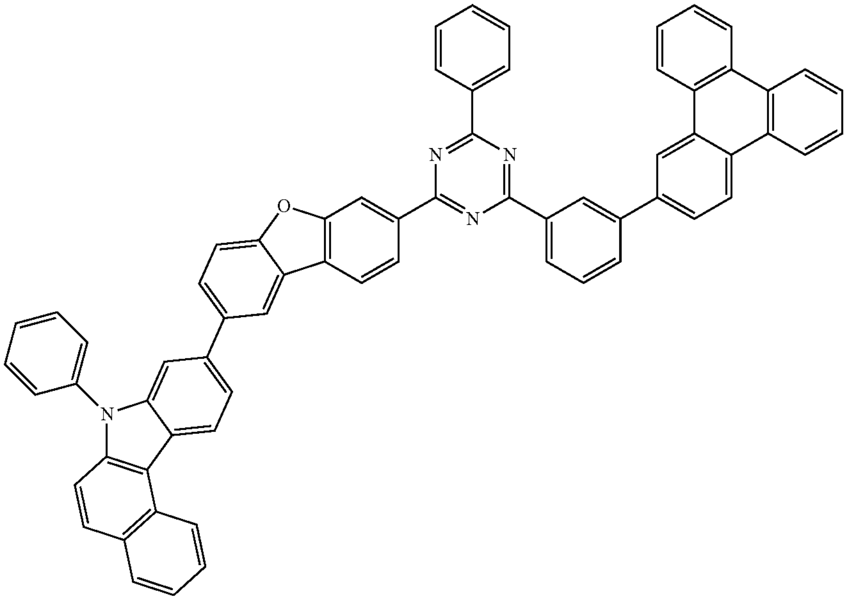
2-101
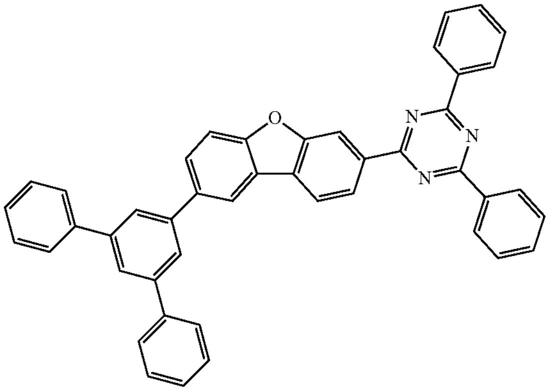
2-102
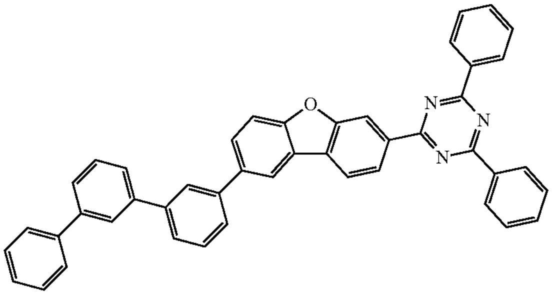

-continued
2-103
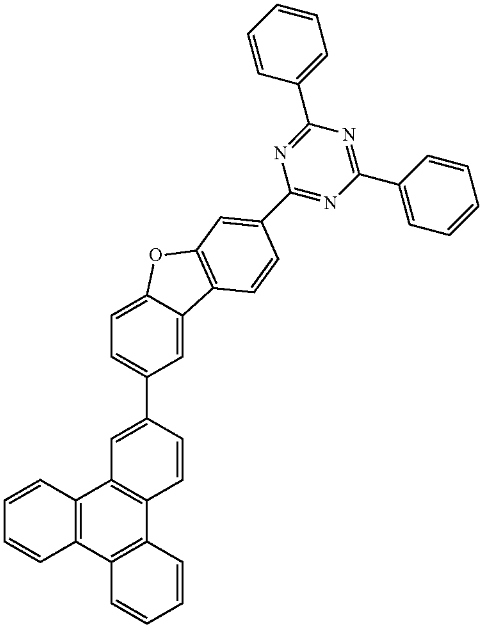
2-104
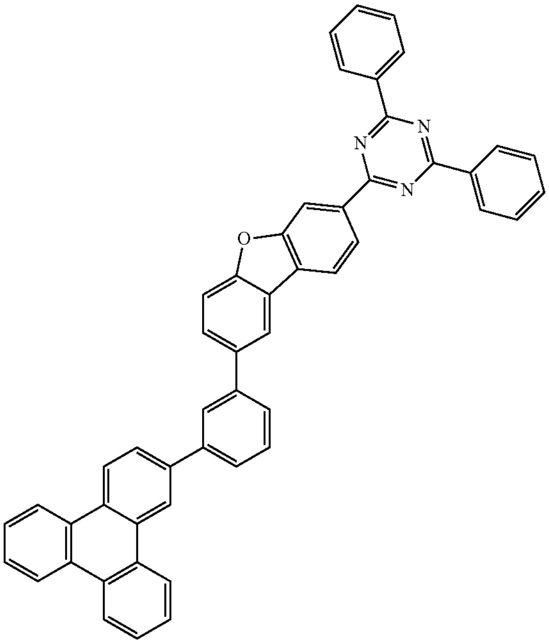
3-1
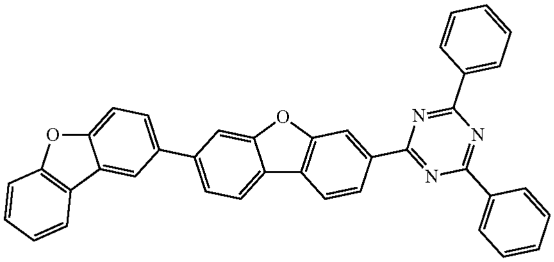
3-2
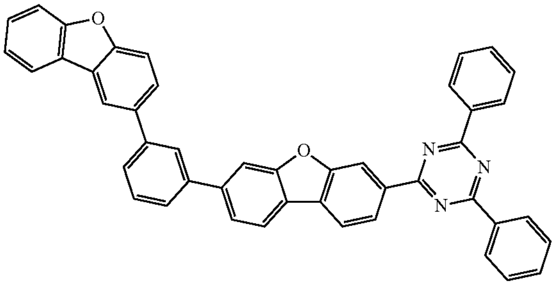
3-3
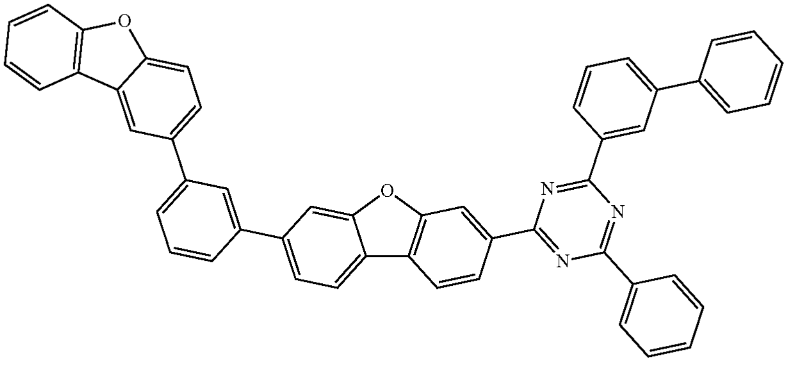

-continued
3-4
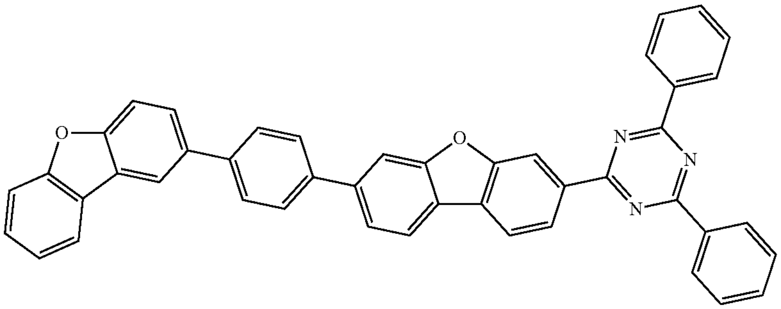
3-5
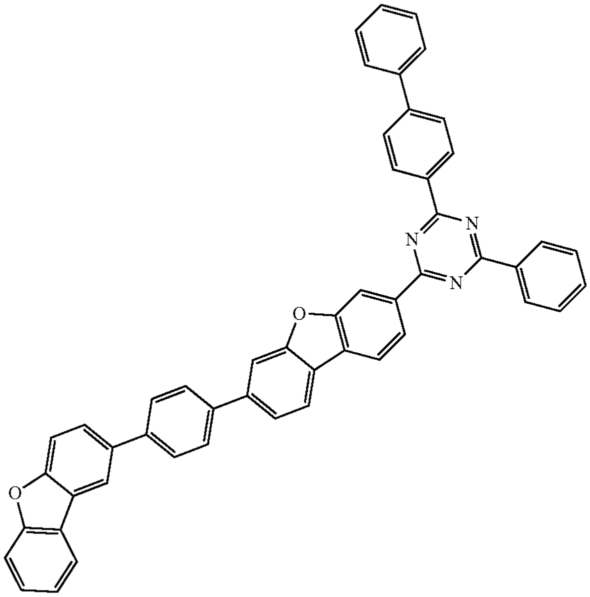
3-6
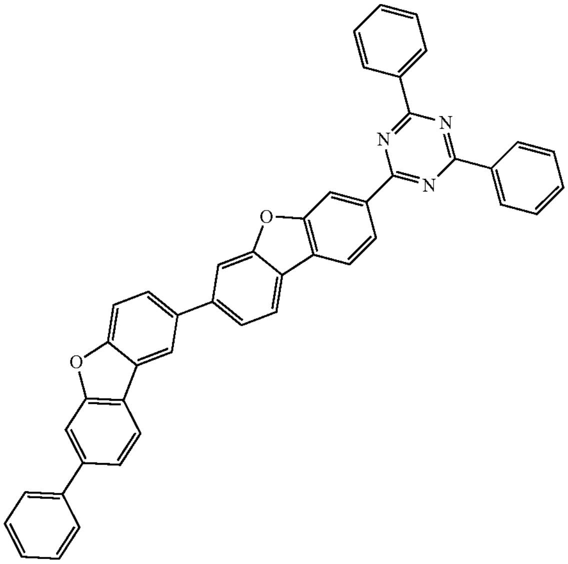
3-7
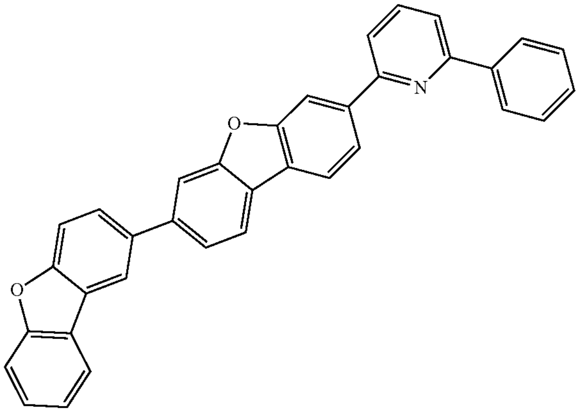

-continued
3-8
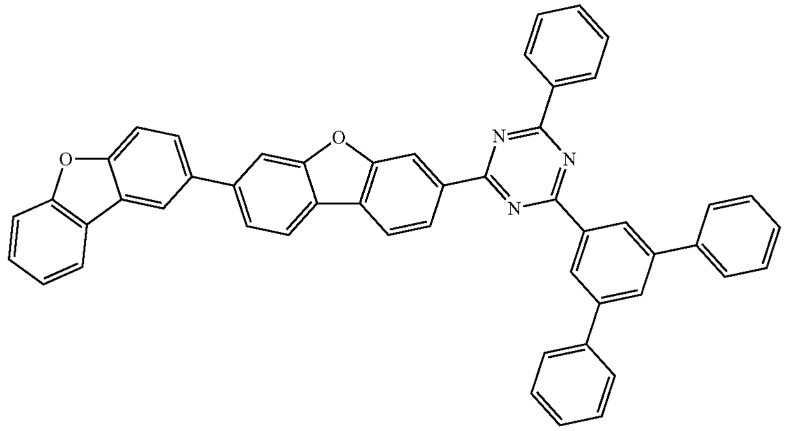
3-9
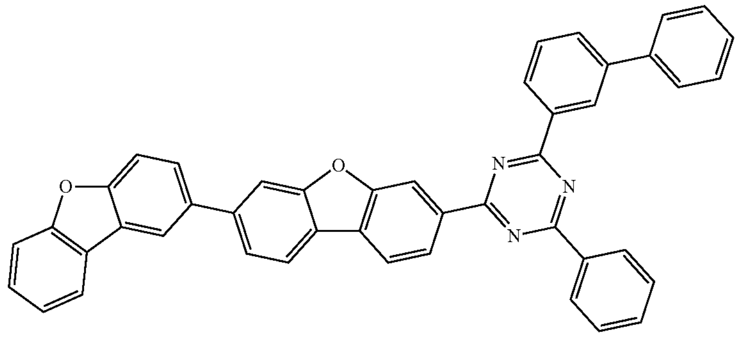
3-10
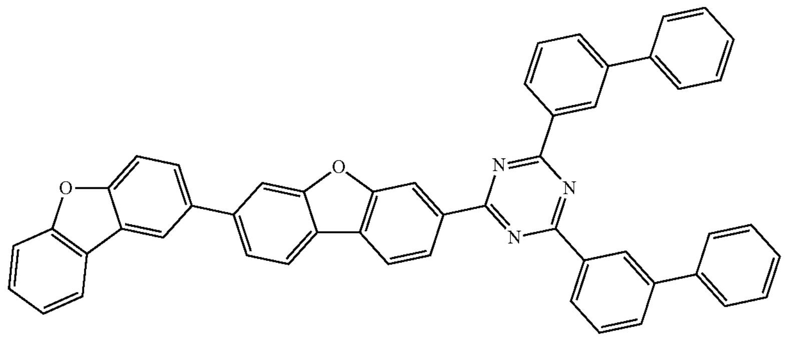

-continued
3-11
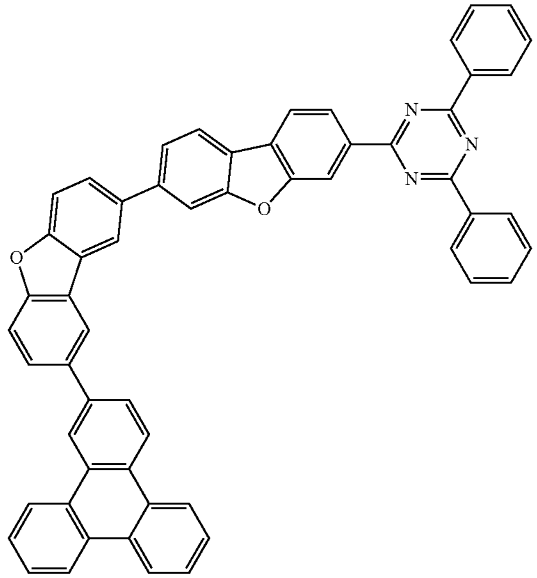
3-12
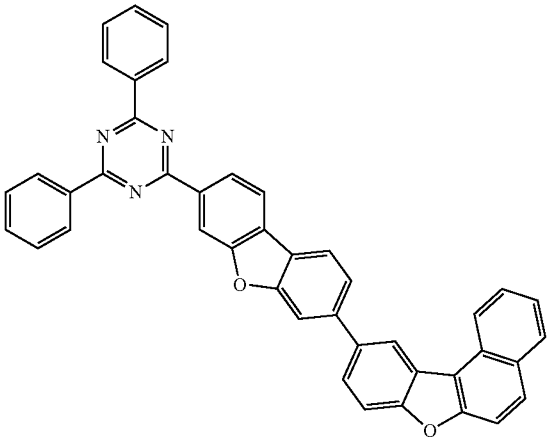
3-13
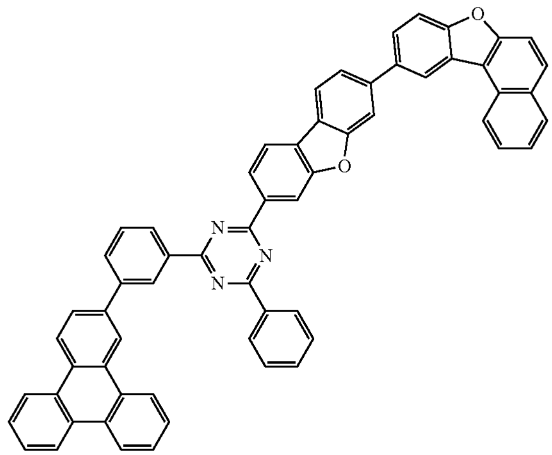
3-14
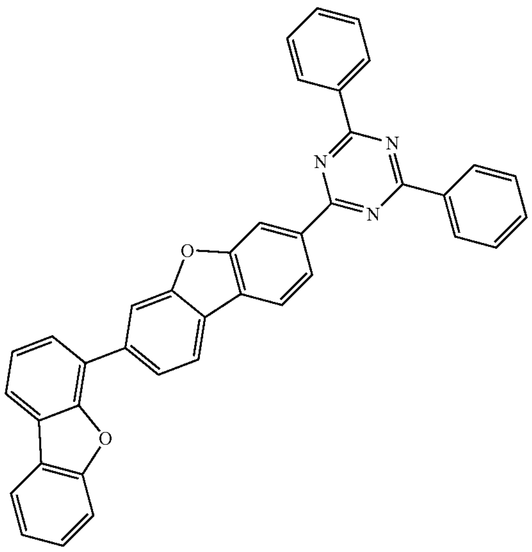

-continued
3-15
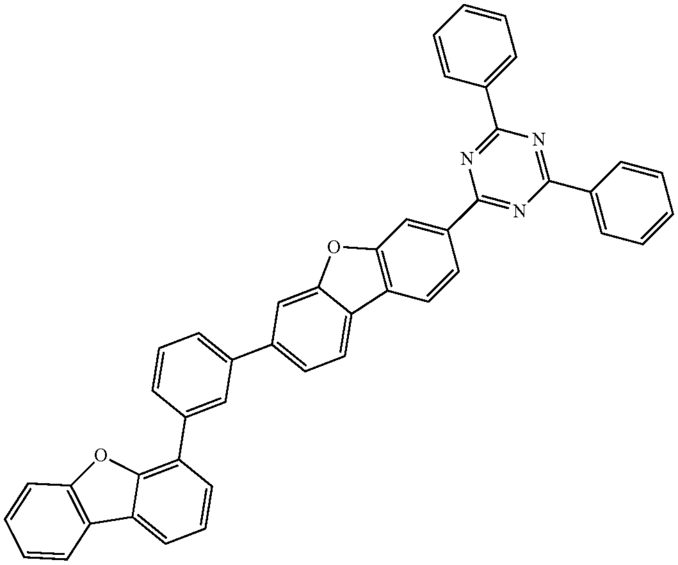
3-16
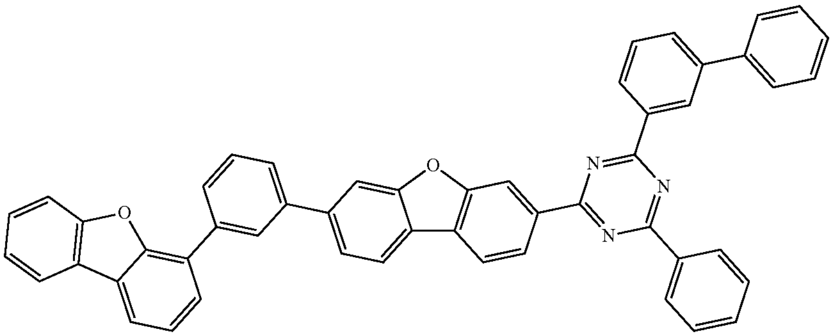
3-17
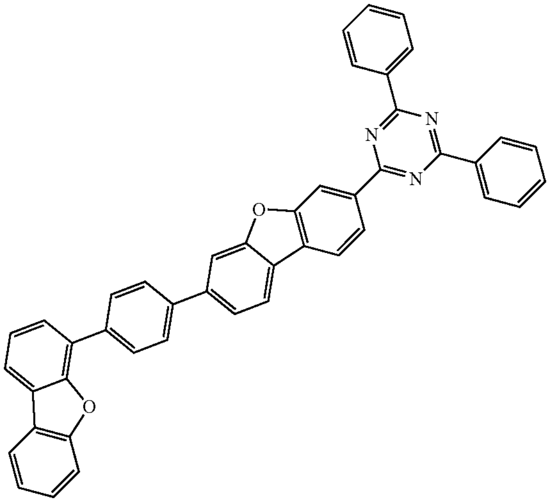
3-18
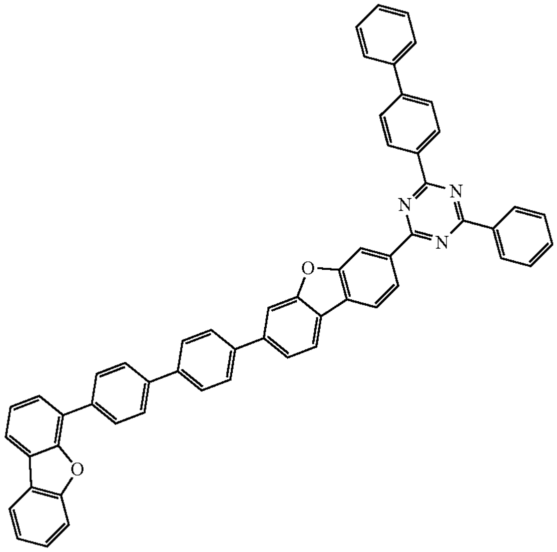

-continued
3-19
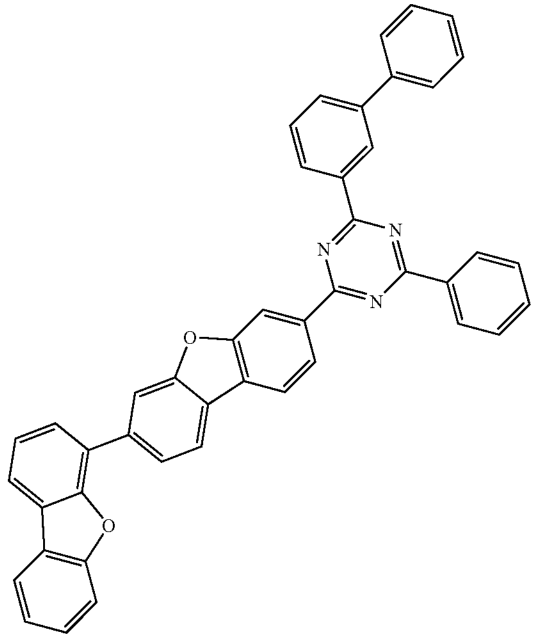
3-20
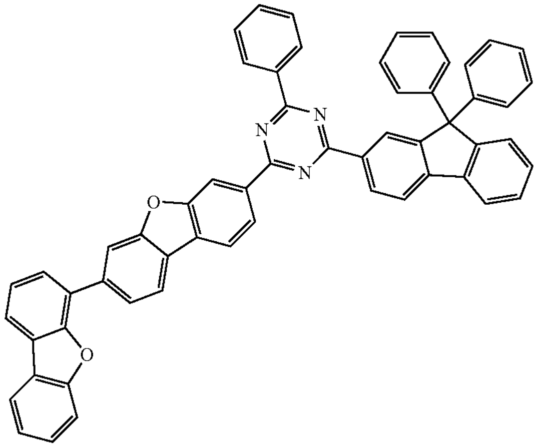
3-21
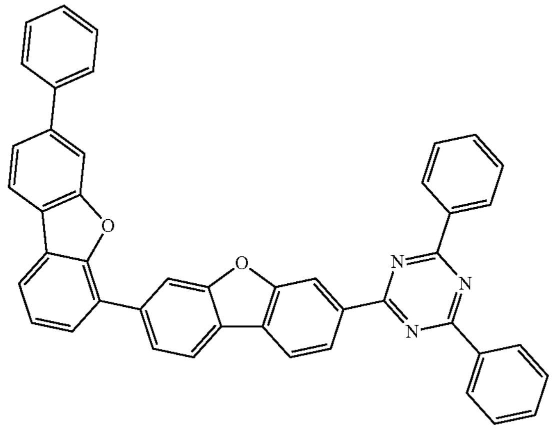
3-22
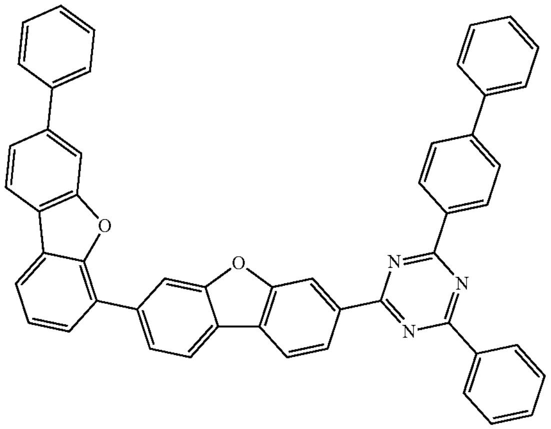
3-23
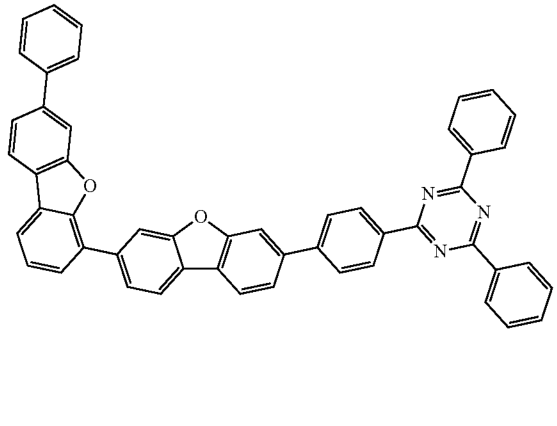
3-24
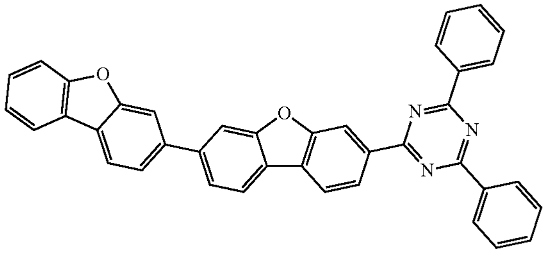

-continued
3-25
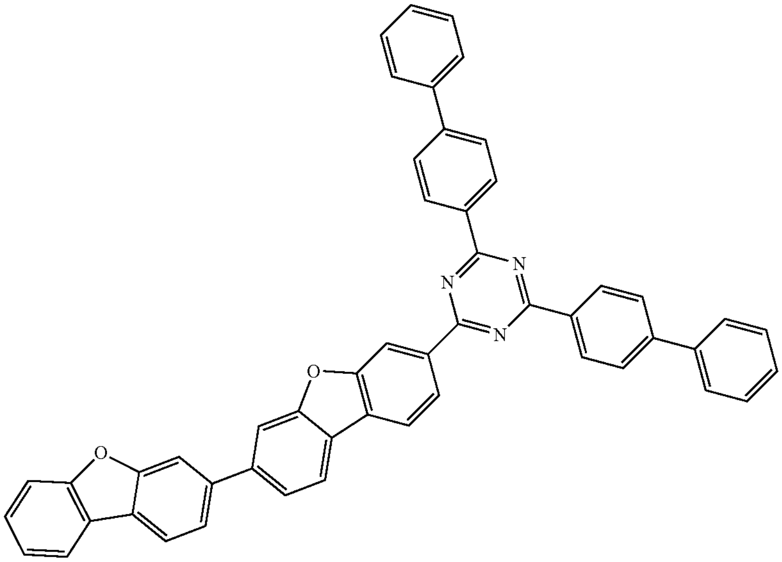
3-26
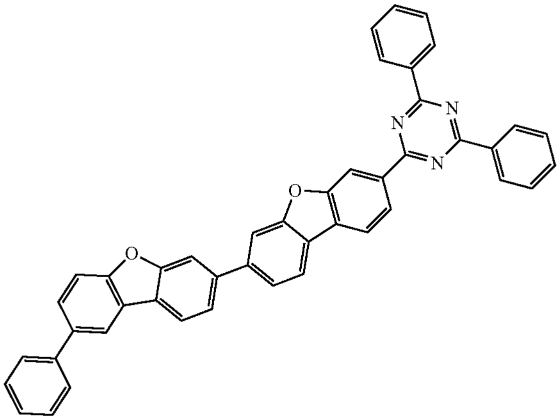
3-27
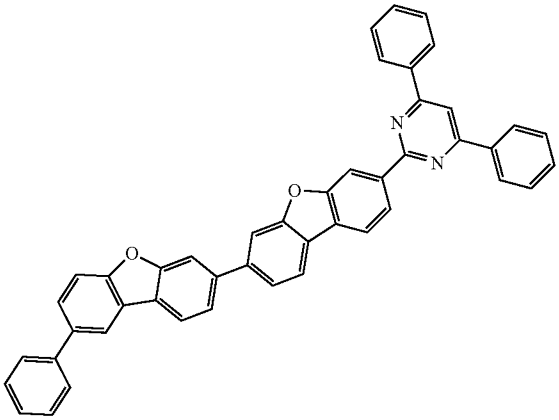
3-28
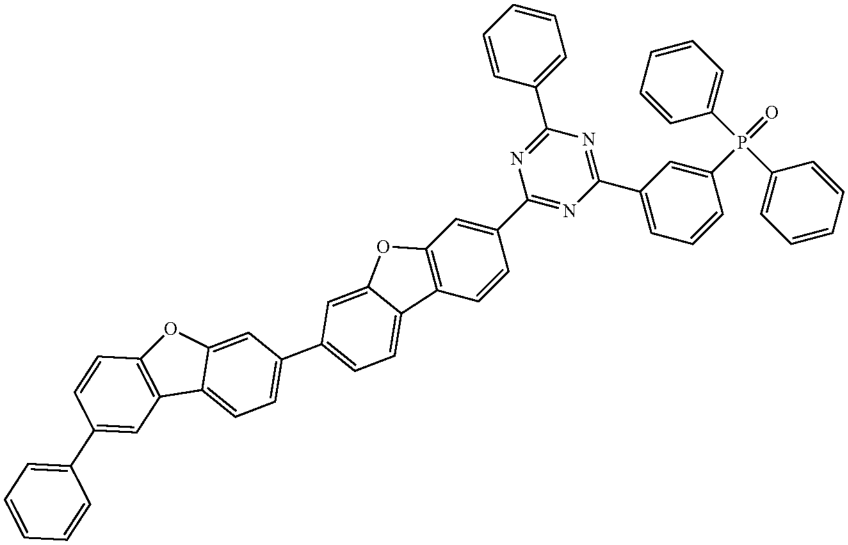

-continued
3-29
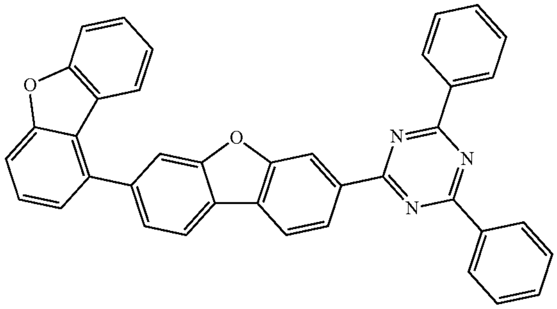
3-30
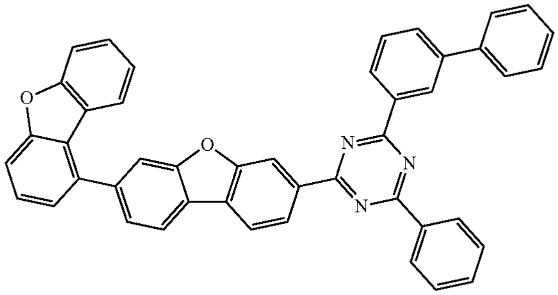
3-31
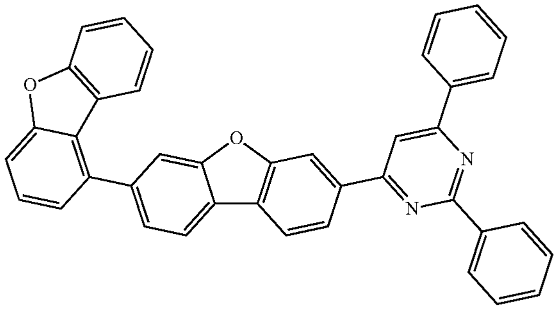
3-32
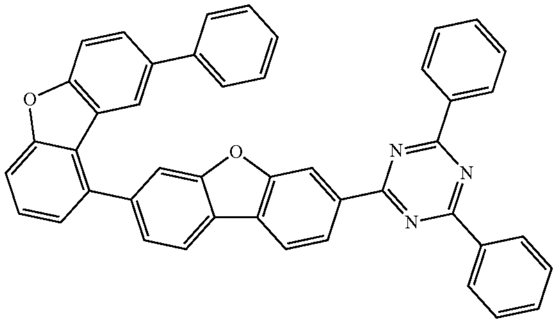
3-33
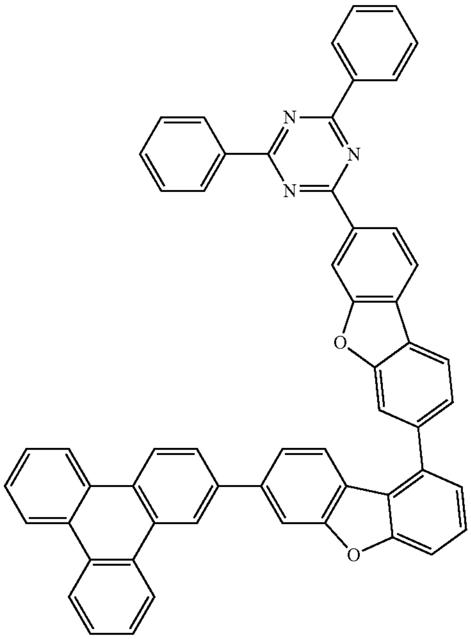
3-34
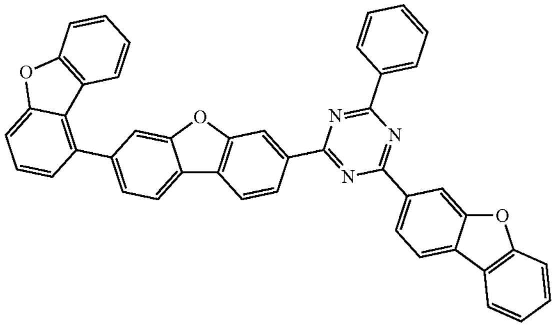

-continued
3-35
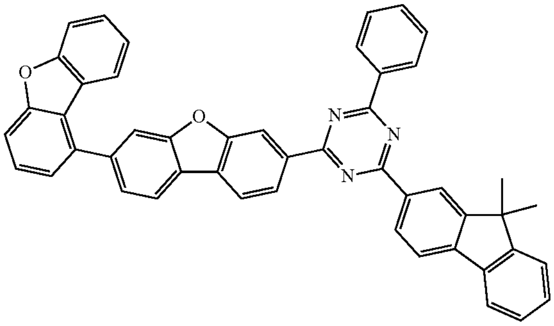
3-36
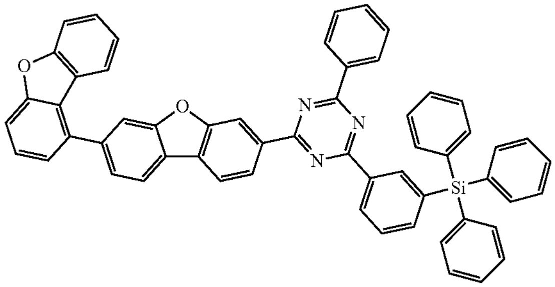
3-37
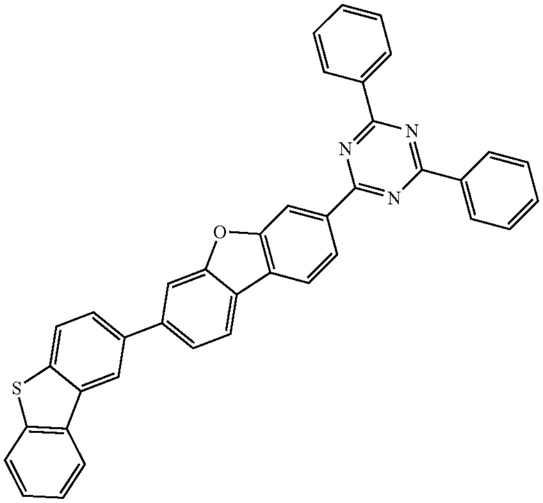
3-38
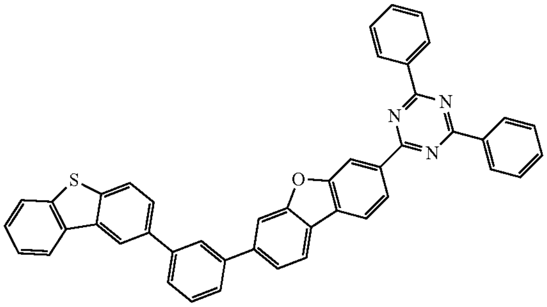
3-39
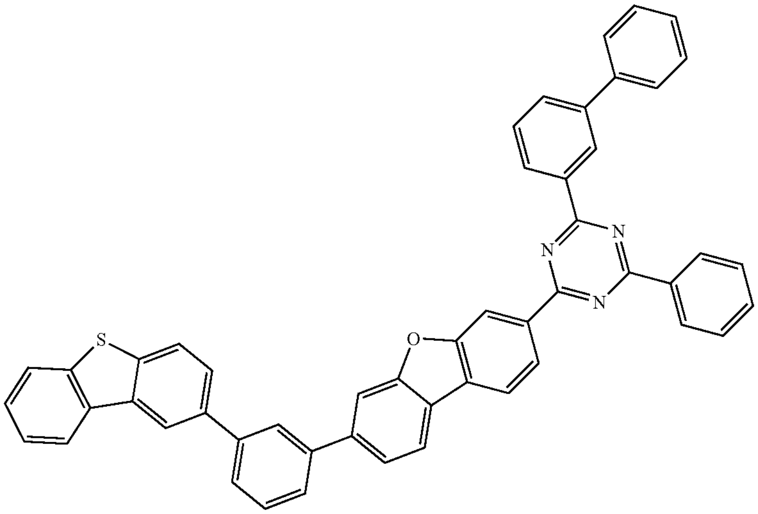

-continued
3-40
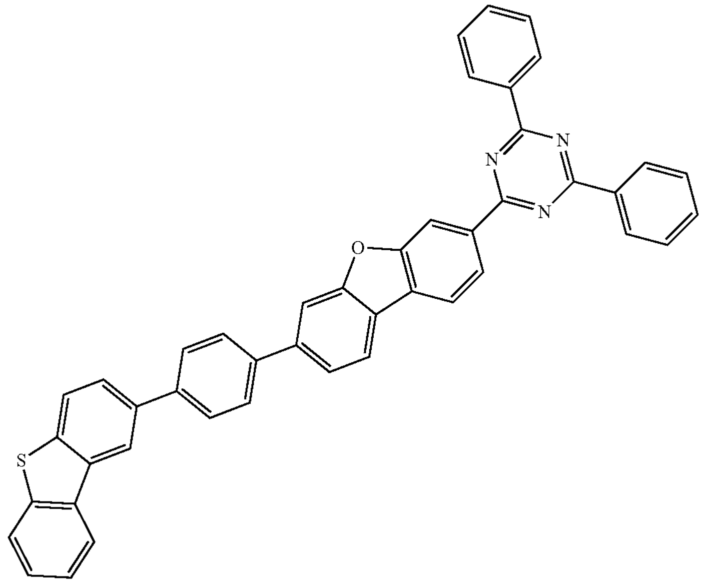
3-41
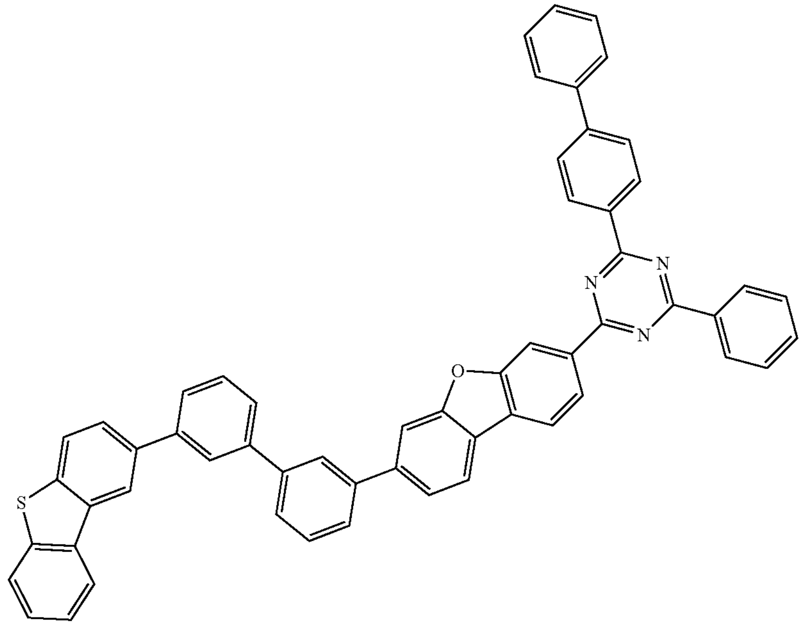

-continued
3-42
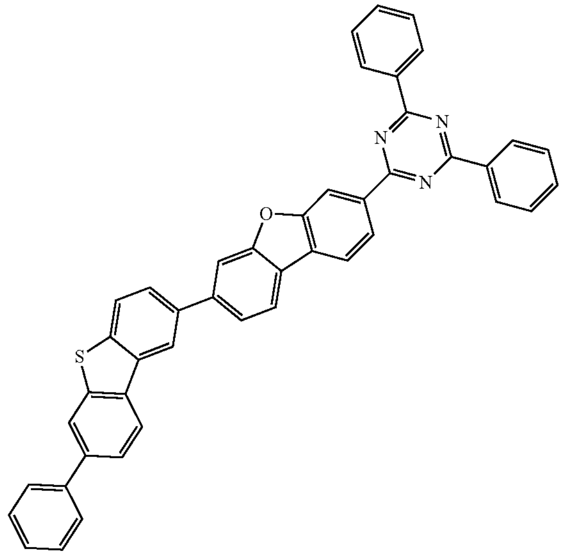
3-43
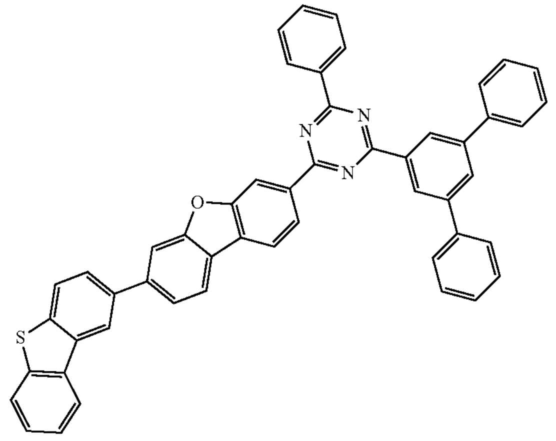
3-44
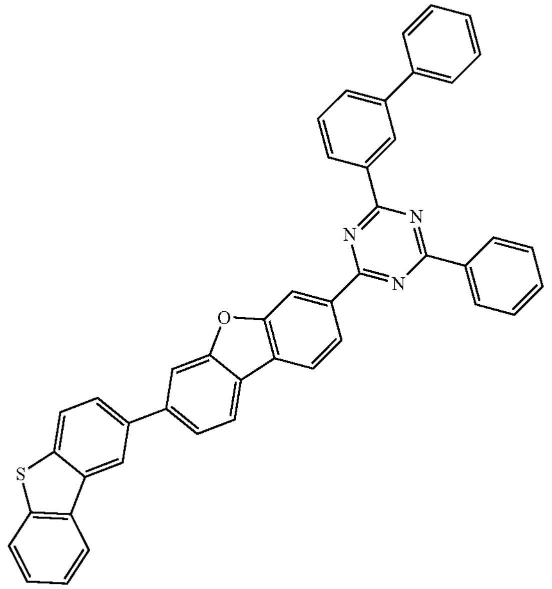
3-45
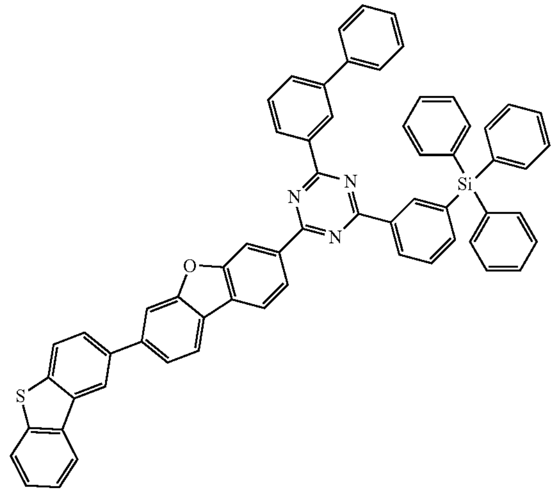

-continued
3-46
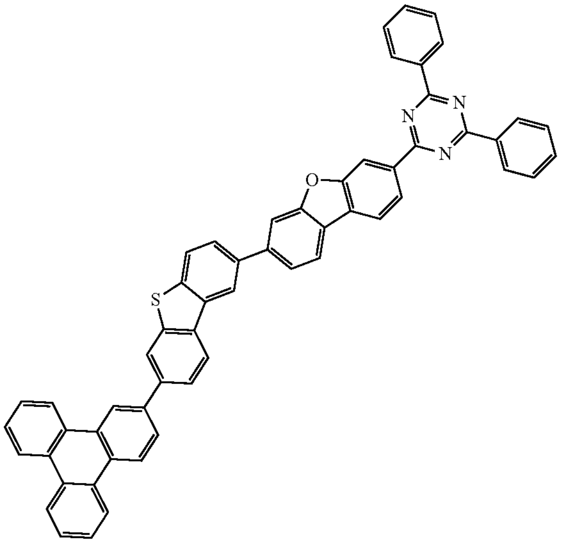
3-47
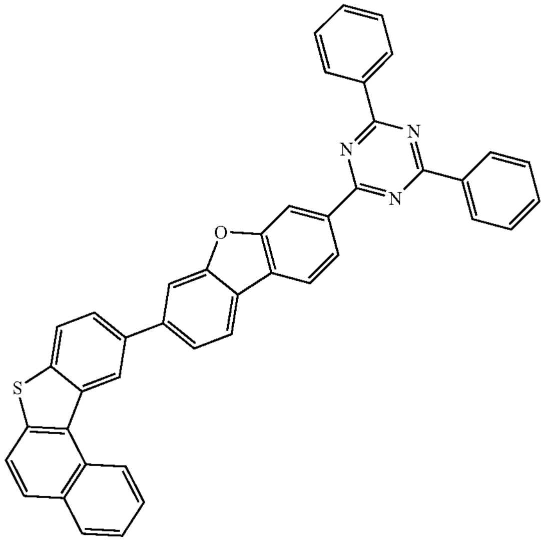
3-48
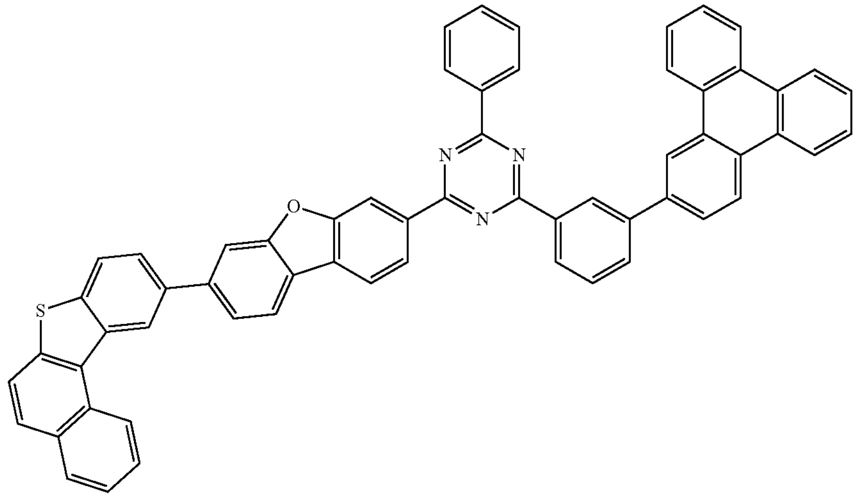
3-49
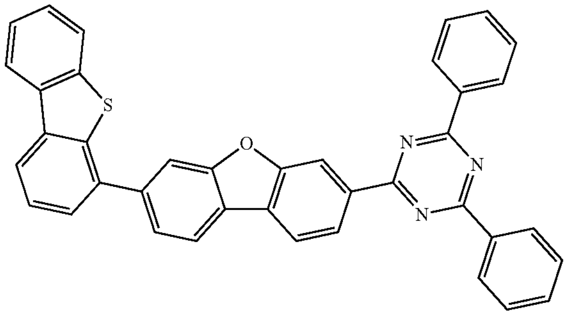

-continued
3-50
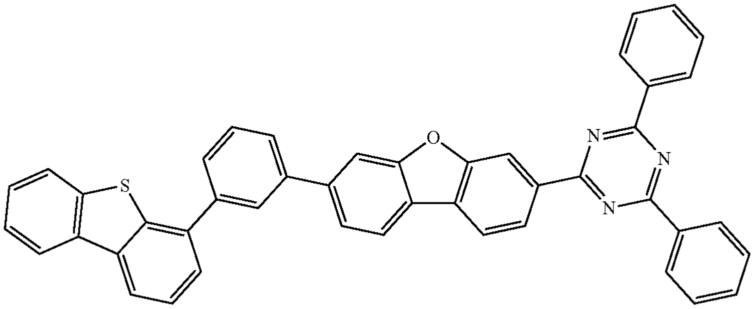
3-51
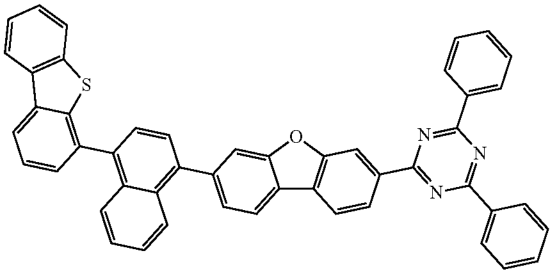
3-52
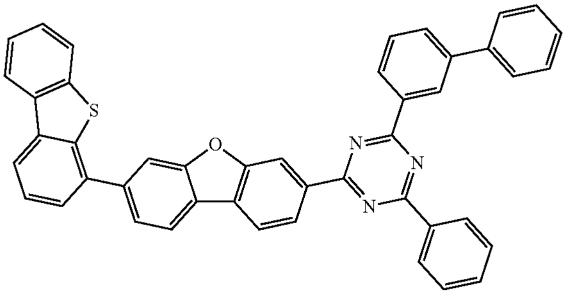
3-53
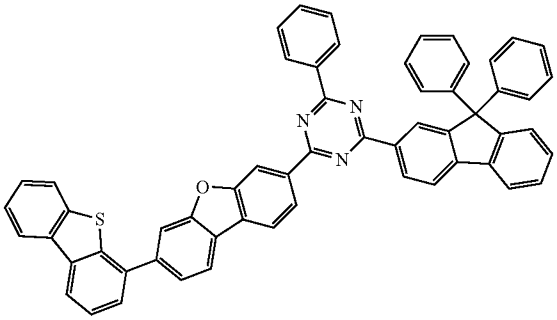
3-54
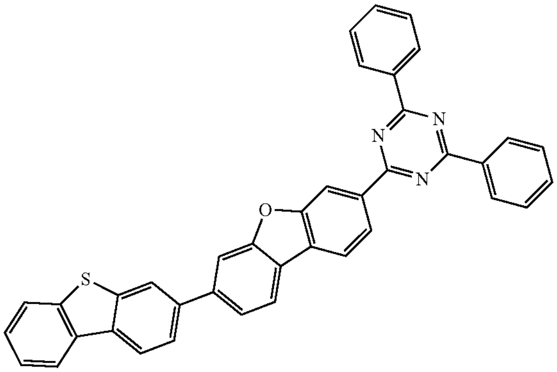
3-55
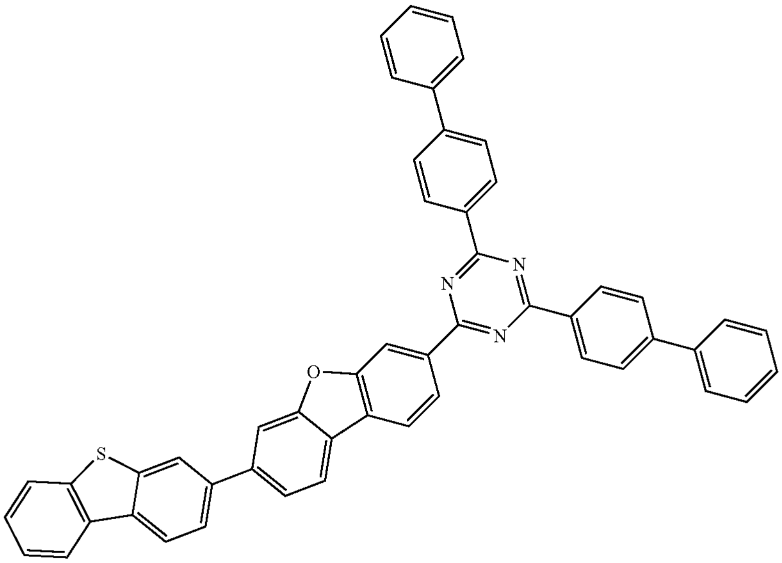

-continued
3-56
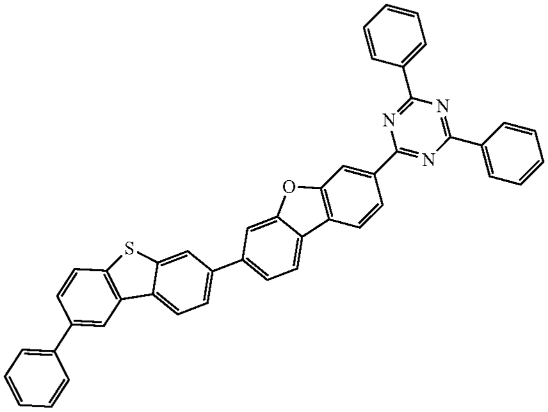
3-57
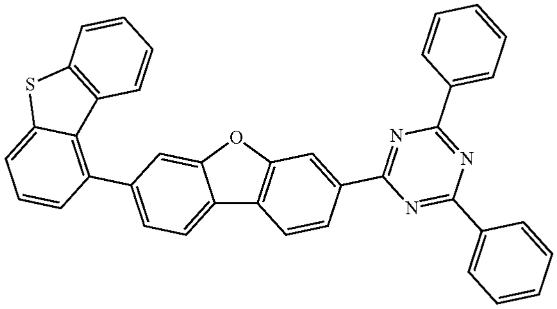
3-58
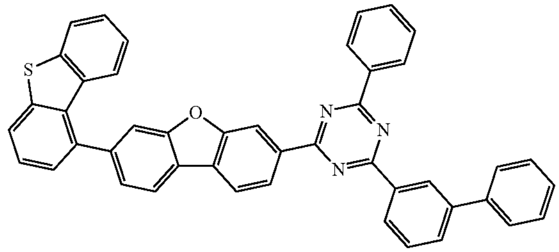
3-59
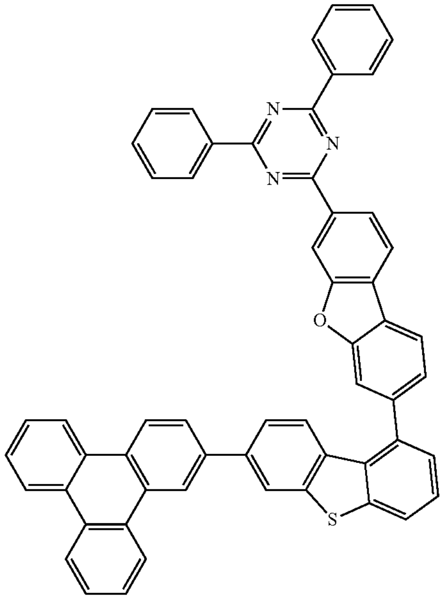
3-60
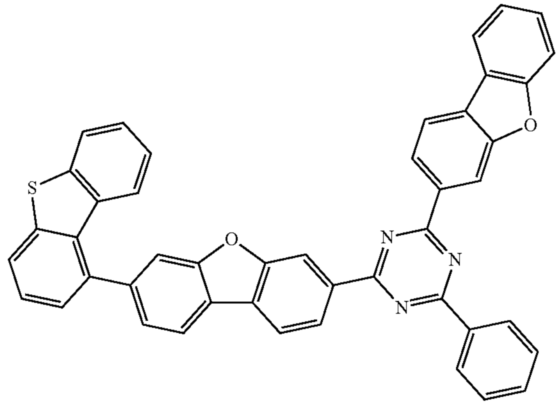
3-61
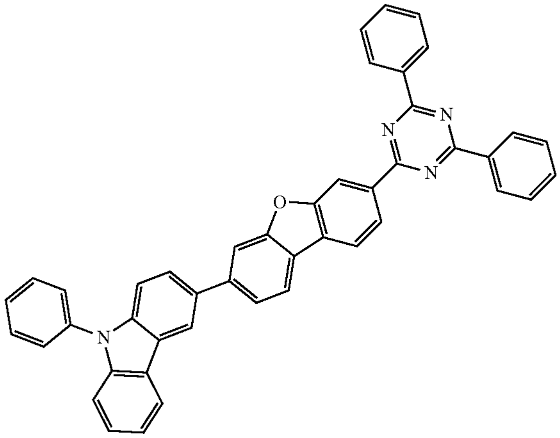

-continued
3-62
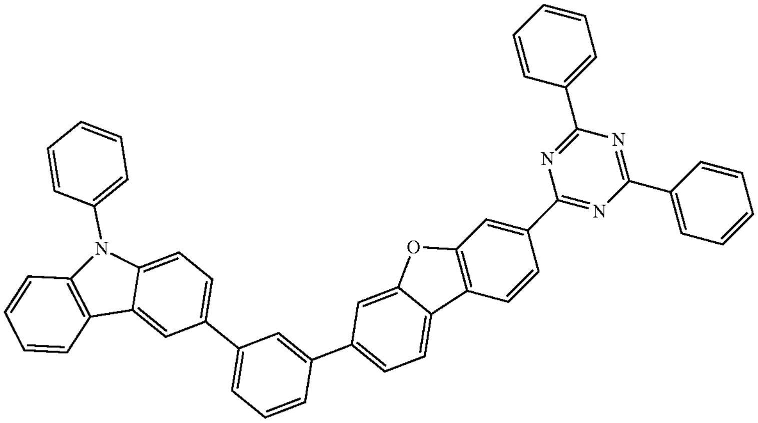
3-63
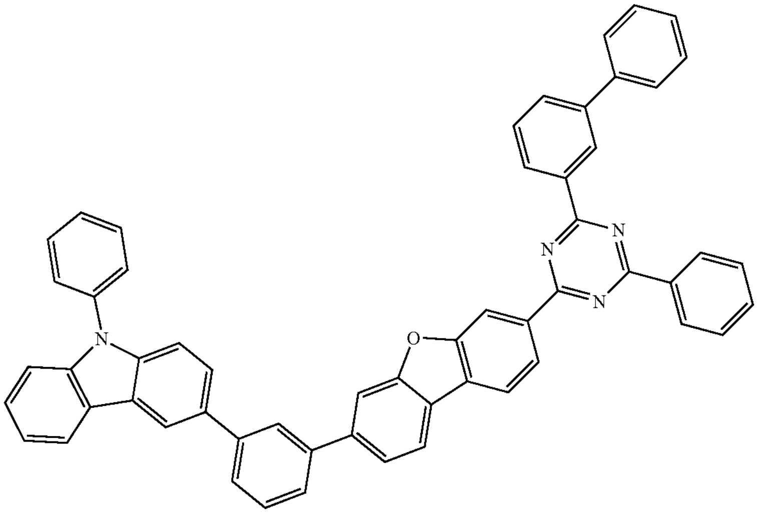
3-64
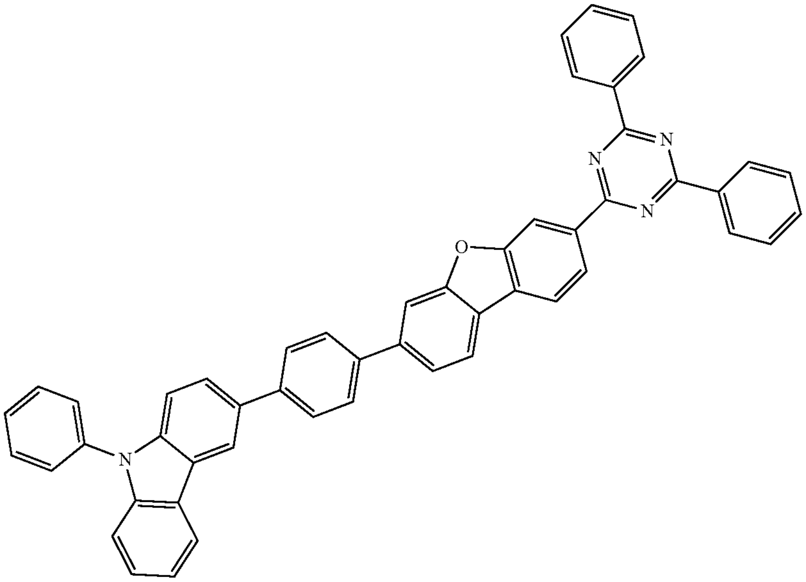

-continued
3-65
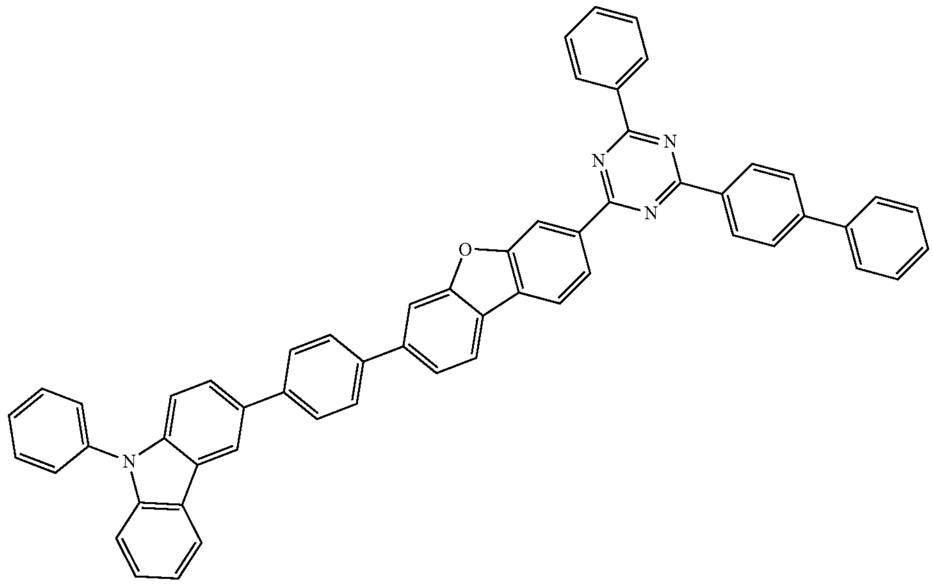
3-66
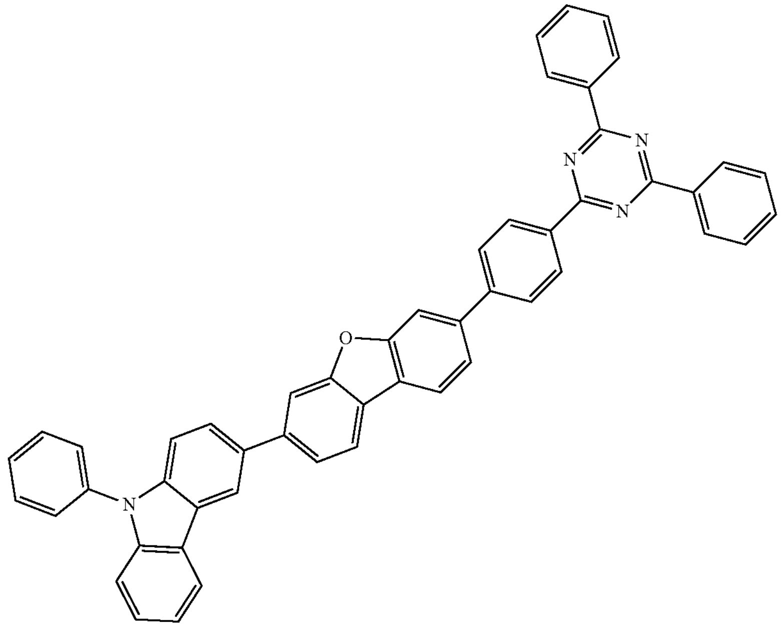

-continued
3-67
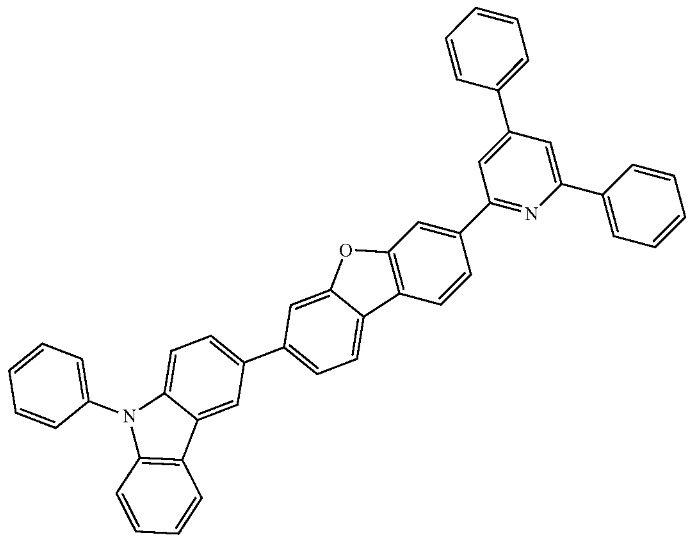
3-68
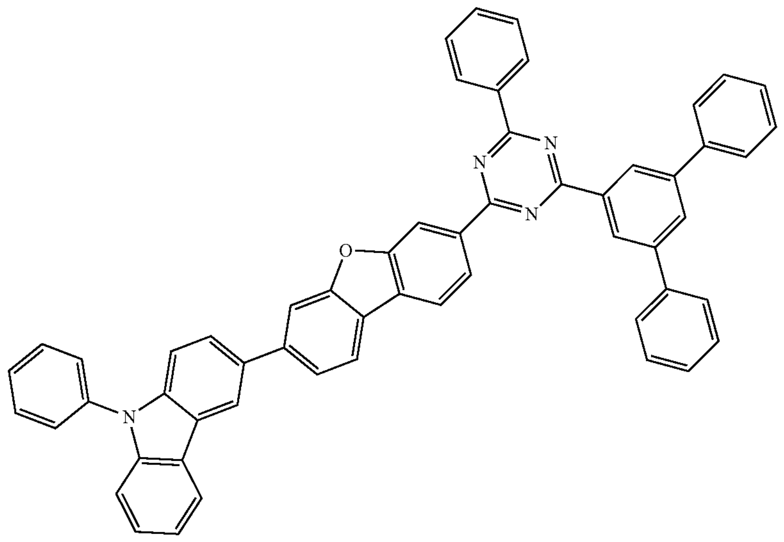

-continued
3-69
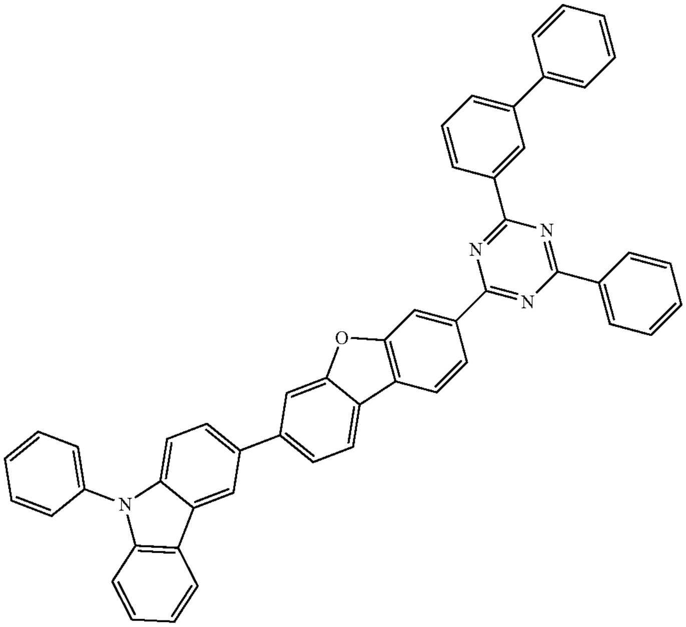
3-70
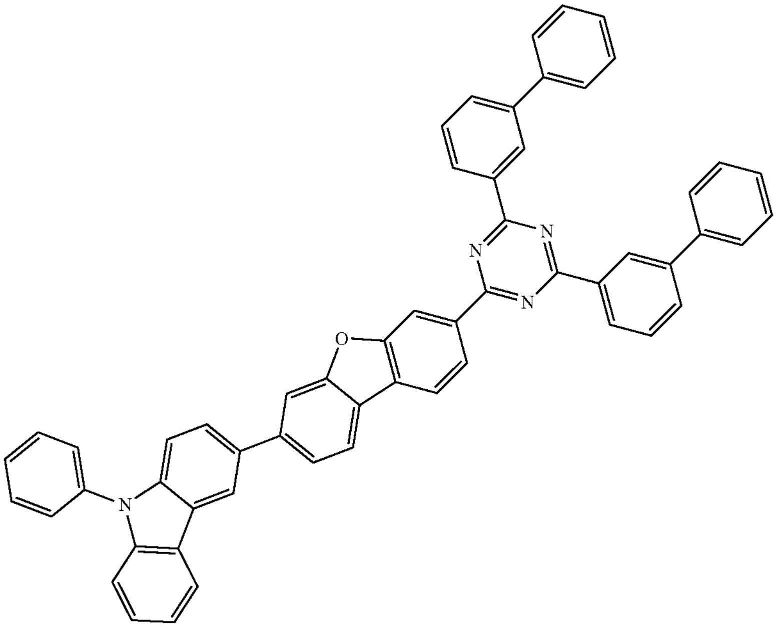

-continued
3-71
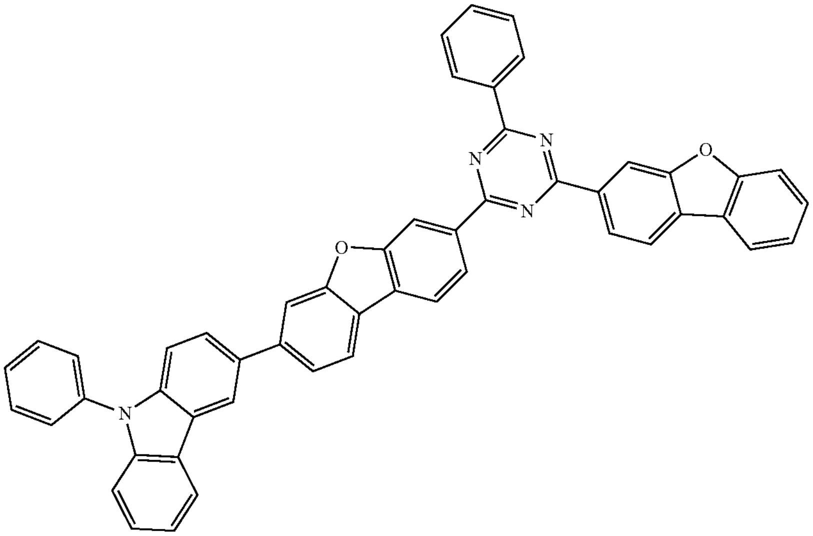
3-72
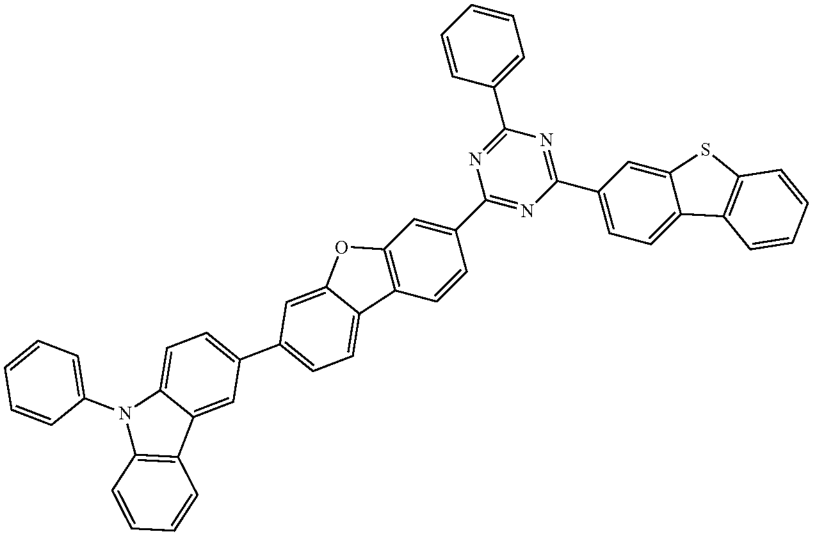
3-73
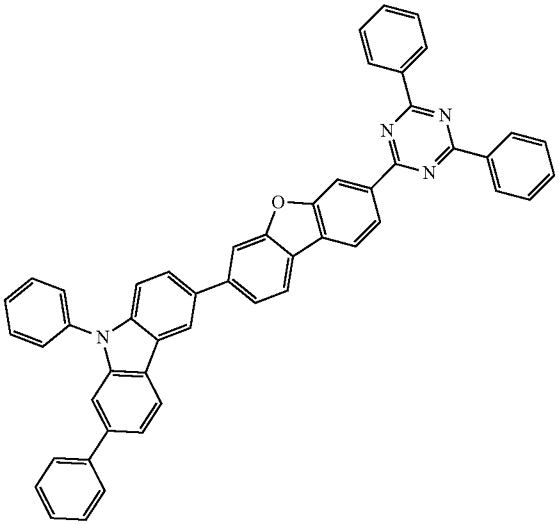
3-74
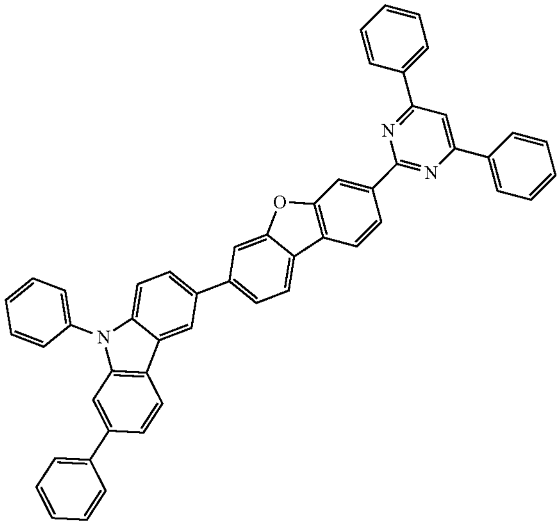

-continued
3-75
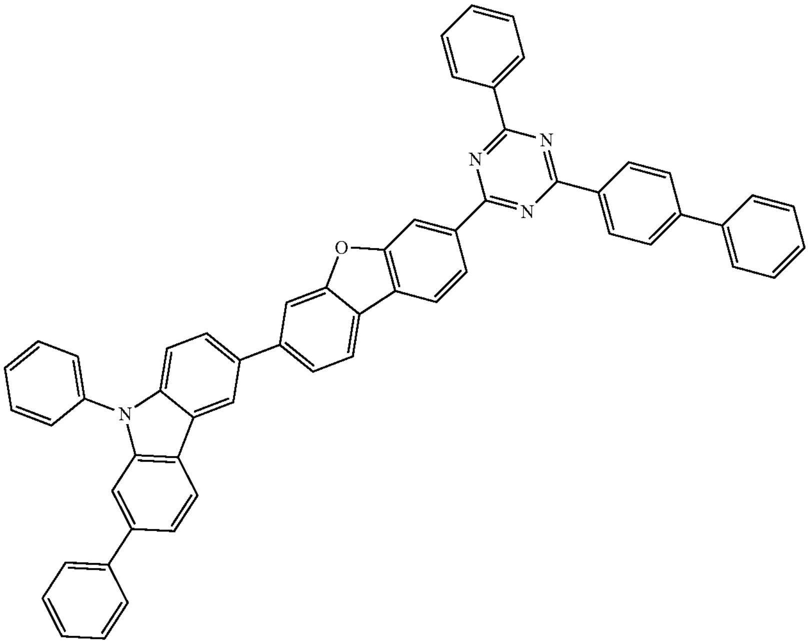
3-76
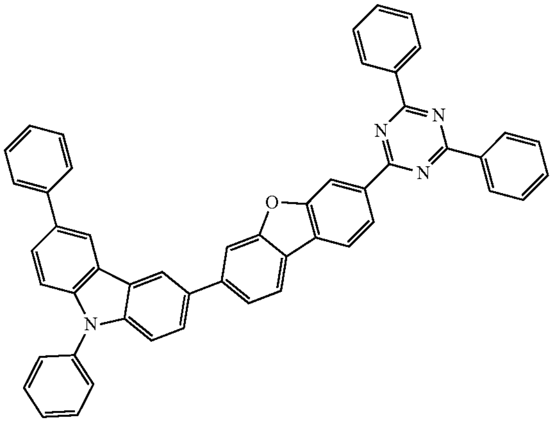
3-77
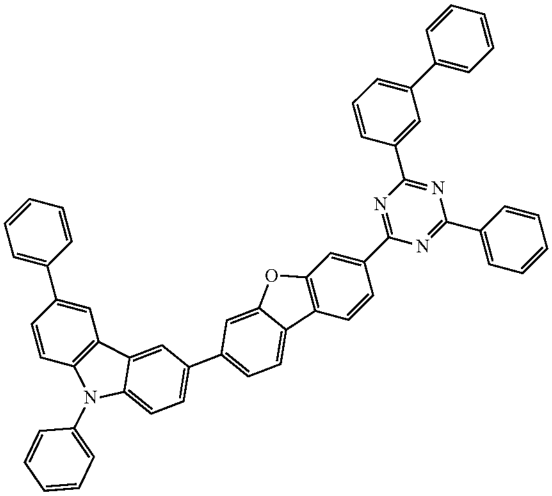

-continued
3-78
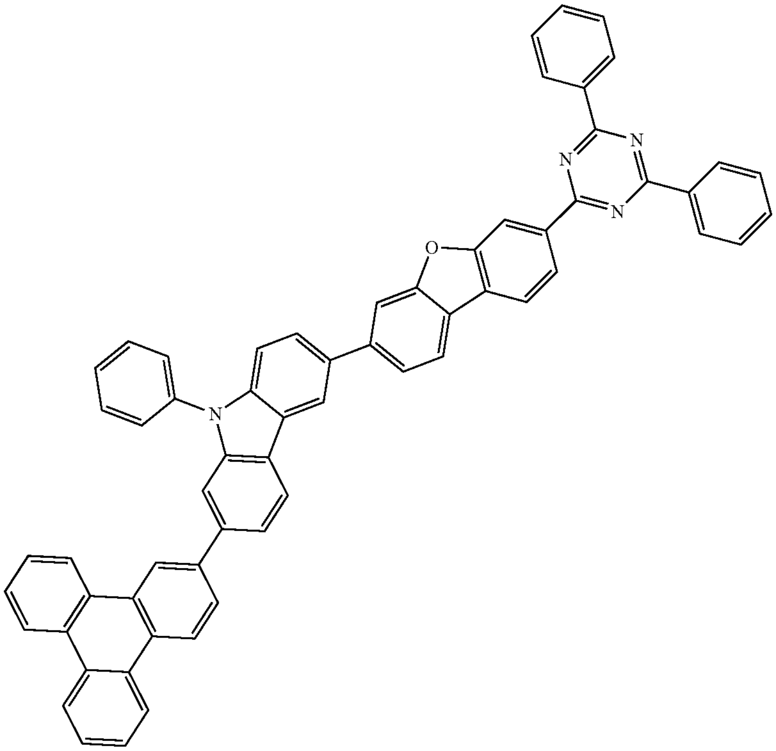
3-79
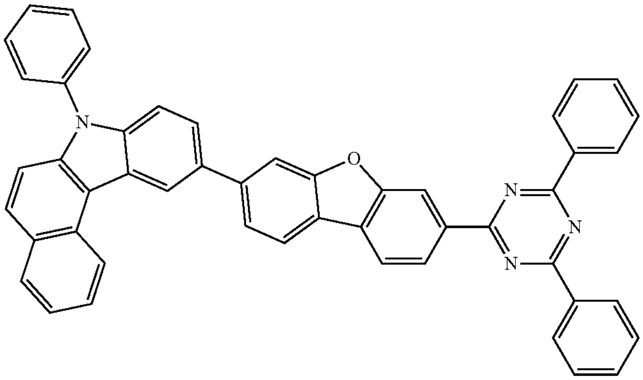

-continued
3-80
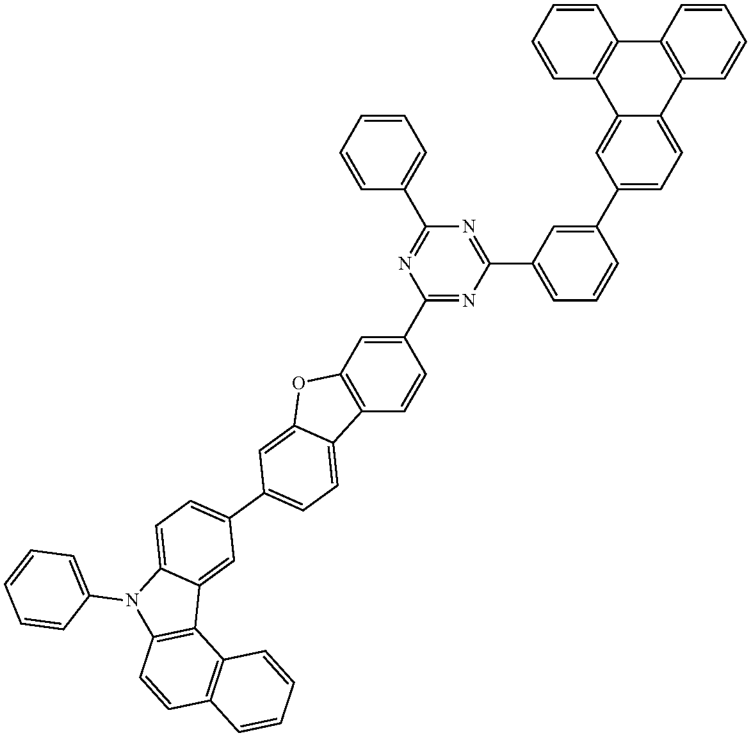
3-81
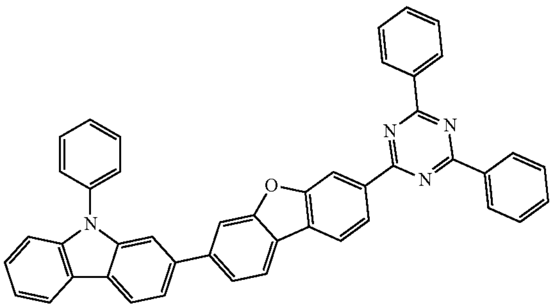
3-82
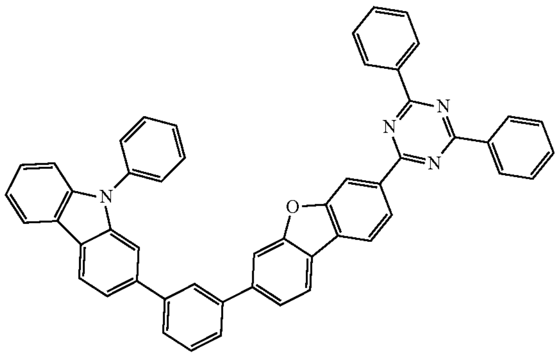
3-83
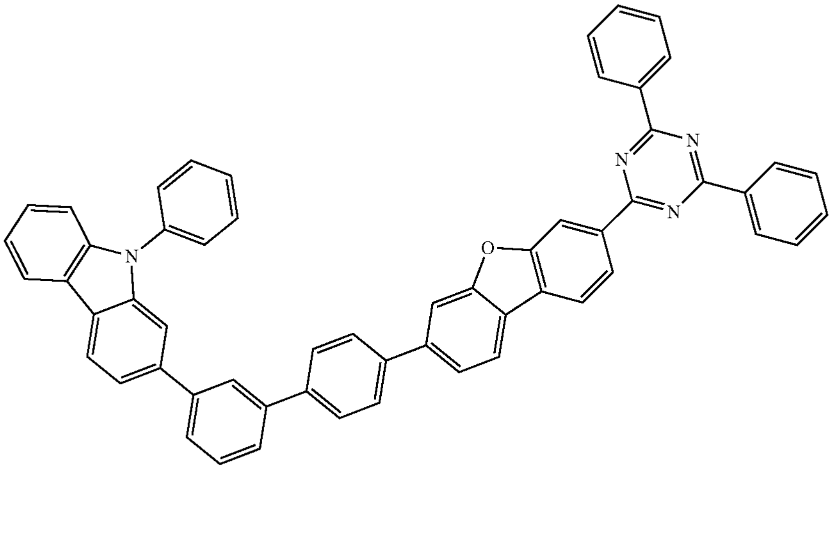

-continued
3-84
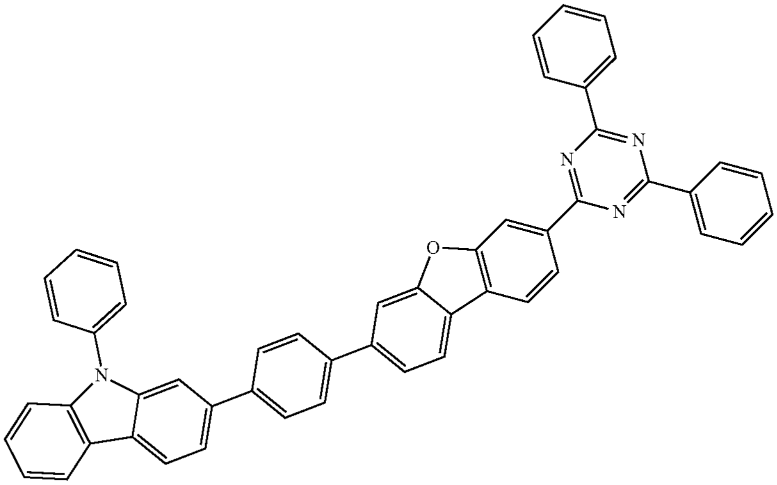
3-85
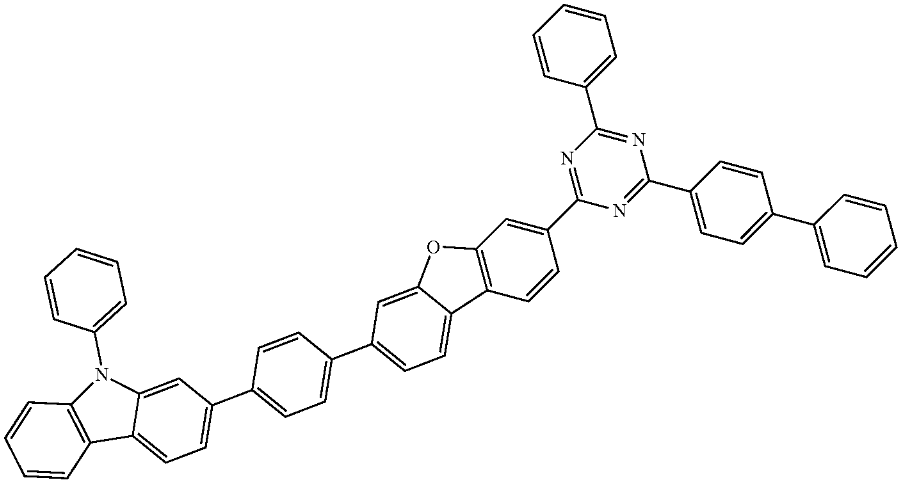
3-86
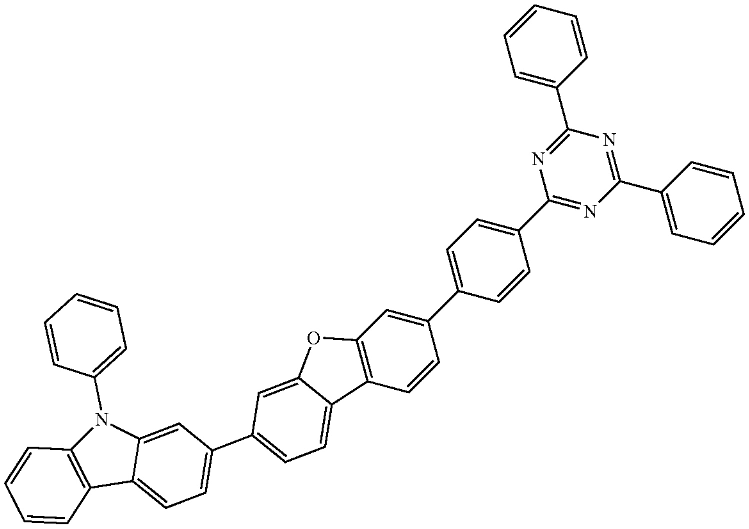

-continued
3-87
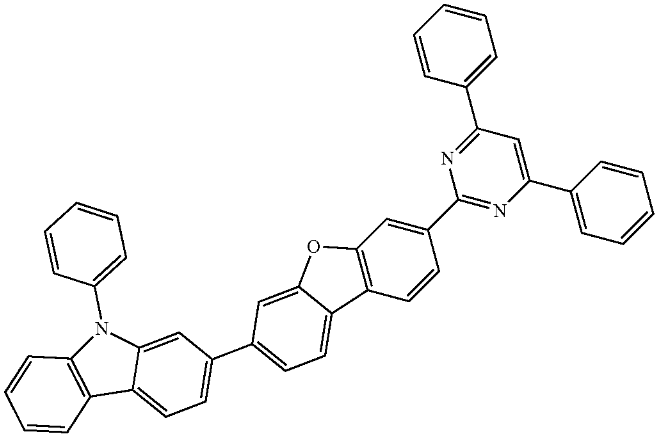
3-88
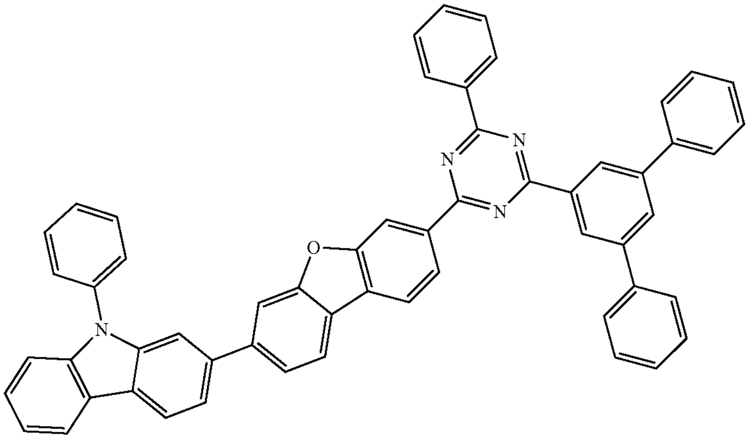
3-89
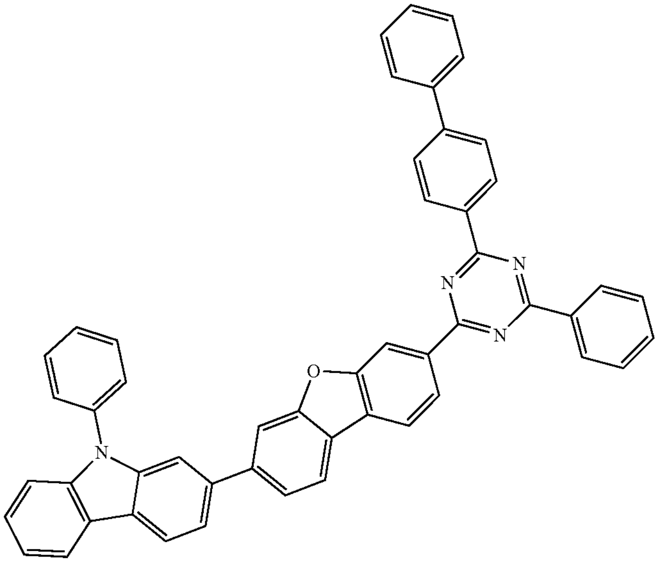

-continued
3-90
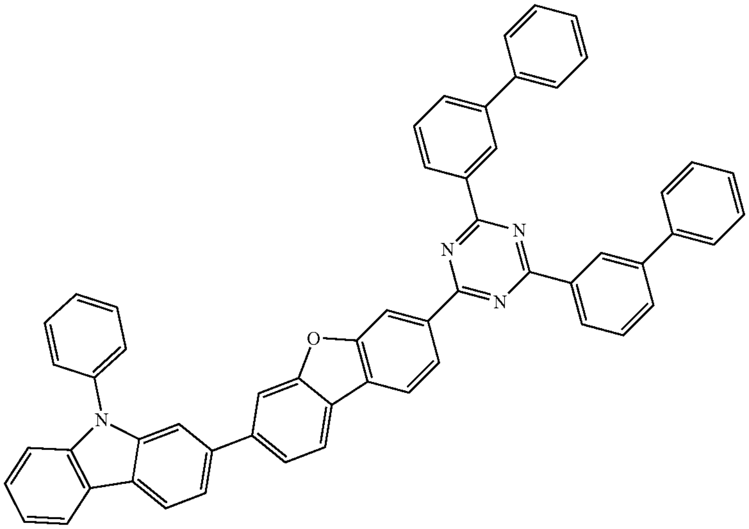
3-91
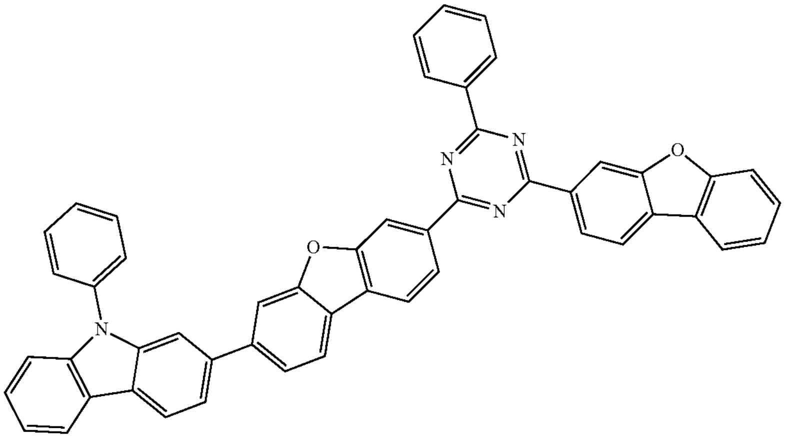
3-92
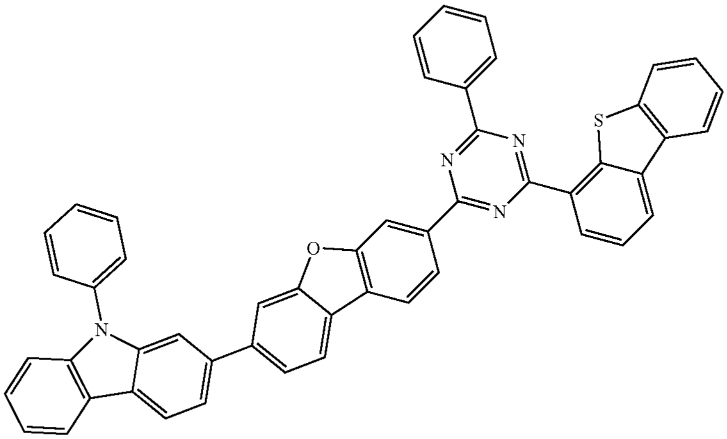

-continued
3-93
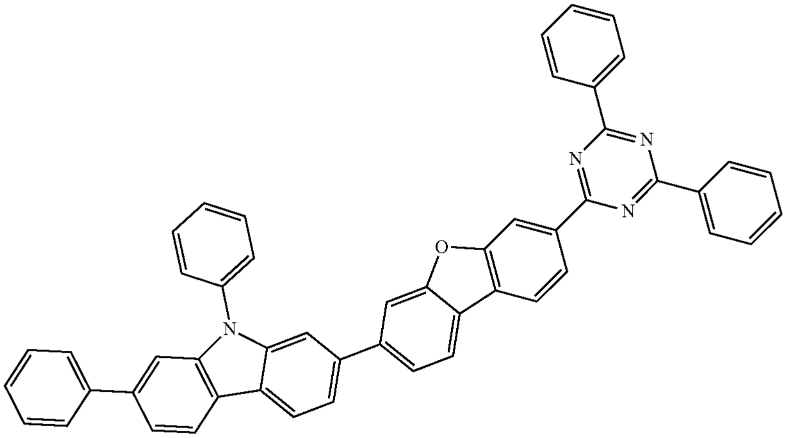
3-94
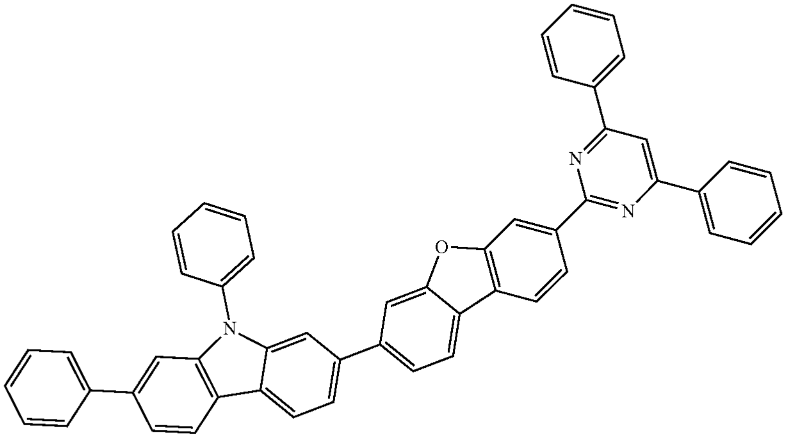
3-95
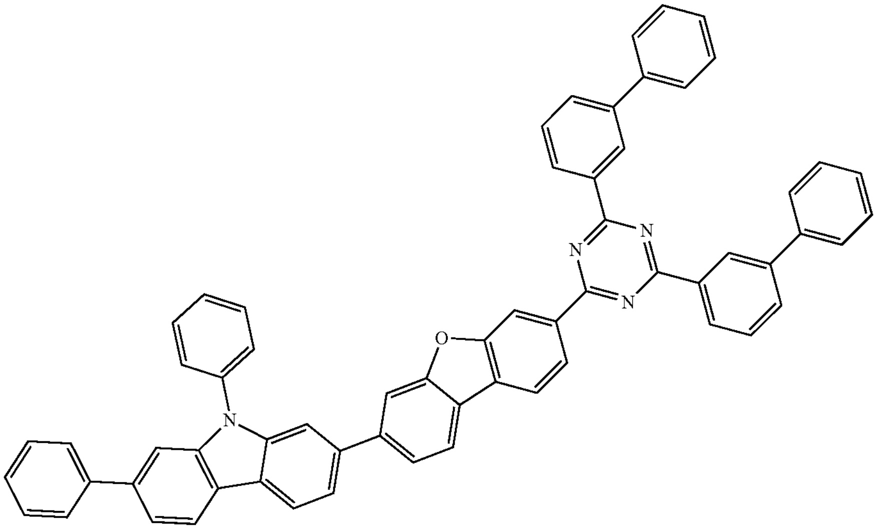

-continued
3-96
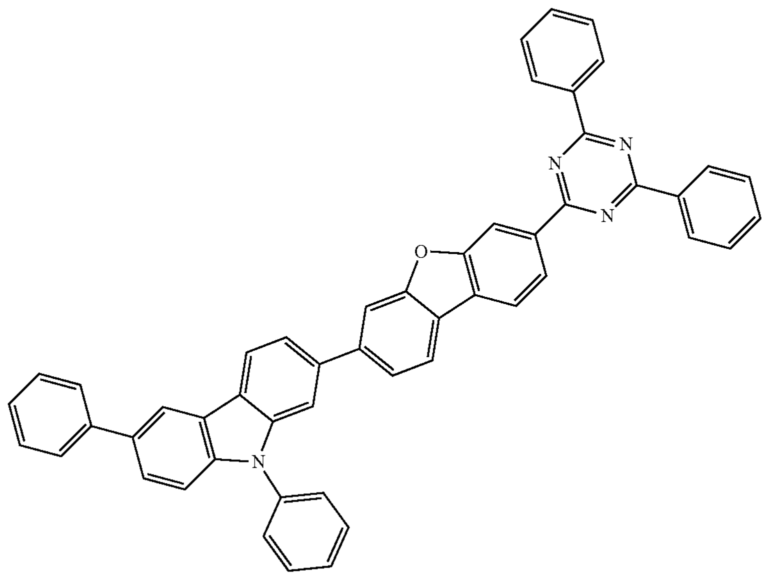
3-97
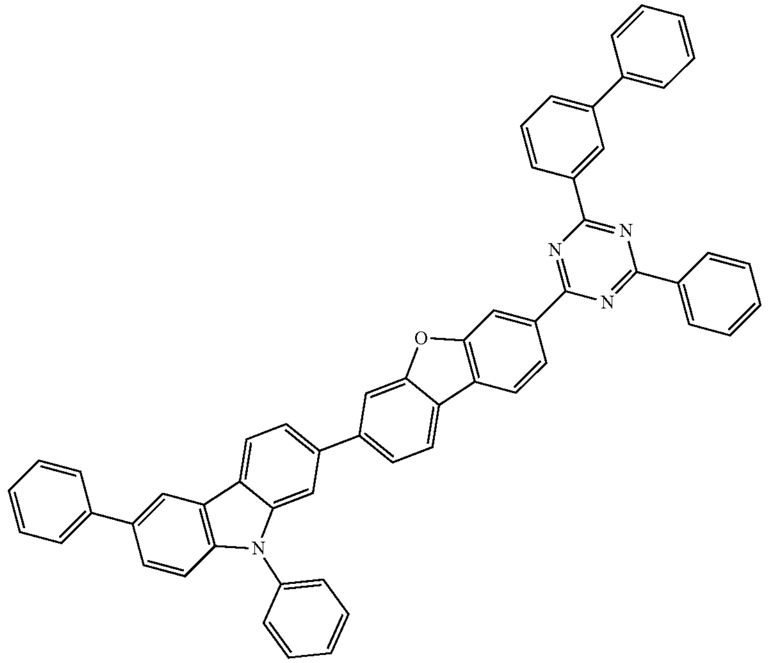

-continued
3-98
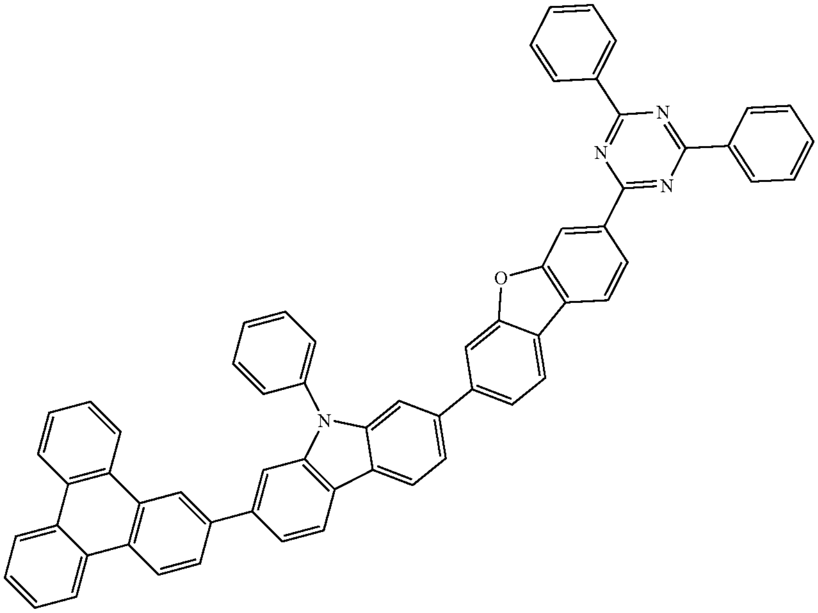
3-99
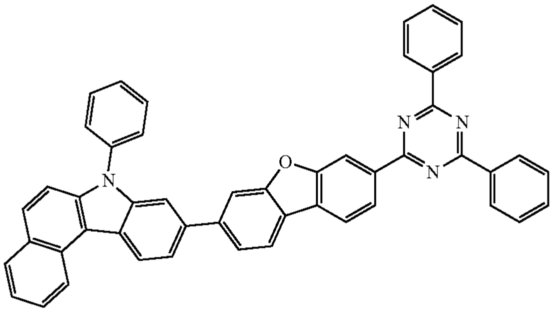
3-100
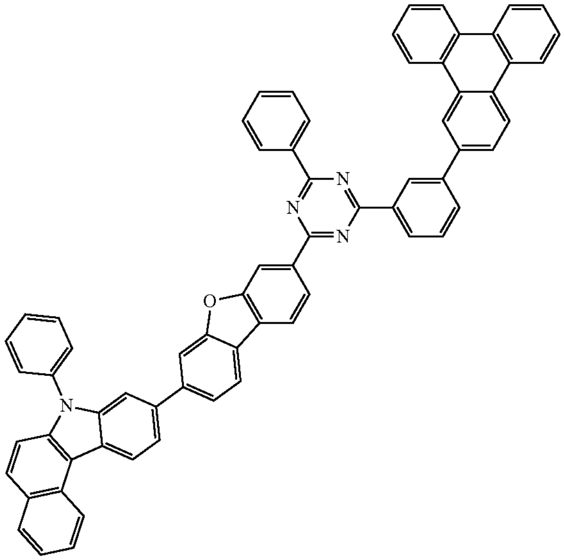
3-101
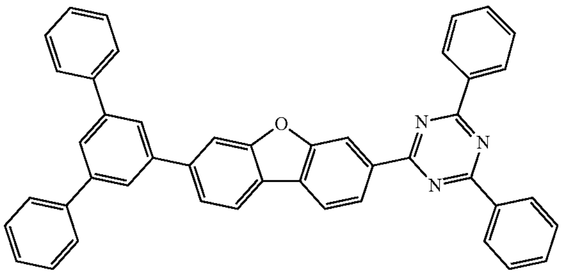
3-102
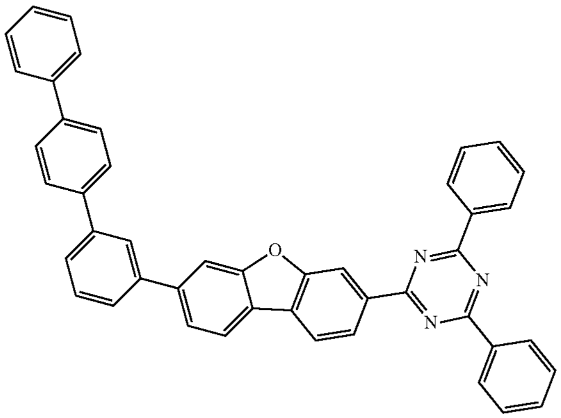

-continued
3-103
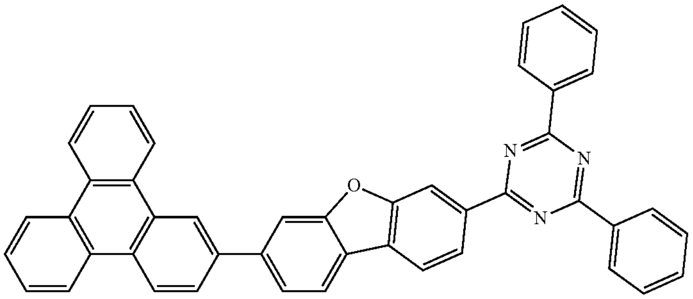
3-104
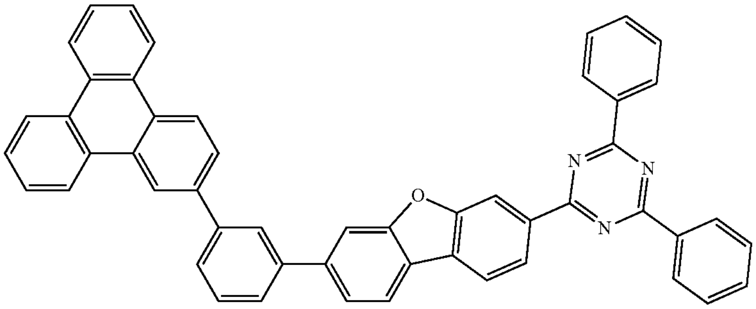
4-1
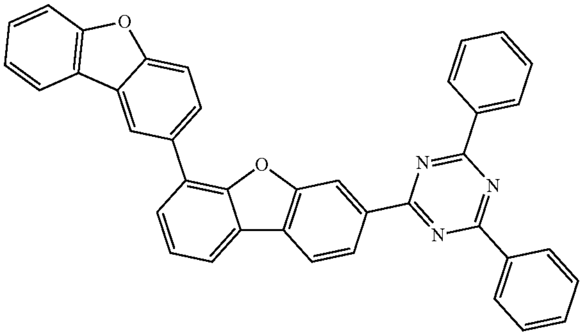
4-2
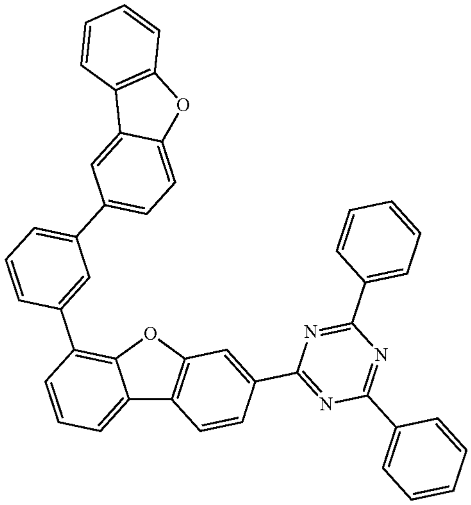

-continued
4-3
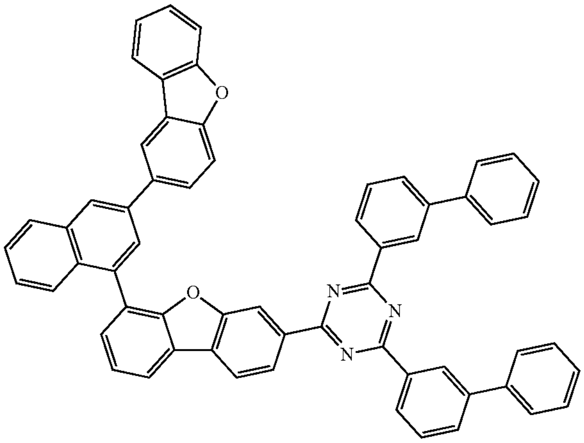
4-4
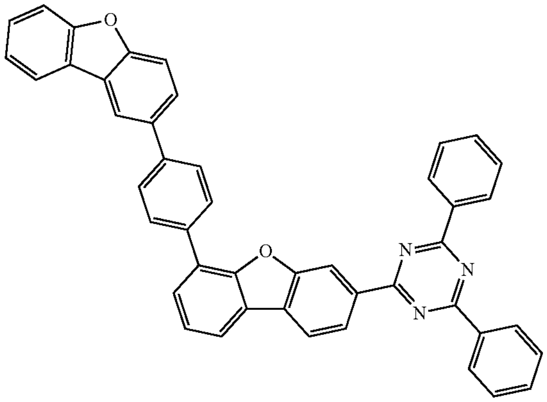
4-5
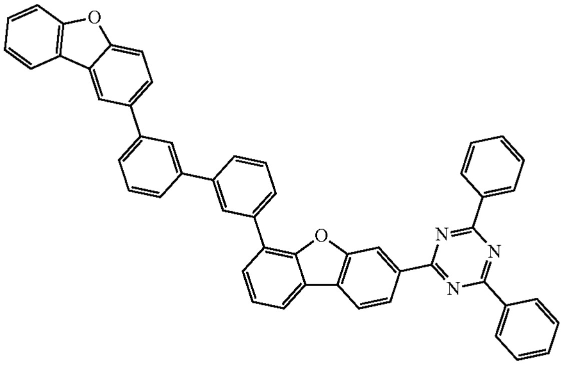
4-6
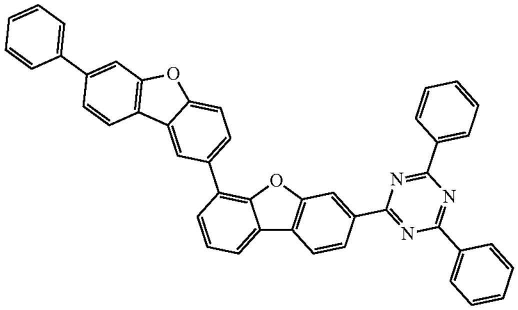
4-7
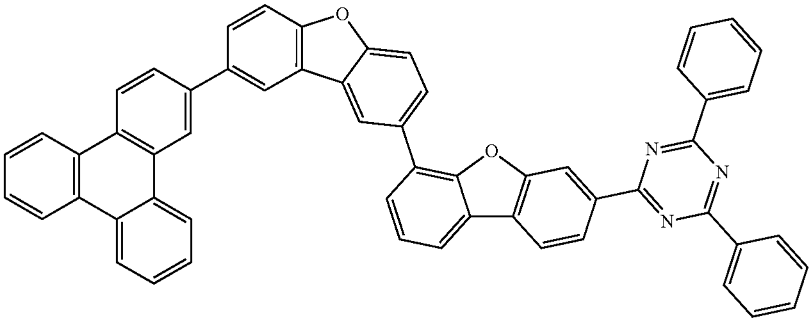
4-8
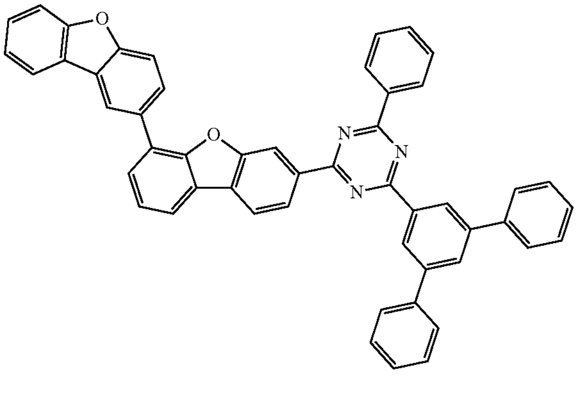
4-9
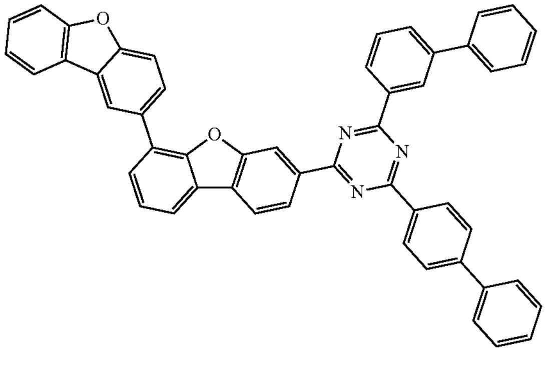

-continued
4-10
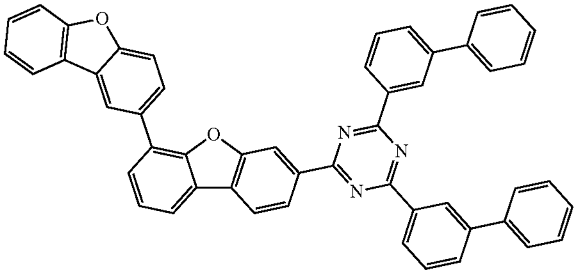
4-11
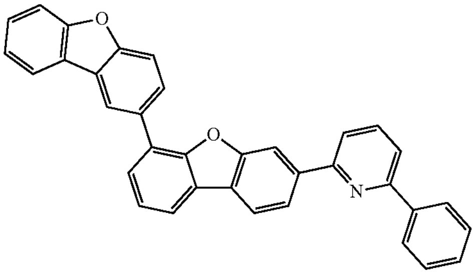
4-12
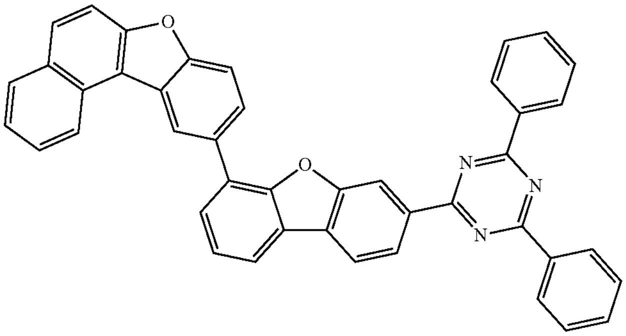
4-13
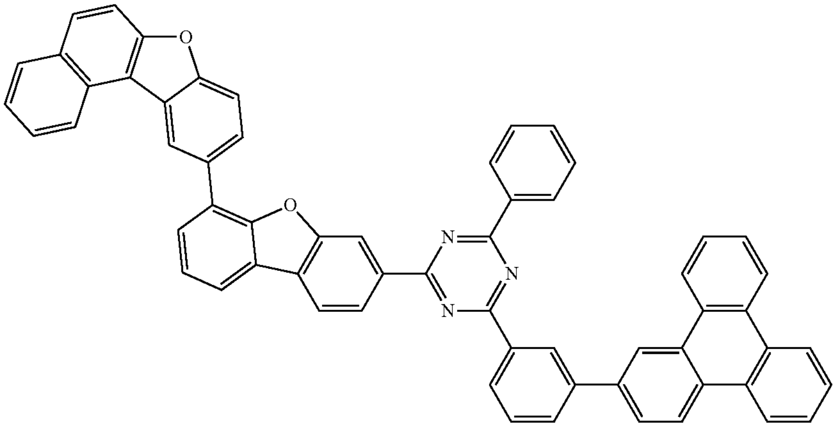
4-14
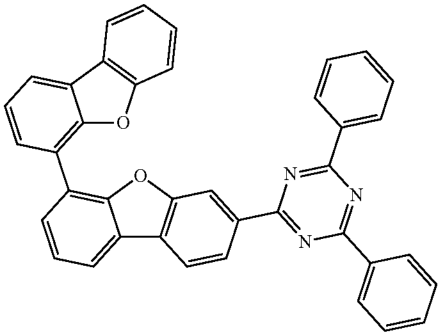
4-15
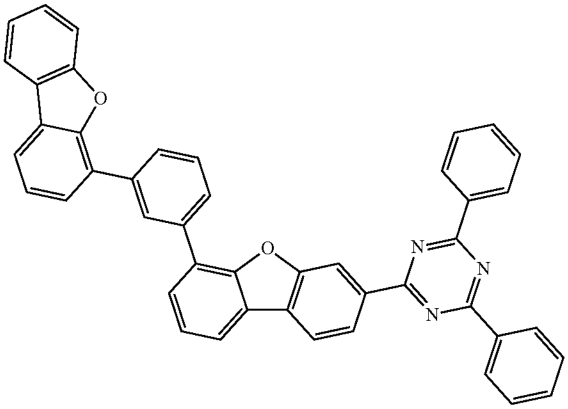

-continued
4-16
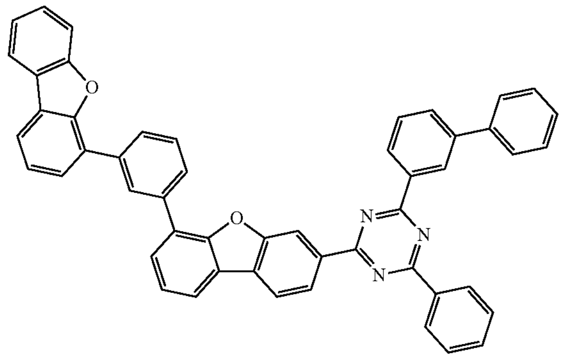
4-17
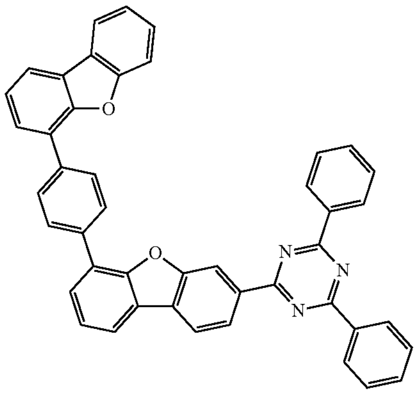
4-18
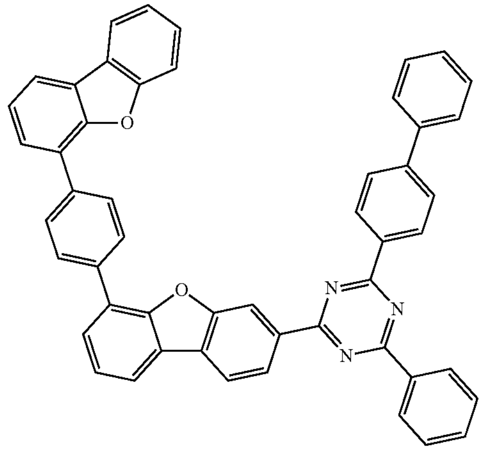
4-19
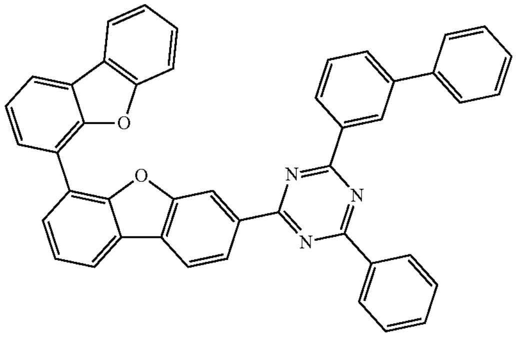
4-20
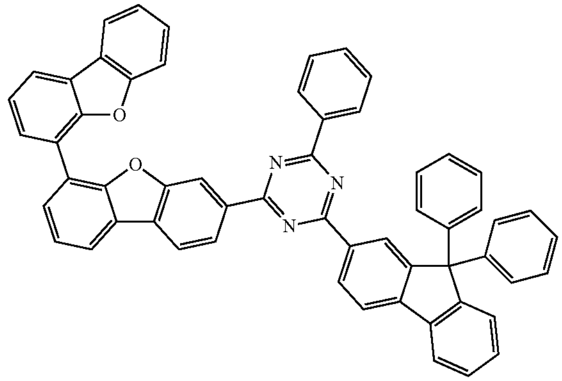
4-21
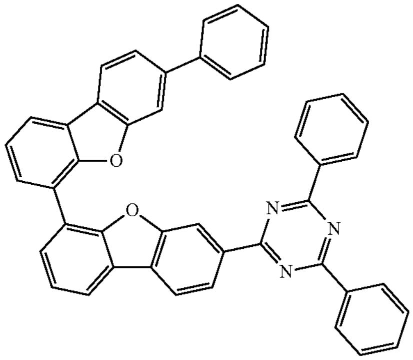
4-22
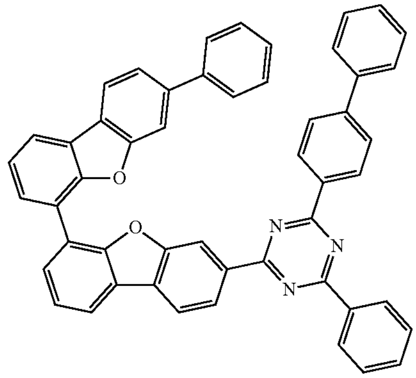
4-23
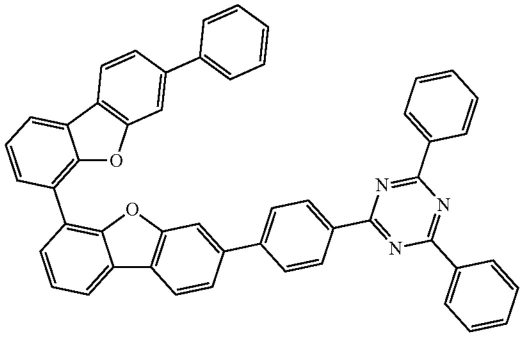

-continued
4-24
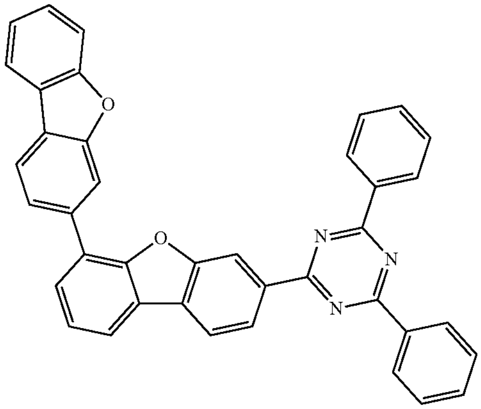
4-25
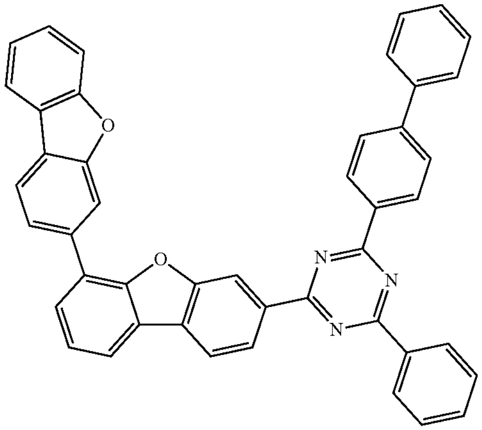
4-26
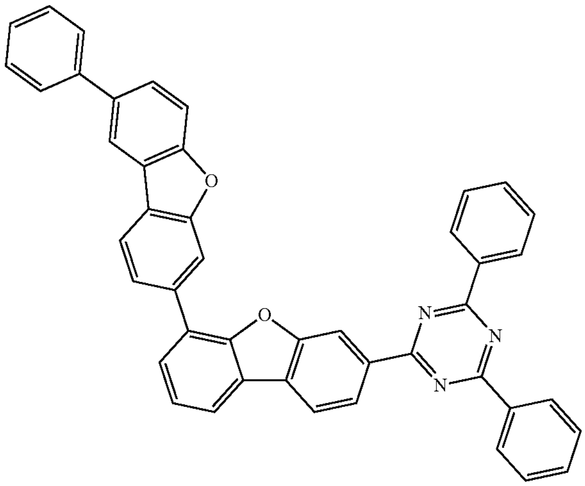
4-27
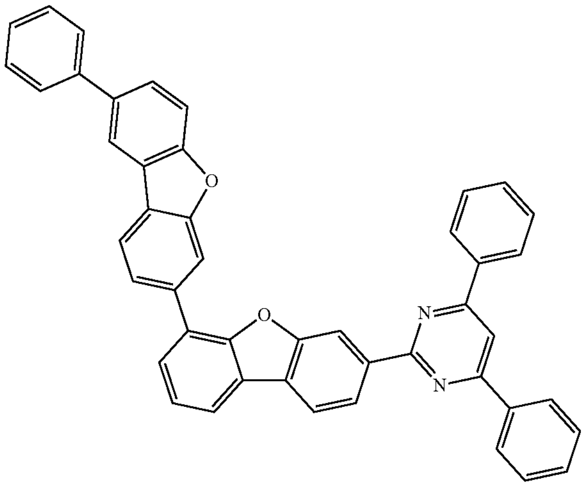
4-28
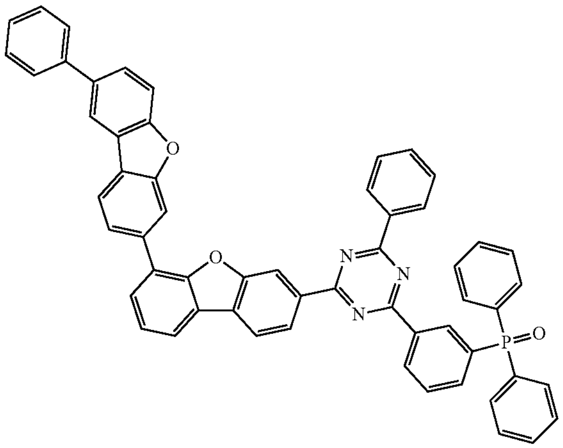
4-29
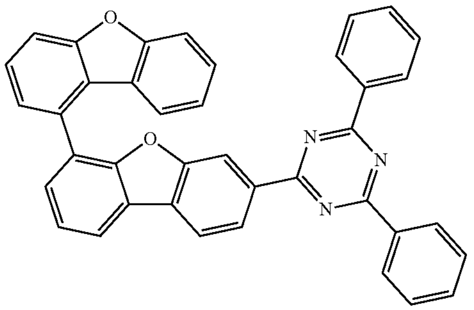

-continued
4-30
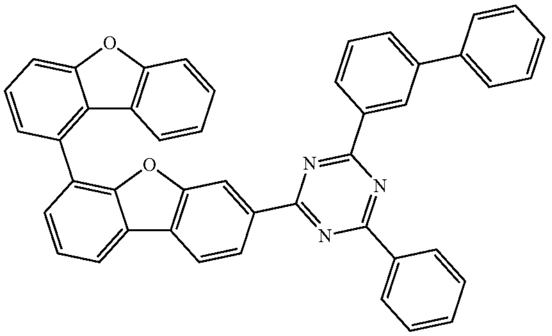
4-31
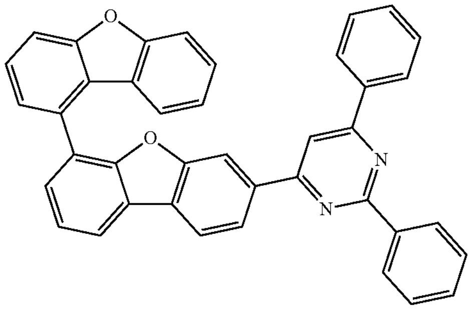
4-32
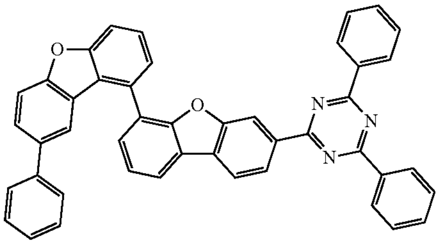
4-33
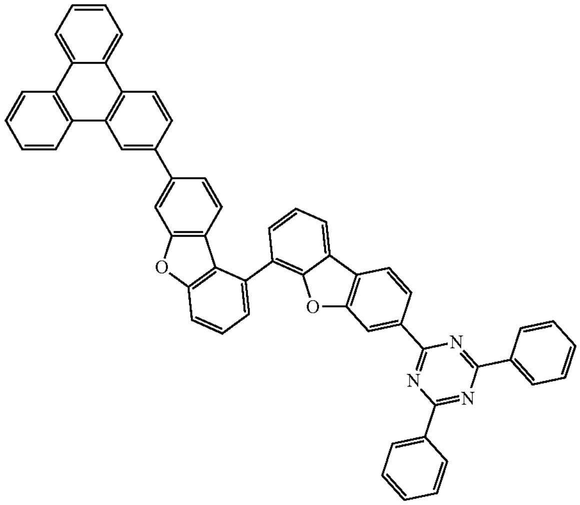
4-34
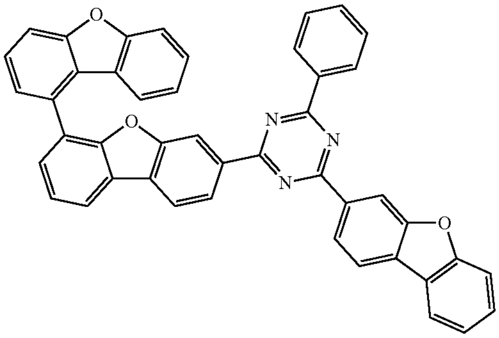
4-35
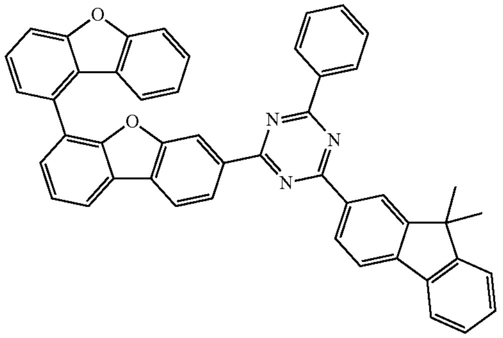
4-36
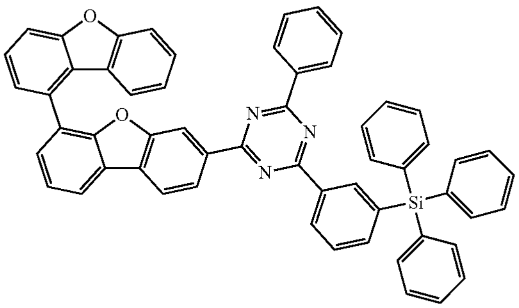
4-37
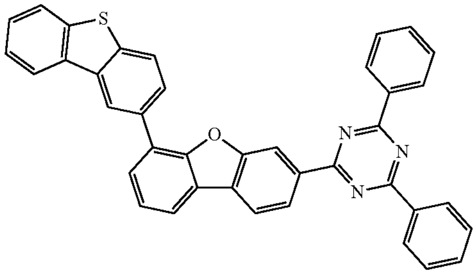

-continued
4-38
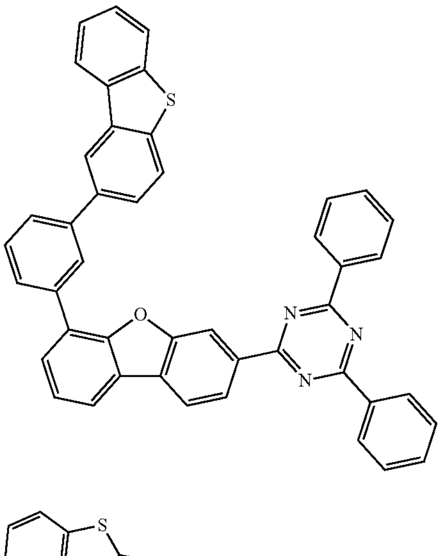
4-39
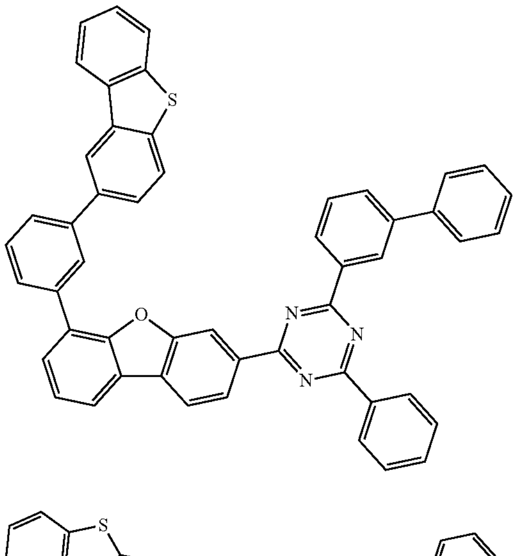
4-40
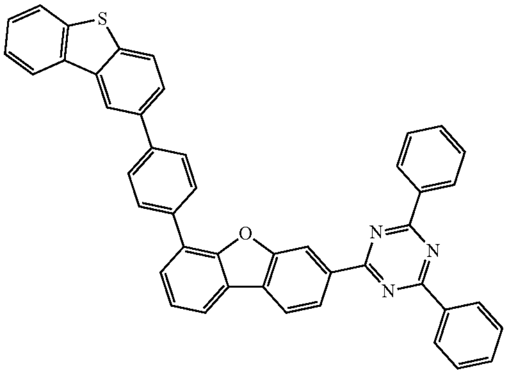
4-41
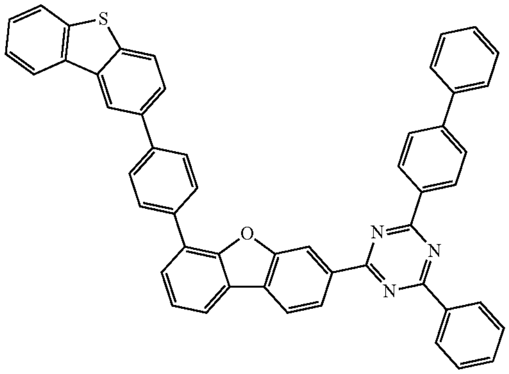
4-42
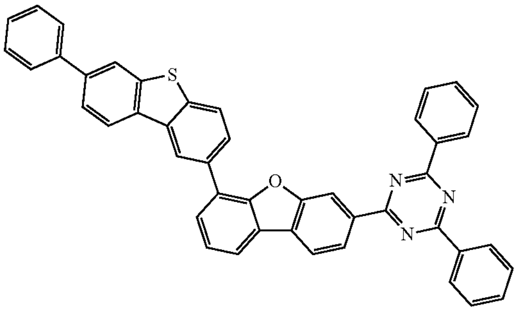
4-43
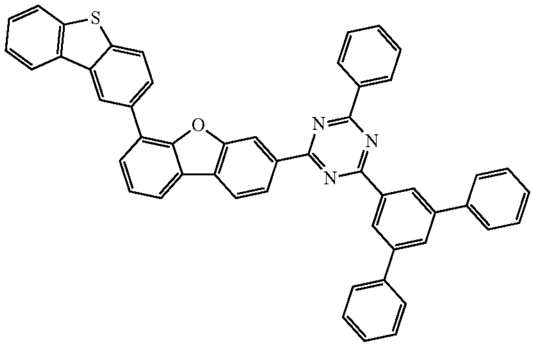
4-44
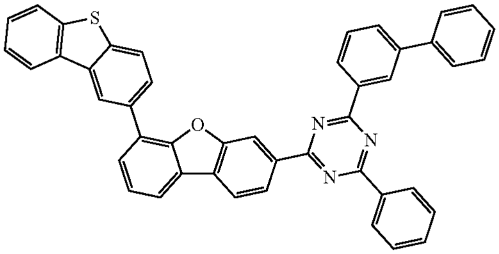
4-45
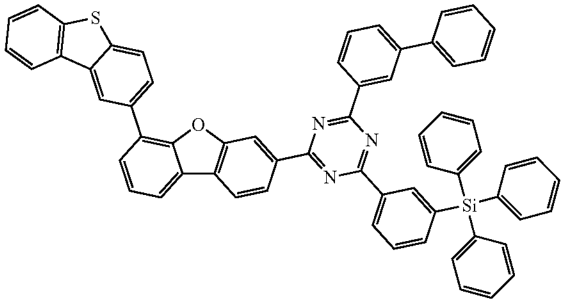

-continued
4-46
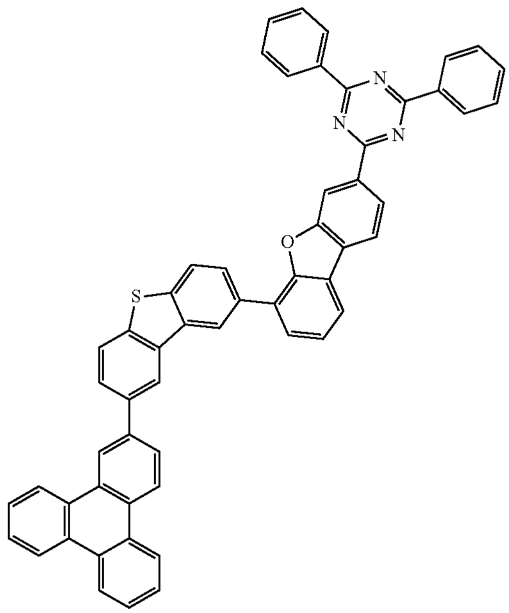
4-47
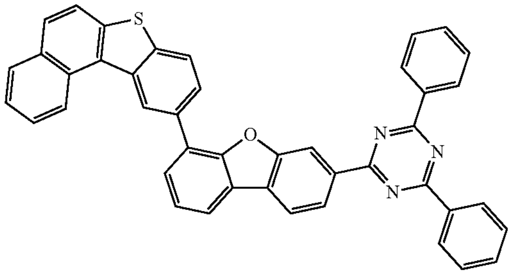
4-48
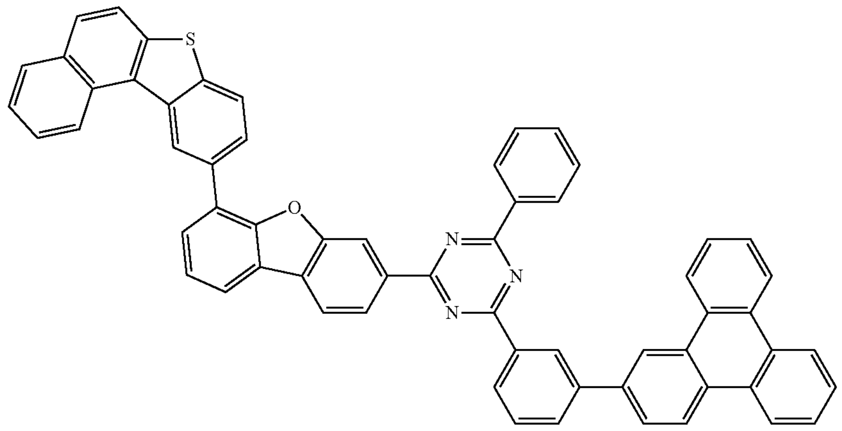
4-49
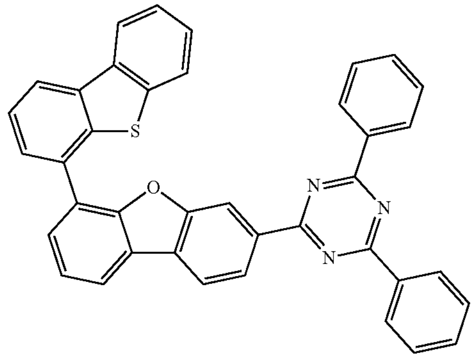
4-50
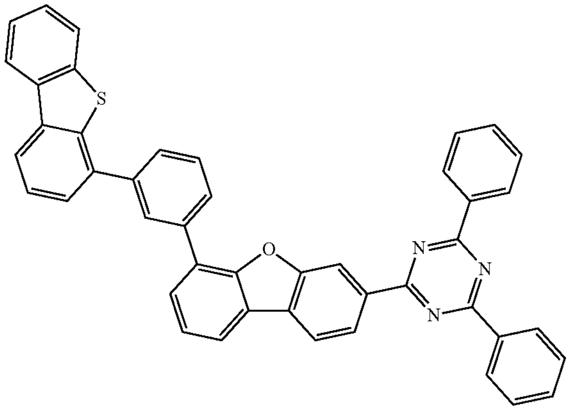

-continued
4-51
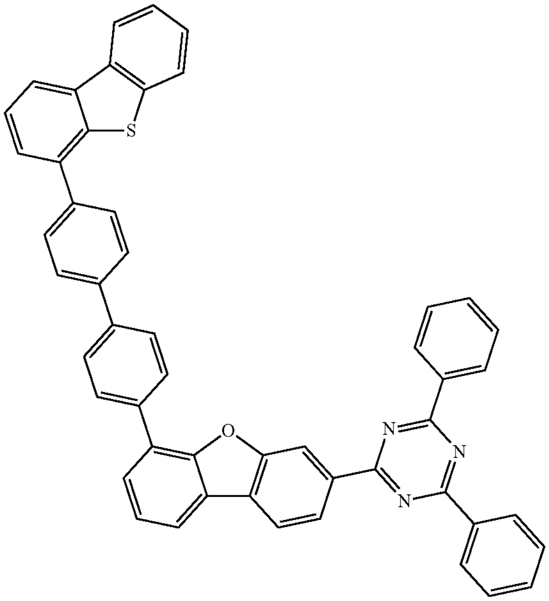
4-52
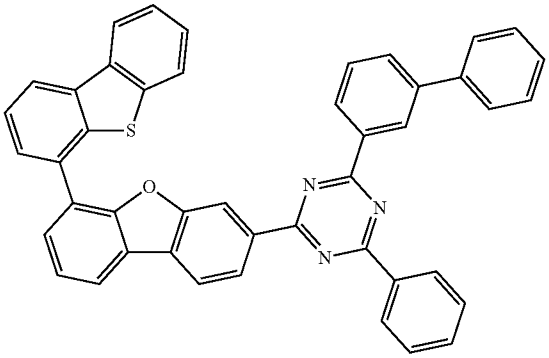
4-53
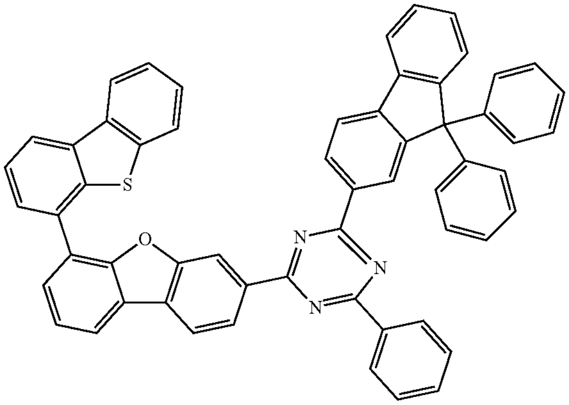
4-54
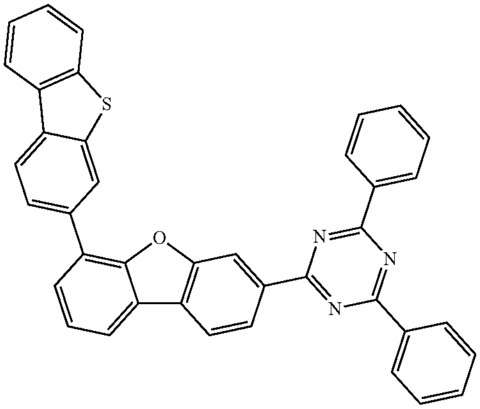
4-55
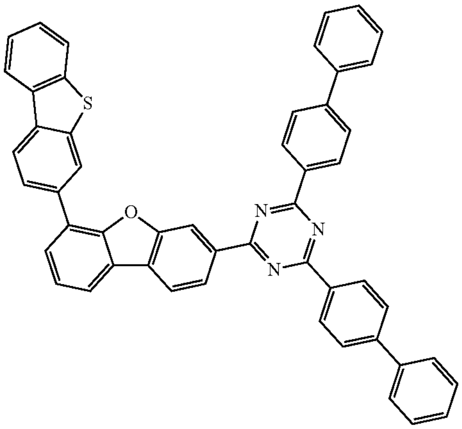
4-56
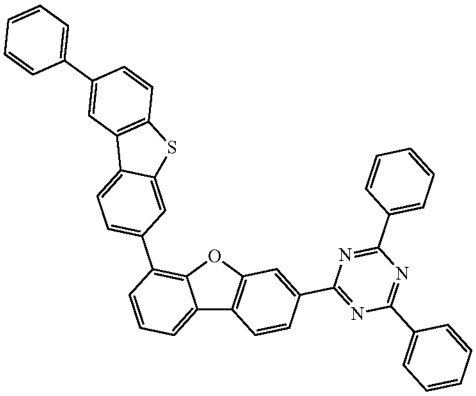

-continued
4-57
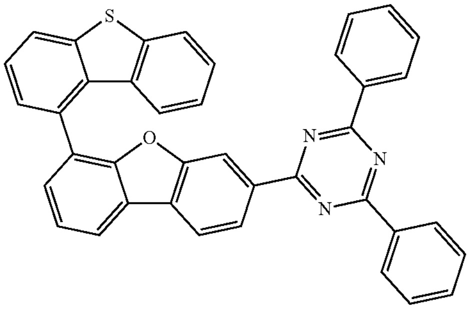
4-58
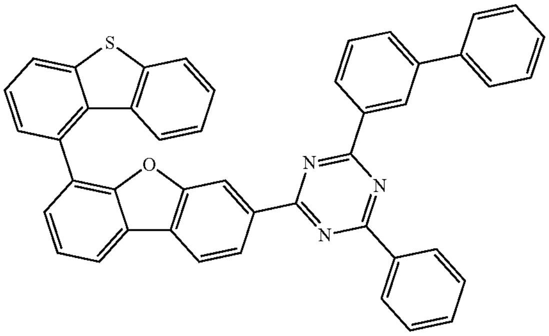
4-59
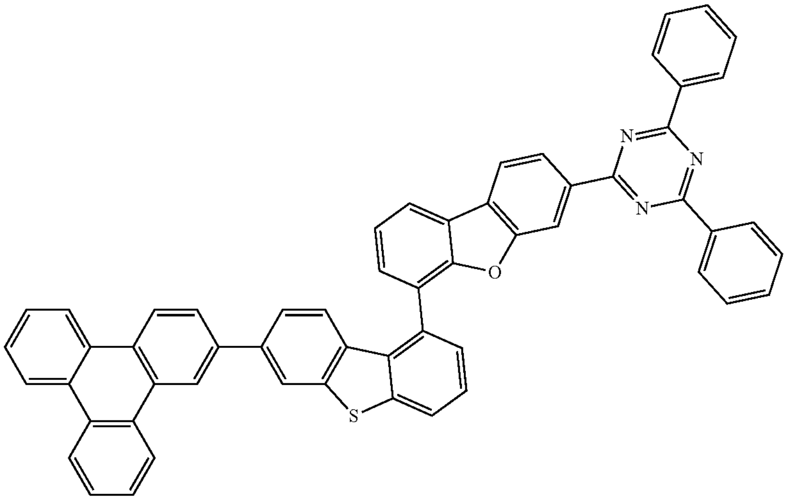
4-60
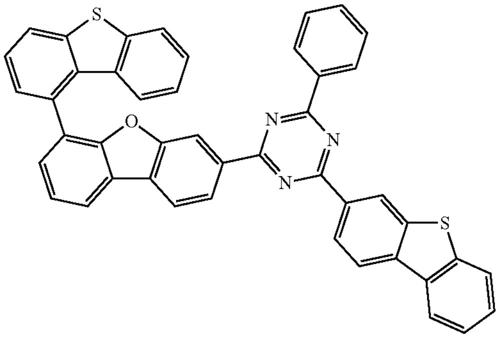
4-61
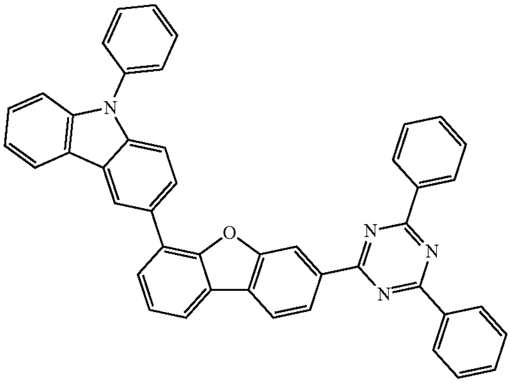

-continued
4-62
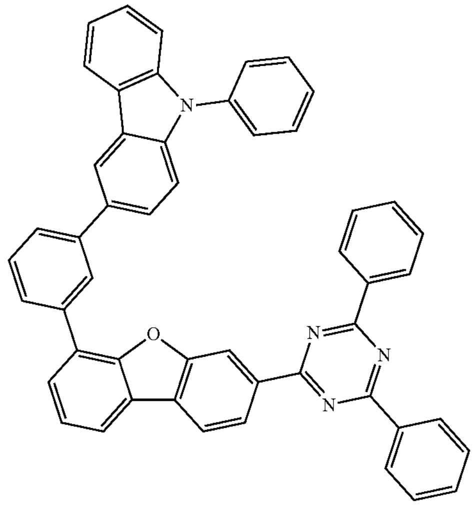
4-63
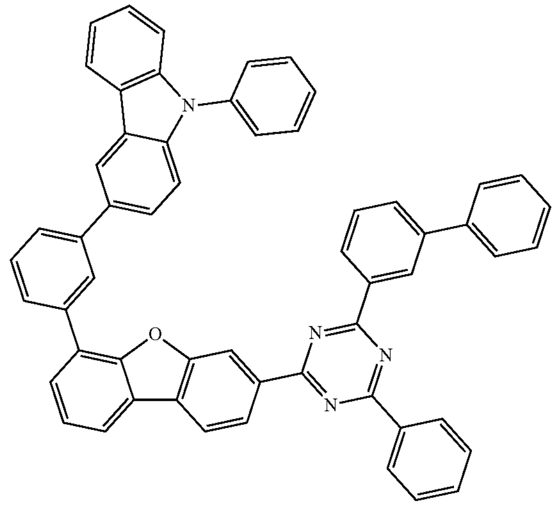
4-64
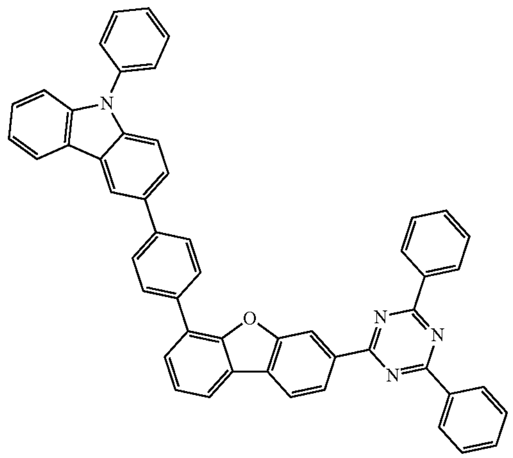
4-65
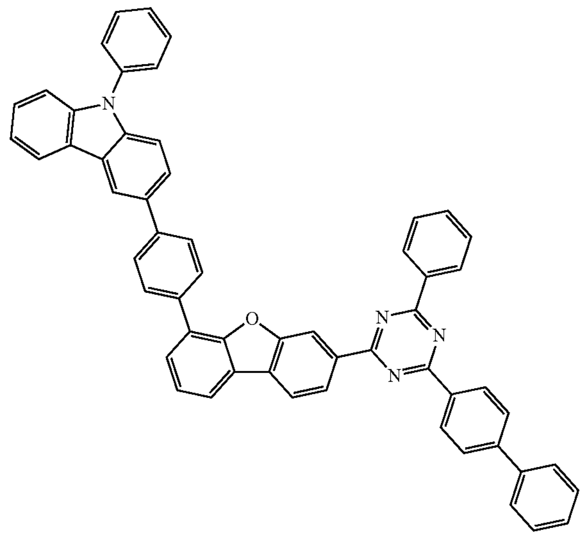
4-66
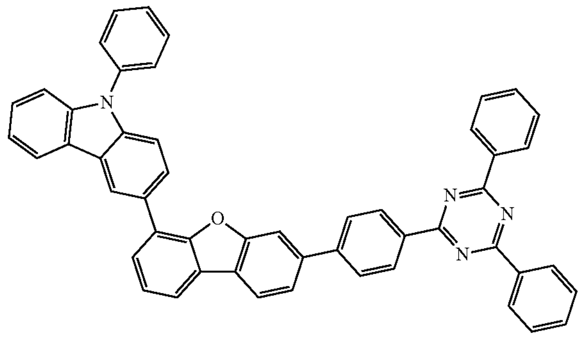
4-67
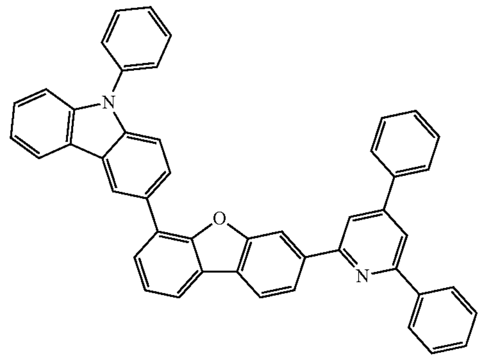

-continued
4-68
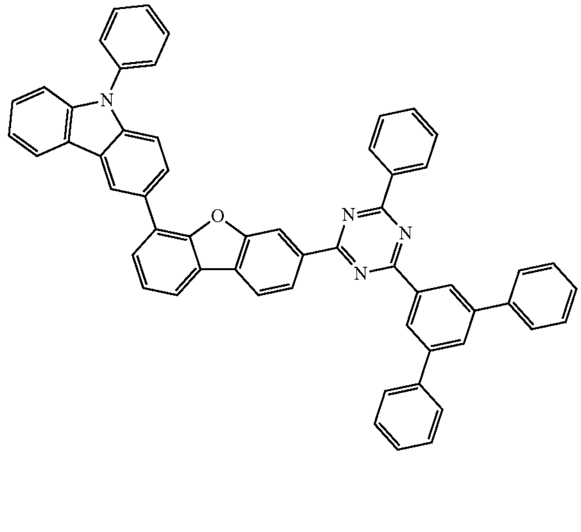
4-69
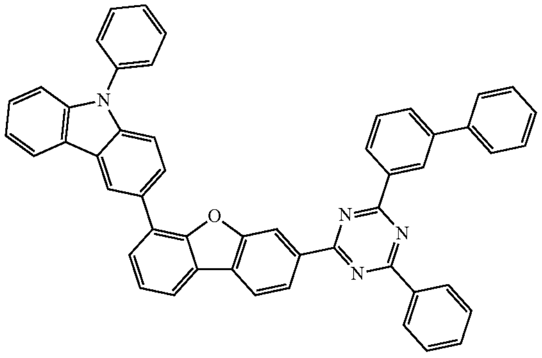
4-70
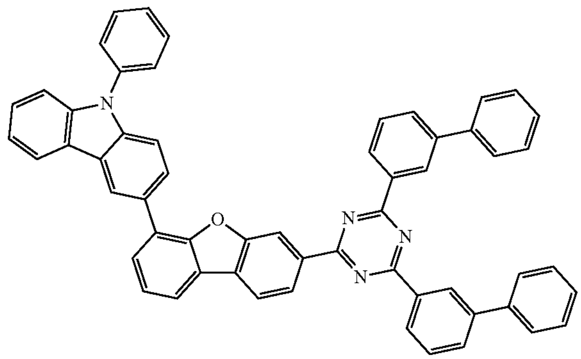
4-71
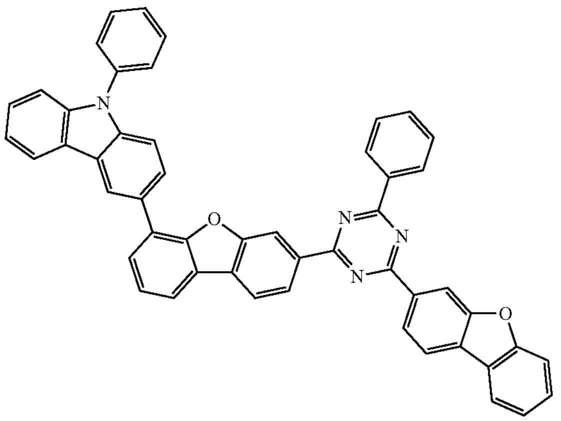
4-72
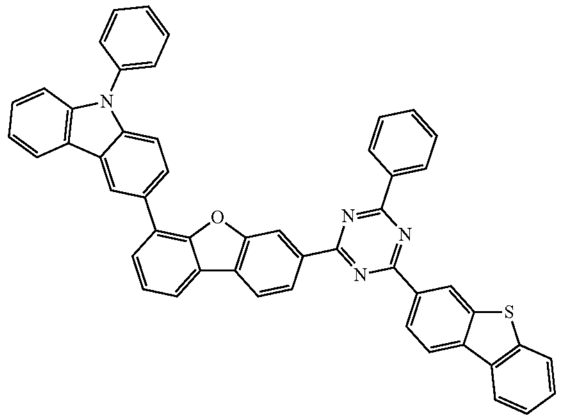
4-73
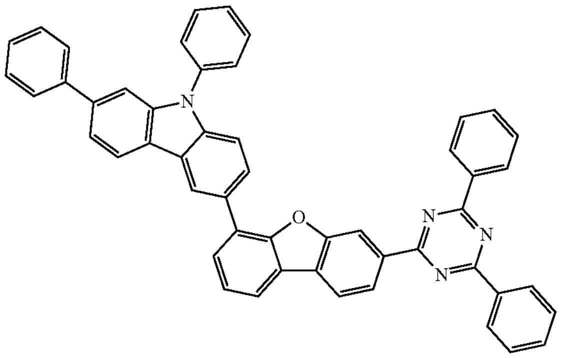

-continued
4-74
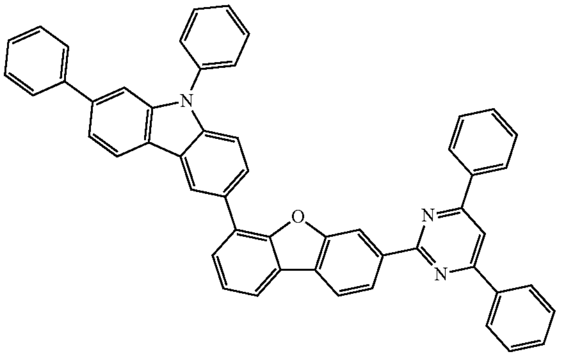
4-75
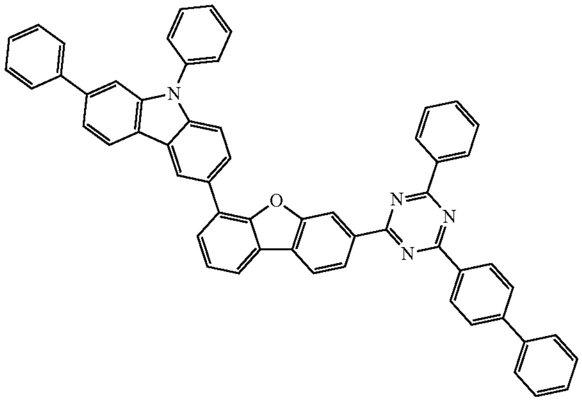
4-76
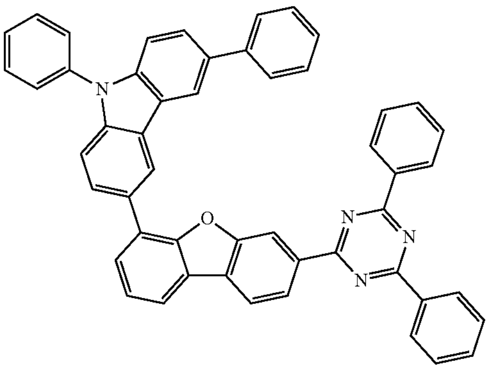
4-77
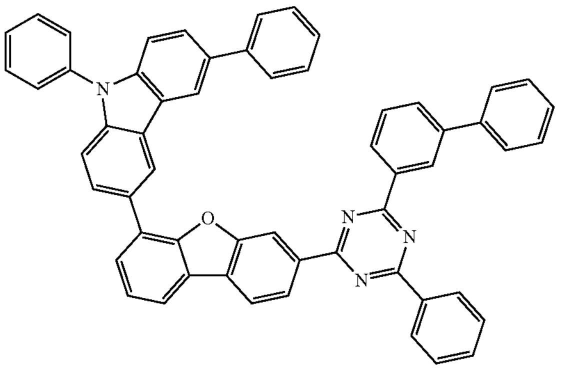
4-78
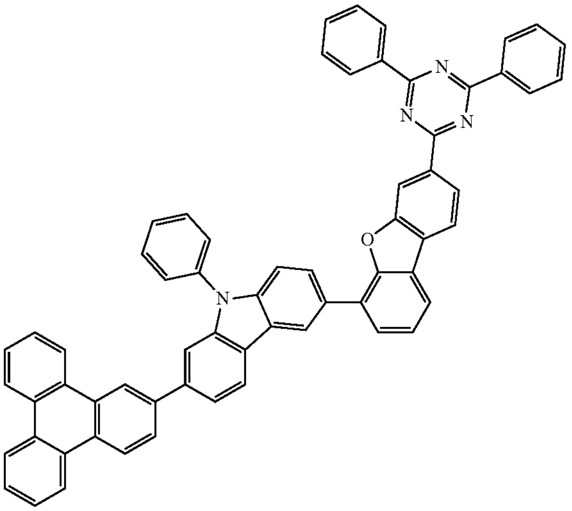
4-79
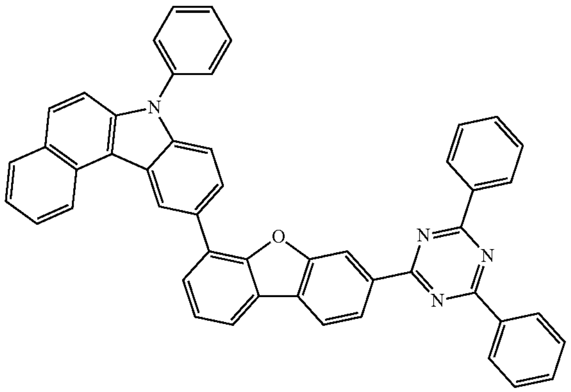

-continued
4-80
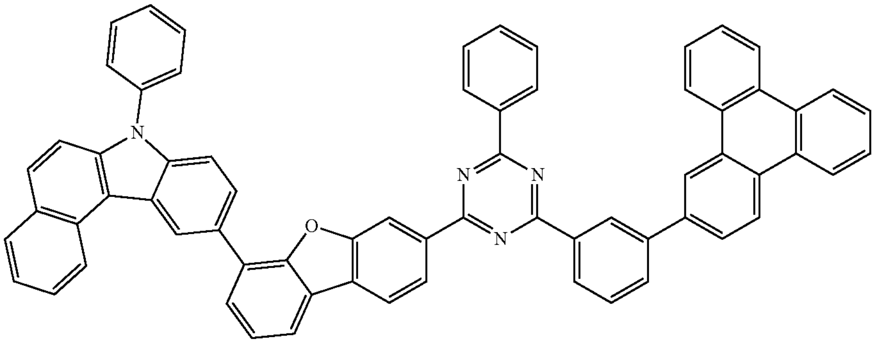
4-81
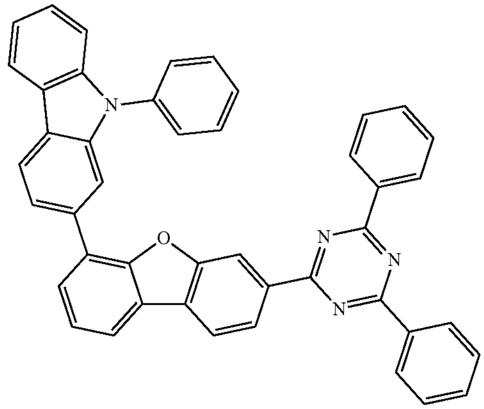
4-82
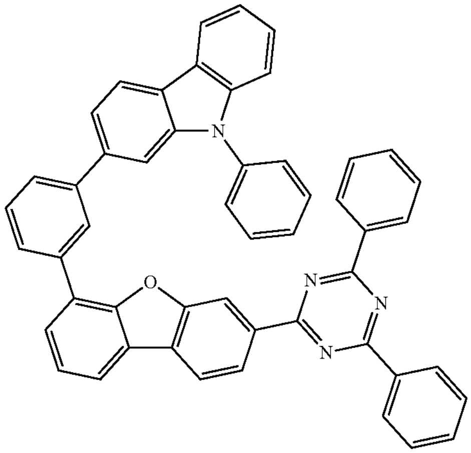
4-83
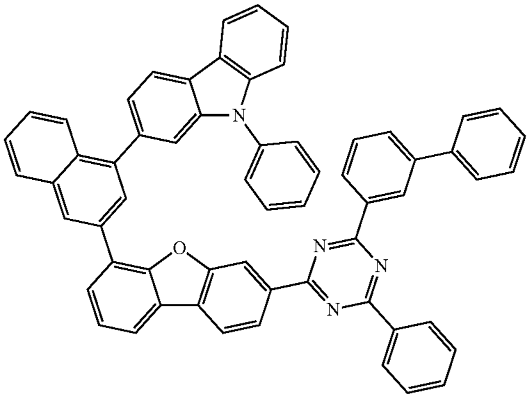
4-84
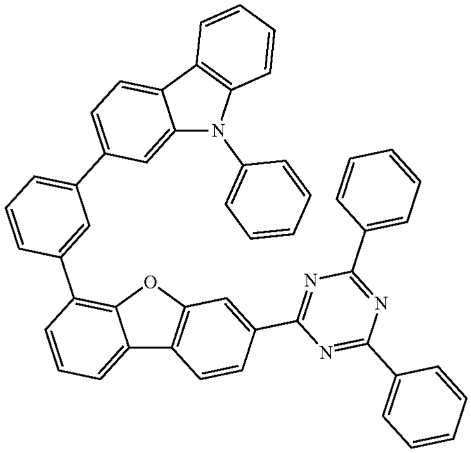
4-85
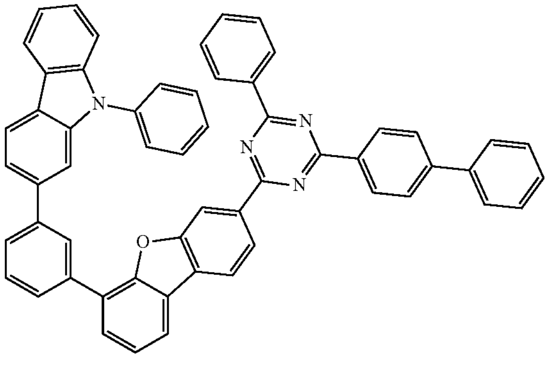
4-86
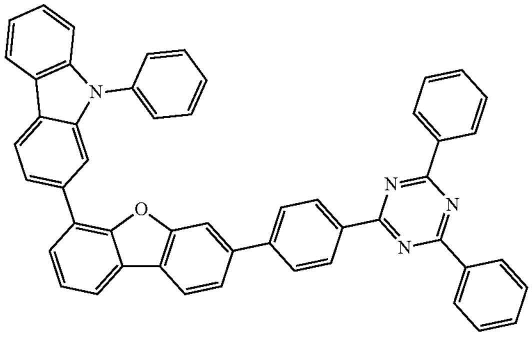

-continued
4-87
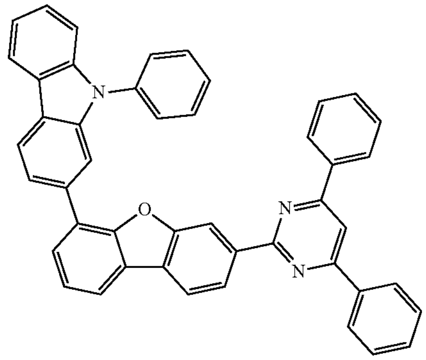
4-88
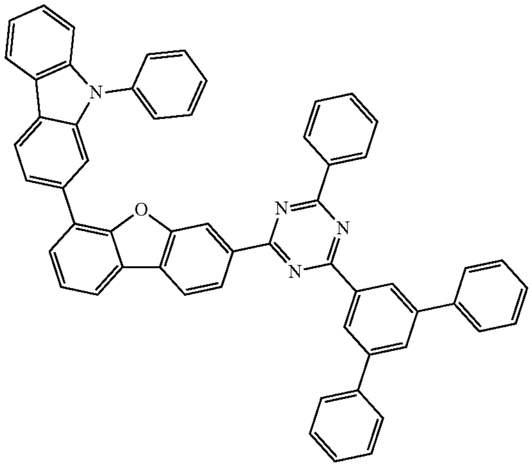
4-89
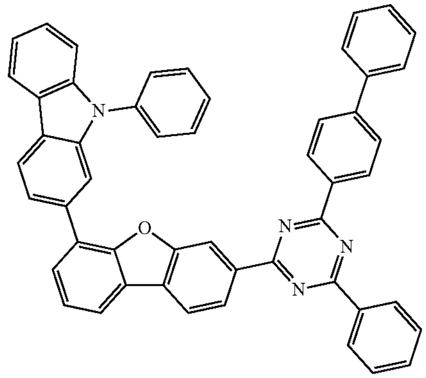
4-90
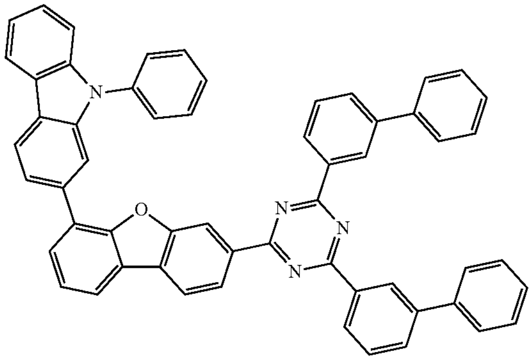
4-91
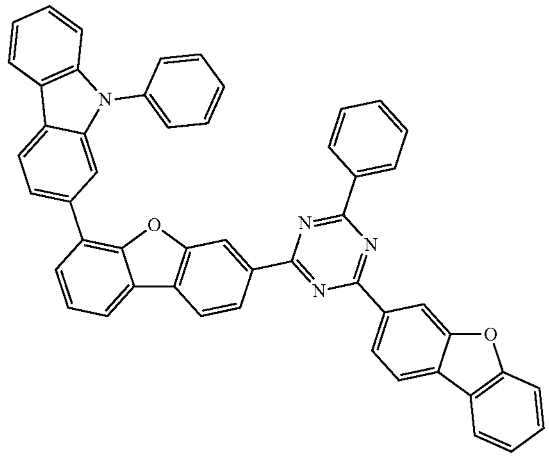
4-92
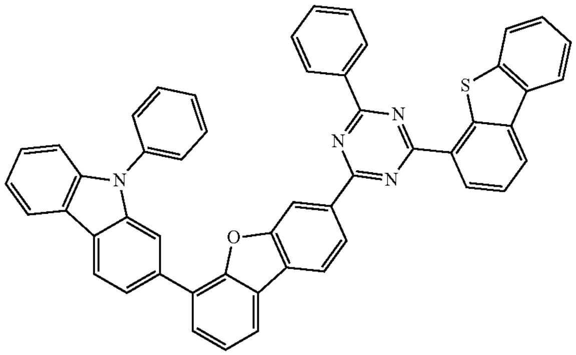

-continued
4-93
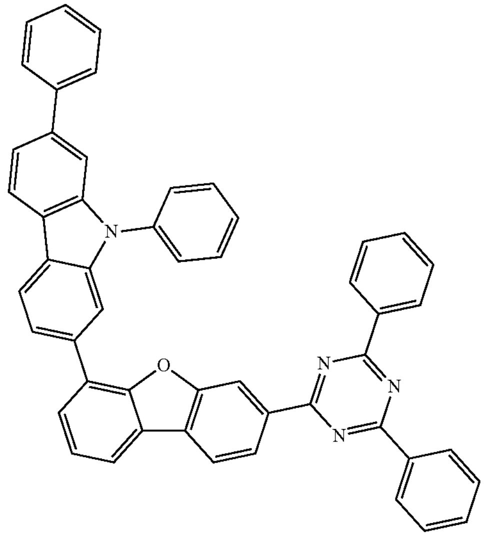
4-94
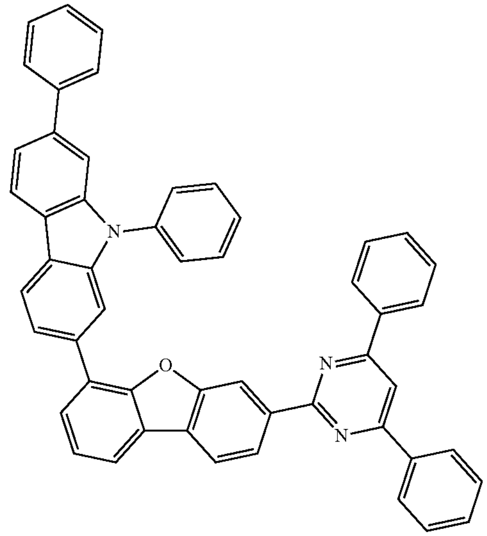
4-95
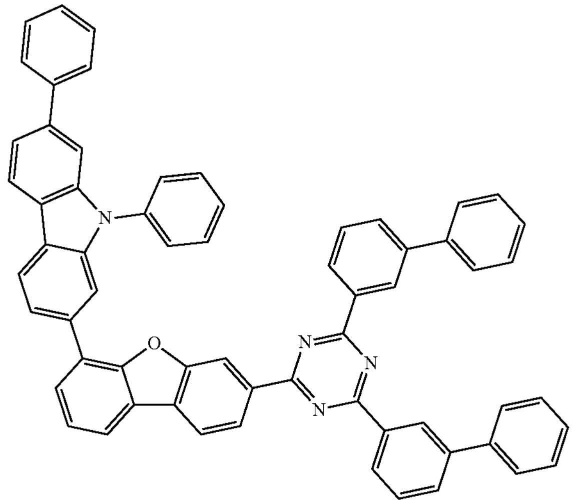
4-96
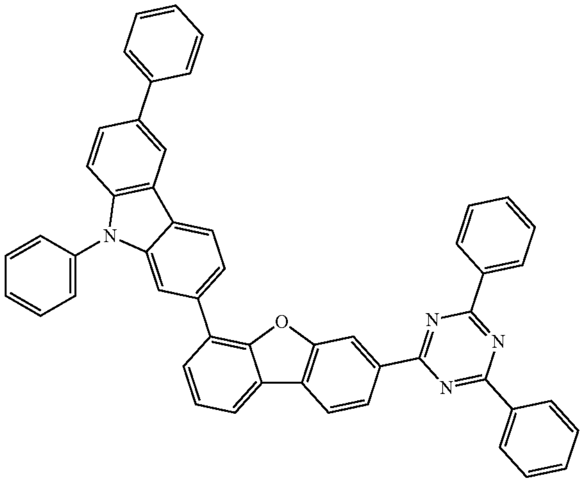
4-97
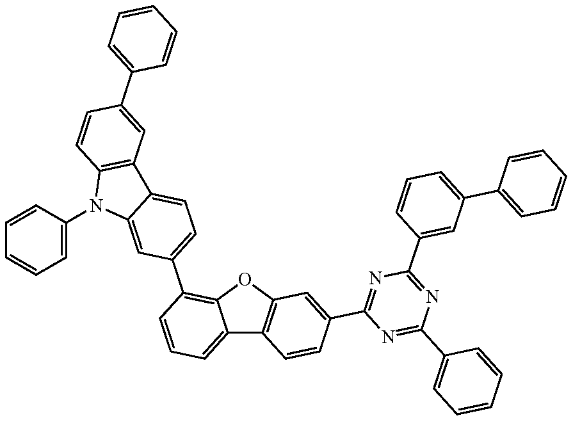
4-98
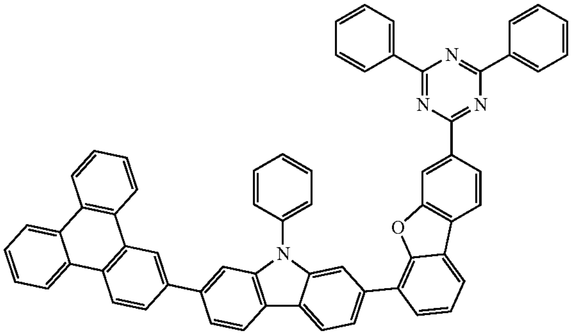

-continued
4-99
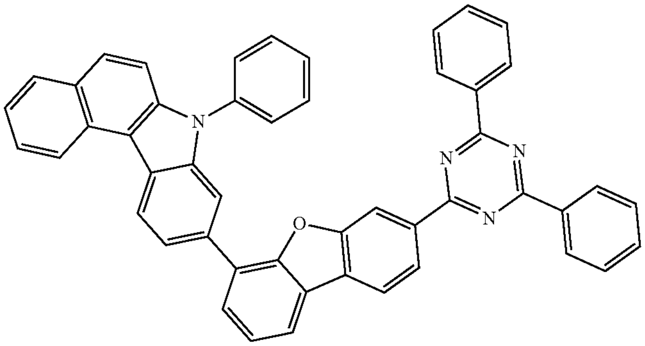
4-100
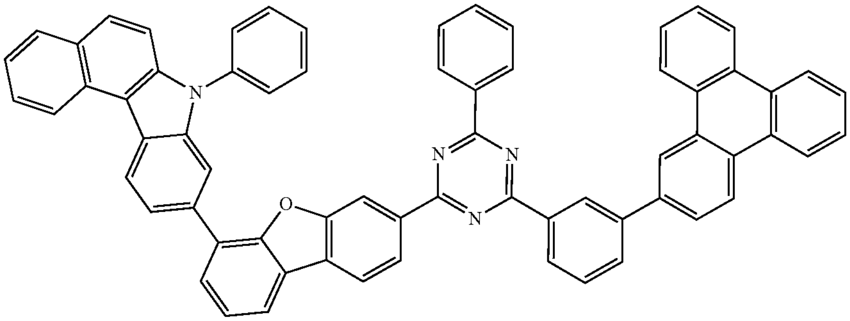
4-101
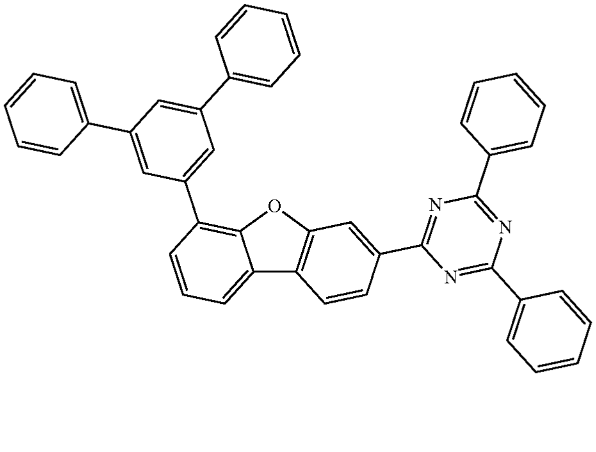
4-102
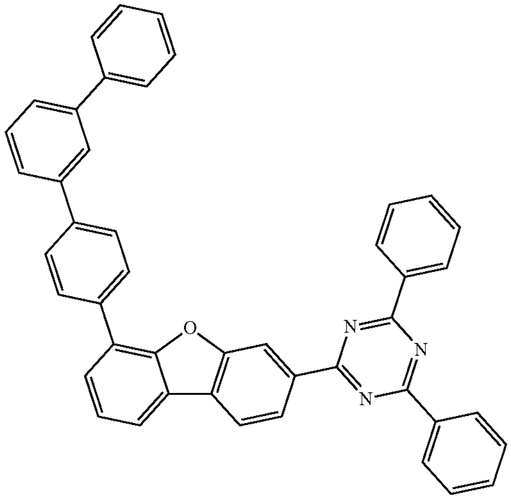

-continued
4-103
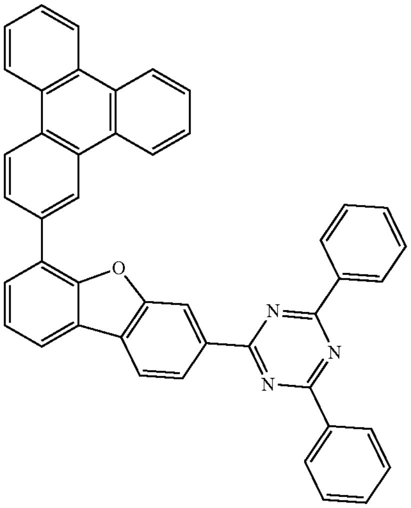
4-104
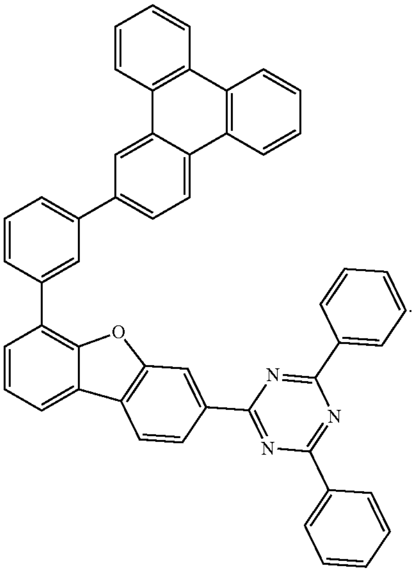
6. The organic light emitting device of claim 1, wherein any one of the Chemical Formulae 2-7 to 2-9 is represented by any one of the following compounds:
5-121
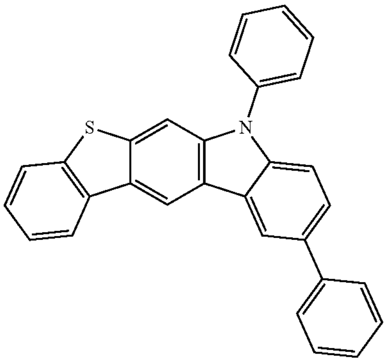
5-122
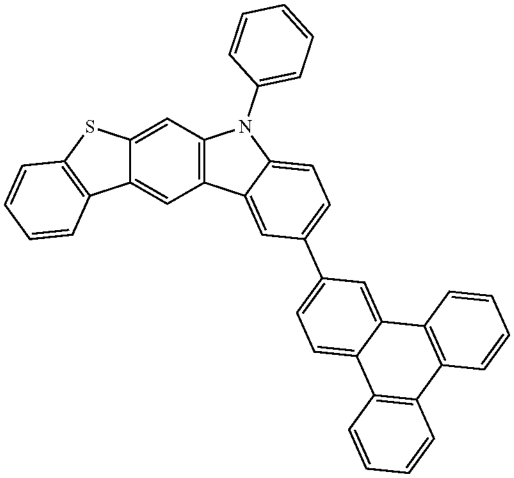
-continued
5-123
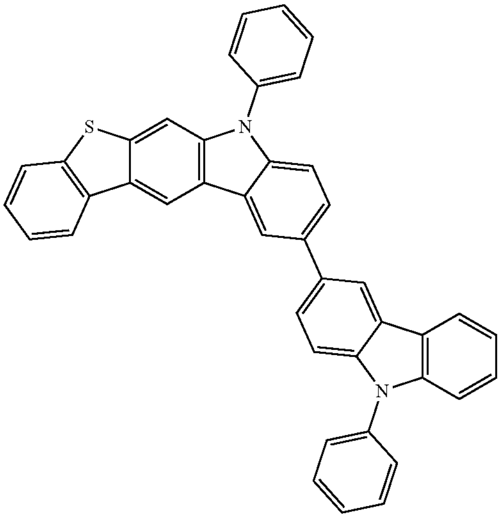
5-124
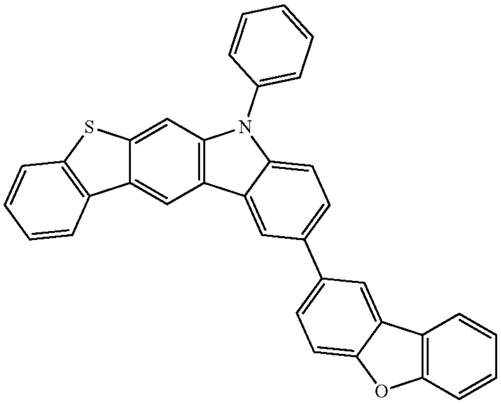

-continued
5-125
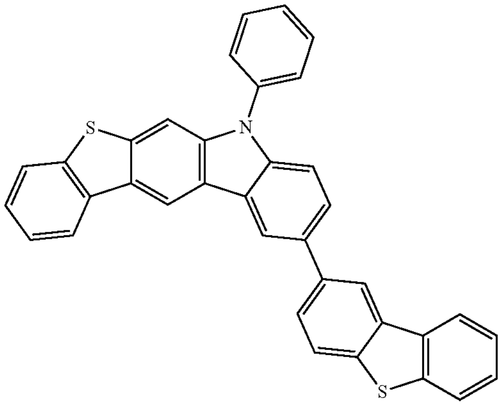
5-126
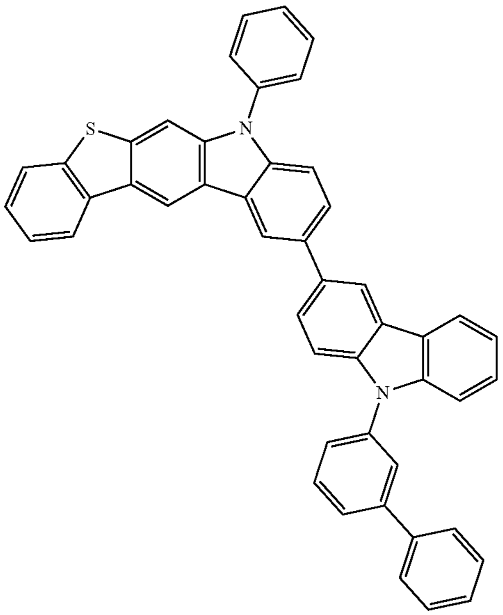
-continued
5-127
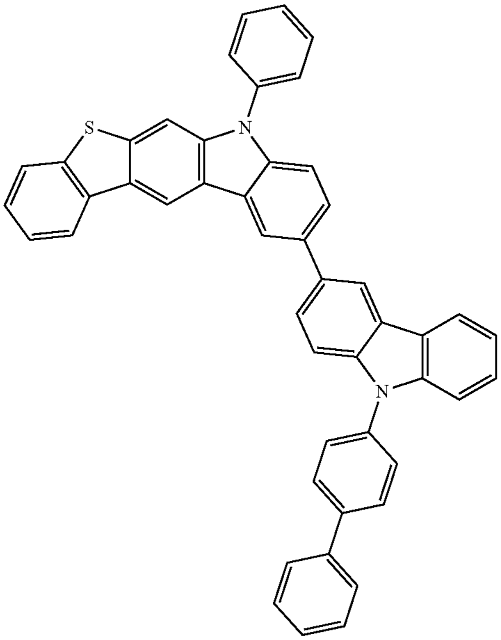
5-128
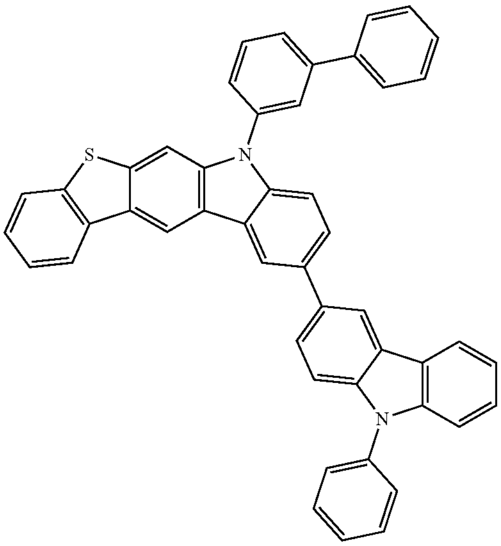

-continued
5-129
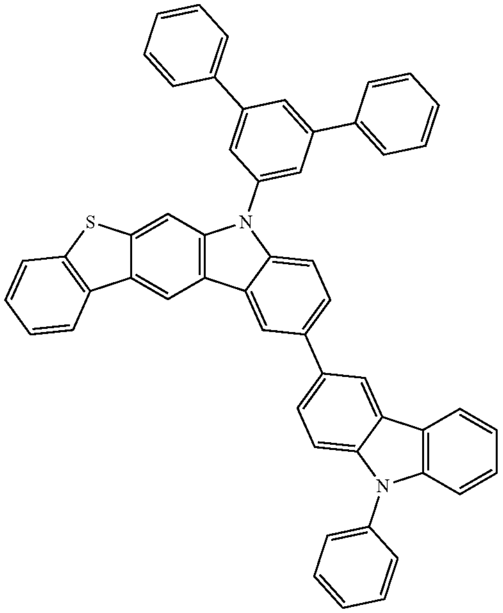
5-130
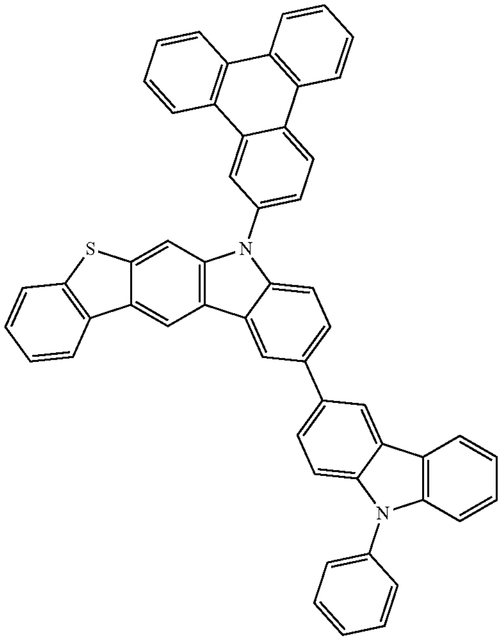
-continued
5-131
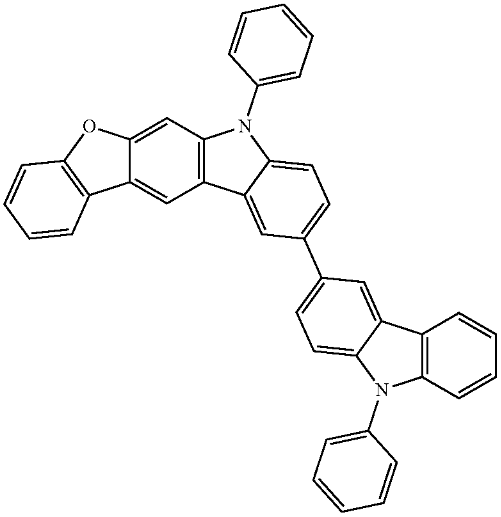
5-132
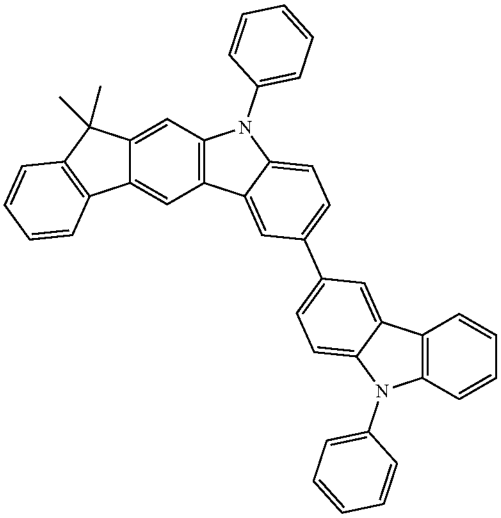
5-133
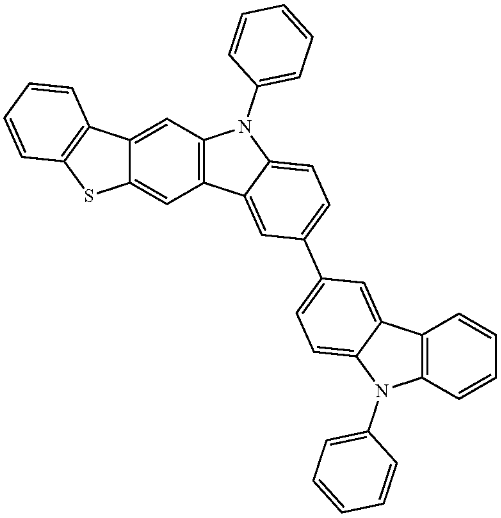

-continued
5-134
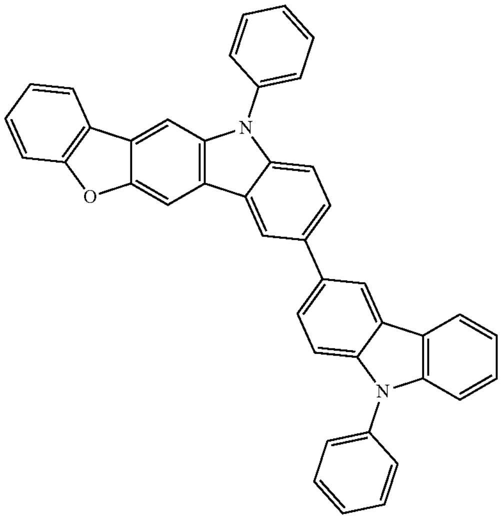
5-135
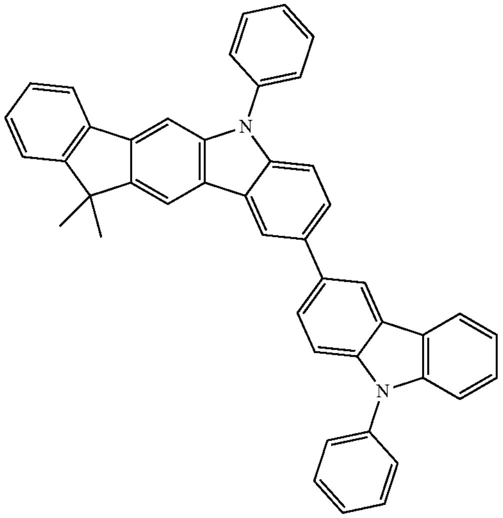
5-136
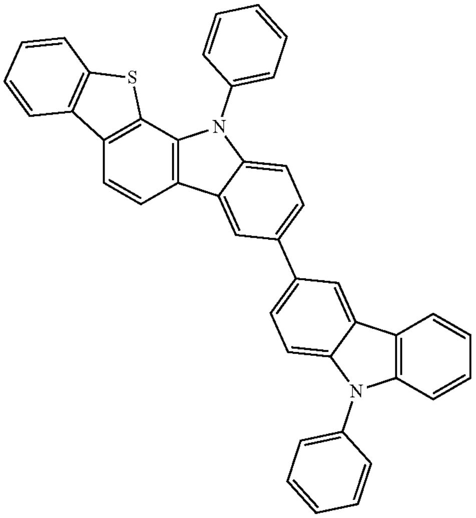
-continued
5-137
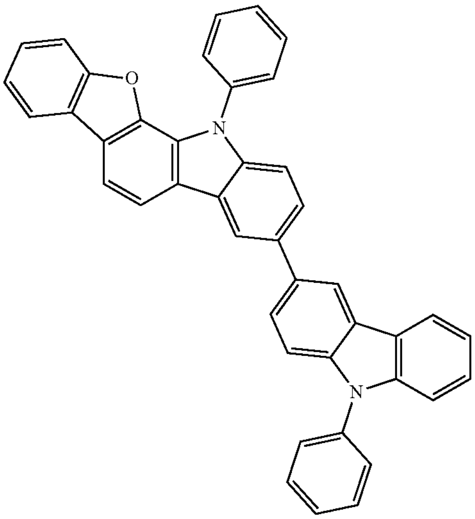
5-138
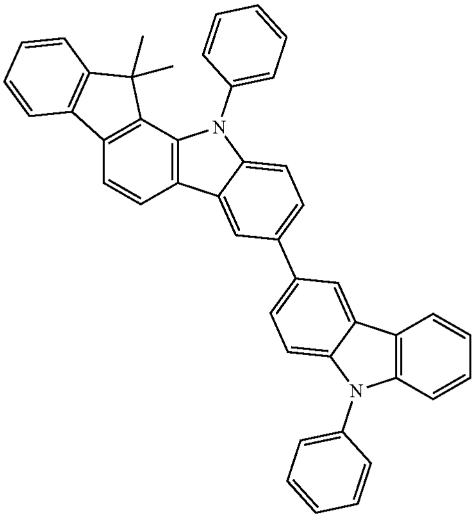
5-139
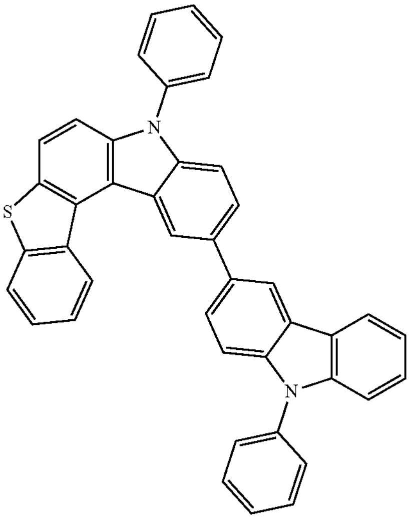

-continued
5-140
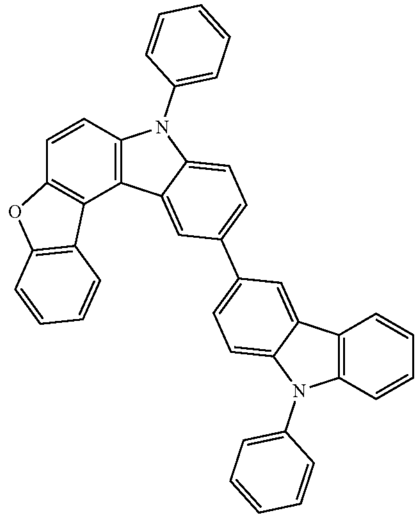
5-141
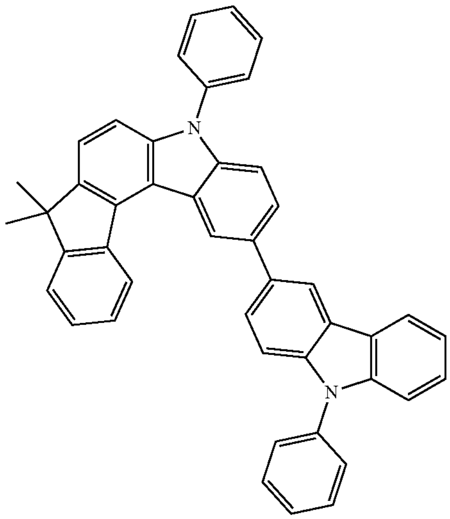
5-142
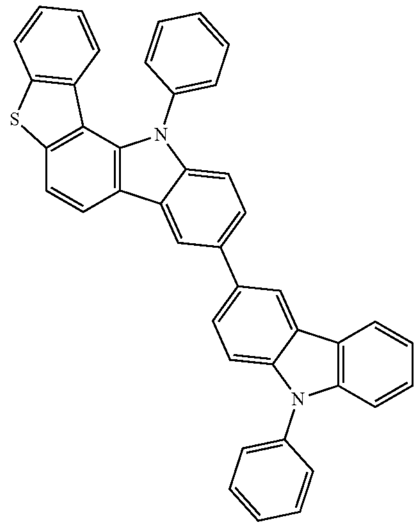
-continued
5-143
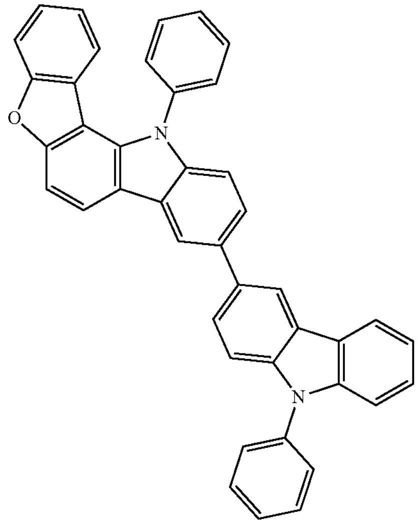
5-144
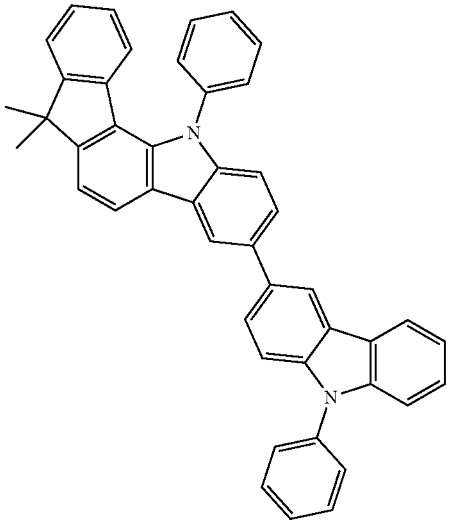
5-145
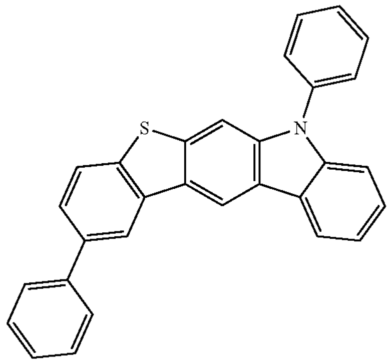

-continued
5-146
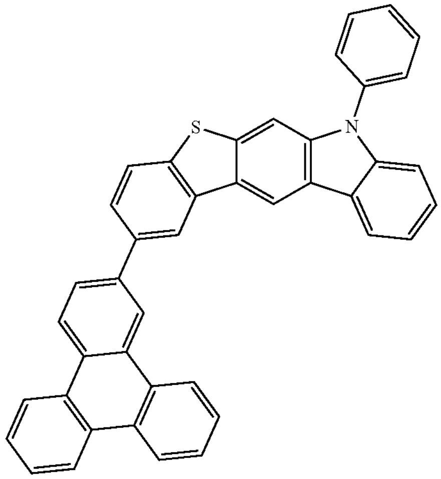
5-147
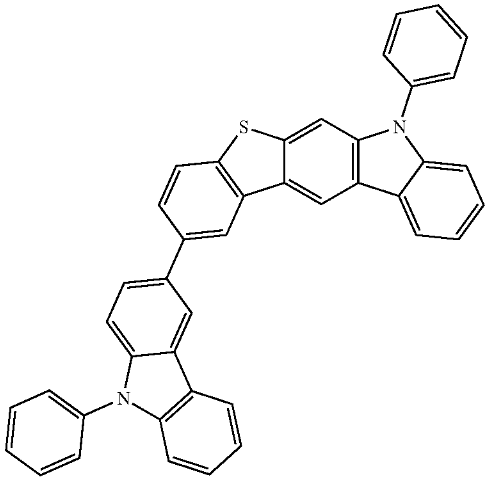
5-148
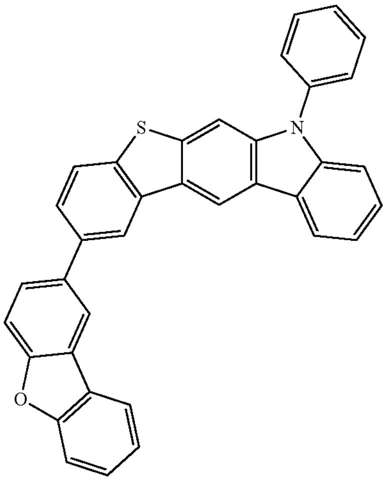
-continued
5-149
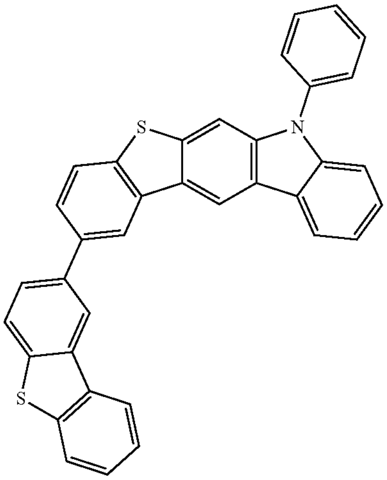
5-150
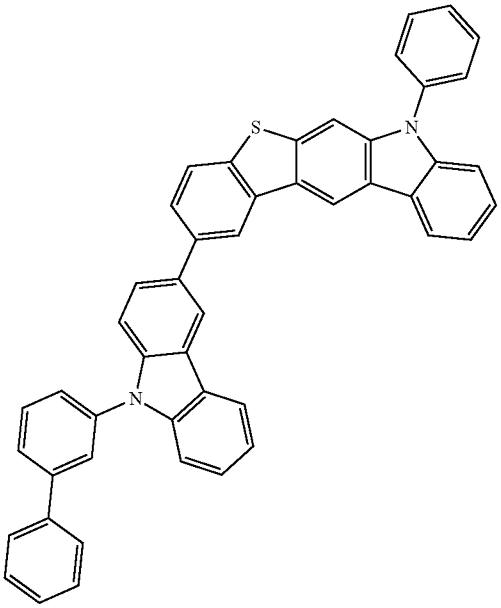
5-151
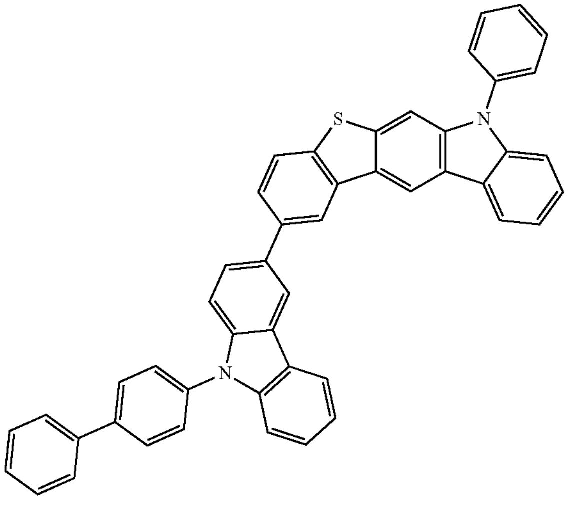

5-152
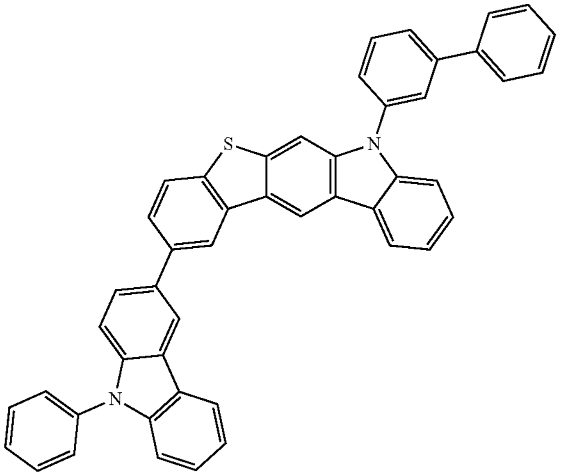
5-153
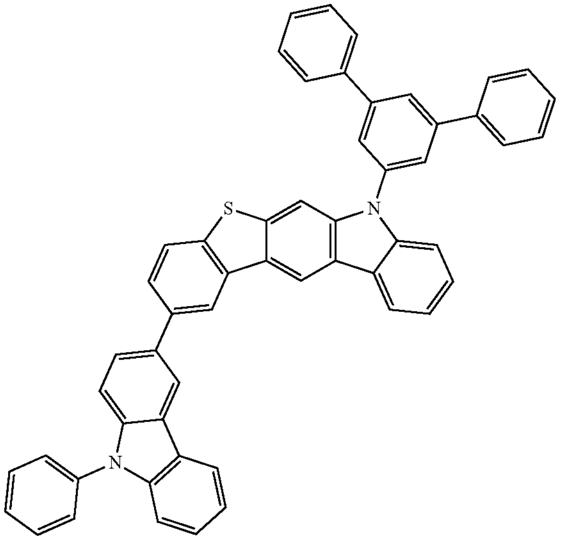
5-154
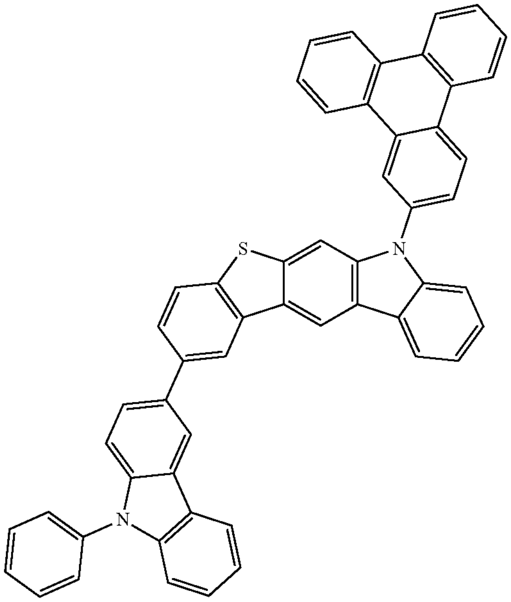
5-155
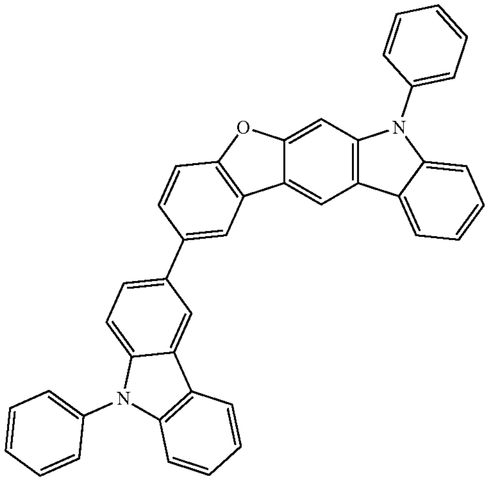
5-156
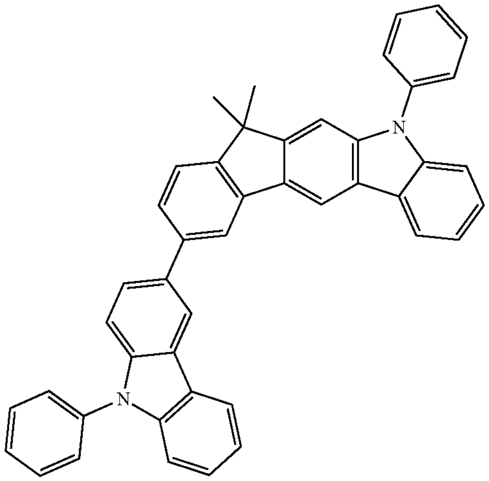

-continued
5-157
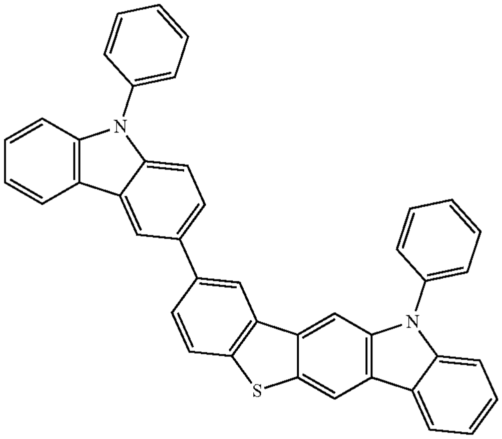
5-158
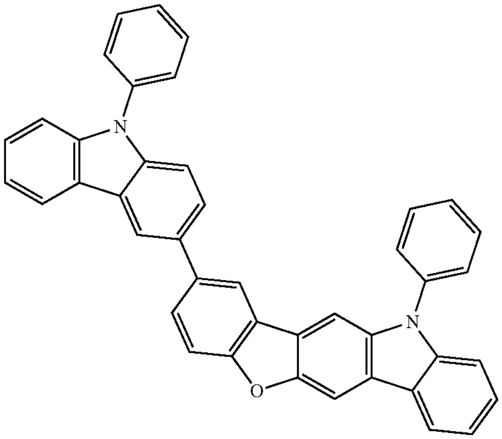
5-159
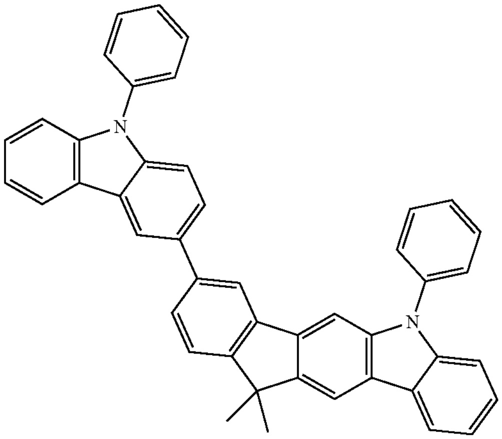
-continued
5-160
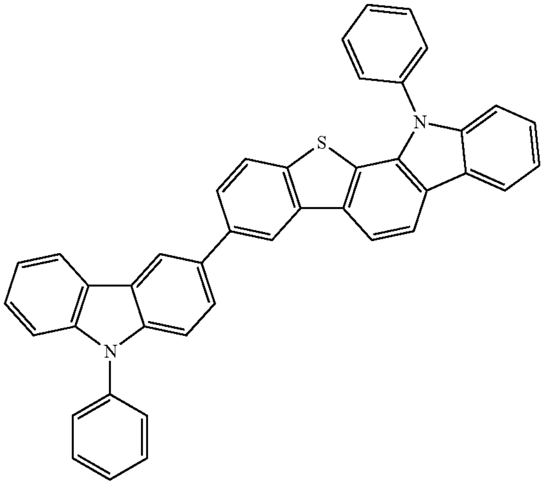
5-161
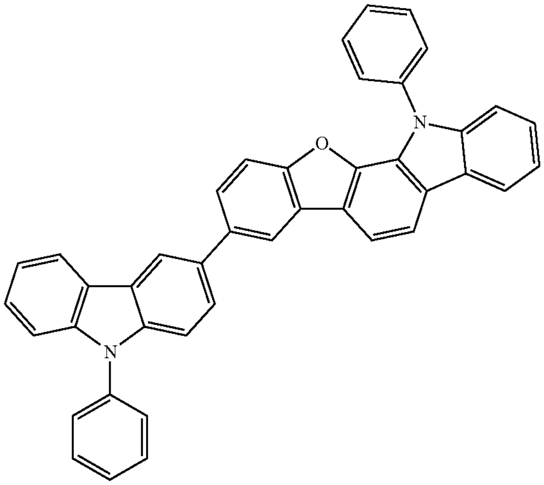
5-162
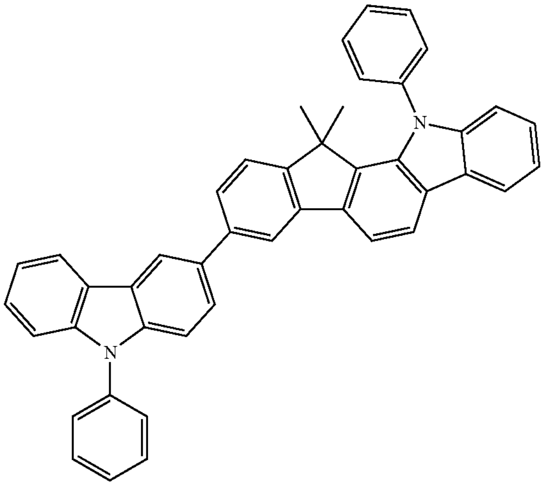

-continued 5-163

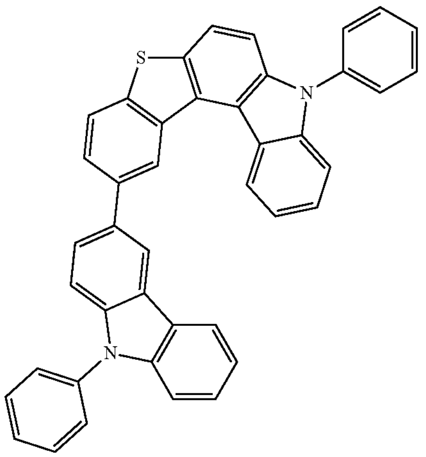

5-164

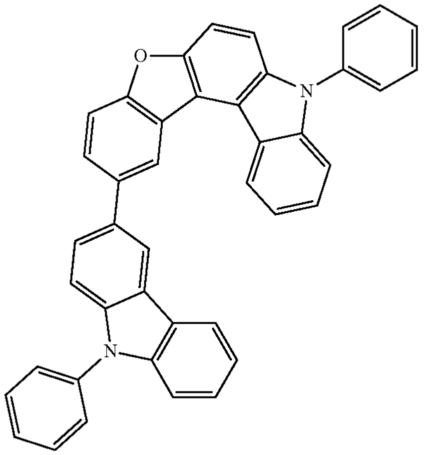

5-165

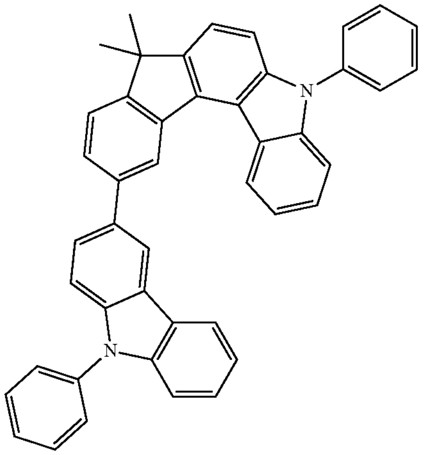

-continued 5-166

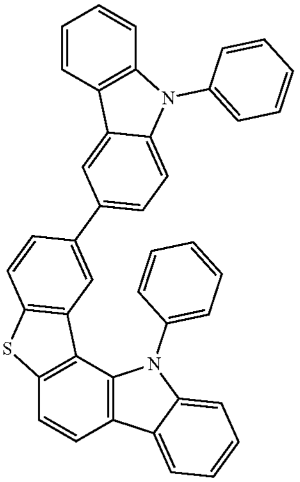

5-167

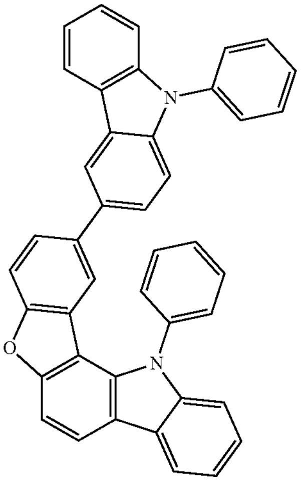

5-168

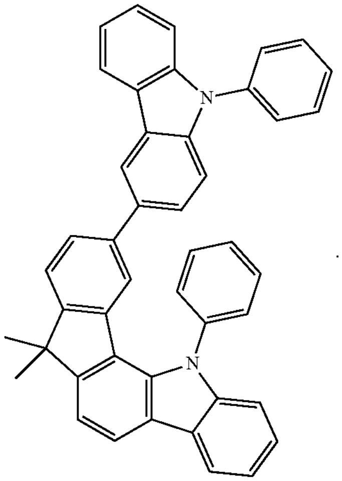

7. The organic light emitting device of claim 1, wherein the organic material layer comprises at least one of a hole blocking layer, an electron injection layer and an electron transfer layer, and the at least one of a hole blocking layer, an electron injection layer and an electron transfer layer comprises the heterocyclic compound represented by Chemical Formula 1 and the heterocyclic compound represented by any one of the Chemical Formulae 2-7 to 2-9.

8. The organic light emitting device of claim 1, wherein the organic material layer comprises a light emitting layer, and the light emitting layer comprises the heterocyclic compound represented by Chemical Formula 1 and the heterocyclic compound represented by any one of the Chemical Formulae 2-7 to 2-9.

9. The organic light emitting device of claim 1, wherein the organic material layer comprises a light emitting layer, the light emitting layer comprises a host material, and the host material comprises the heterocyclic compound represented by Chemical Formula 1 and the heterocyclic compound represented by any one of the Chemical Formulae 2-7 to 2-9.

10. The organic light emitting device of claim 1, further comprising one, two or more layers selected from the group consisting of a light emitting layer, a hole injection layer, a hole transfer layer, an electron injection layer, an electron transfer layer, an electron blocking layer and a hole blocking layer.

11. A composition for an organic material layer of an organic light emitting device, the composition comprising:

a heterocyclic compound represented by the following Chemical Formula 1; and a compound represented by the following any one of the Chemical Formulae 2-7 to 2-9:

[Chemical Formula 1]

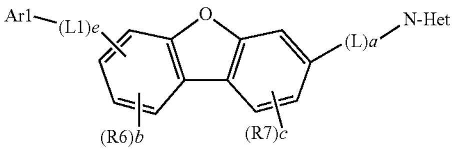

[Chemical Formula 2-7]

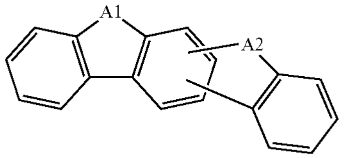

[Chemical Formula 2-8]

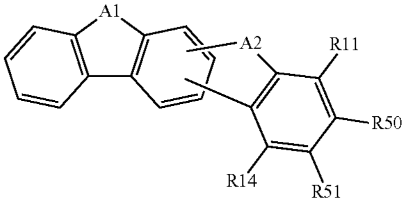

[Chemical Formula 2-9]

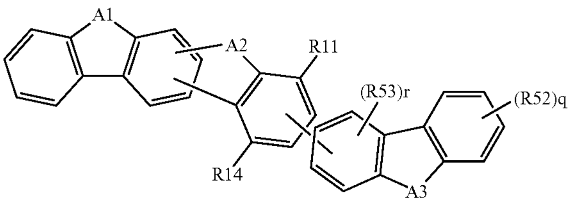

wherein, in Chemical Formulae 1 and 2-7 to 2-9,

N-Het is a pyridine group unsubstituted or substituted with one or more substituents selected from the group consisting of a C1 to C20 alkyl group, a C6 to C40 aryl group, a C2 to C40 heteroaryl group comprising S or O as a heteroatom, —P(═)ORR' and —SiRR'R" or a substituent linking two or more of the substituents; a pyrimidine group unsubstituted or substituted with one or more substituents selected from the group consisting of a C1 to C20 alkyl group, a C6 to C40 aryl group, a C2 to C40 heteroaryl group comprising S or O as a heteroatom, —P(═)ORR' and —SiRR'R" or a substituent linking two or more of the substituents; or a triazine group unsubstituted or substituted with one or more substituents selected from the group consisting of a C1 to C20 alkyl group, a C6 to C40 aryl group, a C2 to C40 heteroaryl group comprising S or O as a heteroatom, —P(═)ORR' and —SiRR'R" or a substituent linking two or more of the substituents, L and L1 are a direct bond; a C6 to C60 monocyclic arylene group; or a C10 to C60 polycyclic arylene group, Ar1 is a substituted or unsubstituted C10 to C60 aryl group, or represented by the following Chemical Formula 1-A;

[Chemical Formula 1-A]

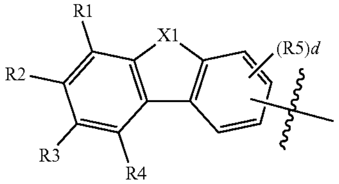

X1 is O; S; or NR22,

R1 to R4 are the same as or different from each other, and each independently hydrogen; a substituted or unsubstituted C1 to C40 alkyl group; a substituted or unsubstituted C6 to C40 aryl group; or a substituted or unsubstituted C2 to C40 heteroaryl group, or two or more groups adjacent to each other bond to each other to form a substituted or unsubstituted C6 to C40 aromatic hydrocarbon ring, A3 is O; S; or NRg;

R50 and R51 are the same as or different from each other, and each independently hydrogen; a phenyl group; or a triphenylenyl group, and at least one thereof is a phenyl group or a triphenylenyl group, Rg is a substituted or unsubstituted C6 to C60 aryl group, R11, R14, R52 and R53 are hydrogen, r is an integer of 0 to 3;

q is an integer of 0 to 4,

R5 to R7 are the same as or different from each other, and each independently selected from the group consisting of hydrogen; and deuterium;

A1 and A2 are the same as or different from each other, and each independently O; S; NRa; or CRbRc;

at least one of A1 and A2 is O; S; or CRbRc;

R22, R, R', and R" are the same as or different from each other, and each independently a C6 to C40 aryl, Ra is a phenyl group unsubstituted or substituted with one or more substituents selected form the group consisting of a phenyl group, a biphenyl group and a triphenylsilyl group; a biphenyl group; a naphthyl group; a terphenyl group; a triphenylenyl group; a dimethylfluorenyl group; a diphenylfluorenyl group; a dibenzofuran group; a dibenzothiophene group; or a carbazole group unsubstituted or substituted with a phenyl group, Rb and Rc are the same as or different from each other, and each independently C1 to C20 alkyl group, b, c and d are an integer of 0 to 3;

and a and e are an integer of 0 to 5,

"substituted or unsubstituted" means being substituted with one or more substituents selected from the group consisting of C1 to C60 linear or branched alkyl; C6 to C60 monocyclic or polycyclic aryl; C2 to C60 monocyclic or polycyclic heteroaryl; —SiRR'R"; and —P(=O)RR'; or being unsubstituted, or being substituted with a substituent linking two or more substituents selected from among the substituents illustrated above, or being unsubstituted.

12. The composition for an organic material layer of an organic light emitting device of claim 11, wherein the heterocyclic compound represented by Chemical Formula 1 and the heterocyclic compound represented by any one of the Chemical Formulae 2-7 to 2-9 have a weight ratio of 1:10 to 10:1 in the composition.

13. A method for manufacturing an organic light emitting device, the method comprising:

preparing a substrate;

forming a first electrode on the substrate, forming one or more organic material layers on the first electrode; and forming a second electrode on the organic material layer, wherein the forming of organic material layers comprises forming one or more organic material layers using the composition for an organic material layer of claim 11.

14. The method for manufacturing an organic light emitting device of claim 13, wherein the forming of organic material layers is forming using a thermal vacuum deposition method after pre-mixing the heterocyclic compound of Chemical Formula 1 and the heterocyclic compound of any one of the Chemical Formulae 2-7 to 2-9.

* * * * *